United States Patent
Casale et al.

(10) Patent No.: US 12,018,023 B2
(45) Date of Patent: Jun. 25, 2024

(54) HETEROCONDENSED PYRIDONES COMPOUNDS AND THEIR USE AS IDH INHIBITORS

(71) Applicant: NERVIANO MEDICAL SCIENCES S.R.L., Nerviano (IT)

(72) Inventors: Elena Casale, Varese (IT); Francesco Casuscelli, Dairago Milan (IT); Teresa Disingrini, Vanzago Milan (IT); Paola Magnaghi, Nerviano Milan (IT); Beatrice Malgesini, San Lorenzo di Parabiago Milan (IT); Ilaria Motto, Nerviano Milan (IT); Stefano Nuvoloni, Genoa (IT)

(73) Assignee: NERVIANO MEDICAL SCIENCES S.R.L., Nerviano (IT)

( * ) Notice: Subject to any disclaimer, the term of this patent is extended or adjusted under 35 U.S.C. 154(b) by 649 days.

(21) Appl. No.: 17/056,450

(22) PCT Filed: May 16, 2019

(86) PCT No.: PCT/EP2019/062605
§ 371 (c)(1),
(2) Date: Nov. 18, 2020

(87) PCT Pub. No.: WO2019/224096
PCT Pub. Date: Nov. 28, 2019

(65) Prior Publication Data
US 2021/0206759 A1    Jul. 8, 2021

(30) Foreign Application Priority Data

May 21, 2018    (EP) .................................... 18173430

(51) Int. Cl.
C07D 471/04 (2006.01)
A61K 31/519 (2006.01)
A61K 45/06 (2006.01)

(52) U.S. Cl.
CPC .......... *C07D 471/04* (2013.01); *A61K 31/519* (2013.01); *A61K 45/06* (2013.01)

(58) Field of Classification Search
CPC .... A61K 31/519; A61K 45/06; C07D 471/04; A61P 35/00
See application file for complete search history.

(56) References Cited

FOREIGN PATENT DOCUMENTS

| WO | 98/33798 A2 | 8/1998 |
|---|---|---|
| WO | 2005/047284 A1 | 5/2005 |
| WO | 2007/044813 A1 | 4/2007 |
| WO | 2008/021389 A2 | 2/2008 |
| WO | 2014/141104 A1 | 9/2014 |

OTHER PUBLICATIONS

Lima et al., Bioisosterism: A Useful Strategy for Molecular Modification and Drug Design, Current Medicinal Chemistry, vol. 12, No. 1, 23-49, 2005. (Year: 2005).*
International Search Report dated Jul. 10, 2019 received in International Application No. PCT/EP2019/062605.
Indian Examination Report dated May 9, 2022 received in Indian Application No. 202047054683, together with an English-language translation.

* cited by examiner

*Primary Examiner* — Kortney L. Klinkel
*Assistant Examiner* — Padmaja S Rao
(74) *Attorney, Agent, or Firm* — Scully, Scott, Murphy & Presser, P.C.

(57) ABSTRACT

The present invention relates to certain substituted heterocondensed pyridone analogues of formula (I) which modulate the activity of Isocitrate Dehydrogenase (IDH). The compounds of this invention are therefore useful in treating diseases caused by mutated IDH1 and/or mutated IDH2 enzyme and/or IDH1 wild type enzyme, in particular cancer, cell proliferative disorders and immune-related disorders. The present invention also provides methods for preparing these compounds, pharmaceutical compositions comprising these compounds, and methods of treating diseases utilizing pharmaceutical compositions comprising these compounds.

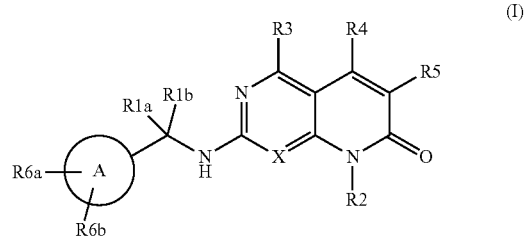

16 Claims, No Drawings

HETEROCONDENSED PYRIDONES COMPOUNDS AND THEIR USE AS IDH INHIBITORS

The present invention relates to certain substituted heterocondensed pyridone analogues, which modulate the activity of Isocitrate Dehydrogenase (IDH). The compounds of this invention are therefore useful in treating diseases caused by mutated IDH1 and/or mutated IDH2 enzyme and/or IDH1 wild type enzyme. The present invention also provides methods for preparing these compounds, pharmaceutical compositions comprising these compounds, and methods of treating diseases utilizing pharmaceutical compositions comprising these compounds.

BACKGROUND OF THE INVENTION

Isocitrate dehydrogenases (IDHs) represent a family of metal dependent oxidoreductases involved in cellular metabolism. These enzymes catalyze the oxidative decarboxylation of isocitrate to alpha-ketoglutarate generating carbon dioxide and NADH or NADPH in the process.

Three different members of this family have been identified: IDH1 and IDH2 that are structurally related homodimers and use $NADP^+$ as electron acceptor, and IDH3 that is a heterotrimeric complex and uses instead $NAD^+$ as electron acceptor.

IDH1 is localized in the cytoplasm and peroxisomes and represent a major source of NADPH production for cells, while IDH2 is localized in the mitochondria as an integral part of the tricarboxylic acid cycle (TCA). The human IDH1 gene encodes a protein of 414 amino acids whose amino acid sequence can be found as UniProtKB accession no. O75874. The human IDH2 gene encodes a protein of 452 amino acid whose amino acid sequence can be found as UniProtKB accession no. P48735.

Somatic heterozygous mutations in isocitrate dehydrogenase 1 (IDH1) were identified in approximately 80% of grade II-Ill gliomas and in secondary glioblastomas (see Balss, J. Acta Neuropathol, 2008, 116, 597-602, Watanabe, T., Am. J. Pathol, 2009, 174, 1149-1153, Yan, H. N. Engl. J. Med. 2009, 360, 765-773). IDH1 mutations were also found in 50% of chondrosarcoma (see Amary MF, J. Pathol 2011, 224, 334-43), in 15%-20% of intrahepatic cholangiocarcinoma (see Borger D R, Oncol. 2012, 17, 72-9), and at lower frequency (<5%) in other solid tumors (e.g. glioblastomas, colorectal cancer, esophageal cancer, bladder cancer, melanoma, prostate carcinoma, breast adenocarcinoma (see Cerami E, Cancer Discov. 2012, 2, 401-4).

IDH1 and IDH2 mutations were also observed in a number of hematopoietic neoplasms, most commonly in 10%-15% acute myeloid leukemia (AML) (see, e.g. Mardis ER, N Engl J. Med. 2009, 361, 1058-66, Gross S, J. Exp. Med. 2010, 207, 339-44, Marcucci G, J. Clin. Oncol. 2010, 28, 2348-55) and 20% of angio-immunoblastic T-cell lymphoma (see Cairns R A, Blood 2012, 119, 1901-3).

Interestingly the same mutations in IDH1 or IDH2 were identified in the majority of enchondromas and spindle cell hemangiomas in patients with the Ollier disease and Maffuci syndrome, nonhereditary skeletal disorders (see Amary et al., Nature Genetics, 2011, 1261-1265; and Pansuriya T C, Nat. Genet. 2011, 43, 1256-61).

All mutations have been found in heterozygosity in a mutual exclusive way and in specific tissues. These mutations reside in the catalytic domain of the enzyme responsible for 2-oxoglutarate coordination, and involve mainly Arg 132 (R132) in IDH1 and Arg 140 (R140) or Arg 172 (R172) in IDH2, that can mutate to different aminoacids. Other mutations were also identified in IDH1 although with very low frequency (e.g. Arg 100, and Gly 97; Dang L, Nature, 2009, 462, 739-44). In all cases these points of mutation of Arg to Cys, His, Lys, Leu or Ser abolish magnesium binding and prevent the conversion of isocitrate to alpha-ketoglutarate. Instead, the mutated enzymes acquired a neomorphic activity that converts the alpha-ketoglutarate into R(−)-2-hydroxyglutarate (R-2-HG) (See P. S. Ward et al., Cancer Cell, 2010, 17, 225). In general, the production of 2-HG is enantiospecific, resulting in generation of the D-enantiomer (also known as R enantiomer or R-2-HG). R(−)-2-hydroxyglutarate was shown to act as an oncometabolite, mainly through the inhibition of several DNA and histone demethylases. The consequence at cellular level is an epigenetic reprogramming, leading to a different transcriptional asset, that induce dedifferentiation and tumorigenesis.

IDH1 over-expression was shown to sustain a less differentiated tumor cell state, to promote growth, to accelerate tumor progression and to reduce susceptibility to RTK-targeting therapies in glioblasoma (GBM) and other solid and systemic cancer models. At molecular level, diminished IDH1 activity results in reduced α-ketoglutarate (α-KG) and NADPH production, exhaustion of reduced glutathione, increased levels of reactive oxygen species (ROS), and enhanced histone methylation and differentiation markers expression. Pharmacological inhibition of IDH1 with a small molecule reduces GBM tumor burden and increases the survival of PDX mice. These data suggest also that cancer-associated IDH1 upregulation represents an actionable ("druggable") cancer-promoting mechanism and provide the rationale for the evaluation of wild-type IDH1 inhibitors as anti-neoplastic agents (see Calvert et al., 2017, Cell Reports 19, 1858-1873).

The inhibition of activity of IDH enzymes is therefore a potential therapeutic treatment option for tumors and other IDH related disorders.

Accordingly, there is a strong medical need for therapeutic agents active against diseases caused by and/or associated with mutated IDH enzymes, and/or IDH wt over-functions, and several efforts are ongoing to develop inhibitors, in particular small molecule inhibitors, of their alpha hydroxyl neomorphic activity.

Certain pyrido-pyridin-7-one derivatives having biological activity as kinase inhibitors are disclosed in WO2005/047284 in the name of Hoffmann La Roche.

Other pyrido-pyrimidin-7-one compounds useful as kinase inhibitors are disclosed in WO2007044813, in the name of Exelixis Inc., and in WO2008/034008 in the name of Deciphera Pharmaceuticals Lcc.

The inventors have now found that compounds of formula (I), described below, are inhibitors of mutated IDH1 and/or mutated IDH2 and/or IDH1 wild type enzymes and are thus useful to treat diseases caused by high level of 2-HG, or caused by IDH wt over-functions.

Accordingly, a first object of the present invention is a substituted heterocondensed pyridone derivative of formula (I):

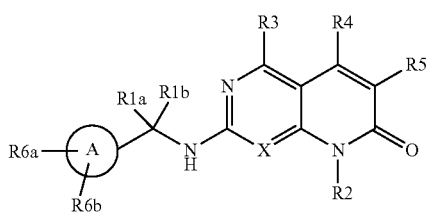

(I)

wherein:
X is nitrogen or —CH—
R1a is hydrogen or an optionally substituted straight or branched $(C_1-C_6)$alkyl;
R1b is an optionally substituted $(C_1-C_6)$alkyl, or together with the atom to which they are bound, R1a and R1b may form a $(C_3-C_6)$cycloalkyl;
A is a $(C_3-C_6)$cycloalkyl, aryl or heteroaryl;
R6a and R6b are each independently selected from hydrogen, halogen, cyano, an optionally substituted straight or branched $(C_1-C_6)$alkyl, $(C_3-C_6)$cycloalkyl, cycloalkyl-alkyl, $(C_2-C_6)$alkenyl, $(C_2-C_6)$alkynyl, aryl, heteroaryl, heterocyclyl, —OR7, NR7R8, —COOR7, —SO$_2$R7, —CONR7R8, —CH(R14)OR7 and —CH(R14)NR7R8;
wherein:
R14 is hydrogen or an optionally substituted straight or branched $(C_1-C_6)$alkyl;
R7 and R8 are each independently hydrogen or a group selected from an optionally substituted straight or branched $(C_1-C_6)$alkyl, $(C_3-C_6)$cycloalkyl, aryl, heteroaryl, heterocyclyl, aryl-alkyl, heteroaryl-alkyl, heterocyclyl-alkyl, heterocyclyl-C(O)-alkyl, heterocyclyl-C(O)-alkenyl, heterocyclyl-C(O)-alkynyl or, together with the nitrogen atom to which they are bound, R7 and R8 form a 5- to 7-membered heteroaryl or heterocyclyl group optionally containing one additional heteroatom selected from 0, S and NR9;
wherein:
R9 is hydrogen, an optionally substituted straight or branched $(C_1-C_6)$alkyl, —COOR10 or —COR11;
wherein:
R10 is hydrogen or an optionally substituted straight or branched $(C_1-C_6)$alkyl;
R11 is an optionally substituted straight or branched $(C_1-C_6)$alkyl, $(C_2-C_6)$alkenyl or $(C_2-C_6)$alkynyl;
R2 is an optionally substituted group selected from straight or branched $(C_1-C_6)$alkyl, $(C_3-C_6)$cycloalkyl-$(C_1-C_6)$alkyl, aryl-$(C_1-C_6)$alkyl, and heterocyclyl-$(C_1-C_6)$alkyl;
R3 is hydrogen, chloro, cyano, CONH$_2$, NH$_2$, NR13R13a, OR12, or an optionally substituted group selected from straight or branched $(C_1-C_6)$alkyl, $(C_3-C_6)$cycloalkyl-$(C_1-C_6)$alkyl, aryl and heteroaryl;
wherein:
R12 is an optionally substituted straight or branched $(C_1-C_6)$alkyl;
R13, R13a are each independently selected from hydrogen or optionally substituted straight or branched $(C_1-C_6)$alkyl;
R4 is hydrogen or an optionally substituted straight or branched $(C_1-C_6)$alkyl;
R5 is hydrogen, fluoro, cyano, an optionally substituted straight or branched $(C_1-C_6)$alkyl or —OR12,
wherein:
R12 is as described above;
or a pharmaceutically acceptable salt thereof.

Preferred compounds of formula (I) are the compounds wherein:
R3 is hydrogen, chloro, cyano, CONH$_2$, NH$_2$, NR13R13a, OR12, or an optionally substituted straight or branched $(C_1-C_6)$alkyl;
wherein:
R12 is an optionally substituted straight or branched $(C_1-C_6)$alkyl;
R13, R13a are each independently selected from hydrogen or optionally substituted straight or branched $(C_1-C_6)$alkyl;
R5 is hydrogen, fluoro or —OR12,
wherein:
R12 is as described above; and
R1a, R1b, A, X, R6a, R6b, R2 and R4 are as defined above.

More preferred compounds of formula (I) are the compounds wherein:
R6a and R6b are each independently selected from hydrogen, halogen, cyano, an optionally substituted straight or branched $(C_1-C_6)$alkyl, $(C_2-C_6)$alkenyl, $(C_2-C_6)$alkynyl, aryl, heteroaryl, heterocyclyl, —OR7, NR7R8, —COOR7, —SO$_2$R7, —CONR7R8, —CH(R14)OR7 and —CH(R14)NR7R8;
wherein:
R7, R8 and R14 are as defined above;
R5 is hydrogen or fluoro; and
R1a, R1b, A, X, R2, R3 and R4 are as defined above.

Most preferred compounds of formula (I) are the compounds wherein:
A is aryl or heteroaryl;
R3 is hydrogen, cyano, CONH$_2$, NH$_2$, NR13R13a, or an optionally substituted straight or branched $(C_1-C_6)$alkyl;
wherein:
R13, R13a are each independently selected from hydrogen or optionally substituted straight or branched $(C_1-C_6)$alkyl; and
R1a, R1b, R6a, R6b, X, R2, R4 and R5 are as defined above.

Preferred specific compounds of formula (I), or a pharmaceutically acceptable salt thereof, are the compounds listed below:
methyl 4-{(1S)-1-[(8-benzyl-7-oxo-pyrido[2,3-d]pyrimidin-2-yl)amino]ethyl}benzoate (cpd 1);
methyl 4-{(1S)-1-[(8-ethyl-7-oxo-pyrido[2,3-d]pyrimidin-2-yl)amino]ethyl}benzoate (cpd 2);
methyl 4-[(1S)-1-{[8-(methoxymethyl)-7-oxo-pyrido[2,3-d]pyrimidin-2-yl]amino}ethyl]benzoate (cpd 3);
methyl 4-{(1S)-1-[(8-methyl-7-oxo-pyrido[2,3-d]pyrimidin-2-yl)amino]ethyl}benzoate (cpd 4);
methyl 4-[(1S)-1-{[8-(2-methylpropyl)-7-oxo-pyrido[2,3-d]pyrimidin-2-yl]amino}ethyl]benzoate (cpd 5);
methyl 4-[(1S)-1-{[8-(4-fluorobenzyl)-7-oxo-pyrido[2,3-d]pyrimidin-2-yl]amino}ethyl]benzoate (cpd 6);
methyl 4-[(1S)-1-{[8-(3,5-difluorobenzyl)-7-oxo-pyrido[2,3-d]pyrimidin-2-yl]amino}ethyl]benzoate (cpd 7);
methyl 4-[(1S)-1-({8-[4-fluoro-2-(trifluoromethyl)benzyl]-7-oxo-pyrido[2,3-d]pyrimidin-2-yl}amino)ethyl]benzoate (cpd 8);
methyl 4-[(1S)-1-{[7-oxo-8-(propan-2-yl)-pyrido[2,3-d]pyrimidin-2-yl]amino}ethyl]benzoate (cpd 9);

methyl 4-[(1S)-1-({8-[(3-methyloxetan-3-yl)methyl]-7-oxo-pyrido[2,3-d]pyrimidin-2-yl}amino)ethyl]benzoate (cpd 10);

methyl 4-[(1S)-1-{[8-(2,2-dimethylpropyl)-7-oxo-pyrido[2,3-d]pyrimidin-2-yl]amino}ethyl]benzoate (cpd 11);

2-{[(1S)-1-cyclohexylethyl]amino}-8-ethylpyrido[2,3-d]pyrimidin-7(8H)-one (cpd 12);

8-ethyl-2-{[(1S)-1-(4-methoxyphenyl)ethyl]amino}pyrido[2,3-d]pyrimidin-7(8H)-one (cpd 13);

2-{[(1S)-1-(4-chlorophenyl)ethyl]amino}-8-ethylpyrido[2,3-d]pyrimidin-7(8H)-one (cpd 14);

2-{[(1S)-1-(4-chlorophenyl)ethyl]amino}-8-(pentan-3-yl)pyrido[2,3-d]pyrimidin-7(8H)-one (cpd 15);

8-benzyl-2-{[(1S)-1-(4-chlorophenyl)ethyl]amino}pyrido[2,3-d]pyrimidin-7(8H)-one (cpd 16);

2-{[(1S)-1-(4-chlorophenyl)ethyl]amino}-8-(2-fluoroethyl)pyrido[2,3-d]pyrimidin-7(8H)-one (cpd 17);

2-{[(1S)-1-(4-chlorophenyl)ethyl]amino}-8-(2,2,2-trifluoroethyl)pyrido[2,3-d]pyrimidin-7(8H)-one (cpd 18);

2-{[(1S)-1-(4-chlorophenyl)ethyl]amino}-8-(2-methylpropyl)pyrido[2,3-d]pyrimidin-7(8H)-one (cpd 19);

2-{[(1S)-1-(4-chlorophenyl)ethyl]amino}-8-(cyclopropylmethyl)pyrido[2,3-d]pyrimidin-7(8H)-one (cpd 20);

2-{[(1S)-1-(4-chlorophenyl)ethyl]amino}-8-(4-methoxybenzyl)pyrido[2,3-d]pyrimidin-7(8H)-one (cpd 21);

2-{[(1S)-1-(4-chlorophenyl)ethyl]amino}-8-(2-fluorobenzyl)pyrido[2,3-d]pyrimidin-7(8H)-one (cpd 22);

2-{[(1S)-1-(4-chlorophenyl)ethyl]amino}-8-(3,4-difluorobenzyl)pyrido[2,3-d]pyrimidin-7(8H)-one (cpd 23);

2-{[(1S)-1-(4-chlorophenyl)ethyl]amino}-8-[3-(trifluoromethyl)benzyl]pyrido[2,3-d]pyrimidin-7(8H)-one (cpd 24);

2-{[(1S)-1-(4-chlorophenyl)ethyl]amino}-8-(2,4-difluorobenzyl)pyrido[2,3-d]pyrimidin-7(8H)-one (cpd 25);

2-{[(1S)-1-(4-chlorophenyl)ethyl]amino}-8-[4-(trifluoromethoxy)benzyl]pyrido[2,3-d]pyrimidin-7(8H)-one (cpd 26);

4-{[2-{[(1S)-1-(4-chlorophenyl)ethyl]amino}-7-oxopyrido[2,3-d]pyrimidin-8(7H)-yl]methyl}benzonitrile (cpd 27);

2-{[(1S)-1-(4-chlorophenyl)ethyl]amino}-8-(4-fluorobenzyl)pyrido[2,3-d]pyrimidin-7(8H)-one (cpd 28);

2-{[(1S)-1-(4-chlorophenyl)ethyl]amino}-8-(3,5-difluorobenzyl)pyrido[2,3-d]pyrimidin-7(8H)-one (cpd 29);

2-{[(1S)-1-(4-chlorophenyl)ethyl]amino}-8-(3-methoxybenzyl)pyrido[2,3-d]pyrimidin-7(8H)-one (cpd 30);

2-{[(1S)-1-(4-chlorophenyl)ethyl]amino}-8-(2,6-difluorobenzyl)pyrido[2,3-d]pyrimidin-7(8H)-one (cpd 31);

2-{[(1S)-1-(4-chlorophenyl)ethyl]amino}-4-methyl-8-(2-methylpropyl)pyrido[2,3-d]pyrimidin-7(8H)-one (cpd 32);

8-(2,2-dimethylpropyl)-2-{[(1S)-1-(4-methoxyphenyl)ethyl]amino}pyrido[2,3-d]pyrimidin-7(8H)-one (cpd 33);

2-{[(1S)-1-(4-bromophenyl)ethyl]amino}-8-(2,2-dimethylpropyl)pyrido[2,3-d]pyrimidin-7(8H)-one (cpd 34);

2-{[(1S)-1-(4-bromophenyl)ethyl]amino}-8-(3-hydroxy-2,2-dimethylpropyl)pyrido[2,3-d]pyrimidin-7(8H)-one (cpd 35);

8-(2,2-dimethylpropyl)-2-{[(1S)-1-(naphthalen-2-yl)ethyl]amino}pyrido[2,3-d]pyrimidin-7(8H)-one (cpd 36);

methyl 2,2-dimethyl-3-[2-{[(1S)-1-(naphthalen-2-yl)ethyl]amino}-7-oxopyrido[2,3-d]pyrimidin-8(7H)-yl]propanoate (cpd 37);

8-(3-hydroxy-2,2-dimethylpropyl)-2-{[(1S)-1-(naphthalen-2-yl)ethyl]amino}pyrido[2,3-d]pyrimidin-7(8H)-one (cpd 38);

8-(2,2-dimethylpropyl)-2-{[(1R)-1-phenylethyl]amino}pyrido[2,3-d]pyrimidin-7(8H)-one (cpd 39);

8-(2,2-dimethylpropyl)-2-{[(1S)-1-phenylethyl]amino}pyrido[2,3-d]pyrimidin-7(8H)-one (cpd 40);

8-(2,2-dimethylpropyl)-2-[(2-phenylpropan-2-yl)amino]pyrido[2,3-d]pyrimidin-7(8H)-one (cpd 41);

8-(2,2-dimethylpropyl)-2-[(1-phenylcyclopropyl)amino]pyrido[2,3-d]pyrimidin-7(8H)-one (cpd 42);

8-(2,2-dimethylpropyl)-2-[(1-phenylcyclobutyl)amino]pyrido[2,3-d]pyrimidin-7(8H)-one (cpd 43);

8-(2,2-dimethylpropyl)-2-{[1-(tricyclo[3.3.1.1$^{3,7}$]dec-1-yl)ethyl]amino}pyrido[2,3-d]pyrimidin-7(8H)-one (cpd 44);

8-[(3-methyloxetan-3-yl)methyl]-2-{[(1S)-1-(naphthalen-2-yl)ethyl]amino}pyrido[2,3-d]pyrimidin-7(8H)-one (cpd 45);

8-(2-hydroxy-2-methylpropyl)-2-{[(1S)-1-phenylethyl]amino}pyrido[2,3-d]pyrimidin-7(8H)-one (cpd 46);

8-(2,2-Dimethyl-propyl)-6-fluoro-2-((S)-1-phenyl-ethylamino)-8H-pyrido[2,3-d]pyrimidin-7-one (cpd 47);

Methyl 4-[(1S)-1-{[8-(2-hydroxy-2-methylpropyl)-7-oxo-7,8-dihydropyrido[2,3-d]pyrimidin-2-yl]amino}ethyl]benzoate (cpd 48);

8-(2,2-dimethylpropyl)-2-{[(1S)-1-(4-phenoxyphenyl)ethyl]amino}pyrido[2,3-d]pyrimidin-7(8H)-one (cpd 49);

2-{[(1S)-1-(6-chloro-2-oxo-quinolin-3-yl)ethyl]amino}-8-(2,2-dimethylpropyl)pyrido[2,3-d]pyrimidin-7(8H)-one (cpd 50);

8-benzyl-2-{[(1S)-1-(5-chloro-1H-benzimidazol-2-yl)ethyl]amino}pyrido[2,3-d]pyrimidin-7(8H)-one (cpd 51);

8-benzyl-2-({(1S)-1-[3-(4-chlorophenyl)-1,2,4-oxadiazol-5-yl]ethyl}amino)pyrido[2,3-d]pyrimidin-7(8H)-one (cpd 52);

2-({(1S)-1-[3-(4-chlorophenyl)-1,2,4-oxadiazol-5-yl]ethyl}amino)-8-(2,2-dimethylpropyl)pyrido[2,3-d]pyrimidin-7(8H)-one (cpd 53);

8-(2,2-dimethylpropyl)-2-{[(1S)-1-(4-oxo-3,4-dihydroquinazolin-2-yl)ethyl]amino}pyrido[2,3-d]pyrimidin-7(8H)-one (cpd 54);

2-{[(1S)-1-{4-[(4,4-difluoropiperidin-1-yl)methyl]phenyl}ethyl]amino}-8-(3-hydroxy-2,2-dimethylpropyl)pyrido[2,3-d]pyrimidin-7(8H)-one (cpd 55);

4-(4-{(S)-1-[8-(3-Hydroxy-2,2-dimethyl-propyl)-7-oxo-7,8-dihydro-pyrido[2,3-d]pyrimidin-2-ylamino]-ethyl}-benzyl)-piperazine-1-carboxylic acid tert-butyl ester (cpd 56);

2-{(S)-1-[4-(3,3-Difluoro-piperidin-1-ylmethyl)-phenyl]-ethylamino}-8-(2,2-dimethyl-propyl)-6-fluoro-8H-pyrido[2,3-d]pyrimidin-7-one (cpd 57);

2-{(S)-1-[4-(3,3-Difluoro-piperidin-1-ylmethyl)-phenyl]-ethylamino}-8-(2,2-dimethyl-propyl)-6-methoxy-8H-pyrido[2,3-d]pyrimidin-7-one (cpd 58);

4-(4-{(S)-1-[8-(2,2-Dimethyl-propyl)-7-oxo-7,8-dihydro-pyrido[2,3-d]pyrimidin-2-ylamino]-ethyl}-benzyl)-piperazine-1-carboxylic acid tert-butyl ester (cpd 59);

2-{[(1S)-1-{4-[(3,3-difluoropiperidin-1-yl)methyl]phenyl}ethyl]amino}-8-(2,2-dimethylpropyl)-5-methylpyrido[2,3-d]pyrimidin-7(8H)-one (cpd 60);

8-(butan-2-yl)-2-{[(1S)-1-{4-[(3,3-difluoropiperidin-1-yl)methyl]phenyl}ethyl]amino}pyrido[2,3-d]pyrimidin-7(8H)-one (cpd 61);

8-[(2S)-butan-2-yl]-2-{[(1S)-1-{4-[(3,3-difluoropiperidin-1-yl)methyl]phenyl}ethyl]amino}pyrido[2,3-d]pyrimidin-7(8H)-one (cpd 62);

ethyl 2-[2-{[(1S)-1-{4-[(3,3-difluoropiperidin-1-yl)methyl]phenyl}ethyl]amino}-7-oxopyrido[2,3-d]pyrimidin-8(7H)-yl]propanoate (cpd 63);

2-[2-{[(1S)-1-{4-[(3,3-difluoropiperidin-1-yl)methyl]phenyl}ethyl]amino}-7-oxopyrido[2,3-d]pyrimidin-8(7H)-yl]propanenitrile (cpd 64);

2-{[(1S)-1-{4-[(3,3-difluoropiperidin-1-yl)methyl]phenyl}ethyl]amino}-8-[(2S)-3-methylbutan-2-yl]pyrido[2,3-d]pyrimidin-7(8H)-one (cpd 65);

8-[(1S)-1-cyclohexylethyl]-2-{[(1S)-1-{4-[(3,3-difluoropiperidin-1-yl)methyl]phenyl}ethyl]amino}-pyrido[2,3-d]pyrimidin-7(8H)-one (cpd 66);

2-{[(1S)-1-{4-[(4,4-difluoropiperidin-1-yl)methyl]-3-fluorophenyl}ethyl]amino}-8-[(2S)-3-methylbutan-2-yl]pyrido[2,3-d]pyrimidin-7(8H)-one (cpd 67);

2-({(1S)-1-[3-fluoro-4-(morpholin-4-ylmethyl)phenyl]ethyl}amino)-8-[(2S)-3-methylbutan-2-yl]pyrido[2,3-d]pyrimidin-7(8H)-one (cpd 68);

2-{[(1S)-1-{4-[(3,3-difluoropiperidin-1-yl)methyl]phenyl}ethyl]amino}-8-[(2S)-3,3-dimethylbutan-2-yl]pyrido[2,3-d]pyrimidin-7(8H)-one (cpd 69);

8-(2,2-dimethylpropyl)-2-{[(1S)-1-phenylpropyl]amino}pyrido[2,3-d]pyrimidin-7(8H)-one (cpd 70);

2-{[(1S)-1-(4-chlorophenyl)ethyl]amino}-8-(3-hydroxybenzyl)pyrido[2,3-d]pyrimidin-7(8H)-one (cpd 71);

2-{[(1S)-1-(4-chlorophenyl)ethyl]amino}-8-(4-hydroxybenzyl)pyrido[2,3-d]pyrimidin-7(8H)-one (cpd 72);

4-[(1S)-1-{[8-(2,6-difluorobenzyl)-7-oxo-pyrido[2,3-d]pyrimidin-2-yl]amino}ethyl]benzoic acid (cpd 73);

4-[(1S)-1-{[8-(2-fluorobenzyl)-7-oxo-pyrido[2,3-d]pyrimidin-2-yl]amino}ethyl]benzoic acid (cpd 74);

4-[(1S)-1-{[8-(2,6-difluorobenzyl)-7-oxo-pyrido[2,3-d]pyrimidin-2-yl]amino}ethyl]-N-(4,4-difluorocyclohexyl)benzamide (cpd 75);

4-[(1S)-1-{[8-(2,6-difluorobenzyl)-7-oxo-pyrido[2,3-d]pyrimidin-2-yl]amino}ethyl]-N-(1-methylpiperidin-4-yl)benzamide (cpd 76);

8-(2,6-difluorobenzyl)-2-{[(1S)-1-{4-[(4,4-difluoropiperidin-1-yl)carbonyl]phenyl}ethyl]amino}pyrido[2,3-d]pyrimidin-7 (8H)-one (cpd 77);

4-[(1S)-1-{[8-(2,6-difluorobenzyl)-7-oxo-pyrido[2,3-d]pyrimidin-2-yl]amino}ethyl]-N-(tetrahydro-2H-pyran-4-yl)benzamide (cpd 78);

N-(4,4-difluorocyclohexyl)-4-[(1S)-1-{[8-(2,2-dimethylpropyl)-7-oxo-pyrido[2,3-d]pyrimidin-2-yl]amino}ethyl]benzamide (cpd 79);

N-cyclopentyl-4-[(1S)-1-{[8-(2,2-dimethylpropyl)-7-oxo-pyrido[2,3-d]pyrimidin-2-yl]amino}ethyl]benzamide (cpd 80), N-cyclohexyl-4-[(1S)-1-{[8-(2,2-dimethylpropyl)-7-oxo-pyrido[2,3-d]pyrimidin-2-yl]amino}ethyl]benzamide (cpd 81);

2-chloro-N-(4,4-difluorocyclohexyl)-4-(1-{[8-(2,2-dimethylpropyl)-7-oxo-pyrido[2,3-d]pyrimidin-2-yl]amino}ethyl) benzamide (cpd 82);

2-{[(1S)-1-{4-[(4,4-difluoropiperidin-1-yl)carbonyl]phenyl}ethyl]amino}-8-(2,2-dimethylpropyl)pyrido[2,3-d]pyrimidin-7(8H)-one (cpd 83);

N-(4,4-difluorocyclohexyl)-4-(1-{[8-(2,2-dimethylpropyl)-7-oxo-pyrido[2,3-d]pyrimidin-2-yl]amino}ethyl)-2-fluorobenzamide (cpd 84);

N-(3,3-difluorocyclobutyl)-4-[(1S)-1-{[8-(2,2-dimethylpropyl)-7-oxo-pyrido[2,3-d]pyrimidin-2-yl]amino}ethyl]benzamide (cpd 85);

4-[(1S)-1-{[8-(2,2-dimethylpropyl)-7-oxo-pyrido[2,3-d]pyrimidin-2-yl]amino}ethyl]benzamide (cpd 86);

8-(2,2-dimethylpropyl)-2-{[(1S)-1-{4-[(4-hydroxypiperidin-1-yl)carbonyl]phenyl}ethyl]amino}pyrido[2,3-d]pyrimidin-7(8H)-one (cpd 87);

2-chloro-N-(4,4-difluorocyclohexyl)-4-[(1S)-1-{[8-(2,2-dimethylpropyl)-7-oxo-7,8-dihydropyrido[2,3-d]pyrimidin-2-yl]amino}ethyl]benzamide (cpd 88);

N-(4,4-difluorocyclohexyl)-4-[(1S)-1-{[8-(2,2-dimethylpropyl)-7-oxo-7,8-dihydropyrido[2,3-d]pyrimidin-2-yl]amino}ethyl]-2-fluorobenzamide (cpd 89);

8-(2,2-dimethylpropyl)-2-({(1S)-1-[3-fluoro-4-(hydroxymethyl)phenyl]ethyl}amino)pyrido[2,3-d]pyrimidin-7(8H)-one (cpd 90);

2-({(1S)-1-[4-(hydroxymethyl)phenyl]ethyl}amino)-8-(2-methylpropyl)pyrido[2,3-d]pyrimidin-7(8H)-one (cpd 91);

8-(2,6-difluorobenzyl)-2-({(1S)-1-[4-(hydroxymethyl)phenyl]ethyl}amino)pyrido[2,3-d]pyrimidin-7(8H)-one (cpd 92);

2-({(1S)-1-[4-(hydroxymethyl)phenyl]ethyl}amino)-8-(2-hydroxy-2-methylpropyl)pyrido[2,3-d]pyrimidin-7(8H)-one (cpd 93);

2-{[(1S)-1-{4-[(4,4-difluoropiperidin-1-yl)methyl]-3-fluorophenyl}ethyl]amino}-8-(2,2-dimethylpropyl)pyrido[2,3-d]pyrimidin-7(8H)-one (cpd 94);

2-{[(1S)-1-{4-[(4,4-difluoropiperidin-1-yl)methyl]phenyl}ethyl]amino}-8-(2-methylpropyl)pyrido[2,3-d]pyrimidin-7(8H)-one (cpd 95);

8-benzyl-2-[(1-{4-[(4,4-difluoropiperidin-1-yl)methyl]phenyl}ethyl)amino]pyrido[2,3-d]pyrimidin-7(8H)-one (cpd 96);

2-[(1-{4-[(4,4-difluoropiperidin-1-yl)methyl]phenyl}ethyl)amino]-8-(2-fluorobenzyl)pyrido[2,3-d]pyrimidin-7(8H)-one (cpd 97);

8-(2,6-difluorobenzyl)-2-[(1-{4-[(4,4-difluoropiperidin-1-yl)methyl]phenyl}ethyl)amino]pyrido[2,3-d]pyrimidin-7(8H)-one (cpd 98);

8-(2,6-difluorobenzyl)-2-{[(1S)-1-{4-[(4,4-difluoropiperidin-1-yl)methyl]phenyl}ethyl]amino}pyrido[2,3-d]pyrimidin-7(8H)-one (cpd 99);

2-[(1-{4-[(4,4-difluoropiperidin-1-yl)methyl]phenyl}ethyl)amino]-8-(2-fluoroethyl)pyrido[2,3-d]pyrimidin-7(8H)-one (cpd 100);

2-{[(1S)-1-{4-[(4,4-difluoropiperidin-1-yl)methyl]phenyl}ethyl]amino}-8-propylpyrido[2,3-d]pyrimidin-7(8H)-one (cpd 101);

2-({(1S)-1-[4-(azepan-1-ylmethyl)phenyl]ethyl}amino)-8-propylpyrido[2,3-d]pyrimidin-7(8H)-one (cpd 102);

2-{[(1S)-1-{4-[(4-acetylpiperazin-1-yl)methyl]phenyl}ethyl]amino}-8-propylpyrido[2,3-d]pyrimidin-7(8H)-one (cpd 103);

2-{[(1S)-1-{4-[(4,4-difluoropiperidin-1-yl)methyl]phenyl}ethyl]amino}-8-(2-methylpropyl)pyrido[2,3-d]pyrimidin-7(8H)-one (cpd 104);

2-{[(1S)-1-{4-[(4,4-difluoropiperidin-1-yl)methyl]phenyl}ethyl]amino}-8-(2,2-dimethylpropyl)pyrido[2,3-d]pyrimidin-7(8H)-one (cpd 105);

2-{[(1S)-1-{4-[(4,4-difluoropiperidin-1-yl)methyl]phenyl}ethyl]amino}-8-(2,2,2-trifluoroethyl)pyrido[2,3-d]pyrimidin-7(8H)-one (cpd 106);

8-[2,3-difluoro-2-(fluoromethyl)propyl]-2-{[(1S)-1-{4-[(4,4-difluoropiperidin-1-yl)methyl]phenyl}ethyl]amino}pyrido[2,3-d]pyrimidin-7(8H)-one (cpd 107);

2-{[(1S)-1-{4-[(4,4-difluoropiperidin-1-yl)methyl]phenyl}ethyl]amino}-8-[3,3,3-trifluoro-2-(trifluoromethyl)propyl] pyrido [2,3-d]pyrimidin-7(8H)-one (cpd 108);

8-(cyclobutylmethyl)-2-{[(1S)-1-{4-[(4,4-difluoropiperidin-1-yl)methyl]phenyl}ethyl]amino}pyrido[2,3-d]pyrimidin-7(8H)-one (cpd 109);

8-(2,2-dimethylpropyl)-2-({(1S)-1-[4-(morpholin-4-ylmethyl)phenyl]ethyl}amino)pyrido[2,3-d]pyrimidin-7(8H)-one (cpd 110);

8-(2,2-dimethylpropyl)-2-({(1S)-1-[4-(pyrrolidin-1-ylmethyl)phenyl]ethyl}amino)pyrido[2,3-d]pyrimidin-7(8H)-one (cpd 111);

2-{[(1S)-1-{4-[(4,4-difluoropiperidin-1-yl)methyl]phenyl}ethyl]amino}-8-(2-methylbenzyl)pyrido[2,3-d]pyrimidin-7(8H)-one (cpd 112);

8-(cyclohexylmethyl)-2-{[(1S)-1-{4-[(4,4-difluoropiperidin-1-yl)methyl]phenyl}ethyl]amino}pyrido[2,3-d]pyrimidin-7(8H)-one (cpd 113);

2-{[(1S)-1-{4-[(4,4-difluoropiperidin-1-yl)methyl]phenyl}ethyl]amino}-8-(2-methoxyethyl)pyrido[2,3-d]pyrimidin-7(8H)-one (cpd 114);

2-{[(1S)-1-{4-[(4,4-difluoropiperidin-1-yl)methyl]phenyl}ethyl]amino}-8-[4-fluoro-2-(trifluoromethyl)benzyl]pyrido[2,3-d]pyrimidin-7(8H)-one (cpd 115);

2-{[(1S)-1-{4-[(4,4-difluoropiperidin-1-yl)methyl]phenyl}ethyl]amino}-8-(3,3,3-trifluoro-2,2-dimethylpropyl)pyrido[2,3-d]pyrimidin-7(8H)-one (cpd 116);

2-{[(1S)-1-{4-[(3,3-difluoropiperidin-1-yl)methyl]phenyl}ethyl]amino}-8-(2,2-dimethylpropyl)pyrido[2,3-d]pyrimidin-7(8H)-one (cpd 117);

2-{[(1S)-1-{4-[(4,4-difluoropiperidin-1-yl)methyl]phenyl}ethyl]amino}-4-methyl-8-(2-methylpropyl)pyrido[2,3-d]pyrimidin-7(8H)-one (cpd 118);

2-{[(1S)-1-{4-[(4,4-difluoropiperidin-1-yl)methyl]phenyl}ethyl]amino}-8-(2-hydroxy-2-methylpropyl)pyrido[2,3-d]pyrimidin-7(8H)-one (cpd 119);

2-{[(1S)-1-{4-[(4,4-difluoropiperidin-1-yl)methyl]phenyl}ethyl]amino}-8-[2-(hydroxymethyl)-2-methylpentyl]pyrido[2,3-d]pyrimidin-7(8H)-one (cpd 120);

2,2-dimethyl-3-[2-{[(1S)-1-(naphthalen-2-yl)ethyl]amino}-7-oxopyrido[2,3-d]pyrimidin-8(7H)-yl]propanoic acid (cpd 121);

2,2-dimethyl-3-[2-{[(1S)-1-(naphthalen-2-yl)ethyl]amino}-7-oxopyrido[2,3-d]pyrimidin-8(7H)-yl]propanamide (cpd 122);

N,2,2-trimethyl-3-[7-oxo-2-{[(1S)-1-phenylethyl]amino}pyrido[2,3-d]pyrimidin-8(7H)-yl]propanamide (cpd 123);

N,N,2,2-tetramethyl-3-[7-oxo-2-{[(1S)-1-phenylethyl]amino}pyrido[2,3-d]pyrimidin-8(7H)-yl]propanamide (cpd 124);

2,2-dimethyl-N-(3-methylphenyl)-3-[7-oxo-2-{[(1S)-1-phenylethyl]amino}pyrido[2,3-d]pyrimidin-8(7H)-yl]propanamide (cpd 125);

N-(2-hydroxyethyl)-2,2-dimethyl-3-[7-oxo-2-{[(1S)-1-phenylethyl]amino}pyrido[2,3-d]pyrimidin-8(7H)-yl]propanamide (cpd 126);

N-(3-hydroxypropyl)-2,2-dimethyl-3-[7-oxo-2-{[(1S)-1-phenylethyl]amino}pyrido[2,3-d]pyrimidin-8(7H)-yl]propanamide (cpd 127);

N-[3-(1-hydroxyethyl)phenyl]-2,2-dimethyl-3-[7-oxo-2-{[(1S)-1-phenylethyl]amino}pyrido[2,3-d]pyrimidin-8(7H)-yl]propanamide (cpd 128);

2,2-dimethyl-3-[2-{[(1S)-1-(naphthalen-2-yl)ethyl]amino}-7-oxopyrido[2,3-d]pyrimidin-8(7H)-yl]propanenitrile (cpd 129);

8-(2,2-dimethylpropyl)-2-({(1S)-1-[4-(1-methyl-1H-pyrazol-4-yl)phenyl]ethyl}amino)pyrido[2,3-d]pyrimidin-7(8H)-one (cpd 130);

8-(2,2-dimethylpropyl)-2-({(1S)-1-[4-(pyridin-4-yl)phenyl]ethyl}amino)pyrido[2,3-d]pyrimidin-7(8H)-one (cpd 131);

8-(2,2-dimethylpropyl)-2-({(1S)-1-[4-(2-fluoropyridin-4-yl)phenyl]ethyl}amino)pyrido[2,3-d]pyrimidin-7(8H)-one (cpd 132)

8-(2,2-dimethylpropyl)-2-({(1S)-1-[4-(thiophen-3-yl)phenyl]ethyl}amino)pyrido[2,3-d]pyrimidin-7(8H)-one (cpd 133);

4'-[(1S)-1-{[8-(2,2-dimethylpropyl)-7-oxo-7,8-dihydropyrido[2,3-d]pyrimidin-2-yl]amino}ethyl]biphenyl-2-carbonitrile (cpd 134);

8-(3-hydroxy-2,2-dimethylpropyl)-2-({(1S)-1-[4-(1-methyl-1H-pyrazol-4-yl)phenyl]ethyl}amino)pyrido[2,3-d]pyrimidin-7(8H)-one (cpd 135);

8-(3-hydroxy-2,2-dimethylpropyl)-2-({(1S)-1-[4-(thiophen-3-yl)phenyl]ethyl}amino)pyrido[2,3-d]pyrimidin-7(8H)-one (cpd 136);

8-(2,2-dimethylpropyl)-2-({(1S)-1-[4-(methylsulfonyl)phenyl]ethyl}amino)pyrido[2,3-d]pyrimidin-7(8H)-one (cpd 137);

8-(2,2-dimethylpropyl)-2-({(1S)-1-[4-(piperazin-1-ylmethyl)phenyl]ethyl}amino)pyrido[2,3-d]pyrimidin-7(8H)-one dihydrochloride (cpd 138);

2-{[(1S)-1-{4-[(4-acryloylpiperazin-1-yl)methyl]phenyl}ethyl]amino}-8-(2,2-dimethylpropyl)pyrido[2,3-d]pyrimidin-7(8H)-one (cpd 139);

2-{[(1S)-1-{4-[(4-acryloylpiperazin-1-yl)methyl]phenyl}ethyl]amino}-8-(3-hydroxy-2,2-dimethylpropyl)pyrido[2,3-d]pyrimidin-7(8H)-one (cpd 140);

2-{[(1S)-1-{4-[(4-acryloylpiperazin-1-yl)methyl]-3-fluorophenyl}ethyl]amino}-8-(2,2-dimethylpropyl)pyrido[2,3-d]pyrimidin-7(8H)-one (cpd 141);

2-{[(1S)-1-{4-[(4-acryloylpiperazin-1-yl)carbonyl]phenyl}ethyl]amino}-8-(2,2-dimethylpropyl)pyrido[2,3-d]pyrimidin-7(8H)-one (cpd 142);

2-({(1S)-1-[4-({4-[(2E)-but-2-enoyl]piperazin-1-yl}methyl)phenyl]ethyl}amino)-8-(2,2-dimethylpropyl)pyrido[2,3-d]pyrimidin-7(8H)-one (cpd 143);

8-(2,2-dimethylpropyl)-2-{[(1S)-1-(4-{[4-(2-methylacryloyl)piperazin-1-yl]methyl}phenyl)ethyl]amino} pyrido[2,3-d]pyrimidin-7(8H)-one (cpd 144);

8-(2,2-Dimethyl-propyl)-2-[(S)-1-(4-hydroxy-phenyl)-ethylamino]-8H-pyrido[2,3-d]pyrimidin-7-one (cpd 145);

4-(4-{(S)-1-[8-((S)-1,2-Dimethyl-propyl)-7-oxo-7,8-dihydro-pyrido[2,3-d]pyrimidin-2-ylamino]-ethyl}-phenoxy)-piperidine-1-carboxylic acid benzyl ester (cpd 146);

2-{[(1S)-1-{4-[(3,3-difluoroazetidin-1-yl)methyl]phenyl}ethyl]amino}-8-(2,2-dimethylpropyl)pyrido[2,3-d]pyrimidin-7(8H)-one (cpd 147);

2-{[(1S)-1-{4-[(3,3-difluoropyrrolidin-1-yl)methyl]phenyl}ethyl]amino}-8-(2,2-dimethylpropyl)pyrido[2,3-d]pyrimidin-7(8H)-one (cpd 148);

8-[(2R)-butan-2-yl]-2-{[(1S)-1-{4-[(3,3-difluoropiperidin-1-yl)methyl]phenyl}ethyl]amino}pyrido[2,3-d]pyrimidin-7(8H)-one (cpd 149);

2-{[(1S)-1-(4-{[(2R,6S)-2,6-dimethylmorpholin-4-yl]methyl}-3-fluorophenyl)ethyl]amino}-8-[(2S)-3-methylbutan-2-yl]pyrido[2,3-d]pyrimidin-7(8H)-one (cpd 150);

2-{[(1S)-1-(4-{[(2R,6S)-2,6-dimethylmorpholin-4-yl]methyl}-2-fluorophenyl)ethyl]amino}-8-(2,2-dimethylpropyl) pyrido[2,3-d]pyrimidin-7(8H)-one (cpd 151);

2-{[(1S)-1-{4-[(4,4-difluoropiperidin-1-yl)methyl]-2-fluorophenyl}ethyl]amino}-8-(2,2-dimethylpropyl)pyrido[2,3-d]pyrimidin-7(8H)-one (cpd 152);

8-(2,2-dimethylpropyl)-2-({(1S)-1-[2-fluoro-4-(morpholin-4-ylmethyl)phenyl]ethyl}amino)pyrido[2,3-d]pyrimidin-7(8H)-one (cpd 153);

4-(4-{(S)-1-[8-(2,2-Dimethyl-propyl)-7-oxo-7,8-dihydro-pyrido[2,3-d]pyrimidin-2-ylamino]-ethyl}-phenoxy)-piperidine-1-carboxylic acid tert-butyl ester (cpd 154);

8-((S)-1,2-Dimethyl-propyl)-2-{(S)-1-[4-(piperidin-4-yloxy)-phenyl]-ethylamino}-8H-pyrido[2,3-d]pyrimidin-7-one (cpd 155);

2-{(S)-1-[4-(1-Acryloyl-piperidin-4-yloxy)-phenyl]-ethylamino}-8-(2,2-dimethyl-propyl)-8H-pyrido[2,3-d]pyrimidin-7-one (cpd 156);

8-(2,2-dimethylpropyl)-2-{[(1S)-1-(4-{[4-(2-methylpropanoyl)piperazin-1-yl]methyl}phenyl)ethyl]amino}pyrido[2,3-d]pyrimidin-7(8H)-one (cpd 157);

2-{[(1S)-1-(4-{[4-(cyclopropylcarbonyl)piperazin-1-yl]methyl}phenyl)ethyl]amino}-8-(2,2-dimethylpropyl)pyrido[2,3-d]pyrimidin-7(8H)-one (cpd 158);

2-{(S)-1-[4-(1-Acryloyl-piperidin-4-yloxy)-phenyl]-ethylamino}-8-((S)-1,2-dimethyl-propyl)-8H-pyrido[2,3-d]pyrimidin-7-one (cpd 159);

8-((S)-1,2-Dimethyl-propyl)-2-{(S)-1-[4-(1-isobutyryl-piperidin-4-yloxy)-phenyl]-ethylamino}-8H-pyrido[2,3-d]pyrimidin-7-one (cpd 160);

2-{(S)-1-[4-(4-Acryloyl-piperazin-1-ylmethyl)-phenyl]-ethylamino}-8-((S)-1,2-dimethyl-propyl)-8H-pyrido[2,3-d]pyrimidin-7-one (cpd 161);

8-((S)-1,2-Dimethyl-propyl)-2-((S)-1-{4-[4-(2-methylacryloyl)-piperazin-1-ylmethyl]-phenyl}-ethylamino)-8H-pyrido[2,3-d]pyrimidin-7-one (cpd 162);

2-{[(1S)-1-(4-bromophenyl)ethyl]amino}-8-[(2S)-3-methylbutan-2-yl]pyrido[2,3-d]pyrimidin-7(8H)-one (cpd 163);

2-{[(1S)-1-(4-{[(2R,6S)-2,6-dimethylmorpholin-4-yl]methyl}phenyl)ethyl]amino}-8-[(2S)-1,1,1-trifluoropropan-2-yl]pyrido[2,3-d]pyrimidin-7(8H)-one (cpd 164);

4'-[(1S)-1-({8-[(2S)-3-methylbutan-2-yl]-7-oxo-7,8-dihydropyrido[2,3-d]pyrimidin-2-yl}amino)ethyl]biphenyl-2-carbonitrile (cpd 165);

2-({(1S)-1-[4-(2-fluoropyridin-4-yl)phenyl]ethyl}amino)-8-[(2S)-3-methylbutan-2-yl]pyrido[2,3-d]pyrimidin-7(8H)-one (cpd 166);

tert-butyl 4-{4-[(1S)-1-({8-[(2S)-3-methylbutan-2-yl]-7-oxo-7,8-dihydropyrido[2,3-d]pyrimidin-2-yl}amino)ethyl]phenyl}-3,6-dihydropyridine-1(2H)-carboxylate (cpd 167);

2-({(1S)-1-[4-(1-acryloyl-1,2,3,6-tetrahydropyridin-4-yl)phenyl]ethyl}amino)-8-[(2S)-3-methylbutan-2-yl]pyrido[2,3-d]pyrimidin-7(8H)-one (cpd 168);

2-{[(1S)-1-{4-[(4-acryloylpiperazin-1-yl)methyl]phenyl}ethyl]amino}-8-[(2S)-1,1,1-trifluoropropan-2-yl]pyrido[2,3-d]pyrimidin-7(8H)-one (cpd 169);

2-{[(1S)-1-{4-[(3,3-difluoropiperidin-1-yl)methyl]phenyl}ethyl]amino}-8-(propan-2-yl)pyrido[2,3-d]pyrimidin-7(8H)-one (cpd 170);

8-[(1S)-1-cyclopropylethyl]-2-{[(1S)-1-(4-{[(2R,6S)-2,6-dimethylmorpholin-4-yl]methyl}-3-fluorophenyl) ethyl]amino}pyrido[2,3-d]pyrimidin-7(8H)-one (cpd 171);

2-{[(1S)-1-(6-chloro-2-oxo-1,2-dihydroquinolin-3-yl)ethyl]amino}-8-[(2S)-3-methylbutan-2-yl]pyrido[2,3-d]pyrimidin-7(8H)-one (cpd 172);

8-[(2S)-3-methylbutan-2-yl]-2-({(1S)-1-[4-(morpholin-4-yl)phenyl]ethyl}amino)pyrido[2,3-d]pyrimidin-7(8H)-one (cpd 173);

benzyl 4-{4-[(1S)-1-({8-[(2S)-3-methylbutan-2-yl]-7-oxo-7,8-dihydropyrido[2,3-d]pyrimidin-2-yl}amino)ethyl]phenyl}piperazine-1-carboxylate (cpd 174);

2-({(1S)-1-[4-(4-acryloylpiperazin-1-yl)phenyl]ethyl}amino)-8-[(2S)-3-methylbutan-2-yl]pyrido[2,3-d]pyrimidin-7(8H)-one (cpd 175);

8-[(2S)-3-methylbutan-2-yl]-2-({(1S)-1-[4-(piperazin-1-yl)phenyl]ethyl}amino)pyrido[2,3-d]pyrimidin-7(8H)-one (cpd 176);

2-({(1S)-1-[4-(4-ethylpiperazin-1-yl)phenyl]ethyl}amino)-8-[(2S)-3-methylbutan-2-yl]pyrido[2,3-d]pyrimidin-7(8H)-one (cpd 177);

benzyl 4-{2-fluoro-4-[(1S)-1-({8-[(2S)-3-methylbutan-2-yl]-7-oxo-7,8-dihydropyrido[2,3-d]pyrimidin-2-yl}amino)ethyl]phenyl}piperazine-1-carboxylate (cpd 178);

2-({(1S)-1-[4-(4-acryloylpiperazin-1-yl)-3-fluorophenyl]ethyl}amino)-8-[(2S)-3-methylbutan-2-yl]pyrido[2,3-d]pyrimidin-7(8H)-one (cpd 179);

8-[(2S)-3-methylbutan-2-yl]-2-({(1S)-1-[6-(piperazin-1-yl)pyridin-3-yl]ethyl}amino)pyrido[2,3-d]pyrimidin-7(8H)-one (cpd 180);

2-({(1S)-1-[6-(4-acryloylpiperazin-1-yl)pyridin-3-yl]ethyl}amino)-8-[(2S)-3-methylbutan-2-yl]pyrido[2,3-d]pyrimidin-7(8H)-one (cpd 181);

2-{[(1S)-1-{4-[(4-acryloylpiperazin-1-yl)methyl]phenyl}ethyl]amino}-8-(2-azidoethyl)pyrido[2,3-d]pyrimidin-7(8H)-one (cpd 182);

2-{[(1S)-1-{4-[(4-acryloylpiperazin-1-yl)methyl]-3-fluorophenyl}ethyl]amino}-8-(propan-2-yl)pyrido[2,3-d]pyrimidin-7(8H)-one (cpd 183);

2-{[(1S)-1-{4-[(4-acryloylpiperazin-1-yl)methyl]phenyl}ethyl]amino}-8-(propan-2-yl)pyrido[2,3-d]pyrimidin-7(8H)-one (cpd 184);

tert-butyl 4-(4-{(1S)-1-[(8-ethyl-7-oxo-7,8-dihydropyrido[2,3-d]pyrimidin-2-yl)amino]ethyl}benzyl)piperazine-1-carboxylate (cpd 185);

2-{[(1S)-1-{4-[(4-acryloylpiperazin-1-yl)methyl]phenyl}ethyl]amino}-8-ethylpyrido[2,3-d]pyrimidin-7(8H)-one (cpd 186);

2-{[(1S)-1-{4-[1-(4-acryloylpiperazin-1-yl)propyl]phenyl}ethyl]amino}-8-(propan-2-yl)pyrido[2,3-d]pyrimidin-7(8H)-one (cpd 187);

8-[(2S)-3-methylbutan-2-yl]-2-{[(1S)-1-{4-[(4-methyl-3-oxopiperazin-1-yl)methyl]phenyl}ethyl]amino}pyrido[2,3-d]pyrimidin-7(8H)-one (cpd 188);

tert-butyl 4-(4-{(1S)-1-[(8-ethyl-7-oxo-7,8-dihydropyrido[2,3-d]pyrimidin-2-yl)amino]ethyl}benzoyl)piperazine-1-carboxylate (cpd 189);

2-{[(1S)-1-{4-[(4-acryloylpiperazin-1-yl)carbonyl]phenyl}ethyl]amino}-8-ethylpyrido[2,3-d]pyrimidin-7(8H)-one (cpd 190);

2-{[(1S)-1-{4-[(4-acryloylpiperazin-1-yl)carbonyl]-3-fluorophenyl}ethyl]amino}-8-[(2S)-3-methylbutan-2-yl]pyrido[2,3-d]pyrimidin-7(8H)-one (cpd 191);

N-(1-acryloylpiperidin-4-yl)-2-fluoro-4-[(1S)-1-{[7-oxo-8-(propan-2-yl)-7,8-dihydropyrido[2,3-d]pyrimidin-2-yl]amino}ethyl]benzamide (cpd 192);

tert-butyl 6-[(1S)-1-({8-[(2S)-3-methylbutan-2-yl]-7-oxo-7,8-dihydropyrido[2,3-d]pyrimidin-2-yl}amino)ethyl]-3',6'-dihydro-3,4'-bipyridine-1'(2'H)-carboxylate (cps 193);

2-{[(1S)-1-(1'-acryloyl-1',2',3',6'-tetrahydro-3,4'-bipyridin-6-yl)ethyl]amino}-8-[(2S)-3-methylbutan-2-yl]pyrido[2,3-d]pyrimidin-7(8H)-one (cpd 194);

2-({(1S)-1-[1'-(cyclopropylcarbonyl)-1',2',3',6'-tetrahydro-3,4'-bipyridin-6-yl]ethyl}amino)-8-[(2S)-3-methylbutan-2-yl]pyrido[2,3-d]pyrimidin-7(8H)-one (cpd 195);

8-[(2S)-3-methylbutan-2-yl]-2-({(1S)-1-[2'-(trifluoromethyl)-3,4'-bipyridin-6-yl]ethyl}amino)pyrido[2,3-d]pyrimidin-7(8H)- one (cpd 196);

2-{[(1S)-1-(2'-fluoro-3,4'-bipyridin-6-yl)ethyl]amino}-8-[(2S)-3-methylbutan-2-yl]pyrido[2,3-d]pyrimidin-7(8H)-one (cpd 197);

2-{[(1S)-1-{4-[(4-acryloylpiperazin-1-yl)methyl] phenyl}ethyl]amino}-8-[(2S)-1-fluoropropan-2-yl] pyrido[2,3-d]pyrimidin-7(8H)-one (cpd 198);

2-{[(1S)-1-{4-[(4-acryloylpiperazin-1-yl)methyl] phenyl}ethyl]amino}-8-[(2S)-1-hydroxypropan-2-yl] pyrido[2,3-d]pyrimidin-7(8H)-one (cpd 199);

tert-butyl 4-{4-[(1S)-1-{[4-cyano-8-(2,2-dimethylpropyl)-7-oxo-7,8-dihydropyrido[2,3-d]pyrimidin-2-yl]amino} ethyl]benzyl}piperazine-1-carboxylate (cpd 200);

2-{[(1S)-1-{4-[(4-acryloylpiperazin-1-yl)methyl] phenyl}ethyl]amino}-8-(2,2-dimethylpropyl)-4-ethoxy-pyrido[2,3-d]pyrimidin-7(8H)-one (cpd 201);

2-{[(1S)-1-{4-[(4-acryloylpiperazin-1-yl)methyl] phenyl}ethyl]amino}-8-(2,2-dimethylpropyl)-4-(methylamino)pyrido[2,3-d]pyrimidin-7(8H)-one (cpd 202);

2-{[(1S)-1-{4-[(4-acryloylpiperazin-1-yl)methyl] phenyl}ethyl]amino}-4-(dimethylamino)-8-(propan-2-yl) pyrido[2,3-d]pyrimidin-7(8H)-one (cpd 203);

2-{[(1S)-1-{4-[(4-acryloylpiperazin-1-yl)methyl] phenyl}ethyl]amino}-7-oxo-8-(propan-2-yl)-7,8-dihydropyrido[2,3-d]pyrimidine-4-carbonitrile (cpd 204);

2-{[(1S)-1-{4-[(4-acryloylpiperazin-1-yl)methyl] phenyl}ethyl]amino}-4-[(2,4-dimethoxybenzyl)amino]-8-(propan-2-yl) pyrido[2,3-d]pyrimidin-7(8H)-one (cpd 205);

2-{[(1S)-1-{4-[(4-acryloylpiperazin-1-yl)methyl] phenyl}ethyl]amino}-4-amino-8-(propan-2-yl)pyrido[2,3-d]pyrimidin-7(8H)-one (cpd 206);

2-{[(1S)-1-(4-{[(2R)-4-acryloyl-2-methylpiperazin-1-yl] methyl}phenyl)ethyl]amino}-8-ethylpyrido[2,3-d]pyrimidin-7(8H)-one (cpd 207);

2-{[(1S)-1-(4-{[(3R)-4-acryloyl-3-methylpiperazin-1-yl] methyl}phenyl)ethyl]amino}-8-ethylpyrido[2,3-d]pyrimidin-7(8H)-one (cpd 208);

2-{[(1S)-1-(4-{[(2R)-4-acryloyl-2-(propan-2-yl)piperazin-1-yl]methyl}phenyl)ethyl]amino}-8-ethylpyrido[2,3-d] pyrimidin-7(8H)-one (cpd 209);

2-{[(1S)-1-(4-{[(2S)-4-acryloyl-2-methylpiperazin-1-yl] methyl}phenyl)ethyl]amino}-8-ethylpyrido[2,3-d]pyrimidin-7(8H)-one (cpd 210);

2-{[(1S)-1-(4-{[(3S)-4-acryloyl-3-methylpiperazin-1-yl] methyl}phenyl)ethyl]amino}-8-ethylpyrido[2,3-d]pyrimidin-7(8H)-one (cpd 211);

2-{[(1S)-1-(4-{[(2S)-4-acryloyl-2-(propan-2-yl)piperazin-1-yl]methyl}phenyl)ethyl]amino}-8-ethylpyrido[2,3-d] pyrimidin-7(8H)-one (cpd 212);

2-{[(1S)-1-{6-[(4-acryloylpiperazin-1-yl)methyl]pyridin-3-yl}ethyl]amino}-8-(propan-2-yl)pyrido[2,3-d]pyrimidin-7(8H)-one (cpd 213);

2-{[(1S)-1-{4-[1-(4-acryloylpiperazin-1-yl)propyl] phenyl}ethyl]amino}-8-ethylpyrido[2,3-d]pyrimidin-7(8H)-one (cpd 214);

2-{[(1S)-1-{4-[1-(4-acryloylpiperazin-1-yl)propyl] phenyl}ethyl]amino}-8-methylpyrido[2,3-d]pyrimidin-7(8H)-one (cpd 215);

2-{[(1S)-1-{4-[1-(4-acryloylpiperazin-1-yl)propyl] phenyl}ethyl]amino}-8-(2,6-difluorobenzyl)pyrido[2,3-d]pyrimidin-7(8H)-one (cpd 216);

2-{[(1S)-1-{4-[(4-acryloylpiperazin-1-yl)methyl] phenyl}ethyl]amino}-8-(4-ethynyl-2-fluorobenzyl) pyrido[2,3-d]pyrimidin-7(8H)-one (cpd 217);

2-{[(1S)-1-{4-[1-(4-acryloylpiperazin-1-yl)propyl] phenyl}ethyl]amino}-8-cyclopropylpyrido[2,3-d]pyrimidin-7(8H)-one (cpd 218);

2-{[(1S)-1-{4-[1-(4-acryloylpiperazin-1-yl)-2-cyclopropyl-ethyl]phenyl}ethyl]amino}-8-ethylpyrido[2,3-d]pyrimidin-7(8H)-one (cpd 219);

2-{[(1S)-1-{4-[1-(4-acryloylpiperazin-1-yl)-2-cyclopropyl-ethyl]phenyl}ethyl]amino}-8-(propan-2-yl)pyrido[2,3-d] pyrimidin-7(8H)-one (cpd 220);

2-{[(1S)-1-(4-{1-[4-(2-methylacryloyl)piperazin-1-yl] propyl}phenyl)ethyl]amino}-8-(propan-2-yl)pyrido[2,3-d]pyrimidin-7(8H)-one (cpd 221);

2-({(1S)-1-[4-(1-{4-[(2E)-but-2-enoyl]piperazin-1-yl}propyl)phenyl]ethyl}amino)-8-(propan-2-yl)pyrido[2,3-d]pyrimidin-7(8H)-one (cpd 222);

2-{[(1S)-1-(4-{[(3R)-1-acryloylpyrrolidin-3-yl] oxy}phenyl)ethyl]amino}-8-ethylpyrido[2,3-d]pyrimidin-7(8H)-one (cpd 223);

2-{[(1S)-1-(4-{[(3S)-1-acryloylpyrrolidin-3-yl]oxy}phenyl) ethyl]amino}-8-ethylpyrido[2,3-d]pyrimidin-7(8H)-one (cpd 224);

phenyl 4-[(1S)-1-{4-[(1S)-1-{[7-oxo-8-(propan-2-yl)-7,8-dihydropyrido[2,3-d]pyrimidin-2-yl]amino}ethyl] phenyl} propyl]piperazine-1-carboxylate (cpd 225);

phenyl 4-[(1R)-1-{4-[(1S)-1-{[7-oxo-8-(propan-2-yl)-7,8-dihydropyrido[2,3-d]pyrimidin-2-yl]amino}ethyl]phenyl} propyl]piperazine-1-carboxylate (cpd 226);

2-{[(1S)-1-{4-[(1S)-1-(4-acryloylpiperazin-1-yl)propyl] phenyl}ethyl]amino}-8-(propan-2-yl)pyrido[2,3-d]pyrimidin-7(8H)-one (cpd 227);

2-{[(1S)-1-{4-[(1R)-1-(4-acryloylpiperazin-1-yl)propyl] phenyl}ethyl]amino}-8-(propan-2-yl)pyrido[2,3-d]pyrimidin-7(8H)-one (cpd 228);

2-{[(1R)-1-{4-[(1R)-1-(4-acryloylpiperazin-1-yl)propyl] phenyl}ethyl]amino}-8-(propan-2-yl)pyrido[2,3-d]pyrimidin-7(8H)-one (cpd 229);

2-{[(1S)-1-{4-[(1S)-1-(4-acryloylpiperazin-1-yl)-2-cyclopropylethyl]phenyl}ethyl]amino}-8-(propan-2-yl)pyrido [2,3-d]pyrimidin-7(8H)-one (cpd 230);

2-{[(1S)-1-{4-[(1R)-1-(4-acryloylpiperazin-1-yl)-2-cyclopropylethyl]phenyl}ethyl]amino}-8-(propan-2-yl)pyrido [2,3-d]pyrimidin-7(8H)-one (cpd 231);

4-{4-[(S)-1-(1-Ethyl-2-oxo-1,2-dihydro-[1,6]naphthyridin-7-ylamino)-ethyl]-benzyl}-piperazine-1-carboxylic acid tert-butyl ester (cpd 232);

4-(1-{4-[(S)-1-(1-Ethyl-2-oxo-1,2-dihydro-[1,6]naphthyridin-7-ylamino)-ethyl]-phenyl}-propyl)-piperazine-1-carboxylic acid tert-butyl ester (cpd 233);

4-((S)-1-{4-[(S)-1-(1-Ethyl-2-oxo-1,2-dihydro-[1,6]naphthyridin-7-ylamino)-ethyl]-phenyl}-propyl)-piperazine-1-carboxylic acid phenyl ester (cpd 234);

7-{(S)-1-[4-(3,3-Difluoro-piperidin-1-ylmethyl)-phenyl]-ethylamino}-1-(2,2-dimethyl-propyl)-1H-[1,6]naphthyridin-2-one (cpd 235);

7-{(S)-1-[4-(4-Acryloyl-piperazin-1-ylmethyl)-phenyl]-ethylamino}-1-ethyl-1H-[1,6]naphthyridin-2-one (cpd 236);

7-((S)-1-{4-[1-(4-Acryloyl-piperazin-1-yl)-propyl]-phenyl}-ethylamino)-1-ethyl-1H-[1,6]naphthyridin-2-one (cpd 237);

7-((S)-1-{4-[(S)-1-(4-Acryloyl-piperazin-1-yl)-propyl]-phenyl}-ethylamino)-1-ethyl-1H-[1,6]naphthyridin-2-one (cpd 238);

7-{[(1S)-1-{4-[(1S)-1-(4-acryloylpiperazin-1-yl)propyl] phenyl}ethyl]amino}-1-(propan-2-yl)-1,6-naphthyridin-2 (1H)-one (cpd 239);

2-{[(1S)-1-{4-[1-(4-propanoylpiperazin-1-yl)propyl] phenyl}ethyl]amino}-8-(propan-2-yl)pyrido[2,3-d]pyrimidin-7(8H)-one (cpd 240);

1-acryloyl-4-{4-[(1S)-1-{[7-oxo-8-(propan-2-yl)-7,8-dihydropyrido[2,3-d]pyrimidin-2-yl]amino}ethyl] phenyl}piperidine-4-carbonitrile (cpd 241);

2-{[(1S)-1-(4-{(1S)-1-[4-(3-chloropropanoyl)piperazin-1-yl]-2-cyclopropylethyl}phenyl)ethyl]amino}-8-(propan-2-yl) pyrido[2,3-d]pyrimidin-7(8H)-one (cpd 242);

2-{[(1S)-1-(4-{(1R)-1-[4-(3-hydroxypropanoyl)piperazin-1-yl]propyl}phenyl)ethyl]amino}-8-(propan-2-yl)pyrido[2,3-d]pyrimidin-7(8H)-one (cpd 243);

2-[(1-{4-[1-(4-acryloylpiperazin-1-yl)-2-cyclopropylethyl]phenyl}cyclopropyl)amino]-8-(propan-2-yl)pyrido[2,3-d]pyrimidin-7(8H)-one (cpd 244);

2-[(1-{4-[(1R)-1-(4-acryloylpiperazin-1-yl)-2-cyclopropylethyl]phenyl}cyclopropyl)amino]-8-(propan-2-yl)pyrido[2,3-d]pyrimidin-7(8H)-one (cpd 245);

2-[(1-{4-[(1S)-1-(4-acryloylpiperazin-1-yl)-2-cyclopropylethyl]phenyl}cyclopropyl)amino]-8-(propan-2-yl)pyrido[2,3-d]pyrimidin-7(8H)-one (cpd 246);

2-[(1-{4-[1-(4-acryloylpiperazin-1-yl)propyl]phenyl}cyclopropyl)amino]-8-(propan-2-yl)pyrido[2,3-d]pyrimidin-7(8H)-one (cpd 247);

2-[(1-{4-[(1R)-1-(4-acryloylpiperazin-1-yl)propyl]phenyl}cyclopropyl)amino]-8-(propan-2-yl)pyrido[2,3-d]pyrimidin-7(8H)-one (cpd 248);

2-[(1-{4-[(1S)-1-(4-acryloylpiperazin-1-yl)propyl]phenyl}cyclopropyl)amino]-8-(propan-2-yl)pyrido[2,3-d]pyrimidin-7(8H)-one (cpd 249);

2-{[(1S)-1-{4-[(2E)-pent-2-en-3-yl]phenyl}ethyl]amino}-8-(propan-2-yl)pyrido[2,3-d]pyrimidin-7(8H)-one (cpd 250); and 7-{[(1S)-1-{4-[(1S)-1-(4-acryloylpiperazin-1-yl)-2-cyclopropylethyl]phenyl}ethyl]amino}-1-(propan-2-yl)-1,6-naphthyridin-2(1H)-one (cpd 251).

If a stereogenic center or another form of an asymmetric center is present in a compound of the present invention, all forms of such optical isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

Pharmaceutically acceptable salts of the compounds of formula (I) include the salts with inorganic or organic acids, e.g. nitric, hydrochloric, hydrobromic, sulfuric, perchloric, phosphoric, acetic, trifluoroacetic, propionic, glycolic, lactic, oxalic, fumaric, malonic, malic, maleic, tartaric, citric, benzoic, cinnamic, mandelic, methanesulphonic, isethionic and salicylic acid.

Pharmaceutically acceptable salts of the compounds of formula (I) also include the salts with inorganic or organic bases, e.g. alkali or alkaline-earth metals, especially sodium, potassium, calcium, ammonium or magnesium hydroxides, carbonates or bicarbonates, acyclic or cyclic amines.

With the term "$(C_1-C_6)$alkyl", we intend an aliphatic $(C_1-C_6)$ hydrocarbon chain, containing carbon-carbon single bonds only, which can be straight or branched. Representative examples include, but are not limited to, methyl, ethyl, n-propyl, isopropyl, n-butyl, isobutyl, tert-butyl, sec-butyl, n-pentyl, n-hexyl, and the like.

With the term "$(C_3-C_6)$cycloalkyl", we intend, unless otherwise provided, 3- to 6-membered all-carbon monocyclic ring, which may contain one or more double bonds, but does not have a completely conjugated π-electron system.

Examples of $(C_3-C_6)$cycloalkyl groups, without limitation, are cyclopropyl, cyclobutyl, cyclopentyl, cyclopentenyl, cyclohexanyl, cyclohexenyl and cyclohexadienyl. The $(C_3-C_6)$cycloalkyl ring can be optionally further fused or linked to aromatic and non-aromatic carbocyclic or heterocyclic rings.

With the term "heterocyclyl", we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyranyl, tetrahydropyranyl, pyrrolidinyl, pyrrolinyl, imidazolinyl, imidazolidinyl, pyrazolidinyl, pyrazolinyl, thiazolinyl, thiazolidinyl, dihydrofuranyl, tetrahydrofuranyl, tetrahydropyridinyl, 1,3-dioxolanyl, piperidinyl, piperazinyl, morpholinyl and the like. The heterocyclyl ring can be optionally further fused or linked to aromatic and non-aromatic carbocyclic or heterocyclic rings.

With the term "$(C_2-C_6)$alkenyl", we intend an aliphatic straight or branched $(C_2-C_6)$ hydrocarbon chain containing at least one carbon-carbon double bond. Representative examples include, but are not limited to, ethenyl, 1-propenyl, 2-propenyl, 1- or 2-butenyl, and the like.

With the term "$(C_2-C_6)$alkynyl", we intend an aliphatic straight or branched $(C_2-C_6)$ hydrocarbon chain containing at least one carbon-carbon triple bond. Representative examples include, but are not limited to, ethynyl, 1-propynyl, 2-propynyl, 1- or 2-butynyl, and the like.

With the term "$(C_1-C_6)$alkoxy", we intend any of the above defined $(C_1-C_6)$alkyl linked to the rest of the molecule through an oxygen atom (—O—).

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non limiting examples of such aryl groups are phenyl, α- or β-naphthyl, α- or β-tetrahydronaphthalenyl, biphenyl, and indanyl groups.

The term "heteroaryl" refers to aromatic heterocyclic rings, typically 5- to 7-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, furanyl, oxazolyl, isoxazolyl, pyrazolyl, thiophenyl, thiadiazolyl, isoxazolyl, isothiazolyl, oxadiazolyl, indazolyl, cinnolinyl, benzo[1,3]dioxolyl, benzo[1,4]dioxinyl, benzothiazolyl, benzothiophenyl, benzofuranyl, isoindolinyl, benzoimidazolyl, benzoxazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl, benzopyranyl, 2,3-dihydrobenzoxazinyl, 2,3-dihydroquinoxalinyl and the like.

With the term "halogen", we intend fluoro, chloro, bromo or iodo.

With the term "polyfluorinated $(C_1-C_6)$alkyl" or "polyfluorinated $(C_1-C_6)$alkoxy", we intend any of the above defined $(C_1-C_6)$alkyl or $(C_1-C_6)$alkoxy groups which are substituted by more than one fluoro atom such as, for instance, trifluoromethyl, trifluoroethyl, 1,1,1,3,3,3-hexafluoropropyl, trifluoromethoxy and the like.

With the term "hydroxy$(C_1-C_6)$alkyl" we intend any of the above defined $(C_1-C_6)$alkyl groups, bearing a hydroxyl group such as, for instance, hydroxymethyl, 2-hydroxyethyl, 3-hydroxypropyl and the like.

According to the present invention and unless otherwise provided, A, R1, R2, R3, R4, R5 and R6 may be optionally substituted, in any of their free positions, by one or more groups, for instance 1 to 6 groups, independently selected from: hydroxyl, hydroxy($C_1$-$C_6$)alkyl, halogen, nitro, oxo group (=O), cyano, ($C_1$-$C_6$)alkyl, polyfluorinated ($C_1$-$C_6$) alkyl, polyfluorinated ($C_1$-$C_6$)alkoxy, ($C_2$-$C_6$)alkenyl, ($C_2$-$C_6$)alkynyl, aryl, aryl($C_1$-$C_6$)alkyl, ($C_1$-$C_6$)alkylaryl, aryl ($C_1$-$C_6$)alkoxy, heteroaryl, heteroaryl($C_1$-$C_6$)alkyl, ($C_1$-$C_6$) alkylheteroaryl, heterocyclyl, heterocyclyl($C_1$-$C_6$)alkyl, ($C_1$-$C_6$)alkylheterocyclyl, ($C_1$-$C_6$)alkylheterocyclyl($C_1$-$C_6$) alkyl, tri($C_1$-$C_6$)alkylsilyl, ($C_3$-$C_7$)cycloalkyl, ($C_1$-$C_6$) alkoxy, aryloxy, heterocyclyloxy, methylenedioxy, ($C_1$-$C_6$) alkylcarbonyloxy, arylcarbonyloxy, di($C_1$-$C_6$)alkylaminoheterocyclyl($C_1$-$C_6$)alkyl, ($C_3$-$C_7$)cycloalkenyloxy, heterocyclylcarbonyloxy, ($C_1$-$C_6$)alkylideneaminooxy, carboxy, ($C_1$-$C_6$)alkoxycarbonyl, aryloxycarbonyl, ($C_3$-$C_7$)cycloalkyloxycarbonyl, amino, heterocyclyl($C_1$-$C_6$)alkoxycarbonylamino, ureido, ($C_1$-$C_6$)alkylamino, amino($C_1$-$C_6$) alkyl, di($C_1$-$C_6$)alkylamino, arylamino, diarylamino, heterocyclylamino, formylamino, ($C_1$-$C_6$)alkylcarbonylamino, arylcarbonylamino, heterocyclylcarbonylamino, aminocarbonyl, ($C_1$-$C_6$)alkylaminocarbonyl, di($C_1$-$C_6$)alkylaminocarbonyl, arylaminocarbonyl, heteroarylaminocarbonyl, arylaminocarbonyl($C_1$-$C_6$)alkyl, ($C_3$-$C_7$)cycloalkylaminocarbonyl, heterocyclylaminocarbonyl, ($C_1$-$C_6$)alkoxycarbonylamino, hydroxyaminocarbonyl, ($C_1$-$C_6$)alkoxyimino, ($C_1$-$C_6$)alkylsulfonylamino, arylsulfonylamino, heterocyclylsulfonylamino, formyl, ($C_1$-$C_6$)alkylcarbonyl, arylcarbonyl, ($C_3$-$C_7$)cycloalkylcarbonyl, heterocyclylcarbonyl, heterocyclylcarbonyl($C_1$-$C_6$)alkyl, ($C_1$-$C_6$)alkylsulfonyl, polyfluorinated ($C_1$-$C_6$)alkylsulfonyl, arylsulfonyl, aminosulfonyl, ($C_1$-$C_6$)alkylaminosulfonyl, di($C_1$-$C_6$)alkylaminosulfonyl, arylaminosulfonyl, heterocyclylaminosulfonyl, arylthio, ($C_1$-$C_6$)alkylthio; in their turn, whenever appropriate, each of the above substituents may be further substituted by one or more of the aforementioned groups.

From all of the above, it is clear to the skilled person that any group which name is a composite name such as, for instance, "arylamino" has to be intended as conventionally construed by the parts from which it derives, e.g. by an amino group which is substituted by aryl, wherein aryl is as above defined.

Likewise, any of the terms such as, for instance, ($C_1$-$C_6$) alkylthio, ($C_1$-$C_6$)alkylamino, di($C_1$-$C_6$)alkylamino, ($C_1$-$C_6$)alkoxycarbonyl, ($C_1$-$C_6$)alkoxycarbonylamino, heterocyclylcarbonyl, heterocyclylcarbonylamino, ($C_3$-$C_7$) cycloalkyloxycarbonyl and the like, include groups wherein the ($C_1$-$C_6$)alkyl, ($C_1$-$C_6$)alkoxy, aryl, ($C_3$-$C_7$)cycloalkyl and heterocyclyl moieties are as above defined.

The present invention also provides processes for the preparation of the compound of general formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by apparent modifications to those skilled in the art, for instance by appropriately protecting interfering groups, by suitably replacing reagents with others known in the art, or by making routine modifications of reaction conditions. Alternatively, other reactions referred to herein or known in the art will be recognized as having adaptability for preparing other compounds of the invention. The compounds of this invention can be prepared from readily available starting materials using the following general methods and procedures. Unless otherwise indicated, the starting materials are known compounds or may be prepared from known compounds according to well known procedures. It will be appreciated that, where typical or preferred process conditions (i.e., reaction temperatures, times, mole ratios of reactants, solvents, pressures) are described, different process conditions can also be used unless otherwise stated. Optimum reaction conditions may vary with the particular reactants or solvent used, but such conditions can be determined by one skilled in the art by routine optimization procedures.

The compound of general formula (I), as defined above, can be prepared according to the general synthetic processes described in Scheme 1, starting from an intermediate compound of formula (II):

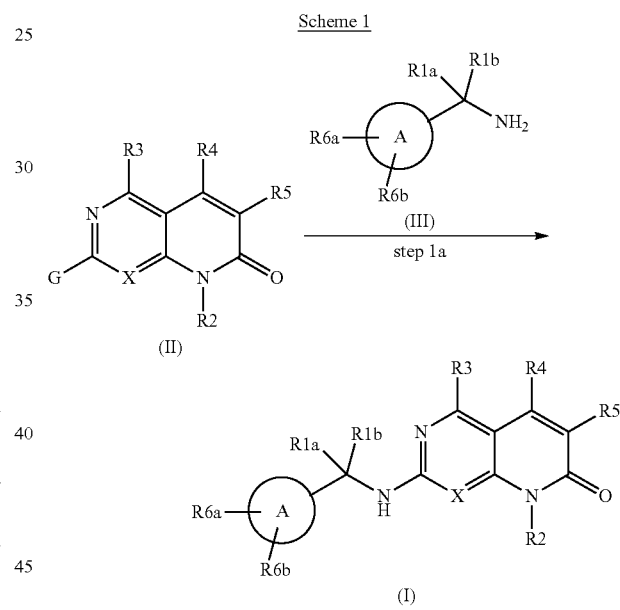

Accordingly, a process of the present invention comprises the following steps:

Step 1a) reacting a compound of formula (II):

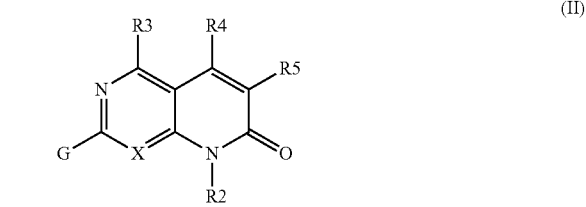

wherein G is chloro, $MeS(O)_2$—, or $MeS(O)$—; R2 is an optionally substituted group selected from straight or branched ($C_1$-$C_6$)alkyl, ($C_3$-$C_6$)cycloalkyl-($C_1$-$C_6$)alkyl, aryl-($C_1$-$C_6$)alkyl, and heterocyclyl-($C_1$-$C_6$)alkyl; X is nitrogen or —CH—, R3 is hydrogen, chloro, cyano, $CONH_2$, NH₂, NR13R13a, OR12, or an optionally substituted group selected from straight or branched $(C_1-C_6)$alkyl, $(C_3-C_6)$cycloalkyl-$(C_1-C_6)$alkyl, aryl and heteroaryl; R4 is hydrogen or an optionally substituted straight or branched $(C_1-C_6)$alkyl; R5 is hydrogen, fluoro, cyano, an optionally substituted straight or branched $(C_1-C_6)$alkyl or OR12, wherein R12 is an optionally substituted straight or branched $(C_1-C_6)$alkyl and R13, R13a are each independently selected from hydrogen or optionally substituted straight or branched $(C_1-C_6)$alkyl; with an compound of formula (III):

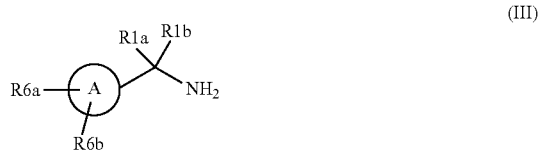

wherein R1a is hydrogen or an optionally substituted straight or branched $(C_1-C_6)$alkyl; R1b is an optionally substituted $(C_1-C_6)$alkyl, or together with the atom to which they are bound, R1a and R1b may form a $(C_3-C_6)$cycloalkyl; A is a $(C_3-C_6)$ cycloalkyl, aryl or heteroaryl; R6a and R6b are each independently selected from hydrogen, halogen, cyano, an optionally substituted straight or branched $(C_1-C_6)$alkyl, $(C_3-C_6)$cycloalkyl, cycloalkyl-alkyl, $(C_2-C_6)$alkenyl, $(C_2-C_6)$alkynyl, aryl, heteroaryl, heterocyclyl, —OR7, NR7R8, —COOR7, —SO₂R7, —CONR7R8, —CH(R14)OR7, and —CH(R14)NR7R8 wherein R14 is hydrogen or an optionally substituted straight or branched $(C_1-C_6)$alkyl and R7 and R8 are each independently hydrogen or a group selected from an optionally substituted straight or branched $(C_1-C_6)$alkyl, $(C_3-C_6)$cycloalkyl, aryl, heteroaryl, heterocyclyl, aryl-alkyl, heteroaryl-alkyl, heterocyclyl-alkyl, heterocyclyl-C(O)-alkyl, heterocyclyl-C(O)-alkenyl, heterocyclyl-C(O)-alkynyl or, together with the nitrogen atom to which they are bound, R7 and R8 form a 5- to 7-membered heteroaryl or heterocyclyl group optionally containing one additional heteroatom selected from O, S and NR9; wherein R9 is hydrogen, an optionally substituted straight or branched $(C_1-C_6)$alkyl, —COOR10 or —COR11; wherein R10 is hydrogen or an optionally substituted straight or branched $(C_1-C_6)$alkyl; R11 is an optionally substituted straight or branched $(C_1-C_6)$alkyl, $(C_2-C_6)$alkenyl or $(C_2-C_6)$alkynyl;

to yield a compound of general formula (I), wherein A, R1a, R1b, R2, R3, R4, R5, R6a and R6b are as defined above.

The compound of formula (II) can be prepared following the synthetic Scheme 2 or Scheme 4 reported below: compound of formula (II) wherein G is MeS(O)₂— or MeS(O)— can be prepared following the Scheme 2:

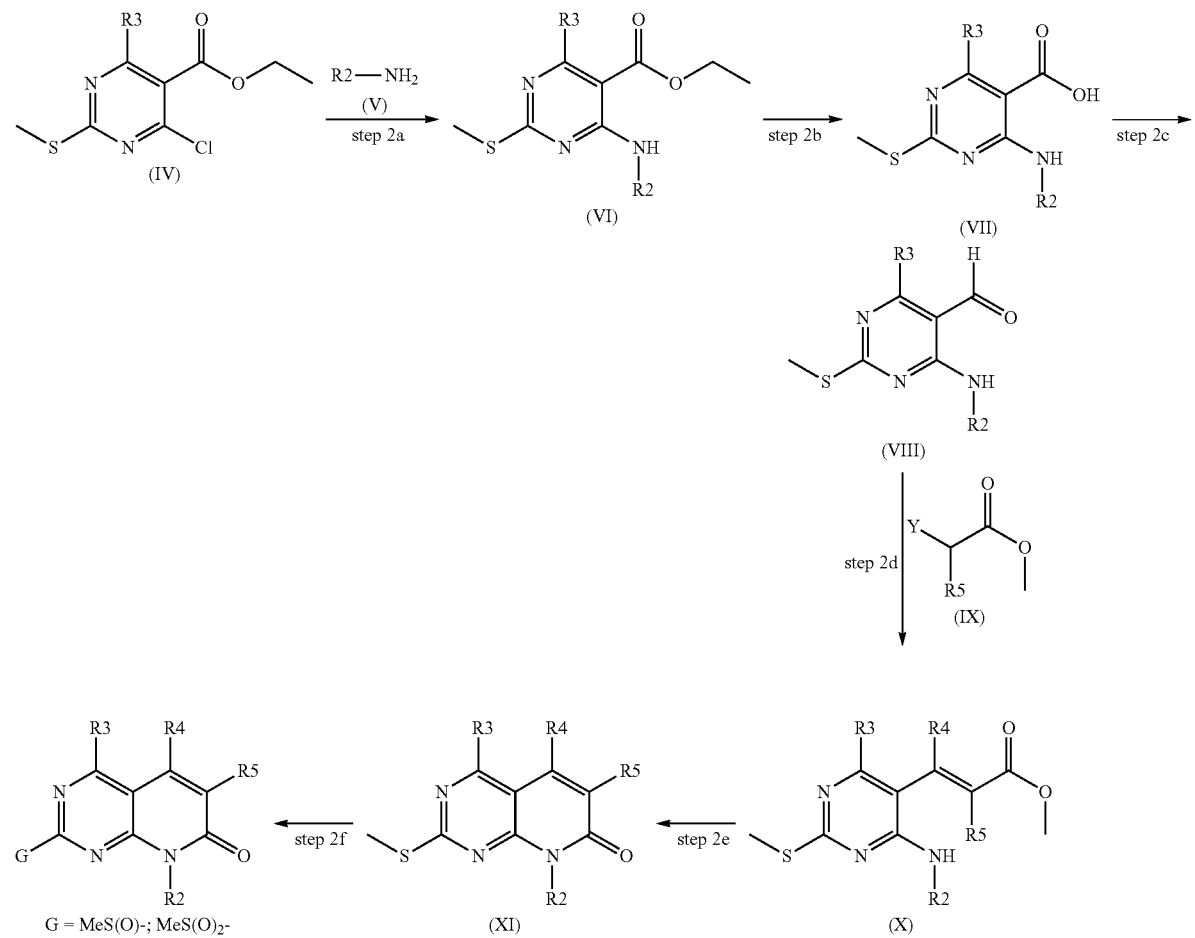

Step 2a) substituting the chlorine of an intermediate compound of formula (IV):

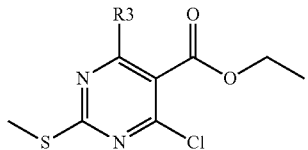

wherein R3 is hydrogen, or an optionally substituted straight or branched (C$_1$-C$_6$)alkyl, with an amine intermediate compound of formula (V):

R2-NH$_2$ (V)

wherein R2 is as defined above;

Step 2b) reacting a compound of formula (VI):

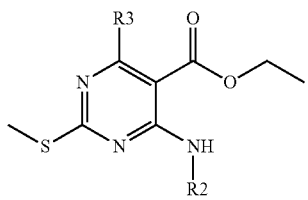

wherein R2 and R3 are as defined above, with a reducing agent;

Step 2c) reacting the resultant compound of formula (VII):

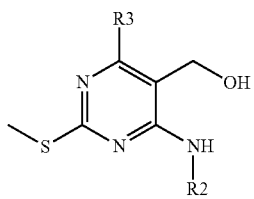

wherein R2 and R3 are as defined above, with an appropriate oxydant reagent;

Step 2d) reacting the resultant compound of formula (VIII):

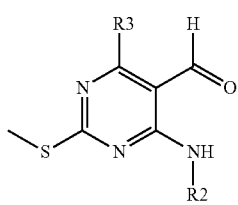

wherein R2 and R3 are as defined above, with an compound of formula (IX):

wherein Y is a suitable leaving group for Wittig or Horner-Wadsworth-Emmons reaction (or HWE reaction) such as triphenylphosphorane or diethylphosphonate, and R5 is hydrogen or fluoro, or an optionally substituted straight or branched (C$_1$-C$_6$)alkyl;

Step 2e) cyclize an intermediate compound of formula (X):

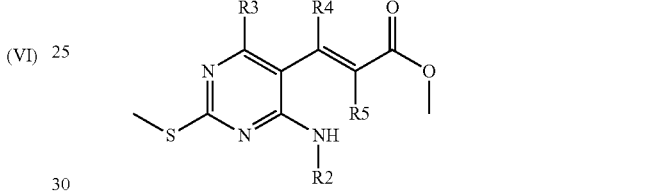

wherein R2, R3, R4 and R5 are as defined above under basic conditions, to obtained the intermediate compound of formula (XI);

Step 2f) mixing the resultant intermediate compound of formula (XI):

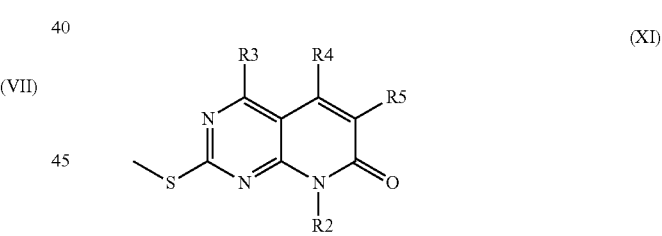

wherein R2, R3, R4 and R5 are as defined above, with a oxydant reagent, to give a compound of formula (II) wherein G is MeS(O)$_2$—, or MeS(O)— and R2, R3, R4 and R5 are as defined above;

alternatively compounds of formula (XI) can be prepared following Scheme 3 below:

Scheme 3

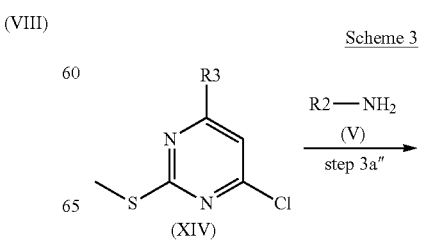

-continued

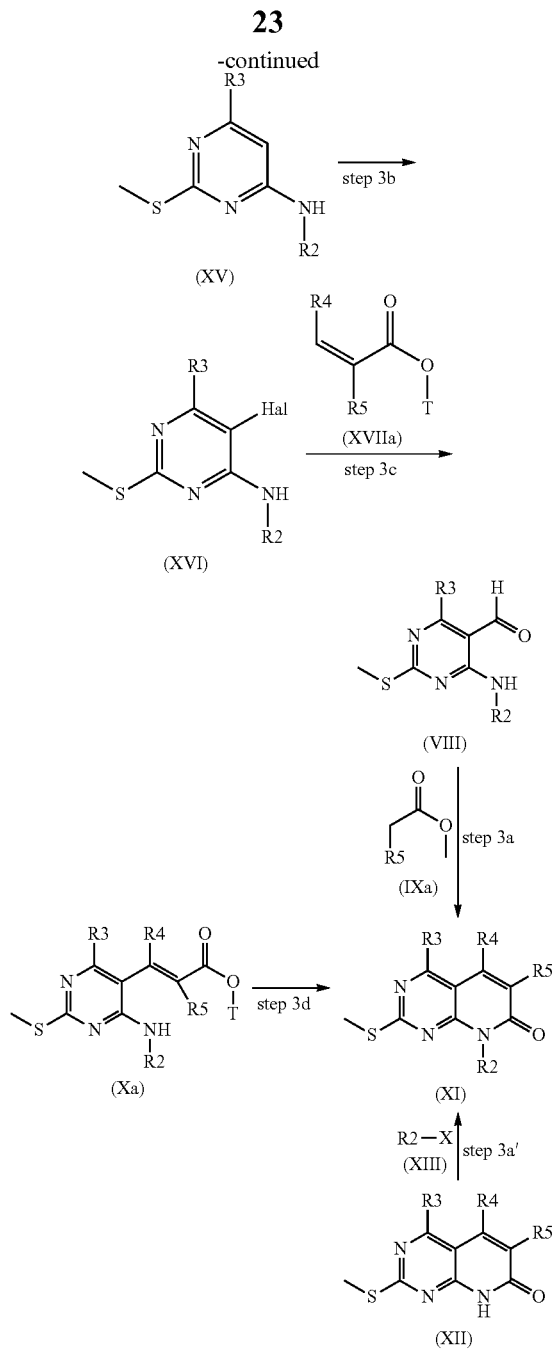

Step 3a) reacting a compound of formula (VIII):

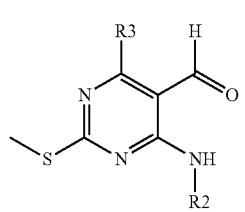

wherein R2, is as defined above, and R3 is hydrogen, chloro or an optionally substituted straight or branched (C$_1$-C$_6$) alkyl; with a compound of formula (IXa):

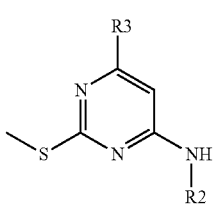

wherein R5 is hydrogen or OR12, wherein R12 is an optionally substituted straight or branched (C$_1$-C$_6$)alkyl, to yield a compound of formula (XI) wherein R2, R3 and R4 are as defined above and R5 is hydrogen or OR12 wherein R12 is an optionally substituted straight or branched (C$_1$-C$_6$)alkyl;

or

Step 3a') alkylating the intermediate compound of formula (XII):

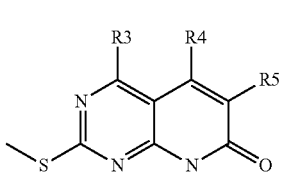

wherein, R3 and R4 are as defined above and R5 is hydrogen, fluoro, cyano, an optionally substituted straight or branched (C$_1$-C$_6$)alkyl or OR12, wherein R12 is an optionally substituted straight or branched (C$_1$-C$_6$)alkyl, with an alkylating agent of formula R2-X (XIII), wherein X is bromine, iodine, —OMs —OTs or hydroxy and R2 is as defined above, to give a compound of formula (XI) wherein R2, R3, R5 and R5 are as defined above;

or

Step 3a") reacting a compound of formula (XIV):

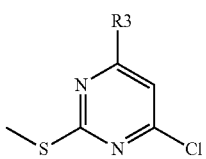

wherein R3 is as defined above, with a compound of formula (V):

R2-NH$_2$  (V)

wherein R2 is as defined above;

Step 3b) reacting the resultant intermediate compound of formula (XV):

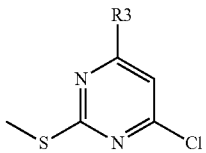

wherein R3 and R2 are as defined above, with a halogenation reagent;

Step 3c) reacting the intermediate compound of formula (XVI):

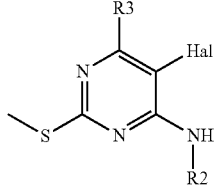

(XVI)

with a compound of formula (XVIIa):

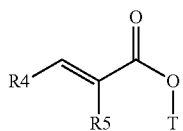

(XVIIa)

wherein R4 is hydrogen or an optionally substituted straight or branched $(C_1-C_6)$alkyl, R5 is hydrogen and T is a straight or branched $(C_1-C_6)$alkyl;

Step 3d) cyclize an intermediate compound of formula (Xa):

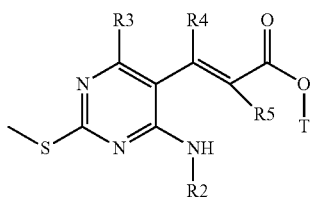

(Xa)

wherein R2, R3, R4, R5 and T are as defined above under basic conditions, so to obtain the intermediate compound of formula (XI), wherein R4 is hydrogen or an optionally substituted straight or branched $(C_1-C_6)$alkyl, R5 is hydrogen and R2 and R3 are as defined above.

If desired, converting a first compound of formula (XI) into a second compound of formula (XI) by operating according to well-known synthetic conditions.

Examples of possible conversions are those reported below:

conv. A) converting a compound of formula (XI):

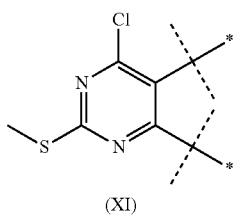

(XI)     (XI)

wherein R3 is chloro, into a compound of formula (XI) wherein R3 is CN, by reacting with a source of cyanide, following the condition known in the art for palladium-catalyzed cyanation of aryl halides;

conv. B) converting a compound of formula (XI):

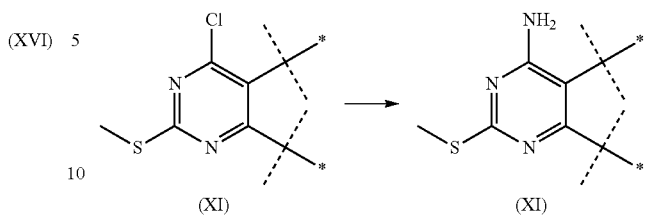

(XI)     (XI)

wherein R3 is chloro, into a compound of formula (XI) wherein R3 is NH2, by reacting with amonia;

conv. C) converting a compound of formula (XI):

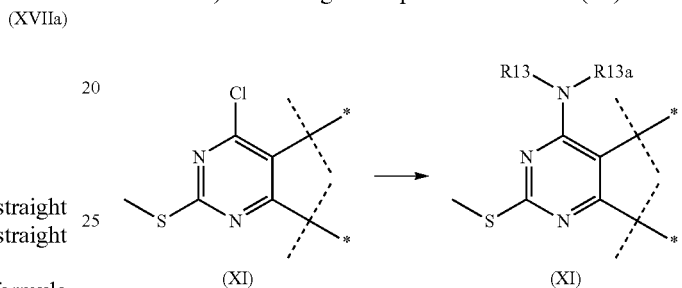

(XI)     (XI)

wherein R3 is chloro, into a compound of formula (XI) wherein R3 is NR13R13a, by reacting with an amine NR13R13a wherein R13 and R13a are each independently selected from hydrogen or optionally substituted straight or branched $(C_1-C_6)$alkyl;

conv. D) converting a compound of formula (XI):

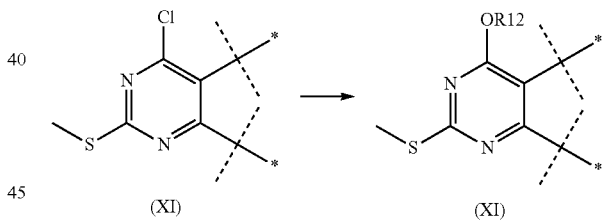

(XI)     (XI)

wherein R3 is chloro, into a compound of formula (XI) wherein R3 is OR12, by reacting with an alcohol R12-OH wherein R12 is an optionally substituted straight or branched $(C_1-C_6)$alkyl;

conv. E) converting a compound of formula (XI):

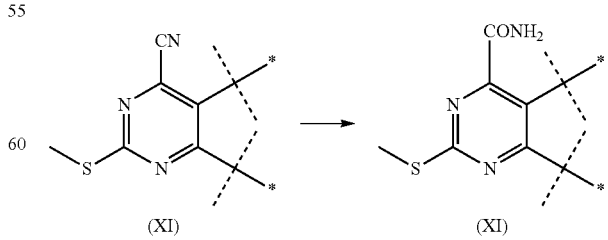

(XI)     (XI)

wherein R3 is cyano, into a compound of formula (XI) wherein R3 is $CONH_2$, by hydrolysis with a suitable agent;

conv. F) converting a compound of formula (XI):

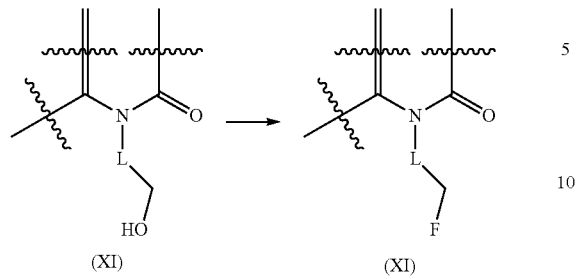

wherein R2 is a group of formula L-CH$_2$OH, into a compound of formula (XI), wherein R2 is a group of formula L-CH$_2$F wherein L is an optionally substituted group selected straight or branched (C$_1$-C$_6$)alkyl, (C$_3$-C$_6$)cycloalkyl-(C$_1$-C$_6$)alkyl, aryl-(C$_1$-C$_6$)alkyl, and heterocyclyl-(C$_1$-C$_6$)alkyl, by reacting with a fluorination agent.

The compound of formula (II) wherein G is chloro and X is nitrogen or —CH—, can be prepared following the Scheme 4 below:

Scheme 4

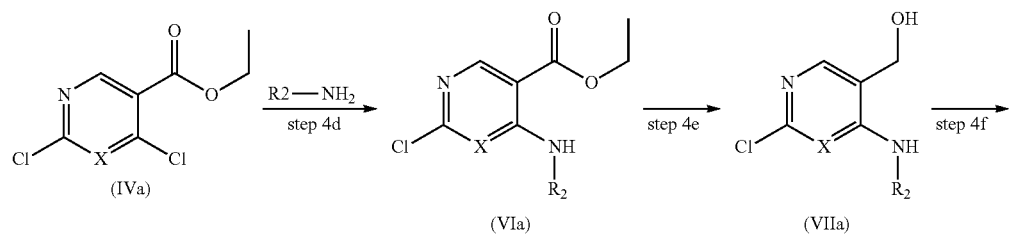

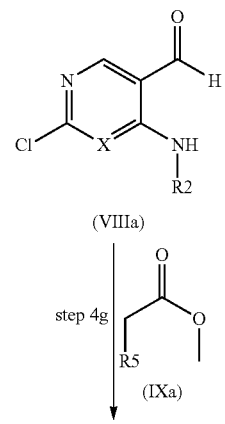

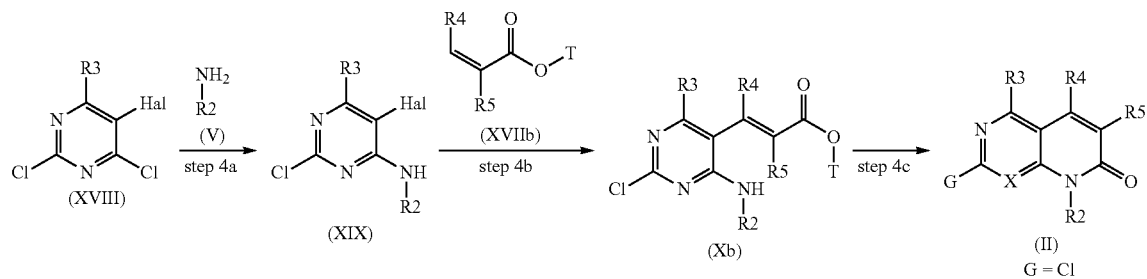

Step 4a) reacting a compound of formula (XVIII):

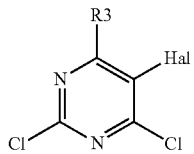
(XVIII)

wherein R3 is hydrogen or an optionally substituted straight or branched (C$_1$-C$_6$)alkyl, and Hal is preferably bromo or iodo, with an intermediate compound of formula (V):

R2-NH$_2$ (V)

wherein R2 is as defined above;

Step 4b) mixing the obtained intermediate compound of formula (XIX):

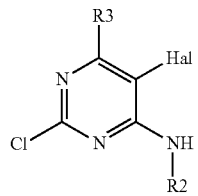
(XIX)

wherein R2, R3 and Hal are as defined above, with a reagent of formula (XVIIb):

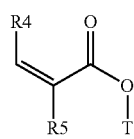
(XVIIb)

wherein R4 is hydrogen or an optionally substituted straight or branched (C$_1$-C$_6$) alkyl, R5 and T are hydrogen;

Step 4c) cyclize an intermediate compound of formula (X):

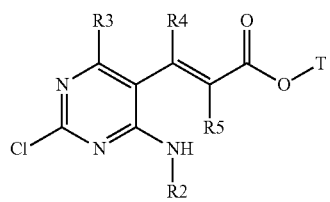
(Xb)

wherein R2, R3, R4, R5 and T are as defined above, with addition of acetic anhydride, to obtain the intermediate compound of formula (II) wherein G is chloro, R4 is hydrogen or an optionally substituted straight or branched (C$_1$-C$_6$) alkyl, R5 is hydrogen and R2 and R3 are as defined above;

Step 4d) substituting the chlorine of an intermediate compound of formula (IVa):

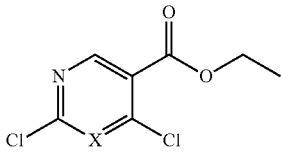
(IVa)

wherein X is N, or —CH, with an amine intermediate compound of formula (V):

R2-NH$_2$ (V)

wherein R2 is as defined above;

Step 4e) reacting a compound of formula (VIa):

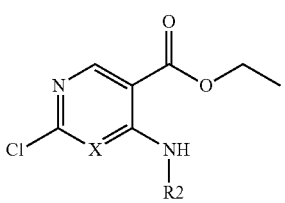
(VIa)

wherein X is N, or —CH and R2 is as defined above, with a reducing agent;

Step 4f) reacting the resultant compound of formula (VIIa):

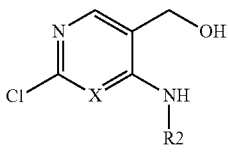
(VIIa)

wherein X is N, or —CH and R2 is as defined above, with an appropriate oxydant reagent;

Step 4g) reacting the resultant compound of formula (VIIIa):

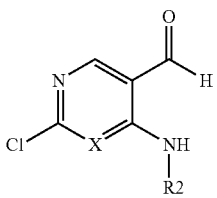
(VIIIa)

wherein R2 is as defined above, with an compound of formula (IXa):

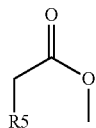

(IXa)

wherein R5 is hydrogen or OR12, wherein R12 is an optionally substituted straight or branched ($C_1$-$C_6$)alkyl, to yield a compound of formula (II) wherein G is chloro and X is nitrogen or —CH—, R2 is as defined above, R3 and R4 are hydrogen and R5 is hydrogen or OR12 wherein R12 is an optionally substituted straight or branched ($C_1$-$C_6$)alkyl;

According to step 1a, the replacement of a leaving group such as methylsulphone, methylsulphoxide or chloro intermediate of formula (II) with an intermediate of formula (Iii) is carried out using an organic base such as DIPEA, CsF as reaction accelerator, in a suitable solvent such as ACN, DMSO, and a temperature ranging from 60 to 120° C. under conventional heating or microwave irradiation, for a time ranging from 1 to 24 h; alternatively, and more in particular when G is chloro the reaction can be accomplished under conditions well known by one skilled in the art. For example, the halide can be displaced by a Buchwald-Hartwig amination reaction with the a suitable palladium source such as PEPPSI precatalyst and a base such as $Cs_2CO_3$, in a solvent such as toluene or ACN, a temperature ranging from 60 to 110° C. under conventional heating or microwave irradiation, and for a time ranging from 1 to 24 h According to step 2a, substitution of chlorine of compound of formula (IV) with an amine of formula $R_2$—$NH_2$ (V) can be carried out neat or in the presence of a suitable base, such as $Na_2CO_3$, $K_2CO_3$, $Cs_2CO_3$, TEA, DIPEA and the like, in a suitable solvent, such as DMF, DMA, ACN, DMSO and the like, at a temperature ranging from room temperature to reflux.

According to step 2b, of the process the reduction of an ester of formula (VI), to obtain a compound of formula (VII) can be performed in different ways and experimental conditions well known in the art. A reducing agent such as lithium aluminium hydride or the like, in a suitable solvent such as THF at a temperature ranging from 0° C. to room temperature from 2 to about 24 h can be used. Preferably, the reaction is conveniently performed with lithium aluminium hydride in THF at room temperature.

According to step 2c of the process, the oxidation of an intermediate of formula (VII) to aldehyde of formula (VIII) can be carried out in the presence of Manganese(II)dioxide, Pyridinium chlorochromate, o-Iodoxybenzoic acid (IBX), Tetrapropylammonium perruthenate (TPAP), 4-Methylmorpholine N-oxide or Sodium hypochlorite/TEMPO/$Bu_4NHSO_4$, in a solvent such as DCM, ACN, THF, EtOAc, Acetone or chloroform at room temperature.

According to step 2d of the process, the aldehyde of formula (VIII) is reacted with a phosphorane of formula (IX) in the Wittig reaction conditions such as, in the presence of a base as TEA, LiHMDS, KHMDS, NaH, KOtBu, and the like, in a suitable solvent such as THF, $Et_2O$ and the like, at a temperature ranging from −20° C. to room temperature, or alternatively the aldehyde of formula (VIII) is reacted with a phosphonate of formula (IX) in the Homer-Wadsworth-Emmons reaction (or HWE reaction) conditions such as in the presence of a base as LiOH, NaOH, TEA, NaH, and the like, in a suitable solvent such as THF, at room temperature.

According to step 2e of the process, the cyclization of an intermediate of formula (X) to give a compound of formula (XI), can be carried out in the presence of a suitable base, such as TEA, DBU, DABCO and the like, in a suitable solvent, such as DMF, DMA, DIPEA and the like, at a temperature approximately to reflux for a time ranging from 1 to 24 h.

According to step 2f, the oxidation of methylthio group of an intermediate of formula (XI) to yield a compound of formula (II) wherein G is MeS$(O)_2$— or MeS(O), can be carried out in the presence of an oxidant agent well-known to those skilled in the art, such as, for instance, oxone or m-chloroperbenzoic acid and the like, in a suitable solvent such as DCM, or at room temperature for a time ranging from 1 to 4 h.

According to step 3a, the Knovenegal-type condensation of an intermediate of formula (VIII) with an intermediate of formula (IXa), can be carried out in the presence of a suitable base, such as $Na_2CO_3$, $K_2CO_3$, LiOH, $Cs_2CO_3$, Potassium t-butoxide, LiHMDS, KHMDS and the like, in a suitable solvent, such as THF, DMF, DMA, and the like, at a temperature ranging from 0° C. to reflux for a time ranging from 1 to 24 h in classical thermal conditions or in a microwave apparatus.

According to step 3a', the alkylation of an intermediate of formula (XII) with an intermediate of formula (XIII), wherein X is bromine, iodine, —OMs or —OTs, can be carried out in the presence of a suitable base, such as $Na_2CO_3$, $K_2CO_3$, $Cs_2CO_3$, NaH, KH and the like, in a suitable solvent, such as DMF, DMA, ACN, acetone, THF and the like, at a temperature ranging from 0° C. to reflux. When is used an intermediate of formula (XIII), wherein X is hydroxy, the reaction is preferentially carried out under Mitsunobu alkylation conditions in the presence of a suitable reagent such as, for instance, diethylazodicarboxylate (DEAD), diisopropylazodicarboxylate (DIAD), ditertbutylazodicarboxylate (DBAD), 1,1'-(azodicarbonyl)dipiperidine (ADDP), and a phosphine reagent such as, for instance, trimethylphosphine, tritertbutylphosphine, triphenylphosphine and the like, in a suitable solvent, such as THF, DMF, DCM, toluene, benzene and the like, at a temperature ranging from 0° C. to 65° C.

According to step 3a", substitution of chlorine of compound of formula (XIV) with an amine of formula (V) can be carried out as described above in step 2a to obtain a compound of formula (XV).

According to step 3b, the intermediate of formula (XV) is reacted with a halogenatin agent. The said reaction is performed with halogenating reagent such as NBS or NIS, in a suitable solvent such as DCM or DMF, from −10° C. to room temperature in a period of time varying from 2 hours to about 18 hours. Preferably, the reaction is carried out under neutral conditions in the presence of iodine and silver trifluoroacetate, in DCM at a temperature ranging from 0° C. to room temperature and for a time varying from 2 hours to overnight.

According to step 3c, the intermediate of formula (XVI) is reacted with a derivative of formula (XVIIa) in Heck type reaction, in the presence of a catalyst such as Pd(OAc)$_2$ and (+) BINAP, and in the presence of a base such as TEA, in a suitable solvent, such as DMF, DMA and the like. The reaction is heated at 100° C. for approximately overnight or less as needed for the reaction to go to completion in classical thermal conditions or in a microwave apparatus.

According to step 3d, the compound of formula (Xa) is cyclized under condition reported in step 2f so to afford the compound of formula (XI).

According to conv. A of the process an heteroaryl chloride of formula (XI) can be reacted in different ways and experimental conditions known in the art as nucleophylic aromatic substitution with a source of cyanide such as sodium cyanide, potassium cyanide or alternatively by using ZnCN, CuCN or potassium hexacyanoferrate(II) as a source of cyanide in the presence of palladium(II) acetate as catalyst, sodium carbonate, potassium carbonate or cesium carbonate as base, in a suitable solvent such as DMF, N-methylpyrrolidone, or DMA, from 80° C. to reflux, for a time ranging from 4 to about 24 hours (J. Org. Chem. 2005, 70, 1508-1510, Org. Lett., 2011, 13 (4), pp 648-651).

According to conv. B of the process a heteroaryl chloride of formula (XI) can be reacted in different ways and experimental conditions with ammonium hydroxide (30%) in acetonitrile at reflux for a time ranging from 4 to about 24 hours.

According to conv. C of the process an heteroaryl chloride of formula (XI) can be reacted in different ways and experimental conditions with amines of formula NR13R13a in suitable solvent such as acetonitrile, DMF, DMA from rt to reflux for a time ranging from 2 to about 24 hours.

According to conv. D of the process an heteroaryl chloride of formula (XI) can be reacted in different ways and experimental conditions with alcohol of formula OR12 in suitable solvent such as acetonitrile, THF, in the presence of potassium carbonate, cesium carbonate, from rt to reflux for a time ranging from 2 to about 24 hours.

According to conv. E of the process a heteroaryl nitrile of formula (XI) can be reacted with acetamide in the presence of 1,4-dioxanne, in the presence of Pd(OAc)$_2$, at reflux for a time ranging from 4 to about 24 hours.

According to conv. F of the process conversion of an alcohol of formula (XI) into the corresponding fluoro derivative, can be accomplished in different ways, and experimental conditions known in the art. Preferably the transformation of an alcohol into a aliphatic fluoro derivative is obtained by reaction with perfluoro-1-butanesulfonyl fluoride and NEt$_3$(HF)$_3$ in acetonitrile at 0° C. for 2 h (see, e.g. Yin, J.; et al. *Org. Lett.* 2004, 1465-1468).

According to step 4a, substitution of chlorine of compound of formula (XVIII) with an amine of formula (V) can be carried out as described above in step 2a.

According to step 4b, the intermediate of formula (XIX) is reacted with a acrylic or crotonic acid of formula (XVIIb) in Heck type reaction, in the presence of a catalyst such as dichlorobis(benzonitrile)palladium (II) and tri-o-tolyl-phosphine, and in the presence of a base such as TEA, in a suitable solvent, such as THF, DMF, DMA and the like.

The reaction is heated to approximately 100° C. for approximately overnight or less as needed for the reaction to go to completion in classical thermal conditions or in a microwave apparatus.

According to step 4c of the process the cyclization of an intermediate of formula (Xb) can be carried out in the presence of acetic anhydride and the like, in a suitable solvent, such as THF, DMF, DMA and the like, at a temperature approximately to reflux for a time ranging from 1 to 24 h to give a compound of formula (II), as defined above.

According to step 4d of the process the substitution of chlorine of compound of formula (IVa) with an amine of formula (V) to obtain a compound of formula (VIa) can be carried out as described above in step 2a.

According to step 4e, of the process the reduction of an ester of formula (VIa), to obtain a compound of formula (VIIa) can be performed as described above in step 2b.

According to step 4f of the process, the oxidation of an intermediate of formula (VIIa) to aldehyde of formula (VIIIa) can be carried out as described above in step 2b.

According to Step 4 g, the compound of formula (VIIIa) is cyclized under condition reported in step 3a so to afford the compound of formula (II) wherein G is chloro and X is nitrogen or —CH—.

A first compound of general formula (I) can be conveniently converted into a second compound of general formula (I) by operating according to well-known synthetic conditions.

Examples of possible conversions are those reported below:

conv. 1) converting a compound of formula (I):

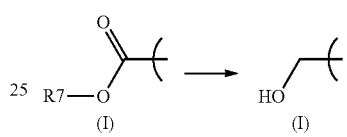

wherein R6a is a group of formula —COOR7, R7 is an optionally substituted straight or branched (C$_1$-C$_6$) alkyl, into a compound of formula (I) wherein R6a is a group of formula —CH$_2$OH, by reacting with a suitable reducing reagent;

conv. 2) converting a compound of formula (I):

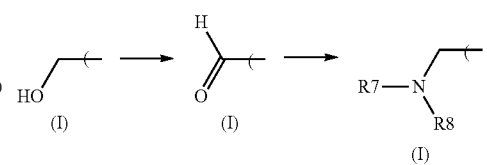

wherein R6a is a group of formula —CH$_2$OH, into a compound of formula (I) wherein R6a is a group —CH(R14)NR7R8 wherein R14 is hydrogen, by first converting the group —CH$_2$OH into the corresponding aldehyde —CHO then, reacting the resulting derivative with a compound of formula R7R8NH (XX), wherein R6 and R7 are as defined above, under reductive amination conditions in the presence of a suitable reducing agents;

conv. 3) converting a compound of formula (I):

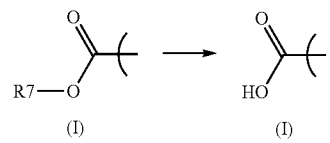

wherein R6a is a group of formula —COOR7, wherein R7 is an optionally substituted straight or branched (C$_1$-C$_6$) alkyl, into a compound of formula (I), wherein R6a is a group of formula —COOH under acidic or basic conditions;

conv. 4) converting a compound of the formula (I):

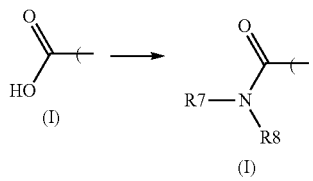

wherein R6a is a group of formula —COOH, into a compound of formula (I), wherein R6a is a group of formula a group —CONR7R8, wherein R7 and R8 are as defined above by reaction with a compound of formula R7R8NH (XX), in the presence of suitable amide coupling agents;

conv. 5) converting a compound of formula (I):

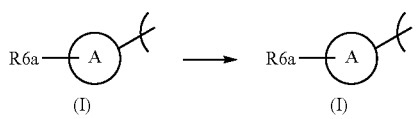

wherein A is aryl or heteroaryl and R6a is chloro, bromo or iodo, into a compound of formula (I), wherein R6a is an optionally substituted group selected from $(C_1-C_6)$alkyl, $(C_2-C_6)$alkenyl, $(C_2-C_6)$alkynyl, $(C_3-C_7)$cycloalkyl, heterocyclyl, aryl, heteroaryl, by reaction with a reagent of formula R6aQ (XXI), wherein R6a is as defined above and Q is a group selected from boronic acid, boronic ester, and —Sn$[(C_1-C_6)$alkyl$]_3$, under Pd-based catalyzed cross-coupling conditions;

conv. 6) converting a compound of formula (I):

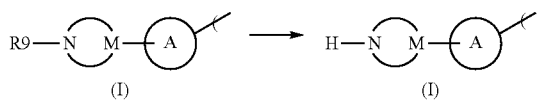

wherein R6a is a linker group M of formula —CH(R14)NR7R8 or —CONR7R8 or NR7R8 wherein R14 is hydrogen or an optionally substituted straight or branched $(C_1-C_6)$alkyl, R7 and R8 together with the nitrogen atom to which they are bound, may form a 5 to 7 membered heterocyclyl group optionally containing one additional group such as N—R9, wherein R9 is a suitable protecting group, into a compound of formula (I), wherein A is as defined above and R9 is hydrogen, under basic or acid hydrogenation conditions;

conv. 7) converting a compound of formula I:

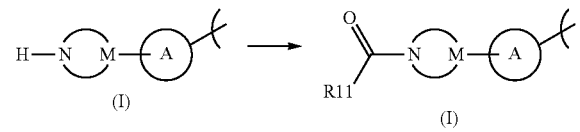

wherein R6a is a linker group M of formula —CH(R14)NR7R8, or —CONR7R8 or NR7R8 wherein R14 is hydrogen or an optionally substituted straight or branched $(C_1-C_6)$alkyl, R7 and R8 together with the nitrogen atom to which they are bound, may form a 5 to 7 membered heterocyclyl group optionally containing one additional group such as N—R9, wherein R9 is hydrogen, into a compound of formula (I) wherein A, is as defined above and R9 is —COR11, wherein R11 is an optionally substituted straight or branched $(C_1-C_6)$alkyl, $(C_2-C_6)$ alkenyl or $(C_2-C_6)$ alkynyl, by reaction with a reagent of formula R11COW (XXII), wherein R11 is as defined above and W is OH or Cl;

conv. 8) converting a compound of formula (I):

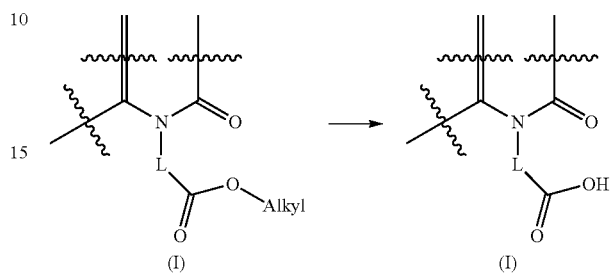

wherein R2 is a group of formula L-COOAlkyl wherein L is an optionally substituted group selected straight or branched $(C_1-C_6)$alkyl, $(C_3-C_6)$cycloalkyl-$(C_1-C_6)$alkyl, aryl-$(C_1-C_6)$alkyl, and heterocyclyl-$(C_1-C_6)$alkyl, into a compound of formula (I) wherein R2 is a group of formula L-COOH, wherein L is as defined above; under acidic or basic conditions;

conv. 9) converting a compound of formula (I):

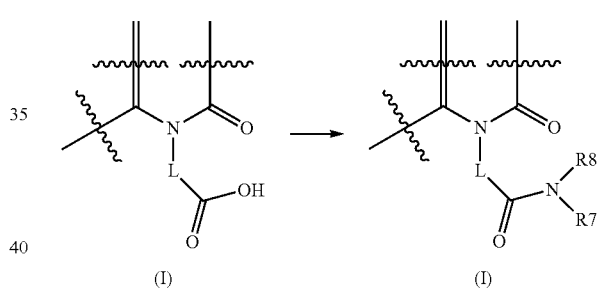

wherein R2 is a group of formula L-COOH, wherein L is as defined above, into a compound of formula (I), wherein R2 is a group of formula L-CONR7R8, wherein L, R7 and R8 are as defined above, by reaction with a compound of formula R7R8NH (XX), in the presence of a amide coupling agents;

conv. 10) converting a compound of formula (I):

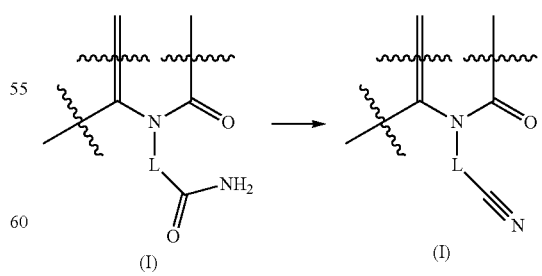

wherein R2 is a group of formula L-CONH$_2$ wherein L is as defined above, into a compound of formula (I), wherein R2 is a group of formula L-CN, wherein L is as defined above, by reaction with a dehydration agent;

conv. 11) converting a compound of formula (I):

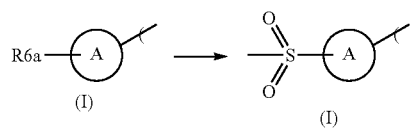

wherein A is aryl or heteroaryl and R6a is chloro, bromo or iodo, into a compound of formula (I), wherein R6a is methylsulphonyl group, under cross-coupling reaction conditions;

conv. 12) converting a compound of formula (I):

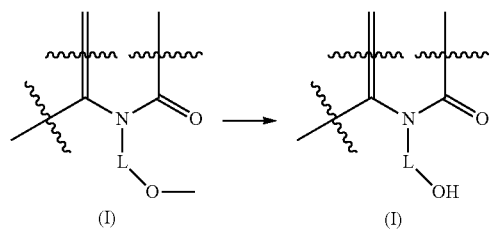

wherein L is a group selected from aryl($C_1$-$C_6$)alkyl, and heterocyclyl-($C_1$-$C_6$) alkyl, into a compound of formula (I) wherein L is defined above, under strong Lewis acid conditions;

conv. 13) converting a compound of formula (I):

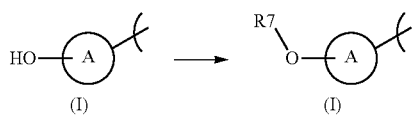

wherein R6a is a phenolic group, into a compound of formula (I) wherein R6a is a group OR7 wherein R7 is as defined above, by reaction with a reagent of formula R7-X (XXIII), wherein R7 is as defined above and X is hydroxy, bromine, iodine, —OMs or —OTs;

conv. 14) converting a compound of formula (I):

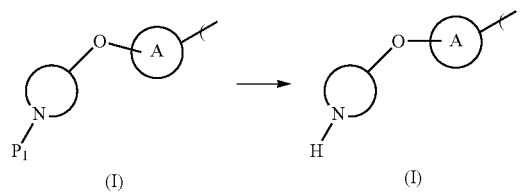

wherein A is as defined above and R6a is a group —OR7 wherein R7 is heterocyclyl group and P1 is a suitable protecting group, into a compound of formula (I), wherein A is as defined above and R7 is heterocyclyl, according to procedure well known in the art (see e.g. Green, Theodora W. and Wuts, Peter G. M.—Protective Groups in Organic Synthesis, Third Edition) such as, e.g. under basic or acid hydrogenation;

conv. 15) converting a compound of formula (I):

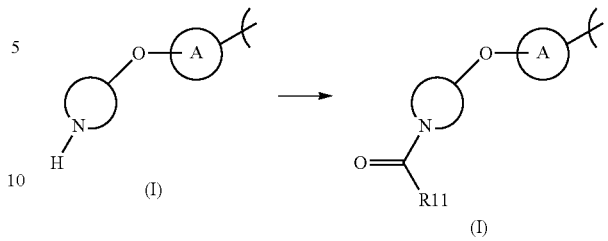

wherein A is as defined above and R6a is a group —OR7 wherein R7 is a heterocyclyl group, into a compound of formula (I), wherein A and R11 are as defined above, by reaction with a reagent of formula R11COW, (XXII) wherein R11 is as defined above and W is OH or Cl.

conv. 16) converting a compound of formula (I):

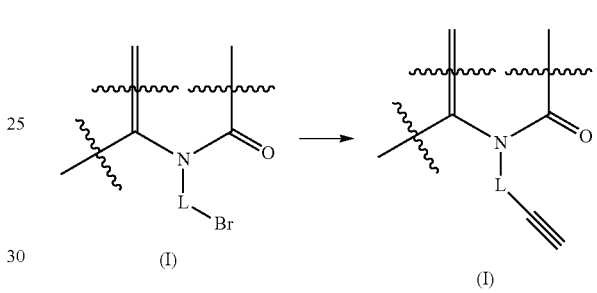

wherein L is a group selected from aryl($C_1$-$C_6$)alkyl, and heterocyclyl-($C_1$-$C_6$)-alkyl, into a compound of formula (I) wherein L is defined above, under Sonogashira reaction.

According to conv. 1 of the process an ester of formula (I) can be reacted in different ways and experimental conditions known in the art with a reducing agent to obtain the corresponding alcohol compound of formula (I). For example, lithium aluminium hydride or the like, in a suitable solvent such as THF at a temperature ranging from 0° C. to room temperature from 2 to about 24 h. Preferably, the reaction is conveniently performed with lithium aluminium hydride in THF at room temperature.

According to conv. 2 of the process at first the oxidation of an intermediate of formula (I) can be carried out in the presence of Manganese (II) dioxide, Pyridinium chlorochromate, o-Iodoxybenzoic acid (IBX), Tetrapropylammonium perruthenate (TPAP), 4-Methylmorpholine N-oxide (NMO), Sodium hypochlorite/TEMPO/$Bu_4NHSO_4$, in a solvent such as methylene chloride, ACN, THF, EtOAc, acetone or chloroform at room temperature to provide the aldehyde of formula (I). Then, the aldehyde intermediate is further reacted in reductive amination conditions with a reagent of formula (XX), in the presence of a reductive agent such as $NaBH_4$, $NaCNBH_3$, $NaBH(OAc)_3$ and the like, in a solvent such as MeOH, EtOH, 2,2,2-trifluoroethanol and the like, at a temperature ranging from rt to 40° C. and for a time ranging from 1 to about 12 h. Said reducing reaction can be optionally carried out in the presence of a suitable catalyst such as AcOH, TFA and the like.

According to conv. 3, the reaction is carried out with aqueous alkaline solutions, such as aqueous LiOH, NaOH or KOH, or in acidic conditions, for instance with AcOH, TFA or HCl, in an organic solvent, such as a lower alcohol, THF, DMF, DCM or 1,4-dioxane or mixtures thereof, at a temperature ranging from rt to about 80° C. and for a time ranging from about 1 to about 12 h.

According to conv. 4, the amidation of a compound of formula (I), is carried out in the presence of a suitable primary or secondary amine of formula (XX), under basic conditions, preferably with DIPEA or TEA, in a suitable solvent such as DCM, DMF, THF, 1,4-dioxane or DMA, in the presence of a suitable condensing agent, for instance dicyclohexylcarbodiimide (DCC), 1-ethyl-3-(3'-dimethylaminopropyl)carbodiimide (EDC), 3,4-dihydro-3-hydroxy-4-oxo-1,2,3-benzotriazine (DHBT), O-benzotriazolyltetramethylisouronium tetrafluoroborate (TBTU), benzotriazol-1-yloxytripyrrolidinophosphonium hexafluorophosphate (PyBOP), or 2-(1H-benzotriazole-1-yl)-1,1,3,3-tetramethyluronium hexafluorophosphate (HBTU) at a temperature ranging from about −10° C. to reflux and for a suitable time, for instance from about 30 minutes to about 96 h. Said reaction is optionally carried out in the presence of a suitable catalyst such as DMAP, or in the presence of a further coupling reagent such as N-hydroxybenzotriazole (HOBT); or alternatively, conversion can be also carried out, for example through a mixed anhydride method, by using an alkyl chloroformate such as ethyl, isopropyl, benzyl chloroformate, in the presence of a tertiary amine, such as TEA, DIPEA or pyridine, in a suitable solvent, such as, for instance toluene, DCM, THF, DMF and the like, at rt; or alternatively the carboxylic acid is converted first into the corresponding acyl chloride by reaction with an activating agent such as thionyl chloride, oxalyl chloride, cyanuric chloride or 1-chloro-N,N,2-trimethylpropenylamine (Ghosez's reagent) neat or in a suitable solvent, such as toluene or DCM, optionally in the presence of a catalytic amount of DMF, at a temperature ranging from about −10° C. to reflux and for a suitable time, for instance from about 30 minutes to about 4 h. Then, said acyl chloride is reacted with a suitable primary or secondary amine of formula (XX), in a suitable solvent such as DCM, chloroform, THF, diethyl ether, 1,4-dioxane, ACN, toluene, or DMF and the like at a temperature ranging from about −10° C. to reflux and for a suitable time, for instance from about 30 minutes to about 96 h, in the presence of a suitable base such as TEA, DIPEA or pyridine.

According to conv. 5, reaction of a compound of the formula (I) with a compound of general formula (XXI), is performed under standard Suzuki coupling conditions using a Pd-based catalyst, such as Pd(dppf)Cl$_2$, PdCl$_2$(PPh$_3$)$_2$ and Pd(PPh$_3$)$_4$, with a suitable base such as Na$_2$CO$_3$, Cs$_2$CO$_3$, K$_3$PO$_4$, in a suitable solvent such as 1,4-dioxane, 1,4-dioxane/water, THF, DMF, toluene and the like, at temperatures ranging from rt to 130° C., in classical thermal conditions, or in a microwave apparatus for a time period ranging from 1 hour to 48 h.

According to conv. 6, deprotection of a compound of formula (I) is performed under acidic conditions, such as for instance TFA, HCl and the like in a solvent such as DCM, 1,4-dioxane, or with a catalytic amount of CuCl in a suitable solvent such as MeOH, EtOH or a mixture EtOH/water at a temperature ranging from rt to reflux and for a time ranging from 1 to about 12 h.

According to conv. 7, converting a compound of the formula (I), wherein an amine group is present, into the corresponding carboxamide derivative, by reaction with a compound of formula (XXII). It is clear to the skilled person that this reaction can be accomplished in a variety of ways and operative conditions, which are widely known in the art for the preparation of carboxamides (see e.g. Scott, C. J. et al. J. Med. Chem. 2005, 48, 1344-1358; Amino Acids, Peptides and Proteins in Organic Chemistry: Building Blocks, Catalysis and Coupling Chemistry, Volume 3; Andrew B. Hughes, Ayman El-Faham, Fernando Albericio). As an example, when an acyl chloride is used, the reaction is performed in a suitable solvent such as for instance, DCM, THF, 1,4-dioxane, ACN, or DMF or the like at a temperature ranging from about −10° C. to reflux and for a suitable time, for instance from about 30 minutes to about 96 hours. The reaction is carried out in the presence of an opportune proton scavenger such as triethylamine, N,N-diisopropylethylamine or pyridine; or when a carboxylic acid is involved, the reaction is carried out in the presence of a coupling agent such as, for instance, 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N'-propylmethyl polystyrene or N-cyclohexylcarbodiimide-N'-methyl polystyrene, in a suitable solvent such as, for instance, dichloromethane, tetrahydrofuran, 1,4-dioxane, acetonitrile, N,N-dimethylformamide at a temperature ranging from about −10° C. to reflux and for a time from about 30 minutes to about 48 hours. The said reaction is optionally carried out in the presence of a suitable catalyst, for instance 4-dimethylaminopyridine, or in the presence of a further coupling agent such as N-hydroxybenzotriazole.

According to conv. 8, the reaction is performed as described as for conv. 3.

According to conv. 9, the reaction is performed as described as for conv. 4.

According to conv. 10 converting the amide of formula (I) into the corresponding nitrile by reaction with a dehydrating agent such as trifluoroacetic anhydride, used as solvent, at a temperature ranging from rt to reflux for a time period ranging from 1 to 4 h.

According to conv. 11, conversion of a compound of formula (I) into the corresponding methylsulphonyl compound of formula (I) is performed, through any of the cross-coupling reactions suitable for the formation of C—S bonds (*Org. Lett.,* 2002, 4, pp 4423-4425). Said reactions, imply a coupling with sodium methansulphinate in the presence of CuI in a suitable solvent such as DMSO and the like, at a temperature ranging from 90° C. to 130° C. for a time ranging from 6 to 24 h.

According to conv. 12 of the process, conversion of compound of formula (I) into the corresponding hydroxy derivative of formula (I) is carried out by reaction with a Lewis acid such as BBr$_3$, AlCl$_3$ or the like in a suitable solvent such as DCM, at a temperature of 0° C. for a time ranging from 1 to 4 h.

According to conv. 13 of the process, a reaction of a compound of the formula (I) with a reagent of formula (XXIII), wherein X is bromine, iodine, —OMs or —OTs, can be carried out in the presence of a suitable base, such as Na$_2$CO$_3$, K$_2$CO$_3$, Cs$_2$CO$_3$, NaH, KH and the like, in a suitable solvent, such as DMF, DMA, ACN, acetone, THF and the like, at a temperature ranging from 0° C. to reflux. When an intermediate of formula (XXIII), wherein X is hydroxy is used, the reaction is preferentially carried out under Mitsunobu alkylation conditions in the presence of a suitable reagent such as, for instance, diethylazodicarboxylate (DEAD), diisopropylazodicarboxylate (DIAD), ditertbutylazodicarboxylate (DBAD), 1,1'-(azodicarbonyl)dipiperidine (ADDP), and a phosphine reagent such as, for instance, trimethylphosphine, tritertbutylphosphine, triphenylphosphine and the like, in a suitable solvent, such as THF, DMF, DCM, toluene, benzene and the like, at a temperature ranging from 0° C. to 65° C.

According to conv. 14, the reaction is performed as described as for conv. 6.

According to conv. 15, the reaction is performed as described as for conv. 7.

From all of the above it is clear to the skilled person that any compound of formula (I) bearing a functional group which can be further derivatized to another functional group, by working according to methods well known in the art thus leading to other compounds of the formula (I), is intended to be comprised within the scope of the present invention.

When preparing the compounds of general formula (I) according to any of the above variants of the process, optional functional groups within the starting materials, the reagents or the intermediates thereof, and which could give rise to unwanted side reactions, need to be properly protected according to conventional techniques (see e.g., Green, Theodora W. and Wuts, Peter G. M.—Protective Groups in Organic Synthesis, Third Edition, John Wiley & Sons Inc., New York (NY), 1999). Likewise, the conversion of these latter into the free deprotected compounds may be carried out according to known procedures.

The compounds of every general formula can be further transformed in other compounds of the same general formula according to methods well known in the literature, as reported in the experimental section.

According to any variant of the process for preparing the compounds of the formula (I), the starting materials and any other reactants are known or easily prepared according to known methods.

The compounds of the formula (III) can be prepared as described in WO2014141104A1 and WO2017/019429.

The compounds of the formula (IV), (V), (VIIIa), (IX), (IXa), (IXb), (XII), (XIII), (XIV), (XVIIa), (XVIIb) and (XVIII), are either commercially available or can be prepared with known methods.

The final compounds may be isolated and purified using conventional procedures, for example chromatography and/or crystallization and salt formation.

The compounds of general formula (I) as defined above can be converted into pharmaceutically acceptable salts.

The compounds of general formula (I) as defined above, or the pharmaceutically acceptable salts thereof, can be subsequently formulated with a pharmaceutically acceptable carrier or diluent to provide a pharmaceutical composition.

The synthesis of a compound of general formula (I), according to the synthetic processes described above, can be conducted in a stepwise manner, whereby each intermediate is isolated and purified if needed by standard purification techniques, like, for example, column chromatography, before carrying out the subsequent reaction.

Alternatively, two or more steps of the synthetic sequence can be carried out in a so-called "one-pot" procedure, as known in the art, whereby only the compound resultant from the two or more steps is isolated and purified.

In cases where a compound of general formula (I) contains one or more asymmetric centers, said compound can be separated into the single stereoisomers by procedures known to those skilled in the art. Such procedures comprise standard chromatographic techniques, including chromatography using a chiral stationary phase, or crystallization.

General methods for separation of compounds containing one or more asymmetric centers are reported, for instance, in Jacques, Jean; Collet, Andre; Wilen, Samuel H., Enantiomers, Racemates, and Resolutions, John Wiley & Sons Inc., New York (NY), 1981.

The present invention also provides a method of treating a disease caused by and/or associated with increased 2-hydroxyglutarate level, which comprises administering to a mammal, preferably a human, in need thereof, an effective amount of a compound of formula (I) as defined above.

Furthermore the present invention provides a compound of formula (I) or a pharmaceutically acceptable salt thereof, as defined above, for use in a method of treating a disease caused by and/or associated with increased 2-hydroxyglutarate level, which comprises administering to a mammal, preferably a human, in need thereof, an effective amount of a compound of formula (I) as defined above.

Additionally, the present invention provides a method of treating a disease caused by and/or associated with mutated IDH enzymes or with IDH wt over-functions, which comprises administering to a mammal, preferably a human, in need thereof, an effective amount of a compound of formula (I) as defined above.

Moreover the invention provides a compound of formula (I) or a pharmaceutically acceptable salt thereof, as defined above, for use in a method of treating a disease caused by and/or associated with mutated IDH enzymes or with IDH wt over-functions, which comprises administering to a mammal, preferably a human, in need thereof, an effective amount of a compound of formula (I) as defined above.

Preferably the disease is selected from the group consisting of cancer, cell proliferative disorders, immune-related disorders. More preferably, the disease is cancer.

According to a most preferred embodiment of the present invention the cancer is selected from the group consisting of: carcinomas, such as bladder, breast, kidney, liver, colon, lung, including small cell lung cancer, esophagus, gallbladder, ovary, pancreas, stomach, cervix, prostate, and skin, including squamous cell carcinoma; hematopoietic tumors of lymphoid lineage including leukemia, acute lymphocitic leukemia, acute lymphoblastic leukemia, B-cell lymphoma, angioimmunoblastic T-cell lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including glioma, glioblastoma, glioblastoma multiforme, astrocytoma, oligodendroglioma, paraglioma, neuroblastoma, and schwannomas; and other tumors, including melanoma, seminoma, teratocarcinoma, osteosarcoma, xeroderma pigmentosum, keratoxanthoma, thyroid cancers, such as papillary thyroid carcinoma and medullary thyroid carcinoma, Kaposi's sarcoma, chondrosarcoma, and cholangiocarcinoma.

Other preferred diseases caused by and/or associated with mutated IDH enzymes or IDH wt over-functions, are cellular proliferation disorders such as, for example, benign prostate hyperplasia, familial adenomatosis, polyposis, neurofibromatosis, psoriasis, vascular smooth cell proliferation associated with atherosclerosis, pulmonary fibrosis, arthritis, glomerulonephritis and post-surgical stenosis and restenosis.

Further preferred diseases caused by and/or associated with mutated IDH enzymes with increased 2-hydroxyglutarate level are for example, Ollier disease or Mafucci syndrome.

Additional preferred diseases caused by and/or associated with mutated IDH enzymes or IDH wt over-functions, are immune-related disorders including but not limited to: transplant rejection, skin disorders like psoriasis, allergies, asthma and autoimmune-mediated diseases such as rheumatoid arthritis (RA), systemic lupus erythematosus (SLE), Crohn's disease and amyotrophic lateral sclerosis. Optionally, the methods of the present invention further comprise treating a mammal in need thereof in combination with radiation therapy or chemotherapy regimen.

Moreover, the present invention provides a compound of formula (I), or a pharmaceutically acceptable salt thereof, as defined above, for use in a method of treating a mammal in need thereof in combination with radiation therapy or in combination with a chemotherapy regimen.

In one embodiment the chemotherapy regimen comprises at least one cytostatic or cytotoxic agent.

Cytostatic or cytotoxic agents include, but are not limited to, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, aromatase inhibitors, inhibitors of kinesins, therapeutic monoclonal antibodies, inhibitors of mTOR, histone deacetylase inhibitors, inhibitors of hypoxic response, PD-1 antagonists, or antigen binding fragment thereof, which specifically binds to PD-1 or PD-L1.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g. to humans, can be administered by the usual routes and the dosage level depends upon the age, weight, and conditions of the patient and administration route.

For example, a suitable dosage adopted for oral administration of a compound of formula (I) may range from about to about 1000 mg per dose, from 1 to 5 times daily. The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or through intravenous and/or intrathecal and/or intraspinal injection or infusion.

The pharmaceutical compositions containing the compounds of the invention are usually prepared following conventional methods and are administered in a suitable pharmaceutical form.

For example, the solid oral forms may contain, together with the active compound, diluents, e.g. lactose, dextrose, saccharose, sucrose, cellulose, corn starch or potato starch; lubricants, e.g. silica, talc, stearic acid, magnesium or calcium stearate, and/or polyethylene glycols; binding agents, e.g. starches, arabic gum, gelatine methylcellulose, carboxymethylcellulose or polyvinyl pyrrolidone; disintegrating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g. syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g. cocoa butter, polyethylene glycol, a polyoxyethylene sorbitan fatty acid ester surfactant or lecithin.

The present invention also provides a pharmaceutical composition comprising a therapeutically effective amount of a compound of formula (I) or a pharmaceutically acceptable salt thereof, as defined above, and at least one pharmaceutically acceptable excipient, carrier or diluent.

The present invention further provides a pharmaceutical composition of a compound of formula (I) further comprising one or more chemotherapeutic agents. Chemotherapeutic agents included, but are not limited to, cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, aromatase inhibitors, inhibitors of kinesins, therapeutic monoclonal antibodies, inhibitors of mTOR, histone deacetylase inhibitors, inhibitors of hypoxic response, PD-1 antagonists, or antigen binding fragment thereof, which specifically binds to PD-1 or PD-L1 and the like.

Moreover the invention provides an in vitro method for inhibiting mutated IDH protein activity which comprises contacting the said protein with an effective amount of a compound of formula (I) as defined above.

Additionally, the invention provides a product comprising a compound of formula (I) or a pharmaceutically acceptable salt thereof, as defined above, and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Finally, the invention provides the use of a compound of formula (I) or a pharmaceutically acceptable salt thereof, as defined above, in the manufacture of a medicament with anticancer activity.

EXPERIMENTAL PART

The short forms and abbreviations used herein have the following meaning:

| | |
|---|---|
| g gram | mg milligram |
| mL milliliter | μL microliter |
| mM millimolar | mmol millimole |
| μM (micromolar) | MHz (Mega-Hertz) |
| h hour(s) | Hz (Hertz) |
| mm (millimetres) | min (minutes) |
| μm (micron) | M (molar) |
| BSA bovine serum albumine | DTT dithiothreitol |
| NADPH Nicotinamide adenine dinucleotide phosphate | Rt retention time |
| 2-HG 2-Hydroxy glutaric acid | KOtBu (potassium tert-butoxide) |
| rt (room temperature) | TEA (triethylamine) |
| DMAP (4-dimethylaminopyridine) | DME (1,2-dimethoxyethane) |
| TFA (trifluoroacetic acid) | $Na_2SO_4$ (sodium sulphate) |
| AcOH (acetic acid) | ESI (electrospray ionization) |
| $Na_2CO_3$ (sodium carbonate) | $K_2CO_3$ (potassium carbonate) |
| $CS_2CO_3$ (caesium carbonate) | $K_3PO_4$ (potassium phosphate) |
| LiOH (lithium hydroxide) | NaOH (sodium hydroxide) |
| KOH (potassium hydroxide) | p-TsOH (p-toluensulfonic acid) |
| EtOAc (ethyl acetate) | LiHMDS (lithium bis(trimethylsilyl)amide) |
| NMP (N-methyl-2-pyrrolidone) | NaH (sodium hydride) |
| DMA (N,N-dimethylacetamide) | KH (potassium hydride) |
| DMF (N,N-dimethylformamide) | DCM (dichloromethane) |
| DIPEA (N,N-diisopropyl-N-ethylamine) | hex (hexane) |
| THF (tetrahydrofuran) | DMSO (dimethylsulfoxide) |
| MeOH (methanol) | ACN (acetonitrile) |
| EtOH (ethanol) | Bn (benzyl) |
| -OMs (mesylate) | -OTs (tosylate) |
| HOBT (N-hydroxy-benzotriazole) | DCC (1,3-dicyclohexylcarbodiimide) |
| NMR Nuclear magnetic resonance | MS Mass spectroscopy |
| m/z mass to charge ratio | LC Liquid chromatography |
| $MgCl_2$ Magnesium chloride | |
| EDCl (1-ethyl-3-(3-dimethylaminopropyl)carbodiimide hydrochloride) | |
| TBTU (N,N,N',N'-tetramethyl-O-(benzotriazol-1-yl)uronium-tetrafluoroborate) | |
| RP-HPLC (reverse phase high performance liquid chromatography) | |

Biochemical Assay
In Vitro Assays for IDH1m (R132H or R132C) and $IDH2^{R172K}$ Inhibitors IDH mutated enzyme activity converting alpha-ketoglutarate to 2-hydroxyglutaric acid is measured using a NADPH depletion assay. In the assay the remaining cofactor is measured at the end of the reaction with the addition of a catalytic excess of diaphorase and resazurin, to generate a fluorescent signal in proportion to the amount of NADPH remaining. IDH1 WT enzyme as well as mutated isoforms $IDH1^{R132H}$, $IDH1^{R132C}$, and $IDH2^{R172K}$ enzymes are commercially available proteins (see e.g. Sino Biological, Abcam, Active Motif or Creative BioMart).

$IDH1^{R132H}$ homodimer enzyme are diluted to 8 nM, in 10 μL of Assay Buffer (150 mM NaCl, 50 mM Tris-HCl pH 7.6, 10 mM $MgCl_2$, 0.001% Triton X-100, 4 mM β-mercaptoethanol); 0.2 uL of test compound, previously serially diluted 1 to 3, >10 experimental points from 1 mM in DMSO, is added and the mixture is incubated for 15 minutes at room temperature. The reaction is started with the addition of 10 μL of Substrate Mix (12 uM NADPH, 3.4 mM alpha-ketoglutarate in Assay Buffer) and the mixture is incubated for 60 minutes at room temperature. The reaction is terminated with the addition of 5 μl of Detection Buffer (100 μg/mL diaphorase, 30 μM resazurin, in IX Assay Buffer), and is incubated for 15 minute before reading on a ViewLux as platereader at Ex544/Em590.

Compounds are assayed for their activity against $IDH1^{R132C}$ following the same assay as above with the following modifications: $IDH1^{R132C}$ and alpha-ketoglutarate final concentrations in the Assay Buffer is 2 nM and 0.14 mM, respectively.

Compounds are assayed for their activity against $IDH2^{R172K}$ following the same assay as above with the following modifications: $IDH2^{R172K}$ and alpha-ketoglutarate final concentrations in the Assay Buffer is 16 nM and 0.55 mM, respectively.

Enzymatic Assay for IDH1 Wild-Type (WT)

IDH1WT enzymatic activity converting isocitric acid to alpha-ketoglutarate is measured using a NADPH forming assay. In the assay the forming cofactor is measured in continuous with the addition of a catalytic excess of diaphorase and resazurin, to generate a fluorescent signal in proportion to the amount of NADPH forming.

Compounds were preincubated with the enzyme, then the reaction was started by the addition of $NADP^+$, isocitrate, diaphorase and a corresponding substrate, resazurin. Diaphorase reduces resazurin to the highly fluorescent resorufin with the concomitant oxidation of NADPH to NADP. Specifically, 0.2 uL of test compound, previously serially diluted 1 to 3, 10 experimental points from 1 mM in DMSO, was added to 0.016 nM IDH1WT enzyme in 10 μL of Assay Buffer (150 mM NaCl, 50 mM Tris-HCl pH 7.6, 10 mM MgCl2, 0.001% Triton X-100, 4 mM β-mercaptoethanol); the mixture is incubated for 15 minutes at room temperature. The reaction is started with the addition of 10 μL of Substrate Mix (400 μM $NADP^+$, 40 μM iso-citrate, 5 ugr/mL Diaphorase and 7 μM resazurin in Assay Buffer), the mixture is incubated at room temperature and the reaction is reading on a ViewLux as platereader at Ex544/Em590 in continuous.

Biochemical Activity

Biochemical potencies on mutants $IDH1^{R132H}$, $IDH1^{R132C}$ and $IDH2^{R172K}$ of representative compounds, which were determined according to the above described assays, are reported in Table 1 as $IC_{50}$ values (μM), while biochemical potencies on IDH1 wild type enzyme, determined according to the above described assays, are reported in Table 2 as $IC_{50}$ values (μM).

TABLE 1

| Cpd_number | $IDH1^{R132H}$ IC50(μM) | $IDH1^{R132C}$ IC50(μM) | $IDH2^{R172K}$ IC50(μM) |
|---|---|---|---|
| 1 | 1.829 | 0.622 | |
| 5 | 1.128 | 0.45 | |
| 6 | 3.335 | 1.336 | 6.645 |
| 7 | 2.963 | 1.41 | |
| 8 | 2.436 | 1.385 | |
| 9 | 1.53 | 0.604 | |
| 10 | 3.852 | 1.923 | |
| 11 | 0.362 | 0.181 | 6.1 |
| 12 | 3.481 | 1.775 | 5.02 |
| 14 | 1.742 | 0.85 | 5.733 |
| 16 | 1.003 | 0.46 | 2.696 |
| 17 | 4.907 | 1.893 | |
| 18 | 4.07 | 1.551 | |
| 19 | 0.41 | 0.203 | 6.68 |
| 20 | 0.74 | 0.332 | 5.02 |
| 21 | 2.491 | 0.586 | |
| 22 | 0.451 | 0.195 | 2.986 |
| 23 | 2.088 | 0.891 | 3.494 |
| 24 | 3.527 | 1.722 | 2.96 |
| 25 | 1.943 | 0.524 | |
| 26 | 2.361 | 1.257 | 2.204 |
| 27 | 1.071 | 0.336 | 2.595 |
| 28 | 1.476 | 0.59 | 2.514 |
| 30 | 1.343 | 0.406 | 2.523 |
| 31 | 0.323 | 0.147 | 2.2 |
| 32 | 3.769 | 1.151 | |
| 33 | 0.461 | 0.19 | |
| 34 | 0.219 | 0.135 | 3.35 |
| 35 | 0.211 | 0.>106 | 5.053 |
| 36 | 0.178 | 0.>105 | 6.543 |
| 37 | 1.481 | 0.805 | 4.847 |
| 38 | 0.137 | 0.067 | 7.51 |
| 40 | 0.16 | 0.071 | |
| 41 | 2.464 | 1.408 | |
| 42 | 1.383 | 0.951 | |
| 43 | 1.642 | 1.047 | |
| 44 | 1.09 | 0.811 | |
| 45 | 0.554 | 0.206 | |
| 47 | 1.811 | 0.597 | |
| 49 | 0.118 | 0.067 | 4.355 |
| 50 | 0.068 | 0.038 | 2.509 |
| 52 | 1.758 | 0.786 | |
| 53 | 0.941 | 0.529 | |
| 55 | 0.137 | 0.065 | |
| 57 | 0.543 | 0.208 | |
| 60 | 0.341 | 0.139 | |
| 61 | 0.071 | 0.038 | 5.023 |
| 62 | 0.082 | 0.044 | 5.7 |
| 63 | 0.29 | 0.123 | |
| 64 | 0.21 | 0.133 | |
| 65 | 0.02 | 0.011 | |
| 66 | 0.161 | 0.094 | 4.537 |
| 67 | 0.037 | 0.015 | 7.36 |
| 68 | 0.078 | 0.029 | |
| 69 | 0.036 | 0.022 | |
| 70 | 0.478 | 0.177 | |
| 71 | 2.479 | 0.964 | 4.833 |
| 72 | 2.589 | 1.236 | |
| 75 | 0.407 | 0.431 | |
| 76 | 2.38 | 3.635 | |
| 77 | 0.207 | 0.209 | |
| 78 | 0.896 | 1.381 | |
| 79 | 0.529 | 0.357 | |
| 80 | 0.444 | 0.282 | |
| 81 | 0.288 | 0.172 | |
| 82 | 0.146 | 0.134 | |
| 83 | 0.347 | 0.196 | 4.261 |
| 84 | 0.19 | 0.15 | |
| 85 | 1.767 | 1.462 | |
| 88 | 0.138 | 0.097 | |
| 89 | 0.112 | 0.075 | |
| 90 | 0.697 | 0.391 | |
| 92 | 0.713 | 0.715 | |
| 94 | 0.071 | 0.03 | 5.568 |
| 95 | 0.425 | 0.162 | 5.156 |
| 96 | 0.801 | 0.42 | 5.02 |
| 97 | 0.524 | 0.323 | 5.03 |
| 98 | 0.366 | 0.217 | 5.344 |
| 99 | 0.201 | 0.132 | 3.626 |
| 100 | 3.064 | 1.595 | |
| 101 | 0.575 | 0.271 | 2.667 |
| 102 | 4.325 | 2.803 | |
| 103 | 1.593 | 0.634 | |
| 104 | 0.276 | 0.121 | 5.132 |
| 105 | 0.105 | 0.055 | 4.727 |
| 106 | 1.227 | 0.667 | 2.91 |
| 107 | 0.722 | 0.459 | |
| 108 | 0.459 | 0.307 | |
| 109 | 0.334 | 0.218 | 5.681 |
| 110 | 0.238 | 0.104 | |
| 111 | 4.038 | 1.423 | |
| 112 | 0.19 | 0.178 | |
| 113 | 0.367 | 0.282 | 5.508 |
| 114 | 2.371 | 1.913 | |
| 115 | 0.672 | 0.825 | |
| 116 | 0.176 | 0.101 | 5.02 |
| 117 | 0.055 | 0.029 | 5.509 |
| 118 | 1.296 | 0.923 | |
| 119 | 2.232 | 1.164 | |
| 120 | 0.221 | 0.108 | |
| 121 | 3.904 | 1.635 | |
| 122 | 0.717 | 0.386 | |
| 129 | 0.197 | 0.098 | 6.68 |
| 130 | 0.18 | 0.093 | 5.03 |
| 131 | 0.284 | 0.17 | |
| 132 | 0.194 | 0.124 | 6.114 |
| 133 | 0.218 | 0.141 | 5.051 |
| 134 | 0.152 | 0.061 | 6.115 |
| 135 | 0.4 | 0.202 | |
| 136 | 0.122 | 0.054 | |
| 137 | 3.468 | 1.299 | |
| 138 | 2.258 | 0.777 | |
| 139 | 0.042 | 0.021 | 0.264 |
| 140 | 0.249 | 0.115 | 3.226 |
| 141 | 0.038 | 0.031 | 0.213 |
| 142 | 0.176 | 0.214 | 0.552 |
| 143 | 0.236 | 0.066 | |
| 144 | 0.078 | 0.025 | |
| 145 | 3.561 | 1.322 | |
| 146 | 0.059 | 0.016 | 1.417 |
| 147 | 0.473 | 0.173 | |
| 148 | 0.187 | 0.109 | 5.828 |
| 149 | 0.085 | 0.048 | 3.326 |
| 150 | 0.02 | 0.008 | |
| 151 | 0.095 | 0.02 | |
| 152 | 0.158 | 0.065 | 5.617 |
| 153 | 0.226 | 0.041 | |
| 154 | 0.199 | 0.079 | 5.383 |
| 155 | 0.455 | 0.147 | |
| 156 | 0.139 | 0.091 | 0.476 |
| 157 | 0.162 | 0.051 | |
| 158 | 0.126 | 0.04 | |
| 159 | 0.077 | 0.037 | 0.51 |
| 160 | 0.068 | 0.031 | |
| 161 | 0.022 | 0.013 | 0.299 |
| 162 | 0.084 | 0.03 | |
| 163 | 0.163 | 0.087 | 6.6 |
| 164 | 0.759 | 0.406 | |
| 165 | 0.157 | 0.085 | 5.663 |
| 166 | 0.179 | 0.093 | 7.569 |

TABLE 1-continued

| Cpd_number | IDH1$^{R132H}$ IC50(μM) | IDH1$^{R132C}$ IC50(μM) | IDH2$^{R172K}$ IC50(μM) |
|---|---|---|---|
| 167 | 0.03 | 0.023 | 2.562 |
| 168 | 0.029 | 0.016 | 0.137 |
| 169 | 0.193 | 0.179 | 0.414 |
| 170 | 0.167 | 0.09 | 3.111 |
| 171 | 0.169 | 0.055 | |
| 172 | 0.179 | 0.056 | 3.586 |
| 173 | 0.575 | 0.144 | |
| 174 | 0.042 | 0.032 | |
| 175 | 0.065 | 0.066 | 0.442 |
| 176 | 3.51 | 1.909 | |
| 177 | 0.978 | 0.401 | |
| 178 | 0.046 | 0.03 | 5.02 |
| 179 | 0.123 | 0.063 | 2.355 |
| 180 | 999 | 3.541 | |
| 181 | 0.175 | 0.351 | 0.878 |
| 182 | 0.103 | 0.061 | |
| 183 | 0.052 | 0.039 | |
| 184 | 0.126 | 0.227 | 0.201 |
| 185 | 2.373 | 1.271 | |
| 186 | 0.392 | 0.811 | 0.431 |
| 187 | 0.002 | 0.002 | 0.018 |
| 188 | 0.33 | 0.12 | |
| 189 | 3.769 | 0.811 | |
| 190 | 1.938 | 3.598 | 0.679 |
| 191 | 0.07 | 0.116 | 0.902 |
| 192 | 0.227 | 0.252 | 0.645 |
| 193 | 0.126 | 0.089 | |
| 194 | 0.338 | 0.2 | 1.791 |
| 195 | 0.593 | 0.184 | |
| 196 | 0.955 | 0.141 | |
| 197 | 2.343 | 0.405 | |
| 198 | 0.132 | 0.401 | 0.248 |
| 199 | 1.403 | 1.529 | 0.717 |
| 201 | 0.42 | 0.173 | |
| 202 | 0.666 | 0.104 | |
| 206 | 0.013 | 0.015 | 0.098 |
| 207 | | 0.624 | |
| 208 | | 0.213 | |
| 209 | | 0.046 | |
| 210 | | 0.183 | |
| 211 | | 0.525 | |
| 212 | | 0.061 | |
| 214 | 0.004 | 0.002 | 0.015 |
| 215 | | 0.004 | |
| 216 | | 0.001 | |
| 217 | | 0.015 | |
| 218 | | 0.013 | |
| 219 | 0.001 | 0.001 | 0.006 |
| 220 | 0.001 | 0.001 | 0.015 |
| 221 | | 0.068 | |
| 222 | | 0.147 | |
| 223 | | 1.673 | |
| 224 | | 1.697 | |
| 227 | 0.007 | 0.005 | 0.049 |
| 228 | 0.002 | 0.002 | 0.025 |
| 229 | 0.083 | 0.044 | 0.386 |
| 230 | 0.001 | 0.001 | 0.011 |
| 231 | 0.001 | 0.001 | 0.014 |
| 232 | | 0.330 | |
| 235 | 0.128 | 0.048 | 5.11 |
| 236 | | 0.105 | |
| 237 | 0.004 | 0.004 | 0.027 |
| 238 | 0.004 | 0.004 | 0.025 |
| 239 | 0.002 | 0.002 | 0.020 |
| 240 | | 0.068 | |
| 241 | 0.272 | 0.196 | 0.146 |
| 242 | | 0.010 | |
| 243 | | 0.020 | |
| 244 | 0.002 | 0.003 | 0.021 |
| 245 | 0.002 | 0.002 | 0.020 |
| 246 | 0.002 | 0.001 | 0.019 |
| 247 | 0.005 | 0.004 | 0.035 |
| 248 | 0.004 | 0.002 | 0.030 |
| 249 | 0.005 | 0.003 | 0.033 |
| 251 | | 0.002 | |

TABLE 2

| Cpd_number | IDH1wt IC50 (μM) |
|---|---|
| 67 | 1.709 |
| 94 | 1.326 |
| 105 | 2.045 |
| 117 | 1.583 |
| 139 | 0.720 |
| 140 | 4.848 |
| 141 | 1.825 |
| 144 | 6.798 |
| 156 | 2.540 |
| 159 | 1.731 |
| 161 | 0.908 |
| 162 | 3.896 |
| 168 | 0.758 |
| 169 | 2.847 |
| 175 | 1.171 |
| 181 | 2.137 |
| 183 | 0.899 |
| 184 | 2.869 |
| 186 | 5.460 |
| 187 | 0.541 |
| 191 | 2.986 |
| 206 | 0.221 |
| 213 | 4.286 |
| 214 | 0.064 |
| 219 | 0.052 |
| 220 | 0.053 |
| 227 | 0.109 |
| 228 | 0.0273 |
| 229 | 0.839 |
| 230 | 0.039 |
| 231 | 0.122 |
| 237 | 0.091 |
| 241 | 0.117 |
| 244 | 0.220 |
| 245 | 0.224 |
| 246 | 0.231 |
| 247 | 0.215 |
| 248 | 0.216 |
| 249 | 0.215 |

Cellular Assay for IDHm Inhibitors

Cell lines HT-1080 (commercially available) and U87-MG-IDH1$^{R132H}$ (obtained in analoy to the procedure reported in *J. Mol. Neurosci* 2013, 50, 165-71) are maintained in E-MEM 10% FCS and incubated at 37° C. in a humidified 5% $CO_2$ atmosphere. Stably transfected U87-MG cell lines are also supplemented with 500 μg/mL G418.

Cells are seeded into 96 well black flat bottom plates at a density of 500 cells/well in 100 μL complete medium. After 24 hr the medium is replaced with 200 uL of fresh medium and compounds (dissolved into DMSO) are administrated to the cells using D300E Digital Dispenser (Tecan).

After 72 hr of incubation 100 uL from each well are collected and used for 2HG (R(−)-2-hydroxyglutarate) quantification.

Levels of 2-HG in cell culture media are determined by LC-MS/MS. Cell supernatants (100 μL/well) are treated with 1 M aqueous trichloroacetic acid containing 130 μM of the internal standard 2-HG-d3 (20 μL/well) in a 96-well plate.

The plates are sealed, mildly vortexed for 60 minutes, centrifuged at 4,000 RPM for 15 minutes, placed in a refrigerated autosampler taking care not to shake them, and aliquots of the upper part of the samples are directly injected in the chromatographic system. Calibration standards are obtained by ten fold dilution of aqueous 2-HG stock solutions with blank cell culture medium and denatured exactly in the same way as described above for samples. Samples and standards are assayed for 2-HG by reversed phase chromatography on a $C_{18}$ column eluted with aqueous 0.15% formic acid and briefly washed with 90% methanol at the end of the run. 2-HG is determined by negative ion electrospray ionization with the internal standard method on a triple quadrupole mass spectrometer monitoring the MRM transitions 147>129 (2-HG) and 150>132 (2-HG-d3). 2-HG inhibition was calculated by comparing treated versus control data using Assay Explore (Symyx) software, with IC50 determined using a sigmoidal fitting algorithm.

Table 3 and Table 4 report the $IC_{50}$ values (µM) of representative compounds on the inhibition of 2HG production in two cell lines U87MG_IDH1 R132H and HT-1080 ($IDH1^{R132C}$), determined according to the above described assay.

TABLE 3

| Cpd_number | U87MG_IDH1R132H 2-HG IC50 (µM) |
| --- | --- |
| 36 | 4.042 |
| 38 | 2.642 |
| 49 | 0.507 |
| 50 | 2.531 |
| 62 | 0.462 |
| 65 | 0.179 |
| 66 | 0.691 |
| 67 | 0.2 |
| 68 | 0.646 |
| 69 | 0.078 |
| 75 | 1.189 |
| 77 | 3.034 |
| 82 | 1.323 |
| 83 | 2.064 |
| 89 | 0.501 |
| 94 | 0.370 |
| 99 | 1.385 |
| 104 | 1.770 |
| 105 | 0.417 |
| 109 | 1.813 |
| 110 | 2.61 |
| 112 | 1.610 |
| 113 | 2.538 |
| 116 | 0.612 |
| 117 | 0.177 |
| 129 | 3.841 |
| 130 | 4.839 |
| 132 | 3.220 |
| 134 | 0.874 |
| 136 | 2.909 |
| 139 | 0.008 |
| 140 | 0.010 |
| 141 | 0.024 |
| 150 | 0.127 |
| 151 | 0.321 |
| 156 | 0.289 |
| 159 | 0.081 |
| 170 | 0.637 |
| 175 | 0.021 |
| 219 | 0.0004 |
| 220 | 0.0005 |
| 227 | 0.0004 |
| 228 | 0.0006 |
| 229 | 0.013 |
| 230 | 0.0004 |
| 237 | 0.0010 |

TABLE 4

| Cpd_number | HT1080 2-HG IC50 (µM) |
| --- | --- |
| 49 | 0.307 |
| 62 | 0.169 |
| 65 | 0.082 |
| 66 | 0.353 |
| 67 | 0.067 |
| 68 | 0.315 |
| 89 | 0.505 |
| 94 | 0.203 |
| 105 | 0.116 |
| 110 | 0.590 |
| 116 | 0.311 |
| 117 | 0.155 |
| 139 | 0.022 |
| 140 | 0.108 |
| 142 | 0.075 |
| 143 | 0.517 |
| 170 | 0.442 |
| 183 | 0.021 |
| 184 | 0.028 |
| 187 | <0.001 |
| 191 | 0.040 |
| 206 | 0.0101 |
| 209 | 0.0302 |
| 212 | 0.0531 |
| 214 | 0.0021 |
| 215 | 0.0023 |
| 216 | 0.0011 |
| 217 | 0.0082 |
| 218 | 0.0021 |
| 219 | 0.0004 |
| 220 | 0.0003 |
| 221 | 0.1424 |
| 222 | 0.1680 |
| 224 | 1.0668 |
| 227 | 0.0014 |
| 228 | 0.0008 |
| 229 | 0.0200 |
| 230 | 0.0004 |
| 231 | 0.0003 |
| 237 | 0.0004 |
| 238 | 0.0009 |
| 239 | 0.0009 |
| 241 | 0.0647 |
| 242 | 0.0045 |
| 243 | 0.038 |
| 244 | 0.0016 |
| 245 | 0.0010 |
| 246 | 0.0021 |
| 247 | 0.0030 |
| 248 | 0.0031 |
| 249 | 0.0029 |
| 251 | 0.0023 |

Representative compounds of the invention when tested in cell lines having the mutated form of IDH1 as reported in table 3 and Table 4, showed dose dependent inhibition of cellular production of 2-HG with potency lower then 5 µM. As expected the compounds showed any effect on the cellular proliferation even at the highest dose (10 uM).

Preparation of Compounds of Formula (I)

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

With the aim at better illustrating the present invention, without posing any limitation to it, the following examples are given.

As used herein the symbols and conventions used in the processes, schemes and examples are consistent with those used in the contemporary scientific literature, for example, the *Journal of the American Chemical* Society or the *Journal of Biological Chemistry.*

Compound names are IUPAC names, generated by using ACD Name (by Advanced Chemistry Development, Inc.).

Unless otherwise noted, all materials, including anhydrous solvent such as DMF, THF, DCM, were obtained from commercial suppliers, of the best grade and used without further purification. All reactions involving air- or moisture-sensitive compounds were performed under nitrogen or argon atmosphere.

General Purification and Analytical Methods

Flash Chromatography was performed on silica gel (Merck grade 9395, 60 A).

The HPLC equipment consisted of a Waters Alliance™ HT 2795 system equipped with a Waters 996 PDA detector and Waters mod. ZO 2000 single quadrupole mass spectrometer, equipped with an electrospray (ESI) ion source. Instrument control, data acquisition and data processing were provided by Empower 2 and MassLynx 4.1 softwares. HPLC was carried out at 25° C. at a flow rate of 1.2 mL/min using a YMC-Triart C18 (4,6×50 mm, 3 µm) column.

Mobile phase B was ammonium acetate 5 mM pH=5.2 buffer with acetonitrile (95:5), and mobile phase C was $H_2O$/acetonitrile (5:95); the gradient was from 10 to 90% C in 5 minutes then ramp to 100% C in 0.1 minutes. The injection volume was 10 µL. The mass spectrometer operated in positive and in negative ion mode, the capillary voltage was set up at 3.5 kV ($ES^+$) and 2.8 kV ($ES^-$); cone voltage was 14 V ($ES^+$) and 28 V ($ES^-$); the source temperature was 120° C.; full scan, mass range from 100 to 800 amu was set up.

The preparative HPLC equipment consisted of a Shimadzu HPLC system equipped with SCL-8A System Controller, two LC-8A Pumps, SPD-6A UV Spectrophotometric Detector and manual Rheodyne injection system. Data acquisition (analogic signal) and data processing were provided by Empower 2 software. Purification was carried out at 25° C. at a flow rate of 15 mL/min using a Waters X-Terra MS RP18 (150×30 mm, 10 µm) column. Mobile phase A was 0.1% TFA in water/acetonitrile (95:5) or, alternatively, Mobile phase A was 0.05% $NH_3$ in water/acetonitrile (95:5) and mobile phase B was $H_2O$/acetonitrile (5:95); the gradient was from 10 to 90% B in 15 minutes then ramp to 100% B in 0.1 minutes. Injection volume max 500 µL.

$^1$H-NMR spectra were recorded at a constant temperature of 28° C. on a Varian INOVA 400 spectrometer operating at 400.5 MHz and equipped with a 5 mm $^1H\{^{15}N-^{31}P\}$ z-axis PFG Indirect Detection probe and on a Varian INOVA 500 spectrometer operating at 499.7 MHz and equipped with a 5 mm $^1H\{^{13}C-^{15}N\}$ triple resonance Indirect Detection probe. Chemical shifts were referenced with respect to the residual solvent signals (DMSO-$d_6$: 2.50 ppm for $^1$H). Data are reported as follows: chemical shift (δ), multiplicity (s=singlet, d=doublet, t=triplet, q=quartet, br. s=broad singlet, dd=doublet of doublets, ddd=doublet of doublets of doublets, m=multiplet), coupling constants (J, Hz) and number of protons.

As formerly reported (M. Colombo, F. R. Sirtori, V. Rizzo, Rapid Commun Mass Spectrom 2004, 18(4), 511-517), ESI(+) high-resolution mass spectra (HRMS) were obtained on a Q-Tof Ultima (Waters, Manchester, UK) mass spectrometer directly connected with an Agilent 1100 micro-HPLC system (Palo Alto, US).

Preparation 1

Step 1: 4-(2,2-Dimethyl-propylamino)-2-methylsulfanyl-pyrimidine-5-carboxylic acid ethyl ester [(VI), R2=2,2-Dimethyl-propyl, R3=H] Step 2a

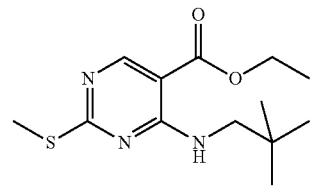 [SMILES: CCOC(=O)c1cnc(SC)nc1NCC(C)(C)C]

4-chloro-2-(methylsulfanyl)pyrimidine-5-carboxylic acid ethyl ester (2.0 g, 8.59 mmol) was dissolved in THF (20.0 mL) to which triethylamine (1.8 mL, 12.89 mmol) and neopentylamine (1.1 mL, 9.45 mmol) was added and stirred for 1 hour at reflux. The precipitated salts were filtered and the solvent evaporated under reduced pressure. The resulting oil was dissolved in $Et_2O$, washed with sodium water, and then dried over $Na_2SO_4$. The salts were filtered, and the solvent was evaporated under vacuum to give the product (1.50 g, 62% yield) which is carried on without further purification.

$^1$H NMR (500 MHz, DMSO-$d_6$) δ=8.55 (s, 1H), 8.39 (t, J=5.9 Hz, 1H), 4.29 (q, J=7.2 Hz, 2H), 3.38 (d, J=6.1 Hz, 2H), 2.47 (s, 3H), 1.30 (t, J=7.1 Hz, 3H), 0.93 (s, 9H). LCMS: m/z 284 [M+H]+@ r.t. 7.86 min. HRMS (ESI) calcd for $C_{13}H_{21}N_3O_2S$ [M+H]$^+$ 284.1427 found 284.1429.

According to the same method, but employing 1-amino-2-methylpropan-2-ol, the following compound was prepared:

4-(2-Hydroxy-2-methyl-propylamino)-2-methylsulfanyl-pyrimidine-5-carboxylic acid ethyl ester [(VI), R2=2-Hydroxy-2-methyl-propylamino, R3=H]

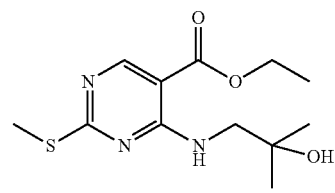 [SMILES: CCOC(=O)c1cnc(SC)nc1NCC(C)(C)O]

The title compound was obtained as a colourless oil (64% yield);

$^1$H NMR (500 MHz, DMSO-$d_6$) δ=8.55 (s, 1H), 8.48 (t, J=5.3 Hz, 1H), 4.76 (s, 1H), 4.28 (q, J=7.0 Hz, 2H), 3.45 (d, J=5.5 Hz, 2H), 2.47 (s, 3H), 1.30 (t, J=7.1 Hz, 3H), 1.13 (s, 6H). LCMS: m/z 286 [M+H]+@ r.t. 5.64 min.

HRMS (ESI) calcd for $C_{12}H_{19}N_3O_3S$ [M+H]$^+$ 286.1220 found 286.1225;

ethyl 4-{[(2S)-3-methylbutan-2-yl]amino}-2-(methylsulfanyl)pyrimidine-5-carboxylate [(VI), R2=(2S)-3-methylbutan-2-yl, R3=H]

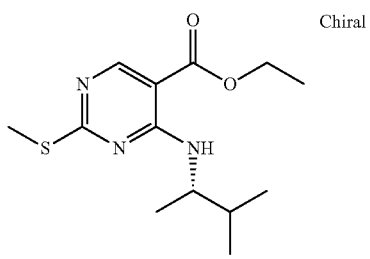 [SMILES: CCOC(=O)c1cnc(SC)nc1N[C@@H](C)C(C)C]

The title compound was obtained as a colourless oil (71% yield);

$^1$H NMR (500 MHz, DMSO-d$_6$) δ=8.55 (s, 1H), 8.20 (d, J=8.39 Hz, 1H), 4.28 (dq, J=1.14, 7.09 Hz, 2H), 4.18 (dqd, J=5.11, 6.76, 8.30 Hz, 1H), 2.47 (s, 3H), 1.79-1.92 (m, 1H), 1.30 (t, J=7.09 Hz, 3H), 1.14 (d, J=6.71 Hz, 3H), 0.91 (d, J=6.86 Hz, 3H), 0.89 (d, J=6.71 Hz, 3H). LCMS: m/z 284 [M+H]$^+$@ r.t. 7.89 min. HRMS (ESI) calcd for C$_{13}$H$_{22}$N$_3$O$_2$S [M+H]$^+$ 284.1427 found 284.1430;

ethyl 4-{[(2S)-3,3-dimethylbutan-2-yl]amino}-2-(methylsulfanyl)pyrimidine-5-carboxylate [(VI), R2=(2S)-3-methylbutan-2-yl, R3=H]

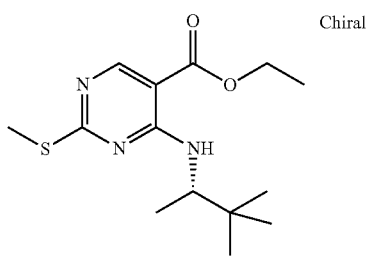 [SMILES: CCOC(=O)c1cnc(SC)nc1N[C@@H](C)C(C)(C)C]

The title compound was obtained as a light yellow oil (56% yield);

$^1$H NMR (500 MHz, DMSO-d$_6$) δ=8.55 (s, 1H), 8.32 (d, J=9.00 Hz, 1H), 4.23-4.34 (m, 2H), 4.19 (qd, J=6.77, 9.13 Hz, 1H), 2.47 (s, 3H), 1.30 (t, J=7.09 Hz, 3H), 1.11 (d, J=6.86 Hz, 3H), 0.92 (s, 9H). LCMS: m/z 298 [M+H]$^+$@ r.t. 8.14 min. HRMS (ESI) calcd for C$_{14}$H$_{24}$N$_3$O$_2$S [M+H]$^+$ 298.1584 found 298.1583.

Ethyl 2-(methylsulfanyl)-4-{[(2S)-1,1,1-trifluoropropan-2-yl]amino}pyrimidine-5-carboxylate [(VI), R2=(2S)-3-methylbutan-2-yl, R3=H]

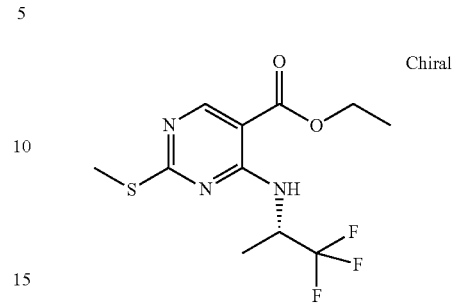

The title compound was obtained as a light yellow oil (56% yield).

$^1$H NMR (500 MHz, DMSO-d$_6$) δ=8.66 (s, 1H), 8.35 (d, J=9.00 Hz, 1H), 5.17-5.36 (m, J=7.27, 8.75 Hz, 1H), 4.31 (q, J=7.02 Hz, 2H), 1.41 (d, J=7.02 Hz, 3H), 1.31 (t, J=7.09 Hz, 3H). LCMS: m/z 310 [M+H]$^+$@ r.t. 7.22 min.

HRMS (ESI) calcd for C$_{11}$H$_{15}$F$_3$N$_3$O$_2$S [M+H]$^+$ 310.0832 found 310.0832.

6-Chloro-4-(2,2-dimethyl-propylamino)-nicotinic acid ethyl ester [(VIa), R2=2,2-Dimethyl-propyl, X=CH]

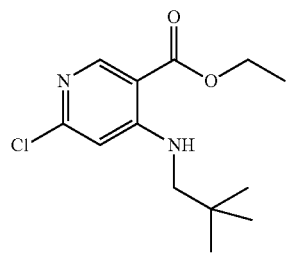 [SMILES: CCOC(=O)c1cnc(Cl)cc1NCC(C)(C)C]

$^1$H NMR (DMSO-d$_6$) δ=8.53 (s, 1H), 8.25 (t, J=5.6 Hz, 1H), 6.92 (s, 1H), 4.31 (q, J=7.2 Hz, 2H), 3.09 (d, J=5.6 Hz, 2H), 1.31 (t, J=7.1 Hz, 3H), 0.95 (s, 9H). LCMS: m/z 271 [M+H]$^+$@ r.t. 7.55 min.

HRMS (ESI) calcd for C$_{13}$H$_{20}$ClN$_2$O$_2$[M+H]$^+$ 271.1208 found 271.1208.

6-Chloro-4-ethylamino-nicotinic acid ethyl ester [(VIa), R2=Ethyl, X=CH]

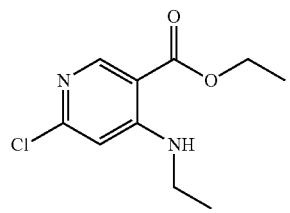

The title compound was obtained as a light yellow oil (80% yield).

1H NMR (DMSO-d6) δ 8.52 (s, 1H), 8.05 (t, J=5.2 Hz, 1H), 6.80 (s, 1H), 4.29 (q, J=7.2 Hz, 2H), 3.25-3.32 (m, 2H), 1.31 (t, J=7.1 Hz, 3H), 1.17 (t, J=7.2 Hz, 3H). LCMS: m/z 229 [M+H]⁺@ r.t. 6.27 min.

HRMS (ESI) calcd for $C_{10}H_{14}ClN_2O_2[M+H]^+$ 229.0739 found 229.0745.

6-Chloro-4-isopropylamino-nicotinic acid ethyl ester [(VIa), R2=propan-2-yl, X=CH]

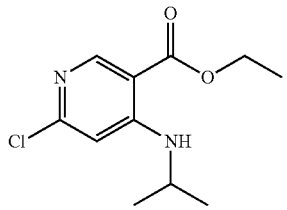 [SMILES: CCOC(=O)c1cnc(Cl)cc1NC(C)C]

¹H NMR (DMSO-d₆) δ=8.53 (s, 1H), 7.98 (d, J=7.9 Hz, 1H), 6.84 (s, 1H), 4.29 (q, J=7.1 Hz, 2H), 3.80-3.93 (m, 1H), 1.31 (t, J=7.1 Hz, 3H), 1.19 (d, J=6.4 Hz, 6H). LCMS: m/z 243 [M+H]⁺@ r.t. 6.72 min.

HRMS (ESI) calcd for $C_{11}H_{16}ClN_2O_2[M+H]^+$ 243.0895 found 243.0901.

Preparation 2

[4-(2,2-Dimethyl-propylamino)-2-methylsulfanyl-pyrimidin-5-yl]-methanol [(VII), R2=2,2-Dimethyl-propyl, R3=H] Step 2b

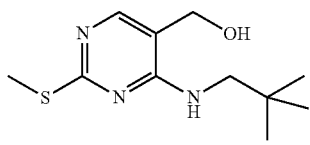 [SMILES: CSc1ncc(CO)c(NCC(C)(C)C)n1]

LiAlH₄ (11.1 mL, 10.58 mmol, 4% in THF) is added to a solution of 4-(2,2-Dimethyl-propylamino)-2-methylsulfanyl-pyrimidine-5-carboxylic acid ethyl ester (1.5 g, 5.29 mmol) in THF (15 mL) at ~5° C. over 15 minutes. After stirring for 1 hour, ice water (0.40 mL) and 15% aqueous NaOH (0.40 mL) are added, followed by additional ice water (1.2 mL). After 30 minutes the quenched reaction mixture is filtered and the filter cake is washed with AcOEt. The combined organic washes are dried over Na₂SO₄ and filtered. The solvent was evaporated under vacuum to give the product (1.25 g, 98% yield) which is used without further purification.

¹H NMR (500 MHz, DMSO-d₆) δ=7.80 (s, 1H), 6.61 (t, J=6.0 Hz, 1H), 5.27 (t, J=5.3 Hz, 1H), 4.36 (d, J=5.0 Hz, 2H), 3.28 (d, J=6.3 Hz, 2H), 2.40 (s, 3H), 0.89 (s, 9H). LCMS: m/z 242 [M+H]⁺@ r.t. 5.64 min. HRMS (ESI) calcd for $C_{11}H_{19}N_3O\,S\,[M+H]^+$ 242.1322 found 242.1319.

The following compound is prepared essentially by the same method of preparation:

1-(5-Hydroxymethyl-2-methylsulfanyl-pyrimidin-4-ylamino)-2-methyl-propan-2-ol [(VII), R2=methyl-propan-2-ol, R3=H]

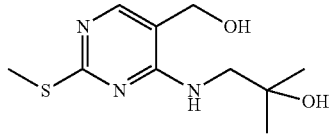 [SMILES: CSc1ncc(CO)c(NCC(C)(C)O)n1]

The title compound was obtained as a white solid (77% yield);

¹H NMR (500 MHz, DMSO-d₆) δ=7.81 (s, 1H), 6.61 (t, J=5.7 Hz, 1H), 5.27 (t, J=5.2 Hz, 1H), 4.66 (s, 1H), 4.36 (d, J=5.2 Hz, 2H), 3.36 (d, J=5.8 Hz, 2H), 2.40 (s, 3H), 1.11 (s, 6H). LCMS: m/z 244 [M+H]⁺@ r.t. 3.83 min.

HRMS (ESI) calcd for $C_{10}H_{17}N_3O_2S\,[M+H]^+$ 244.1114 found 244.1111;

[4-{[(2S)-3-methylbutan-2-yl]amino}-2-(methylsulfanyl)pyrimidin-5-yl]methanol [(VII), R2=(2S)-3-methylbutan-2-yl, R3=H]

Chiral

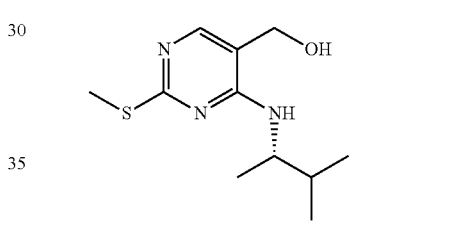

The title compound was obtained as a colourless oil (65% yield);

¹H NMR (500 MHz, DMSO-d₆) δ=7.79 (s, 1H), 6.37 (d, J=8.08 Hz, 1H), 5.21 (t, J=5.49 Hz, 1H), 4.33 (d, J=5.49 Hz, 2H), 4.00-4.11 (m, 1H), 2.40 (s, 3H), 1.82 (qd, J=6.71, 13.27 Hz, 1H), 1.10 (d, J=6.71 Hz, 3H), 0.88 (d, J=6.71 Hz, 3H), 0.87 (d, J=6.86 Hz, 3H). LCMS: m/z 242 [M+H]⁺@ r.t. 5.63 min. HRMS (ESI) calcd for $C_{11}H20N_3O\,S\,[M+H]^+$ 242.1322 found 242.1320;

[4-{[(2S)-3,3-dimethylbutan-2-yl]amino}-2-(methylsulfanyl)pyrimidin-5-yl]methanol [(VII), R2=(2S)-3,3-dimethylbutan-2-yl, R3=H]

Chiral

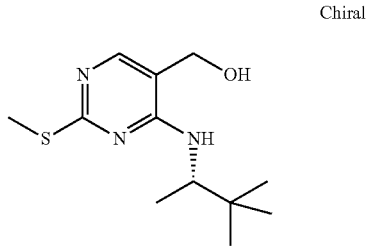 [SMILES: CSc1ncc(CO)c(N[C@@H](C)C(C)(C)C)n1]

The title compound was obtained as a colourless oil (65% yield);

¹H NMR (500 MHz, DMSO-d₆) δ=7.79 (s, 1H), 6.28 (d, J=9.00 Hz, 1H), 5.35 (t, J=5.26 Hz, 1H), 4.32-4.42 (m, 2H), 4.16 (qd, J=6.84, 9.07 Hz, 1H), 2.40 (s, 3H), 1.08 (d, J=6.71 Hz, 3H), 0.90 (s, 9H). LCMS: m/z 256 [M+H]⁺@r.t. 6.0 min. HRMS (ESI) calcd for $C_{12}H_{22}N_3O S$ [M+H]⁺ 256.1478 found 256.1475;

[2-(methylsulfanyl)-4-{[(2S)-1,1,1-trifluoropropan-2-yl]amino}pyrimidin-5-yl]methanol [(VII), R2=(2S)-1,1,1-trifluoropropan-2-yl, R3=H]

Chiral

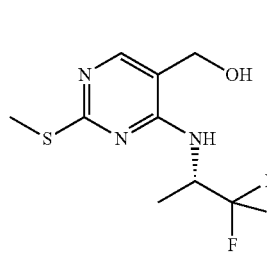

The title compound was obtained as a colourless oil (60% yield).
LCMS: m/z 268 [M+H]⁺@ r.t. 5.45 min.

(6-Chloro-4-ethylamino-pyridin-3-yl)-methanol [(VIIa), R2=Ethyl, X=CH]

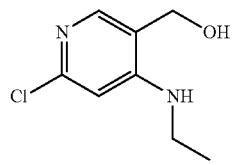

¹H NMR (DMSO-d₆) δ=7.77 (s, 1H), 6.49 (s, 1H), 6.11 (t, J=5.1 Hz, 1H), 5.18 (t, J=5.4 Hz, 1H), 4.37 (d, J=5.3 Hz, 2H), 3.17 (qd, J=7.1, 5.7 Hz, 2H), 1.15 (t, J=7.2 Hz, 3H). LCMS: m/z 187 [M+H]⁺@ r.t. 4.06 min.
HRMS (ESI) calcd for $C_8H_{12}N_2OCl$ [M+H]⁺ 187.0633 found 187.0638.

(6-Chloro-4-isopropylamino-pyridin-3-yl)-methanol [(VIIa), R2=propan-2-yl, X=CH]

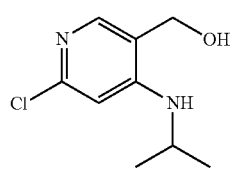

¹H NMR (DMSO-d₆) δ=7.76 (s, 1H), 6.53 (s, 1H), 5.81 (d, J=7.8 Hz, 1H), 5.24 (t, J=5.4 Hz, 1H), 4.38 (d, J=5.2 Hz, 2H), 3.65-3.77 (m, 1H), 1.16 (d, J=6.4 Hz, 6H). LCMS: m/z 201 [M+H]⁺@ r.t. 2.74 min.
HRMS (ESI) calcd for $C_9H_{14}ClN_2O$ [M+H]⁺ 201.0789 found 201.0787.

[6-Chloro-4-(2,2-dimethyl-propylamino)-pyridin-3-yl]-methanol [(VIIa), R2=2,2-Dimethyl-propyl, X=CH]

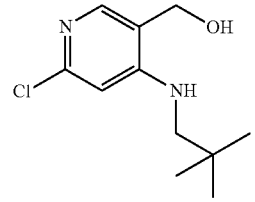

¹H NMR (DMSO-d₆) δ=7.73 (s, 1H), 6.62 (s, 1H), 6.08 (t, J=5.9 Hz, 1H), 5.40 (t, J=5.3 Hz, 1H), 4.45 (d, J=5.2 Hz, 2H), 2.98 (d, J=5.9 Hz, 2H), 0.93 (s, 9H). LCMS: m/z 229 [M+H]⁺@ r.t. 5.59 min.
HRMS (ESI) calcd for $C_{11}H_{18}ClN_2O$ [M+H]⁺ 229.1102 found 229.1105.

Preparation 3

4-(2,2-Dimethyl-propylamino)-2-methylsulfanyl-pyrimidine-5-carbaldehyde [(VIII), R2=2,2-Dimethyl-propyl, R3=H] Step 2c

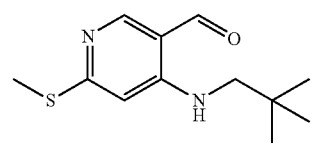 [SMILES: CSc1cc(NCC(C)(C)C)c(C=O)cn1]

[4-(2,2-Dimethyl-propylamino)-2-methylsulfanyl-pyrimidin-5-yl]-methanol (1.25 g, 5.17 mmol) was dissolved in DCM (30 mL) to which MnO₂ (3.15 g, 36.19 mmol) was added. The resulting suspension was stirred overnight. The solids were removed by filtration through a celite pad, which was washed with further DCM. The solvent was evaporated in vacuo to obtain the product (1.17 g, 95% yield).
¹H NMR (500 MHz, DMSO-d₆) δ=9.77 (s, 1H), 8.78 (t, J=5.6 Hz, 1H), 8.54 (s, 1H), 3.40 (d, J=6.3 Hz, 2H), 2.50 (s, 3H), 0.92 (s, 9H). LCMS: m/z 240 [M+H]⁺@ r.t. 6.74 min.
HRMS (ESI) calcd for $C_{11}H~N_3OS$ [M+H]⁺ 240.1165 found 240.1166.
According to the same method the following compound was prepared:

4-(2-Hydroxy-2-methyl-propylamino)-2-methylsulfanyl-pyrimidine-5-carbaldehyde [(VIII), R2=2-Hydroxy-2-methyl-propyl, R3=H]

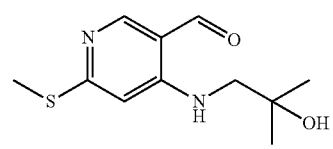 [SMILES: CSc1cc(NCC(C)(C)O)c(C=O)cn1]

The title compound was obtained in quantitative yield;
¹H NMR (500 MHz, DMSO-d₆) δ=9.76 (s, 1H), 8.84 (t, J=5.3 Hz, 1H), 8.54 (s, 1H), 4.79 (s, 1H), 3.47 (d, J=5.6 Hz, 2H), 1.13 (s, 6H). LCMS: m/z 242 [M+H]⁺@ r.t. 4.53 min.

HRMS (ESI) calcd for C$_{10}$H$_{15}$N$_3$O$_2$S [M+H]$^+$ 242.0958 found 242.0957;

4-{[(2S)-3-methylbutan-2-yl]amino}-2-(methylsulfanyl)pyrimidine-5-carbaldehyde [(VIII), R2=(2S)-3-methylbutan-2-yl, R3=H]

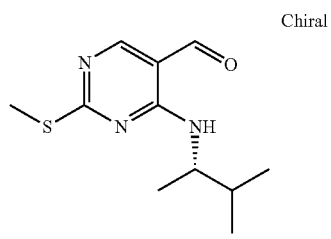 [SMILES: CSc1ncc(C=O)c(N[C@@H](C)C(C)C)n1]

The title compound was obtained as a colourless oil (90% yield);
$^1$H NMR (500 MHz, DMSO-d$_6$) δ=9.75 (s, 1H), 8.57 (d, J=8.69 Hz, 1H), 8.54 (s, 1H), 4.15-4.26 (m, 1H), 2.50 (s, 3H), 1.79-1.93 (m, 1H), 1.15 (d, J=6.71 Hz, 3H), 0.91 (d, J=6.86 Hz, 3H), 0.89 (d, J=6.86 Hz, 3H). LCMS: m/z 240 [M+H]$^+$@ r.t. 6.77 min. HRMS (ESI) calcd for C$_{11}$H$_{18}$N$_3$O S [M+H]$^+$ 240.1165 found 240.1168;

4-{[(2S)-3,3-dimethylbutan-2-yl]amino}-2-(methylsulfanyl)pyrimidine-5-carbaldehyde [(VIII), R2=(2S)-3,3-dimethylbutan-2-yl, R3=H]

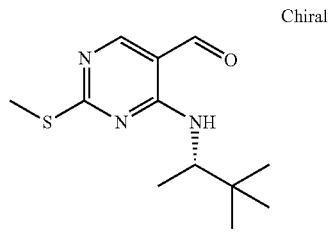 [SMILES: CSc1ncc(C=O)c(N[C@@H](C)C(C)(C)C)n1]

The title compound was obtained as a colourless oil (92% yield);
$^1$H NMR (500 MHz, DMSO-d$_6$) δ=9.76 (s, 1H), 8.70 (d, J=9.00 Hz, 1H), 8.54 (s, 1H), 4.21 (qd, J=6.77, 9.28 Hz, 1H), 2.50 (s, 3H), 1.13 (d, J=6.86 Hz, 3H), 0.92 (s, 9H). LCMS: m/z 254 [M+H]$^+$@ r.t. 7.07 min. HRMS (ESI) calcd for C$_{12}$H$_{20}$N$_3$O S [M+H]$^+$ 254.1322 found 254.1324;

2-(methylsulfanyl)-4-{[(2S)-1,1,1-trifluoropropan-2-yl]amino}pyrimidine-5-carbaldehyde [(VIII), R2=(2S)-1,1,1-trifluoropropan-2-yl, R3=H]

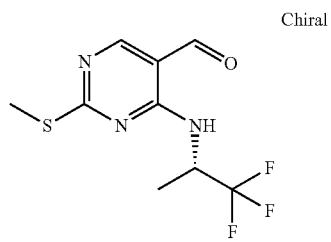 [SMILES: CSc1ncc(C=O)c(N[C@@H](C)C(F)(F)F)n1]

The title compound was obtained as a colourless oil (90% yield).
$^1$H NMR (500 MHz, DMSO-d$_6$) δ=9.82 (s, 1H), 8.69 (s, 1H), 8.66 (d, J=9.15 Hz, 1H), 5.19-5.39 (m, 1H), 2.53 (s, 3H), 1.43 (d, J=7.02 Hz, 3H). LCMS: m/z 266 [M+H]$^+$@ r.t. 6.13 min. HRMS (ESI) calcd for C$_9$H$_{11}$F$_3$N$_3$OS [M+H]$^+$ 266.0570 found 266.0572.

2-(methylsulfanyl)-4-(propan-2-ylamino)pyrimidine-5-carbaldehyde [(VIII), R2=propan-2-yl, R3=H]

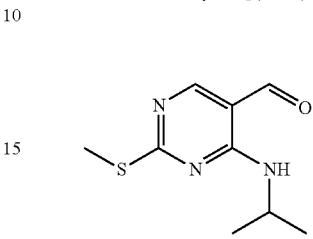

The title compound was obtained as a colourless oil (92% yield).
$^1$H NMR (500 MHz, DMSO-d$_6$) δ=9.74 (s, 1H), 8.53 (s, 1H), 8.45 (d, J=7.32 Hz, 1H), 4.28-4.44 (m, 1H), 2.50 (s, 3H), 1.24 (d, J=6.56 Hz, 6H). LCMS: m/z 212 [M+H]$^+$@ r.t. 5.9 min. HRMS (ESI) calcd for C$_9$H$_{14}$N$_3$O S [M+H]$^+$ 212.0852 found 212.0856.

2-(methylsulfanyl)-4-{[(2S)-1-(tetrahydro-2H-pyran-2-yloxy)propan-2-yl]amino}pyrimidine-5-carbaldehyde [(VIII), R2=(2S)-1-(tetrahydro-2H-pyran-2-yloxy, R3=H]

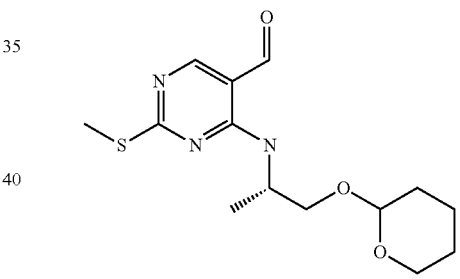

The title compound was obtained as a colourless oil (89% yield).
$^1$H NMR (500 MHz, DMSO-d$_6$) δ=9.75 (s, 1H), 8.53 (s, 1H), (d, J=7.78 Hz, 1H), 8.55 (s, 1H), 4.65 (dd, J=2.9, 4.27 Hz, 1H), 4.45-4.56 (m, 1H), 2.50 (s, 3H), 3.69-3.77 (m, 2H), 3.39-3.50 (m, 2H), 2.49 (s, 3H), 1.40-1.73 (m, 6H), 1.25 (d, J=6.56 Hz, 6H). LCMS: m/z 312 [M+H]$^+$@ r.t. 10.47 min. HRMS (ESI) calcd for C$_{14}$H$_{22}$N$_3$O$_3$S [M+H]$^+$312.1377 found 312.1375.

2-chloro-4-(propan-2-ylamino)pyrimidine-5-carbaldehyde [(VIIIa), R2=propan-2-yl, R3=H]

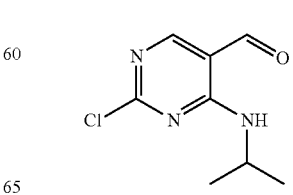

LCMS: m/z 200 [M+H]$^+$@ r.t. 4.87 min.

6-Chloro-4-ethylamino-pyridine-3-carbaldehyde [(VIIIa), R2=propan-2-yl, X=CH]

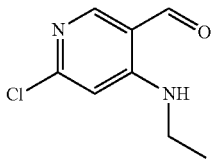

$^1$H NMR (DMSO-d$_6$) δ=9.86 (d, J=0.6 Hz, 1H), 8.56 (t, J=4.7 Hz, 1H), 8.44 (s, 1H), 6.85 (s, 1H), 3.34 (s, 2H), 1.17 (t, J=7.2 Hz, 3H). LCMS: m/z 185 [M+H]$^+$@ r.t. 4.89 min.

HRMS (ESI) calcd for C$_8$H$_{10}$ClN$_2$O [M+H]$^+$ 185.0476 found 185.0481.

6-Chloro-4-isopropylamino-pyridine-3-carbaldehyde [(VIIIa), R2=propan-2-yl, X=CH]

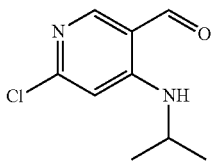

$^1$H NMR (DMSO-d$_6$) δ=9.85 (d, J=0.5 Hz, 1H), 8.40-8.49 (m, 2H), 6.90 (s, 1H), 3.90 (dt, J=7.9, 6.5 Hz, 1H), 1.20 (d, J=6.4 Hz, 6H). LCMS: m/z 199 [M+H]$^+$@ r.t. 7.84 min. HRMS (ESI) calcd for C$_9$H$_{12}$ClN$_2$O [M+H]$^+$ 199.0633 found 199.0632.

6-Chloro-4-(2,2-dimethyl-propylamino)-pyridine-3-carbaldehyde [(VIIIa), R2=2,2-Dimethyl-propyl, X=CH]

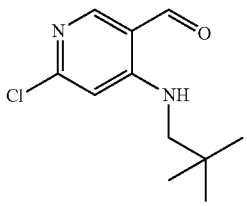

$^1$H NMR (DMSO-d$_6$) δ=9.88 (s, 1H), 8.76 (t, J=5.6 Hz, 1H), 8.45 (s, 1H), 7.00 (s, 1H), 3.14 (d, J=6.1 Hz, 2H), 0.94 (s, 9H). LCMS: m/z 279 [M+H]$^+$@ r.t. 6.46 min. HRMS (ESI) calcd for C$_{11}$H$_{16}$ClN$_2$O [M+H]$^+$ 227.0946 found 227.0949.

Preparation 4

(E)-3-[4-(2-Hydroxy-2-methyl-propylamino)-2-methylsulfanyl-pyrimidin-5-yl]-acrylic acid methyl ester [(X), R2=2-Hydroxy-2-methyl-propyl, R3=R4=R5=H] step 2d

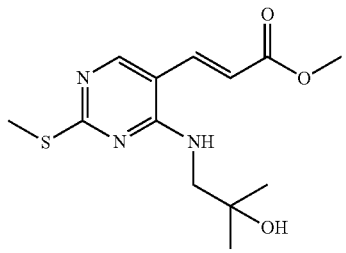

4-(2-Hydroxy-2-methyl-propylamino)-2-methylsulfanyl-pyrimidine-5-carbaldehyde (500.0 mg, 2.07 mmol) was dissolved in THF (7 mL) to which methyl (triphenylphosphoranylidene)acetate (831.3 mg, 2.49 mmol) was added. The resulting suspension was stirred at reflux for 1 hour. The reaction mixture was allowed to cool to room temperature, then was diluted with AcOEt, and washed with water followed by brine. The organic phases were separated and dried over Na$_2$SO$_4$, filtered, and concentrated in vacuo. The crude material was purified through silica gel column chromatography (50 to 70% AcOEt\hexane) to give the title product (498.7 mg, 81% yield).

$^1$H NMR (500 MHz, DMSO-d$_6$) δ=8.37 (s, 1H), 7.79 (d, J=16.0 Hz, 1H), 7.49-7.45 (m, 1H), 6.52 (d, J=15.7 Hz, 1H), 4.62 (s, 1H), 3.72 (s, 3H), 3.44 (d, J=6.1 Hz, 2H), 2.44 (s, 3H), 1.13-1.01 (m, 6H).

LCMS: m/z 298 [M+H]$^+$@ r.t. 5.06 min.

HRMS (ESI) calcd for C$_{13}$H$_{19}$N$_3$O$_3$S [M+H]$^+$ 298.1220 found 298.1217.

Preparation 5

8-(2-Hydroxy-2-methyl-propyl)-2-methylsulfanyl-8H-pyrido[2,3-d]pyrimidin-7-one [(XI), R2=2-Hydroxy-2-methyl-propyl, R3=R4=R5=H] Step 2e

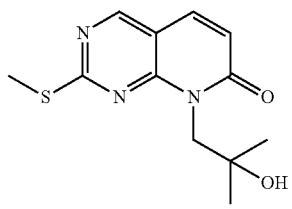 [SMILES: CSc1ncc2ccc(=O)n(CC(C)(C)O)c2n1]

(E)-3-[4-(2-Hydroxy-2-methyl-propylamino)-2-methylsulfanyl-pyrimidin-5-yl]-acrylic acid methyl ester (495.0 mg, 1.66 mmol) was dissolved in DIPEA (7.0 mL) to which DBU (0.25 mL, 1.66 mmol) was added and stirred at reflux overnight. The reaction mixture was allowed to cool to room temperature, then was diluted with DCM, and washed with water followed by saturated NH$_4$Cl. The organic phases were separated and dried over Na$_2$SO$_4$, filtered, and concentrated in vacuo. The crude material was purified through silica gel column chromatography (1 to 10% MeOHDCM) to give the title product (350.7 mg, 79% yield).

$^1$H NMR (500 MHz, DMSO-d$_6$) δ=8.88 (s, 1H), 7.94 (d, J=9.5 Hz, 1H), 6.65 (d, J=9.5 Hz, 1H), 4.53 (s, 1H), 4.44 (s, 2H), 2.60 (s, 3H), 1.10 (s, 6H). LCMS: m/z 266 [M+H]$^+$@ r.t. 4.50 min. HRMS (ESI) calcd for C$_{12}$H$_{15}$N$_3$O$_2$S [M+H]$^+$ 266.0958 found 266.0965;

8-[(2S)-butan-2-yl]-2-(methylsulfanyl)pyrido[2,3-d]pyrimidin-7(8H)-one [(XI), R2=(2S)-butan-2-yl, R3=R4=R5=H]

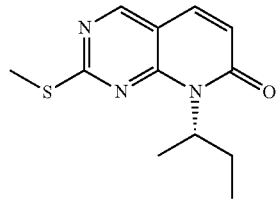 [SMILES: CC[C@H](C)n1c(=O)ccc2cnc(SC)nc21]

$^1$H NMR (500 MHz, DMSO-d$_6$) δ=8.86 (s, 1H), 7.90 (d, J=9.46 Hz, 1H), 6.59 (br. s., 1H), 5.39 (br. s., 1H), 2.59 (s, 3H), 2.23 (br. s., 1H), 1.90 (br. s., 1H), 1.52 (br. s., 3H), 0.73 (t, J=7.47 Hz, 3H).

Preparation 6

8-(2,2-Dimethyl-propyl)-6-fluoro-2-methylsulfanyl-8H-pyrido[2,3-d]pyrimidin-7-one [(XI), R2=2,2-Dimethyl-propyl, R3=R4=H, R5=F] step 3a

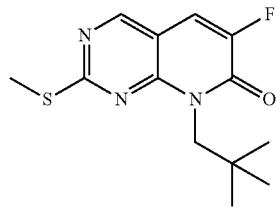 [SMILES: CSc1ncc2cc(F)c(=O)n(CC(C)(C)C)c2n1]

Lithium hydroxide monohydrate (26.1 mg, 0.62 mmol) was added to a solution of ethyl (diethoxyphosphoryl)(fluoro)acetate (0.10 mL, 0.50 mmol) and 4-(2,2-Dimethyl-propylamino)-2-methylsulfanyl-pyrimidine-5-carbaldehyde (100.0 mg, 0.41 mmol) in THF (5.0 mL). The solution was stirred overnight at room temperature, in this condition there is a spontaneous cyclization of the acrylic ester intermediate to the title compound.

The reaction mixture was diluted with DCM, and washed with water followed by brine. The organic phases were separated and dried over Na$_2$SO$_4$, filtered, and concentrated in vacuo. The crude material was purified through silica gel column chromatography (10 to 30% AcOEt\hexane) to give the product (50.2 mg, 43% yield). $^1$H NMR (500 MHz, DMSO-d$_6$) δ=8.88 (s, 1H), 7.92 (d, J=9.0 Hz, 1H), 4.33 (br. s., 2H), 2.61 (s, 3H), 0.93 (s, 9H). LCMS: m/z 282 [M+H]$^+$@ r.t. 6.59 min. HRMS (ESI) calcd for C$_{13}$H$_{16}$FN$_3$S [M+H]$^+$ 282.1071 found 282.1069.

Preparation 7

8-(2,2-Dimethyl-propyl)-6-methoxy-2-methylsulfanyl-8H-pyrido[2,3-d]pyrimidin-7-one [(XI), R2=2,2-Dimethyl-propyl, R3=R4=H, R5=OMe] step 3a

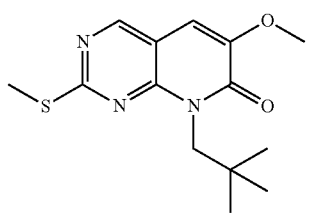

4-(2,2-Dimethyl-propylamino)-2-methylsulfanyl-pyrimidine-5-carbaldehyde (120.0 g, 0.50 mmol) and ethyl methoxyacetate (0.062 mL, 0.62 mmol) were stirred in toluene (4.0 mL) at 0° C. under nitrogen. Potassium t-butoxide (61.4 mg, 0.55 mmol) was added gradually. The mixture was stirred to room temperature, and then to 65° C. for 48 hours. The reaction mixture was concentrated in vacuo and triturated with AcOEt to remove the remaining starting aldehyde. The remaining solid was further purified through silica gel column chromatography (30 to 90% AcOEt\hexane) to give the title product (38.8 mg, 24% yield).

$^1$H NMR (500 MHz, DMSO-d$_6$) δ=8.80 (s, 1H), 7.27 (s, 1H), 4.33 (br. s., 2H), 3.84 (s, 3H), 2.58 (s, 3H), 0.90 (s, 9H). LCMS: m/z 294 [M+H]$^+$@ r.t. 6.24 min. HRMS (ESI) calcd for C$_{14}$H$_{19}$N$_3$O$_2$S [M+H]$^+$ 294.1271 found 294.1273.

Preparation 8

8-[(2S)-3-methylbutan-2-yl]-2-(methylsulfanyl)pyrido[2,3-d]pyrimidin-7(8H)-one [(XI), R2=(2S)-3-methylbutan-2-yl, R3=R4=R5=H] step 3a

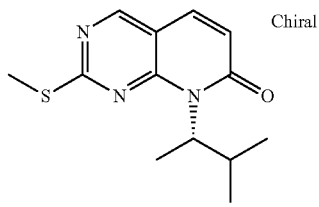 [SMILES: CSc1ncc2ccc(=O)n([C@@H](C)C(C)C)c2n1]

LiHMDS (4 mL of 1 M in THF solution, 4 mmol) was added to THF (15 mL) at −78° C. and treated with EtOAc (0.5 mL, 4.64 mmol). The solution was stirred at −78° C. for 10 min, then solid 4-{[(2S)-3-methylbutan-2-yl]amino}-2-(methylsulfanyl)pyrimidine-5-carbaldehyde (280 mg, 1.16 mmol) was added in one portion and the solution was stirred at −78° C. for 10 min then removed from the cooling bath warmed to RT for 3 h. The reaction was cooled in an ice bath and quenched with saturated solution of NH$_4$Cl and extracted with EtOAc (2×1 mL), dried over Na$_2$SO$_4$, filtered and concentrated. Purification with chromatographic column eluent Hex/EtOAc 8:2 to give an off-white solid of the title compound (250 mg, 80% yield).

$^1$H NMR (500 MHz, DMSO-d$_6$) δ=8.87 (s, 1H), 7.91 (d, J=9.30 Hz, 1H), 6.45-6.72 (m, 1H), 4.86-5.45 (m, 1H), 2.58 (s, 3H), 1.37-1.65 (m, 3H), 1.03 (br. s., 3H), 0.59 (d, J=13.42

Hz, 3H). LCMS: m/z 264 [M+H]+@ r.t. 6.26 min. HRMS (ESI) calcd for $C_{13}H_{18}N_3OS$ [M+H]+ 264.1165 found 264.1174

According to the same method the following compounds were prepared:

8-[(2S)-3,3-dimethylbutan-2-yl]-2-(methylsulfanyl) pyrido[2,3-d]pyrimidin-7(8H)-one [(XI), R2=(2S)-3, 3-dimethylbutan-2-yl, R3=R4=R5=H]

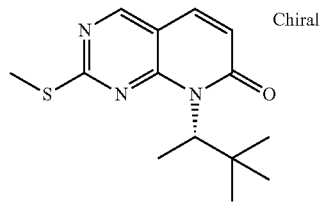 [SMILES: CSc1ncc2ccc(=O)n([C@@H](C)C(C)(C)C)c2n1]

LCMS: m/z 278 [M+H]+@ r.t. 7.02 min;

2-(methylsulfanyl)-8-[(2S)-1,1,1-trifluoropropan-2-yl]pyrido[2,3-d]pyrimidin-7(8H)-one [(XI), R2=(2S)-1,1,1-trifluoropropan-2-yl, R3=R4=R5=H]

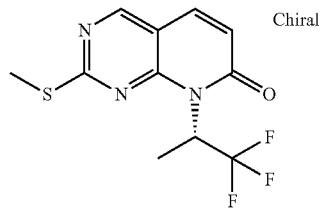 [SMILES: CSc1ncc2ccc(=O)n([C@@H](C)C(F)(F)F)c2n1]

$^1$H NMR (500 MHz, DMSO-$d_6$) δ=8.95 (s, 1H), 8.92 (s, 1H), 8.00 (d, J=9.46 Hz, 1H), 7.98 (d, J=9.61 Hz, 1H), 6.73 (d, J=9.46 Hz, 1H), 6.61 (d, J=9.46 Hz, 1H), 6.32-6.46 (m, 1H), 6.05-6.19 (m, 1H), 2.59 (s, 3H), 2.58 (s, 3H), 1.88 (d, J=7.32 Hz, 3H), 1.75 (d, J=7.02 Hz, 3H). LCMS: m/z 290 [M+H]+@ r.t. 5.91 min. HRMS (ESI) calcd for $C_{11}H_{11}F_3N_3OS$ [M+H]+ 290.0570 found 290.0569.

2-(methylsulfanyl)-8-(propan-2-yl)pyrido[2,3-d] pyrimidin-7(8H)-one [(XI), R2=propan-2-yl, R3=R4=R5=H]

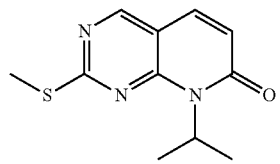 [SMILES: CSc1ncc2ccc(=O)n(C(C)C)c2n1]

$^1$H NMR (500 MHz, DMSO-$d_6$) δ=8.86 (s, 1H), 7.88 (d, J=9.46 Hz, 1H), 6.57 (d, J=9.46 Hz, 1H), 5.68 (br. s., 1H), 2.60 (s, 3H), 1.54 (d, J=7.02 Hz, 6H). LCMS: m/z 236 [M+H]+@ r.t. 9.10 min. HRMS (ESI) calcd for $C_{11}H_{14}N_3OS$ [M+H]+ 236.0852 found 236.0861.

2-(methylsulfanyl)-8-[(2S)-1-(tetrahydro-2H-pyran-2-yloxy)propan-2-yl]pyrido[2,3-d]pyrimidin-7(8H)-one [(XI), R2=(2S)-1-(tetrahydro-2H-pyran-2-yloxy)propan-2-yl, R3=R4=R5=H]

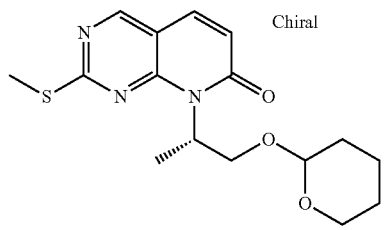 [SMILES: CSc1ncc2ccc(=O)n([C@@H](C)COC3CCCCO3)c2n1]

$^1$H NMR (500 MHz, DMSO-$d_6$) δ=8.87 (s, 1H), 7.90 (d, J=9.46 Hz, 1H), 6.59 (br. s., 1H), 5.40-6.04 (m, 1H), 4.60 (s, 1H), 4.00 (m, 2H), 3.73 (m, 2H), 3.41 (br. s, 2H), 2.59 (s, 3H), 1.07-1.73 (m, 9H). LCMS: m/z 336 [M+H]+@ r.t. 9.82 min. HRMS (ESI) calcd for $C_{16}H_{22}N_3O_3S$ [M+H]+ 336.1377 found 336.1372.

4-chloro-8-(2,2-dimethylpropyl)-2-(methylsulfanyl) pyrido[2,3-d]pyrimidin-7(8H)-one [(XI), R2=2,2-dimethylpropyl, R3=Cl, R4=R5=H]

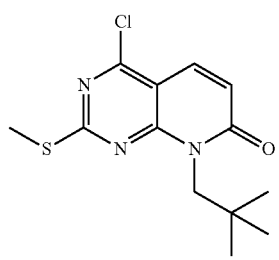 [SMILES: CSc1nc(Cl)c2ccc(=O)n(CC(C)(C)C)c2n1]

$^1$H NMR (500 MHz, DMSO-$d_6$) δ=7.99 (d, J=9.76 Hz, 1H), 6.72 (d, J=9.76 Hz, 1H), 4.30 (br. s., 2H), 2.62 (s, 3H), 0.91 (s, 9H). LCMS: m/z 298 [M+H]+@ r.t. 7.13 min. HRMS (ESI) calcd for $C_{13}H_{17}ClN_3OS$ [M+H]+ 298.0776 found 298.0783.

7-Chloro-1-ethyl-1H-[1,6]naphthyridin-2-one [(II), G=Cl, X=CH, R2=Ethyl, R3=R4=R5=H]

$^1$H NMR (DMSO-$d_6$) δ=8.74 (s, 1H), 8.02 (d, J=9.6 Hz, 1H), 7.69 (s, 1H), 6.71 (d, J=9.6 Hz, 1H), 4.21 (q, J=7.2 Hz, 2H), 1.17 (t, J=7.2 Hz, 3H). LCMS: m/z 209 [M+H]+@ r.t. 4.28 min.

HRMS (ESI) calcd for $C_{10}H_{10}ClN_2O$ [M+H]+ 209.0476 found 209.0485.

7-Chloro-1-isopropyl-1H-[1,6]naphthyridin-2-one [(II), G=Cl, X=CH, R2=propan-2-yl, R3=R4=R5=H]

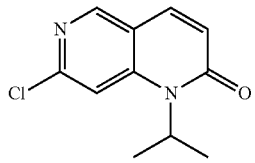

¹H NMR (DMSO-d₆) δ=8.71 (s, 1H), 7.96 (d, J=9.5 Hz, 1H), 7.79 (br. s., 1H), 6.63 (d, J=9.5 Hz, 1H), 5.14 (br. s., 1H), 1.50 (d, J=6.9 Hz, 6H). LCMS: m/z 223 [M+H]⁺@ r.t. 7.11 min.
HRMS (ESI) calcd for $C_{11}H_{12}ClN_2O$ [M+H]⁺ 223.0633 found 223.0633.

7-Chloro-1-(2,2-dimethyl-propyl)-1H-[1,6]naphthyridin-2-one [(II), G=Cl, X=CH, R2=Ethyl, R3=R4=R5=H]

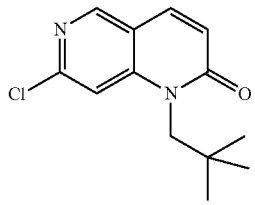 [SMILES: CC(C)(C)Cn1c(=O)ccc2cnc(Cl)cc21]

¹H NMR (DMSO-d₆) δ:=8.71 (s, 1H), 8.01 (d, J=9.5 Hz, 1H), 7.84 (s, 1H), 6.72 (d, J=9.5 Hz, 1H), 4.18 (br. s., 2H), 0.91 (s, 9H). LCMS: m/z 251 [M+H]⁺@ r.t. 5.79 min.
HRMS (ESI) calcd for $C_{13}H_{16}ClN_2O$ [M+H]⁺ 251.0946 found 251.0949.

Preparation 9

2-chloro-8-(propan-2-yl)pyrido[2,3-d]pyrimidin-7(8H)-one [(XI), R2=(2S)-3-methylbutan-2-yl, R3=R4=R5=H] Step 4g

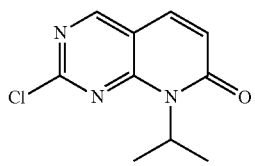

LiHMDS (8 mL of 1 M in THF solution, 18 mmol) was added to THF (20 mL) at −78° C. and treated with EtOAc (1.6 mL, 18.1 mmol). The solution was stirred at −78° C. for 10 min, then a THF solution (10 mL) of 2-chloro-4-(propan-2-ylamino)pyrimidine-5-carbaldehyde (0.9 g, 4.5 mmol) was added dropwise and the solution was stirred at −78° C. for 10 min then removed from the cooling bath and warmed to RT for 3 h. The reaction was cooled in an ice bath and quenched with saturated solution of NH₄Cl and extracted with EtOAc (2×1 mL), dried over Na₂SO₄, filtered and concentrated. Purification with chromatographic column eluent Hex/EtOAc 8:2 to give a off-white solid of the title compound (100 mg, 10% yield).
LCMS: m/z 224 [M+H]⁺@ r.t. 4.26 min.

Preparation 10

2-(methylsulfanyl)-7-oxo-8-(2,2 dimethylpropyl)-7,8-dihydropyrido[2,3-d]pyrimidine-4-carbonitrile [(XI), R2=2,2-dimethylpropyl, R3=CN, R4=R5=H] conv. A

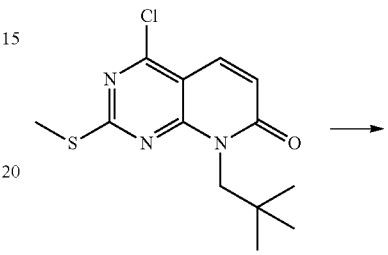

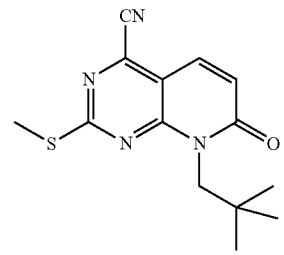

4-Chloro-8-(2,2-dimethyl-propyl)-2-methylsulfanyl-8H-pyrido[2,3-d]pyrimidin-7-one (60 mg, 0.2 mmol) was dissolved in DMSO (4.5 mL) to which triethylamine (300 µL) and NaCN (18 mg, 0.2 mmol) was added and stirred for 1 hour at 50° C. Water was then added 10 mL and extracted with AcOEt two times. The organic phases were washed with brine, and then dried over Na₂SO₄. The salts were filtered, and the solvent was evaporated in vacuo. The crude product was purified on SiO₂ chromatographic column eluent Exane/AcOEt 8/2 to give the product (12 mg, 20% yield).
¹H NMR (500 MHz, DMSO-d₆) δ=7.94 (d, J=9.61 Hz, 1H), 6.83 (d, J=9.61 Hz, 1H), 4.28 (br. s., 2H), 2.63 (s, 3H), 0.91 (s, 3H). LCMS: m/z 289 [M+H]⁺@ r.t. 7.09 min.
HRMS (ESI) calcd for $C_{14}H_{17}N_4OS$ [M+H]⁺ 289.1118 found 289.1122.

Preparation 11

4-amino-2-(methylsulfanyl)-8-(propan-2-yl)pyrido[2,3-d]pyrimidin-7(8H)-one [(XI), R2=propan-2-yl, R3=NH₂, R4=R5=H] conv. B

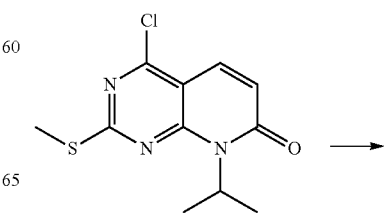

-continued

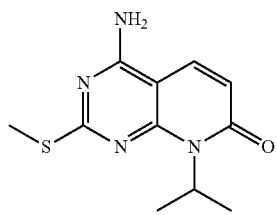

4-Chloro-8-isopropyl-2-methylsulfanyl-8H-pyrido[2,3-d]pyrimidin-7-one (50 mg, 0.15 mmol) ain NH₄OH 30% was heated to 60° C. for 3 hours. The product precipitate and was filtered off in quantitative yield. No further purification was made.

LCMS: m/z 251 [M+H]⁺@ r.t. 9.33 min. HRMS (ESI) calcd for $C_{11}H_{15}N_4OS$ [M+H]⁺ 251.0961 found 251.0961.

Preparation 12

4-(methylamino)-2-(methylsulfanyl)-8-(2,2-dimethylpropyl)pyrido[2,3-d]pyrimidin-7(8H)-one [(XI), R2=2,2-dimethylpropyl, R3=N(H)Me, R4=R5=H] conv. C

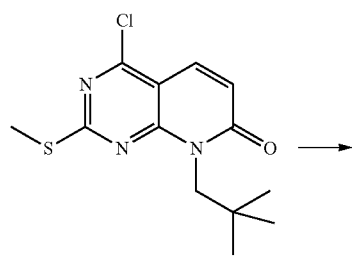

4-Chloro-8-(2,2-dimethyl-propyl)-2-methylsulfanyl-8H-pyrido[2,3-d]pyrimidin-7-one (40 mg, 0.13 mmol) was dissolved in THF (4 mL) to which methylamine 1.0 M in EtOH (100 μL) was added and stirred for 12 hour at room temperature. Water was then added 10 mL and extracted with AcOEt two times. The organic phases were washed with brine, and then dried over Na₂SO₄. The salts were filtered, and the solvent was evaporated in vacuo. The crude product was purified on SiO₂ chromatographic column DCM/MeOH 98/2 to give the product (33 mg, 85% yield).

¹H NMR (500 MHz, DMSO-d₆) δ=8.11 (q, J=4.02 Hz, 1H), 8.01 (d, J=9.61 Hz, 1H), 6.39 (d, J=9.61 Hz, 1H), 4.27 (br. s., 2H), 2.93 (d, J=4.42 Hz, 3H), 2.52 (s, 3H), 0.89 (s, 9H). LCMS: m/z 293 [M+H]⁺@ r.t. 6.63 min. HRMS (ESI) calcd for $C_{14}H_{21}N_4OS$ [M+H]⁺ 293.1431 found 293.1436.

Preparation 13

4-ethoxy-2-(methylsulfanyl)-8-(propan-2-yl)pyrido[2,3-d]pyrimidin-7(8H)-one [(XI), R2=2,2-dimethylpropyl, R3=OEt, R4=R5=H] conv. D

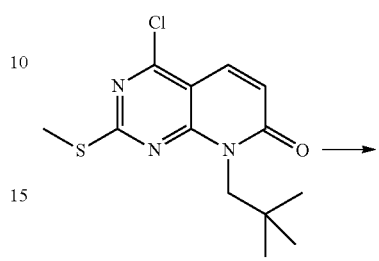

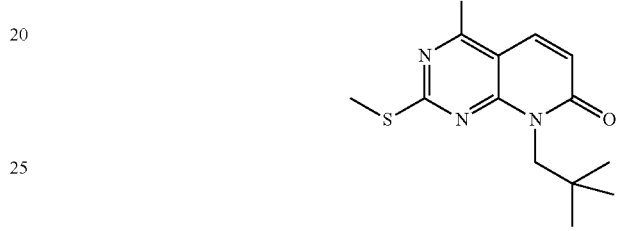

4-Chloro-8-(2,2-dimethyl-propyl)-2-methylsulfanyl-8H-pyrido[2,3-d]pyrimidin-7-one (50 mg, 0.17 mmol) was dissolved in EtOH (4 mL) in the presence of K₂CO₃ (46 mg, 0.34 mmol) was added and stirred for 12 hour at room temperature. Water was then added 10 mL and extracted with AcOEt two times. The organic phases were washed with brine, and then dried over Na₂SO₄. The salts were filtered, and the solvent was evaporated in vacuo. The crude product was purified on SiO₂ chromatographic column DCM/MeOH 98/2 to give the product (40 mg, 76% yield).

¹H NMR (500 MHz, DMSO-d₆) δ=7.86 (d, J=9.61 Hz, 1H), 6.51 (d, J=9.61 Hz, 1H), 4.50 (q, J=7.07 Hz, 2H), 4.29 (br. s., 2H), 2.59 (s, 3H), 1.38 (t, J=7.09 Hz, 3H), 0.90 (s, 9H). LCMS: m/z 308 [M+H]⁺@ r.t. 7.09 min. HRMS (ESI) calcd for $C_{15}H_{22}N_3O_2S$ [M+H]⁺ 308.1427 found 308.1428.

Preparation 14

8-[(2S)-1-fluoropropan-2-yl]-2-(methylsulfanyl)pyrido[2,3-d]pyrimidin-7(8H)-one [(XI), R2=(2S)-1-fluoropropan-2-yl, R3=R4=R5=H] conv. F

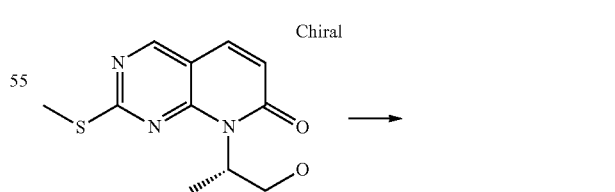

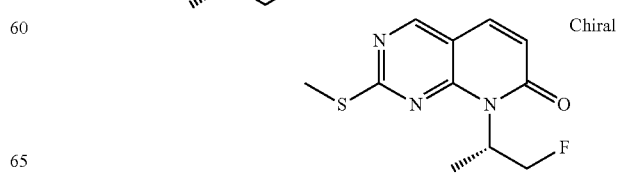

To a solution of 8-[(2S)-1-hydroxypropan-2-yl]-2-(methylsulfanyl)pyrido[2,3-d]pyrimidin-7(8H)-one (100 mg, 0.40 mmol) in MeCN (1.5 mL) were added triethylamine (509 µL, 3.66 mmol) and perfluoro-1-butanesulfonyl fluoride (214.4 µL, 1.194 mmol) followed by $NEt_3(HF)_3$ (198 µL, 1.213 mmol) and the resulting mixture was stirred at room temperature for 12 hours. The reaction mixture was diluted with water (6 mL) and extracted with DCM (3×6 mL). Combined organics fractions were washed with brine (6 mL), dried over $Na_2SO_4$, filtered and concentrated to dryness to give the crude product. Flash column chromatography (diethyl ether) gave 86.7 mg (86%) of the desired product.

$^1$H NMR (500 MHz, DMSO-$d_6$) δ=8.90 (s, 1H), 7.94 (d, J=9.46 Hz, 1H), 6.61 (d, J=9.46 Hz, 1H), 5.85 (br. s., 1H), 5.11 (td, J=8.00, 48.00 Hz, 1H), 4.84 (ddd, J=5.60, 8.70, 46.20 Hz, 1H), 2.59 (s, 3H), 1.49 (d, J=6.86 Hz, 3H). LCMS: m/z 254 [M+H]$^+$@ r.t. 8.06 min. HRMS (ESI) calcd for $C_{13}H_{17}FN_3OS$ [M+H]$^+$ 254.0758 found 254.0762.

Preparation 15

8-benzyl-2-(methylsulfanyl)pyrido[2,3-d]pyrimidin-7(8H)-one [(XI), R2=benzyl, R3=R4=R5=H] step 3a'

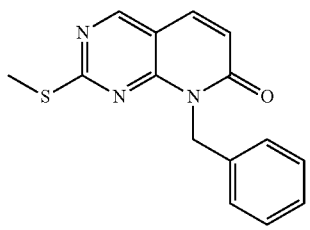 [SMILES: CSc1ncc2ccc(=O)n(Cc3ccccc3)c2n1]

A mixture of 2-(methylsulfanyl)pyrido[2,3-d]pyrimidin-7(8H)-one (100 mg, 0.52 mmol), cesium carbonate (337 mg, 1.04 mmol), and benzyl bromide (133 mg, 0.78 mmol) in anhydrous DMF (2 mL) was purged with nitrogen and heated in a sealed tube at 90° C. for 1 h. The reaction mixture was allowed to cool to room temperature and diluted with water. The product precipitated, filtered and washed with water. To afford 8-benzyl-2-(methylsulfanyl)pyrido[2,3-d]pyrimidin-7(8H)-one as a yellow solid (117 mg, 80% yield).

$^1$H NMR (500 MHz, DMSO-$d_6$) δ 8.91 (s, 1H), 8.00 (d, J=9.46 Hz, 1H), 7.17-7.35 (m, 5H), 6.71 (d, J=9.46 Hz, 1H), 5.50 (s, 2H), 2.50 (s, 3H). LCMS: m/z 284 [M+H]$^+$ r.t. 5.92 min. HRMS (ESI) calcd for $C_{15}H_{14}N_3OS$ [M+H]$^+$ 284.0852 found 284.0865.

According to the same method, but employing the appropriate alkylating reagent, the following compounds were prepared:

8-ethyl-2-(methylsulfanyl)pyrido[2,3-d]pyrimidin-7(8H)-one [(XI), R2=ethyl, R3=R4=R5=H]

The title compound was obtained as a yellow oil (65% yield).

$^1$H NMR (401 MHz, DMSO-$d_6$) δ 8.88 (s, 1H), 7.93 (d, J=9.40 Hz, 1H), 6.62 (d, J=9.52 Hz, 1H), 4.32 (q, J=7.04 Hz, 2H), 2.60 (s, 3H), 1.22 (t, J=7.02 Hz, 3H). LCMS: m/z 222 [M+H]$^+$ r.t. 4.95 min. HRMS (ESI) calcd for $C_{10}H_{12}N_3OS$ [M+H]$^+$ 222.0696 found 222.07; 2-(methylsulfanyl)-8-(propan-2-yl)pyrido[2,3-d]pyrimidin-7(8H)-one [(XI), R2=isopropyl, R3=R4=R5=H]:

The title compound was obtained as a light yellow foam (70% yield).

$^1$H NMR (401 MHz, DMSO-$d_6$) δ 8.85 (s, 1H), 7.87 (d, J=9.52 Hz, 1H), 6.57 (d, J=9.40 Hz, 1H), 5.69 (td, J=6.93, 13.73 Hz, 1H), 2.60 (s, 3H), 1.54 (d, J=6.96 Hz, 6H). LCMS: m/z 236 [M+H]$^+$ r.t. 5.53 min. HRMS (ESI) calcd for $C_{11}H_{14}N_3OS$ [M+H]$^+$ 236.0852 found 236.0861.

8-(4-bromo-2-fluorobenzyl)-2-(methylsulfanyl)pyrido[2,3-d]pyrimidin-7(8H)-one [(XI), R2=4-bromo-2-fluorobenzyl, R3=R4=R5=H]

The title compound was obtained as a off-white foam (75% yield).

$^1$H NMR (500 MHz, DMSO-d6) δ =8.93 (s, 1H), 8.02 (d, J=9.46 Hz, 1H), 7.57 (dd, J=1.83, 9.91 Hz, 1H), 7.29 (dd, J=1.68, 8.39 Hz, 1H), 6.96 (t, J=8.24 Hz, 1H), 6.71 (d, J=9.61 Hz, 1H), 5.48 (s, 2H), 2.44 (s, 3H). LCMS: m/z 379 [M+H]$^+$ r.t. 6.71 min. HRMS (ESI) calcd for $C_{15}H_{12}BrFN_3S$ [M+H]$^+$ 379.9863 found 379.9872.

Preparation 16

4-methyl-2-(methylsulfanyl)pyrido[2,3-d]pyrimidin-7(8H)-one [(XI), R2=H, R3=Me, R4=R5=H]

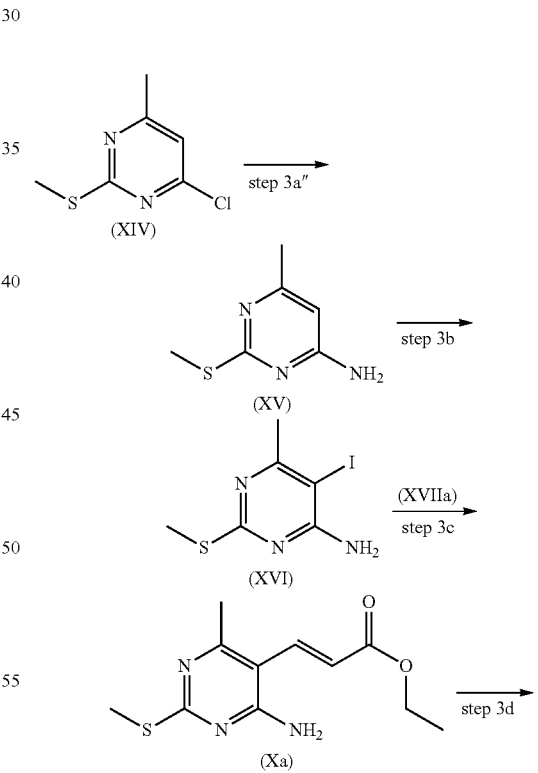

Step 3a″: To a mixture of 4-chloro-6-methyl-2-(methylthio)pyrimidine (1 g, 5.7 mmol) in 5 mL of acetonitrile was added 2 mL of a solution of amonium hydroxide 28% in water. The reaction was heated to 120° C. for 72 h. After competition, the mixture was cooled down to r.t. and diluted with water and a precipitate was observed. The solid was filtered and dried under vacuum to afford 6-methyl-2-(methylsulfanyl)pyrimidin-4-amine (0.76 g, 86% yield).

$^1$H NMR (401 MHz, DMSO-d$_6$) δ=6.75 (br. s., 2H), 5.96 (d, J=0.46 Hz, 1H), 2.36-2.38 (m, 3H), 2.13 (s, 3H)

Step 3b: To the solution of 6-methyl-2-(methylsulfanyl)pyrimidin-4-amine (1.1 g, 7.06 mmol) in 7 mL of methanol was added iodine monochloride (1.5 g, 9.24 mmol) in small portions at 0° C. Then the reaction mixture was stirred overnight. After evaporation of solvent, the residue was triturated with acetone, and the product 5-iodo-6-methyl-2-(methylsulfanyl)pyrimidin-4-amine was collected by filtration (1.32 g 66% yield).

LCMS: m/z 282 [M+H]$^+$ r.t. 5.65 min.

Step 3c: To the solution of 5-iodo-6-methyl-2-(methylsulfanyl)pyrimidin-4-amine (1.49 g, 4.9 mmol), in DMA (10 mL) were added ethylacrylate (1.06 mL, 9.8 mmol), Pd(OAc)$_2$ (0.22 g, 0.98 mmol), (+) BINAP (0.61 g, 0.98 mmol), and TEA (2 mL, 14.7 mmol). Then the reaction mixture was heated to 100° C. and reacted overnight. After evaporation of solvent, the residue was diluted with water and the aqueous layer was extracted with ethyl acetate. The solvent was evaporated in vacuo, yielding the desired intermediate ethyl (2E)-3-[4-amino-6-methyl-2-(methylsulfanyl)pyrimidin-5-yl]prop-2-enoate (0.5 g, 21% yield).

LCMS: m/z 254 [M+H]$^+$ r.t. 6.53 min.

Step 3d: To a solution of ethyl (2E)-3-[4-amino-6-methyl-2-(methylsulfanyl)pyrimidin-5-yl]prop-2-enoate (0.5 g, 1.9 mmol), in DIPEA (2 mL), was added 1,8-diazabicyclo[5.4.0]undec-7-ene (DBU, 1 mL) at reflux for 15 h. After evaporation of volatiles, the residue was triturated with acetone to afford the desired product 4-methyl-2-(methylsulfanyl)pyrido[2,3-d]pyrimidin-7(8H)-one (0.14 g 35% yield). $^1$H NMR (401 MHz, DMSO-d$_6$) δ=12.30 (br. s., 1H), 8.05 (d, J=9.76 Hz, 1H), 6.47 (d, J=9.76 Hz, 1H), 2.61 (s, 3H), 2.54 (s, 3H). LCMS: m/z 208 [M+H]$^+$@ r.t. 3.84 min. HRMS (ESI) calcd for C$_{13}$H$_{21}$N$_3$O$_2$S [M+H]$^+$ 208.0539 found 208.0545.

Preparation 17

8-benzyl-2-(methylsulfonyl)pyrido[2,3-d]pyrimidin-7(8H)-one [(II), G=Me-S(O)$_2$—, R2=benzyl, R3=R4=R5=H] Step 2f

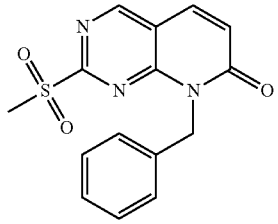 [SMILES: CS(=O)(=O)c1ncc2ccc(=O)n(Cc3ccccc3)c2n1]

8-benzyl-2-(methylsulfanyl)pyrido[2,3-d]pyrimidin-7(8H)-one (110 mg, 0.388 mmol) was dissolved in 5 mL DCM. To the stirring solution, m-CPBA (251 mg, 1.55 mmol) was added. The reaction was allowed to stir for 2 h at room temperature. LCMS indicated reaction had gone to completion. Sample was diluted with 10 mL of DCM, and washed twice with saturated NaHCO$_3$, followed by brine. The organic phase was separated and dried over Na$_2$SO$_4$, filtered, and concentrated in vacuo. The solvent was evaporated to provide 8-benzyl-2-(methylsulfonyl)pyrido[2,3-d]pyrimidin-7(8H)-one (105 mg, 86% yield) as a yellow solid.

$^1$H NMR (401 MHz, DMSO-d$_6$) δ=9.32 (s, 1H), 8.17 (d, J=9.64 Hz, 1H), 7.36-7.42 (m, 2H), 7.19-7.34 (m, 3H), 6.99 (d, J=9.52 Hz, 1H), 5.52 (s, 2H), 3.39 (s, 3H)8.91 (s, 1H), 8.00 (d, J=9.46 Hz, 1H), 7.17-7.35 (m, 5H), 6.71 (d, J=9.46 Hz, 1H), 5.50 (s, 2H). LCMS: m/z 316 [M+H]$^+$ r.t. 4.80 min. HRMS (ESI) calcd for C$_{15}$H$_{14}$N$_3$O$_3$S [M+H]$^+$ 316.0751 found 316.0760.

According to the same method the following compounds were prepared:

8-(2-Hydroxy-2-methyl-propyl)-2-methanesulfonyl-8H-pyrido[2,3-d]pyrimidin-7-one [(II), G=Me-S(O)$_2$—, R2=2-Hydroxy-2-methyl-propyl, R3=R4=R5=H]

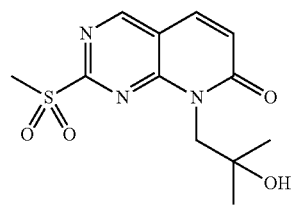 [SMILES: CC(C)(O)Cn1c(=O)ccc2cnc(S(C)(=O)=O)nc21]

$^1$H NMR (500 MHz, DMSO-d$_6$) δ=9.29 (s, 1H), 8.12 (d, J=9.6 Hz, 1H), 6.94 (d, J=9.5 Hz, 1H), 4.50 (s, 1H), 4.44 (s, 2H), 3.47 (s, 3H), 1.12 (s, 6H). LCMS: m/z 320 [M+H]$^+$@ r.t. 3.35 min HRMS (ESI) calcd for C$_{12}$H$_{15}$N$_3$O$_4$S [M+H]$^+$ 320.0675 found 320.0677;

8-(3-Hydroxy-2,2-dimethyl-propyl)-2-methanesulfonyl-8H-pyrido[2,3-d]pyrimidin-7-one [(II), G=Me-S(O)$_2$—, R2=3-Hydroxy-2,2-dimethyl-propyl, R3=R4=R5=H]

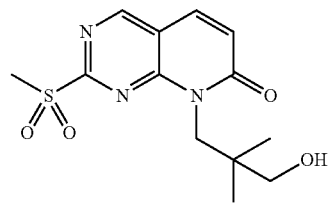 [SMILES: CC(C)(CO)Cn1c(=O)ccc2cnc(S(C)(=O)=O)nc21]

$^1$H NMR (500 MHz, DMSO-d$_6$) δ=9.29 (s, 1H), 8.12 (d, J=9.6 Hz, 1H), 6.94 (d, J=9.5 Hz, 1H), 4.57 (t, J=5.8 Hz, 1H), 4.35 (br. s., 2H), 3.47 (s, 3H), 3.20 (d, J=5.8 Hz, 2H), 0.83 (s, 6H). LCMS: m/z 312 [M+H]$^+$@ r.t. 3.76 min. HRMS (ESI) calcd for C$_{13}$H$_{17}$N$_3$O$_4$S [M+H]$^+$ 312.1013 found 312.1016;

8-(2,2-Dimethyl-propyl)-6-fluoro-2-methanesulfonyl-8H-pyrido[2,3-d]pyrimidin-7-one [(II), G=Me-S(O)$_2$—, R2=2,2-Dimethyl-propyl, R3=R4=H, R5=F]

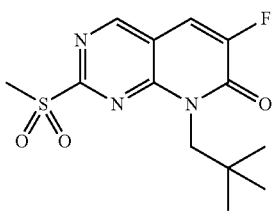 [SMILES: CC(C)(C)Cn1c(=O)c(F)cc2cnc(S(C)(=O)=O)nc21]

$^1$H NMR (500 MHz, DMSO-d$_6$) δ=9.29 (s, 1H), 8.11 (d, J=8.7 Hz, 1H), 4.34 (br. s., 2H), 3.47 (s, 3H), 0.94 (s, 9 H). LCMS: m/z 314 [M+H]$^+$@ r.t. 5.21 min. HRMS (ESI) calcd for C$_{13}$H$_{16}$N$_3$O$_3$FS [M+H]$^+$ 314.0969 found 314.0967;

8-(2,2-Dimethyl-propyl)-2-methanesulfonyl-6-methoxy-8H-pyrido[2,3-d]pyrimidin-7-one [(II), G=Me-S(O)$_2$—, R2=2,2-Dimethyl-propyl, R3=R4=H, R5=OMe]

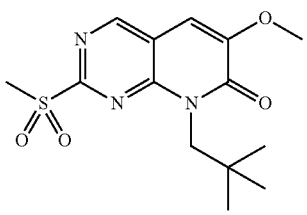

$^1$H NMR (500 MHz, DMSO-d$_6$) δ=9.17 (s, 1H), 7.45 (s, 1H), 4.35 (br. s., 2H), 3.92 (s, 3H), 3.43 (s, 3H), 1.16 (s, 0 H), 0.92 (s, 9H). LCMS: m/z 326 [M+H]$^+$@ r.t. 4.91 min. HRMS (ESI) calcd for C$_{14}$H$_{19}$N$_3$O$_4$S [M+H]$^+$ 326.1169 found 326.1164;

8-[(2S)-3-methylbutan-2-yl]-2-(methylsulfonyl)pyrido[2,3-d]pyrimidin-7(8H)-one [(II), G=Me-S(O)$_2$—, R2=(2S)-3-methylbutan-2-yl, R3=R4=R5=H]

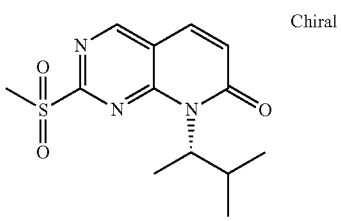 [SMILES: CC(C)[C@H](C)n1c(=O)ccc2cnc(S(C)(=O)=O)nc21]

Purification with chromatographic column eluent Hex/EtOAc 8:2 to give a off-white solid of the title compound (250 mg 95% Yield).
$^1$H NMR (500 MHz, DMSO-d$_6$) δ=9.29 (s, 1H), 8.10 (d, J=9.46 Hz, 1H), 6.71-7.06 (m, 1H), 4.83-5.43 (m, 1H), 3.45 (s, 3H), 1.41-1.68 (m, 3H), 1.05 (d, J=6.56 Hz, 3H), 0.59 (br. s., 3H). LCMS: m/z 296 [M+H]$^+$@ r.t. 4.92 min.

HRMS (ESI) calcd for C$_{13}$H$_{18}$N$_3$O$_3$S [M+H]$^+$ 296.1064 found 296.1065;

8-[(2S)-3,3-dimethylbutan-2-yl]-2-(methylsulfonyl)pyrido[2,3-d]pyrimidin-7(8H)-one [(II), G=Me-S(O)$_2$—, R2=(2S)-3,3-dimethylbutan-2-yl, R3=R4=R5=H]

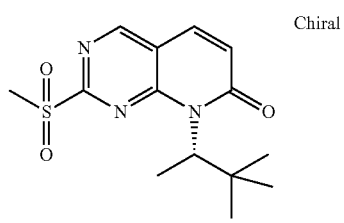 [SMILES: C[C@H](n1c(=O)ccc2cnc(S(C)(=O)=O)nc21)C(C)(C)C]

Purification with chromatographic column eluent Hex/EtOAc 8:2 to give a off-white solid of the title compound (50 mg 95% Yield). LCMS: m/z 310 [M+H]$^+$@ r.t. 5.07 min.

2-(methylsulfonyl)-8-(propan-2-yl)pyrido[2,3-d]pyrimidin-7(8H)-one [(II), G=Me-S(O)$_2$—, R2=propan-2-yl, R3=R4=R5=H]

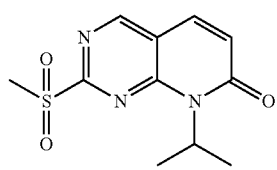 [SMILES: CC(C)n1c(=O)ccc2cnc(S(C)(=O)=O)nc21]

Purification with chromatographic column eluent Hex/EtOAc 8:2 to give a off-white solid of the title compound (479 mg 69% Yield).
$^1$H NMR (500 MHz, DMSO-d$_6$) δ=9.27 (s, 1H), 8.07 (d, J=9.46 Hz, 1H), 6.88 (d, J=9.46 Hz, 1H), 5.65 (spt, J=6.80 Hz, 1H), 3.46 (s, 3H), 1.56 (d, J=7.02 Hz, 6H). LCMS: m/z 268 [M+H]$^+$@ r.t. 4.48 min. HRMS (ESI) calcd for C$_{11}$H$_{13}$N$_3$O$_3$S [M+H]$^+$ 268.0751 found 268.0746;

8-[(2S)-1-fluoropropan-2-yl]-2-(methylsulfonyl)pyrido[2,3-d]pyrimidin-7(8H)-one one [(II), G=Me-S(O)2-,_R2=(2S)-1-fluoropropan-2-yl, R3=R4=R5=H]

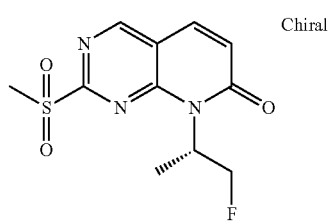

$^1$H NMR (500 MHz, DMSO-d$_6$) δ=9.31 (s, 1H), 8.13 (d, J=9.61 Hz, 1H), 6.92 (d, J=9.61 Hz, 1H), 5.81 (br. s., 1H), 5.12 (td, J=8.50, 47.90 Hz, 1H), 4.87 (ddd, J=5.80, 9.30, 46.20 Hz, 1H), 3.47 (s, 3H), 1.52 (d, J=7.02 Hz, 3H).

LCMS: m/z 286 [M+H]⁺@ r.t. 3.74 min. HRMS (ESI) calcd for $C_{11}H_{13}FN_3O_3S$ [M+H]⁺ 286.0656 found 286.0654;

8-[(2S)-1-hydroxypropan-2-yl]-2-(methylsulfonyl)pyrido[2,3-d]pyrimidin-7(8H)-one [(II), G=Me-S(O)2-,_R2=(2S)-1-hydroxypropan-2-yl, R3=R4=R5=H]

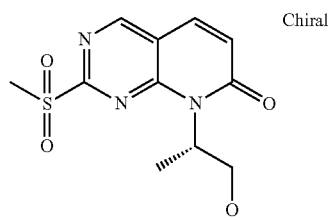 [SMILES: C[C@@H](CF)n1c(=O)ccc2cnc(S(C)(=O)=O)nc21]

¹H NMR (500 MHz, DMSO-d₆) δ=9.27 (s, 1H), 8.08 (d, J=9.46 Hz, 1H), 6.88 (d, J=9.46 Hz, 1H), 5.54 (br. s., 1H), 4.83 (t, J=5.95 Hz, 1H), 4.02-4.23 (m, 1H), 3.70-3.87 (m, 1H), 3.45 (s, 3H), 1.47 (d, J=6.86 Hz, 3H). LCMS: m/z 284 [M+H]⁺@ r.t. 3.74 min. HRMS (ESI) calcd for $C_{11}H_{14}N_3O_4S$ [M+H]⁺ 284.07 found 284.0702.

8-(4-bromo-2-fluorobenzyl)-2-(methylsulfonyl)pyrido[2,3-d]pyrimidin-7(8H)-one [(II), G=Me-S(O)2—, R2=4-bromo-2-fluorobenzyl, R3=R4=R5=H]

Purification with chromatographic column eluent Hex/EtOAc 7:3 to give a off-white solid of the title compound (90% Yield).

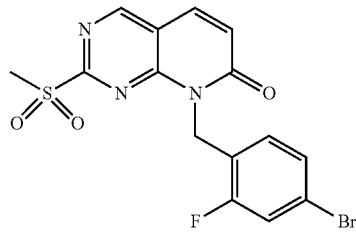 [SMILES: CS(=O)(=O)c1ncc2ccc(=O)n(Cc3ccc(Br)cc3F)c2n1]

1H NMR (500 MHz, DMSO-d6) δ=9.34 (s, 1H), 8.19 (d, J=9.61 Hz, 1H), 7.57 (dd, J=1.83, 9.91 Hz, 1H), 7.29 (dd, J=1.75, 8.31 Hz, 1H), 7.12 (t, J=8.31 Hz, 1H), 6.99 (d, J=9.61 Hz, 1H), 5.51 (s, 2H), 3.37 (s, 3H). LCMS: m/z 411 [M+H]⁺@ r.t. 5.52 min. HRMS (ESI) calcd for $C_{15}H_2BrFN_3O_3S$ [M+H]⁺ 411.9762 found 411.9763.

Preparation 18

2-Chloro-8-(2,2-dimethyl-propyl)-5-methyl-8H-pyrido[2,3-d]pyrimidin-7-one [(II), G=Cl, R2=2,2-dimethyl-propyl, R3=H, R4=Me, R5=H] Steps 4a, 4b and 4c

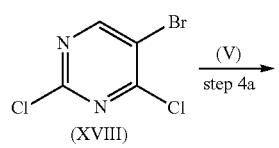

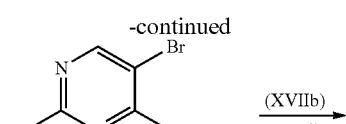

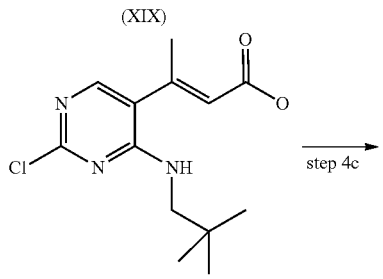

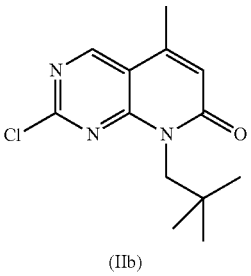

Step 4a: 5-bromo-2,4-dichloropyrimidine (1.0 g, 4.38 mmol) was dissolved in THF (20.0 mL) to which triethylamine (0.94 mL, 6.57 mmol) and neopentylamine (0.45 mL, 5.25 mmol) was added and stirred for 2 hour at room temperature. The precipitated salts were filtered and the solvent evaporated under reduced pressure. The resulting oil was dissolved in Et₂O, washed with brine, and then dried over Na₂SO₄. The salts were filtered, and the solvent was evaporated under vacuum to give the product (1.13 g, 70% yield) which is carried on without further purification.

¹H NMR (500 MHz, DMSO-d₆) δ=8.24 (s, 1H), 7.46 (t, J=6.25 Hz, 1H), 3.26 (d, J=6.41 Hz, 2H), 0.88 (s, 9H).

LCMS: m/z 278 [M+H]⁺@ r.t. 6.98 min. HRMS (ESI) calcd for $C_9H_{14}BrClN_3O$ [M+H]⁺ 278.0054 found 278.0058;

Step 4b: A 3-necked round bottom flask was charged with (5-Bromo-2-chloro-pyrimidin-4-yl)-(2,2-dimethyl-propyl)-amine (200.0 mg, 0.72 mmol), crotonic acid (154.4 mg, 1.79 mmol), DIPEA (0.50 mL, 2.94 mmol) and THF (2.5 mL). The mixture was degassed by applying 3 vacuum/argon cycles then tri-o-tolyl-phosphine (4.4 mg, 0.014 mmol) and dichlorobis(benzonitrile)palladium(II) (5.5 mg, 0.014 mmol) were added. The mixture was degassed again by applying 3 vacuum/argon cycles then heated to 75° C. and stirred under argon for 20 h;

Step 4c: Then, acetic anhydride (0.17 mL, 1.79 mmol) was added and the mixture further stirred at 75° C. for 2 h. The reaction was quenched with water and the mixture allowed to cool down at room temperature. The reaction mixture was diluted with Et₂O, and washed with water followed by brine. The organic phases were separated and dried over Na₂SO₄, filtered, and concentrated in vacuo. The crude material was purified through silica gel column chromatography (10 to 30% AcOEt\hexane) to give the title product (90.8 mg, 48% yield). $^1$H NMR (500 MHz, DMSO-$d_6$) δ=9.04 (s, 1H), 6.66 (q, J=1.2 Hz, 1H), 4.20 (s, 2H), 2.47 (d, J=1.2 Hz, 3H), 0.90 (s, 9H). LCMS: m/z 266 [M+H]$^+$@ r.t. 6.50 min. HRMS (ESI) calcd for $C_{13}H_{16}N_3OCl$ [M+H]$^+$ 266.1055 found 266.1065.

Preparation 19

Preparation of 4-[4-((S)-1-Amino-ethyl)-phenoxy]-piperidine-1-carboxylic acid benzyl ester hydrochloride [(III), A=phenyl, R1a=H, R1b=Me, R6a=O—R7, R6b=H, R7=4-piperidine-1-carboxylic acid benzyl ester]

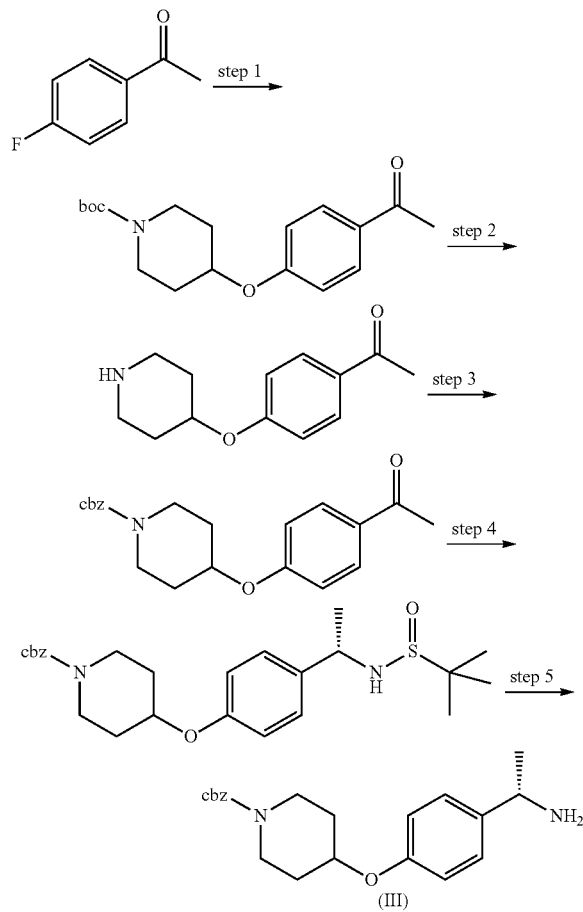

Step 1: 4-fluoroacetophenone (0.691 g, 5.0 mmol) was dissolved in DMF (10.0 mL) to which cesium carbonate (3.26 g, 10.0 mmol) and 1-(tert-butoxycarbonyl)-4-hydroxypiperidine (2.01 g, 10.0 mmol) was added and stirred for 2 days at 100° C. The cesium carbonate was filtered off and the solution was diluted with ether and washed with water (3×10 mL), and then dried over $Na_2SO_4$. The crude material was purified through silica gel column chromatography (10 to 70% AcOEt\hexane) to give 4-(4-Acetyl-phenoxy)-piperidine-1-carboxylic acid tert-butyl ester (547.5 mg, 34% yield).

$^1$H NMR (500 MHz, DMSO-$d_6$) δ=7.86-7.95 (m, 2H), 7.02-7.12 (m, 2H), 4.71 (tt, J=8.1, 3.8 Hz, 1H), 3.61-3.71 (m, 2H), 3.19 (br. s., 2H), 1.87-1.98 (m, 2H), 1.46-1.60 (m, 2H), 1.40 (s, 9H). LCMS: m/z 342 [M+Na]$^+$@ r.t. 6.68 min. HRMS (ESI) calcd for $C_{18}H_{25}NNaO_4$ [M+Na]$^+$ 342.1676 found 342.1677.

Step 2: To a solution of 4-(4-acetyl-phenoxy)-piperidine-1-carboxylic acid tert-butyl ester (250.0 mg) in dioxane (4.0 mL) is added HCl (4 M in dioxane, 1.0 mL). The mixture is stirred overnight at room temperature and it is then concentrated to dryness to provide a white solid which is dried under vacuum to give the compound 1-[4-(Piperidin-4-yloxy)-phenyl]-ethanone hydrochloride as a white solid (220.0 mg).

$^1$H NMR (500 MHz, DMSO-$d_6$) δ=8.63 (br. s., 2H), 7.86-8.01 (m, 2H), 7.04-7.17 (m, 2H), 4.80 (tt, J=7.6, 3.6 Hz, 1H), 3.21-3.28 (m, 2H), 3.09 (ddd, J=12.7, 8.8, 3.5 Hz, 2H), 2.52 (s, 3H), 2.12 (ddq, J=10.2, 7.1, 3.5 Hz, 2H), 1.76-1.90 (m, 2H). LCMS: m/z 220 [M+H]$^+$@ r.t. 3.32 min.

HRMS (ESI) calcd for $C_{13}H_{18}ClNO_2$ [M+H]$^+$ 220.1332 found 220.1338.

Step 3: 1-[4-(Piperidin-4-yloxy)-phenyl]-ethanone (215.0 mg, 0.841 mmol) was dissolved in DCM (5.0 mL) to which TEA (0.35 mL, 2.522 mmol) and benzyl chloroformate (0.27 mL, 1.009 mmol) were added. The resulting solution was stirred overnight at room temperature. The reaction mixture was washed with water followed by brine. The organic phases were separated and dried over $Na_2SO_4$, filtered, and concentrated in vacuo. The crude material was purified through silica gel column chromatography (10 to 70% AcOEt\hexane) to give 4-(4-Acetyl-phenoxy)-piperidine-1-carboxylic acid benzyl ester (210.1 mg, 70% yield).

$^1$H NMR (500 MHz, DMSO-$d_6$) δ=7.86-7.95 (m, 2H), 7.27-7.42 (m, 5H), 7.03-7.12 (m, 2H), 5.08 (s, 2H), 4.69-4.79 (m, 1H), 3.65-3.83 (m, 2H), 3.20-3.41 (m, 2H), 2.51 (br. s., 3H), 1.96 (ddd, J=9.4, 6.1, 2.8 Hz, 2H), 1.50-1.65 (m, 2H). LCMS: m/z 376 [M+Na]$^+$@ r.t. 6.66 min.

HRMS (ESI) calcd for $C_{21}H_{23}NaNO_4$ [M+Na]$^+$ 376.1519 found 376.1526.

Step 4: A mixture of tetraethoxytitanium (0.237 mL, 1.132 mmol), (S)-2-methylpropane-2-sulfinamide (68.2 mg, 0.566 mmol), and 4-(4-Acetyl-phenoxy)-piperidine-1-carboxylic acid benzyl ester (200.0 mg, 0.566 mmol) in THF (15.0 mL) was heated to 80° C. overnight and then cooled to room temperature. To this mixture was added $NaBH_4$ (107.0 mg, 2.829 mmol) at 0° C. The mixture was then slowly warmed up to room temperature in about 5 hours. MeOH (3 mL) was added to quench excess $NaBH_4$ and was followed by the addition of water. The resulting mixture was filtered to remove solids and the aqueous phase was extracted with EtOAc twice, dried over $Na_2SO_4$ and concentrated. The crude material was purified through silica gel column chromatography (0 to 10% MeOHDCM) to give 4-{4-[(S)-1-((S)-2-Methyl-propane-2-sulfinylamino)-ethyl]-phenoxy}-piperidine-1-carboxylic acid benzyl ester (185.6 mg, 72% yield). $^1$H NMR (500 MHz, DMSO-$d_6$) δ=7.30-7.42 (m, 5H), 7.28 (d, J=8.5 Hz, 2H), 6.92 (d, J=8.7 Hz, 2H), 5.49 (d, J=6.7 Hz, 1H), 5.08 (s, 2H), 4.55 (tt, J=7.8, 3.9 Hz, 1H), 4.30 (quin, J=6.8 Hz, 1H), 3.61-3.84 (m, 2H), 3.22-3.32 (m, 2H), 1.91 (ddd, J=9.5, 6.2, 2.9 Hz, 2H), 1.46-1.61 (m, 2H), 1.36 (d, J=6.9 Hz, 3H), 1.10 (s, 9H). LCMS: m/z 459 [M+H]$^+$@ r.t. 6.93 min. HRMS (ESI) calcd for $C_{25}H_{34}N_2O_4S$ [M+H]$^+$ 459.2312 found 459.2305

Step 5: To a solution of 4-{4-[(S)-1-((S)-2-Methyl-propane-2-sulfinylamino)-ethyl]-phenoxy}-piperidine-1-carboxylic acid benzyl ester (150 mg) in MeOH (5 mL) was added HCl (2 mL, 8.0 mmol, 4 M in 1,4-dioxane). The mixture was stirred at room temperature overnight. To this mixture was added 6 mL of ethyl ether and the resulting precipitate was collected by filtration, washed with ethyl ether (2×10 mL), and then dried to title product (quantitative yield).

$^1$H NMR (500 MHz, DMSO-d$_6$) δ=8.18 (br. s., 3H), 7.39 (d, J=8.8 Hz, 2H), 7.28-7.45 (m, 5H), 7.03 (d, J=8.8 Hz, 2H), 5.08 (s, 2H), 4.61 (tt, J=7.8, 3.7 Hz, 1H), 4.34 (spt, J=6.1 Hz, 1H), 1.74-1.98 (m, 2H), 1.54 (dtd, J=12.8, 8.6, 3.9 Hz, 2H), 1.46 (d, J=6.9 Hz, 3H). LCMS: m/z 377 [M+Na]$^+$@ r.t. 5.36 min.

HRMS (ESI) calcd for C$_{21}$H$_{27}$Cl NaN$_2$O$_3$[M+Na]$^+$ 377.1835 found 377.1835

Preparation 20

Preparation of benzyl 4-{4-[(1S)-1-aminoethyl]-2-fluorophenyl}piperazine-1-carboxylate hydrochloride [(III), A=phenyl, R1a=H, R1b=Me, R6a=NR7R8, R6b=H, R7=4-piperazine-1-carboxylic acid benzyl ester]

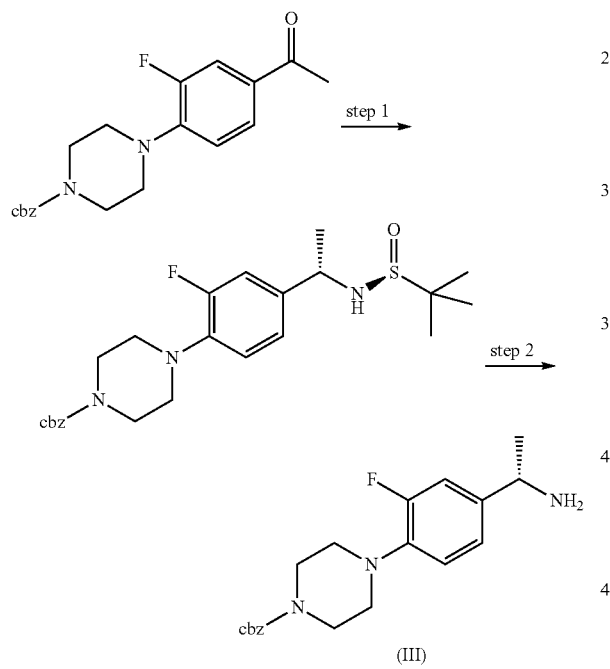

Step 1 A mixture of tetraethoxytitanium (0.456 mL, 2 mmol), (S)-2-methylpropane-2-sulfinamide (131 mg, 1 mmol), and benzyl 4-(4-acetyl-2-fluorophenyl)piperazine-1-carboxylate (356.0 mg, 1 mmol) in THF (15.0 mL) was heated to 80° C. overnight and then cooled to room temperature. To this mixture was added NaBH$_4$ (185.0 mg, 4 mmol) at 0° C. The mixture was then slowly warmed up to room temperature in about 5 hours. MeOH (3 mL) was added to quench excess NaBH$_4$ and was followed by the addition of water. The resulting mixture was filtered to remove solids and the aqueous phase was extracted with EtOAc twice, dried over Na$_2$SO$_4$ and concentrated. The crude material was purified through silica gel column chromatography (0 to 10% MeOHDCM) to give benzyl 4-{4-[(1S)-1-{[(S)-tert-butylsulfinyl]amino}ethyl]-2-fluorophenyl} piperazine-1-carboxylate (256 mg, 55% yield). 1H NMR (500 MHz, DMSO-d6) δ=7.29-7.42 (m, 5H), 7.20 (dd, J=1.83, 13.88 Hz, 1H), 7.11 (dd, J=1.75, 8.31 Hz, 1H), 6.99 (t, J=8.69 Hz, 1H), 5.61 (d, J=7.47 Hz, 1H), 5.10 (s, 2H), 4.31 (quin, J=6.83 Hz, 1H), 3.55 (br. s., 4H), 2.96 (t, J=4.58 Hz, 4H), 1.35 (d, J=6.71 Hz, 3H), 1.10 (s, 9H). LCMS: m/z 462 [M+H]$^+$@ r.t. 6.85 min. HRMS (ESI) calcd for C$_{24}$H$_{33}$FN$_3$O$_3$S [M+H]$^+$ 462.2221 found 462.2232.

Step 2: To a solution of benzyl 4-{4-[(1 S)-1-{[(S)-tert-butylsulfinyl]amino}ethyl]-2-fluorophenyl}piperazine-1-carboxylate (250 mg) in MeOH (5 mL) was added HCl (2 mL, 8.0 mmol, 4 M in 1,4-dioxane). The mixture was stirred at room temperature overnight. To this mixture was added 6 mL of ethyl ether and the resulting precipitate was collected by filtration, washed with ethyl ether (2×10 mL), and then dried to title product (quantitative yield).

$^1$H NMR (500 MHz, DMSO-d$_6$) δ=0.8.29 (br. s., 3H), 7.28-7.43 (m, 6H), 7.23 (dd, J=1.98, 8.39 Hz, 1H), 7.09 (t, J=8.85 Hz, 1H), 5.11 (s, 2H), 4.36 (quin, J=5.91 Hz, 1H), 3.56 (br. s., 4H), 2.89-3.07 (m, J=4.58 Hz, 4H), 1.46 (d, J=6.71 Hz, 3H). LCMS: m/z 341 [M(-NH$_3$)+H]$^+$@ r.t. 5.4 min.

HRMS (ESI) calcd for C$_{20}$H$_{25}$FN$_3$O$_2$[M(-NH$_3$)+H]$^+$ 341.1160 found 341.1164.

According to the same method, the following compounds were prepared:

Preparation of benzyl 4-{4-[(1S)-1-aminoethyl]-2-fluorophenyl}piperazine-1-carboxylate hydrochloride [(III), A=phenyl, R1a=H, R1b=Me, R6a=NR7R8, R6b=H, R7=4-piperazine-1-carboxylic acid benzyl ester]

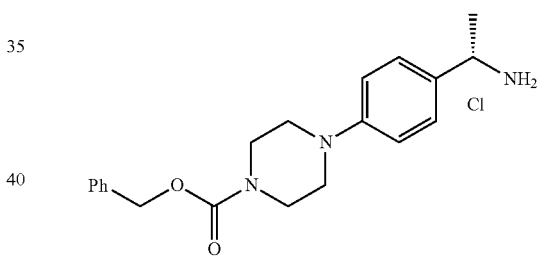

$^1$H NMR (500 MHz, DMSO-d$_6$) δ=0.8.19 (br. s., 3H), 7.36-7.42 (m, 4H), 7.34 (d, J=8.69 Hz, 3H), 7.00 (d, J=8.85 Hz, 2H), 5.10 (s, 2H), 4.30 (spt, J=6.30 Hz, 1H), 3.54 (br. s., 4H), 3.15 (d, J=4.88 Hz, 4H), 1.46 (d, J=6.71 Hz, 3H). LCMS: m/z 340 [M+H]$^+$@ r.t. 5.06 min. HRMS (ESI) calcd for C$_{20}$H$_{26}$N$_3$O$_2$ [M+H]$^+$ 340.2020 found 340.2018.

Preparation 21 tert-butyl 4-{1-[4-(1-aminocyclopropyl)phenyl]-2-cyclopropylethyl}piperazine-1-carboxylate [(III), A=phenyl, R1a and R1b=cyclopropyl, R6a=4-CH(R14)NR7R8, R6b=H, R7-R8=4-piperazine-1-carboxylic acid benzyl ester, R14=cyclopropylmethyl]

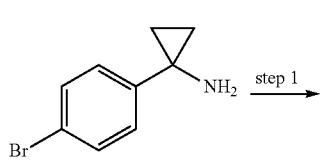

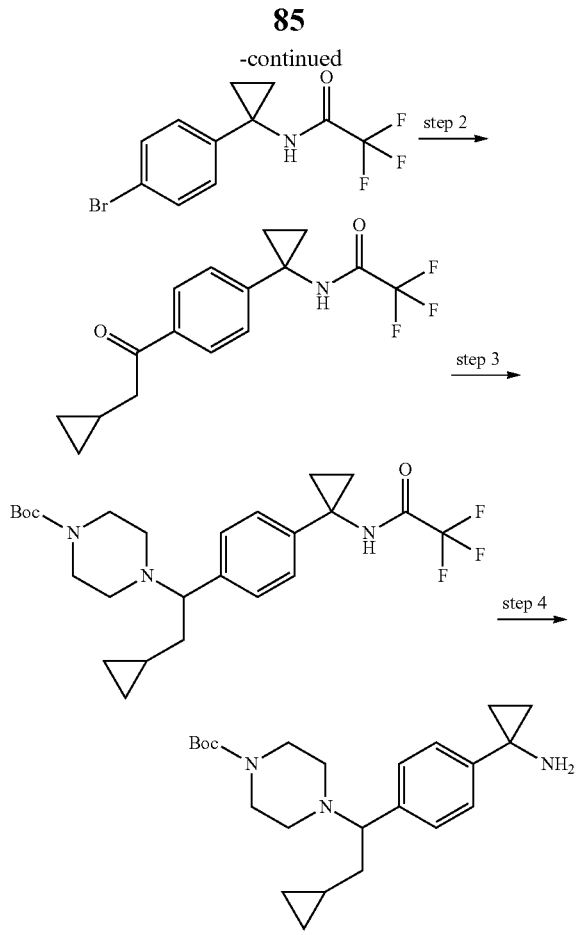

Step 1. To a solution of 1-(4-bromophenyl)cyclopropanamine (1.0 g, 4.71 mmol), in ACN (6.5 ml) at 0° C. was slowly added trifluoroacetic anhydride (0.72 ml, 5.26 mmol, 1.1 eq.) in the presence of TEA (1.31 ml, 9.42 mmol, 2 eq.). The mixture is stirred at the same temperature for 15 min. then the cool bath was revoved and left warmup at r.t. for 1 h. A mixture of water (10 ml) and brine (5 ml) was added and the slurry was stirred for 15 min. The precipitate was filtered under vacuum and the solid washed with n-Hexane, and dried in oven under vacuum, to obtain N-[1-(4-bromophenyl)cyclopropyl]-2,2,2-trifluoroacetamide as a white solid (1.4 g 96%).

$^1$H NMR (500 MHz, DMSO-d$_6$) δ=0.10.22 (s, 1H), 7.47-7.56 (m, 2H), 7.08-7.17 (m, 2H), 1.20-1.31 (m, 4H).

Step 2. n-Butyl lithium 1.6 M in hexane, (5.67 ml, 9.07 mmol, 2 eq.) was added dropwise to a solution of N-[1-(4-bromophenyl)cyclopropyl]-2,2,2-trifluoroacetamide (1.4 g, 4.54 mmol), in THF dry (45 ml) at −78° C. and then stirred for additional 40 min. under Argon. To the solution was added N-Methoxy-N-methylcyclopropaneacetamide (0.845 g 5.90 mmol, 1.3 eq.) dissolved in THF (1 ml). The mixture was stirred at −78° C. for 45 min, saturated aqueous amonium chloride (50 ml) was added, and the mixture was warmed to r.t. The layers were separated and the organic phase was washed with brine and dried over Na$_2$SO$_4$, filtered and concentrated under reduced pressure. The solid was dissolved in a small amount of DCM and then hexane (25 ml) was added dropwise with vigorous stirring to give a white solid. The solid was collect via filtration, washed with a small amount of hexane, and dried in vacuo to give N-{1-[4-(cyclopropylacetyl)phenyl]cyclopropyl}-2,2,2-trifluoroacetamide (0.915 g, 65%).

$^1$H NMR (500 MHz, DMSO-d$_6$) δ=10.27 (s, 1H), 7.89 (d, J=8.69 Hz, 2H), 7.24 (d, J=8.54 Hz, 2H), 2.90 (d, J=6.71 Hz, 2H), 1.29-1.41 (m, 3H), 0.96-1.09 (m, 1H), 0.44-0.53 (m, 2H), 0.11-0.17 (m, 2H).

Step 3 Titanium (IV) isopropoxide (2.14 ml, 7.2 mmol, 5 eq.) was added to a solution of N-{1-[4-(cyclopropylacetyl)phenyl]cyclopropyl}-2,2,2-trifluoroacetamide (0.45 g, 1.44 mmol) and tert-butyl piperazine-1-carboxylate (0.644 g, 3.45 mmol, 2.4 eq.), in THF (8 ml) and stirred at 60° C. overnight. The mixture was cooled to room temperature and MeOH (3 ml) was added followed by the portion-wise addition of sodium cyanoborohydride (0.18 g, 2.88 mmol, 2 eq.). The mixture was stirred at room temperature for 8 hours and then water (15 ml) and MeOH (4 ml) were added and the mixture was stirred at r.t. overnight. The mixture iiwas filtered to remove solids and the solids were rinsed with MeOH and water. Most of volatiles were removed and the residue was extracted with EtOAc (2×). The combined organic extracts were dried over Na$_2$SO$_4$, filtered, and concentrated. The crude was purified via column chromatography eluting with a gradient DCM/hexane/EtOAc from 300/300/0 to 300/300/100 to afford tert-butyl 4-[2-cyclopropyl-1-(4-{1-[(trifluoroacetyl)amino]cyclopropyl}phenyl)ethyl]piperazine-1-carboxylate as white foam (0.46 g, 66%).

$^1$H NMR (500 MHz, DMSO-d$_6$) δ=10.15 (s, 1H), 7.19 (d, J=8.39 Hz, 2H), 7.08 (d, J=8.39 Hz, 2H), 3.42 (dd, J=5.72, 9.07 Hz, 1H), 3.16-3.31 (m, 4H), 2.22 (br. s., 4H), 1.69-1.81 (m, 1H), 1.50-1.60 (m, 1H), 1.34 (s, 9H), 1.21-1.29 (m, 4H), 0.25-0.44 (m, 3H), −0.11-0.03 (m, 2H).

Step 4 Aqueous KOH (2 M, 8 ml), iwas added to a solution of tert-butyl 4-[2-cyclopropyl-1-(4-{1-[(trifluoroacetyl)amino]cyclopropyl}phenyl)ethyl]piperazine-1-carboxylate (0.46 g), in EtOH (15 ml) and the resulting mixture was stirred at room temperature for 48 hours. The volatiles were removed under reduced pressure and to the residue was added sat. aqueous NaHCO$_3$ and partitioned with DCM. The combined organic extracts were dried over anhydrous Na2SO4, filtered, and concentrated in vacuo, to give tert-butyl 4-{1-[4-(1-aminocyclopropyl)phenyl]-2-cyclopropylethyl}piperazine-1-carboxylate as light yellow viscous oil (0.358 g, 97%).

$^1$H NMR (500 MHz, DMSO-d$_6$) δ=7.23 (d, J=8.24 Hz, 2H), 7.13 (d, J=8.24 Hz, 2H), 3.42 (dd, J=5.49, 9.00 Hz, 1H), 3.25 (d, J=4.27 Hz, 4H), 2.22 (br. s., 5H), 1.73-1.83 (m, 1H), 1.55 (s, 1H), 1.33 (s, 9H), 0.85-0.97 (m, 4H), 0.34-0.45 (m, 1H), 0.25-0.32 (m, 2H), −0.02 (d, J=18.76 Hz, 2H).

Example 1

Methyl 4-{(1S)-1-[(8-benzyl-7-oxo-pyrido[2,3-d]pyrimidin-2-yl)amino]ethyl}benzoate [(I), X=N, R2=Benzyl, A=Phenyl, R1a=H, R1b=Me, R6a=—COOMe, R6b=H, R3=R4=R5=H] step 1a, cpd 1

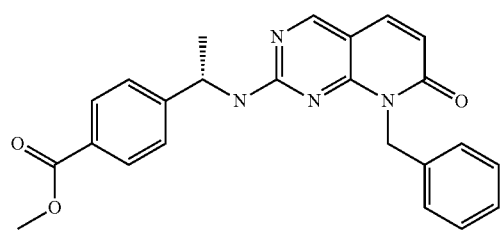

To a solution of compound 8-benzyl-2-(methylsulfonyl)pyrido[2,3-d]pyrimidin-7(8H)-one (100 mg, 0.32 mmol) in ACN (2 mL) was added (S)-methyl 4-(1-aminoethyl)benzoate (86 mg, 0.48 mmol). The reaction was heated to 90° C. for 2 hours. The reaction mixture was diluted with EtOAc (4 mL) and washed with water (5 mL) and brine (5 mL). The organic layer was dried over $Na_2SO_4$, filtered and concentrated. The crude material was purified on silica gel column chromatography (DCM/EtOAc 8/2) provided the title compound as a light yellow foam (100 mg, 76% yield).

$^1$H NMR (401 MHz, DMSO-$d_6$) δ=8.63 (s, 1H), 8.50 (d, J=7.20 Hz, 1H), 7.79 (d, J=8.18 Hz, 2H), 7.75 (d, J=9.52 Hz, 1H), 7.41 (d, J=8.06 Hz, 2H), 7.08-7.19 (m, 3H), 7.04 (d, J=5.61 Hz, 2H), 6.28 (d, J=9.52 Hz, 1H), 5.44 (d, J=14.04 Hz, 1H), 5.11 (d, J=14.40 Hz, 1H), 5.07 (quin, J=7.00 Hz, 1H), 3.83 (s, 3H), 1.44 (d, J=6.96 Hz, 3H).

LCMS: m/z 415 [M+H]$^+$ r.t. 6.21 min. HRMS (ESI) calcd for $C_{24}H_{23}N_4O_3$ [M+H]$^+$ 415.1765 found 415.177.

According to the same method, the following compounds were prepared:

Methyl 4-{(1S)-1-[(8-ethyl-7-oxo-pyrido[2,3-d]pyrimidin-2-yl)amino]ethyl}benzoate [(I), X=N, R2=Ethyl, A=Phenyl, R1a=H, R1b=Me, R6a=—COOMe, R6b=H, R3=R4=R5=H] cpd 2

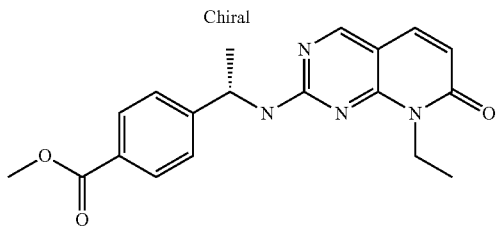

$^1$H NMR (401 MHz, DMSO-$d_6$) δ=8.59 (s, 1H), 8.49 (d, J=6.6 Hz, 1H), 7.85-7.94 (m, 2H), 7.67 (d, J=9.3 Hz, 1H), 7.54 (d, J=8.3 Hz, 1H), 6.21 (d, J=9.2 Hz, 1H), 5.08 (quin, J=6.9 Hz, 1H), 4.15 (dq, J=12.7, 6.6 Hz, 1H), 3.90-4.06 (m, 1H), 3.82 (s, 3H), 1.49 (d, J=7.2 Hz, 3H), 0.87 (t, J=6.8 Hz, 3H). LCMS: m/z 353 [M+H]$^+$ r.t. 5.61 min. HRMS (ESI) calcd for $C_{19}H_{21}N_4O_3$ [M+H]$^+$ 353.1608 found 353.1602;

Methyl 4-[(1S)-1-{[8-(methoxymethyl)-7-oxo-pyrido[2,3-d]pyrimidin-2-yl]amino}ethyl]benzoate [(I), X=N, R2=methoxymethyl, A=Phenyl, R1a=H, R1b=Me, R6a=—COOMe, R6b=H, R3=R4=R5=H] cpd 3

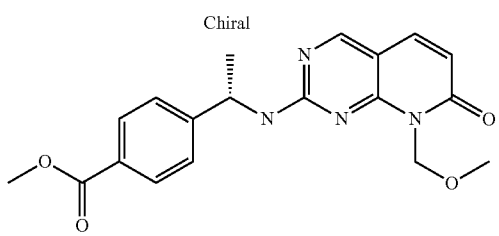

$^1$H NMR (401 MHz, DMSO-$d_6$) δ=8.61 (s, 1H), 8.57 (d, J=7.63 Hz, 1H), 7.91 (d, J=8.24 Hz, 2H), 7.73 (d, J=9.30 Hz, 1H), 7.55 (d, J=8.24 Hz, 2H), 6.23 (d, J=9.46 Hz, 1H), 5.50 (d, J=9.00 Hz, 1H), 5.36 (d, J=9.15 Hz, 1H), 5.14 (quin, J=7.09 Hz, 1H), 3.82 (s, 3H), 3.11 (s, 3H), 1.49 (d, J=7.02 Hz, 3H).

LCMS: m/z 369 [M+H]$^+$ r.t. 5.24 min. HRMS (ESI) calcd for $C_{19}H_{21}N_4O_4$ [M+H]$^+$ 369.1558 found 369.1567;

methyl 4-{(1S)-1-[(8-methyl-7-oxo-pyrido[2,3-d]pyrimidin-2-yl)amino]ethyl}benzoate [(I), X=N, R2=methyl, A=Phenyl, R1a=H, R1b=Me, R6a=—COOMe, R6b=H, R3=R4=R5=H] cpd 4

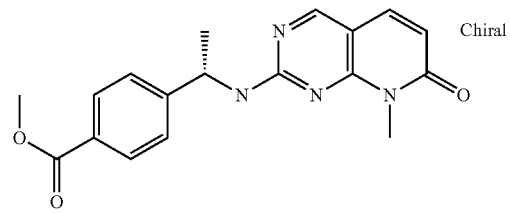

$^1$H NMR (401 MHz, DMSO-$d_6$) δ=8.96 (br. s., 1H), 8.05 (d, J=8.54 Hz, 1H), 7.91 (d, J=7.93 Hz, 2H), 7.58 (d, J=7.02 Hz, 2H), 6.68 (d, J=8.54 Hz, 1H), 5.25-5.46 (m, 1H), 3.92 (br. s., 3H), 3.82 (s, 3H), 1.50 (d, J=7.02 Hz, 3H).

LCMS: m/z 339 [M+H]$^+$ r.t. 5.67 min. HRMS (ESI) calcd for $C_{18}H_{19}N_4O_3$ [M+H]$^+$ 339.1452 found 339.1443;

methyl 4-[(1S)-1-{[8-(2-methylpropyl)-7-oxo-pyrido[2,3-d]pyrimidin-2-yl]amino}ethyl]benzoate [(I), X=N, R2=2-methylpropyl, A=Phenyl, R1a=H, R1b=Me, R6a=—COOMe, R6b=H, R3=R4=R5=H] cpd 5

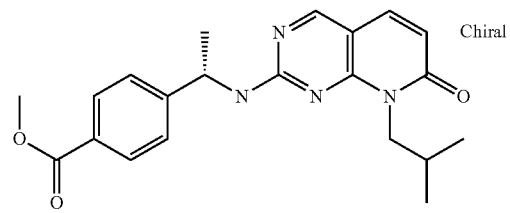

$^1$H NMR (401 MHz, DMSO-$d_6$) δ=8.60 (s, 1H), 8.47 (d, J=6.47 Hz, 1H), 7.91 (d, J=8.30 Hz, 2H), 7.69 (d, J=9.15 Hz, 1H), 7.51 (d, J=8.18 Hz, 2H), 6.22 (d, J=9.15 Hz, 1H), 5.07 (quin, J=6.87 Hz, 1H), 3.92 (dd, J=7.81, 12.08 Hz, 1H), 3.82 (s, 3H), 3.77 (dd, J=7.60, 12.00 Hz, 1H), 1.88 (tt, J=6.74, 13.64 Hz, 1H), 1.49 (d, J=7.08 Hz, 3H), 0.72 (d, J=6.71 Hz, 3H), 0.57 (d, J=6.47 Hz, 3H). LCMS: m/z 381 [M+H]$^+$ r.t. 6.2 min. HRMS (ESI) calcd for $C_{21}H_{25}N_4O_3$ [M+H]$^+$ 381.1921 found 381.1915;

methyl 4-[(1S)-1-{[8-(4-fluorobenzyl)-7-oxo-pyrido[2,3-d]pyrimidin-2-yl]amino}ethyl]benzoate [(I), X=N, R2=4-fluorobenzyl, A=Phenyl, R1a=H, R1b=Me, R6a=—COOMe, R6b=H, R3=R4=R5=H] cpd 6

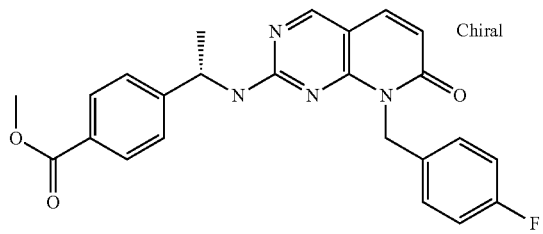

$^1$H NMR (500 MHz, DMSO-d$_6$) δ=8.60 (s, 1H), 8.47 (d, J=6.47 Hz, 1H), 7.91 (d, J=8.30 Hz, 2H), 7.69 (d, J=9.15 Hz, 1H), 7.51 (d, J=8.18 Hz, 2H), 6.22 (d, J=9.15 Hz, 1H), 5.07 (quin, J=6.87 Hz, 1H), 3.92 (dd, J=7.81, 12.08 Hz, 1H), 3.82 (s, 3H), 3.77 (dd, J=7.60, 12.00 Hz, 1H), 1.88 (tt, J=6.74, 13.64 Hz, 1H), 1.49 (d, J=7.08 Hz, 3H), 0.72 (d, J=6.71 Hz, 3H), 0.57 (d, J=6.47 Hz, 3H). LCMS: m/z 433 [M+H]$^+$ r.t. 6.29 min. HRMS (ESI) calcd for C$_{24}$H$_{22}$FN$_4$O$_3$[M+H]$^+$ 433.1671 found 433.1685;

methyl 4-[(1S)-1-{[8-(3,5-difluorobenzyl)-7-oxo-pyrido[2,3-d]pyrimidin-2-yl]amino}ethyl]benzoate [(I), X=N, R2=3,5-difluorobenzyl, A=Phenyl, R1a=H, R1b=Me, R6a=—COOMe, R6b=H, R3=R4=R5=H] cpd 7

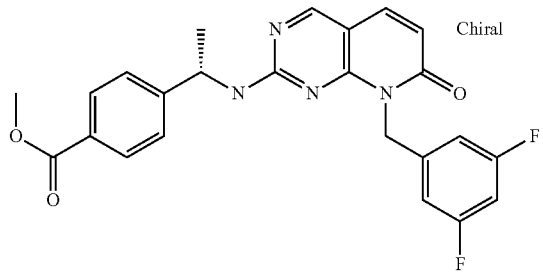

$^1$H NMR (500 MHz, DMSO-d$_6$) δ=8.60 (s, 1H), 8.47 (d, J=6.47 Hz, 1H), 7.91 (d, J=8.30 Hz, 2H), 7.69 (d, J=9.15 Hz, 1H), 7.51 (d, J=8.18 Hz, 2H), 6.22 (d, J=9.15 Hz, 1H), 5.07 (quin, J=6.87 Hz, 1H), 3.92 (dd, J=7.81, 12.08 Hz, 1H), 3.82 (s, 3H), 3.77 (dd, J=7.60, 12.00 Hz, 1H), 1.88 (tt, J=6.74, 13.64 Hz, 1H), 1.49 (d, J=7.08 Hz, 3H), 0.72 (d, J=6.71 Hz, 3H), 0.57 (d, J=6.47 Hz, 3H). LCMS: m/z 451 [M+H]$^+$ r.t. 6.36 min. HRMS (ESI) calcd for C$_{24}$H$_{21}$F$_2$N$_4$O$_3$[M+H]$^+$ 451.1576 found 451.1584;

methyl-4-[(1S)-1-({8-[4-fluoro-2-(trifluoromethyl)benzyl]-7-oxo-pyrido[2,3-d]pyrimidin-2-yl}amino)ethyl]benzoate [(I), X=N, R2=4-fluoro-2-(trifluoromethyl)benzyl, A=Phenyl, R1a=H, R1b=Me, R6a=—COOMe, R6b=H, R3=R4=R5=H] cpd 8

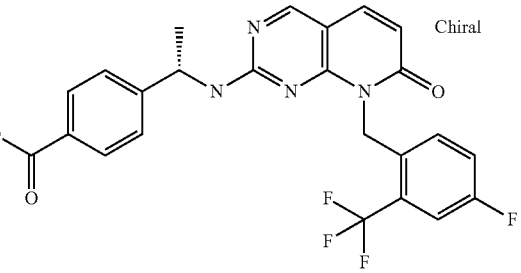

$^1$H NMR (500 MHz, DMSO-d$_6$) δ=8.70 (s, 1H), 8.55 (d, J=6.71 Hz, 1H), 7.85 (d, J=9.30 Hz, 1H), 7.57 (dd, J=2.44, 9.15 Hz, 1H), 7.52 (d, J=8.24 Hz, 2H), 7.11 (d, J=8.39 Hz, 2H), 7.05 (dt, J=2.29, 8.39 Hz, 1H), 6.24-6.35 (m, 2H), 5.49 (d, J=16.01 Hz, 1H), 5.30 (d, J=15.71 Hz, 1H), 4.80 (quin, J=7.02 Hz, 1H), 3.81 (s, 3H), 1.31-1.47 (m, 3H). LCMS: m/z 501 [M+H]$^+$ r.t. 6.65 min. HRMS (ESI) calcd for C$_{25}$H$_{21}$F$_4$N$_4$O$_3$[M+H]$^+$ 501.1545 found 501.1541;

methyl 4-[(1S)-1-{[7-oxo-8-(propan-2-yl)-pyrido[2,3-d]pyrimidin-2-yl]amino}ethyl]benzoate [(I), X=N, R2=is-pr, A=Phenyl, R1a=H, R1b=Me, R6a=—COOMe, R6b=H, R3=R4=R5=H] cpd 9

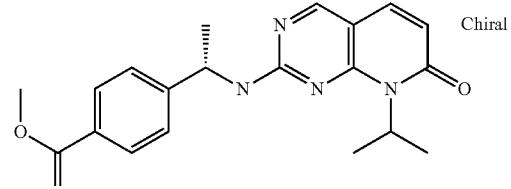

$^1$H NMR (500 MHz, DMSO-d$_6$) δ=8.50-8.63 (m, 1H), 8.22-8.49 (m, 1H), 7.90 (d, J=8.39 Hz, 2H), 7.62 (d, J=8.85 Hz, 1H), 7.52 (d, J=8.08 Hz, 2H), 6.16 (d, J=8.85 Hz, 1H), 5.39-5.79 (m, 1H), 5.00-5.33 (m, 1H), 3.81 (s, 3H), 1.49 (d, J=6.86 Hz, 3H), 0.97-1.39 (m, 6H). LCMS: m/z 367 [M+H]$^+$ r.t. 5.98 min. HRMS (ESI) calcd for C$_{20}$H$_{23}$N$_4$O$_3$ [M+H]$^+$ 367.1765 found 367.1757;

methyl 4-[(1S)-1-({8-[(3-methyloxetan-3-yl)methyl]-7-oxo-pyrido[2,3-d]pyrimidin-2-yl}amino)ethyl]benzoate [(I), X=N, R2=7-oxo-8-(3-methyl-oxetan-3-yl), A=Phenyl, R1a=H, R1b=Me, R6a=—COOMe, R6b=H, R3=R4=R5=H] cpd 10

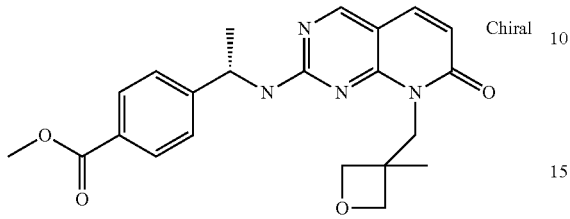

LCMS: m/z 409 [M+H]$^+$ r.t. 5.2 min. HRMS (ESI) calcd for $C_{22}H_{25}N_4O_4$ [M+H]$^+$ 409.1871 found 409.1873;

methyl 4-[(1S)-1-{[8-(2,2-dimethylpropyl)-7-oxo-pyrido[2,3-d]pyrimidin-2-yl]amino}ethyl]benzoate [(I), X=N, R2=2,2-dimethylpropyl, A=Phenyl, R1a=H, R1b=Me, R6a=—COOMe, R6b=H, R3=R4=R5=H] cpd 11

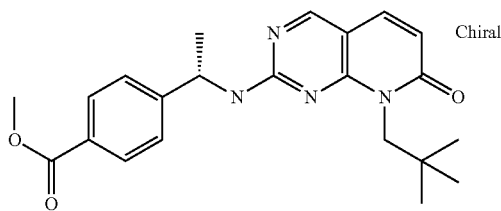

$^1$H NMR (500 MHz, DMSO-d$_6$) δ=8.59 (s, 1H), 8.47 (d, J=7.32 Hz, 1H), 7.91 (d, J=8.08 Hz, 2H), 7.68 (d, J=9.15 Hz, 1H), 7.49-7.56 (m, 2H), 6.23 (d, J=9.30 Hz, 1H), 5.12 (t, J=6.79 Hz, 1H), 4.01-4.25 (m, 1H), 3.93 (d, J=12.51 Hz, 1H), 3.82 (s, 3H), 1.48 (d, J=7.02 Hz, 3H), 0.42-1.00 (m, 9H). LCMS: m/z 395 [M+H]$^+$ r.t. 6.44 min.
HRMS (ESI) calcd for $C_{22}H_{27}N_4O_3$ [M+H]$^+$ 395.2078 found 395.2077;

2-{[(1S)-1-cyclohexylethyl]amino}-8-ethylpyrido[2,3-d]pyrimidin-7(8H)-one [(I), X=N, R2=Ethyl, A=cyclohexyl, R1a=H, R1b=Me, R6a=R6b=H, R3=R4=R5=H] cpd 12

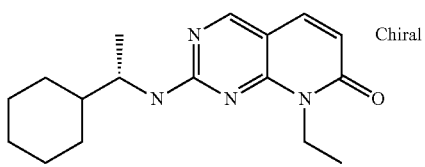

$^1$H NMR (401 MHz, DMSO-d$_6$) δ=8.54 (s, 1H), 7.61-7.75 (m, 2H), 6.21 (d, J=9.28 Hz, 1H), 4.12-4.35 (m, 2H), 3.85-3.95 (m, 1H), 1.48-1.79 (m, 6H), 0.90-1.25 (m, 11H). LCMS: m/z 301 [M+H]$^+$ r.t. 6.94 min. HRMS (ESI) calcd for $C_{17}H_{25}N_4O$ [M+H]$^+$ 301.2023 found 301.2029;

8-ethyl-2-{[(1S)-1-(4-methoxyphenyl)ethyl]amino}pyrido[2,3-d]pyrimidin-7(8H)-one [(I), X=N, R2=Ethyl, A=phenyl, R1a=H, R1b=Me, R6a=4-methoxy, R6b=H, R3=R4=R5=H] cpd 13

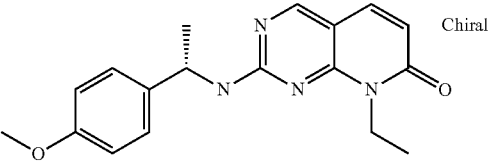

$^1$H NMR (401 MHz, DMSO-d$_6$) δ=8.56 (s, 1H), 8.33 (d, J=7.45 Hz, 1H), 7.67 (d, J=9.28 Hz, 1H), 7.26-7.38 (m, 2H), 6.79-6.92 (m, 2H), 6.21 (d, J=9.40 Hz, 1H), 5.01 (quin, J=7.42 Hz, 1H), 4.15-4.34 (m, 1H), 4.02-4.15 (m, 1H), 3.70 (s, 3H), 1.46 (d, J=6.96 Hz, 3H), 1.02 (t, J=6.71 Hz, 3H). LCMS: m/z 325 [M+H]$^+$ r.t. 5.73 min. HRMS (ESI) calcd for $C_{18}H_{21}N_4O_2$ [M+H]$^+$ 325.1659 found 325.1663;

2-{[(1S)-1-(4-chlorophenyl)ethyl]amino}-8-ethylpyrido[2,3-d]pyrimidin-7(8H)-one [(I), X=N, R2=Ethyl, A=phenyl, R1a=H, R1b=Me, R6a=4-Cl, R6b=H, R3=R4=R5=H] cpd 14

$^1$H NMR (401 MHz, DMSO-d$_6$) δ=8.58 (s, 1H), 8.43 (d, J=7.32 Hz, 1H), 7.67 (d, J=9.40 Hz, 1H), 7.39-7.45 (m, 2H), 7.33-7.38 (m, 2H), 6.22 (d, J=9.52 Hz, 1H), 4.87-5.14 (m, 2H), 4.14-4.26 (m, 1H), 3.99-4.07 (m, 1H), 1.47 (d, J=7.08 Hz, 3H), 0.94 (t, J=6.77 Hz, 3H). LCMS: m/z 329 [M+H]$^+$ r.t. 6.24 min. HRMS (ESI) calcd for $C_{17}H_{18}ClN_4O$ [M+H]$^+$ 329.1164 found 329.1167;

2-{[(1S)-1-(4-chlorophenyl)ethyl]amino}-8-(pentan-3-yl)pyrido[2,3-d]pyrimidin-7(8H)-one [(I), X=N, R2=pentan-3-yl, A=phenyl, R1a=H, R1b=Me, R6a=4-Cl, R6b=H, R3=R4=R5=H] cpd 15

$^1$H NMR (401 MHz, DMSO-d$_6$) δ=8.89 (s, 1H), 8.09 (d, J=8.67 Hz, 1H), 8.01 (d, J=8.67 Hz, 1H), 7.33-7.48 (m, 4H), 6.63 (d, J=8.54 Hz, 1H), 5.11-5.47 (m, 2H), 1.57-1.78 (m, 4H), 1.43-1.51 (m, 3H), 0.77-0.96 (m, 6H).

LCMS: m/z 371 [M+H]⁺ r.t. 7.78 min. HRMS (ESI) calcd for $C_{20}H_{24}ClN_4O$ [M+H]⁺ 371.1633 found 371.1642; 8-benzyl-2-{[(1S)-1-(4-chlorophenyl)ethyl]amino}pyrido[2,3-d]pyrimidin-7(8H)-one [(I), X=N, R2=benzyl, A=phenyl, R1a=H, R1b=Me, R6a=4-Cl, R6b=H, R3=R4=R5=H] cpd 16

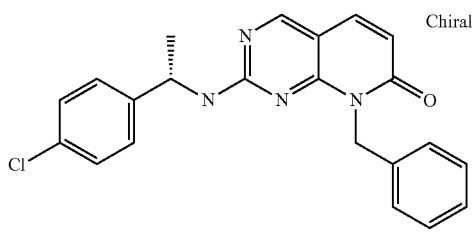 [SMILES: C[C@H](Nc1ncc2ccc(=O)n(Cc3ccccc3)c2n1)c1ccc(Cl)cc1]

¹H NMR (500 MHz, DMSO-d₆) δ=8.62 (s, 1H), 8.47 (d, J=7.63 Hz, 1H), 7.75 (d, J=9.30 Hz, 1H), 7.26-7.30 (m, 2H), 7.22-7.26 (m, 2H), 7.15-7.20 (m, 3H), 7.08 (d, J=6.10 Hz, 2H), 6.28 (d, J=9.46 Hz, 1H), 5.46 (d, J=14.18 Hz, 1H), 5.17 (d, J=14.03 Hz, 1H), 4.99-5.07 (m, 1H), 1.41 (d, J=7.02 Hz, 3H). LCMS: m/z 391 [M+H]⁺ r.t. 6.86 min. HRMS (ESI) calcd for $C_{22}H_{20}ClN_4O$ [M+H]⁺ 391.132 found 391.1324;

2-{[(1S)-1-(4-chlorophenyl)ethyl]amino}-8-(2-fluoroethyl)pyrido[2,3-d]pyrimidin-7(8H)-one [(I), X=N, R2=2-fluoroethyl, A=phenyl, R1a=H, R1b=Me, R6a=4-Cl, R6b=H, R3=R4=R5=H] cpd 17

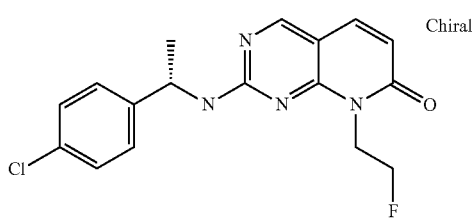 [SMILES: C[C@H](Nc1ncc2ccc(=O)n(CCF)c2n1)c1ccc(Cl)cc1]

¹H NMR (500 MHz, DMSO-d₆) δ=8.61 (s, 1H), 8.52 (d, J=6.86 Hz, 1H), 7.72 (d, J=9.30 Hz, 1H), 7.38-7.43 (m, 2H), 7.33-7.38 (m, 2H), 6.24 (d, J=9.30 Hz, 1H), 4.96-5.04 (m, 1H), 4.26-4.75 (m 4H), 1.45 (d, J=7.02 Hz, 3H).

LCMS: m/z 347 [M+H]⁺ r.t. 6.03 min. HRMS (ESI) calcd for $C_{17}H_{17}ClFN_4O$ [M+H]⁺ 347.107 found 347.1069;

2-{[(1S)-1-(4-chlorophenyl)ethyl]amino}-8-(2,2,2-trifluoroethyl)pyrido[2,3-d]pyrimidin-7(8H)-one [(I), X=N, R2=2,2,2-trifluoroethyl, A=phenyl, R1a=H, R1b=Me, R6a=4-Cl, R6b=H, R3=R4=R5=H] cpd 18

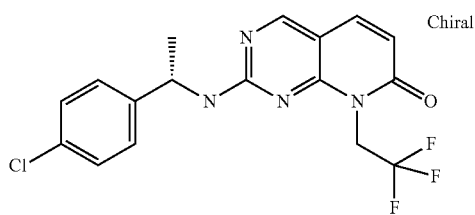 [SMILES: C[C@H](Nc1ncc2ccc(=O)n(CC(F)(F)F)c2n1)c1ccc(Cl)cc1]

¹H NMR (500 MHz, DMSO-d₆) δ=8.65 (s, 1H), 8.63 (m, 1H), 7.79 (d, J=9.46 Hz, 1H), 7.38-7.42 (m, 2H), 7.33-7.38 (m, 2H), 6.29 (d, J=9.46 Hz, 1H), 5.14-5.24 (m, 1H), 4.99-5.07 (m, 1H), 4.74-4.87 (m, 1H), 1.41-1.52 (m, 3H). LCMS: m/z 383 [M+H]⁺ r.t. 6.61 min. HRMS (ESI) calcd for $C_7H_{15}ClF_3N_4O$ [M+H]⁺ 383.0881 found 383.0893;

2-{[(1S)-1-(4-chlorophenyl)ethyl]amino}-8-(2-methylpropyl)pyrido[2,3-d]pyrimidin-7(8H)-one [(I), X=N, R2=2-methylpropyl, A=phenyl, R1a=H, R1b=Me, R6a=4-Cl, R6b=H, R3=R4=R5=H] cpd 19

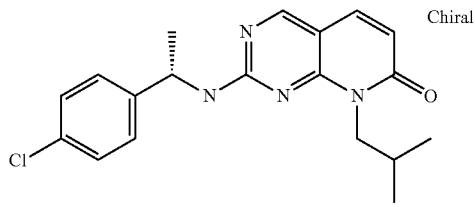 [SMILES: CC(C)Cn1c(=O)ccc2cnc(N[C@@H](C)c3ccc(Cl)cc3)nc21]

¹H NMR (500 MHz, DMSO-d₆) δ=8.59 (s, 1H), 8.41 (d, J=7.45 Hz, 1H), 7.69 (d, J=9.28 Hz, 1H), 7.27-7.46 (m, 4H), 6.23 (d, J=9.28 Hz, 1H), 5.01 (quin, J=6.87 Hz, 1H), 3.95 (dd, J=7.51, 12.14 Hz, 1H), 3.68-3.89 (m, 1H), 1.92 (spt, J=6.60 Hz, 1H), 1.46 (d, J=7.08 Hz, 3H), 0.75 (d, J=6.59 Hz, 3H), 0.62 (d, J=6.59 Hz, 3H). LCMS m/z 357 [M+H]⁺ r.t. 6.86 min. HRMS (ESI) calcd for $C_{19}H_{22}ClN_4O$ [M+H]⁺ 357.1477 found 357.148;

2-{[(1S)-1-(4-chlorophenyl)ethyl]amino}-8-(cyclopropylmethyl)pyrido[2,3-d]pyrimidin-7(8H)-one [(I), X=N, R2=cyclopropylmethyl, A=phenyl, R1a=H, R1b=Me, R6a=4-Cl, R6b=H, R3=R4=R5=H] cpd 20

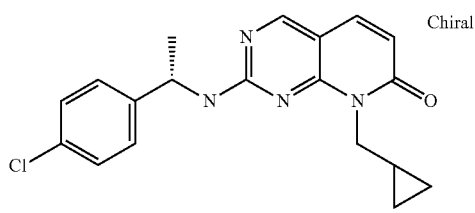 [SMILES: C[C@H](Nc1ncc2ccc(=O)n(CC3CC3)c2n1)c1ccc(Cl)cc1]

$^1$H NMR (500 MHz, DMSO-d$_6$) δ=8.60 (s, 1H), 8.46 (d, J=6.86 Hz, 1H), 7.70 (d, J=9.30 Hz, 1H), 7.18-7.44 (m, 4H), 6.24 (d, J=9.15 Hz, 1H), 4.82-5.06 (m, 1H), 4.04 (dd, J=6.86, 12.66 Hz, 1H), 3.76-3.89 (m, 1H), 1.46 (d, J=7.02 Hz, 3H), 0.89-1.03 (m, 1H), 0.24-0.35 (m, 4H). LCMS: m/z 355 [M+H]$^+$ r.t. 6.67 min. HRMS (ESI) calcd for C$_{19}$H$_{20}$ClN$_4$O [M+H]$^+$ 355.132 found 357.1424;

2-{[(1S)-1-(4-chlorophenyl)ethyl]amino}-8-(4-methoxybenzyl)pyrido[2,3-d]pyrimidin-7(8H)-one [(I), X═N, R2=4-methoxybenzyl, A=phenyl, R1a=H, R1b=Me, R6a=4-Cl, R6b=H, R3=R4=R5=H] cpd 21

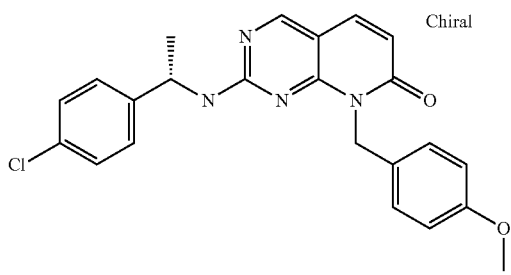 [SMILES: COc1ccc(Cn2c(=O)ccc3cnc(N[C@@H](C)c4ccc(Cl)cc4)nc32)cc1]

$^1$H NMR (500 MHz, DMSO-d$_6$) δ=8.62 (s, 1H), 8.48 (d, J=7.47 Hz, 1H), 7.72 (d, J=9.30 Hz, 1H), 7.26-7.35 (m, 4H), 7.01 (d, J=8.39 Hz, 2H), 6.67 (d, J=8.54 Hz, 2H), 6.26 (d, J=9.30 Hz, 1H), 5.37 (d, J=13.88 Hz, 1H), 5.05-5.14 (m, 2H), 3.68 (s, 3H), 1.45 (d, J=7.02 Hz, 3H). LCMS: m/z 421 [M+H]$^+$ r.t. 6.75 min. HRMS (ESI) calcd for C$_{23}$H$_{22}$ClN$_4$O$_2$ [M+H]$^+$ 421.1426 found 357.1442;

2-{[(1S)-1-(4-chlorophenyl)ethyl]amino}-8-(2-fluorobenzyl)pyrido[2,3-d]pyrimidin-7(8H)-one [(I), X═N, R2=2-fluorobenzyl, A=phenyl, R1a=H, R1b=Me, R6a=4-Cl, R6b=H, R3=R4=R5=H] cpd 22

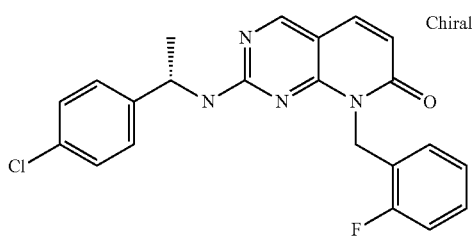 [SMILES: C[C@H](Nc1ncc2ccc(=O)n(Cc3ccccc3F)c2n1)c1ccc(Cl)cc1]

$^1$H NMR (500 MHz, DMSO-d$_6$) δ=8.64 (s, 1H), 8.13-8.52 (m, 1H), 7.80 (d, J=9.30 Hz, 1H), 7.24-7.41 (m, 2H), 7.11-7.24 (m, 4H), 6.90-7.09 (m, 1H), 6.52-6.84 (m, 1H), 6.31 (d, J=9.30 Hz, 1H), 5.49 (d, J=15.10 Hz, 1H), 5.20-5.32 (m, 1H), 4.82-4.95 (m, 1H), 1.32-1.49 (m, 3H). LCMS: m/z 409 [M+H]$^+$ r.t. 6.9 min. HRMS (ESI) calcd for C$_{22}$H$_{19}$ClFN$_4$O [M+H]$^+$ 409.1226 found 409.123;

2-{[(1S)-1-(4-chlorophenyl)ethyl]amino}-8-(3,4-difluorobenzyl)pyrido[2,3-d]pyrimidin-7(8H)-one [(I), X═N, R2=3,4-difluorobenzyl, A=phenyl, R1a=H, R1b=Me, R6a=4-Cl, R6b=H, R3=R4=R5=H] cpd 23

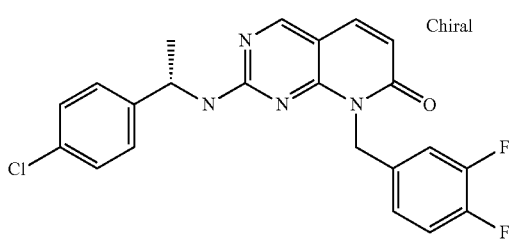 [SMILES: C[C@H](Nc1ncc2ccc(=O)n(Cc3ccc(F)c(F)c3)c2n1)c1ccc(Cl)cc1]

$^1$H NMR (500 MHz, DMSO-d$_6$) δ=8.56-8.70 (m, 1H), 8.52 (d, J=7.47 Hz, 1H), 7.76 (d, J=9.30 Hz, 1H), 7.32-7.44 (m, 1H), 7.13-7.30 (m, 4H), 6.97-7.08 (m, 1H), 6.71-6.87 (m, J=5.03 Hz, 1H), 6.28 (d, J=9.30 Hz, 1H), 5.34-5.50 (m, 1H), 4.88-5.28 (m, 2H), 1.38-1.51 (m, 3H). LCMS: m/z 427 [M+H]$^+$ r.t. 6.9 min. HRMS (ESI) calcd for C$_{22}$H$_{18}$ClF$_2$N$_4$O [M+H]$^+$ 427.1132 found 427.1137;

2-{[(1S)-1-(4-chlorophenyl)ethyl]amino}-8-[3-(trifluoromethyl)benzyl]pyrido[2,3-d]pyrimidin-7(8H)-one [(I), X═N, R2=3-(trifluoromethyl)benzyl, A=phenyl, R1a=H, R1b=Me, R6a=4-Cl, R6b=H, R3=R4=R5=H] cpd 24

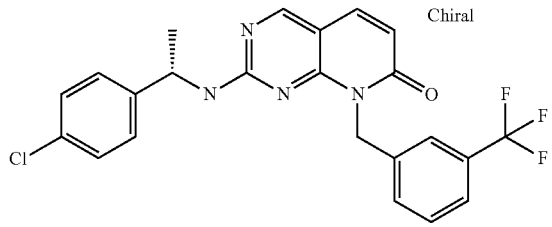 [SMILES: C[C@H](Nc1ncc2ccc(=O)n(Cc3cccc(C(F)(F)F)c3)c2n1)c1ccc(Cl)cc1]

$^1$H NMR (500 MHz, DMSO-d$_6$) δ=8.56-8.72 (m, 1H), 8.31-8.53 (m, 1H), 7.70-7.80 (m, 1H), 7.51-7.66 (m, 2H), 7.39 (t, J=7.63 Hz, 1H), 7.21-7.28 (m, 3H), 7.17 (d, J=8.39 Hz, 2H), 6.30 (d, J=9.30 Hz, 1H), 5.58 (d, J=14.49 Hz, 1H), 5.22 (d, J=14.95 Hz, 1H), 4.89-5.05 (m, 1H), 1.32-1.49 (m, 3H). LCMS: m/z 459 [M+H]$^+$ r.t. 7.34 min. HRMS (ESI) calcd for C$_{22}$H$_{19}$ClF$_3$N$_4$O [M+H]$^+$ 459.1194 found 459.1192;

2-{[(1S)-1-(4-chlorophenyl)ethyl]amino}-8-(2,4-difluorobenzyl)pyrido[2,3-d]pyrimidin-7(8H)-one one [(I), X=N, R2=2,4-difluorobenzyl, A=phenyl, R1a=H, R1b=Me, R6a=4-Cl, R6b=H, R3=R4=R5=H] cpd 25

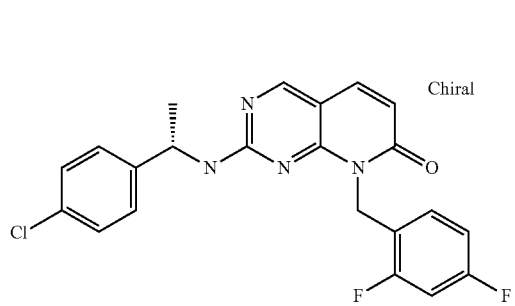 [SMILES: C[C@H](Nc1ncc2ccc(=O)n(Cc3ccc(F)cc3F)c2n1)c1ccc(Cl)cc1]

¹H NMR (500 MHz, DMSO-d₆) δ=8.57-8.73 (m, 1H), 8.49 (d, J=7.63 Hz, 1H), 7.79 (d, J=9.30 Hz, 1H), 7.31-7.42 (m, 1H), 7.13-7.28 (m, 4H), 6.53-7.00 (m, 2H), 6.30 (d, J=9.46 Hz, 1H), 5.42 (d, J=14.64 Hz, 1H), 5.20 (d, J=14.95 Hz, 1H), 4.80-4.99 (m, 1H), 1.33-1.47 (m, 3H). LCMS: m/z 427 [M+H]⁺ r.t. 6.97 min. HRMS (ESI) calcd for C₂₂H₁₈ClF₂N₄O [M+H]⁺ 427.1132 found 427.1136;

2-{[(1S)-1-(4-chlorophenyl)ethyl]amino}-8-[4-(trifluoromethoxy)benzyl]pyrido[2,3-d]pyrimidin-7(8H)-one [(I), X=N, R2=4-(trifluoromethoxy)benzyl, A=phenyl, R1a=H, R1b=Me, R6a=4-Cl, R6b=H, R3=R4=R5=H] cpd 26

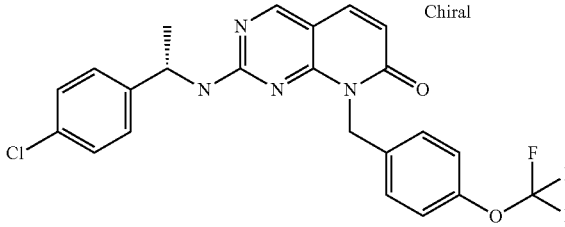

¹H NMR (500 MHz, DMSO-d₆) δ=8.57-8.68 (m, 1H), 8.27-8.54 (m, 1H), 7.64-7.80 (m, 1H), 7.33-7.48 (m, 1H), 7.30 (d, J=8.39 Hz, 2H), 7.21-7.25 (m, 2H), 7.08-7.19 (m, 3H), 6.28 (d, J=9.30 Hz, 1H), 5.40-5.55 (m, 1H), 4.99-5.28 (m, 2H), 1.38-1.49 (m, 3H). LCMS: m/z 475 [M+H]⁺ r.t. 7.46 min. HRMS (ESI) calcd for C₂₂H₁₉ClF₃N₄O₂ [M+H]⁺ 475.1143 found 475.114;

4-{[2-{[(1S)-1-(4-chlorophenyl)ethyl]amino}-7-oxopyrido[2,3-d]pyrimidin-8(7H)-yl]methyl}benzonitrile [(I), X=N, R2=4-cyanobenzyl, A=phenyl, R1a=H, R1b=Me, R6a=4-Cl, R6b=H, R3=R4=R5=H] cpd 27

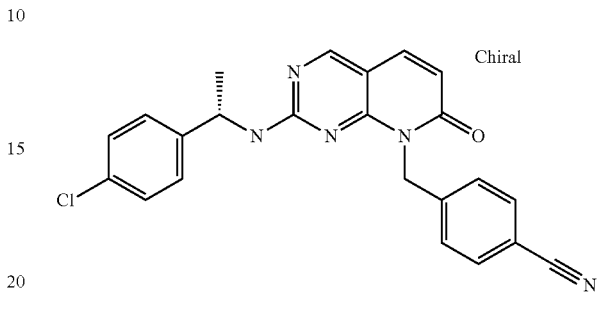

¹H NMR (500 MHz, DMSO-d₆) δ=8.65 (s, 1H), 8.51 (d, J=7.32 Hz, 1H), 7.79 (d, J=9.46 Hz, 1H), 7.62 (d, J=8.08 Hz, 2H), 7.17-7.25 (m, 2H), 7.14 (d, J=7.63 Hz, 4H), 6.29 (d, J=9.30 Hz, 1H), 5.54 (d, J=15.10 Hz, 1H), 5.20 (d, J=15.10 Hz, 1H), 4.92 (quin, J=7.28 Hz, 1H), 1.38 (d, J=7.02 Hz, 3H).

LCMS: m/z 416 [M+H]⁺ r.t. 6.4 min. HRMS (ESI) calcd for C₂₃H₁₉ClN₄O [M+H]⁺ 416.1273 found 416.129;

2-{[(1S)-1-(4-chlorophenyl)ethyl]amino}-8-(4-fluorobenzyl)pyrido[2,3-d]pyrimidin-7(8H)-one [(I), X=N, R2=4-fluorobenzyl, A=phenyl, R1a=H, R1b=Me, R6a=4-Cl, R6b=H, R3=R4=R5=H] cpd 28

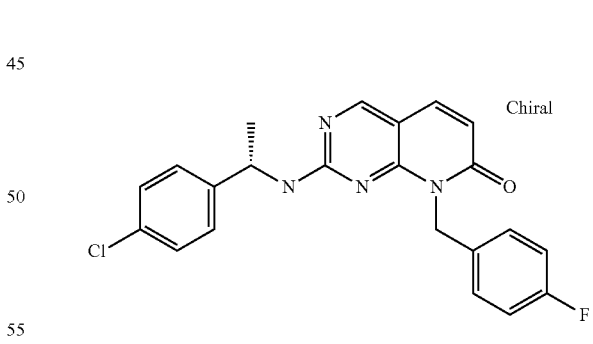

¹H NMR (500 MHz, DMSO-d₆) δ=8.63 (s, 1H), 8.50 (d, J=7.47 Hz, 1H), 7.75 (d, J=9.30 Hz, 1H), 7.28-7.33 (m, 2H), 7.22-7.28 (m, 2H), 7.08 (dd, J=5.80, 7.93 Hz, 2H), 6.95 (t, J=8.85 Hz, 2H), 6.27 (d, J=9.30 Hz, 1H), 5.42 (d, J=14.34 Hz, 1H), 5.12 (d, J=14.18 Hz, 1H), 5.04 (quin, J=6.98 Hz, 1H), 1.43 (d, J=6.86 Hz, 3H). LCMS: m/z 409 [M+H]⁺ r.t. 6.4 min. HRMS (ESI) calcd for C₂₂H₁₉ClFN₄O [M+H]⁺ 409.1226 found 409.1228;

2-{[(1S)-1-(4-chlorophenyl)ethyl]amino}-8-(3,5-difluorobenzyl)pyrido[2,3-d]pyrimidin-7(8H)-one [(I), X=N, R2=3,5-difluorobenzyl, A=phenyl, R1a=H, R1b=Me, R6a=4-Cl, R6b=H, R3=R4=R5=H] cpd 29

2-{[(1S)-1-(4-chlorophenyl)ethyl]amino}-8-(2,6-difluorobenzyl)pyrido[2,3-d]pyrimidin-7(8H)-one [(I), X=N, R2=2,6-difluorobenzyl A=phenyl, R1a=H, R1b=Me, R6a=4-Cl, R6b=H, R3=R4=R5=H] cpd 31

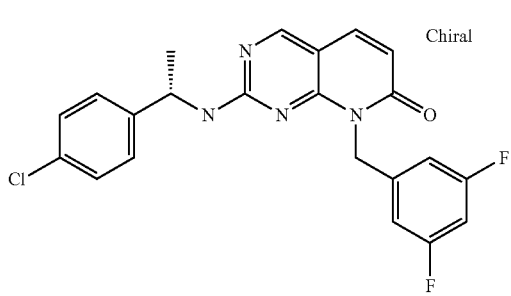 [SMILES: C[C@H](Nc1ncc2ccc(=O)n(Cc3cc(F)cc(F)c3)c2n1)c1ccc(Cl)cc1]

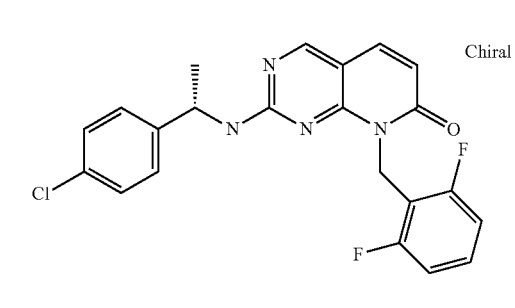

$^1$H NMR (500 MHz, DMSO-d$_6$) δ=8.65 (s, 1H), 8.53 (d, J=7.78 Hz, 1H), 7.78 (d, J=9.30 Hz, 1H), 7.25 (d, J=8.24 Hz, 2H), 7.17 (d, J=8.39 Hz, 2H), 7.05 (tt, J=2.30, 9.50 Hz, 1H), 6.69 (d, J=6.71 Hz, 2H), 6.29 (d, J=9.46 Hz, 1H), 5.50 (d, J=14.79 Hz, 1H), 5.16 (d, J=15.10 Hz, 1H), 4.98 (quin, J=7.10 Hz, 1H), 1.39 (d, J=7.02 Hz, 3H).

LCMS: m/z 427 [M+H]$^+$ r.t. 6.99 min. HRMS (ESI) calcd for C$_{22}$H$_{18}$ClF$_2$N$_4$O [M+H]$^+$ 427.1132 found 427.1139;

$^1$H NMR (500 MHz, DMSO-d$_6$) δ=8.60 (s, 1H), 8.09-8.47 (m, J=8.08 Hz, 1H), 7.74 (d, J=9.30 Hz, 1H), 7.26-7.43 (m, 3H), 7.21 (d, J=8.24 Hz, 2H), 6.87-7.05 (m, 2H), 6.24 (d, J=9.30 Hz, 1H), 5.56 (d, J=14.95 Hz, 1H), 5.30 (d, J=14.95 Hz, 1H), 4.98-5.05 (m, 1H), 1.32-1.48 (m, 3H). LCMS: m/z 427 [M+H]$^+$ r.t. 6.84 min. HRMS (ESI) calcd for C$_{22}$H$_{18}$ClF$_2$N$_4$O [M+H]$^+$ 427.1132 found 427.1135;

2-{[(1S)-1-(4-chlorophenyl)ethyl]amino}-8-(3-methoxybenzyl)pyrido[2,3-d]pyrimidin-7(8H)-one [(I), X=N, R2=3-methoxybenzyl A=phenyl, R1a=H, R1b=Me, R6a=4-Cl, R6b=H, R3=R4=R5=H] cpd 30

2-{[(1S)-1-(4-chlorophenyl)ethyl]amino}-4-methyl-8-(2-methylpropyl)pyrido[2,3-d]pyrimidin-7(8H)-one [(I), X=N, R2=2-methylpropyl, A=phenyl, R1a=H, R1b=Me, R6a=4-Cl, R6b=H, R3=Me, R4=R5=H] cpd 32

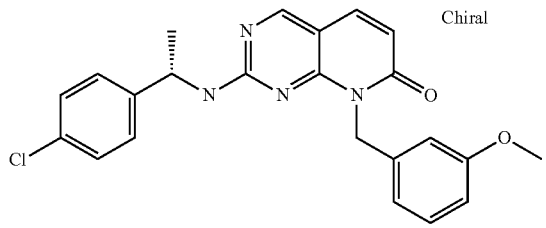 [SMILES: COc1cccc(Cn2c(=O)ccc3cnc(N[C@@H](C)c4ccc(Cl)cc4)nc32)c1]

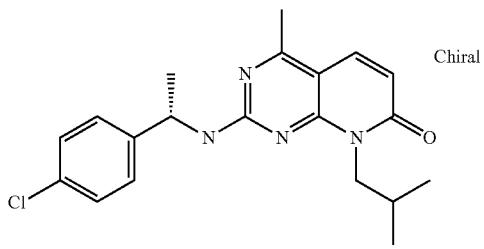 [SMILES: Cc1nc(N[C@@H](C)c2ccc(Cl)cc2)nc2c1ccc(=O)n2CC(C)C]

$^1$H NMR (500 MHz, DMSO-d$_6$) δ=8.56-8.69 (m, 1H), 8.47 (d, J=7.78 Hz, 1H), 7.76 (d, J=9.46 Hz, 1H), 7.24-7.30 (m, 2H), 7.20 (d, J=8.24 Hz, 2H), 7.10 (t, J=7.85 Hz, 1H), 6.79 (dd, J=2.13, 7.93 Hz, 1H), 6.70 (br. s., 1H), 6.61 (d, J=7.47 Hz, 1H), 6.29 (d, J=9.30 Hz, 1H), 5.45 (d, J=14.34, 1H), 5.16 (d, J=14.49 Hz, 1H), 4.96-5.07 (m, 1H), 3.64-3.73 (m, 3H), 1.37-1.49 (m, 3H). LCMS: m/z 421 [M+H]$^+$ r.t. 6.79 min. HRMS (ESI) calcd for C$_{23}$H$_{22}$ClN$_4$O$_2$[M+H]$^+$ 421.1426 found 421.1436;

$^1$H NMR (500 MHz, DMSO-d$_6$) δ=8.36 (d, J=7.02 Hz, 1H), 7.87 (d, J=9.61 Hz, 1H), 7.28-7.43 (m, 4H), 6.20 (d, J=9.61 Hz, 1H), 4.98 (d, J=10.83 Hz, 1H), 3.96 (dd, J=7.40, 11.97 Hz, 1H), 3.79-3.87 (m, J=11.74 Hz, 1H), 1.79-1.97 (m, 1H), 1.43 (d, J=7.02 Hz, 3H), 1.23 (s, 3H), 0.73 (d, J=6.86 Hz, 3H), 0.60 (d, J=6.71 Hz, 3H).

LCMS: m/z 371 [M+H]$^+$ r.t. 7.11 min. HRMS (ESI) calcd for C$_{20}$H$_{24}$ClN$_4$O [M+H]$^+$ 371.1633 found 371.1633;

8-(2,2-dimethylpropyl)-2-{[(1S)-1-(4-methoxyphe-nyl)ethyl]amino}pyrido[2,3-d]pyrimidin-7(8H)-one [(I), X=N, R2=2,2-dimethylpropyl, A=phenyl, R1a=H, R1b=Me, R6a=4-MeO, R6b=H, R3=R4=R5=H] cpd 33

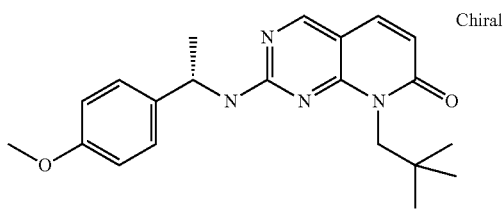 [SMILES: COc1ccc([C@H](C)Nc2ncc3ccc(=O)n(CC(C)(C)C)c3n2)cc1]

$^1$H NMR (500 MHz, DMSO-d$_6$) δ=8.52-8.57 (m, 1H), 8.32 (d, J=7.63 Hz, 1H), 7.67 (d, J=9.15 Hz, 1H), 7.29 (d, J=8.54 Hz, 2H), 6.86 (d, J=8.54 Hz, 2H), 6.22 (d, J=9.30 Hz, 1H), 5.01-5.36 (dq, J=7.6, 6.90, Hz, 1H), 3.87-4.44 (m, 2H), 3.70 (s, 3H), 1.44 (d, J=7.02 Hz, 3H), 0.58-1.02 (m, 9H). LCMS: m/z 367 [M+H]$^+$ r.t. 6.6 min. HRMS (ESI) calcd for C$_{21}$H$_{27}$N$_4$O$_2$ [M+H]$^+$ 367.2129 found 367.2132;

2-{[(1S)-1-(4-bromophenyl)ethyl]amino}-8-(2,2-dimethylpropyl)pyrido[2,3-d]pyrimidin-7(8H)-one [(I), X=N, R2=2,2-dimethylpropyl, A=phenyl, R1a=H, R1b=Me, R6a=4-Br, R6b=H, R3=R4=R5=H] cpd 34

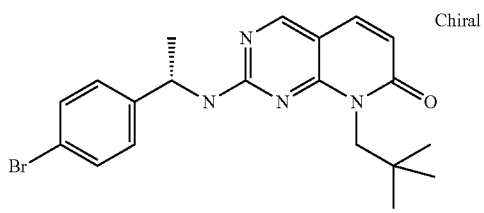 [SMILES: C[C@H](Nc1ncc2ccc(=O)n(CC(C)(C)C)c2n1)c1ccc(Br)cc1]

$^1$H NMR (500 MHz, DMSO-d$_6$) δ=8.58 (s, 1H), 8.40 (d, J=7.47 Hz, 1H), 7.68 (d, J=9.30 Hz, 1H), 7.50 (d, J=8.40 Hz, 2H), 7.34 (d, J=8.39 Hz, 2H), 6.23 (d, J=9.30 Hz, 1H), 5.04 (quin, J=6.90 Hz, 1H), 3.96-4.25 (m, 2H), 1.45 (d, J=7.02 Hz, 3H), 0.75 (br. s., 9H). LCMS: m/z 415 [M+H]$^+$ r.t. 7.21 min. HRMS (ESI) calcd for C$_{20}$H$_{24}$BrN$_4$O [M+H]$^+$ 415.1128 found 415.1135;

2-{[(1S)-1-(4-bromophenyl)ethyl]amino}-8-(3-hy-droxy-2,2-dimethylpropyl)pyrido[2,3-d]pyrimidin-7(8H)-one [(I), X=N, R2=3-hydroxy-2,2-dimethyl-propyl, A=phenyl, R1a=H, R1b=Me, R6a=4-Br, R6b=H, R3=R4=R5=H] cpd 35

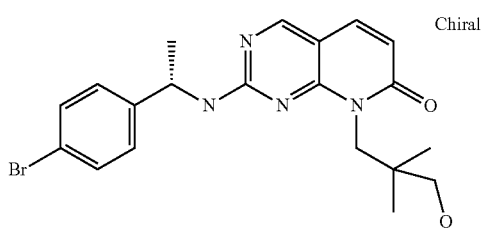 [SMILES: C[C@H](Nc1ncc2ccc(=O)n(CC(C)(C)CO)c2n1)c1ccc(Br)cc1]

$^1$H NMR (500 MHz, DMSO-d$_6$) δ=8.52-8.67 (m, 1H), 8.47 (d, J=7.63 Hz, 1H), 7.72 (d, J=9.30 Hz, 1H), 7.46-7.53 (m, 2H), 7.37 (d, J=8.24 Hz, 2H), 6.26 (d, J=9.15 Hz, 1H), 4.94-5.35 (m, J=6.94, 6.94 Hz, 1H), 4.60 (br. s., 1H), 4.01-4.28 (m, 2H), 3.06 (br. s., 2H), 1.45 (d, J=7.02 Hz, 3H), 0.62 (br. s., 6H). LCMS: m/z 431 [M+H]$^+$ r.t. 6.25 min. HRMS (ESI) calcd for C$_{20}$H$_{24}$BrN$_4$O$_2$[M+H]$^+$ 431.1077 found 431.1085;

8-(2,2-dimethylpropyl)-2-{[(1S)-1-(naphthalen-2-yl)ethyl]amino}pyrido[2,3-d]pyrimidin-7(8H)-one [(I), X=N, R2=2,2-dimethylpropyl, A=2-naphthalenyl, R1a=H, R1b=Me, R6a=R6b=H, R3=R4=R5=H] cpd 36

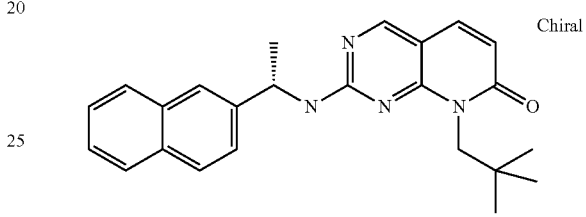

$^1$H NMR (500 MHz, DMSO-d$_6$) δ=8.59 (s, 1H), 8.49 (d, J=7.47 Hz, 1H), 7.76-7.92 (m, 4H), 7.66 (d, J=9.30 Hz, 1H), 7.58 (dd, J=1.45, 8.46 Hz, 1H), 7.41-7.48 (m, 2H), 6.20 (d, J=9.30 Hz, 1H), 5.25 (quin, J=7.32 Hz, 1H), 3.90-4.36 (m, 2H), 1.56 (d, J=7.02 Hz, 3H), 0.50-1.04 (m, 9H). LCMS: m/z 387 [M+H]$^+$ r.t. 7.27 min. HRMS (ESI) calcd for C$_{24}$H$_{27}$N$_4$O [M+H]$^+$ 387.218 found 387.2178;

methyl 2,2-dimethyl-3-[2-{[(1S)-1-(naphthalen-2-yl)ethyl]amino}-7-oxopyrido[2,3-d]pyrimidin-8(7H)-yl]propanoate [(I), X=N, R2=methyl-2,2-dimethyl-3-propanoate, A=2-naphthalenyl, R1a=H, R1b=Me, R6a=R6b=H, R3=R4=R5=H] cpd 37

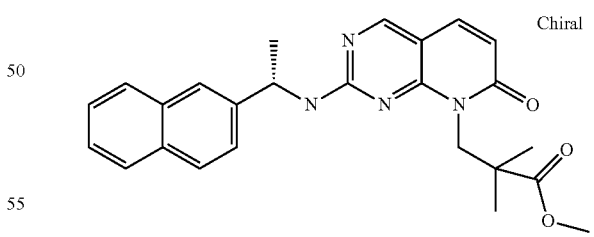

$^1$H NMR (500 MHz, DMSO-d$_6$) δ=8.60 (s, 1H), 8.55 (d, J=7.47 Hz, 1H), 7.80-7.92 (m, 4H), 7.68 (d, J=9.30 Hz, 1H), 7.58 (dd, J=1.45, 8.46 Hz, 1H), 7.38-7.50 (m, 2H), 6.18 (d, J=9.30 Hz, 1H), 5.12-5.32 (m, J=7.17 Hz, 1H), 4.21-4.28 (m, 2H), 3.42 (s, 3H), 1.56 (d, J=7.02 Hz, 3H), 1.07-1.11 (m, 3H), 0.83 (s, 3H). LCMS: m/z 431 [M+H]+r.t. 6.63 min. HRMS (ESI) calcd for C$_{25}$H$_{27}$N$_4$O$_3$ [M+H]$^+$ 431.2078 found 431.2076;

8-(3-hydroxy-2,2-dimethylpropyl)-2-{[(1S)-1-(naphthalen-2-yl)ethyl]amino}pyrido[2,3-d]pyrimidin-7(8H)-one [(I), X=N, R2=3-hydroxy-2,2-dimethyl-propyl, A=2-naphthalenyl, R1a=H, R1b=Me, R6a=R6b=H, R3=R4=R5=H] cpd 38

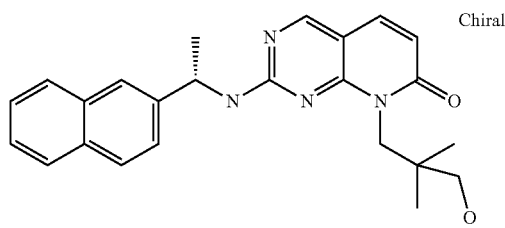 [SMILES: C[C@H](Nc1ncc2ccc(=O)n(CC(C)(C)CO)c2n1)c1ccc2ccccc2c1]

$^1$H NMR (500 MHz, DMSO-d$_6$) δ=8.61 (s, 1H), 8.55 (d, J=7.32 Hz, 1H), 7.79-7.92 (m, 4H), 7.71 (d, J=9.30 Hz, 1H), 7.60 (d, J=8.54 Hz, 1H), 7.37-7.52 (m, 2H), 6.23 (d, J=9.30 Hz, 1H), 5.08-5.47 (m, J=7.32, 7.32 Hz, 1H), 4.50-4.69 (m, 1H), 3.96-4.40 (m, 2H), 3.00-3.16 (m, 2H), 1.56 (s, 3H), 0.80-0.86 (m, 3H), 0.68-0.74 (m, 3H).
LCMS: m/z 403 [M+H]$^+$ r.t. 6.34 min. HRMS (ESI) calcd for C$_{24}$H$_{27}$N$_4$O$_2$ [M+H]$^+$ 403.2129 found 403.214;

8-(2,2-dimethylpropyl)-2-{[(1R)-1-phenylethyl]amino}pyrido[2,3-d]pyrimidin-7(8H)-one [(I), X=N, R2=2,2-dimethyl-propyl, A=phenyl, R1a=H, R1b=Me, R6a=R6b=H, R3=R4=R5=H] cpd 39

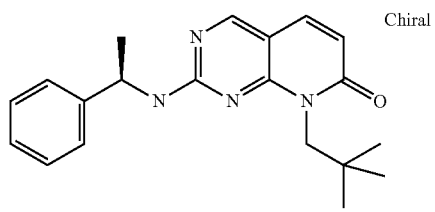 [SMILES: C[C@@H](Nc1ncc2ccc(=O)n(CC(C)(C)C)c2n1)c1ccccc1]

$^1$H NMR (500 MHz, DMSO-d$_6$) δ=8.50-8.60 (m, 1H), 8.05-8.43 (m, 1H), 7.67 (d, J=9.30 Hz, 1H), 7.36-7.42 (m, 2H), 7.26-7.33 (m, 2H), 7.15-7.22 (m, 1H), 6.22 (d, J=9.30 Hz, 1H), 5.01-5.30 (m, 1H), 3.79-4.33 (m, 2H), 1.46 (d, J=7.02 Hz, 3H), 0.66-0.99 (m, 9H). LCMS: m/z 337 [M+H]$^+$ r.t. 6.73 min. HRMS (ESI) calcd for C$_{20}$H$_{25}$N$_4$O [M+H]$^+$ 337.2023 found 337.2025;

8-(2,2-dimethylpropyl)-2-{[(1S)-1-phenylethyl]amino}pyrido[2,3-d]pyrimidin-7(8H)-one [(I), X=N, R2=2,2-dimethyl-propyl, A=phenyl, R1a=H, R1b=Me, R6a=R6b=H, R3=R4=R5=H] cpd 40

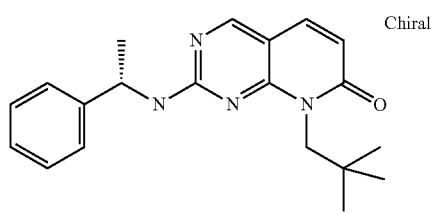 [SMILES: C[C@H](Nc1ncc2ccc(=O)n(CC(C)(C)C)c2n1)c1ccccc1]

$^1$H NMR (500 MHz, DMSO-d$_6$) δ=8.57 (s, 1H), 8.39 (d, J=7.63 Hz, 1H), 7.67 (d, J=9.15 Hz, 1H), 7.38 (d, J=7.63 Hz, 2H), 7.30 (t, J=7.55 Hz, 2H), 7.16-7.21 (m, 1H), 6.22 (d, J=9.30 Hz, 1H), 5.08 (t, J=7.09 Hz, 1H), 3.98-4.28 (m, 2H), 1.46 (d, J=7.02 Hz, 3H), 0.77 (br. s., 9H). LCMS: m/z 337 [M+H]$^+$ r.t. 6.73 min. HRMS (ESI) calcd for C$_{20}$H$_{25}$N$_4$O [M+H]$^+$ 337.2023 found 337.2024;

8-(2,2-dimethylpropyl)-2-[(2-phenylpropan-2-yl)amino]pyrido[2,3-d]pyrimidin-7(8H)-one [(I), X=N, R2=2,2-dimethyl-propyl, A=phenyl, R1a=R1b=Me, R6a=R6b=H, R3=R4=R5=H] cpd 41

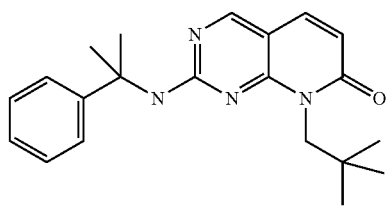 [SMILES: CC(C)(C)Cn1c(=O)ccc2cnc(NC(C)(C)c3ccccc3)nc21]

$^1$H NMR (500 MHz, DMSO-d$_6$) δ=8.57 (br. s., 1H), 8.15 (br. s., 1H), 7.64 (d, J=8.85 Hz, 1H), 7.38 (d, J=6.71 Hz, 2H), 7.25 (t, J=7.63 Hz, 2H), 7.11-7.16 (m, 1H), 6.20 (d, J=9.30 Hz, 1H), 3.73 (br. s., 2H), 1.71 (s, 6H), 0.54 (br. s., 9H). LCMS: m/z 351 [M+H]$^+$ r.t. 7.02 min. HRMS (ESI) calcd for C$_{21}$H$_{27}$N$_4$O [M+H]$^+$ 351.218 found 351.2176;

8-(2,2-dimethylpropyl)-2-[(1-phenylcyclopropyl)amino]pyrido[2,3-d]pyrimidin-7(8H)-one [(I), X=N, R2=2,2-dimethyl-propyl, A=phenyl, R1a-R1b=cyclopropyl, R6a=R6b=H, R3=R4=R5=H] cpd 42

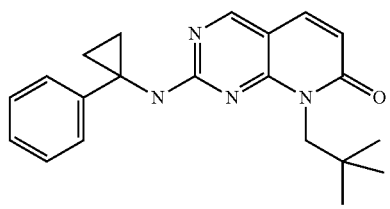 [SMILES: CC(C)(C)Cn1c(=O)ccc2cnc(NC3(c4ccccc4)CC3)nc21]

$^1$H NMR (500 MHz, DMSO-d$_6$) δ=8.64 (s, 1H), 8.60 (s, 1H), 7.68-7.72 (m, 1H), 7.22 (d, J=7.32 Hz, 2H), 7.16-7.19 (m, 2H), 7.06-7.13 (m, 1H), 6.25 (d, J=9.30 Hz, 1H), 3.87-4.29 (m, 2H), 1.23-1.38 (m, 2H), 0.90-0.95 (m, 2H), 0.61 (s, 9H). LCMS: m/z 349 [M+H]$^+$ r.t. 6.71 min. HRMS (ESI) calcd for C$_{21}$H$_{25}$N$_4$O [M+H]$^+$ 349.2023 found 349.2021;

8-(2,2-dimethylpropyl)-2-[(1-phenylcyclobutyl)
amino]pyrido[2,3-d]pyrimidin-7(8H)-one [(I),
X=N, R2=2,2-dimethyl-propyl, A=phenyl, R1a-
R1b=cyclobutyl, R6a=R6b=H, R3=R4=R5=H] cpd
43

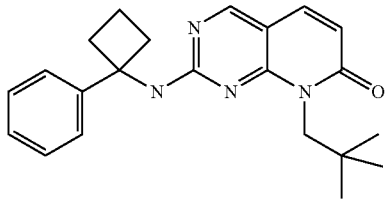 [SMILES: CC(C)(C)Cn1c(=O)ccc2cnc(NC3(c4ccccc4)CCC3)nc21]

$^1$H NMR (500 MHz, DMSO-d$_6$) δ=8.69 (s, 1H), 8.58 (s, 1H), 7.65 (d, J=9.00 Hz, 1H), 7.45-7.52 (m, 2H), 7.29 (t, J=8.01 Hz, 2H), 7.10-7.18 (m, 1H), 6.20 (d, J=9.30 Hz, 1H), 3.88 (br. s., 2H), 1.90-2.13 (m, 4H), 0.9-0.94 (m, 2H), 0.57 (s, 9H). LCMS: m/z 363 [M+H]$^+$ r.t. 7.16 min. HRMS (ESI) calcd for C$_{22}$H$_{27}$N$_4$O [M+H]$^+$ 363.218 found 363.2187;

8-(2,2-dimethylpropyl)-2-{[1-(tricyclo[3.3.1.1$^{3,7}$]
dec-1-yl)ethyl]amino}pyrido[2,3-d]pyrimidin-7(8H)-
one [(I), X=N, R2=2,2-dimethyl-propyl,
A=adamantanyl, R1a=H, R1b=Me, R6a=R6b=H,
R3=R4=R5=H] cpd 44

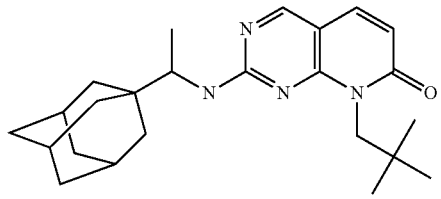 [SMILES: CC(Nc1ncc2ccc(=O)n(CC(C)(C)C)c2n1)C12CC3CC(CC(C3)C1)C2]

$^1$H NMR (500 MHz, DMSO-d$_6$) δ 8.53 (s, 1H), 7.57-7.72 (m, 1H), 7.17-7.56 (m, 1H), 6.07-6.29 (m, 1H), 4.20 (br. s., 2H), 3.84-4.05 (m, 1H), 1.94 (br. s., 3H), 1.39-1.71 (m, 12H), 1.05 (d, J=6.86 Hz, 3H), 0.86-0.96 (m, 9H).
LCMS: m/z 395 [M+H]$^+$ r.t. 8.81 min. HRMS (ESI) calcd for C$_{24}$H$_{34}$N$_4$O [M+H]$^+$ 395.2806 found 395.2813;

8-[(3-methyloxetan-3-yl)methyl]-2-{[(1S)-1-(naph-
thalen-2-yl)ethyl]amino}pyrido[2,3-d]pyrimidin-7
(8H)-one [(I), X=N, R2=(3-methyloxetan-3-yl)
methyl, A=2-naphthalenyl, R1a=H, R1b=Me,
R6a=R6b=H, R3=R4=R5=H] cpd 45

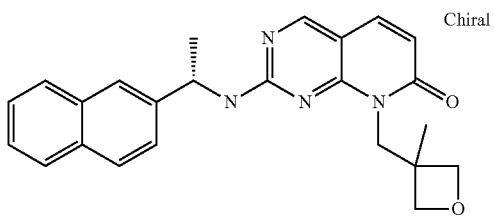 [SMILES: C[C@H](Nc1ncc2ccc(=O)n(CC3(C)COC3)c2n1)c1ccc2ccccc2c1]

Chiral $^1$H NMR (500 MHz, DMSO-d$_6$) δ=8.65 (s, 1H), 8.60 (d, J=7.02 Hz, 1H), 7.78-7.91 (m, 3H), 7.74 (d, J=9.30 Hz, 1H), 7.54 (d, J=8.39 Hz, 1H), 7.39-7.52 (m, 3H), 6.23 (d, J=9.30 Hz, 1H), 4.99-5.46 (m, J=6.63, Hz, 1H), 4.66-4.69 (m, 1H), 4.56 (d, J=5.80 Hz, 1H), 4.38 (d, J=6.10 Hz, 1H), 4.35 (d, J=5.80 Hz, 1H), 4.19-4.25 (m, 1H), 4.03-4.12 (m, 1H), 1.49-1.62 (m, 3H), 1.20-1.43 (m, 3H). LCMS: m/z 401 [M+H]$^+$ r.t. 6.0 min. HRMS (ESI) calcd for C$_{24}$H$_{25}$N$_4$O$_2$ [M+H]$^+$ 401.1972 found 401.1973;

8-(2-Hydroxy-2-methyl-propyl)-2-((S)-1-phenyl-
ethylamino)-8H-pyrido[2,3-d]pyrimidin-7-one [(I),
X=N, R2=2-Hydroxy-2-methyl-propyl, A=Phenyl,
R1a=H, R1b=Me, R6a=R6b=H, R3=R4=R5=H]
cpd 46

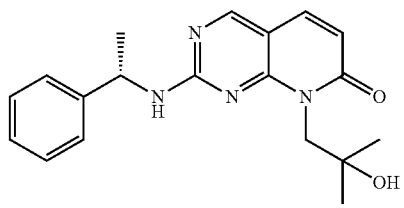 [SMILES: C[C@H](Nc1ncc2ccc(=O)n(CC(C)(C)O)c2n1)c1ccccc1]

$^1$H NMR (500 MHz, DMSO-d$_6$) δ=8.63 (s, 1H), 8.51 (d, J=7.8 Hz, 1H), 7.74 (d, J=9.3 Hz, 1H), 7.41-7.37 (m, 2 H), 7.30 (t, J=7.6 Hz, 2H), 7.23-7.14 (m, 1H), 6.28 (d, J=9.3 Hz, 1H), 5.05 (quin, J=7.2 Hz, 1H), 4.58 (s, 1H), 4.29 (d, J=13.3 Hz, 1H), 4.17 (d, J=13.3 Hz, 1H), 1.46 (d, J=7.3 Hz, 3H), 1.04 (s, 3H), 0.86 (br. s., 3H). LCMS: m/z 339 [M+H]$^+$@ r.t. 5.45 min. HRMS (ESI) calcd for C$_{19}$H$_{22}$N$_4$O$_2$ [M+H]$^+$ 339.1816 found 339.1812;

8-(2,2-Dimethyl-propyl)-6-fluoro-2-((S)-1-phenyl-
ethylamino)-8H-pyrido[2,3-d]pyrimidin-7-one [(I),
X=N, R2=2,2-Dimethyl-propyl, A=Phenyl,
R1a=H, R1b=Me, R6a=R6b=H, R3=R4=H, R5=F]
cpd 47

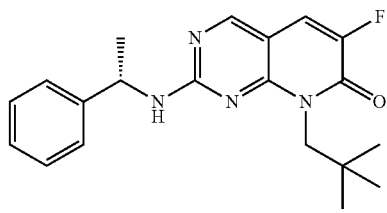 [SMILES: C[C@H](Nc1ncc2cc(F)c(=O)n(CC(C)(C)C)c2n1)c1ccccc1]

$^1$H NMR (500 MHz, DMSO-d$_6$) δ=8.58 (s, 1H), 8.39 (d, J=7.3 Hz, 1H), 7.69 (d, J=9.5 Hz, 1H), 7.38 (d, J=7.5 Hz, 2H), 7.30 (t, J=7.5 Hz, 2H), 7.24-7.13 (m, 1H), 5.06 (quin, J=6.9 Hz, 1H), 5.31-4.95 (m, 1H), 4.33-4.02 (m, 2H), 1.46 (d, J=7.0 Hz, 3H), 0.78 (br. s., 9H). LCMS: m/z 355 [M+H]$^+$@ r.t. 7.10 min. HRMS (ESI) calcd for C$_{20}$H$_{23}$FN$_4$O [M+H]$^+$ 355.1929 found 355.1926;

4-{(S)-1-[8-(2-Hydroxy-2-methyl-propyl)-7-oxo-7,
8-dihydro-pyrido[2,3-d]pyrimidin-2-ylamino]-
ethyl}-benzoic acid methyl ester [(I), X=N, R2=2-
Hydroxy-2-methyl-propyl, A=Phenyl, R1a=H,
R1b=Me, R6a=—COOMe, R6b=H, R3=R4=R5=H]
cpd 48

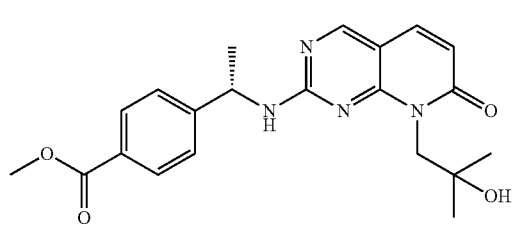 [SMILES: COC(=O)c1ccc([C@H](C)Nc2ncc3ccc(=O)n(CC(C)(C)O)c3n2)cc1]

$^1$H NMR (500 MHz, DMSO-d$_6$) δ=8.64 (s, 1H), 8.57 (d, J=7.2 Hz, 1H), 7.95-7.86 (m, 2H), 7.74 (d, J=9.2 Hz, 1H), 7.54 (d, J=7.9 Hz, 2H), 6.28 (d, J=9.3 Hz, 1H), 5.11 (quin, J=6.9 Hz, 1H), 4.55 (s, 1H), 4.25 (d, J=13.1 Hz, 1H), 4.11 (d, J=13.1 Hz, 1H), 3.82 (s, 3H), 1.48 (d, J=7.0 Hz, 3H), 1.01 (s, 3H), 0.83 (br. s., 3H). LCMS: m/z 397 [M+H]$^+$ @ r.t. 5.32 min. HRMS (ESI) calcd for C$_{21}$H$_{24}$N$_4$O$_4$ [M+H]$^+$ 397.1871 found 397.1868;

8-(2,2-dimethylpropyl)-2-{[(1S)-1-(4-phenoxyphe-
nyl)ethyl]amino}pyrido[2,3-d]pyrimidin-7(8H)-one
[(I), X=N, R2=2,2-dimethylpropyl, A=phenyl,
R1a=H, R1b=Me, R6a=4-phenoxy, R6b=H,
R3=R4=R5=H] cpd 49

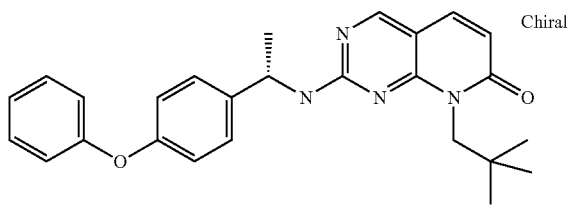 [SMILES: C[C@H](Nc1ncc2ccc(=O)n(CC(C)(C)C)c2n1)c1ccc(Oc2ccccc2)cc1]

$^1$H NMR (500 MHz, DMSO-d$_6$) δ=8.58 (s, 1H), 8.38 (d, J=7.47 Hz, 1H), 7.68 (d, J=9.30 Hz, 1H), 7.33-7.41 (m, 4H), 7.10 (t, J=7.32 Hz, 1H), 6.95 (t, J=7.78 Hz, 4H), 6.24 (d, J=9.30 Hz, 1H), 5.91 (m, 1H), 4.00-4.10 (m, 2H), 1.47 (d, J=7.02 Hz, 3H), 0.90-0.94 (m, 6H), 0.74-0.81 (m, 3H). LCMS: m/z 429 [M+H]$^+$ r.t. 7.66 min. HRMS (ESI) calcd for C$_{26}$H$_{29}$N$_4$O$_2$ [M+H]$^+$ 429.2285 found 429.2289.

Example 2

Preparation of 2-{[(1S)-1-(6-chloro-2-oxo-quinolin-
3-yl)ethyl]amino}-8-(2,2-dimethylpropyl)pyrido[2,
3-d]pyrimidin-7(8H)-one [(I), X=N, R2=2,2-dim-
ethylpropyl, A=2-oxo-quinolin-3-yl, R1a=H,
R1b=Me, R6a=6-chloro, R6b=H, R3=R4=R5=H]
step 1a cpd 50

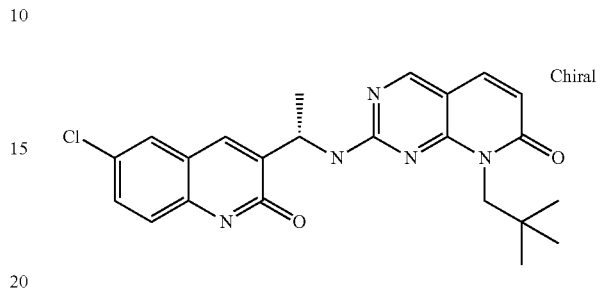

To a solution of compound 8-(2,2-dimethylpropyl)-2-(methylsulfonyl)pyrido[2,3-d]pyrimidin-7(8H)-one (50 mg, 0.17 mmol) in ACN (1 mL) and DIPEA (123 µL, 0.68 mM) was added 3-[(1S)-1-aminoethyl]-6-chloroquinolin-2(1H)-one hydrochloride (prepared as reported in WO2016171755) (65 mg, 0.255 mmol). The reaction was heated to 90° C. for 4 hours. The reaction mixture was diluted with EtOAc (4 mL) and washed with water (5 mL) and brine (5 mL). The organic layer was dried over Na$_2$SO$_4$, filtered and concentrated. The crude material was purified on silica gel column chromatography (DCM/EtOAc/EtOH 7/2/1) provided the title compound as a off-white solid (44 mg, 60% yield).

$^1$H NMR (500 MHz, DMSO-d$_6$) δ=12.05 (s, 1H), 8.61 (s, 1H), 8.35 (d, J=7.17 Hz, 1H), 7.61-7.75 (m, 3H), 7.46 (dd, J=8.77, 2.21 Hz, 1H), 7.30 (d, J=8.85 Hz, 1H), 6.23 (d, J=9.30 Hz, 1H), 5.26 (quin, J=6.94 Hz, 1H), 3.82-4.42 (m, 2H), 1.43 (d, J=6.86 Hz, 3H), 0.52-1.02 (m, 9H). LCMS: m/z 438 [M+H]$^+$ r.t. 5.88 min. HRMS (ESI) calcd for C$_{23}$H$_{25}$ClN$_5$O$_2$[M+H]$^+$ 438.1692 found 438.1692.

According to the same method, the following compounds were prepared:

8-benzyl-2-{[(1S)-1-(5-chloro-1H-benzimidazol-2-
yl)ethyl]amino}pyrido[2,3-d]pyrimidin-7(8H)-one
[(I), X=N, R2=benzyl, A=1H-benzimidazol-2-yl,
R1a=H, R1b=Me, R6a=5-chloro, R6b=H,
R3=R4=R5=H] cpd 51

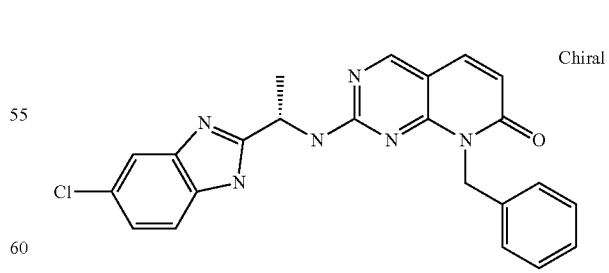

$^1$H NMR (500 MHz, DMSO-d$_6$) δ=12.09-12.60 (m, 1H), 8.59-8.74 (m, 1H), 8.40 (d, J=7.32 Hz, 1H), 7.78 (d, J=9.46 Hz, 1H), 7.58 (s, 1H), 7.54 (d, J=8.54 Hz, 1H), 7.12-7.18 (m, 1H), 7.09 (d, J=7.32 Hz, 2H), 6.86-7.05 (m, 3H), 6.31 (d, J=9.30 Hz, 1H), 5.28-5.51 (m, 2H), 5.08-5.16 (m, 1H), 1.55-1.65 (m, 3H). LCMS: m/z 431 [M+H]+ r.t. 5.57 min. HRMS (ESI) calcd for $C_{23}H_{20}ClN_6O$ [M+H]$^+$ 431.1382 found 431.139;

2-({(1S)-1-[3-(4-chlorophenyl)-1,2,4-oxadiazol-5-yl]ethyl}amino)-8-(2,2-dimethylpropyl)pyrido[2,3-d]pyrimidin-7(8H)-one [(I), X=N, R2=2,2-dimethylpropyl, A=1,2,4-oxadiazol-5-yl, R1a=H, R1b=Me, R6a=3-(4-chlorophenyl), R6b=H, R3=R4=R5=H]
cpd 52

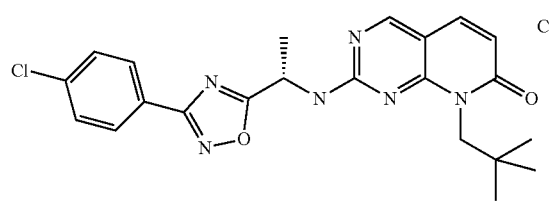

$^1$H NMR (500 MHz, DMSO-d$_6$) δ=8.51-8.71 (m, 2H), 7.93-8.01 (m, 2H), 7.74 (d, J=9.46 Hz, 1H), 7.63 (d, J=8.54 Hz, 2H), 6.30 (d, J=9.30 Hz, 1H), 5.31-5.59 (m, J=7.17 Hz, 1H), 3.85-4.35 (m, 3H), 1.69 (d, J=7.17 Hz, 3H), 1.59 (m, 9H). LCMS: m/z 439 [M+H]$^+$ r.t. 7.23 min. HRMS (ESI) calcd for $C_{22}H_{24}ClN_6O_2$[M+H]$^+$ 439.1644 found 439.164;

8-benzyl-2-({(1S)-1-[3-(4-chlorophenyl)-1,2,4-oxadiazol-5-yl]ethyl}amino)pyrido[2,3-d]pyrimidin-7(8H)-one [(I), X=N, R2=benzyl, A=1,2,4-oxadiazol-5-yl, R1a=H, R1b=Me, R6a=3-(4-chlorophenyl), R6b=H, R3=R4=R5=H] cpd 53

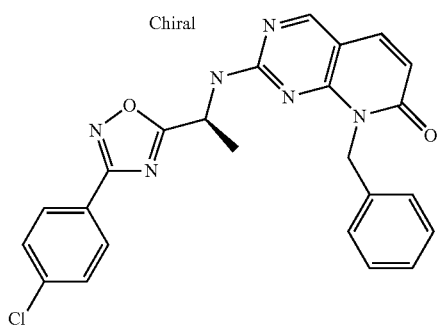 [SMILES: C[C@H](Nc1ncc2ccc(=O)n(Cc3ccccc3)c2n1)c1nc(-c2ccc(Cl)cc2)no1]

$^1$H NMR (500 MHz, DMSO-d$_6$) δ=8.72 (s, 1H), 8.69 (d, J=6.84 Hz, 1H), 7.91 (d, J=8.54 Hz, 2H), 7.81 (d, J=9.28 Hz, 1H), 7.61 (d, J=8.54 Hz, 2H), 6.96-7.17 (m, 5H), 6.35 (d, J=9.15 Hz, 1H), 5.39 (quin, J=7.00 Hz, 1H), 5.36 (d, J=13.79 Hz, 1H), 5.15 (d, J=14.28 Hz, 1H), 1.63 (d, J=7.08 Hz, 3H). LCMS: m/z 459 [M+H]$^+$ r.t. 6.97 min.

HRMS (ESI) calcd for $C_{24}H_{20}ClN_6O_2$[M+H]$^+$ 459.1331 found 459.1336;

8-(2,2-dimethylpropyl)-2-{[(1S)-1-(4-oxo-3,4-dihydroquinazolin-2-yl)ethyl]amino}pyrido[2,3-d]pyrimidin-7(8H)-one one [(I), X=N, R2=2,2-dimethylpropyl, A=4-oxo-3,4-dihydroquinazolin-2-yl, R1a=H, R1b=Me, R6a=R6b=H, R3=R4=R5=H]
cpd 54

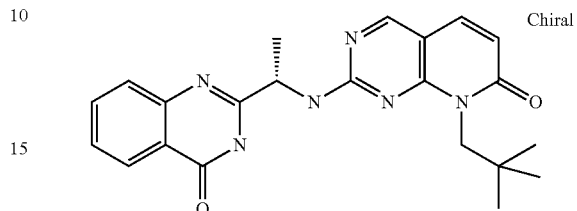

$^1$H NMR (500 MHz, DMSO-d$_6$) δ=12.37 (br. s., 1H), 8.64 (s, 1H), 8.00-8.12 (m, 2H), 7.64-7.79 (m, 2H), 7.56 (d, J=8.24 Hz, 1H), 7.42-7.53 (m, 2H), 6.25 (d, J=9.30 Hz, 1H), 4.91 (t, J=6.79 Hz, 1H), 3.90-4.07 (m, 1H), 1.56 (d, J=7.02 Hz, 3H), 0.70 (br. s., 9H). LCMS: m/z 405 [M+H]$^+$ r.t. 5.17 min. HRMS (ESI) calcd for $C_{22}H_{25}N_6O_2$ [M+H]$^+$ 405.2034 found 405.2041.

Example 3

Step 8: 2-{(S)-1-[4-(4,4-Difluoro-piperidin-1-ylmethyl)-phenyl]-ethylamino}-8-(3-hydroxy-2,2-dimethyl-propyl)-8H-pyrido[2,3-d]pyrimidin-7-one [(I), X=N, R2=3-hydroxy-2,2-dimethylpropyl, A=phenyl, R1a=H, R1b=Me, R6a=4-CH$_2$NR7R8, R6b=H, R7-R8=4,4-difluoropiperidin-1-yl, R3=R4=R5=H] step 1a, cpd 55

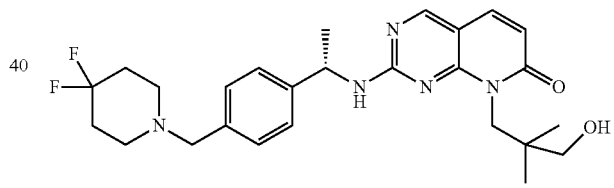

(S)-1-[4-(4,4-difluoro-piperidin-1-ylmethyl)-phenyl]-ethylamine (prepared as reported in WO2017019429) 13.5 mg, 0.053 mmol) was dissolved in DMSO (0.5 mL). To this solution is then sequentially added 8-(3-hydroxy-2,2-dimethyl-propyl)-2-methanesulfonyl-8H-pyrido[2,3-d]pyrimidin-7-one (15 mg, 0.048 mmol), CsF (8.0 mg, 0.053 mmol) and DIPEA (0.01 mL, 0.058 mmol). The reaction mixture is then heated at 75° C. for 4 hours and then allowed to warm to room temperature. The reaction mixture is slowly poured over cold water/brine. The precipitated solids are filtered, washed with water, and dried under vacuum. The dried solid obtained (16.1 mg, 69% yield) is taken forward without further purification.

$^1$H NMR (500 MHz, DMSO-d$_6$) δ=8.60 (s, 1H), 8.43 (d, J=7.5 Hz, 1H), 7.72 (d, J=9.3 Hz, 1H), 7.36 (d, J=7.6 Hz, 2H), 7.23 (d, J=7.8 Hz, 2H), 6.25 (d, J=9.2 Hz, 1H), 5.11 (quin, J=6.7 Hz, 1H), 4.56 (br. s., 1H), 4.35-3.88 (m, 2H), 3.48 (s, 2H), 3.04 (br. s., 2H), 2.43 (br. s., 4H), 1.91 (t, J=13.3 Hz, 4H), 1.46 (d, J=7.0 Hz, 3H), 1.04-0.31 (m, 6H). LCMS: m/z 486 [M+H]$^+$@ r.t. 6.22 min. HRMS (ESI) calcd for $C_{26}H_{34}F_2N_5O_2$[M+H]$^+$ 486.2675 found 486.2670.

According to the same method, the following compounds were prepared:

4-(4-{(S)-1-[8-(3-Hydroxy-2,2-dimethyl-propyl)-7-oxo-7,8-dihydro-pyrido[2,3-d]pyrimidin-2-ylamino]-ethyl}-benzyl)-piperazine-1-carboxylic acid tert-butyl ester [(I), X=N, R2=3-hydroxy-2,2-dimethylpropyl, A=phenyl, R1a=H, R1b=Me, R6a=4-CH$_2$NR7R8, R6b=H, R7-R8=4-piperazine-1-carboxylic acid tert-butyl ester, R3=R4=R5=H] cpd 56

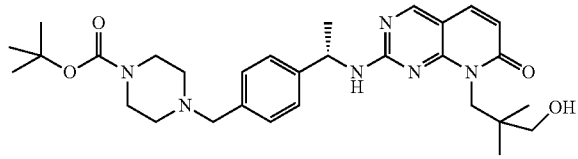 [SMILES: C[C@H](Nc1ncc2ccc(=O)n(CC(C)(C)CO)c2n1)c1ccc(CN2CCN(C(=O)OC(C)(C)C)CC2)cc1]

$^1$H NMR (500 MHz, DMSO-d$_6$) δ=8.60 (s, 1H), 8.43 (d, J=7.3 Hz, 1H), 7.72 (d, J=9.3 Hz, 1H), 7.35 (d, J=7.8 Hz, 2H), 7.22 (d, J=7.8 Hz, 2H), 6.25 (d, J=9.3 Hz, 1H), 5.11 (quin, J=7.2 Hz, 1H), 4.57 (br. s., 1H), 4.37-3.89 (m, 2H), 3.41 (s, 2H), 3.27 (br. s., 4H), 3.04 (br. s., 2H), 2.26 (br. s., 4H), 1.46 (d, J=6.9 Hz, 3H), 1.37 (s, 9H), 0.70 (br. s., 6H). LCMS: m/z 551 [M+H]$^+$@ r.t. 6.42 min. HRMS (ESI) calcd for C$_{30}$H$_{43}$N$_6$O$_4$ [M+H]$^+$ 551.3341 found 551.3344;

2-{(S)-1-[4-(3,3-Difluoro-piperidin-1-ylmethyl)-phenyl]-ethylamino}-8-(2,2-dimethyl-propyl)-6-fluoro-8H-pyrido[2,3-d]pyrimidin-7-one [(I), X=N, R2=2,2-dimethylpropyl, A=phenyl, R1a=H, R1b=Me, R6a=4-CH$_2$NR7R8, R6b=F, R7-R8=3,3-difluoropiperidin-1-yl, R3=R4=H, R5=F] cpd 57

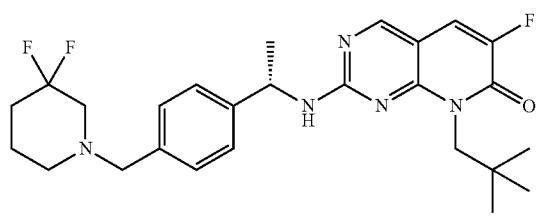 [SMILES: C[C@H](Nc1ncc2cc(F)c(=O)n(CC(C)(C)C)c2n1)c1ccc(CN2CCCC(F)(F)C2)cc1]

$^1$H NMR (500 MHz, DMSO-d$_6$) δ=8.58 (s, 1H), 8.37 (d, J=7.2 Hz, 1H), 7.69 (d, J=9.3 Hz, 1H), 7.33 (d, J=8.1 Hz, 2H), 7.26-7.11 (m, 2H), 5.04 (quin, J=7.0 Hz, 1H), 4.39-3.88 (m, 2H), 3.59-3.44 (m, 2H), 2.60-2.52 (m, 2H), 2.36 (br. s., 2H), 1.83 (qd, J=7.0, 13.5 Hz, 2H), 1.62 (quin, J=5.9 Hz, 2H), 1.46 (d, J=7.0 Hz, 3H), 0.72 (br. s., 9H). LCMS: m/z 488 [M+H]$^+$@ r.t. 7.55 min. HRMS (ESI) calcd for C$_{26}$H$_{33}$F$_3$N$_5$O [M+H]$^+$ 488.2632 found 488.2637;

2-{(S)-1-[4-(3,3-Difluoro-piperidin-1-ylmethyl)-phenyl]-ethylamino}-8-(2,2-dimethyl-propyl)-6-methoxy-8H-pyrido[2,3-d]pyrimidin-7-one [(I), X=N, R2=2,2-dimethylpropyl, A=phenyl, R1a=H, R1b=Me, R6a=4-CH$_2$NR7R8, R6b=H, R7-R8=3,3-difluoropiperidin-1-yl, R3=R4=H, R5=OMe] cpd 58

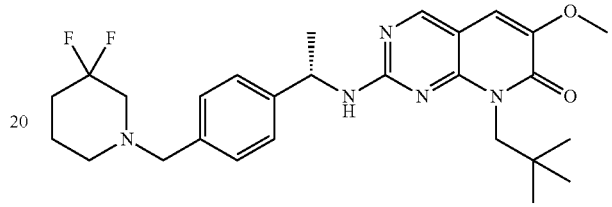

$^1$H NMR (500 MHz, DMSO-d$_6$) δ=8.50 (br. s., 1H), 8.01 (br. s., 1H), 7.33 (d, J=8.1 Hz, 2H), 7.20 (d, J=8.1 Hz, 2H), 7.07 (s, 1H), 5.01 (br. s., 1H), 4.38-3.95 (m, 2H), 3.73 (s, 3H), 3.50 (d, J=2.0 Hz, 2H), 2.57-2.43 (m, 4H), 1.90-1.76 (m, 2H), 1.67-1.57 (m, 2H), 1.44 (d, J=7.0 Hz, 3H), 0.70 (br. s., 9H).

LCMS: m/z 500 [M+H]$^+$@ r.t. 7.21 min. HRMS (ESI) calcd for C$_{27}$H$_{36}$F$_2$N$_5$O$_2$[M+H]$^+$ 500.2832 found 500.2827;

4-(4-{(S)-1-[8-(2,2-Dimethyl-propyl)-7-oxo-7,8-dihydro-pyrido[2,3-d]pyrimidin-2-ylamino]-ethyl}-benzyl)-piperazine-1-carboxylic acid tert-butyl ester [(I), X=N, R2=2,2-dimethylpropyl, A=phenyl, R1a=H, R1b=Me, R6a=4-CH$_2$NR7R8, R6b=H, R7-R8=4-piperazine-1-carboxylic acid tert-butyl ester, R3=R4=R5=H] cpd 59

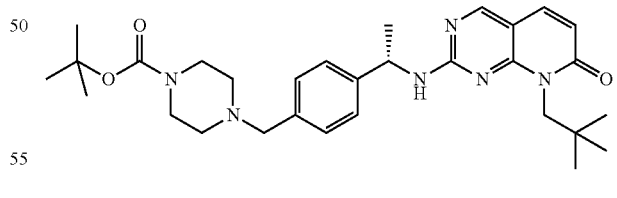

$^1$H NMR (500 MHz, DMSO-d$_6$) δ=8.57 (s, 1H), 8.36 (d, J=7.5 Hz, 1H), 7.67 (d, J=9.3 Hz, 1H), 7.32 (d, J=7.9 Hz, 2H), 7.22 (d, J=7.9 Hz, 2H), 6.22 (d, J=9.3 Hz, 1H), 5.06 (quin, J=7.0 Hz, 1H), 4.34-3.89 (m, 2H), 3.42 (s, 2H), 3.27 (br. s., 4H), 2.26 (br. s., 4H), 1.45 (d, J=7.0 Hz, 3H), 1.37 (s, 9H), 0.73 (br. s., 9H). LCMS: m/z 535 [M+H]$^+$@r.t. 7.43 min. HRMS (ESI) calcd for C$_{30}$H$_{43}$N$_6$O$_3$ [M+H]$^+$ 535.3391 found 535.3387;

2-{(S)-1-[4-(3,3-Difluoro-piperidin-1-ylmethyl)-phenyl]-ethylamino}-8-(2,2-dimethyl-propyl)-5-methyl-8H-pyrido [2,3-d]pyrimidin-7-one [(I), X=N, R2=2,2-dimethylpropyl, A=phenyl, R1a=H, R1b=Me, R6a=4-CH$_2$NR7R8, R6b=H, R7-R8=3,3-difluoropiperidin-1-yl, R3=R5=H, R4=Me] cpd 60

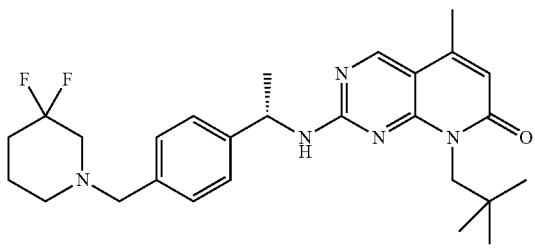 [SMILES: Cc1cc(=O)n(CC(C)(C)C)c2nc(N[C@@H](C)c3ccc(CN4CCCC(F)(F)C4)cc3)ncc12]

$^1$H NMR (500 MHz, DMSO-d$_6$) δ=8.64 (s, 1H), 8.32 (d, J=7.3 Hz, 1H), 7.32 (d, J=8.1 Hz, 2H), 7.21 (d, J=8.1 Hz, 2H), 6.09 (s, 1H), 5.05 (quin, J=7.0 Hz, 1H), 4.27-3.86 (m, 4H), 3.56-3.44 (m, 2H), 2.61-2.52 (m, 2H), 2.32 (s, 3H), 1.84 (tt, J=6.9, 13.6 Hz, 2H), 1.61 (quin, J=5.9 Hz, 2H), 1.46 (d, J=7.2 Hz, 3H), 1.01-0.47 (m, 9H). LCMS: m/z 484 [M+H]$^+$@ r.t. 7.48 min. HRMS (ESI) calcd for C$_{27}$H$_{36}$F$_2$N$_5$O [M+H]$^+$ 484.2883 found 484.2874;

8-(butan-2-yl)-2-{[(1S)-1-{4-[(3,3-difluoropiperidin-1-yl)methyl]phenyl}ethyl]amino}pyrido[2,3-d]pyrimidin-7(8H)-one [(I), X=N, R2=-butan-2-yl, A=phenyl, R1a=H, R1b=Me, R6a=4-CH$_2$NR7R8, R6b=H, R7-R8=3,3-difluoropiperidin-1-yl, R3=R4=R5=H] cpd 61

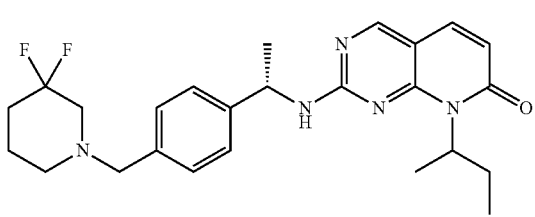 [SMILES: CCC(C)n1c(=O)ccc2cnc(N[C@@H](C)c3ccc(CN4CCCC(F)(F)C4)cc3)nc21]

$^1$H NMR (500 MHz, DMSO-d$_6$) δ=8.56 (br. s., 1H), 8.08-8.43 (m, 1H), 7.58-7.73 (m, 1H), 7.30 (br. s., 2H), 7.16-7.25 (m, 2H), 6.17 (br. s., 1H), 4.83-5.46 (m, 2H), 3.44-3.55 (m, 2H), 2.53-2.61 (m, 2H), 2.30-2.41 (m, 2H), 1.74-1.93 (m, J=6.79, 13.46, 13.46 Hz, 2H), 1.56-1.71 (m, 2H), 1.38-1.56 (m, 8H), 0.30-1.21 (m, 3H). LCMS: m/z 456 [M+H]$^+$@ r.t. 7.04 min. HRMS (ESI) calcd for C$_{25}$H$_{32}$F$_2$N$_5$O [M+H]$^+$ 456.257 found 456.2567;

8-[(2S)-butan-2-yl]-2-{[(1S)-1-{4-[(3,3-difluoropiperidin-1-yl)methyl]phenyl}ethyl]amino}pyrido[2,3-d]pyrimidin-7(8H)-one [(I), X=N, R2=-(2S)-butan-2-yl, A=phenyl, R1a=H, R1b=Me, R6a=4-CH$_2$NR7R8, R6b=H, R7-R8=3,3-difluoropiperidin-1-yl, R3=R4=R5=H] cpd 62

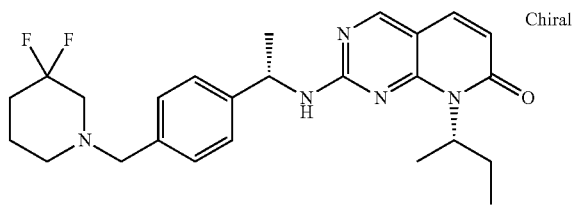 [SMILES: CC[C@H](C)n1c(=O)ccc2cnc(N[C@@H](C)c3ccc(CN4CCCC(F)(F)C4)cc3)nc21]

$^1$H NMR (500 MHz, DMSO-d$_6$) δ=8.56 (br. s., 1H), 8.08-8.43 (m, 1H), 7.58-7.73 (m, 1H), 7.30 (br. s., 2H), 7.16-7.25 (m, 2H), 6.17 (br. s., 1H), 4.83-5.46 (m, 2H), 3.44-3.55 (m, 2H), 2.53-2.61 (m, 2H), 2.30-2.41 (m, 2H), 1.74-1.93 (m, J=6.79, 13.46, 13.46 Hz, 2H), 1.56-1.71 (m, 2H), 1.38-1.56 (m, 8H), 0.30-1.21 (m, 3H). LCMS: m/z 456 [M+H]$^+$@ r.t. 7.03 min. HRMS (ESI) calcd for C$_{25}$H$_{32}$F$_2$N$_5$O [M+H]$^+$ 456.257 found 456.2574;

ethyl 2-[2-{[(1S)-1-{4-[(3,3-difluoropiperidin-1-yl)methyl]phenyl}ethyl]amino}-7-oxopyrido[2,3-d]pyrimidin-8(7H)-yl]propanoate [(I), X=N, R2=ethyl-2-propanoate, A=phenyl, R1a=H, R1b=Me, R6a=4-CH$_2$NR7R8, R6b=H, R7-R8=3,3-difluoropiperidin-1-yl, R3=R4=R5=H] cpd 63

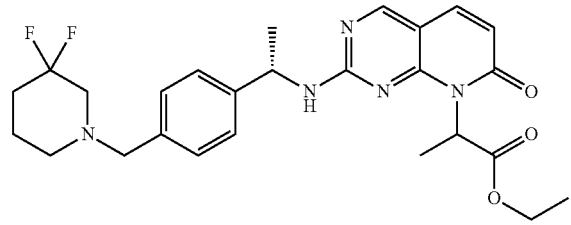 [SMILES: CCOC(=O)C(C)n1c(=O)ccc2cnc(N[C@@H](C)c3ccc(CN4CCCC(F)(F)C4)cc3)nc21]

$^1$H NMR (500 MHz, DMSO-d$_6$) δ=8.59-8.65 (m, 1H), 8.45-8.57 (m, 1H), 7.73 (d, J=9.30 Hz, 1H), 7.36 (dd, J=3.36, 7.93 Hz, 2H), 7.16-7.26 (m, 2H), 6.24 (d, J=13.95 Hz, 1H), 5.66-5.90 (m, 1H), 4.89-5.13 (m, 1H), 3.96-4.06 (m, 2H), 3.46-3.56 (m, 4H), 2.32-2.39 (m, 2H), 1.77-1.92 (m, 2H), 1.61 (br. s., 2H), 1.38-1.54 (m, 3H), 1.17 (d, J=7.17 Hz, 3H), 1.03 (t, J=7.09 Hz, 3H). LCMS: m/z 500 [M+H]$^+$@ r.t. 6.6 min. HRMS (ESI) calcd for C$_{26}$H$_{32}$F$_2$N$_5$O$_4$[M+H]$^+$ 500.2468 found 500.2463;

2-[2-{[(1S)-1-{4-[(3,3-difluoropiperidin-1-yl)
methyl]phenyl}ethyl]amino}-7-oxopyrido[2,3-d]
pyrimidin-8(7H)-yl]propanenitrile [(I), X=N,
R2=2-propanenitrile, A=phenyl, R1a=H, R1b=Me,
R6a=4-CH$_2$NR7R8, R6b=H, R7-R8=3,3-difluoropi-
peridin-1-yl, R3=R4=R5=H] cpd 64

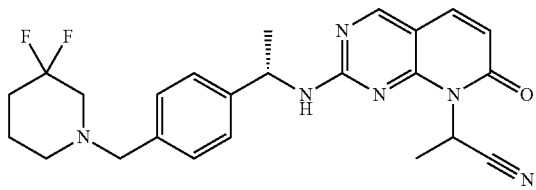 [SMILES: CC(C#N)n1c(=O)ccc2cnc(N[C@@H](C)c3ccc(CN4CCCC(F)(F)C4)cc3)nc21]

$^1$H NMR (500 MHz, DMSO-d$_6$) δ=8.60-8.73 (m, 2H), 7.72-7.80 (m, 1H), 7.42 (d, J=7.93 Hz, 1H), 7.36 (d, J=7.93 Hz, 1H), 7.17-7.28 (m, 2H), 6.23-6.53 (m, 2H), 5.08-5.34 (m, 1H), 3.44-3.55 (m, 2H), 2.53-2.58 (m, 2H), 2.31-2.38 (m, 2H), 1.77-1.88 (m, 2H), 1.56-1.63 (m, 2H), 1.46-1.51 (m, 6H). LCMS: m/z 453 [M+H]$^+$ @ r.t. 6.24 min.

HRMS (ESI) calcd for C$_{24}$H$_{27}$F$_2$N$_6$O [M+H]$^+$ 453.2209 found 453.2198;

2-{[(1S)-1-{4-[(3,3-difluoropiperidin-1-yl)methyl]
phenyl}ethyl]amino}-8-[(2S)-3-methylbutan-2-yl]
pyrido[2,3-d]pyrimidin-7(8H)-one [(I), X=N,
R2=-(2S)-3-methylbutan-2-yl, A=phenyl, R1a=H,
R1b=Me, R6a=4-CH$_2$NR7R8, R6b=H, R7-R8=3,3-
difluoropiperidin-1-yl, R3=R4=R5=H] cpd 65

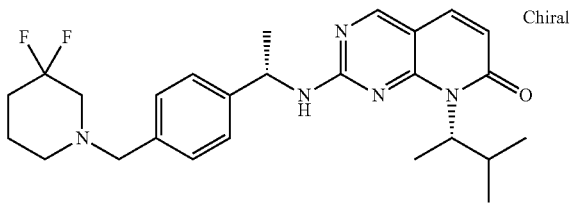 [SMILES: CC(C)[C@H](C)n1c(=O)ccc2cnc(N[C@@H](C)c3ccc(CN4CCCC(F)(F)C4)cc3)nc21]

$^1$H NMR (500 MHz, DMSO-d$_6$) δ=8.54-8.59 (m, 1H), 8.33-8.40 (m, 1H), 7.62-7.66 (d, J=10.8 Hz, 1H), 7.19-7.38 (m, 4H), 6.09-6.23 (m, 1H), 4.97-5.09 (m, 1H), 4.76-4.86 (m, 1H), 3.50 (br., s, 2H), 2.53-2.61 (m, 2H), 2.32-2.39 (m, 2H), 2.02-2.10 (m, 1H), 1.78-1.89 (m, 2H), 1.57-1.65 (m, 2H), 1.44-1.53 (m, 3H), 0.99-1.10 (m, 3H), 0.61-0.77 (m, 3H), 0.06-0.1 (d, J=6.1 Hz, 3H). LCMS: m/z 470 [M+H]$^+$ @ r.t. 7.22 min. HRMS (ESI) calcd for C$_{26}$H$_{34}$F$_2$N$_5$O [M+H]$^+$ 470.2726 found 470.2721;

8-[(1S)-1-cyclohexylethyl]-2-{[(1S)-1-{4-[(3,3-dif-
luoropiperidin-1-yl)methyl]phenyl}ethyl]amino}
pyrido[2,3-d]pyrimidin-7(8H)-one [(I), X=N,
R2=-(1S)-1-cyclohexylethyl, A=phenyl, R1a=H,
R1b=Me, R6a=4-CH$_2$NR7R8, R6b=H, R7-R8=3,3-
difluoropiperidin-1-yl, R3=R4=R5=H] cpd 66

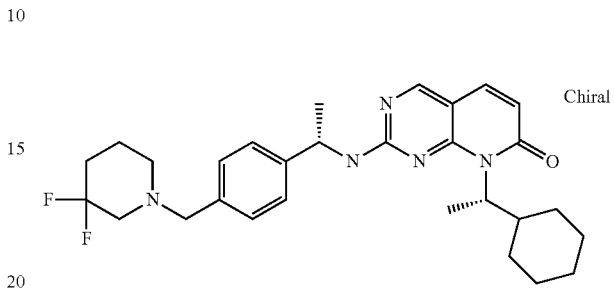

$^1$H NMR (500 MHz, DMSO-d$_6$) δ=8.53-8.59 (m, 1H), 8.35-8.40 (m, 1H), 7.62-7.66 (m, 1H), 7.19-7.38 (m, 4H), 6.08-6.23 (m, 1H), 5.10-5.21 (m, 1H), 4.79-4.97 (m, 1H), 3.47-3.54 (m, 4H), 2.53-2.61 (m, 2H), 2.32-2.39 (m, 2H), 1.74-2.06 (m, 4H), 1.43-1.66 (m, 5H), 0.66-1.44 (m, 9H), 0.42-0.52 (m, 1H). LCMS: m/z 510 [M+H]$^+$ @ r.t. 7.90 min. HRMS (ESI) calcd for C$_{29}$H$_{38}$F$_2$N$_5$O [M+H]$^+$ 510.3039 found 510.3040;

2-{[(1S)-1-{4-[(4,4-difluoropiperidin-1-yl)methyl]-
3-fluorophenyl}ethyl]amino}-8-[(2S)-3-methylbu-
tan-2-yl]pyrido[2,3-d]pyrimidin-7(8H)-one [(I),
X=N, R2=-(2S)-3-methylbutan-2-yl, A=phenyl,
R1a=H, R1b=Me, R6a=4-CH$_2$NR7R8, R6b=F,
R7-R8=4,4-difluoropiperidin-1-yl, R3=R4=R5=H]
cpd 67

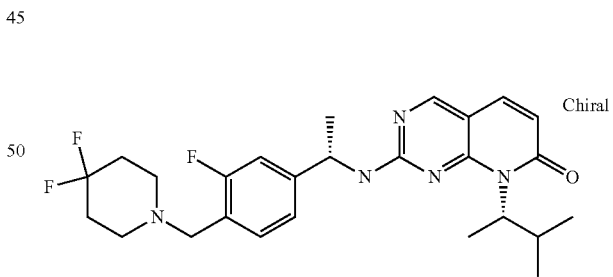

$^1$H NMR (500 MHz, DMSO-d$_6$) δ=8.53-8.61 (m, 1H), 8.34-8.42 (m, 1H), 7.62-7.68 (m, 1H), 7.32 (dd, J=7.63 Hz, 1H), 7.06-7.24 (m, 2H), 6.10-6.24 (m, 1H), 4.95-5.05 (m, 1H), 4.75-4.85 (m, 1H), 3.54 (br. s, 2H), 2.43-2.48 (m, 4H), 1.85-1.97 (m, 5H), 1.44-1.51 (m, 3H), 1.0-1.08 (m, 3H), 0.59-0.76 (m, 3H), 0.06-0.1 (d, J=6.71 Hz, 3H).

LCMS: m/z 488 [M+H]$^+$ r.t. 7.16 min. HRMS (ESI) calcd for C$_{26}$N$_{33}$F$_3$N$_5$O [M+H]$^+$ 488.2632 found 488.2639;

2-({(1S)-1-[3-fluoro-4-(morpholin-4-ylmethyl)phe-
nyl]ethyl}amino)-8-[(2S)-3-methylbutan-2-yl]pyrido
[2,3-d]pyrimidin-7(8H)-one [(I), X═N, R2=-(2S)-
3-methylbutan-2-yl, A=phenyl, R1a=H, R1b=Me,
R6a=4-CH₂NR7R8, R6b=F, R7-R8=morpholin-4-yl,
R3=R4=R5=H] cpd 68

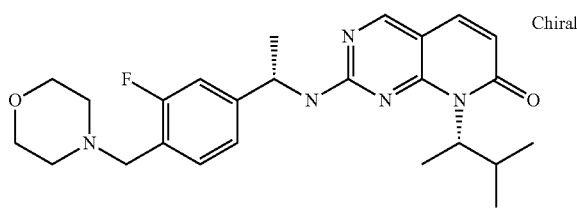 [SMILES: CC(C)[C@H](C)n1c(=O)ccc2cnc(N[C@@H](C)c3ccc(CN4CCOCC4)c(F)c3)nc21]

¹H NMR (500 MHz, DMSO-d₆) δ=8.54-8.61 (m, 1H), 8.33-8.42 (m, 1H), 7.62-7.67 (m, 1H), 7.31 (dd, J=7.63 Hz, 1H), 7.05-7.21 (m, 2H), 6.10-6.25 (m, 1H), 4.94-5.05 (m, 1H), 4.75-4.86 (m, 1H), 3.52 (br. s, 4H), 3.44 (br., s, 2H), 2.33 (br. s., 4H), 1.92-1.97 (m, 1H), 1.43-1.51 (m, 3H), 1.0-1.08 (m, 3H), 0.54-0.76 (m, 3H), 0.05-0.1 (d, J=6.71 Hz, 3H). LCMS: m/z 454 [M+H]⁺ r.t. 6.07 min. HRMS (ESI) calcd for C₂₅H₃₃N₅O₂ [M+H]⁺454.2613 found 454.2612;

2-{[(1S)-1-{4-[(3,3-difluoropiperidin-1-yl)methyl]
phenyl}ethyl]amino}-8-[(2S)-3,3-dimethylbutan-2-
yl]pyrido [2,3-d]pyrimidin-7(8H)-one [(I), X═N,
R2=-(2S)-3,3-dimethylbutan-2-yl, A=phenyl,
R1a=H, R1b=Me, R6a=4-CH₂NR7R8, R6b H,
R7-R8=3,3-difluoropiperidin-1-yl, R3=R4=R5=H]
cpd 69

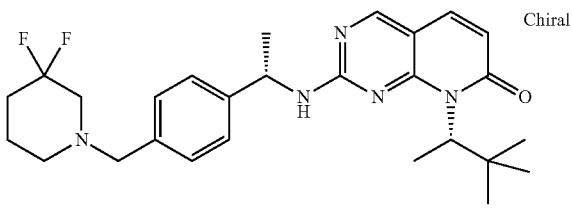 [SMILES: C[C@H](Nc1ncc2ccc(=O)n([C@@H](C)C(C)(C)C)c2n1)c1ccc(CN2CCCC(F)(F)C2)cc1]

¹H NMR (500 MHz, DMSO-d₆) δ=8.54 (s, 1H), 8.38 (d, J=6.56 Hz, ¹H), 7.61 (d, J=9.15 Hz, 1H), 7.30 (d, J=7.93 Hz, 2H), 7.21 (d, J=7.93 Hz, 2H), 6.10 (d, J=9.30 Hz, 1H), 5.41 (q, J=7.02 Hz, 1H), 4.90 (quin, J=6.86 Hz, 1H), 3.45-3.56 (m, 2H), 2.53-2.61 (m, 2H), 2.33-2.40 (m, 2H), 1.78-1.90 (m, 2H), 1.57-1.65 (m, 2H), 1.48 (d, J=6.86 Hz, 3H), 1.15-1.22 (m, 3H), 0.98 (s, 9H). LCMS: m/z 484 [M+H]⁺@ r.t. 7.64 min. HRMS (ESI) calcd for C₂₇H₃₆F₂N₅O [M+H]⁺ 484.2883 found 484.2876;

8-(2,2-dimethylpropyl)-2-{[(1S)-1-phenylpropyl]
amino}pyrido[2,3-d]pyrimidin-7(8H)-one [(I),
X═N, R2=-2,2-dimethylpropyl, A=phenyl, R1a=H,
R1b=Ethyl, R6a=R6b=H, R3=R4=R5=H] cpd 70

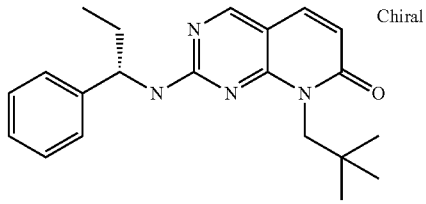 [SMILES: CC[C@H](Nc1ncc2ccc(=O)n(CC(C)(C)C)c2n1)c1ccccc1]

¹H NMR (500 MHz, DMSO-d₆) δ=8.56 (s, 1H), 8.37 (d, J=7.93 Hz, 1H), 7.67 (d, J=9.30 Hz, 1H), 7.38 (d, J=7.17 Hz, 2H), 7.30 (t, J=7.55 Hz, 2H), 7.14-7.25 (m, 1H), 6.22 (d, J=9.30 Hz, 1H), 4.76-5.09 (m, 1H), 3.96-4.32 (m, 2H), 1.65-1.93 (m, 2H), 0.85-0.98 (m, 3H), 0.80 (br. s, 9H). LCMS: m/z 351 [M+H]⁺ r.t. 7.16 min. HRMS (ESI) calcd for C₂₁H₂₇N₄O [M+H]⁺351.2180 found 351.2180.

8-(2,2-Dimethyl-propyl)-2-[(S)-1-(4-hydroxy-phe-
nyl)-ethylamino]-8H-pyrido[2,3-d]pyrimidin-7-one
[(I), X═N, R2=-2,2-dimethylpropyl, A=phenyl,
R1a=H, R1b=Me, R6a=OH, R6b=H,
R3=R4=R5=H] cpd 145

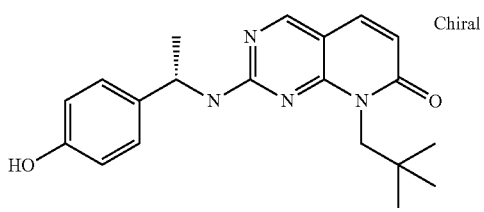 [SMILES: C[C@H](Nc1ncc2ccc(=O)n(CC(C)(C)C)c2n1)c1ccc(O)cc1]

¹H NMR (500 MHz, DMSO-d₆) δ=9.21 (s, 1H), 8.55 (s, 1H), 8.25 (d, J=7.5 Hz, 1H), 7.67 (d, J=9.2 Hz, 1H), 7.17 (d, J=8.4 Hz, 2H), 6.67 (d, J=8.2 Hz, 2H), 6.22 (d, J=9.2 Hz, 1H), 4.88-5.26 (m, 1H), 4.05-4.30 (m, 2H), 1.42 (d, J=7.0 Hz, 3H), 0.82 (br. s, 9H). LCMS: m/z 353 [M+H]⁺@ r.t. 5.78 min
HRMS (ESI) calcd for C₂₀H₂₅N₄O₂ [M+H]⁺ 353.1972 found 353.1976

4-(4-{(S)-1-[8-((S)-1,2-Dimethyl-propyl)-7-oxo-7,8-
dihydro-pyrido[2,3-d]pyrimidin-2-ylamino]-ethyl}-
phenoxy)-piperidine-1-carboxylic acid benzyl ester
[(I), X═N, R2=—(S)-1,2-Dimethyl-propyl),
A=phenyl, R1a=H, R1b=Me, R6a=—O—R7,
R6b=H, R7=4-piperidine-1-carboxylic acid benzyl
ester, R3=R4=R5=H] cpd 146

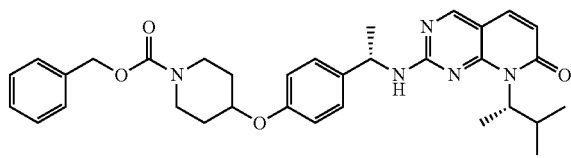 [SMILES: CC(C)[C@H](C)n1c(=O)ccc2cnc(N[C@@H](C)c3ccc(OC4CCN(C(=O)OCc5ccccc5)CC4)cc3)nc21]

¹H NMR (500 MHz, DMSO-d₆) δ=8.50-8.62 (m, 1H), 8.23-8.37 (m, 1H), 7.64 (d, J=9.3 Hz, 1H), 7.15-7.42 (m, 7H), 6.90 (d, J=8.5 Hz, 2H), 6.04-6.29 (m, 1H), 4.77-5.33 (m, 4H), 4.51 (spt, J=4.0 Hz, 1H), 3.68 (br. s., 2H), 3.26 (br. s., 2H), 1.40-2.11 (m, 8H), 0.13-1.19 (m, 9H). LCMS: m/z 570 [M+H]⁺@ r.t. 7.59 min HRMS (ESI) calcd for $C_{33}H_{40}N_5O_4$ [M+H]⁺ 570.3075 found 570.3100

2-{[(1S)-1-{4-[(3,3-difluoroazetidin-1-yl)methyl]phenyl}ethyl]amino}-8-(2,2-dimethylpropyl)pyrido[2,3-d]pyrimidin-7(8H)-one [(I), X=N, R2=2,2-dimethylpropyl, A=phenyl, R1a=H, R1b=Me, R6a=4-CH₂NR7R8, R6b=H, R7-R8=-(3,3-difluoroazetidin-1-yl, R3=R4=R5=H] cpd 147

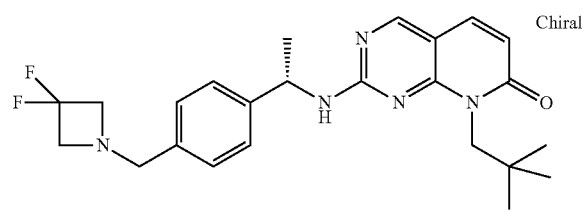 [SMILES: C[C@H](Nc1ncc2ccc(=O)n(CC(C)(C)C)c2n1)c1ccc(CN2CC(F)(F)C2)cc1]

¹H NMR (500 MHz, DMSO-d₆) δ=8.57 (s, 1H), 8.36 (d, J=7.47 Hz, 1H), 7.67 (d, J=9.30 Hz, 1H), 7.33 (d, J=7.93 Hz, 2H), 7.22 (d, J=7.93 Hz, 2H), 6.22 (d, J=9.30 Hz, 1H), 5.07 (quin, J=7.17 Hz, 1H), 3.93-4.32 (m, 2H), 3.65 (s, 2H), 3.54 (t, J=12.43 Hz, 4H), 1.45 (d, J=7.02 Hz, 3H), 0.76 (br. s., 9H). LCMS: m/z 442 [M+H]⁺@ r.t. 6.77 min. HRMS (ESI) calcd for $C_{24}H_{30}N_5O$ [M+H]⁺ 442.2413 found 442.2423.

2-{[(1S)-1-{4-[(3,3-difluoropyrrolidin-1-yl)methyl]phenyl}ethyl]amino}-8-(2,2-dimethylpropyl)pyrido[2,3-d]pyrimidin-7(8H)-one [(I), X=N, R2=2,2-dimethylpropyl, A=phenyl, R1a=H, R1b=Me, R6a=4-CH₂NR7R8, R6b=H, R7-R8=-(3,3-difluoropyrrolidin-1-yl, R3=R4=R5=H] cpd 148

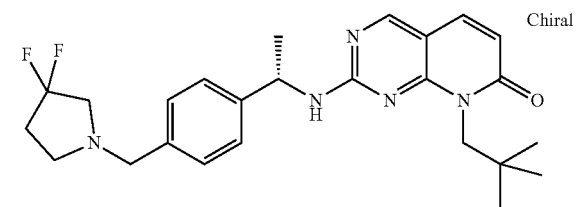 [SMILES: C[C@H](Nc1ncc2ccc(=O)n(CC(C)(C)C)c2n1)c1ccc(CN2CCC(F)(F)C2)cc1]

¹H NMR (500 MHz, DMSO-d₆) δ=8.58 (s, 1H), 8.36 (d, J=7.32 Hz, 1H), 7.67 (d, J=9.30 Hz, 1H), 7.33 (d, J=8.08 Hz, 2H), 7.23 (d, J=7.78 Hz, 2H), 6.22 (d, J=9.15 Hz, 1H), 5.06 (quin, J=7.21 Hz, 1H), 3.87-4.34 (m, 2H), 3.55 (s, 2H), 2.72-2.88 (m, 2H), 2.64 (d, J=6.41 Hz, 2H), 2.13-2.29 (m, 2H), 1.46 (d, J=7.02 Hz, 3H), 0.73 (br. s., 9H).

LCMS: m/z 456 [M+H]⁺@ r.t. 7.13 min. HRMS (ESI) calcd for $C_{25}H_{32}N_5O$ [M+H]⁺ 456.257 found 456.2582.

8-[(2R)-butan-2-yl]-2-{[(1S)-1-{4-[(3,3-difluoropiperidin-1-yl)methyl]phenyl}ethyl]amino}pyrido[2,3-d]pyrimidin-7(8H)-one [(I), X=N, R2=-(2R)-butan-2-yl, A=phenyl, R1a=H, R1b=Me, R6a=4-CH₂NR7R8, R6b=H, R7-R8=-(3,3-difluoropiperidin-1-yl, R3=R4=R5=H] cpd 149

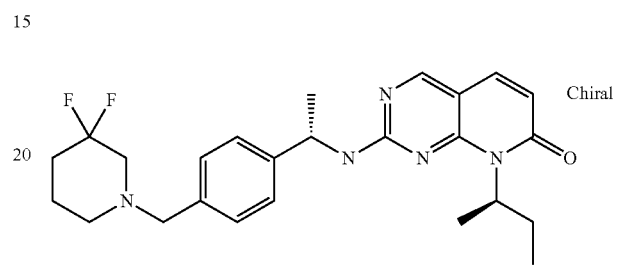

¹H NMR (500 MHz, DMSO-d₆) δ=8.58 (s, 1H), 8.36 (d, J=7.32 Hz, 1H), 7.67 (d, J=9.30 Hz, 1H), 7.33 (d, J=8.08 Hz, 2H), 7.23 (d, J=7.78 Hz, 2H), 6.22 (d, J=9.15 Hz, 1H), 5.06 (quin, J=7.21 Hz, 1H), 3.87-4.34 (m, 2H), 3.55 (s, 2H), 2.72-2.88 (m, 2H), 2.64 (d, J=6.41 Hz, 2H), 2.13-2.29 (m, 2H), 1.46 (d, J=7.02 Hz, 3H), 0.73 (br. s., 9H).

LCMS: m/z 456 [M+H]⁺@ r.t. 7.02 min. HRMS (ESI) calcd for $C_{25}H_{32}F_2N_5O$ [M+H]⁺ 456.257 found 456.2568.

2-{[(1S)-1-(4-{[(2R,6S)-2,6-dimethylmorpholin-4-yl]methyl}-3-fluorophenyl)ethyl]amino}-8-[(2S)-3-methylbutan-2-yl]pyrido[2,3-d]pyrimidin-7(8H)-one [(I), X=N, R2=-(2S)-3-methylbutan-2-yl, A=phenyl, R1a=H, R1b=Me, R6a=4-CH₂NR7R8, R6b F, R7-R8 (2R,6S)-2,6-dimethylmorpholin-4-yl, R3=R4=R5=H] cpd 150

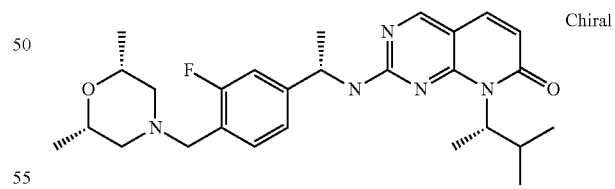

¹H NMR (500 MHz, DMSO-d₆) δ=8.60 (s, 1H), 8.36 (d, J=7.47 Hz, 1H), 7.65 (d, J=9.60 Hz, 1H), 7.30 (t, J=7.47 Hz, 1H), 7.05-7.21 (m, 2H), 6.22 (d, J=9.60 Hz, 1H), 4.95-5.03 (m, 1H), 4.76-4.85 (m, 1H), 3.46-3.54 (m, 2H), 3.43 (s, 2H), 2.59-2.67 (m, 4H), 1.59-1.68 (m, 1H), 1.48 (m, 3H), 0.95-1.08 (m, 9H), 0.73 (d, J=6.25 Hz, 3H), 0.08 (d, J=6.25 Hz, 3H). LCMS: m/z 482 [M+H]⁺@ r.t. 6.77 min. HRMS (ESI) calcd for $C_{27}H_{37}FN_5O_2$ [M+H]⁺ 482.2926 found 482.2931.

121

2-{[(1S)-1-(4-{[(2R,6S)-2,6-dimethylmorpholin-4-yl]methyl}-2-fluorophenyl)ethyl]amino}-8-(2,2-dimethyl propyl)pyrido[2,3-d]pyrimidin-7(8H)-one [(I), X=N, R2=2,2-dimethylpropyl, A=phenyl, R1a=H, R1b=Me, R6a=4-CH$_2$NR7R8, R6b=F, R7-R8=(2R,6S)-2,6-dimethylmorpholin-4-yl, R3=R4=R5=H] cpd 151

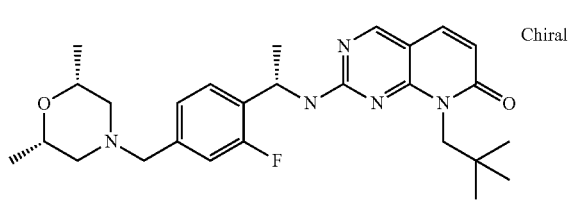 [SMILES: C[C@@H]1CN(Cc2ccc([C@H](C)Nc3ncc4ccc(=O)n(CC(C)(C)C)c4n3)c(F)c2)C[C@H](C)O1 ; "Chiral"]

$^1$H NMR (500 MHz, DMSO-d$_6$) δ=8.59 (s, 1H), 8.44 (d, J=7.32 Hz, 1H), 7.68 (d, J=9.30 Hz, 1H), 7.33 (t, J=8.01 Hz, 1H), 7.08 (d, J=11.13 Hz, 1H), 7.04 (d, J=7.78 Hz, 1H), 6.23 (d, J=9.30 Hz, 1H), 5.33 (quin, J=6.98 Hz, 1H), 3.86-4.35 (m, 2H), 3.47-3.63 (m, 2H), 3.37-3.45 (m, 2H), 2.57-2.71 (m, 2H), 1.54-1.71 (m, 2H), 1.45 (d, J=7.02 Hz, 3H), 0.99 (d, J=6.25 Hz, 6H), 0.70 (br. s., 9H). LCMS: m/z 482 [M+H]$^+$@ r.t. 7.08 min. HRMS (ESI) calcd for C$_{27}$H$_{37}$FN$_5$O$_2$[M+H]$^+$ 482.2926 found 482.2931.

2-{[(1S)-1-{4-[(4,4-difluoropiperidin-1-yl)methyl]-2-fluorophenyl}ethyl]amino}-8-(2,2-dimethylpropyl)pyrido [2,3-d]pyrimidin-7(8H)-one [(I), X=N, R2=2,2-dimethylpropyl, A=phenyl, R1a=H, R1b=Me, R6a=4-CH$_2$NR7R8, R6b=2-F, R7-R8=4,4-difluoropiperidin-1-yl, R3=R4=R5=H] cpd 152

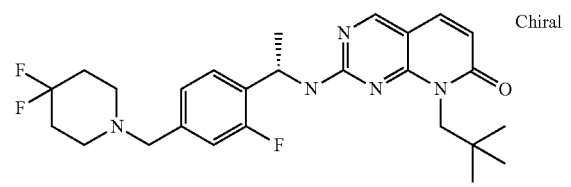 [SMILES: C[C@H](Nc1ncc2ccc(=O)n(CC(C)(C)C)c2n1)c1ccc(CN2CCC(F)(F)CC2)cc1F ; "Chiral"]

$^1$H NMR (500 MHz, DMSO-d$_6$) δ=8.59 (s, 1H), 8.45 (d, J=7.47 Hz, 1H), 7.68 (d, J=9.30 Hz, 1H), 7.35 (t, J=7.85 Hz, 1H), 7.11 (d, J=11.44 Hz, 1H), 7.06 (dd, J=0.92, 7.93 Hz, 1H), 6.24 (d, J=9.30 Hz, 1H), 5.35 (quin, J=7.05 Hz, 1H), 3.92-4.34 (m, 2H), 3.50 (d, J=2.14 Hz, 2H), 2.44 (br. s., 4H), 1.82-2.02 (m, 4H), 1.45 (d, J=7.02 Hz, 3H), 0.71 (br. s., 9H). LCMS: m/z 488 [M+H]$^+$@ r.t. 7.43 min. HRMS (ESI) calcd for C$_{26}$H$_{33}$F$_3$N$_5$O [M+H]$^+$ 488.2632 found 488.2637.

122

8-(2,2-dimethylpropyl)-2-({(1S)-1-[2-fluoro-4-(morpholin-4-ylmethyl)phenyl]ethyl}amino)pyrido[2,3-d]-pyrimidin-7(8H)-one [(I), X=N, R2=2,2-dimethylpropyl, A=phenyl, R1a=H, R1b=Me, R6a=4-CH$_2$NR7R8, R6b=2-F, R7-R8=morpholin-4-yl, R3=R4=R5=H] cpd 153

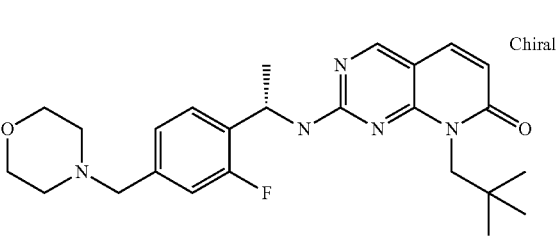 [SMILES: C[C@H](Nc1ncc2ccc(=O)n(CC(C)(C)C)c2n1)c1ccc(CN2CCOCC2)cc1F ; "Chiral"]

$^1$H NMR (500 MHz, DMSO-d$_6$) δ=8.59 (s, 1H), 8.45 (d, J=7.63 Hz, 1H), 7.68 (d, J=9.30 Hz, 1H), 7.34 (t, J=7.93 Hz, 1H), 7.09 (d, J=11.29 Hz, 1H), 7.06 (dd, J=1.07, 7.93 Hz, 1H), 6.23 (d, J=9.30 Hz, 1H), 5.35 (quin, J=7.02 Hz, 1H), 3.86-4.33 (m, 2H), 3.54 (t, J=4.35 Hz, 4H), 3.37-3.45 (m, 2H), 2.31 (br. s., 4H), 1.45 (d, J=7.02 Hz, 3H), 0.72 (br. s., 9H). LCMS: m/z 454 [M+H]$^+$@ r.t. 6.33 min. HRMS (ESI) calcd for C$_{25}$H$_{33}$FN$_5$O$_2$[M+H]$^+$ 454.2613 found 454.2603.

2-{[(1S)-1-(4-bromophenyl)ethyl]amino}-8-[(2S)-3-methylbutan-2-yl]pyrido[2,3-d]pyrimidin-7(8H)-one [(I), X=N, R2=-(2S)-3-methylbutan-2-yl, A=phenyl, R1a=H, R1b=Me, R6a=Br, R6b=H, R3=R4=R5=H] cpd 163

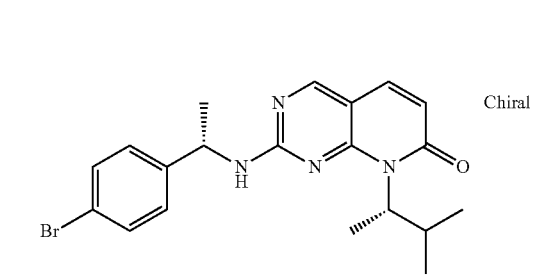 [SMILES: CC(C)[C@H](C)n1c(=O)ccc2cnc(N[C@@H](C)c3ccc(Br)cc3)nc21 ; "Chiral"]

$^1$H NMR (500 MHz, DMSO-d$_6$) δ=8.60 (s, 1H), 8.34 (d, J=7.44 Hz, 1H), 7.65 (d, J=9.70 Hz, 1H), 7.49 (d, J=8.41 Hz, 2H), 7.31 (d, J=8.41 Hz, 2H), 6.23 (d, J=9.70 Hz, 1H), 4.88-4.98 (m, 1H), 4.73-4.85 (m, 1H), 1.66-1.75 (m, 1H), 1.46 (d, J=7.12 Hz, 3H), 1.10 (d, J=6.71 Hz, 3H), 0.71 (d, J=6.41 Hz, 3H), 0.08 (d, J=6.71 Hz, 3H). LCMS m/z 415 [M+H]$^+$@ r.t. 7.14 min. HRMS (ESI) calcd for C$_{20}$H$_{24}$BrN$_4$O [M+H]$^+$ 415.1128 found 415.1143.

2-{[(1S)-1-(4-{[(2R,6S)-2,6-dimethylmorpholin-4-yl]methyl}phenyl)ethyl]amino}-8-[(2S)-1,1,1-trifluoropropan-2-yl]pyrido[2,3-d]pyrimidin-7(8H)-one [(I), X=N, R2=-(2S)-1,1,1-trifluoropropan-2-yl, A=phenyl, R1a=H, R1b=Me, R6a=4-CH₂NR7R8, R6b=H, R7-R8=(2R,6S)-2,6-dimethylmorpholin-4-yl, R3=R4=R5=H] cpd 164

8-[(1S)-1-cyclopropylethyl]-2-{[(1S)-1-(4-{[(2R,6S)-2,6-dimethylmorpholin-4-yl]methyl}-3-fluorophenyl)ethyl]amino}pyrido[2,3-d]pyrimidin-7(8H)-one [(I), X=N, R2=(1S)-1-cyclopropylethyl, A=phenyl, R1a=H, R1b=Me, R6a=4-CH₂NR7R8, R6b=, R7-R8=(2R,6S)-2,6-dimethylmorpholin-4-yl, R3=R4=R5=H] cpd 170

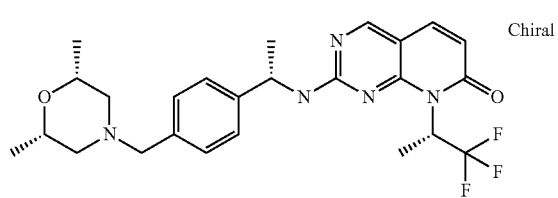 [SMILES: C[C@@H]1CN(Cc2ccc([C@H](C)Nc3ncc4ccc(=O)n([C@@H](C)C(F)(F)F)c4n3)cc2)C[C@H](C)O1 ; "Chiral"]

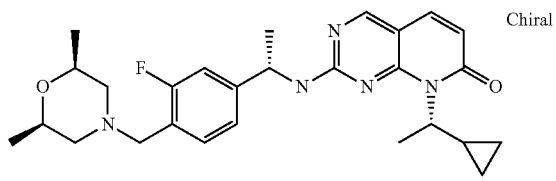

¹H NMR (500 MHz, DMSO-d₆) δ=8.63 (m, 2H), 7.72 (d, J=9.46 Hz, 1H), 7.20-7.31 (m, 4H), 6.18 (d, J=9.45 Hz, 1H), 6.01-6.10 (m, 1H), 4.79 (quin, J=6.7 Hz, 1H), 3.48-3.51 (m, 2H), 3.37-3.45 (m, 2H), 2.57-2.71 (m, 2H), 1.87 (d, J=7.17 Hz, 1H), 1.56-1.71 (m, 3H), 1.46 (d, J=6.86 Hz, 3H), 0.95-1.05 (m, 6H). LCMS: m/z 490 [M+H]⁺@r.t. 6.35 min. HRMS (ESI) calcd for C₂₅H₃₇F₃N₅O₂[M+H]⁺ 490.2425 found 490.2415.

¹H NMR (500 MHz, DMSO-d₆) δ=8.53-8.59 (br. s., 1H), 8.34-8.41 (br. s., 1H), 7.65 (d, J=9.3 Hz, 1H), 7.19-7.33 (m, 4H), 6.14 (d, J=9.3 Hz, 1H), 4.89-5.00 (br. m., 1H), 4.54 (br. m, 1H), 3.52 (br. s., 2H), 3.37 (s., 2H), 2.57-2.67 (m, 4H), 1.80 (m, 1H) 1.41-1.61 (m, 6H), 0.97 (m, 6H), 0.25-0.64 (m, 4H). LCMS: m/z 462 [M+H]⁺@ r.t. 6.26 min. HRMS (ESI) calcd for C₂₇H₃₆N₅O₂ [M+H]⁺ 462.2864 found 462.2872.

2-{[(1S)-1-{4-[(3,3-difluoropiperidin-1-yl)methyl]phenyl}ethyl]amino}-8-(propan-2-yl)pyrido[2,3-d]pyrimidin-7(8H)-one [(I), X=N, R2=propan-2-yl, A=phenyl, R1a=H, R1b=Me, R6a=4-CH₂NR7R8, R6b=, R7-R8=(3,3-difluoropiperidin-1-yl, R3=R4=R5=H] cpd 170

2-{[(1S)-1-(6-chloro-2-oxo-1,2-dihydroquinolin-3-yl)ethyl]amino}-8-[(2S)-3-methylbutan-2-yl]pyrido[2,3-d]pyrimidin-7(8H)-one [(I), X=N, R2=(2S)-3-methylbutan-2-yl, A=2-oxo-quinolin-3-yl, R1a=H, R1b=Me, R6a=6-chloro, R6b=H, R3=R4=R5=H] step 1a, cpd 172

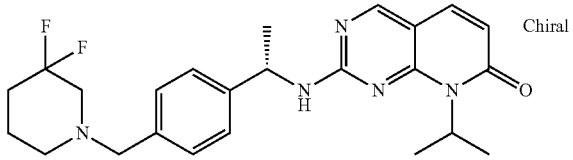 [SMILES: CC(C)n1c(=O)ccc2cnc(N[C@@H](C)c3ccc(CN4CCCC(F)(F)C4)cc3)nc21 ; "Chiral"]

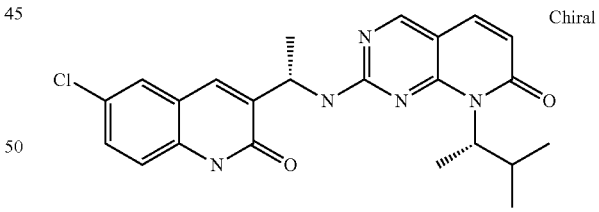

¹H NMR (500 MHz, DMSO-d₆) δ=8.56 (br. s., 1H), 8.36 (d, J=6.71 Hz, 1H), 7.62 (d, J=9.15 Hz, 1H), 7.33 (d, J=7.93 Hz, 2H), 7.21 (d, J=7.93 Hz, 2H), 6.15 (d, J=9.15 Hz, 1H), 5.44-5.56 (br. s., 1H), 4.99 (m, 2H), 3.49 (br. s., 2H), 2.53-2.61 (m, 2H), 2.31-2.35 (m, 2H), 1.74-1.93 (m, J=6.79, 13.46, 13.46 Hz, 2H), 1.56-1.71 (m, 2H), 1.38-1.56 (m, 9H). LCMS: m/z 442 [M+H]⁺@ r.t. 6.77 min. HRMS (ESI) calcd for C₂₄H₃₀F₂N₅O [M+H]⁺ 442.2413 found 442.2418.

¹H NMR (500 MHz, DMSO-d₆) δ=12.04 (s, 1H), 8.63 (s, 1H), 8.27 (d, J=5.95 Hz, 1H), 7.72 (d, J=1.98 Hz, 1H), 7.66 (d, J=9.00 Hz, 1H), 7.55 (s, 1H), 7.46 (dd, J=2.21, 8.62 Hz, 1H), 7.31 (d, J=8.85 Hz, 1H), 6.21 (d, J=9.30 Hz, 1H), 4.93-5.08 (m, 1H), 4.71 (q., J=6.86 Hz, 1H), 1.84-1.93 (m, 1H), 1.47 (d, J=6.86 Hz, 3H), 1.41 (d, J=6.86 Hz, 3H), 0.98 (d, J=6.71 Hz, 3H), 0.61 (d, J=6.41 Hz, 3H). −0.24 (d, J=6.71 Hz, 3H). LCMS: m/z 438 [M+H]⁺ r.t. 5.68 min. HRMS (ESI) calcd for C₂₃H₂₄ClN₅O₂[M+H]⁺ 438.1692 found 438.1685.

8-[(2S)-3-methylbutan-2-yl]-2-({(1S)-1-[4-(morpholin-4-yl)phenyl]ethyl}amino)pyrido[2,3-d]pyrimidin-7(8H)-one [(I), X=N, R2=(2S)-3-methylbutan-2-yl, A=phenyl, R1a=H, R1b=Me, R6a=4-NR7R8, R6b=H, R7-R8=morpholin-4-yl R3=R4=R5=H] step 1a, cpd 173

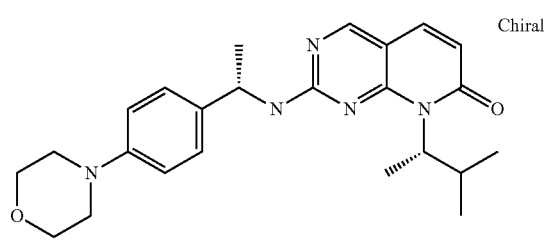 [SMILES: CC(C)[C@H](C)n1c(=O)ccc2cnc(N[C@@H](C)c3ccc(N4CCOCC4)cc3)nc21 ; "Chiral"]

¹H NMR (500 MHz, DMSO-d₆) δ=8.56 (s., 1H), 8.24 (d, J=7.02 Hz, 1H), 7.64 (d, J=9.15 Hz, 1H), 7.23 (d, J=8.69 Hz, 1H), 7.16 (d, J=8.69 Hz, 1H), 6.87 (d, J=8.69 Hz, 2H), 6.19 (d, J=9.15 Hz, 1H), 4.78-5.15 (br. m., 2H), 3.71 (m, 4H), 3.02 (m, 4H), 1.41-1.52 (m, 4H), 0.98-1.22 (m, 3H), 0.61-0.80 (m, 3H), 0.12-0.17 (m, 3H). LCMS: m/z 422 [M+H]⁺ r.t. 6.3 min. HRMS (ESI) calcd for $C_{24}H_{31}N_5O_2$ [M+H]⁺ 422.2551 found 422.2545.

Benzyl-4-{4-[(1S)-1-({8-[(2S)-3-methylbutan-2-yl]-7-oxo-7,8-dihydropyrido[2,3-d]pyrimidin-2-yl}amino) ethyl]phenyl}piperazine-1-carboxylate [(I), X=N, R2=(2S)-3-methylbutan-2-yl, A=phenyl, R1a=H, R1b=Me, R6a=4-NR7R8, R6b=H, R7-R8=benzyl-piperazine-1-carboxylate, R3=R4=R5=H] step 1a, cpd 174

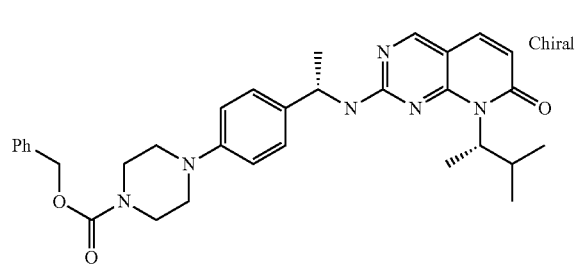 [SMILES: CC(C)[C@H](C)n1c(=O)ccc2cnc(N[C@@H](C)c3ccc(N4CCN(C(=O)OCc5ccccc5)CC4)cc3)nc21 ; "Chiral"]

¹H NMR (500 MHz, DMSO-d₆) δ=8.55 (br. s., 1H), 8.24 (d, J=7.32 Hz, 1H), 7.63 (d, J=9.30 Hz, 1H), 7.28-7.42 (m, 5H), 7.23 (d, J=8.69 Hz, 1H), 7.15 (d, J=8.69 Hz, 1H), 6.89 (d, J=8.69 Hz, 2H), 6.20 (d, J=9.30 Hz, 1H), 5.09 (s, 2H), 4.77-4.97 (br. m., 2H), 3.51 (br. s., 4H), 3.04 (br. s., 4H), 1.41-1.52 (m, 4H), 1.16-1.21 (br. m, 3H), 0.55-0.75 (m, 3H), 0.13 (d, J=6.56 Hz, 3H). LCMS: m/z 555 [M+H]⁺ r.t. 7.38 min. HRMS (ESI) calcd for $C_{32}H_{39}N_6O_3$ [M+H]⁺ 555.3078 found 555.3092.

8-[(2S)-3-methylbutan-2-yl]-2-({(1S)-1-[4-(piperazin-1-yl)phenyl]ethyl}amino)pyrido[2,3-d]pyrimidin-7(8H)-one [(I), X=N, R2=(2S)-3-methylbutan-2-yl, A=phenyl, R1a=H, R1b=Me, R6a=4-NR7R8, R6b=H, R7-R8=piperazin-1-yl, R3=R4=R5=H] step 1a, cpd 176

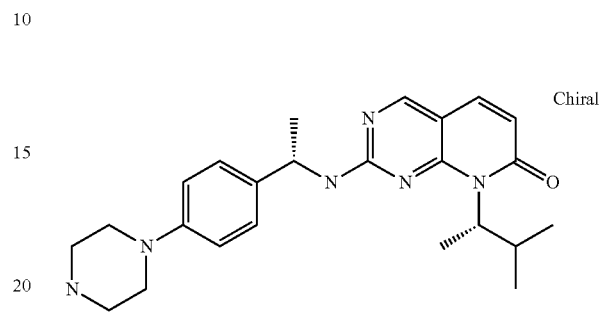

¹H NMR (500 MHz, DMSO-d₆) δ=8.56 (s., 1H), 8.24 (m, 1H), 7.64 (m, 1H), 7.11-7.26 (m, 2H), 6.9 (d, J=8.69 Hz, 2H), 6.19 (m, 1H), 4.78-5.15 (br. m., 2H), 3.21 (m, 4H), 3.14 (m, 4H), 1.41-1.52 (m, 4H), 0.98-1.22 (m, 3H), 0.61-0.80 (m, 3H), 0.12-0.17 (m, 3H). LCMS: m/z 421 [M+H]⁺ r.t. 4.98 min. HRMS (ESI) calcd for $C_{24}H_{33}N_6O$ [M+H]⁺ 421.2711 found 421.2714.

2-({(1S)-1-[4-(4-ethylpiperazin-1-yl)phenyl]ethyl}amino)-8-[(2S)-3-methylbutan-2-yl]pyrido[2,3-d]pyrimidin-7(8H)-one [(I), X=N, R2=(2S)-3-methylbutan-2-yl, A=phenyl, R1a=H, R1b=Me, R6a=4-NR7R8, R6b=H, R7-R8=4-ethylpiperazin-1-yl, R3=R4=R5=H] step 1a, cpd 177

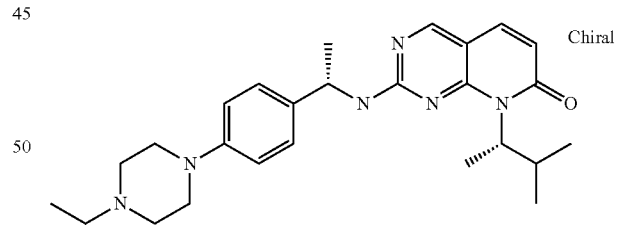

¹H NMR (500 MHz, DMSO-d₆) δ=8.56 (br., s., 1H), 8.25 (d, J07, 0.32 Hz, 1H), 7.63 (d, J=9.30 Hz, 1H), 7.21 (d, J=8.54 Hz, 1H), 7.13 (d, J=8.54 Hz, 1H), 6.85 (d, J=8.54 Hz, 2H), 6.19 (d, J=9.30 Hz, 1H), 4.75-5.19 (m, 2H), 3.05 (br. s., 4H), 2.46 (br. s., 4H), 2.34 (q, J=7.10 Hz, 2H), 1.41-1.52 (m, 4H), 1.03-1.22 (m, 3H), 1.01 (t, J=7.17 Hz, 3H), 0.61-0.79 (m, 3H), 0.14 (d, J=6.56 Hz, 3H). LCMS: m/z 449 [M+H]⁺ r.t. 5.25 min. HRMS (ESI) calcd for $C_{26}H_{37}N_6O$ [M+H]⁺ 449.3024 found 449.3021.

Benzyl 4-{2-fluoro-4-[(1S)-1-({8-[(2S)-3-methylbutan-2-yl]-7-oxo-7,8-dihydropyrido[2,3-d]pyrimidin-2-yl}amino)ethyl]phenyl}piperazine-1-carboxylate [(I), X=N, R2=(2S)-3-methylbutan-2-yl, A=phenyl, R1a=H, R1b=Me, R6a=4-NR7R8, R6b=F, R7-R8=benzyl-piperazine-1-carboxylate, R3=R4=R5=H] step 1a, cpd 178

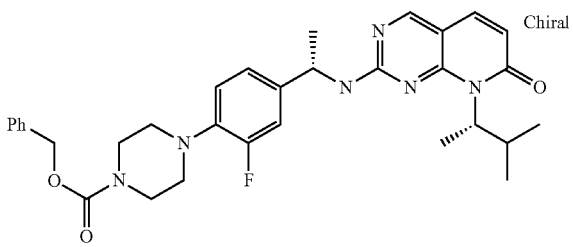 [SMILES: CC(C)[C@H](C)n1c(=O)ccc2cnc(N[C@@H](C)c3ccc(N4CCN(C(=O)OCc5ccccc5)CC4)c(F)c3)nc21 ; "Chiral"]

$^1$H NMR (500 MHz, DMSO-d$_6$) δ=8.59 (s, 1H), (8.29 (d, J=7.17 Hz, 1H), 7.65 (dd, J=3.97, 9.00 Hz, 1H), 7.27-7.42 (m, 5H), 6.95-7.15 (m, 3H), 6.05-6.30 (m, 1H), 5.09 (s, 2H), 4.92 (m, 1H), 4.79 (m, 1H), 3.53 (br. s., 4H), 2.91 (br. s., 4H), 1.95 (m, 1H), 1.41-1.49 (m, 3H), 1.02-1.11 (m, 3H), 0.59-0.77 (m, 3H), 0.09-0.13 (m, 3H). LCMS: m/z 573 [M+H]$^+$ r.t. 7.48 min. HRMS (ESI) calcd for C$_{32}$H$_{38}$FN$_6$O$_3$ [M+H]$^+$ 573.2984 found 573.3004.

8-[(2S)-3-methylbutan-2-yl]-2-({(1S)-1-[6-(piperazin-1-yl)pyridin-3-yl]ethyl}amino)pyrido[2,3-d]pyrimidin-7(8H)-one [(I), X=N, R2=(2S)-3-methylbutan-2-yl, A pyridin-3-yl, R1a=H, R1b=Me, R6a=4-NR7R8, R6b=H, R7-R8=piperazin-1-yl, R3=R4=R5=H] step 1a, cpd 180

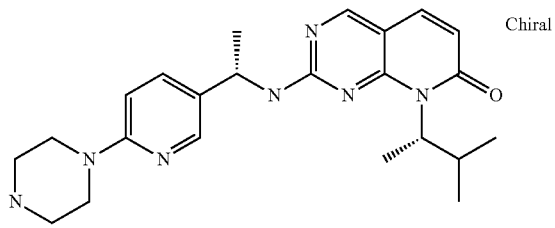 [SMILES: CC(C)[C@H](C)n1c(=O)ccc2cnc(N[C@@H](C)c3ccc(N4CCNCC4)nc3)nc21]

$^1$H NMR (500 MHz, DMSO-d$_6$) δ 8.57 (s, 1H), 8.25 (m, 1H), 8.11 br., s, 1H), 7.65 (d, J=9.30 Hz, 1H), 7.44 (d, J=8.39 Hz, 1H), 6.74 (d, J=8.39 Hz, 1H), 6.22 (d, J=9.30 Hz, 1H), 4.91 (m, 1H), 4.80 (m, 1H), 3.33 (m, 4H), 2.76 (m, 4H), 2.07 (m, 1H), 1.43-1.52 (m, 3H), 0.98-1.08 (m, 3H), 0.55-0.81 (m, 3H), 0.17 (d, J=6.56 Hz, 1H). LCMS: m/z 422 [M+H]$^+$ r.t. 4.63 min. HRMS (ESI) calcd for C$_{23}$H$_{32}$N$_{70}$ [M+H]$^+$ 422.266 found 422.267.

tert-butyl 4-(4-{(1S)-1-[(8-ethyl-7-oxo-7,8-dihydropyrido[2,3-d]pyrimidin-2-yl)amino]ethyl}benzyl)piperazine-1-carboxylate [(I), X=N, R2=ethyl, A=phenyl, R1a=H, R1b=Me, R6a=4-CH$_2$NR7R8, R6b=H, R7-R8=4-piperazine-1-carboxylic acid tert-butyl ester, R3=R4=R5=H] cpd 185

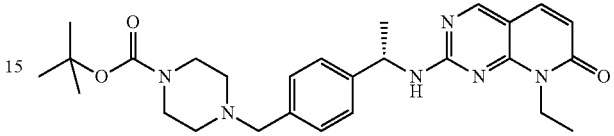

$^1$H NMR (500 MHz, DMSO-d$_6$) δ=8.58 (s, 1H), 8.43 (d, J=7.17 Hz, 1H), 7.66 (d, J=9.30 Hz, 1H), 7.47 (d, J=8.08 Hz, 1H), 7.42 (d, J=8.08 Hz, 1H), 7.33 (d, J=8.08 Hz, 1H), 7.22 (d, J=8.08 Hz, 1H), 6.21 (d, J=9.30 Hz, 1H), 5.03 (q, J=7.1 Hz, 1H), 4.46 (s, 2H), 4.01-4.21 (m, 2H), 3.58 (s, 2H), 3.38-3.47 (br. s, 8H), 1.47 (d, J=7.02 Hz, 3H), 1.38 (s, 9H), 0.89 (m, 3H). LCMS: m/z 493 [M+H]$^+$@r.t. 6.37 min. HRMS (ESI) calcd for C$_2$H$_{36}$N$_6$O$_3$ [M+H]$^+$ 493.2922 found 493.2921;

8-[(2S)-3-methylbutan-2-yl]-2-{[(1S)-1-{4-[(4-methyl-3-oxopiperazin-1-yl)methyl]phenyl}ethyl]amino}-pyrido [2,3-d]pyrimidin-7(8H)-one carboxylate [(I), X=N, R2=(2S)-3-methylbutan-2-yl, A=phenyl, R1a=H, R1b=Me, R6a=4-CH$_2$NR7R8, R6b=H, R7-R8=-4-methyl-3-oxopiperazin-1-yl, R3=R4=R5=H] cpd 188

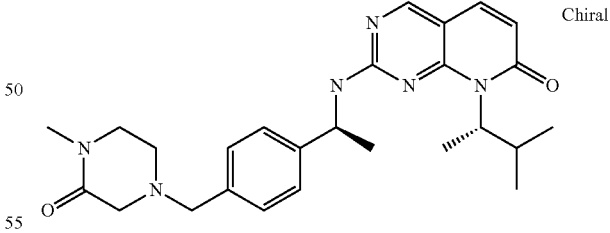

$^1$H NMR (500 MHz, DMSO-d$_6$) δ=8.56 (s. 1H), 8.37 (d, J=7.32 Hz, 1H), 7.64 (d, J=9.30 Hz, 1H), 7.21-7.37 (m, 4H), 6.04-6.29 (m, 1H), 4.69-5.09 (m, 2H), 3.46 (s, 2H), 3.17-3.25 (m, J=4.73 Hz, 2H), 2.91 (br. s., 2H), 2.78 (s, 3H), 2.58 (br. quin, J=4.70 Hz, 2H), 1.44-1.54 (m, 4H), 0.99-1.09 (m, 3H), 0.58-0.76 (m, 3H), 0.08 (d, J=6.56 Hz, 3H). LCMS: m/z 463 [M+H]$^+$@ r.t. 5.52 min. HRMS (ESI) calcd for C$_{27}$H$_{35}$N$_6$O$_2$ [M+H]$^+$ 463.2816 found 463.2819;

tert-butyl 4-(4-{(1S)-1-[(8-ethyl-7-oxo-7,8-dihydro-pyrido[2,3-d]pyrimidin-2-yl)amino]ethyl}benzoyl)piperazine-1-carboxylate [(I), X=N, R2=ethyl, A=phenyl, R1a=H, R1b=Me, R6a=4-CH₂NR7R8, R6b=H, R7-R8=4-piperazine-1-carboxylic acid tert-butyl ester, R3=R4=R5=H] cpd 189

Phenyl 4-[(1S)-1-{4-[(1S)-1-{[7-oxo-8-(propan-2-yl)-7,8-dihydropyrido[2,3-d]pyrimidin-2-yl]amino}ethyl]phenyl}propyl]piperazine-1-carboxylate [(I), X=N, R2=propan-2-yl, A=phenyl, R1a=H, R1b=Me, R6a=4-CHR14NR7R8, R6b=H, R7-R8=4-piperazine-1-carboxylic acid phenyl ester, R14=Ethyl, R3=R4=R5=H] cpd 225

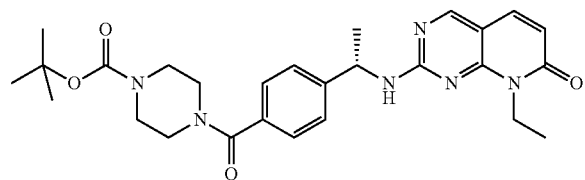 [SMILES: CCn1c(=O)ccc2cnc(N[C@@H](C)c3ccc(C(=O)N4CCN(C(=O)OC(C)(C)C)CC4)cc3)nc21]

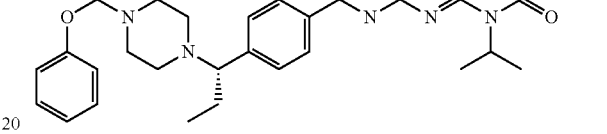

¹H NMR (500 MHz, DMSO-d₆) δ=8.59 (s, 1H), 8.49 (d, J=7.17 Hz, 1H), 7.68 (d, J=9.30 Hz, 1H), 7.46 (d, J=8.24 Hz, 2H), 7.35 (d, J=8.24 Hz, 2H), 6.21 (d, J=9.30 Hz, 1H), 5.05 (quin, J=6.90 Hz, 1H), 3.94-4.35 (m, 2H), 3.37-3.62 (m, 8H), 1.49 (d, J=7.02 Hz, 3H), 1.39 (s, 9H), 0.89 (t, J=6.86 Hz, 3H). LCMS: m/z 507 [M+H]⁺@ r.t. 5.78 min. HRMS (ESI) calcd for C₂₇H₃₅N₆O₄ [M+H]⁺ 507.2715 found 507.2722;

¹H NMR (500 MHz, DMSO-d₆) δ=8.57 (s, 1H), 8.33 (d, J=7.93 Hz, 1H), 7.63 (d, J=9.3 Hz, 1H), 7.36 (d, J=7.78 Hz, 2H), 7.32 (d, J=7.78 Hz, 2H), 7.17 (d, J=7.78 Hz, 2H), 7.16 (d, J=7.78 Hz, 1H), 7.01 (d, J=7.78 Hz, 1H), 6.16 (d, J=9.3 Hz, 2H), 5.48 (br.s, 1H), 5.00 (br. s., 1H), 3.50 (br. s., 4H), 3.36 (m, 1H), 2.30 (br.s., 4H), 1.82-1.92 (m, 1H), 1.63-1.73 (m, 1H), 1.48 (d, J=6.9 Hz, 3H), 0.96 (br. s., 6H), 0.67-0.74 (m, 3H). LCMS: m/z 555 [M+H]+@ r.t. 8.68 min. HRMS (ESI) calcd for C₃₂H₃₉N₆O₃ [M+H]⁺ 555.3078 found 555.3085;

tert-butyl 4-{4-[(1S)-1-{[4-cyano-8-(2,2-dimethyl-propyl)-7-oxo-7,8-dihydropyrido[2,3-d]pyrimidin-2-yl]amino}ethyl]benzyl}piperazine-1-carboxylate [(I), X=N, R2=2,2-dimethylpropyl, A=phenyl, R1a=H, R1b=Me, R6a=4-CH₂NR7R8, R6b=H, R7-R8=4-piperazine-1-carboxylic acid tert-butyl ester, R3=CN, R4=R5=H] cpd 200

Phenyl 4-[(1R)-1-{4-[(1S)-1-{[7-oxo-8-(propan-2-yl)-7,8-dihydropyrido[2,3-d]pyrimidin-2-yl]amino}ethyl]phenyl}propyl]piperazine-1-carboxylate [(I), X=N, R2=propan-2-yl, A=phenyl, R1a=H, R1b=Me, R6a=4-CHR14NR7R8, R6b=H, R7-R8=4-piperazine-1-carboxylic acid phenyl ester, R14=Ethyl, R3=R4=R5=H] cpd 226

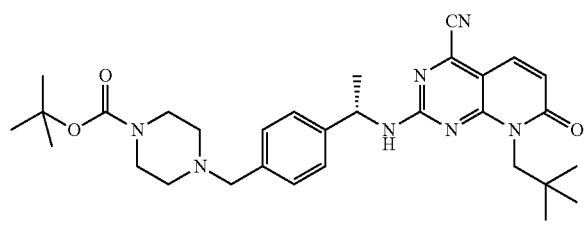 [SMILES: C[C@H](Nc1nc(C#N)c2ccc(=O)n(CC(C)(C)C)c2n1)c1ccc(CN2CCN(C(=O)OC(C)(C)C)CC2)cc1]

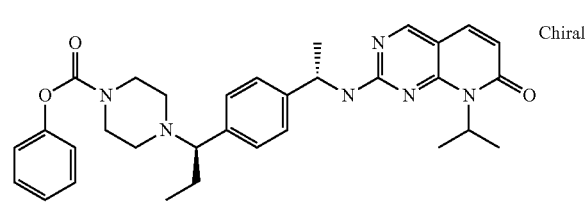 [SMILES: CC[C@H](c1ccc([C@H](C)Nc2ncc3ccc(=O)n(C(C)C)c3n2)cc1)N1CCN(C(=O)Oc2ccccc2)CC1]

¹H NMR (500 MHz, DMSO-d₆) δ=8.93 (d, J=7.47 Hz, 1H), 7.71 (d, J=9.46 Hz, 1H), 7.32 (d, J=8.08 Hz, 2H), 7.23 (d, J=7.78 Hz, 2H), 6.42 (d, J=9.46 Hz, 1H), 5.05 (q, J=7.02 Hz, 1H), 3.96 (dd, J=12.51 Hz, 2H), 3.43 (s, 2H), 3.28 (br. s., 4H), 2.20-2.32 (m, J=4.27 Hz, 4H), 1.46 (d, J=7.02 Hz, 3H), 1.37 (s, 9H), 0.91 (s, 3H), 0.72 (br.s, 6H).
LCMS: m/z 560 [M+H]⁺@ r.t. 10.34 min. HRMS (ESI) calcd for C₃₁H₄₁N₇O₃ [M+H]⁺ 560.3344 found 560.3362;

¹H NMR (500 MHz, DMSO-d₆) δ=8.57 (s, 1H), 8.33 (d, J=7.93 Hz, 1H), 7.63 (d, J=9.3 Hz, 1H), 7.36 (d, J=7.78 Hz, 2H), 7.32 (d, J=7.78 Hz, 2H), 7.17 (d, J=7.78 Hz, 2H), 7.16 (d, J=7.78 Hz, 1H), 7.01 (d, J=7.78 Hz, 1H), 6.16 (d, J=9.3 Hz, 2H), 5.48 (br.s, 1H), 5.00 (br. s., 1H), 3.50 (br. s., 4H), 3.36 (m, 1H), 2.30 (br.s., 4H), 1.82-1.92 (m, 1H), 1.63-1.73 (m, 1H), 1.48 (d, J=6.9 Hz, 3H), 0.96 (br. s., 6H), 0.67-0.74 (m, 3H). LCMS: m/z 555 [M+H]+@ r.t. 8.68 min. HRMS (ESI) calcd for C₃₂H₃₉N₆O₃ [M+H]⁺ 555.3078 found 555.3085.

2-{[(1S)-1-{4-[(2E)-pent-2-en-3-yl]phenyl}ethyl]amino}-8-(propan-2-yl)pyrido[2,3-d]pyrimidin-7(8H)-one [(I), X=N, R2=propan-2-yl, A=phenyl, R1a=H, R1b=Me, R6a=(2E)-pent-2-en-3-yl, R6b=H, R3=R4=R5=H] cpd 250

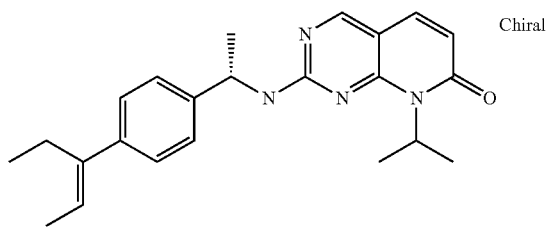 [SMILES: C/C=C(\CC)c1ccc([C@H](C)Nc2ncc3ccc(=O)n(C(C)C)c3n2)cc1]

$^1$H NMR (500 MHz, DMSO-$d_6$) δ=8.51-8.60 (m, 1H), 8.36 (d, J=7.17 Hz, 1H), 7.62 (d, J=9.15 Hz, 1H), 7.25-7.36 (m, 4H), 7.15 (m, 1H), 6.15 (d, J=9.00 Hz, 1H), 5.42-5.82 (m, 1H), 5.00 (br. s., 1H), 2.44 (q, J=7.32 Hz, 2H), 1.74 (d, J=6.71 Hz, 3H), 1.24-1.54 (m, 9H), 0.87 (t, J=7.8 Hz, 3H). LCMS: m/z 377 [M+H]$^+$@ r.t. 13.71 min.

Example 4

2-{[(1S)-1-(4-chlorophenyl)ethyl]amino}-8-(3-hydroxybenzyl)pyrido[2,3-d]pyrimidin-7(8H)-one [(I), X=N, R2=3-hydroxybenzyl, A=phenyl, R1a=H, R1b=Me, R6a=4-Cl, R6b=H, R3=R4=R5=H] conv. 13, cpd 71

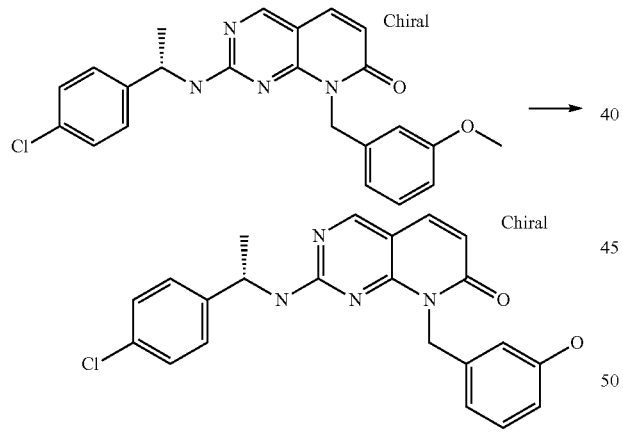

To a stirred suspension of 2-{[(1S)-1-(4-chlorophenyl)ethyl]amino}-8-(3-methoxybenzyl)pyrido[2,3-d]pyrimidin-7(8H)-one (50 mg, 0.12 mM) prepared as described in example 1, in anhydrous dichloromethane (5 mL) was added dropwise, under argon, 1 M BBr$_3$ solution (1 mL, 1 mmol) in DCM at 0° C. The ice bath was removed and the mixture was stirred at room temperature overnight. The reaction was diluted with DCM and washed with NaHCO$_3$ satured solution, then with water and brine. After drying over Na$_2$SO$_4$, the solvent was removed to give a crude that was purified by chromatographic column and eluted with DCM/MeOH 95/5, to afford the title compound (34 mg, 70% yield).

$^1$H NMR (500 MHz, DMSO-$d_6$) δ=9.29 (s, 1H), 8.61 (s, 1H), 8.44 (d, J=7.93 Hz, 1H), 7.76 (d, J=9.46 Hz, 1H), 7.21-7.30 (m, 3H), 7.00 (t, J=7.70 Hz, 1H), 6.60 (d, J=7.63 Hz, 1H), 6.51-6.57 (m, 2H), 6.30 (d, J=9.30 Hz, 1H), 5.37 (d, J=14.18 Hz, 1H), 5.12 (d, J=14.34 Hz, 1H), 4.97-5.07 (m, 1H), 1.38-1.46 (m, 4H).

LCMS: m/z 407 [M+H]$^+$ r.t. 6.05 min. HRMS (ESI) calcd for $C_{22}H_{20}ClN_4O_2$[M+H]$^+$ 407.127 found 407.1276.

According to the same method, the following compounds were prepared:

2-{[(1S)-1-(4-chlorophenyl)ethyl]amino}-8-(4-hydroxybenzyl)pyrido[2,3-d]pyrimidin-7(8H)-one [(I), X=N, R2=4-hydroxybenzyl, A=phenyl, R1a=H, R1b=Me, R6a=4-Cl, R6b=H, R3=R4=R5=H] cpd 72

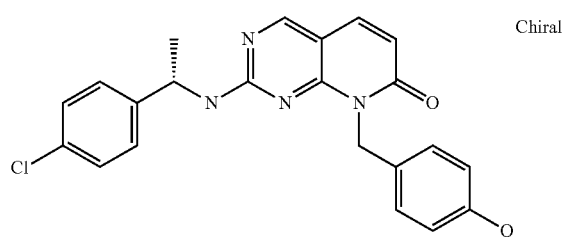 [SMILES: C[C@H](Nc1ncc2ccc(=O)n(Cc3ccc(O)cc3)c2n1)c1ccc(Cl)cc1]

$^1$H NMR (500 MHz, DMSO-$d_6$) δ=9.10-9.70 (m, 1H), 8.61 (s, 1H), 8.48 (d, J=7.63 Hz, 1H), 7.72 (d, J=9.30 Hz, 1H), 7.28-7.38 (m, 4H), 6.96 (d, J=8.39 Hz, 2H), 6.55 (d, J=8.24 Hz, 2H), 6.26 (d, J=9.30 Hz, 1H), 5.32 (d, J=13.88 Hz, 1H), 5.11 (quin, J=6.90 Hz, 1H), 5.05 (d, J=14.03 Hz, 1H), 1.45 (d, J=6.86 Hz, 3H). LCMS: m/z 407 [M+H]$^+$ r.t. 5.93 min. HRMS (ESI) calcd for $C_{22}H_{20}ClN_4O_2$[M+H]$^+$ 407.127 found 407.1274;

Example 5

4-[(1S)-1-{[8-(2,6-difluorobenzyl)-7-oxo-pyrido[2,3-d]pyrimidin-2-yl]amino}ethyl]benzoic acid [(I), X=N, R2=2,6-difluorobenzyl, A=phenyl, R1a=H, R1b=Me, R6a=4-C$_{oo}$H, R6b=H, R3=R4=R5=H] conv. 3, cpd 73

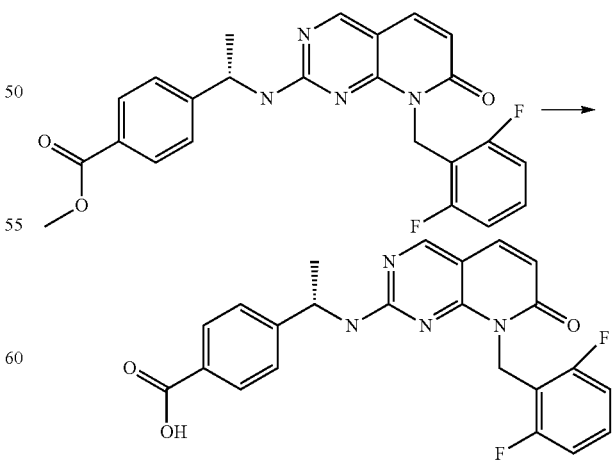

Lithium hydroxyde (0.022 g, 0.52 mmol) was added to a solution of methyl 4-[(1S)-1-{[8-(2,6-difluorobenzyl)-7- oxo-7,8-dihydropyrido[2,3-d]pyrimidin-2-yl]amino}ethyl]benzoate (0.030 g, 0.07 mmol) in THF:water (1:1, 2 mL) and the reaction mixture was stirred at room temperature for 18 h. The solvent (THF) was removed under reduced pressure and the aqueous residue was diluted with water. The aqueous phase was acidified with hydrochloric acid (1 M) until a precipitation occurred, the solid was filtered, washed with water and dried under vacuum, to give the title compound as a white solid (0.029 g, 99% yield).

$^1$H NMR (500 MHz, DMSO-$d_6$) δ=12.77 (br. s., 1H), 8.61 (s, 1H), 8.47 (d, J=7.93 Hz, 1H), 7.66-7.93 (m, 3H), 7.39 (d, J=8.08 Hz, 2H), 7.19-7.35 (m, 1H), 6.87-7.05 (m, 2H), 6.24 (d, J=9.15 Hz, 1H), 5.53 (d, J=15.25 Hz, 1H), 5.28 (d, J=15.25 Hz, 1H), 4.98-5.15 (m, 1H), 1.38-1.53 (m, 3H). LCMS: m/z 437 [M+H]$^+$ r.t. 4.94 min.

HRMS (ESI) calcd for $C_{23}H_{19}F_2N_4O_3$[M+H]$^+$ 437.142 found 437.1413.

According to the same method, the following compounds were prepared:

4-[(1S)-1-{[8-(2-fluorobenzyl)-7-oxo-pyrido[2,3-d]pyrimidin-2-yl]amino}ethyl]benzoic acid [(I), X═N, R2=2-fluorobenzyl, A=phenyl, R1a=H, R1b=Me, R6a=4-COOH, R6b=H, R3=R4=R5=H] cpd 74

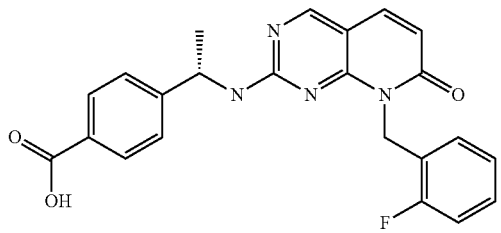 [SMILES: C[C@H](Nc1ncc2ccc(=O)n(Cc3ccccc3F)c2n1)c1ccc(C(=O)O)cc1]

$^1$H NMR (500 MHz, DMSO-$d_6$) δ=12.77 (br. s., 1H), 8.59-8.70 (m, 1H), 8.52 (d, J=7.63 Hz, 1H), 7.80 (d, J=9.30 Hz, 1H), 7.70 (d, J=8.08 Hz, 2H), 7.26-7.48 (m, 2H), 7.16-7.24 (m, 2H), 6.85-7.10 (m, 1H), 6.53-6.81 (m, 1H), 6.31 (d, J=9.30 Hz, 1H), 5.39-5.53 (m, 1H), 5.22 (d, J=15.40 Hz, 1H), 4.85-5.04 (m, 1H), 1.37-1.47 (m, 3H).

LCMS: m/z 419 [M+H]$^+$ r.t. 4.97 min. HRMS (ESI) calcd for $C_{23}H_{20}FN_4O_3$[M+H]$^+$ 419.1514 found 419.1517.

Example 6

4-[(1S)-1-{[8-(2,6-difluorobenzyl)-7-oxo-pyrido[2,3-d]pyrimidin-2-yl]amino}ethyl]-N-(4,4-difluorocyclohexyl)benzamide [(I), X═N, R2=2,6-difluorobenzyl, A=phenyl, R1a=H, R1b=Me, R6a=4-CONR7R8, R6b=H, R7=4,4-difluorocyclohexyl, R8=H, R3=R4=R5=H] conv. 4, cpd 75

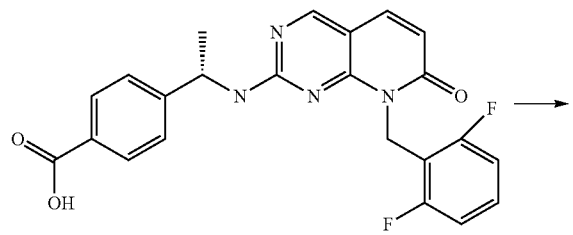

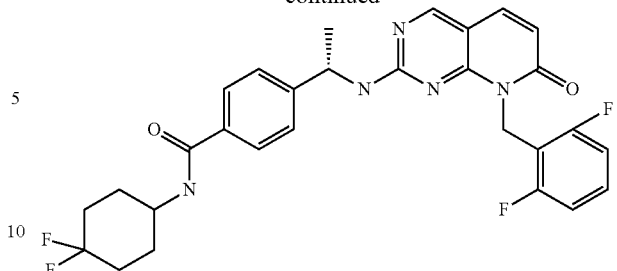

A solution of TBTU (12 mg, 0.04 mmol) in DCM (1 mL) was added to a solution of 4-[(1S)-1-{[8-(2,6-difluorobenzyl)-7-oxo-pyrido[2,3-d]pyrimidin-2-yl]amino}ethyl]benzoic acid (10 mg, 0.02 mmol), DIPEA (10p, 0.06 mmol), and 4,4-difluorocyclohexylamine hydrochloride (6.8 mg g, 0.04 mmol) in DCM (1 mL). The reaction mixture was stirred at room temperature for 12 hours, the solvents were removed in vacuo, the residue was partitioned between DCM and water, the organic layer was dried. The crude was purified by chromatography on a silica gel column (eluent: DCM/EtOAc/EtOH: 60/35/5) to afford the title compound (9.95 g, 90% yield).

$^1$H NMR (500 MHz, DMSO-$d_6$) δ=8.60 (s, 1H), 8.43 (d, J=8.08 Hz, 1H), 8.14 (d, J=7.63 Hz, 1H), 7.73 (d, J=9.46 Hz, 1H), 7.67 (d, J=8.08 Hz, 1H), 7.36 (d, J=8.24 Hz, 1H), 7.26 (t, J=6.86 Hz, 1H), 6.94 (t, J=8.16 Hz, 1H), 6.24 (d, J=9.30 Hz, 1H), 5.53 (d, J=14.79 Hz, 1H), 5.31 (d, J=14.95 Hz, 1H), 4.98-5.12 (m, 1H), 3.88-4.02 (m, 1H), 1.80-2.11 (m, 6H), 1.61 (q, J=12.15 Hz, 2H), 1.32-1.49 (m, 3H). LCMS: m/z 554 [M+H]$^+$ r.t. 4.85 min. HRMS (ESI) calcd for $C_{29}H_{28}F_4N_5O_2$[M+H]$^+$ 554.2174 found 554.2181.

According to this same methodology, but employing suitable substituted derivatives, the following compounds were prepared:

4-[(1S)-1-{[8-(2,6-difluorobenzyl)-7-oxo-pyrido[2,3-d]pyrimidin-2-yl]amino}ethyl]-N-(1-methylpiperidin-4-yl)benzamide [(I), X═N, R2=2,6-difluorobenzyl, A=phenyl, R1a=H, R1b=Me, R6a=4-CONR7R8, R6b=H, R7=N-1-methylpiperidin-4-yl, R8=H, R3=R4=R5=H] cpd 76

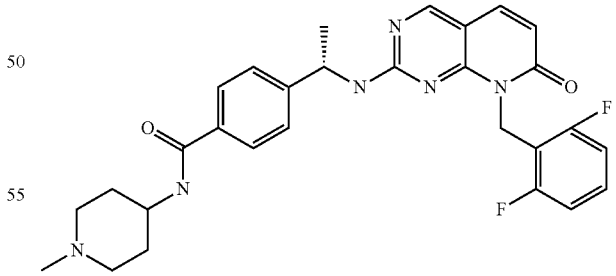

$^1$H NMR (500 MHz, DMSO-$d_6$) δ=8.60 (s, 1H), 8.43 (d, J=7.93 Hz, 1H), 8.07 (d, J=7.78 Hz, 1H), 7.73 (d, J=9.30 Hz, 1H), 7.67 (d, J=8.08 Hz, 2H), 7.35 (d, J=8.08 Hz, 2H), 7.22-7.30 (m, 1H), 6.94 (t, J=8.08 Hz, 2H), 6.24 (d, J=9.30 Hz, 1H), 5.53 (d, J=14.79 Hz, 1H), 5.32 (d, J=14.95 Hz, 1H), 5.05 (quin, J=7.40 Hz, 1H), 3.61-3.78 (m, 1H), 2.75 (d, J=11.29 Hz, 2H), 2.15 (s, 3H), 1.92 (t, J=10.90 Hz, 2H), 1.72 (d, J=11.59 Hz, 2H), 1.55 (tq, J=3.70, 12.10 Hz, 2H), 1.38

(d, J=7.02 Hz, 3H). LCMS: m/z 533 [M+H]$^+$ r.t. 4.82 min. HRMS (ESI) calcd for $C_{29}H_{31}F_2N_6O_2$ [M+H]$^+$ 533.2471 found 533.2473;

8-(2,6-difluorobenzyl)-2-{[(1S)-1-{4-[(4,4-difluoropiperidin-1-yl)carbonyl]phenyl}ethyl]amino}pyrido[2,3-d]pyrimidin-7(8H)-one [(I), X=N, R2=2,6-difluorobenzyl, A=phenyl, R1a=H, R1b=Me, R6a=4-CONR7R8, R6b=H, R7=4,4-difluoropiperidin-1-yl, R8=H, R3=R4=R5=H] cpd 77

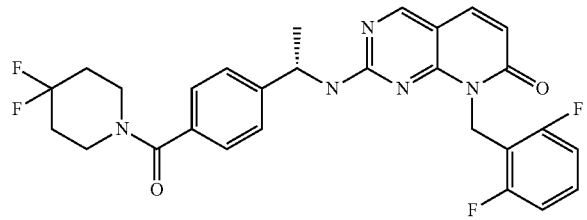 [SMILES: C[C@H](Nc1ncc2ccc(=O)n(Cc3c(F)cccc3F)c2n1)c1ccc(C(=O)N2CCC(F)(F)CC2)cc1]

$^1$H NMR (500 MHz, DMSO-d$_6$) δ=8.61 (s, 1H), 8.43 (d, J=8.39 Hz, 1H), 7.74 (d, J=9.46 Hz, 1H), 7.34-7.39 (m, 2H), 7.31 (d, J=7.93 Hz, 2H), 7.24-7.32 (m, 1H), 6.92-7.01 (m, J=8.08, 8.08 Hz, 2H), 6.25 (d, J=9.30 Hz, 1H), 5.54 (d, J=14.95 Hz, 1H), 5.37 (d, J=15.25 Hz, 1H), 5.04-5.19 (m, 1H), 3.66 (br. s., 2H), 3.40 (br. s, 2H), 2.01 (br. s, 4H), 1.39 (d, J=7.02 Hz, 3H). LCMS: m/z 540 [M+H]$^+$ r.t. 6.03 min. HRMS (ESI) calcd for $C_{28}H_{26}F_4N_5O_2$[M+H]$^+$ 540.2017 found 540.2028;

4-[(1S)-1-{[8-(2,6-difluorobenzyl)-7-oxo-pyrido[2,3-d]pyrimidin-2-yl]amino}ethyl]-N-(tetrahydro-2H-pyran-4-yl) benzamide [(I), X=N, R2=2,6-difluorobenzyl, A=phenyl, R1a=H, R1b=Me, R6a=4-CONR7R8, R6b=H, R7=tetrahydro-2H-pyran-4-yl, R8=H, R3=R4=R5=H] cpd 78

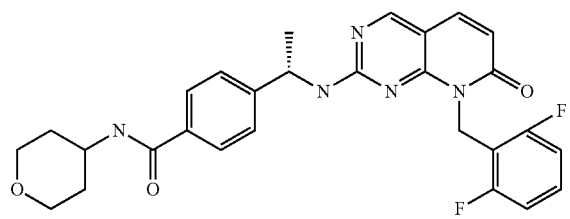 [SMILES: C[C@H](Nc1ncc2ccc(=O)n(Cc3c(F)cccc3F)c2n1)c1ccc(C(=O)NC2CCOCC2)cc1]

$^1$H NMR (500 MHz, DMSO-d$_6$) δ=8.61 (s, 1H), 8.44 (d, J=7.93 Hz, 1H), 8.14 (d, J=7.47 Hz, 1H), 7.73 (d, J=9.30 Hz, 1H), 7.68 (d, J=8.24 Hz, 2H), 7.36 (d, J=8.24 Hz, 2H), 7.22-7.30 (m, 1H), 6.94 (t, J=8.20 Hz, 2H), 6.24 (d, J=9.15 Hz, 1H), 5.53 (d, J=14.95 Hz, 1H), 5.32 (d, J=15.10 Hz, 1H), 4.99-5.09 (m, 1H), 3.92-4.03 (m, 1H), 3.87 (d, J=10.07 Hz, 2H), 3.37 (t, J=11.60 Hz, 2H), 1.73 (tdd, J=2.02, 3.91, 12.64 Hz, 2H), 1.49-1.61 (m, 2H), 1.39 (d, J=6.86 Hz, 3H). LCMS: m/z 520 [M+H]$^+$ r.t. 5.2 min. HRMS (ESI) calcd for $C_{28}H_{28}F_2N_5O_3$[M+H]$^+$ 520.2155 found 520.2153;

N-(4,4-difluorocyclohexyl)-4-[(1S)-1-{[8-(2,2-dimethylpropyl)-7-oxo-pyrido[2,3-d]pyrimidin-2-yl]amino} ethyl]benzamide [(I), X=N, R2=2,2-dimethylpropyl, A=phenyl, R1a=H, R1b=Me, R6a=4-CONR7R8, R6b=H, R7=4,4-difluorocyclohexyl, R8=H, R3=R4=R5=H] cpd 79

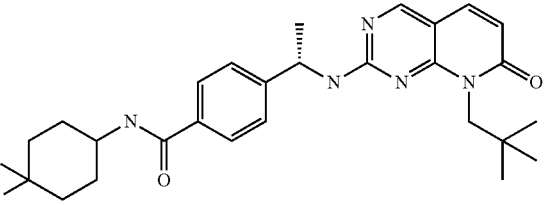

$^1$H NMR (500 MHz, DMSO-d$_6$) δ=8.48-8.62 (m, 1H), 8.44 (d, J=7.32 Hz, 1H), 8.18 (d, J=7.78 Hz, 1H), 7.79 (d, J=8.08 Hz, 2H), 7.68 (d, J=9.30 Hz, 1H), 7.45 (d, J=8.08 Hz, 2H), 6.23 (d, J=9.30 Hz, 1H), 5.11 (quin, J=7.02 Hz, 1H), 3.91-4.07 (m, 3H), 1.81-2.07 (m, 6H), 1.55-1.67 (m, 2H), 1.47 (d, J=7.17 Hz, 3H), 0.67-0.98 (m, 9H).

LCMS: m/z 498 [M+H]$^+$ r.t. 6.27 min. HRMS (ESI) calcd for $C_{27}H_{34}F_2N_5O_2$[M+H]$^+$ 498.2675 found 498.269;

N-cyclopentyl-4-[(1S)-1-{[8-(2,2-dimethylpropyl)-7-oxo-pyrido[2,3-d]pyrimidin-2-yl]amino}ethyl]benzamide [(I), X=N, R2=2,2-dimethylpropyl, A=phenyl, R1a=H, R1b=Me, R6a=4-CONR7R8, R6b=H, R7=-cyclopentyl, R8=H, R3=R4=R5=H] cpd 80

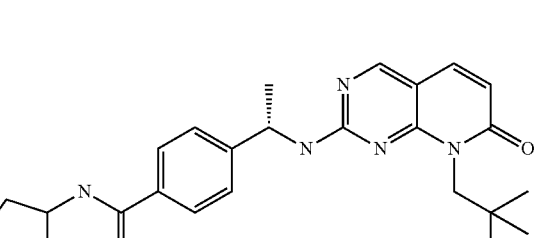

$^1$H NMR (500 MHz, DMSO-d$_6$) δ=8.49-8.66 (m, 1H), 8.43 (d, J=7.47 Hz, 1H), 8.15 (d, J=7.17 Hz, 1H), 7.71-7.83 (m, 2H), 7.67 (d, J=9.30 Hz, 1H), 7.44 (d, J=8.08 Hz, 2H), 6.23 (d, J=9.30 Hz, 1H), 5.12 (t, J=6.79 Hz, 1H), 3.84-4.35 (m, 3H), 1.80-1.90 (m, 2H), 1.60-1.71 (m, 2H), 1.42-1.57 (m, 7H), 0.62-1.00 (m, 9H). LCMS: m/z 498 [M+H]$^+$ r.t. 6.21 min. HRMS (ESI) calcd for $C_{26}H_{34}N_5O_2$ [M+H]$^+$ 448.2707 found 448.2706;

N-cyclohexyl-4-[(1S)-1-{[8-(2,2-dimethylpropyl)-7-oxo-pyrido[2,3-d]pyrimidin-2-yl]amino}ethyl] benzamide [(I), X=N, R2=2,2-dimethylpropyl, A=phenyl, R1a=H, R1b=Me, R6a=4-CONR7R8, R6b=H, R7=cyclohexyl, R8=H, R3=R4=R5=H] cpd 81

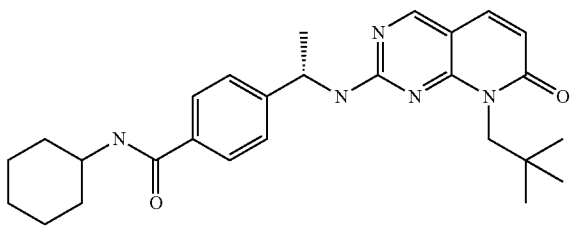 [SMILES: C[C@H](Nc1ncc2ccc(=O)n(CC(C)(C)C)c2n1)c1ccc(C(=O)NC2CCCCC2)cc1]

$^1$H NMR (500 MHz, DMSO-d$_6$) δ=8.48-8.63 (m, 1H), 8.12-8.46 (m, 1H), 8.07 (d, J=8.08 Hz, 1H), 7.71-7.83 (m, 2H), 7.59-7.70 (m, 1H), 7.44 (d, J=8.08 Hz, 2H), 6.23 (d, J=9.30 Hz, 1H), 4.83-5.33 (m, 1H), 3.90-4.35 (m, 2H), 3.73 (d, J=3.51 Hz, 1H), 1.78 (br. s., 2H), 1.71 (br. s., 2H), 1.54-1.65 (m, J=11.74 Hz, 1H), 1.47 (d, J=7.02 Hz, 3H), 1.21-1.35 (m, 4H), 1.04-1.16 (m, 1H), 0.60-0.99 (m, 9H). LCMS: m/z 462 [M+H]$^+$ r.t. 6.51 min. HRMS (ESI) calcd for C$_{27}$H$_{36}$N$_5$O$_2$ [M+H]$^+$ 462.2864 found 462.2861;

2-chloro-N-(4,4-difluorocyclohexyl)-4-(1-{[8-(2,2-dimethylpropyl)-7-oxo-pyrido[2,3-d]pyrimidin-2-yl]amino}ethyl) benzamide [(I), X=N, R2=2,2-dimethylpropyl, A=phenyl, R1a=H, R1b=Me, R6a=4-CONR7R8, R6b=Cl, R7=-4,4-difluorocyclohexyl, R8=H, R3=R4=R5=H] cpd 82

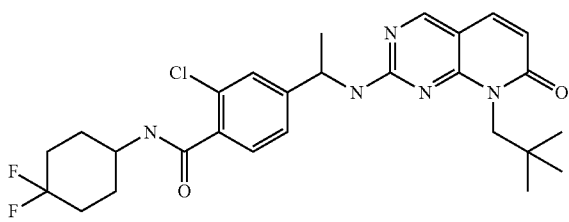 [SMILES: CC(Nc1ncc2ccc(=O)n(CC(C)(C)C)c2n1)c1ccc(C(=O)NC2CCC(F)(F)CC2)c(Cl)c1]

$^1$H NMR (500 MHz, DMSO-d$_6$) δ=8.50-8.64 (m, 1H), 8.46 (d, J=7.32 Hz, 1H), 8.14-8.37 (m, 1H), 7.59-7.72 (m, 1H), 7.50 (d, J=8.54 Hz, 1H), 7.22-7.41 (m, 2H), 6.25 (d, J=9.15 Hz, 1H), 4.97-5.30 (m, 1H), 3.74-4.33 (m, 3H), 1.78-2.09 (m, 6H), 1.50-1.62 (m, 2H), 1.46 (d, J=7.17 Hz, 3H), 0.72-0.99 (m, 9H).
LCMS: m/z 532 [M+H]$^+$ r.t. 6.47 min. HRMS (ESI) calcd for C$_{27}$H$_{33}$ClN$_5$O$_2$[M+H]$^+$ 532.2286 found 532.2276;

2-{[(1S)-1-{4-[(4,4-difluoropiperidin-1-yl)carbonyl]phenyl}ethyl]amino}-8-(2,2-dimethylpropyl) pyrido[2,3-d]pyrimidin-7(8H)-one [(I), X=N, R2=2,2-dimethylpropyl, A=phenyl, R1a=H, R1b=Me, R6a=4-CONR7R8, R6b=H, R7=4,4-difluoropiperidin-1-yl, R8=H, R3=R4=R5=H] cpd 83

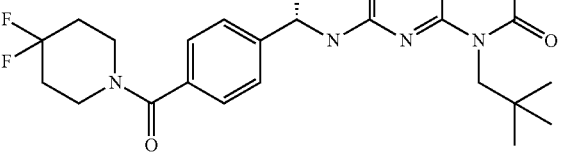

$^1$H NMR (500 MHz, DMSO-d$_6$) δ=8.56 (s, 1H), 8.24 (br. s., 1H), 7.66 (d, J=9.15 Hz, 1H), 7.43-7.48 (m, 2H), 7.33-7.41 (m, 2H), 6.23 (d, J=9.46 Hz, 1H), 5.17 (br. s., 1H), 3.90-4.28 (m, 2H), 3.55 (br. s., 4H), 1.88-2.10 (m, 4H), 1.51 (d, J=7.02 Hz, 3H), 0.78 (br. s., 9H). LCMS: m/z 484 [M+H]$^+$ r.t. 6.18 min. HRMS (ESI) calcd for C$_{26}$H$_{32}$ClF$_2$N$_5$O$_2$ [M+H]$^+$ 484.2519 found 484.2524;

N-(4,4-difluorocyclohexyl)-4-(1-{[8-(2,2-dimethylpropyl)-7-oxo-pyrido[2,3-d]pyrimidin-2-yl]amino}ethyl)-2-fluorobenzamide [(I), X=N, R2=2,2-dimethylpropyl, A=phenyl, R1a=H, R1b=Me, R6a=4-CONR7R8, R6b=F, R7=4,4-difluorocyclohexyl, R8=H, R3=R4=R5=H] cpd 84

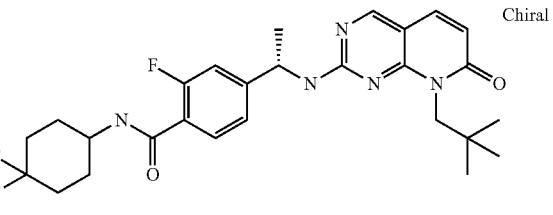

$^1$H NMR (500 MHz, DMSO-d$_6$) δ=8.48-8.64 (m, 1H), 8.44 (d, J=7.32 Hz, 1H), 8.19 (d, J=7.63 Hz, 2H), 7.69 (d, J=9.30 Hz, 1H), 7.05-7.35 (m, 2H), 6.25 (d, J=9.30 Hz, 1H), 4.94-5.29 (m, J=7.17, 7.17 Hz, 1H), 3.81-4.30 (m, 3H), 1.77-2.08 (m, 6H), 1.57 (d, J=10.07 Hz, 2H), 1.46 (d, J=7.02 Hz, 3H), 0.62-0.99 (m, 9H). LCMS: m/z 516 [M+H]$^+$ r.t. 6.47 min. HRMS (ESI) calcd for C$_{27}$H$_{33}$F$_3$N$_5$O$_2$[M+H]$^+$ 516.2581 found 516.2584;

N-(3,3-difluorocyclobutyl)-4-[(1S)-1-{[8-(2,2-dim-
ethylpropyl)-7-oxo-pyrido[2,3-d]pyrimidin-2-yl]
amino}ethyl]benzamide [(I), X=N, R2=2,2-dim-
ethylpropyl, A=phenyl, R1a=H, R1b=Me, R6a=4-
CONR7R8, R6b=H, R7=3,3-difluorocyclobutyl,
R8=H, R3=R4=R5=H] cpd 85

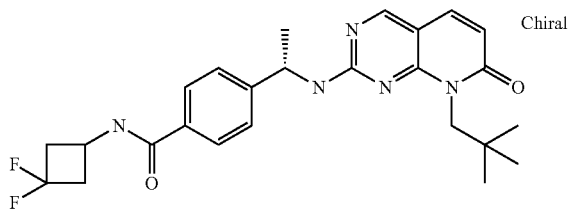 [SMILES: C[C@H](Nc1ncc2ccc(=O)n(CC(C)(C)C)c2n1)c1ccc(C(=O)NC2CC(F)(F)C2)cc1]

$^1$H NMR (500 MHz, DMSO-d$_6$) δ=8.71 (d, J=6.71 Hz, 1H), 8.47-8.63 (m, 1H), 8.44 (d, J=7.32 Hz, 1H), 7.80 (d, J=7.78 Hz, 2H), 7.68 (d, J=9.30 Hz, 1H), 7.26-7.57 (m, 2H), 6.23 (d, J=9.30 Hz, 1H), 5.03-5.31 (m, 1H), 3.88-4.31 (m, 3H), 2.85-3.02 (m, 3H), 2.70-2.80 (m, 1H), 1.47 (d, J=7.02 Hz, 3H), 0.54-1.02 (m, 9H). LCMS: m/z 470 [M+H]$^+$ r.t. 6.05 min. HRMS (ESI) calcd for C$_{25}$H$_{29}$F$_2$N$_5$O$_2$[M+H]$^+$ 470.2362 found 470.2355;

4-[(1S)-1-{[8-(2,2-dimethylpropyl)-7-oxo-pyrido[2,
3-d]pyrimidin-2-yl]amino}ethyl]benzamide [(I),
X=N, R2=2,2-dimethylpropyl, A=phenyl, R1a=H,
R1b=Me, R6a=4-CONH2, R6b=H, R3=R4=R5=H]
cpd 86

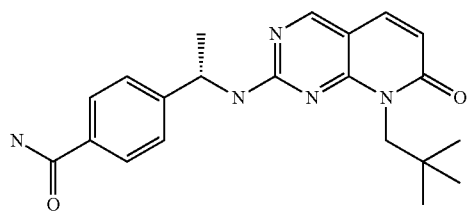 [SMILES: C[C@H](Nc1ncc2ccc(=O)n(CC(C)(C)C)c2n1)c1ccc(C(N)=O)cc1]

$^1$H NMR (500 MHz, DMSO-d$_6$) δ=8.58 (s, 1H), 8.43 (d, J=7.17 Hz, 1H), 7.87 (br. s., 1H), 7.81 (d, J=7.93 Hz, 2H), 7.68 (d, J=9.15 Hz, 1H), 7.44 (d, J=8.08 Hz, 2H), 7.27 (s, 1H), 6.23 (d, J=9.30 Hz, 1H), 4.97-5.38 (m, J=7.09, 7.09 Hz, 1H), 3.81-4.34 (m, 2H), 1.47 (d, J=7.02 Hz, 3H), 0.49-1.04 (m, 9H).

LCMS: m/z 380 [M+H]$^+$ r.t. 5.03 min. HRMS (ESI) calcd for C$_2$H$_{26}$N$_5$O$_2$ [M+H]$^+$ 380.2081 found 380.2093;

8-(2,2-dimethylpropyl)-2-{[(1S)-1-{4-[(4-hy-
droxypiperidin-1-yl)carbonyl]phenyl}ethyl]
amino}pyrido [2,3-d]pyrimidin-7(8H)-one [(I),
X=N, R2=2,2-dimethylpropyl, A=phenyl, R1a=H,
R1b=Me, R6a=4-CONR7R8, R6b=H, R7=4-hy-
droxypiperidin-1-yl, R8=H, R3=R4=R5=H] cpd 87

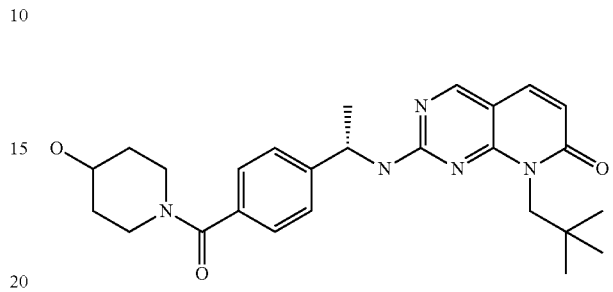

$^1$H NMR (500 MHz, DMSO-d$_6$) δ=8.59 (s, 1H), 8.42 (d, J=7.17 Hz, 1H), 7.68 (d, J=9.30 Hz, 1H), 7.42 (d, J=8.08 Hz, 2H), 7.31 (d, J=7.93 Hz, 2H), 6.23 (d, J=9.30 Hz, 1H), 5.08 (quin, J=6.86 Hz, 1H), 4.78 (d, J=3.81 Hz, 1H), 3.91-4.25 (m, 2H), 3.71 (dq, J=3.28, 7.85 Hz, 1H), 3.42-3.49 (m, 2H), 3.04-3.22 (m, 2H), 1.61-1.79 (m, 2H), 1.48 (d, J=7.02 Hz, 3H), 1.21-1.39 (m, 2H), 0.71 (br. s., 9H). LCMS: m/z 464 [M+H]$^+$ r.t. 5.1 min. HRMS (ESI) calcd for C$_{26}$H$_{34}$N$_5$O$_3$ [M+H]$^+$ 464.2656 found 464.2658;

2-chloro-N-(4,4-difluorocyclohexyl)-4-[(1S)-1-{[8-
(2,2-dimethylpropyl)-7-oxo-7,8-dihydropyrido[2,3-
d]pyrimidin-2-yl]amino}ethyl]benzamide [(I),
X=N, R2=2,2-dimethylpropyl, A=phenyl, R1a=H,
R1b=Me, R6a=4-CONR7R8, R6b=Cl, R7=4,4-dif-
luorocyclohexyl, R8=H, R3=R4=R5=H] cpd 88

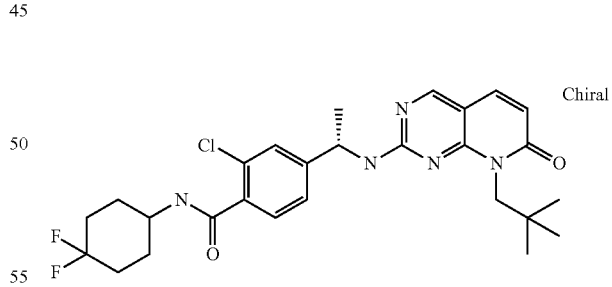

$^1$H NMR (500 MHz, DMSO-d$_6$) δ=8.59 (s, 1H), 8.46 (d, J=7.63 Hz, 1H), 8.36 (d, J=7.32 Hz, 1H), 7.68 (d, J=9.30 Hz, 1H), 7.51 (s, 1H), 7.27-7.43 (m, 2H), 6.25 (d, J=9.15 Hz, 1H), 5.09 (quin, J=6.79 Hz, 1H), 3.97-4.29 (m, 2H), 3.84-3.97 (m, 1H), 1.88-2.11 (m, 4H), 1.85 (d, J=12.66 Hz, 2H), 1.50-1.65 (m, 2H), 1.46 (d, J=7.02 Hz, 3H), 0.84 (br. s., 9H). LCMS: m/z 532 [M+H]$^+$ r.t. 6.58 min. HRMS (ESI) calcd for C$_{27}$H$_{33}$ClF$_2$N$_5$O$_3$ [M+H]$^+$ 532.2286 found 532.2289;

N-(4,4-difluorocyclohexyl)-4-[(1S)-1-{[8-(2,2-dimethylpropyl)-7-oxo-7,8-dihydropyrido[2,3-d]pyrimidin-2-yl]amino}ethyl]-2-fluorobenzamide [(I), X=N, R2=2,2-dimethylpropyl, A=phenyl, R1a=H, R1b=Me, R6a=4-CONR7R8, R6b=F, R7=4,4-difluorocyclohexyl, R8=H, R3=R4=R5=H] cpd 89

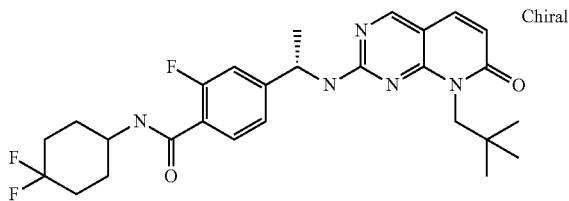 [SMILES: C[C@H](Nc1ncc2ccc(=O)n(CC(C)(C)C)c2n1)c1ccc(C(=O)NC2CCC(F)(F)CC2)c(F)c1]

$^1$H NMR (500 MHz, DMSO-d$_6$) δ=8.48-8.64 (m, 1H), 8.44 (d, J=7.63 Hz, 1H), 8.19 (d, J=7.78 Hz, 1H), 7.69 (d, J=9.30 Hz, 1H), 7.41-7.54 (m, 1H), 7.07-7.34 (m, 2H), 6.25 (d, J=9.30 Hz, 1H), 4.99-5.30 (m, J=6.48, 6.48 Hz, 1H), 3.84-4.31 (m, 3H), 1.78-2.07 (m, 6H), 1.52-1.64 (m, J=10.37 Hz, 2H), 1.46 (d, J=7.02 Hz, 3H), 0.62-0.98 (m, 9H). LCMS: m/z 516 [M+H]$^+$ r.t. 6.48 min. HRMS (ESI) calcd for C$_{27}$H$_{33}$F$_3$N$_5$O$_3$[M+H]$^+$ 516.2581 found 516.2580.

Example 7

8-(2,2-dimethylpropyl)-2-({(1S)-1-[3-fluoro-4-(hydroxymethyl)phenyl]ethyl}amino)pyrido[2,3-d]pyrimidin-7(8H)-one [(I), X=N, R2=2,2-dimethylpropyl, A=phenyl, R1a=H, R1b=Me, R6a=4-CH$_2$OR7, R6b=F, R7=H, R3=R4=R5=H] conv. 1, cpd 90

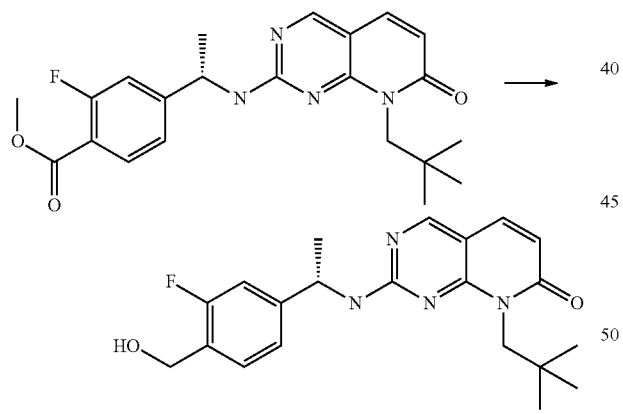

Methyl 4-[(1S)-1-{[8-(2,2-dimethylpropyl)-7-oxo-7,8-dihydropyrido[2,3-d]pyrimidin-2-yl]amino}ethyl]-2-fluorobenzoate (100 mg, 0.24 mmol) was dissolved in 5 mL of dry THF under argon atmosphere at 0° C., and LiAlH$_4$ (1.0 mL of a 1 M solution) was added. The reaction was completed in 30 min, few drops of aqueous NaHCO$_3$ was added to form a colloidal precipitate. The suspension was diluted with EtOAc and decanted to collect the organic fraction. The pooled organic layers were dried, filtered and evaporated to give the wanted product 8-(2,2-dimethylpropyl)-2-({(1S)-1-[3-fluoro-4-(hydroxymethyl)phenyl]ethyl}amino)pyrido[2,3-d]pyrimidin-7(8H)-one as an yellow fluorescent oil.

$^1$H NMR (500 MHz, DMSO-d$_6$) δ=8.58 (s, 1H), 8.38 (d, J=7.32 Hz, 1H), 7.68 (d, J=9.46 Hz, 1H), 7.32-7.42 (m, 1H), 7.19 (d, J=7.78 Hz, 1H), 7.13 (d, J=11.29 Hz, 1H), 6.23 (d, J=9.15 Hz, 1H), 5.17 (t, J=5.72 Hz, 1H), 5.07 (quin, J=7.32 Hz, 1H), 4.47 (d, J=5.64 Hz, 2H), 3.91-4.32 (m, 2H), 1.45 (d, J=7.02 Hz, 3H), 0.77 (br. s., 9H).
LCMS: m/z 385 [M+H]$^+$ r.t. 5.63 min. HRMS (ESI) calcd for C$_{21}$N$_{26}$FN$_4$O$_2$[M+H]$^+$ 385.2035 found 385.2043.

Operating in an analogous way, but employing suitably substituted starting materials, the following compounds were obtained:

2-({(1S)-1-[4-(hydroxymethyl)phenyl]ethyl}amino)-8-(2-methylpropyl)pyrido[2,3-d]pyrimidin-7(8H)-one [(I), X=N, R2=2-methylpropyl, A=phenyl, R1a=H, R1b=Me, R6a=4-CH$_2$OR7, R6b=H, R7=H, R3=R4=R5=H] cpd 91

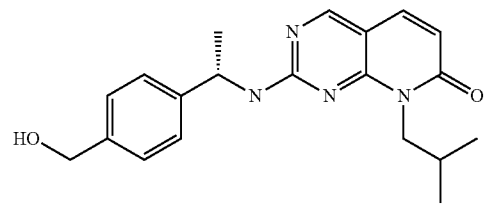 [SMILES: CC(C)Cn1c(=O)ccc2cnc(N[C@@H](C)c3ccc(CO)cc3)nc21]

$^1$H NMR (500 MHz, DMSO-d$_6$) δ=8.57 (s, 1H), 8.51 (d, J=7.78 Hz, 1H), 7.68 (d, J=9.30 Hz, 1H), 7.32 (d, J=8.08 Hz, 2H), 7.23 (d, J=8.08 Hz, 2H), 6.21 (d, J=9.15 Hz, 1H), 5.10 (t, J=5.64 Hz, 1H), 4.92-5.05 (m, 1H), 4.43 (d, J=5.80 Hz, 2H), 3.93-4.00 (m, 1H), 3.84-3.90 (m, 1H), 1.89-1.97 (m, 1H), 1.46 (d, J=7.02 Hz, 3H), 0.78 (d, J=6.71 Hz, 3H), 0.69 (d, J=6.56 Hz, 3H). LCMS: m/z 353 [M+H]$^+$ r.t. 5.29 min. HRMS (ESI) calcd for C$_{20}$N$_{25}$N$_4$O$_2$ [M+H]$^+$ 353.1972 found 353.197;

8-(2,6-difluorobenzyl)-2-({(1S)-1-[4-(hydroxymethyl)phenyl]ethyl}amino)pyrido[2,3-d]pyrimidin-7(8H)-one [(I), X=N, R2=2,6-difluorobenzyl, A=phenyl, R1a=H, R1b=Me, R6a=4-CH$_2$OR7, R6b=H, R7=H, R3=R4=R5=H] cpd 92

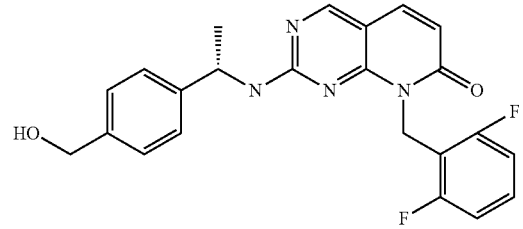 [SMILES: C[C@H](Nc1ncc2ccc(=O)n(Cc3c(F)cccc3F)c2n1)c1ccc(CO)cc1]

$^1$H NMR (500 MHz, DMSO-d$_6$) δ=8.58 (s, 1H), 8.34 (d, J=8.54 Hz, 1H), 7.73 (d, J=9.46 Hz, 1H), 7.27-7.37 (m, 1H), 7.24 (d, J=7.93 Hz, 2H), 7.14 (d, J=7.93 Hz, 2H), 6.98 (t, J=8.24 Hz, 2H), 6.24 (d, J=9.30 Hz, 1H), 5.55 (d, J=15.10 Hz, 1H), 5.37 (d, J=14.79 Hz, 1H), 5.08 (t, J=5.64 Hz, 1H), 5.02 (quin, J=7.50 Hz, 1H), 4.39 (d, J=5.64 Hz, 2H), 1.36 (d, J=7.17 Hz, 3H). LCMS: m/z 423 [M+H]$^+$ r.t. 5.25 min. HRMS (ESI) calcd for C$_{23}$N$_{21}$F$_2$N$_4$O$_2$[M+H]$^+$ 423.1627 found 423.162;

2-({(1S)-1-[4-(hydroxymethyl)phenyl]ethyl}amino)-8-(2-hydroxy-2-methylpropyl)pyrido[2,3-d]pyrimidin-7(8H)-one [(I), X═N, R2=2-hydroxy-2-methylpropyl, A=phenyl, R1a=H, R1b=Me, R6a=4-CH₂OR7, R6b=F, R7=H, R3=R4=R5=H] cpd 93

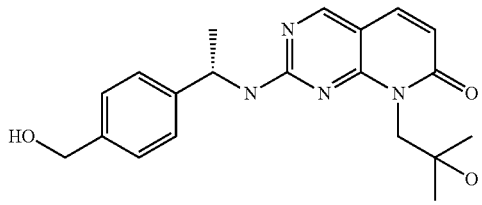 [SMILES: C[C@H](Nc1ncc2ccc(=O)n(CC(C)(C)O)c2n1)c1ccc(CO)cc1]

¹H NMR (500 MHz, DMSO-d₆) δ=8.62 (s, 1H), 8.48 (d, J=7.8 Hz, 1H), 7.73 (d, J=9.3 Hz, 1H), 7.34 (d, J=7.9 Hz, 2H), 7.24 (d, J=8.1 Hz, 2H), 6.27 (d, J=9.3 Hz, 1H), 5.09 (t, J=5.7 Hz, 1H), 5.05 (quin, J=7.2 Hz, 1H), 4.63 (s, 1H), 4.43 (d, J=5.8 Hz, 2H), 4.38-4.18 (m, 2H), 1.45 (d, J=6.9 Hz, 3H), 1.09-0.90 (m, 6H). LCMS: m/z 369 [M+H]⁺ r.t. 4.47 min. HRMS (ESI) calcd for C₂₀N₂₅N₄O₃ [M+H]⁺369.1921 found 369.1921.

Example 8

2-{[(1S)-1-{4-[(4,4-difluoropiperidin-1-yl)methyl]-3-fluorophenyl}ethyl]amino}-8-(2,2-dimethylpropyl)pyrido[2,3-d]pyrimidin-7(8H)-one [(I), X═N, R2=2,2-dimethylpropyl, A=phenyl, R1a=H, R1b=Me, R6a=4-CH₂NR7R8, R6b=F, R7-R8=4,4-difluoropiperidin-1-yl, R3=R4=R5=H] conv. 2, cpd 94

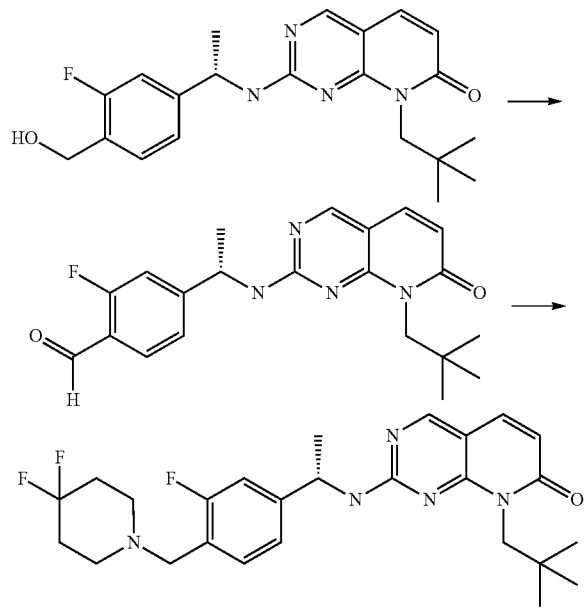

Step 1: Preparation of 4-[(1S)-1-{[8-(2,2-dimethylpropyl)-7-oxo-pyrido[2,3-d]pyrimidin-2-yl]amino}ethyl]-2-fluorobenzaldehyde 8-(2,2-dimethylpropyl)-2-({(1S)-1-[3-fluoro-4-(hydroxymethyl)phenyl]ethyl}amino)pyrido[2,3-d]pyrimidin-7(8H)-one (75 mg, 0.2 mmol) was dissolved in DCM (10 mL) in the presence of manganese dioxide (347 mg, 4.0 mmol) and stirred at room temperature for 18 h. The solution was filtered through a pad of celite and washed with DCM. The filtrated was concentrated to give the corresponding aldehyde used in the next step without further purification.

Step 2: Preparation of the Title Compound

4-[(1S)-1-{[8-(2,2-dimethylpropyl)-7-oxo-pyrido[2,3-d]pyrimidin-2-yl]amino}ethyl]-2-fluorobenzaldehyde (30 mg, 0.08 mmol) was reacted with 4,4-difluoropiperidine hydrochloride (25 mg, 0.16 mmol) in the presence of sodium triacetoxyborohydride (102 mg, 0.48 mmol) in THF for 4 h. When the reaction was complete, it was worked up with NaHCO₃ and AcOEt. The organic phase was evaporated under vacuum and the crude purified by column chromatography with (DCM/EtOAc/EtOH: 7/2/1) to give the title compound.

¹H NMR (500 MHz, DMSO-d₆) δ=8.59 (s, 1H), 8.38 (d, J=7.17 Hz, 1H), 7.68 (d, J=9.30 Hz, 1H), 7.28-7.38 (m, 1H), 7.06-7.24 (m, 2H), 6.24 (d, J=9.15 Hz, 1H), 4.87-5.40 (m, J=7.02, 7.02 Hz, 1H), 3.76-4.40 (m, 2H), 3.55 (s, 2H), 2.47 (br. s., 4H), 1.80-1.97 (m, 4H), 1.46 (d, J=7.02 Hz, 3H), 0.50-1.02 (m, 9H). LCMS: m/z 488 [M+H]+r.t. 7.15 min. HRMS (ESI) calcd for C₂₆N₃₃F₃N₅O [M+H]⁺488.2632 found 488.2636.

According to the same method, but employing others amines, the following compounds were prepared:

2-{[(1S)-1-{4-[(4,4-difluoropiperidin-1-yl)methyl]phenyl}ethyl]amino}-8-(2-methylpropyl)pyrido[2,3-d]pyrimidin-7(8H)-one [(I), X═N, R2=2-methylpropyl, A=phenyl, R1a=H, R1b=Me, R6a=4-CH₂NR7R8, R6b=H, R7-R8=4,4-difluoropiperidin-1-yl, R3=R4=R5=H] cpd 95

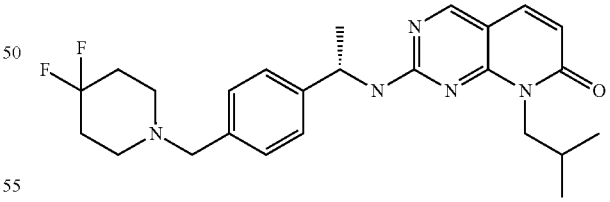

¹H NMR (500 MHz, DMSO-d₆) δ=8.58 (s, 1H), 8.40 (d, J=7.02 Hz, 1H), 7.69 (d, J=9.30 Hz, 1H), 7.30-7.34 (m, 2H), 7.23 (d, J=7.93 Hz, 2H), 6.21 (d, J=9.30 Hz, 1H), 4.99-5.03 (m, 1H), 3.81-4.06 (m, 2H), 3.47 (s, 2H), 2.43 (br. s., 4H), 1.84-2.00 (m, 5H), 1.46 (d, J=7.02 Hz, 3H), 0.72 (d, J=6.56 Hz, 3H), 0.60 (d, J=6.56 Hz, 3H). LCMS: m/z 456 [M+H]⁺ r.t. 6.9 min. HRMS (ESI) calcd for C₂₅N₃₂F₂N₅O [M+H]⁺ 456.257 found 456.257;

145

8-benzyl-2-[(1-{4-[(4,4-difluoropiperidin-1-yl)methyl]phenyl}ethyl)amino]pyrido[2,3-d]pyrimidin-7(8H)-one [(I), X=N, R2=benzyl, A=phenyl, R1a=H, R1b=Me, R6a=4-CH$_2$NR7R8, R6b=H, R7-R8=4,4-difluoropiperidin-1-yl, R3=R4=R5=H] cpd 96

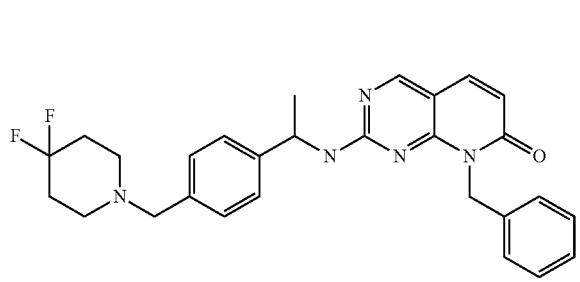 [SMILES: CC(Nc1ncc2ccc(=O)n(Cc3ccccc3)c2n1)c1ccc(CN2CCC(F)(F)CC2)cc1]

$^1$H NMR (500 MHz, DMSO-d$_6$) δ=8.61 (s, 1H), 8.42 (d, J=8.08 Hz, 1H), 7.74 (d, J=9.30 Hz, 1H), 6.98-7.38 (m, 9H), 6.28 (d, J=9.30 Hz, 1H), 5.44 (d, J=14.18 Hz, 1H), 5.20 (d, J=14.18 Hz, 1H), 4.94-5.12 (m, 1H), 3.46 (s, 2H), 2.39-2.46 (m, 4H), 1.83-1.98 (m, 4H), 1.34-1.49 (m, 3H). LCMS: m/z 490 [M+H]$^+$ r.t. 7.87 min. HRMS (ESI) calcd for C$_{28}$N$_{30}$F$_2$N$_5$O [M+H]$^+$490.2413 found 490.2403;

2-[(1-{4-[(4,4-difluoropiperidin-1-yl)methyl]phenyl}ethyl)amino]-8-(2-fluorobenzyl)pyrido[2,3-d]pyrimidin-7(8H)-one [(I), X=N, R2=2-fluorobenzyl, A=phenyl, R1a=H, R1b=Me, R6a=4-CH$_2$NR7R8, R6b=H, R7-R8=4,4-difluoropiperidin-1-yl, R3=R4=R5=H] cpd 97

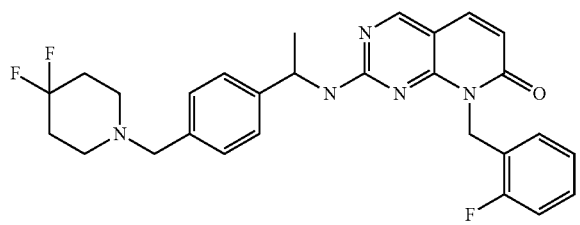 [SMILES: CC(Nc1ncc2ccc(=O)n(Cc3ccccc3F)c2n1)c1ccc(CN2CCC(F)(F)CC2)cc1]

$^1$H NMR (500 MHz, DMSO-d$_6$) δ=8.58-8.67 (m, 1H), 8.07-8.47 (m, 1H), 7.79 (d, J=9.46 Hz, 1H), 7.19-7.36 (m, 2H), 7.15 (d, J=7.93 Hz, 2H), 7.07 (d, J=7.93 Hz, 2H), 6.96 (t, J=7.17 Hz, 1H), 6.54-6.82 (m, 1H), 6.31 (d, J=9.46 Hz, 1H), 5.44-5.55 (m, 1H), 5.24-5.36 (m, 1H), 4.73-5.12 (m, 1H), 3.41-3.48 (m, 2H), 2.42 (br. s., 6H), 1.83-1.99 (m, 4H), 1.32-1.44 (m, 3H). LCMS: m/z 508 [M+H]$^+$ r.t. 8.2 min. HRMS (ESI) calcd for C$_{28}$N$_{29}$F$_3$N$_5$O [M+H]$^+$508.2319 found 508.2307;

146

8-(2,6-difluorobenzyl)-2-[(1-{4-[(4,4-difluoropiperidin-1-yl)methyl]phenyl}ethyl)amino]pyrido[2,3-d]pyrimidin-7(8H)-one [(I), X=N, R2=2,6-difluorobenzyl, A=phenyl, R1a=H, R1b=Me, R6a=4-CH$_2$NR7R8, R6b=H, R7-R8=4,4-difluoropiperidin-1-yl, R3=R4=R5=H] cpd 98

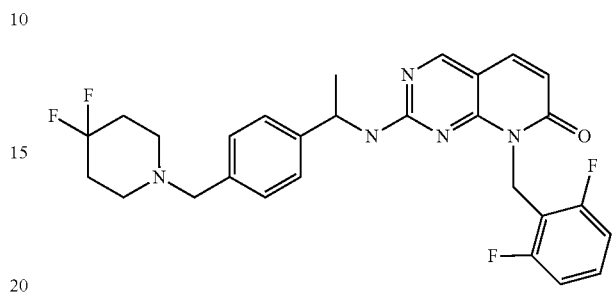

$^1$H NMR (500 MHz, DMSO-d$_6$) δ=8.59 (s, 1H), 8.34 (d, J=8.39 Hz, 1H), 7.73 (d, J=9.30 Hz, 1H), 7.28-7.38 (m, 1H), 7.21-7.28 (m, 2H), 7.13 (d, J=7.93 Hz, 2H), 6.97 (t, J=8.24 Hz, 2H), 6.24 (d, J=9.46 Hz, 1H), 5.55 (d, J=14.95 Hz, 1H), 5.35 (d, J=14.95 Hz, 1H), 4.99-5.13 (m, 1H), 3.43 (s, 2H), 2.42 (br. s., 4H), 1.86-1.97 (m, 4H), 1.31-1.50 (m, 3H). LCMS: m/z 526 [M+H]$^+$ r.t. 8.03 min. HRMS (ESI) calcd for C$_{28}$N$_{28}$F$_4$N$_5$O [M+H]$^+$526.2225 found 526.2216;

8-(2,6-difluorobenzyl)-2-{[(1S)-1-{4-[(4,4-difluoropiperidin-1-yl)methyl]phenyl}ethyl]amino}pyrido[2,3-d]pyrimidin-7(8H)-one [(I), X=N, R2=2,6-difluorobenzyl, A=phenyl, R1a=H, R1b=Me, R6a=4-CH$_2$NR7R8, R6b=H, R7-R8=4,4-difluoropiperidin-1-yl, R3=R4=R5=H] cpd 99

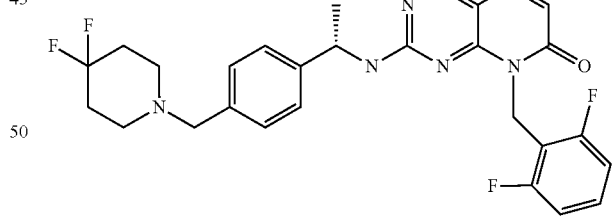

$^1$H NMR (500 MHz, DMSO-d$_6$) δ=8.59 (s, 1H), 8.34 (d, J=8.39 Hz, 1H), 7.73 (d, J=9.30 Hz, 1H), 7.28-7.42 (m, 1H), 7.25 (d, J=7.93 Hz, 2H), 7.09-7.21 (m, 2H), 6.91-7.06 (m, 2H), 6.24 (d, J=9.30 Hz, 1H), 5.55 (d, J=15.10 Hz, 1H), 5.35 (d, J=15.25 Hz, 1H), 4.99-5.28 (m, 1H), 3.43 (s, 1H), 3.34 (br. s., 1H), 2.42 (br. s., 4H), 1.86-1.97 (m, 4H), 1.34-1.49 (m, 3H). LCMS: m/z 526 [M+H]$^+$ r.t. 8.05 min. HRMS (ESI) calcd for C$_{28}$N$_{28}$F$_4$N$_5$O [M+H]+526.2225 found 526.2215;

2-[(1-{4-[(4,4-difluoropiperidin-1-yl)methyl]
phenyl}ethyl)amino]-8-(2-fluoroethyl)pyrido[2,3-d]
pyrimidin-7(8H)-one [(I), X=N, R2=2-fluoroethyl,
A=phenyl, R1a=H, R1b=Me, R6a=4-CH$_2$NR7R8,
R6b=H, R7-R8=4,4-difluoropiperidin-1-yl,
R3=R4=R5=H] cpd 100

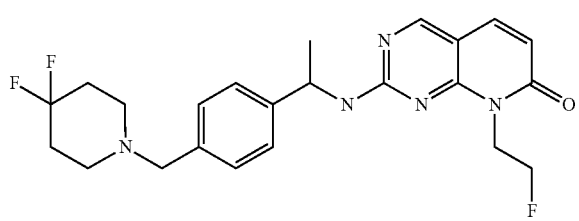 [SMILES: CC(Nc1ncc2ccc(=O)n(CCF)c2n1)c1ccc(CN2CCC(F)(F)CC2)cc1]

$^1$H NMR (500 MHz, DMSO-d$_6$) δ=8.53-8.64 (m, 1H), 8.48 (d, J=7.17 Hz, 1H), 7.69-7.73 (m, 1H), 7.33 (d, J=7.93 Hz, 2H), 7.23 (d, J=8.08 Hz, 2H), 6.15-6.31 (m, 1H), 4.93-5.28 (m, 1H), 4.14-4.52 (m, 4H), 3.47 (s, 2H), 2.43 (br. s., 4H), 1.80-1.97 (m, 4H), 1.46 (d, J=7.17 Hz, 3H). LCMS: m/z 446 [M+H]$^+$ r.t. 5.76 min. HRMS (ESI) calcd for C$_{28}$N$_{27}$F$_3$N$_5$O [M+H]$^+$446.2162 found 446.2162.

2-{[(1S)-1-{4-[(4,4-difluoropiperidin-1-yl)methyl]
phenyl}ethyl]amino}-8-propylpyrido[2,3-d]pyrimi-
din-7(8H)-one [(I), X=N, R2=propyl, A=phenyl,
R1a=H, R1b=Me, R6a=4-CH$_2$NR7R8, R6b=H,
R7-R8=4,4-difluoropiperidin-1-yl, R3=R4=R5=H]
cpd 101

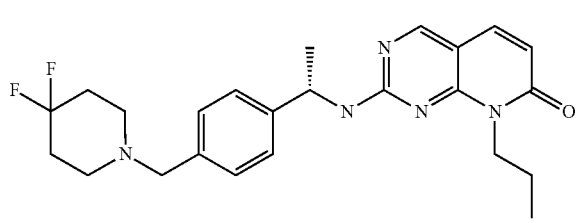 [SMILES: CCCn1c(=O)ccc2cnc(N[C@@H](C)c3ccc(CN4CCC(F)(F)CC4)cc3)nc21]

$^1$H NMR (500 MHz, DMSO-d$_6$) δ=8.53-8.64 (m, 1H), 8.48 (d, J=7.17 Hz, 1H), 7.69-7.73 (m, 1H), 7.33 (d, J=7.93 Hz, 2H), 7.23 (d, J=8.08 Hz, 2H), 6.15-6.31 (m, 1H), 4.93-5.28 (m, 1H), 3.88-4.10 (m, 2H), 3.47 (br. s., 2H), 2.43 (br. s., 4H), 1.80-1.97 (m, 4H), 1.46 (d, J=7.17 Hz, 3H), 1.31-1.40 (m, 2H), 0.78 (t, J=7.32 Hz, 3H). LCMS: m/z 442 [M+H]$^+$ r.t. 6.58 min. HRMS (ESI) calcd for C$_{24}$N$_{30}$F$_2$N$_5$O [M+H]$^+$442.2413 found 442.2411;

2-({(1S)-1-[4-(azepan-1-ylmethyl)phenyl]
ethyl}amino)-8-propylpyrido[2,3-d]pyrimidin-7
(8H)-one [(I), X=N, R2=propyl, A=phenyl,
R1a=H, R1b=Me, R6a=4-CH$_2$NR7R8, R6b=H,
R7-R8=azepan-1-yl, R3=R4=R5=H] cpd 102

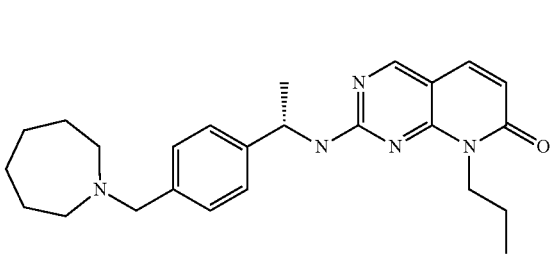 [SMILES: CCCn1c(=O)ccc2cnc(N[C@@H](C)c3ccc(CN4CCCCCC4)cc3)nc21]

$^1$H NMR (500 MHz, DMSO-d$_6$) δ=8.57 (s, 1H), 8.41 (d, J=7.32 Hz, 1H), 7.67 (d, J=9.30 Hz, 1H), 7.31 (d, J=7.63 Hz, 2H), 7.23 (d, J=7.78 Hz, 2H), 6.20 (d, J=9.15 Hz, 1H), 4.95-5.32 (m, 1H), 3.85-4.21 (m, 2H), 3.51-3.58 (m, 2H), 2.54 (br. s., 4H), 1.53 (br. s., 8H), 1.46 (d, J=7.02 Hz, 3H), 1.17-1.42 (m, 2H), 0.79 (t, J=7.40 Hz, 3H). LCMS: m/z 420 [M+H]$^+$ r.t. 4.95 min. HRMS (ESI) calcd for C$_{25}$N$_{34}$N$_5$O [M+H]$^+$420.2758 found 420.2763;

2-{[(1S)-1-{4-[(4-acetylpiperazin-1-yl)methyl]
phenyl}ethyl]amino}-8-propylpyrido[2,3-d]pyrimi-
din-7(8H)-one [(I), X=N, R2=propyl, A=phenyl,
R1a=H, R1b=Me, R6a=4-CH$_2$NR7R8, R6b=H,
R7-R8=4-acetylpiperazin-1-yl, R3=R4=R5=H] cpd
103

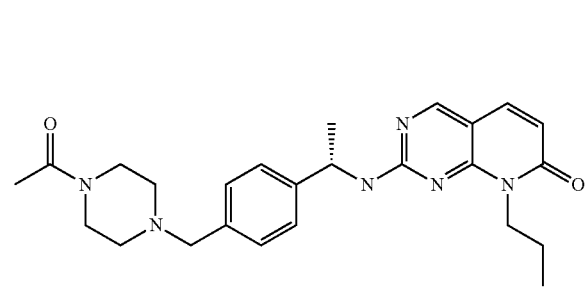 [SMILES: CCCn1c(=O)ccc2cnc(N[C@@H](C)c3ccc(CN4CCN(C(C)=O)CC4)cc3)nc21]

$^1$H NMR (500 MHz, DMSO-d$_6$) δ=8.58 (s, 1H), 8.42 (d, J=7.32 Hz, 1H), 7.67 (d, J=9.30 Hz, 1H), 7.32 (d, J=8.08 Hz, 2H), 7.22 (d, J=7.93 Hz, 2H), 6.20 (d, J=9.30 Hz, 1H), 4.97-5.26 (m, 1H), 3.85-4.12 (m, 2H), 3.43-3.46 (m, 6H), 2.17-2.33 (m, 4H), 1.95 (s, 3H), 1.46 (d, J=7.17 Hz, 3H), 1.22-1.40 (m, 2H), 0.78 (t, J=7.40 Hz, 3H). LCMS: m/z 449 [M+H]$^+$ r.t. 4.97 min. HRMS (ESI) calcd for C$_{25}$N$_{33}$N$_6$O$_2$ [M+H]$^+$449.266 found 449.2663;

2-{[(1S)-1-{4-[(4,4-difluoropiperidin-1-yl)methyl]phenyl}ethyl]amino}-8-(2-methylpropyl)pyrido[2,3-d]pyrimidin-7(8H)-one [(I), X=N, R2=2-propyl, A=phenyl, R1a=H, R1b=Me, R6a=4-CH₂NR7R8, R6b=H, R7-R8=4,4-difluoropiperidin-1-yl, R3=R4 R5=H cpd 104

2-{[(1S)-1-{4-[(4,4-difluoropiperidin-1-yl)methyl]phenyl)ethyl]amino}-8-(2,2,2-trifluoroethyl)pyrido[2,3-d]pyrimidin-7(8H)-one [(I), X=N, R2=2,2,2-trifluoroethyl, A=phenyl, R1a=H, R1b=Me, R6a=4-CH₂NR7R8, R6b=H, R7-R8=4,4-difluoropiperidin-1-yl, R3=R4=R5=H] cpd 106

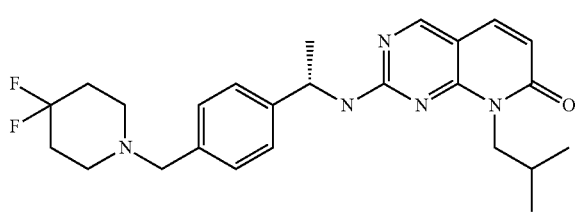 [SMILES: CC(C)Cn1c(=O)ccc2cnc(N[C@@H](C)c3ccc(CN4CCC(F)(F)CC4)cc3)nc21]

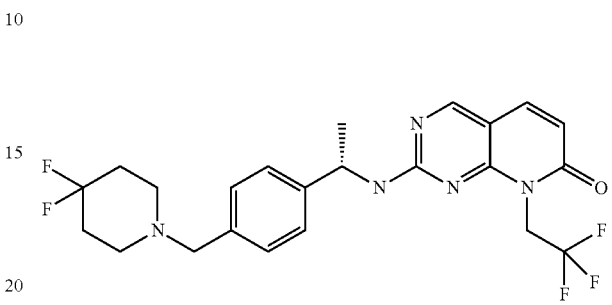

¹H NMR (500 MHz, DMSO-d₆) δ=8.51-8.63 (m, 1H), 8.41 (d, J=7.32 Hz, 1H), 7.69 (d, J=9.15 Hz, 1H), 7.32 (d, J=7.93 Hz, 2H), 7.23 (d, J=8.08 Hz, 2H), 6.14-6.29 (m, 1H), 4.97-5.30 (m, 1H), 3.97 (dd, J=7.40, 12.12 Hz, 1H), 3.83 (dd, J=7.70, 12.28 Hz, 1H), 3.48 (s, 2H), 2.43 (br. s., 4H), 1.83-1.96 (m, 5H), 1.46 (d, J=7.02 Hz, 3H), 0.73 (d, J=6.71 Hz, 3H), 0.60 (d, J=6.56 Hz, 3H). LCMS: m/z 456 [M+H]⁺ r.t. 6.89 min. HRMS (ESI) calcd for $C_{25}N_{32}F_2N_5O$ [M+H]⁺ 456.257 found 456.2564;

¹H NMR (500 MHz, DMSO-d₆) δ=8.61-8.68 (m, 1H), 8.29-8.60 (m, 1H), 7.63-7.84 (m, 1H), 7.33 (d, J=7.78 Hz, 2H), 7.23 (d, J=8.24 Hz, 2H), 6.28 (d, J=9.30 Hz, 1H), 4.98-5.11 (m, 2H), 4.64-4.88 (m, 1H), 3.48 (s, 2H), 2.43 (br. s., 4H), 1.79-1.97 (m, 4H), 1.46 (d, J=7.02 Hz, 3H). LCMS: m/z 482 [M+H]⁺ r.t. 6.64 min. HRMS (ESI) calcd for $C_{23}H_{25}F_5N_5O$ [M+H]⁺482.1974 found 482.1974;

2-{[(1S)-1-{4-[(4,4-difluoropiperidin-1-yl)methyl]phenyl)ethyl]amino)-8-(2,2-dimethylpropyl)pyrido[2,3-d]pyrimidin-7(8H)-one [(I), X=N, R2=2,2-dimethylpropyl, A=phenyl, R1a=H, R1b=Me, R6a=4-CH₂NR7R8, R6b=H, R7-R8=4,4-difluoropiperidin-1-yl, R3=R4=R5=H] cpd 105

8-[2,3-difluoro-2-(fluoromethyl)propyl]-2-{[(1S)-1-{4-[(4,4-difluoropiperidin-1-yl)methyl]phenyl)ethyl]amino) pyrido[2,3-d]pyrimidin-7(8H)-one [(I), X=N, R2=2,3-difluoro-2-(fluoromethyl)propyl, A=phenyl, R1a=H, R1b=Me, R6a=4-CH₂NR7R8, R6b=H, R7-R8=4,4-difluoropiperidin-1-yl, R3=R4=R5=H] cpd 107

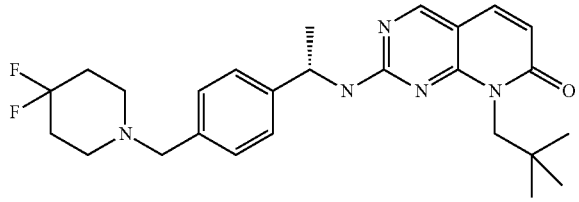 [SMILES: C[C@H](Nc1ncc2ccc(=O)n(CC(C)(C)C)c2n1)c1ccc(CN2CCC(F)(F)CC2)cc1]

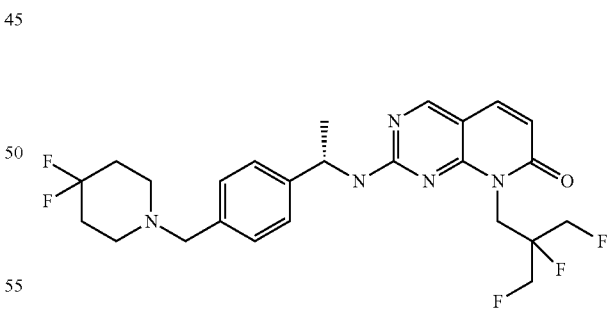

¹H NMR (500 MHz, DMSO-d₆) δ=8.57 (s, 1H), 8.36 (d, J=7.17 Hz, 1H), 7.67 (d, J=9.00 Hz, 1H), 7.31-7.35 (m, 2H), 7.23 (d, J=8.24 Hz, 2H), 6.22 (d, J=9.15 Hz, 1H), 5.04-5.11 (m, 1H), 3.96-4.26 (m, 2H), 3.48 (s, 2H), 2.44 (d, J=4.12 Hz, 4H), 1.84-1.99 (m, 4H), 1.45 (d, J=7.02 Hz, 3H), 0.68-0.94 (m, 9H). LCMS: m/z 470 [M+H]⁺ r.t. 7.23 min. HRMS (ESI) calcd for $C_{26}N_{34}F_2N_5O$ [M+H]⁺470.2726 found 470.2723;

¹H NMR (500 MHz, DMSO-d₆) δ 8.55-8.66 (m, 1H), 8.49 d, 8.08 z, 1H), 7.74 (d, J=9.30 Hz, 1H), 7.37 (d, J=7.78 Hz, 2H), 7.24 (d, J=7.93 Hz, 2H), 6.16-6.34 (m, 1H), 5.18-5.21 (m, 1H), 4.35-4.66 (m, 6H), 3.47 (s, 2H), 2.44 (br. s., 4H), 1.84-1.99 (m, 4H), 1.42-1.53 (m, 3H). LCMS: m/z 510 [M+H]⁺ r.t. 6.42 min. HRMS (ESI) calcd for $C_{25}H_{29}F_5N_5O$ [M+H]⁺510.2287 found 510.228;

2-{[(1S)-1-{4-[(4,4-difluoropiperidin-1-yl)methyl] phenyl]ethyl]amino)-8-[3,3,3-trifluoro-2-(trifluoromethyl) propyl]pyrido[2,3-d]pyrimidin-7(8H)-one [(I), X=N, R2=3,3,3-trifluoro-2-(trifluoromethyl)propyl, A=phenyl, R1a=H, R1b=Me, R6a=4-CH$_2$NR7R8, R6b=H, R7-R8=4,4-difluoropiperidin-1-yl, R3=R4=R5=H] cpd 108

8-(2,2-dimethylpropyl)-2-({(1S)-1-[4-(morpholin-4-ylmethyl)phenyl]ethyl}amino)pyrido[2,3-d]pyrimidin-7(8H)-one [(I), X=N, R2=2,2-dimethylpropyl, A=phenyl, R1a=H, R1b=Me, R6a=4-CH$_2$NR7R8, R6b=H, R7-R8=morpholin-4-yl, R3=R4=R5=H] cpd 110

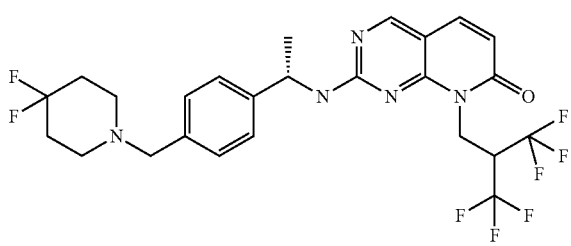 [SMILES: C[C@H](Nc1ncc2ccc(=O)n(CC(C(F)(F)F)C(F)(F)F)c2n1)c1ccc(CN2CCC(F)(F)CC2)cc1]

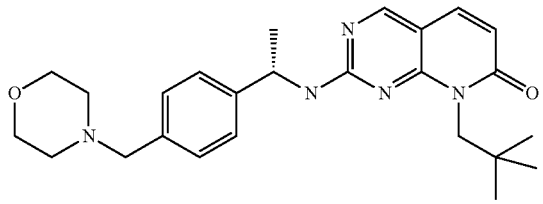 [SMILES: C[C@H](Nc1ncc2ccc(=O)n(CC(C)(C)C)c2n1)c1ccc(CN2CCOCC2)cc1]

$^1$H NMR (500 MHz, DMSO-d$_6$) δ=8.65 (s, 1H), 8.55 (d, J=7.93 Hz, 1H), 7.76 (d, J=9.46 Hz, 1H), 7.26-7.31 (m, 2H), 7.20-7.26 (m, 2H), 6.27 (d, J=9.30 Hz, 1H), 5.04-5.15 (m, 1H), 4.66-4.80 (m, 1H), 4.52 (dd, J=6.41, 13.88 Hz, 1H), 4.09-4.29 (m, J=8.08 Hz, 1H), 3.47 (s, 2H), 2.43 (br. s., 4H), 1.85-1.98 (m, 4H), 1.44-1.53 (m, 3H).

LCMS: m/z 564 [M+H]$^+$ r.t. 7.23 min. HRMS (ESI) calcd for C$_{25}$H$_{26}$F$_8$N$_5$O [M+H]$^+$ 564.2004 found 564.1195;

$^1$H NMR (500 MHz, DMSO-d$_6$) δ=8.57 (s, 1H), 8.36 (d, J=7.47 Hz, 1H), 7.67 (d, J=9.15 Hz, 1H), 7.32 (d, J=7.93 Hz, 2H), 7.22 (d, J=7.93 Hz, 2H), 6.22 (d, J=9.30 Hz, 1H), 4.91-5.31 (m, J=6.90 Hz, 1H), 3.89-4.30 (m, 2H), 3.53 (t, J=4.42 Hz, 4H), 3.39 (s, 2H), 2.30 (br. s., 4H), 1.45 (d, J=7.02 Hz, 3H), 0.47-0.99 (m, 9H). LCMS: m/z 436 [M+H]$^+$ r.t. 5.8 min. HRMS (ESI) calcd for C$_{25}$H$_{34}$N$_5$O$_2$[M+H]$^+$ 436.2707 found 436.2716;

8-(cyclobutylmethyl)-2-{[(1S)-1-{4-[(4,4-difluoropiperidin-1-yl)methyl]phenyl}ethyl]amino}pyrido[2,3-d]pyrimidin-7(8H)-one [(I), X=N, R2=cyclobutylmethyl, A=phenyl, R1a=H, R1b=Me, R6a=4-CH$_2$NR7R8, R6b=H, R7-R8=4,4-difluoropiperidin-1-yl, R3=R4=R5=H] cpd 109

8-(2,2-dimethylpropyl)-2-({(1S)-1-[4-(pyrrolidin-1-ylmethyl)phenyl]ethyl}amino)pyrido[2,3-d]pyrimidin-7(8H)-one [(I), X=N, R2=2,2-dimethylpropyl, A=phenyl, R1a=H, R1b=Me, R6a=4-CH$_2$NR7R8, R6b=H, R7-R8=-pyrrolidin-1-yl, R3=R4=R5=H] cpd 111

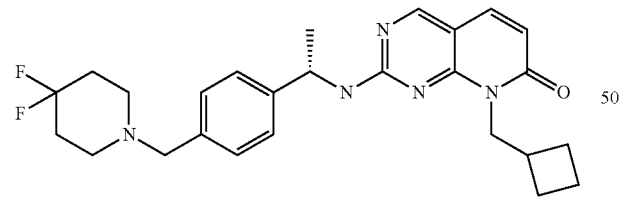

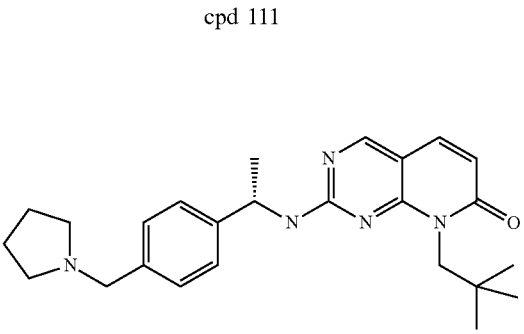

$^1$H NMR (500 MHz, DMSO-d$_6$) δ=8.57 (s, 1H), 8.42 (d, J=7.32 Hz, 1H), 7.66 (d, J=9.30 Hz, 1H), 7.33 (d, J=7.93 Hz, 2H), 7.25 (d, J=7.93 Hz, 2H), 6.20 (d, J=9.30 Hz, 1H), 4.99-5.32 (m, 1H), 4.17 (dd, J=7.24, 12.43 Hz, 1H), 4.06 (dd, J=7.70, 12.43 Hz, 1H), 3.48 (s, 2H), 2.43 (br. s., 4H), 2.10-2.22 (m, 2H), 2.01-2.09 (m, 1H), 1.91 (t, J=13.96 Hz, 4H), 1.66-1.76 (m, 4H), 1.47 (d, J=7.02 Hz, 3H). LCMS: m/z 468 [M+H]$^+$ r.t. 6.96 min. HRMS (ESI) calcd for C$_{26}$H$_{32}$F$_2$N$_5$O [M+H]$^+$ 468.257 found 468.2566;

$^1$H NMR (500 MHz, DMSO-d$_6$) δ=8.47-8.66 (m, 1H), 7.99-8.44 (m, 1H), 7.67 (d, J=9.15 Hz, 1H), 7.31 (d, J=8.08 Hz, 2H), 7.22 (d, J=7.63 Hz, 2H), 6.22 (d, J=9.15 Hz, 1H), 4.95-5.35 (m, J=7.17, 7.17 Hz, 1H), 3.83-4.30 (m, 2H), 3.51 (br. s., 2H), 2.32-2.43 (m, 4H), 1.66 (br. s., 4H), 1.45 (d, J=7.02 Hz, 3H), 0.56-1.00 (m, 9H). LCMS: m/z 420 [M+H]$^+$ r.t. 5.29 min. HRMS (ESI) calcd for C$_{25}$H$_{34}$N$_5$O [M+H]$^+$ 420.2758 found 420.2761.

153

2-{[(1S)-1-{4-[(4,4-difluoropiperidin-1-yl)methyl]phenyl}ethyl]amino}-8-(2-methylbenzyl)pyrido[2,3-d]pyrimidin-7(8H)-one [(I), X=N, R2=2-methylbenzyl, A=phenyl, R1a=H, R1b=Me, R6a=4-CH$_2$NR7R8, R6b=H, R7-R8=4,4-difluoropiperidin-1-yl, R3=R4=R5=H] cpd 112

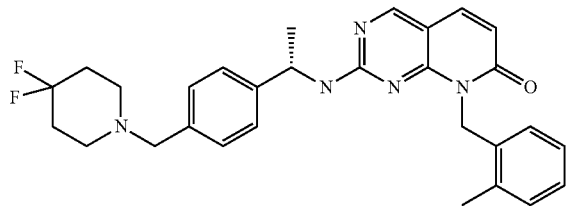 [SMILES: Cc1ccccc1Cn1c(=O)ccc2cnc(N[C@@H](C)c3ccc(CN4CCC(F)(F)CC4)cc3)nc21]

$^1$H NMR (500 MHz, DMSO-d$_6$) δ=8.63 (s, 1H), 8.35 (d, J=8.08 Hz, 1H), 7.80 (d, J=9.30 Hz, 1H) 8.47-7.23 (dd, J=7.78, 7.23, Hz, 1H), 7.11 (dd, J=7.17 Hz, 1H), 7.0.3 (d, J=8.24 Hz, 2H), 7.0 (d, J=8.24 Hz, 2H), 6.92 (dd, J=7.47 Hz, 1H), 6.37 (d, J=7.78 Hz, 1H), 6.32 (d, J=9.30 Hz, 1H), 5.40 (d, J=15.25 Hz, 1H), 5.19 (d, J=15.25 Hz, 1H), 4.82 (m, J=7.32 Hz, 1H), 3.46 (br. s., 2H), 2.43 (s, 3H), 2.38-2.42 (m, 4H), 1.87-1.96 (m, 4H), 1.33 (d, J=6.86 Hz, 3H). LCMS: m/z 504 [M+H]$^+$ r.t. 6.97 min. HRMS (ESI) calcd for C$_{29}$H$_{32}$F$_2$N$_5$O [M+H]$^+$504.257 found 504.2578;

8-(cyclohexylmethyl)-2-{[(1S)-1-{4-[(4,4-difluoropiperidin-1-yl)methyl]phenyl}ethyl]amino}pyrido[2,3-d]pyrimidin-7(8H)-one [(I), X=N, R2=cyclohexylmethyl, A=phenyl, R1a=H, R1b=Me, R6a=4-CH$_2$NR7R8, R6b=H, R7-R8=4,4-difluoropiperidin-1-yl, R3=R4=R5=H] cpd 113

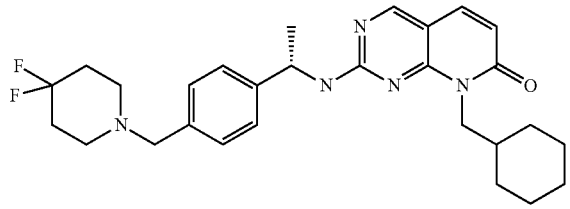 [SMILES: C[C@H](Nc1ncc2ccc(=O)n(CC3CCCCC3)c2n1)c1ccc(CN2CCC(F)(F)CC2)cc1]

$^1$H NMR (500 MHz, DMSO-d$_6$) δ=8.58 (s, 1H), 8.41 (d, J=7.63 Hz, 1H), 7.68 (d, J=9.46 Hz, 1H), 7.33 (d, J=8.08 Hz, 2H), 7.24 (d, J=7.93 Hz, 2H), 6.20 (d, J=9.30 Hz, 1H), 5.08 (quin, J=7.17 Hz, 1H), 4.02 (dd, J=7.40, 12.28 Hz, 1H), 3.87 (dd, J=7.63, 12.35 Hz, 1H), 33.47 (s, 2H), 2.41-2.47 (m, 4H), 1.84-1.96 (m, 4H), 1.58-1.70 (m, 3H), 1.48-1.55 (m, 2H), 1.46 (d, J=7.02 Hz, 3H), 0.89-1.43 m 6H). LCMS: m/z 496 [M+H]$^+$ r.t. 7.52 min. HRMS (ESI) calcd for C$_{28}$H$_{36}$F$_2$N$_5$O [M+H]$^+$496.2883 found 496.2885;

154

2-{[(1S)-1-{4-[(4,4-difluoropiperidin-1-yl)methyl]phenyl}ethyl]amino}-8-(2-methoxyethyl)pyrido[2,3-d]pyrimidin-7(8H)-one [(I), X=N, R2=2-methoxyethyl, A=phenyl, R1a=H, R1b=Me, R6a=4-CH$_2$NR7R8, R6b=H, R7-R8=4,4-difluoropiperidin-1-yl, R3=R4=R5=H] cpd 114

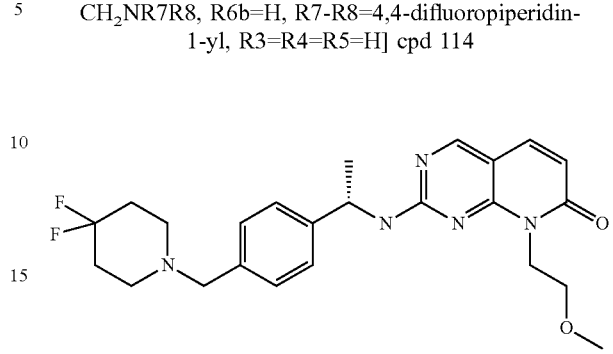

$^1$H NMR (500 MHz, DMSO-d$_6$) δ=8.51-8.61 (m, 1H), 8.18-8.48 (m, 1H), 7.68 (d, J=9.30 Hz, 1H), 7.34 (d, J=7.63 Hz, 2H), 7.23 (d, J=7.93 Hz, 2H), 6.21 (d, J=9.30 Hz, 1H), 4.93-5.30 (m, 1H), 4.28 (t, J=6.25 Hz, 2H), 3.45-3.51 (m, 2H), 3.25-3.30 (m, 2H), 3.15 (s, 3H), 2.43 (br. s., 4H), 1.81-1.96 (m, 4H), 1.46 (d, J=7.02 Hz, 3H). LCMS: m/z 458 [M+H]$^+$ r.t. 5.79 min. HRMS (ESI) calcd for C$_{24}$H$_{30}$F$_2$N$_5$O$_2$ [M+H]$^+$458.2362 found 458.2368;

2-{[(1S)-1-{4-[(4,4-difluoropiperidin-1-yl)methyl]phenyl}ethyl]amino}-8-[4-fluoro-2-(trifluoromethyl)benzyl]pyrido[2,3-d]pyrimidin-7(8H)-one [(I), X=N, R2=4-fluoro-2-(trifluoromethyl)benzyl, A=phenyl, R1a=H, R1b=Me, R6a=4-CH$_2$NR7R8, R6b=H, R7-R8=4,4-difluoropiperidin-1-yl, R3=R4=R5=H] cpd 115

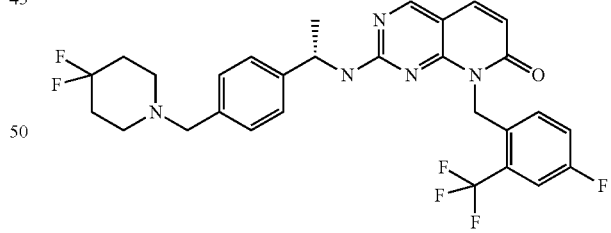

$^1$H NMR (500 MHz, DMSO-d$_6$) δ=8.66 (s, 1H), 8.44 (d, J=7.93 Hz, 1H), 7.85 (d, J=9.30 Hz, 1H), 7.72 (dd, J=2.44, 9.00 Hz, 1H), 7.17-7.25 (m, 1H), 6.93 (s, 4H), 6.55 (dd, J=4.96, 8.31 Hz, 1H), 6.33 (d, J=9.30 Hz, 1H), 5.57 (d, J=16.17 Hz, 1H), 5.45 (d, J=16.17 Hz, 1H), 4.79 (quin, J=7.44 Hz, 1H), 3.38 m, 2H), 2.29-2.45 (m, 4H), 1.82-1.97 (m, 4H), 1.26-1.44 (m, 3H). LCMS: m/z 576 [M+H]$^+$ r.t. 7.37 min. HRMS (ESI) calcd for C$_{29}$H$_{28}$F$_6$N$_5$O [M+H]$^+$ 576.2193 found 576.21938;

2-{[(1S)-1-{4-[(4,4-difluoropiperidin-1-yl)methyl]
phenyl}ethyl]amino}-8-(3,3,3-trifluoro-2,2-dimeth-
ylpropyl) pyrido[2,3-d]pyrimidin-7(8H)-one [(I),
X=N, R2=3,3,3-trifluoro-2,2-dimethylpropyl,
A=phenyl, R1a=H, R1b=Me, R6a=4-CH₂NR7R8,
R6b=H, R7-R8=4,4-difluoropiperidin-1-yl,
R3=R4=R5=H] cpd 116

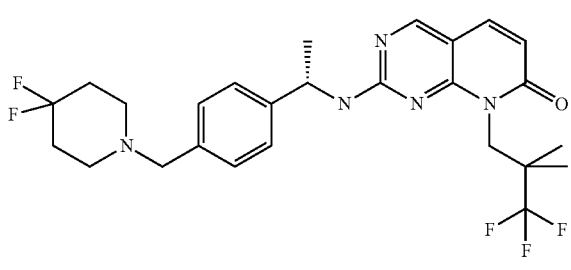 [SMILES: C[C@H](Nc1ncc2ccc(=O)n(CC(C)(C)C(F)(F)F)c2n1)c1ccc(CN2CCC(F)(F)CC2)cc1]

$^1$H NMR (500 MHz, DMSO-$d_6$) δ=8.55-8.64 (m, 1H), 8.48 (d, J=7.78 Hz, 1H), 7.73 (d, J=9.30 Hz, 1H), 7.31 (d, J=7.93 Hz, 2H), 7.23 (d, J=8.08 Hz, 2H), 6.26 (d, J=9.30 Hz, 1H), 5.02-5.29 (m, 1H), 4.31-4.55 (m, 2H), 3.48 (s, 2H), 2.43 (br. s., 4H), 1.85-1.97 (m, 4H), 1.46 (d, J=7.02 Hz, 3H), 0.79-1.17 (m, 6H). LCMS: m/z 524 [M+H]$^+$ r.t. 7.34 min. HRMS (ESI) calcd for $C_{26}H_{31}F_5N_5O$ [M+H]$^+$ 524.2444 found 524.2455;

2-{[(1S)-1-{4-[(3,3-difluoropiperidin-1-yl)methyl]
phenyl}ethyl]amino}-8-(2,2-dimethylpropyl)pyrido
[2,3-d]pyrimidin-7(8H)-one [(I), X=N, R2=2,2-
dimethylpropyl, A=phenyl, R1a=H, R1b=Me,
R6a=4-CH₂NR7R8, R6b=H, R7-R8=3,3-difluoropi-
peridin-1-yl, R3=R4=R5=H] cpd 117

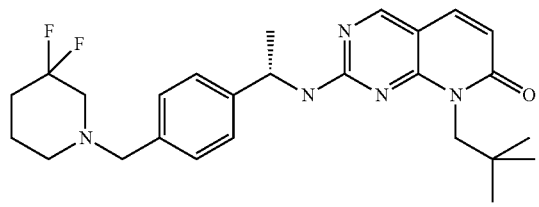 [SMILES: C[C@H](Nc1ncc2ccc(=O)n(CC(C)(C)C)c2n1)c1ccc(CN2CCCC(F)(F)C2)cc1]

$^1$H NMR (500 MHz, DMSO-$d_6$) δ=8.58 (s, 1H), 8.36 (d, J=7.32 Hz, 1H), 7.67 (d, J=9.46 Hz, 1H), 7.33 (d, J=8.08 Hz, 2H), 7.22 (d, J=7.93 Hz, 2H), 6.22 (d, J=9.30 Hz, 1H), 5.06 (quin, J=7.13 Hz, 1H), 3.93-4.23 (m, 2H), 3.46-3.55 (m, 2H), 2.56 (d, J=11.74 Hz, 1H), 2.52 (m, 1H), 2.36 (br. s, 2H), 1.84 (spt, J=6.80 Hz, 2H), 1.61 (quin, J=5.83 Hz, 2H), 1.46 (d, J=7.02 Hz, 3H), 0.71 (br. s., 9H). LCMS: m/z 470 [M+H]$^+$ r.t. 7.31 min. HRMS (ESI) calcd for $C_{26}H_{34}F_2N_5O$ [M+H]$^+$ 470.2726 found 470.272;

2-{[(1S)-1-{4-[(4,4-difluoropiperidin-1-yl)methyl]
phenyl}ethyl]amino}-4-methyl-8-(2-ethylpropyl)
pyrido [2,3-d]pyrimidin-7(8H)-one [(I), X=N,
R2=2-methylpropyl, A=phenyl, R1a=H, R1b=Me,
R6a=4-CH₂NR7R8, R6b=H, R7-R8=4,4-difluoropi-
peridin-1-yl, R3=Me, R4=R5=H] cpd 118

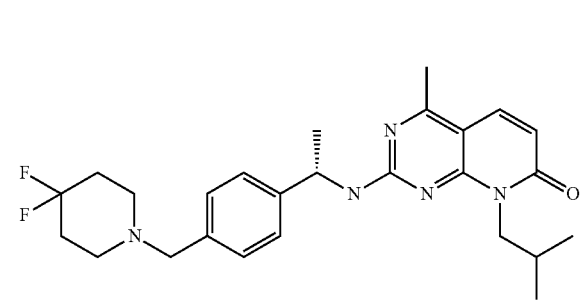 [SMILES: Cc1nc(N[C@@H](C)c2ccc(CN3CCC(F)(F)CC3)cc2)nc2c1ccc(=O)n2CC(C)C]

$^1$H NMR (500 MHz, DMSO-$d_6$) δ=8.33 (d, J=7.47 Hz, 1H), 7.86 (d, J=9.61 Hz, 1H), 7.31 (d, J=7.93 Hz, 2H), 7.22 (d, J=7.93 Hz, 2H), 6.18 (d, J=9.46 Hz, 1H), 4.69-5.40 (m, 1H), 3.94-4.01 (m, 1H), 3.79-3.88 (m, 1H), 3.47 (s, 2H), 2.53 (s, 3H), 2.43 (br. s., 4H), 1.83-1.97 (m, J=13.88, 13.88 Hz, 1H), 1.44 (d, J=7.17 Hz, 3H), 0.72 (d, J=6.71 Hz, 3H), 0.60 (d, J=6.56 Hz, 3H). LCMS: m/z 576 [M+H]$^+$ r.t. 7.01 min. HRMS (ESI) calcd for $C_{26}H_{34}F_2N_5O$ [M+H]$^+$ 470.2726 found 470.2723;

2-{(S)-1-[4-(4,4-Difluoro-piperidin-1-ylmethyl)-
phenyl]-ethylamino}-8-(2-hydroxy-2-methyl-pro-
pyl)-8H-pyrido [2,3-d]pyrimidin-7-one [(I), X=N,
R2=2-hydroxy-2-methylpropyl, A=phenyl, R1a=H,
R1b=Me, R6a=4-CH₂NR7R8, R6b=H, R7-R8=4,4-
difluoropiperidin-1-yl, R3=R4=R5=H₁ cpd 119

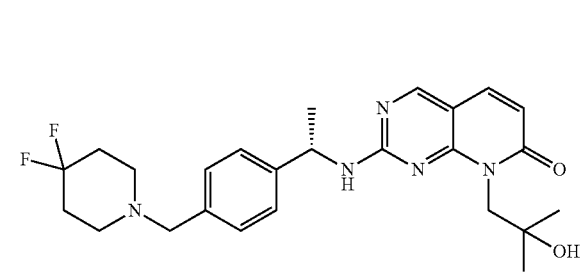 [SMILES: C[C@H](Nc1ncc2ccc(=O)n(CC(C)(C)O)c2n1)c1ccc(CN2CCC(F)(F)CC2)cc1]

$^1$H NMR (500 MHz, DMSO-$d_6$) δ=8.63 (s, 1H), 8.49 (d, J=7.6 Hz, 1H), 7.74 (d, J=9.3 Hz, 1H), 7.34 (d, J=8.1 Hz, 2H), 7.23 (d, J=7.9 Hz, 2H), 6.28 (d, J=9.3 Hz, 1H), 5.04 (quin, J=7.0 Hz, 1H), 4.63-3.73 (m, 3H), 3.48 (s, 2H), 2.44 (d, J=5.3 Hz, 4H), 1.98-1.79 (m, 4H), 1.46 (d, J=7.0 Hz, 3H), 1.26-0.80 (m, 6H). LCMS: m/z 472 [M+H]$^+$ r.t. 6.86 min. HRMS (ESI) calcd for $C_{25}H_{32}F_2N_5O_2$ [M+H]$^+$ 472.2519 found 472.2520;

2-{[(1S)-1-{4-[(4,4-difluoropiperidin-1-yl)methyl]phenyl}ethyl]amino}-8-[2-(hydroxymethyl)-2-methylpentyl]pyrido[2,3-d]pyrimidin-7(8H)-one [(I), X=N, R2=2-hydroxy-2-methylpentyl, A=phenyl, R1a=H, R1b=Me, R6a=4-CH$_2$NR7R8, R6b=H, R7-R8=4,4-difluoropiperidin-1-yl, R3=R4=R5=H] cpd 120

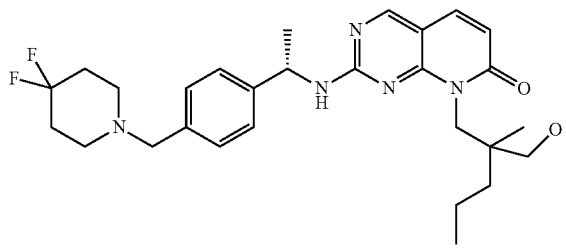 [SMILES: CCCC(C)(CO)Cn1c(=O)ccc2cnc(N[C@@H](C)c3ccc(CN4CCC(F)(F)CC4)cc3)nc21]

$^1$H NMR (500 MHz, DMSO-d$_6$) δ=8.61 (d, J=3.97 Hz, 1H), 8.43 (d, J=7.17 Hz, 1H), 7.73 (d, J=9.15 Hz, 1H), 7.35 (d, J=7.93 Hz, 2H), 7.11-7.28 (m, 2H), 6.26 (d, J=9.30 Hz, 1H), 5.05-5.38 (m, 1H), 4.15-4.48 (m, 3H), 3.48 (s, 2H), 2.86-3.22 (m, 2H), 2.44 (br. s., 4H), 1.92 (t, J=13.80 Hz, 4H), 1.47 (dd, J=2.82, 6.94 Hz, 3H), 1.12-1.46 (m, 4H), 0.82-0.89 (m, 3H), 0.65-0.74 (m, 3H). LCMS: m/z 514 [M+H]$^+$ r.t. 6.99 min. HRMS (ESI) calcd for C$_{28}$H$_{38}$F$_2$N$_5$O$_2$ [M+H]$^+$ 514.2988 found 514.2994.

Example 9

2,2-dimethyl-3-[2-{[(1S)-1-(naphthalen-2-yl)ethyl]amino}-7-oxopyrido[2,3-d]pyrimidin-8(7H)-yl]propanoic acid [(I), X=N, R2=2,2-dimethyl-3-propanoic acid, A=naphthalen-2-yl, R1a=H, R1b=Me, R6a=R6b=H, R3=R4=R5=H] conv. 8, cpd 121

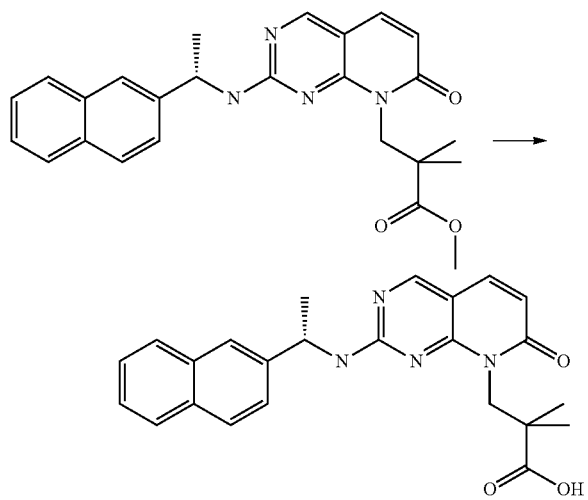

Lithium hydroxyde (0.022 g, 0.52 mmol) was added to a solution of methyl 2,2-dimethyl-3-[2-{[(1S)-1-(naphthalen-2-yl)ethyl]amino}-7-oxopyrido[2,3-d]pyrimidin-8(7H)-yl]propanoate (0.030 g, 0.07 mmol) in THF:water (1:1, 2 mL) and the reaction mixture was stirred at room temperature for 18 h. The solvent (THF) was removed under reduced pressure and the aqueous residue was diluted with water. The aqueous phase was acidified with hydrochloric acid (1 M) until a precipitation occurred, the solid was filtered, washed with water and dried under vacuum, to give the title compound as a white solid (0.029 g, >99%).

$^1$H NMR (500 MHz, DMSO-d$_6$) δ=12.08 (br.s. 1H), 8.57 (s, 1H), 8.50 (d, J=7.47 Hz, 1H), 7.81-7.94 (m, 4H), 7.66 (d, J=9.30 Hz, 1H), 7.59 (dd, J=1.22, 8.54 Hz, 1H), 7.37-7.51 (m, 2H), 6.17 (d, J=9.30 Hz, 1H), 5.19-5.35 (m, J=7.02 Hz, 1H), 4.38 (d, J=12.96 Hz, 1H), 4.27 (d, J=12.81 Hz, 1H), 1.55 (d, J=7.02 Hz, 3H), 1.02 (s, 3H), 0.91 (s, 3H). LCMS: m/z 417 [M+H]$^+$ r.t. 4.74 min. HRMS (ESI) calcd for C$_{24}$H$_{25}$N$_4$O$_3$ [M+H]$^+$ 417.1921 found 417.1924.

Example 10

2,2-dimethyl-3-[2-{[(1S)-1-(naphthalen-2-yl)ethyl]amino}-7-oxopyrido[2,3-d]pyrimidin-8(7H)-yl]propanamide [(I), X=N, R2=2,2-dimethyl-3-propanamide, A=naphthalen-2-yl, R1a=H, R1b=Me, R6a=R6b=H, R8=H, R3=R4=R5=H] conv. 9, cpd 122

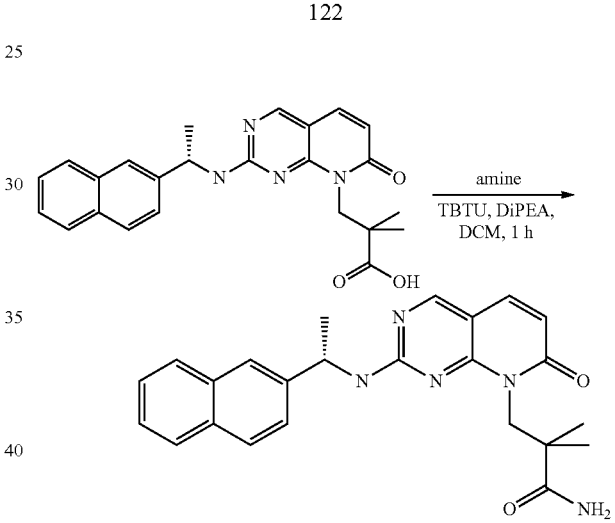

To a solution of TBTU (32 mg, 0.1 mmol) in DCM (2 mL) was added to 2,2-dimethyl-3-[2-{[(1S)-1-(naphthalen-2-yl)ethyl]amino}-7-oxopyrido[2,3-d]pyrimidin-8(7H)-yl]propanoic acid (20 mg, 0.05 mmol), DIPEA (10 μL, 0.06 mmol), and ammonium hydrate 30% (1 mL). The reaction mixture was stirred at room temperature for 16 hours, the solvents were removed in vacuo, the residue was partitioned between DCM and water, and the organic layer was dried. The crude was purified by chromatography on a silica gel column (eluent: DCM/EtOAc/EtOH: 60/30/10) to afford the title compound (18 g, 90% yield).

$^1$H NMR (500 MHz, DMSO-d$_6$) δ=8.56 (s, 1H), 8.49 (d, J=7.78 Hz, 1H), 7.97 (s, 1H), 7.79-7.90 (m, 3H), 7.55-7.69 (m, 2H), 7.40-7.51 (m, 2H), 7.13 (br. s., 1H), 6.91 (br. s., 1H), 6.19 (d, J=9.30 Hz, 1H), 5.33 (t, J=7.24 Hz, 1H), 4.44 (d, J=13.12 Hz, 1H), 4.28 (d, J=12.81 Hz, 1H), 1.55 (d, J=6.86 Hz, 3H), 1.00 (s, 3H), 0.97 (s, 3H).

LCMS: m/z 416 [M+H]$^+$ r.t. 5.42 min. HRMS (ESI) calcd for C$_{24}$H$_{26}$N$_5$O$_2$ [M+H]$^+$ 416.2081 found 416.2088.

According to this same methodology, but employing suitable substituted derivatives, the following compounds were prepared:

N,2,2-trimethyl-3-[7-oxo-2-{[(1S)-1-phenylethyl] amino}pyrido[2,3-d]pyrimidin-8(7H)-yl]propanamide [(I), X=N, R2=N,2,2-trimethyl-3-propanamide, A=phenyl, R1a=H, R1b=Me, R6a=R6b=H, R8=H, R3=R4=R5=H] cpd 123

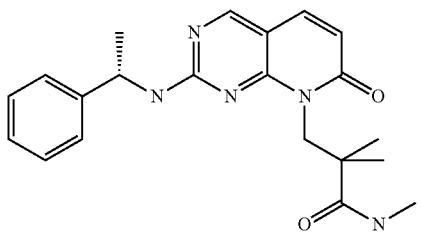 [SMILES: CNC(=O)C(C)(C)Cn1c(=O)ccc2cnc(N[C@@H](C)c3ccccc3)nc21]

¹H NMR (500 MHz, DMSO-d₆) δ=8.49-8.61 (m, 1H), 8.34 (d, J=8.08 Hz, 1H), 7.68-7.98 (m, 1H), 7.66 (d, J=9.30 Hz, 1H), 7.23-7.47 (m, 4H), 7.12-7.22 (m, 1H), 6.20 (d, J=9.30 Hz, 1H), 5.22 (quin, J=6.98 Hz, 1H), 4.17-4.37 (m, 2H), 2.48 (s, 3H), 1.44 (d, J=6.86 Hz, 3H), 0.88-1.11 (m, 6H). LCMS: m/z 380 [M+H]⁺ r.t. 5.03 min.

HRMS (ESI) calcd for $C_{21}H_{26}N_5O_2$ [M+H]⁺ 380.2081 found 380.2086;

N,N,2,2-tetramethyl-3-[7-oxo-2-{[(1S)-1-phenylethyl]amino}pyrido[2,3-d]pyrimidin-8(7H)-yl]propanamide [(I), X=N, R2=N,N,2,2-tetramethyl-3-propanamide, A=phenyl, R1a=H, R1b=Me, R6a=R6b=H, R8=H, R3=R4=R5=H] cpd 124

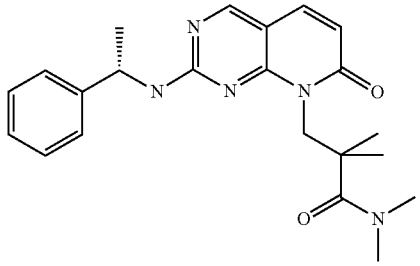

¹H NMR (500 MHz, DMSO-d₆) δ=8.52-8.63 (m, 1H), 8.42 (d, J=7.78 Hz, 1H), 7.69 (d, J=9.46 Hz, 1H), 7.38 (d, J=7.63 Hz, 2H), 7.25-7.32 (m, 2H), 7.12-7.22 (m, 1H), 6.21 (d, J=9.30 Hz, 1H), 5.07 (s, 1H), 4.42 (d, J=5.49 Hz, 2H), 2.79-3.12 (m, 6H), 1.46 (d, J=7.02 Hz, 3H), 0.90-1.17 (m, 6H).

LCMS: m/z 394 [M+H]⁺ r.t. 5.49 min. HRMS (ESI) calcd for $C_{22}H_{28}N_5O_2$ [M+H]⁺ 394.2238 found 394.2246;

2,2-dimethyl-N-(3-methylphenyl)-3-[7-oxo-2-{[(1S)-1-phenylethyl]amino}pyrido[2,3-d]pyrimidin-8(7H)-yl]propanamide [(I), X=N, R2=2,2-dimethyl-N-(3-methylphenyl) propanamide, A=phenyl, R1a=H, R1b=Me, R6a=R6b=H, R8=H, R3=R4=R5=H] cpd 125

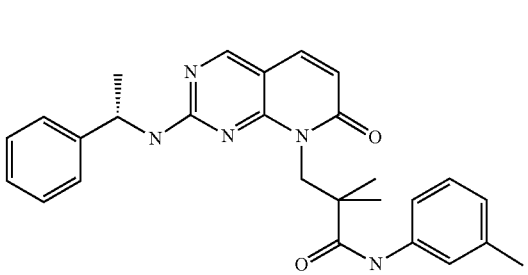

¹H NMR (500 MHz, DMSO-d₆) δ=9.04 (s, 1H), 8.54 (s, 1H), 8.28 (d, J=7.78 Hz, 1H), 7.68 (d, J=9.30 Hz, 1H), 7.28-7.42 (m, 4H), 7.23 (t, J=7.55 Hz, 2H), 7.07-7.19 (m, 2H), 6.84 (d, J=7.47 Hz, 1H), 6.22 (d, J=9.30 Hz, 1H), 4.97-5.19 (m, J=7.24, 7.24 Hz, 1H), 4.13-4.50 (m, 2H), 2.25 (s, 3H), 1.24 (d, J=4.27 Hz, 3H), 1.02-1.19 (m, 6H). LCMS: m/z 456 [M+H]⁺ r.t. 6.61 min. HRMS (ESI) calcd for $C_{27}H_{30}N_5O_2$ [M+H]⁺ 456.2394 found 456.2396;

N-(2-hydroxyethyl)-2,2-dimethyl-3-[7-oxo-2-{[(1S)-1-phenylethyl]amino}pyrido[2,3-d]pyrimidin-8(7H)-yl]propanamide [(I), X=N, R2=N-(2-hydroxyethyl)-2,2-dimethyl-3-propanamide, A=phenyl, R1a=H, R1b=Me, R6a=R6b=H, R8=H, R3=R4=R5=H] cpd 126

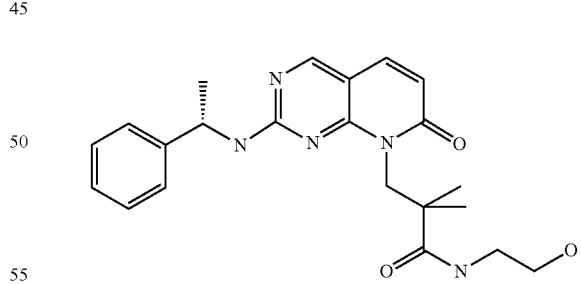

¹H NMR (500 MHz, DMSO-d₆) δ=8.55 (s, 1H), 8.37 (d, J=7.63 Hz, 1H), 7.66 (d, J=9.30 Hz, 1H), 7.43 (d, J=7.47 Hz, 1H), 7.35-7.42 (m, 1H), 7.25-7.34 (m, 3H), 7.10-7.22 (m, 1H), 6.20 (d, J=9.30 Hz, 1H), 5.13-5.29 (m, 1H), 4.57 (t, J=5.57 Hz, 1H), 4.22-4.38 (m, 2H), 2.97-3.18 (m, 4H), 1.41-1.52 (m, 3H), 1.01-1.06 (m, 3H), 0.93-0.98 (m, 3H). LCMS: m/z 410 [M+H]⁺ r.t. 4.78 min. HRMS (ESI) calcd for $C_{22}H_{28}N_5O_3$ [M+H]⁺ 410.2187 found 410.2186;

N-(3-hydroxypropyl)-2,2-dimethyl-3-[7-oxo-2-{[(1S)-1-phenylethyl]amino}pyrido[2,3-d]pyrimidin-8(7H)-yl]propanamide [(I), X=N, R2=N-(2-hydroxyethyl)-2,2-dimethyl-3-propanamide, A=phenyl, R1a=H, R1b=Me, R6a=R6b=H. R8=H. R3=R4=R5=H, cpd 127

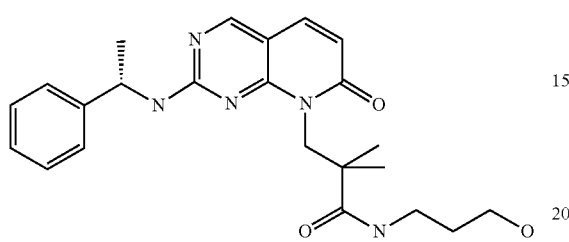

$^1$H NMR (500 MHz, DMSO-d$_6$) δ=8.54 (s, 1H), 8.36 (d, J=7.78 Hz, 1H), 7.66 (d, J=9.30 Hz, 1H), 7.44 (d, J=7.63 Hz, 2H), 7.39 (t, J=5.49 Hz, 1H), 7.28 (t, J=7.63 Hz, 2H), 7.18 (q, J=6.96 Hz, 1H), 6.20 (d, J=9.30 Hz, 1H), 5.14-5.36 (m, J=4.42, 7.17, 7.17 Hz, 1H), 4.19-4.50 (m, 3H), 3.36 (m, 2H), 2.97-3.16 (m, 2H), 1.38-1.60 (m, 5H), 0.94-1.10 (m, 6H). LCMS: m/z 424 [M+H]$^+$ r.t. 4.85 min. HRMS (ESI) calcd for C$_{23}$H$_{30}$N$_5$O$_3$ [M+H]$^+$ 424.2343 found 424.2349;

N-[3-(1-hydroxyethyl)phenyl]-2,2-dimethyl-3-[7-oxo-2-{[(1S)-1-phenylethyl]amino}pyrido[2,3-d]pyrimidin-8(7H)-yl]propanamide [(I), X=N, R2=N-[3-(1-hydroxyethyl)phenyl]-2,2-dimethyl-3-propanamide, A=phenyl, R1a=H, R1b=Me, R6a=R6b=H, R8=H, R3=R4=R5=H] cpd 128

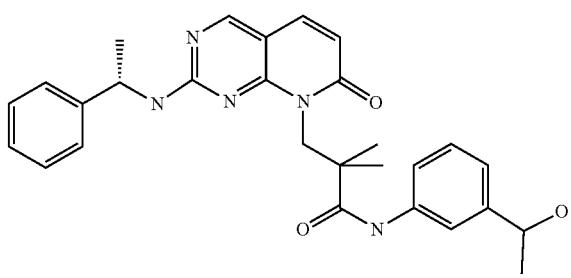

$^1$H NMR (500 MHz, DMSO-d$_6$) δ=9.07-9.26 (m, 1H), 8.47-8.59 (m, 1H), 8.29 (d, J=7.63 Hz, 1H), 7.69 (d, J=9.30 Hz, 1H), 7.42-7.62 (m, 2H), 7.37 (d, J=7.63 Hz, 2H), 7.06-7.33 (m, 5H), 7.00 (d, J=7.63 Hz, 1H), 6.13-6.26 (m, 1H), 4.93-5.27 (m, 1H), 4.54-4.74 (m, 1H), 4.34-4.49 (m, 2H), 1.26-1.33 (m, 6H), 1.16 (br. s, 3H), 1.07 (br. s, 3H). LCMS: m/z 486 [M+H]$^+$ r.t. 5.71 min. HRMS (ESI) calcd for C$_{28}$H$_{32}$N$_5$O$_3$ [M+H]$^+$ 486.25 found 486.2493.

Example 11

2,2-dimethyl-3-[2-{[(1S)-1-(naphthalen-2-yl)ethyl]amino}-7-oxopyrido[2,3-d]pyrimidin-8(7H)-yl]propanenitrile [(I), X=N, R2=2,2-dimethyl-3-propanenitrile, A=phenyl, R1a=H, R1b=Me, R6a=R6b=H, R8=H, R3=R4=R5=H] conv. 10, cpd 129

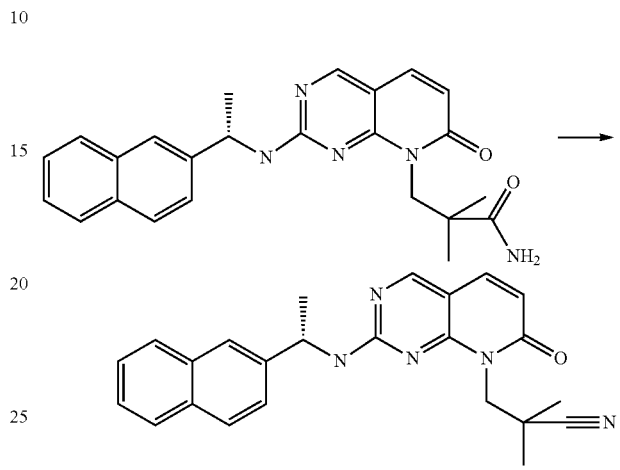

A solution of 2,2-dimethyl-3-[2-{[(1S)-1-(naphthalen-2-yl)ethyl]amino}-7-oxopyrido[2,3-d]pyrimidin-8(7H)-yl]propanamide (10 mg, 0.02 mmol) in 1 mL of trifluoroacetic anhydride was heated at 100° C. for 1 h. The reaction went to completion, the solvent was removed in vacuo and the crude was purified by chromatography on a silica gel column (eluent: DCM/EtOAc/EtOH: 60/35/5) to afford the title compound (7.5 g, 90% yield).

$^1$H NMR (500 MHz, DMSO-d$_6$) δ=8.23-8.70 (m, 2H), 7.81-7.94 (m, 4H), 7.73 (d, J=9.30 Hz, 1H), 7.59 (d, J=8.39 Hz, 1H), 7.34-7.53 (m, 2H), 6.25 (d, J=9.30 Hz, 1H), 5.18-5.51 (m, J=7.05, Hz, 1H), 4.20-4.57 (m, 2H), 1.56 (d, J=7.02 Hz, 3H), 1.04-1.49 (m, 6H). LCMS: m/z 398 [M+H]$^+$ r.t. 6.37 min. HRMS (ESI) calcd for C$_{24}$H$_{24}$N$_5$O [M+H]$^+$ 398.1976 found 398.1985.

Example 12

8-(2,2-dimethylpropyl)-2-({(1S)-1-[4-(1-methyl-1H-pyrazol-4-yl)phenyl]ethyl}amino)pyrido[2,3-d]pyrimidin-7 (8H)-one [(I), X=N, R2=2,2-dimethylpropyl, A=phenyl, R1b=Me, R6a=1-methyl-1H-pyrazol-4-yl, R6b=H, R8=H, R3=R4=R5=H] conv. 5, cpd 130

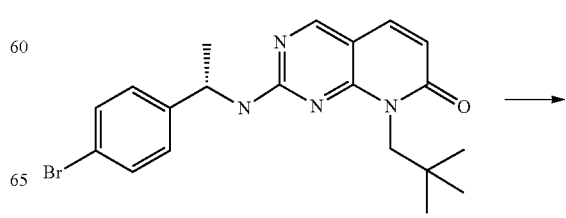

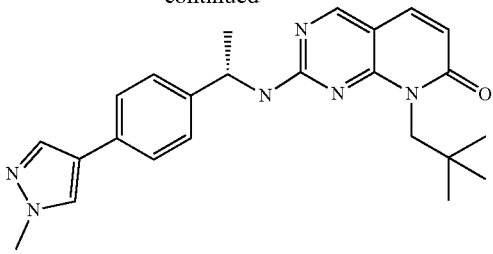

In a 5 mL microwave vial a solution of 2-{[(1S)-1-(4-bromophenyl)ethyl]amino}-8-(2,2-dimethylpropyl)pyrido[2,3-d]pyrimidin-7(8H)-one (30 mg, 0.07 mmol), 1-methyl-4-(4,4,5,5-tetramethyl-1,3,2-dioxaborolan-2-yl)-1 H-pyrazole (29 mg, 0.24 mmol), $CS_2CO_3$ (46 mg, 0.14 mmol) in Dioxane (2 mL) was bubbled $N_2$ for 3 min then $Cl_2Pd(dppf)$ $CH_2Cl_2$ (5 mg, 0.007 mmol) was added. The capped tube was heated to 100° C. for 4 h. After cooling the reaction mixture was diluted with EtOAc (10 mL) and washed with water (10 mL). After separation, the aqueous phase was extracted with EtOAc (3×10 mL). The combined organic layers were dried over $Na_2SO_4$, filtered and concentrated. The crude material was purified through silica gel column chromatography (DCM/EtOAc 8/2) to give an off-white solid (14.5 mg, 50% yield).

$^1$H NMR (500 MHz, DMSO-$d_6$) δ=8.57 (s, 1H), 8.07-8.42 (m, 1H), 8.06 (s, 1H), 7.79 (d, J=0.46 Hz, 1H), 7.67 (d, J=9.30 Hz, 1H), 7.44-7.52 (m, 2H), 7.35 (d, J=8.08 Hz, 2H), 6.22 (d, J=9.15 Hz, 1H), 4.95-5.34 (m, J=6.98, Hz, 1H), 3.99-4.29 (m, 2H), 3.84 (s, 3H), 1.47 (d, J=7.02 Hz, 3H), 0.65-0.98 (m, 9H).

LCMS: m/z 417 [M+H]$^+$ r.t. 6.05 min. HRMS (ESI) calcd for $C_{24}H_{29}N_6O$ [M+H]$^+$ 417.2398 found 417.24.

According to this same methodology, the following compounds were prepared:

8-(2,2-dimethylpropyl)-2-({(1S)-1-[4-(pyridin-4-yl)phenyl]ethyl}amino)pyrido[2,3-d]pyrimidin-7(8H)-one [(I), X=N, R2=2,2-dimethyl-propyl, A=phenyl, R1a=H, R1b=Me, R6a=pyridin-4-yl, R6b=H, R8=H, R3=R4=R5=H] cpd 131

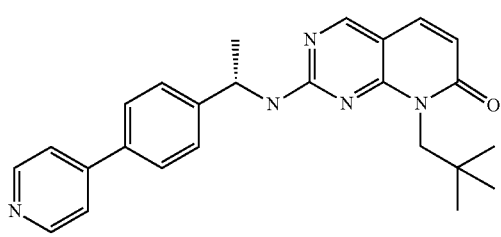

$^1$H NMR (500 MHz, DMSO-$d_6$) δ=8.51-8.65 (m, 3H), 8.46 (d, J=7.32 Hz, 1H), 7.76 (d, J=8.08 Hz, 2H), 7.60-7.70 (m, 3H), 7.53 (d, J=8.08 Hz, 2H), 6.23 (d, J=9.30 Hz, 1H), 4.97-5.42 (m, 1H), 3.88-4.38 (m, 2H), 1.45-1.55 (m, 3H), 0.52-1.04 (m, 9H). LCMS: m/z 414 [M+H]$^+$ r.t. 6.05 min. HRMS (ESI) calcd for $C_{25}H_{28}N_5O$ [M+H]$^+$ 414.2289 found 414.2293;

8-(2,2-dimethylpropyl)-2-({(1S)-1-[4-(2-fluoropyridin-4-yl)phenyl]ethyl}amino)pyrido[2,3-d]pyrimidin-7(8H)-one [(I), X=N, R2=2,2-dimethyl-propyl, A=phenyl, R1a=H, R1b=Me, R6a=2-fluoropyridin-4-yl, R6b=H, R8=H, R3=R4=R5=H] cpd 132

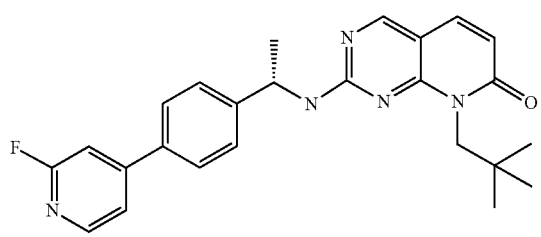

$^1$H NMR (500 MHz, DMSO-$d_6$) δ=8.50-8.63 (m, 1H), 8.47 (d, J=7.47 Hz, 1H), 8.27 (d, J=5.34 Hz, 1H), 7.82 (d, J=8.08 Hz, 2H), 7.60-7.71 (m, 2H), 7.54 (d, J=8.08 Hz, 2H), 7.49 (s, 1H), 6.23 (d, J=9.46 Hz, 1H), 5.03-5.40 (m, 1H), 3.88-4.32 (m, 2H), 1.50 (d, J=7.02 Hz, 3H), 0.55-1.01 (m, 9H).

LCMS: m/z 432 [M+H]$^+$ r.t. 6.72 min. HRMS (ESI) calcd for $C_{25}H_{27}FN_5O$ [M+H]$^+$ 432.2194 found 432.2197;

8-(2,2-dimethylpropyl)-2-({(1S)-1-[4-(thiophen-3-yl)phenyl]ethyl}amino)pyrido[2,3-d]pyrimidin-7(8H)-one one [(I), X=N, R2=2,2-dimethyl-propyl, A=phenyl, R1a=H, R1b=Me, R6a=thiophen-3-yl, R6b=H, R8=H, R3=R4=R5=H] cpd 133

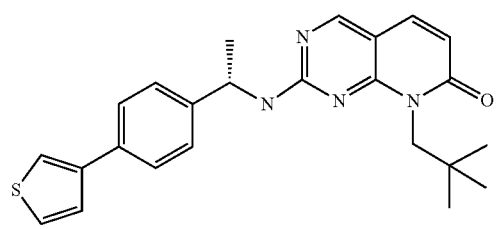

$^1$H NMR (500 MHz, DMSO-$d_6$) δ=8.47-8.66 (m, 1H), 8.41 (d, J=7.17 Hz, 1H), 7.79 (dd, J=1.37, 2.90 Hz, 1H), 7.62-7.72 (m, 2H), 7.61 (dd, J=3.05, 5.03 Hz, 1H), 7.51 (dd, J=1.22, 5.03 Hz, 1H), 7.36-7.45 (m, 2H), 7.34 (d, J=8.39 Hz, 1H), 6.23 (dd, J=6.25, 9.15 Hz, 1H), 4.85-5.38 (m, 1H), 3.84-4.33 (m, 2H), 1.49 (d, J=7.02 Hz, 3H), 0.60-0.99 (m, 9H). LCMS: m/z 419 [M+H]$^+$ r.t. 7.39 min. HRMS (ESI) calcd for $C_{24}H_{27}N_4OS$ [M+H]$^+$ 419.19 found 419.1909, 4'-[(1S)-1-{[8-(2,2-dimethylpropyl)-7-oxo-7,8-dihydropyrido[2,3-d]pyrimidin-2-yl]amino}ethyl]biphenyl-2-carbonitrile [(I), X=N, R2=2,2-dimethylpropyl, A=phenyl, R1a=H, R1b=Me, R6a=-phenyl-2-carbonitrile, R6b=H, R8=H, R3=R4=R5=H] cpd-134

8-(3-hydroxy-2,2-dimethylpropyl)-2-({(1S)-1-[4-(thiophen-3-yl)phenyl]ethyl}amino)pyrido[2,3-d]pyrimidin-7 (8H)-one [(I), X=N, R2=3-hydroxy-2,2-dimethylpropyl, A=phenyl, R1a=H, R1b=Me, R6a=thiophen-3-yl, R6b=H, R8=H, R3=R4=R5=H] cpd 136

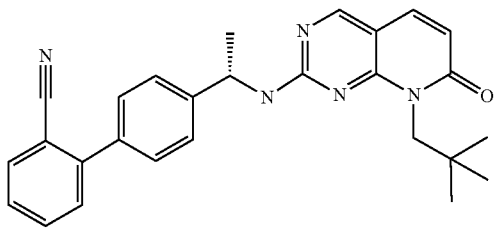

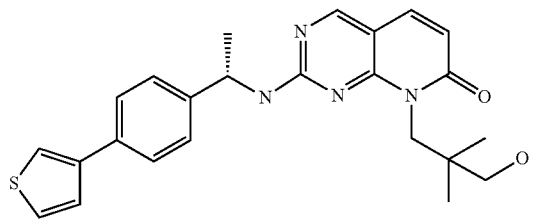

¹H NMR (500 MHz, DMSO-d₆) δ=8.60 (s, 1H), 8.47 (d, J=7.47 Hz, 1H), 7.93 (dd, J=0.76, 7.78 Hz, 1H), 7.77 (dt, J=1.30, 7.74 Hz, 1H), 7.68 (d, J=9.30 Hz, 1H), 7.56-7.60 (m, 2H), 7.54 (br. s, 4H), 6.23 (d, J=9.30 Hz, 1H), 5.17 (quin, J=6.75 Hz, 1H), 3.93-4.33 (m, 2H), 1.53 (d, J=7.02 Hz, 3H), 0.44-1.12 (m, 9H). LCMS: m/z 438 [M+H]+r.t. 7.1 min. HRMS (ESI) calcd for $C_{27}H_{28}N_5O$ [M+H]⁺ 438.2289 found 438.229;

¹H NMR (500 MHz, DMSO-d₆) δ=8.53-8.69 (m, 1H), 8.14-8.51 (m, 1H), 7.80 (dd, J=1.14, 2.82 Hz, 1H), 7.72 (d, J=9.30 Hz, 1H), 7.65 (d, J=8.08 Hz, 2H), 7.57-7.62 (m, 1H), 7.49-7.53 (m, 1H), 7.25-7.48 (m, 2H), 6.20-6.32 (m, 1H), 5.15 (t, J=6.86 Hz, 1H), 4.51-4.71 (m, 1H), 4.05-4.33 (m, 2H), 3.08 (d, J=5.34 Hz, 2H), 1.41-1.53 (m, 3H), 0.47-0.96 (m, 6H). LCMS: m/z 435 [M+H]⁺ r.t. 6.52 min. HRMS (ESI) calcd for $C_{24}H_{27}N_6O_2$ [M+H]⁺ 435.1849 found 435.1852;

8-(3-hydroxy-2,2-dimethylpropyl)-2-({(1S)-1-[4-(1-methyl-1H-pyrazol-4-yl)phenyl]ethyl}amino)pyrido[2,3-d]pyrimidin-7(8H)-one [(I), X=N, R2=3-hydroxy-2,2-dimethylpropyl, A=phenyl, R1a=H, R1b=Me, R6a=1-methyl-1H-pyrazol-4-yl, R6b=H, R8=H, R3=R4=R5=H] cpd 135

4'-[(1S)-1-({8-[(2S)-3-methylbutan-2-yl]-7-oxo-7,8-dihydropyrido[2,3-d]pyrimidin-2-yl}amino)ethyl]biphenyl-2-carbonitrile [(I), X=N, R2=(2S)-3-methylbutan-2-yl, A=phenyl, R1a=H, R1b=Me, R6a=-phenyl-2-carbonitrile, R6b=H, R8=H, R3=R4=R5=H] cpd 165

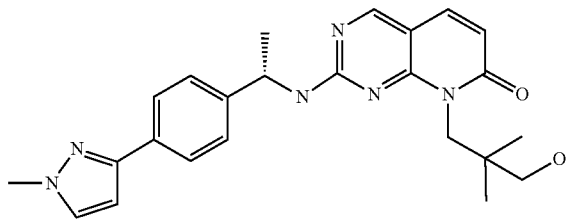

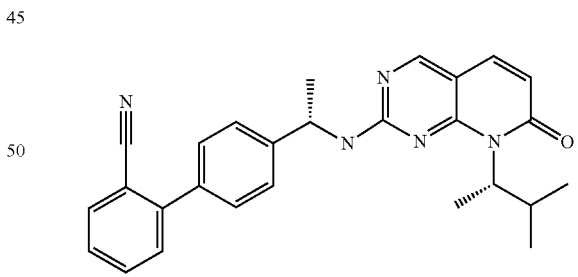

¹H NMR (500 MHz, DMSO-d₆) δ=8.51-8.65 (m, 1H), 8.17-8.46 (m, 1H), 8.06 (s, 1H), 7.79 (s, 1H), 7.72 (d, J=9.30 Hz, 1H), 7.43-7.52 (m, 2H), 7.38 (d, J=7.93 Hz, 2H), 6.25 (d, J=9.30 Hz, 1H), 4.89-5.37 (m, J=7.24, 7.24 Hz, 1H), 4.60 (br. s., 1H), 4.13 (br. s., 2H), 3.84 (s, 3H), 3.07 (d, J=5.49 Hz, 2H), 1.47 (d, J=7.02 Hz, 3H), 0.45-0.94 (m, 6H). LCMS: m/z 433 [M+H]⁺ r.t. 5.24 min. HRMS (ESI) calcd for $C_{24}H_{29}N_6O_2$ [M+H]⁺ 433.2347 found 433.235;

¹H NMR (500 MHz, DMSO-d₆) δ=8.60 (s, 1H), 8.47 (d, J=7.47 Hz, 1H), 7.93 (dd, J=0.76, 7.78 Hz, 1H), 7.77 (dt, J=1.30, 7.74 Hz, 1H), 7.68 (d, J=9.30 Hz, 1H), 7.56-7.60 (m, 2H), 7.54 (br. s, 4H), 6.23 (d, J=9.30 Hz, 1H), 5.17 (quin, J=6.75 Hz, 1H), 3.93-4.33 (m, 2H), 1.53 (d, J=7.02 Hz, 3H), 0.44-1.12 (m, 9H). LCMS: m/z 438 [M+H]+r.t. 6.96 min. HRMS (ESI) calcd for $C_{27}H_{28}N_5O$ [M+H]⁺ 438.2289 found 438.2296.

2-({(1S)-1-[4-(2-fluoropyridin-4-yl)phenyl]ethyl}amino)-8-[(2S)-3-methylbutan-2-yl]pyrido[2,3-d]pyrimidin-7(8H)-one [(I), X=N, R2=(2S)-3-methylbutan-2-yl, A=phenyl, R1a=H, R1b=Me, R6a=2-fluoropyridin-4-yl, R6b=H, R8=H, R3=R4=R5=H] cpd 166

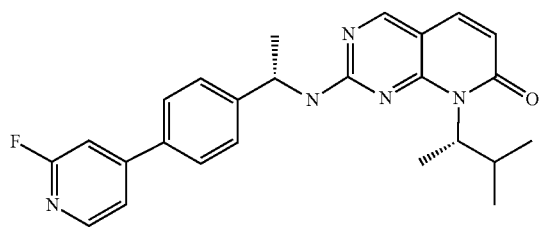

$^1$H NMR (500 MHz, DMSO-d$_6$) δ=8.55-8.61 (m, 1H), 8.40 (d, J=7.47 Hz, 1H), 8.27 (d, J=5.30 Hz, 1H), 7.81 (d, J=8.0 Hz, 2H), 7.62-7.68 (m, 2H), 7.54 (d, J=8.08 Hz, 2H), 7.42-7.52 (m, 2H), 6.22 (d, J=9.30 Hz, 1H), 4.99-5.07 (m, 1H), 4.87-4.96 (m, 1H), 4.73-4.80 (m, 1H), 2.57-2.60 (m, 1H), 1.55 (d, J=7.02 Hz, 3H), 1.0-1.08 (m, 3H), 0.59-0.72 (m, 3H), 0.01 (d, J=6.41 Hz, 3H). LCMS: m/z 432 [M+H]$^+$ r.t. 6.68 min. HRMS (ESI) calcd for C$_{25}$H$_{27}$FN$_5$O [M+H]$^+$ 432.2194 found 432.2197.

tert-butyl 4-{4-[(1S)-1-({8-[(2S)-3-methylbutan-2-yl]-7-oxo-7,8-dihydropyrido[2,3-d]pyrimidin-2-yl}amino) ethyl]phenyl}-3,6-dihydropyridine-1(2H)-carboxylate [(I), X=N, R2=(2S)-3-methylbutan-2-yl, A=phenyl, R1a=H, R1b=Me, R6a=tert-butyl 3,6-dihydropyridine-1(2H)-carboxylate, R6b=H, R8=H, R3=R4=R5=H] cpd 167

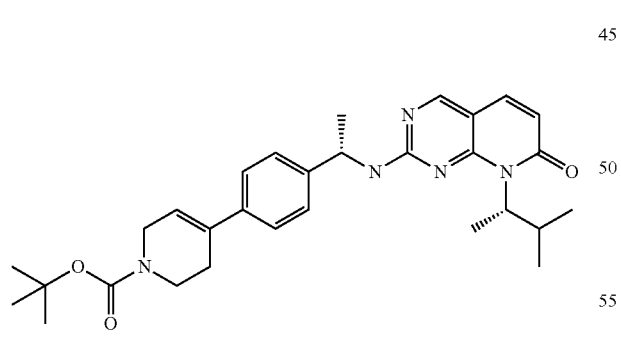

$^1$H NMR (500 MHz, DMSO-d$_6$) δ=8.55-8.61 (m, 1H), 8.40 (d, J=7.47 Hz, 1H), 8.27 (d, J=5.30 Hz, 1H), 7.81 (d, J=8.0 Hz, 2H), 7.62-7.68 (m, 2H), 7.54 (d, J=8.08 Hz, 2H), 7.42-7.52 (m, 2H), 6.22 (d, J=9.30 Hz, 1H), 4.99-5.07 (m, 1H), 4.87-4.96 (m, 1H), 4.73-4.80 (m, 1H), 2.57-2.60 (m, 1H), 1.55 (d, J=7.02 Hz, 3H), 1.0-1.08 (m, 3H), 0.59-0.72 (m, 3H), 0.01 (d, J=6.41 Hz, 3H). LCMS: m/z 518 [M+H]$^+$ r.t. 7.75 min. HRMS (ESI) calcd for C$_{30}$H$_{40}$N$_5$O$_3$ [M+H]$^+$ 518.3126 found 518.3115.

tert-butyl 6-[(1S)-1-({8-[(2S)-3-methylbutan-2-yl]-7-oxo-7,8-dihydropyrido[2,3-d]pyrimidin-2-yl}amino)ethyl]-3',6'-dihydro-3,4'-bipyridine-1'(2'H)-carboxylate [(I), X=N, R2=(2S)-3-methylbutan-2-yl, A=pyridin-2-yl, R1a=H, R1b=Me, R6a=tert-butyl 3,6-dihydropyridine-1(2H)-carboxylate, R6b=H, R8=H, R3=R4=R5=H] cpd 193

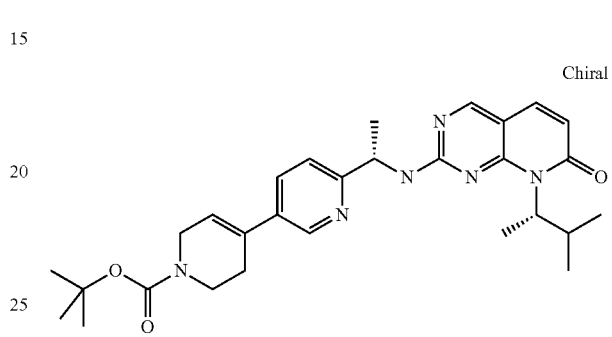

LCMS: m/z 519 [M+H]$^+$ r.t. 6.82 min. HRMS (ESI) calcd for C$_{29}$H$_{39}$N$_6$O$_3$ [M+H]$^+$ 519.3078 found 519.3085.

8-[(2S)-3-methylbutan-2-yl]-2-({(1S)-1-[2'-(trifluoromethyl)-3,4'-bipyridin-6-yl]ethyl}amino)pyrido[2,3-d]pyrimidin-7(8H)-one [(I), X=N, R2=(2S)-3-methylbutan-2-yl, A=pyridin-2-yl, R1a=H, R1b=Me, R6a=2-trifluoromethylpyridin-4-yl, R6b=H, R8=H, R3=R4=R5=H] cpd 196

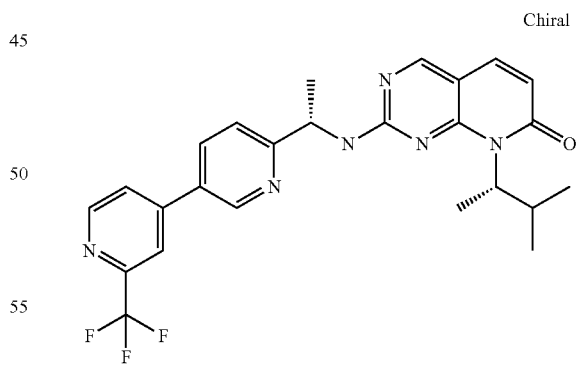

$^1$H NMR (500 MHz, DMSO-d$_6$) δ=9.10 (s, 1H), 8.85 (s, 1H), 8.76 (s, 1H), 8.43 (d, J=6.56 Hz, 1H), 8.29 (d, J=8.39 Hz, 1H), 8.09 (m, 1H), 7.96 (d, J=9.30 Hz, 1H), 7.66 (dd, J=8.85 Hz, 1H), 7.42 (d, J=8.39 Hz, 1H), 6.23 (d, J=9.30 Hz, 1H), 4.70-5.07 (m, 2H), 1.40-1.59 (m, 4H), 0.93-1.02 (m, 3H), 0.59 (d, J=6.25 Hz, 3H), −0.01 (d, J=6.25 Hz, 3H). LCMS: m/z 483 [M+H]$^+$ r.t. 6.29 min. HRMS (ESI) calcd for C$_{25}$H$_{26}$F$_3$N$_6$O [M+H]$^+$ 483.2115 found 483.213.

2-{[(1S)-1-(2'-fluoro-3,4'-bipyridin-6-yl)ethyl]
amino}-8-[(2S)-3-methylbutan-2-yl]pyrido[2,3-d]
pyrimidin-7(8H)-one [(I), X=N, R2=(2S)-3-meth-
ylbutan-2-yl, A=pyridin-2-yl, R1a=H, R1b=Me,
R6a=2-fluoro-pyridin-4-yl, R6b=H, R8=H,
R3=R4=R5=H] cpd 197

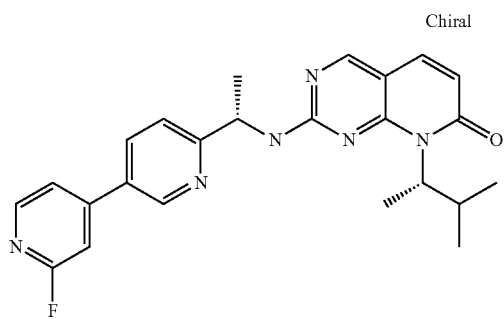

LCMS: m/z 433 [M+H]+ r.t. 5.77 min. HRMS (ESI) calcd for C24H26FN6O [M+H]+ 433.2147 found 433.215.

Example 13

8-(2,2-dimethylpropyl)-2-({(1S)-1-[4-(methylsulfo-
nyl)phenyl]ethyl}amino)pyrido[2,3-d]pyrimidin-7
(8H)-one [(I), X=N, R2=2,2-dimethylpropyl,
A=phenyl, R1a=H, R1b=Me, R6a=methylsulfonyl,
R6b=H, R8=H, R3=R4=R5=H]conv. 11, cpd 137

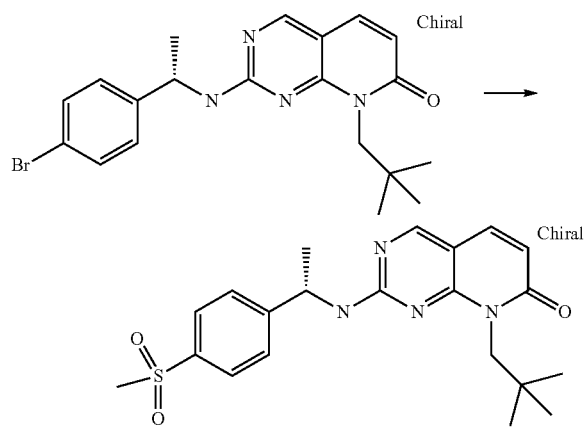

In a 5 mL microwave vial a solution of 2-{[(1S)-1-(4-bromophenyl)ethyl]amino}-8-(2,2-dimethylpropyl)pyrido[2,3-d]pyrimidin-7(8H)-one (30 mg, 0.07 mmol), sodium methanesulfinate (22 mg, 0.21 mmol), CuI (41 mg, 0.21 mmol) in DMSO (2 mL) was added. The capped tube was heated at 120° C. for 6 h. After cooling the reaction mixture was diluted with EtOAc (10 mL) and washed with water (10 mL). After separation, the aqueous phase was extracted with EtOAc (3×10 mL). Combined organics were dried over Na2SO4, filtered and concentrated. The crude material was purified through silica gel column chromatography (DCM/EtOAc 8/2) to give an off-white solid (10 mg, 35% yield).

¹H NMR (500 MHz, DMSO-d6) δ=8.60 (s, 1H), 8.50 (d, J=7.17 Hz, 1H), 7.88 (d, J=8.24 Hz, 2H), 7.68 (d, J=9.30 Hz, 1H), 7.65 (d, J=8.24 Hz, 2H), 6.24 (d, J=9.30 Hz, 1H), 5.00-5.43 (m, J=7.02, 7.02 Hz, 1H), 3.82-4.32 (m, 2H), 3.16 (s, 3H), 1.49 (d, J=7.17 Hz, 3H), 0.51-0.98 (m, 9H). LCMS: m/z 415 [M+H]+ r.t. 5.51 min. HRMS (ESI) calcd for C21H27N4O3S [M+H]+ 415.1799 found 415.1797.

Example 14

8-(2,2-Dimethyl-propyl)-2-[(S)-1-(4-piperazin-1-
ylmethyl-phenyl)-ethyl amino]-8H-pyrido[2,3-d]
pyrimidin-7-one hydrochloride [(I), X=N, R2=2,2-
dimethyl-propyl, A=phenyl, R1a=H, R1b=Me,
R6a=4-CH2NR7R8, R6b=H, R7-R8=4-piperazin-1-
yl, R3=R4=R5=H] conv. 6, cpd 138

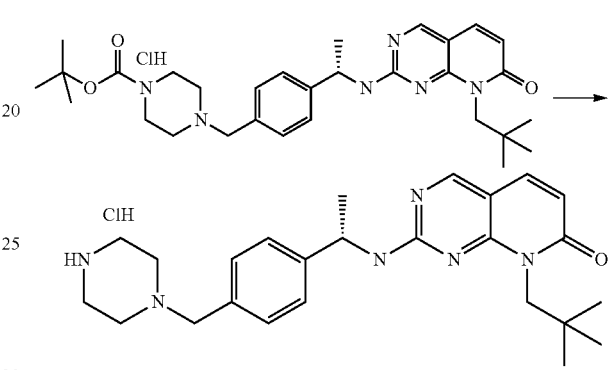

To a solution of 4-(4-{(S)-1-[8-(2,2-Dimethyl-propyl)-7-oxo-7,8-dihydro-pyrido[2,3-d]pyrimidin-2-ylamino]-ethyl}-benzyl)-piperazine-1-carboxylic acid tert-butyl ester (cpd 59) (65.0 mg, 0.122 mmol) in a mixture of dioxane (3.0 mL) and MeOH (1.0 mL) is added HCl (4 M in dioxane, 0.6 mL). The mixture is stirred overnight at room temperature and then concentrated to dryness to provide a white solid which is dried under vacuum to give the title compound as a white solid (57.0 mg, quantitative).

¹H NMR (500 MHz, DMSO-d6) δ=11.72 (br. s., 1H), 9.32 (br. s., 2H), 8.59 (s, 1H), 8.46 (d, J=7.32 Hz, 1H), 7.68 (d, J=9.15 Hz, 1H), 7.54 (br. s., 2H), 7.47 (d, J=7.63 Hz, 2H), 6.24 (d, J=9.30 Hz, 1H), 5.14 (quin, J=6.90 Hz, 1H), 3.93-4.54 (m, 5H), 3.28-3.52 (m, 5H), 1.47 (d, J=7.17 Hz, 3H), 0.79 (br. s., 9H). LCMS (HPLC Method 1): m/z 435 [M+H]+@ r.t. 5.17 min. HRMS (ESI) calcd for C25H35N4O3S [M+H]+ 415.1799 found 415.1797.

Example 15

2-{(S)-1-[4-(4-Acryloyl-piperazin-1-ylmethyl)-phe-
nyl]-ethylamino}-8-(2,2-dimethyl-propyl)-8H-pyrido
[2,3-d]pyrimidin-7-one [(I), X=N, R2=2,2-dim-
ethyl-propyl, A=phenyl, R1a=H, R1b=Me, R6a=4-
CH2NR7R8, R6b=H, R7-R8=4-piperazin-1-yl,
R11=vinyl, R3=R4=R5=H] conv. 7, cpd 139

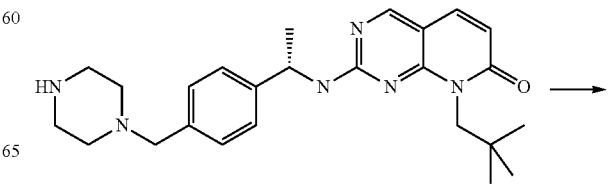

-continued

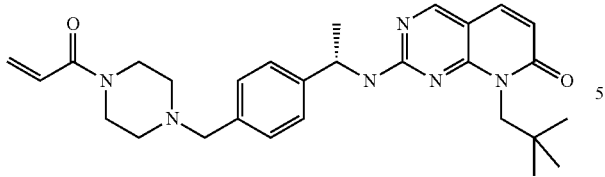

To a solution of 8-(2,2-Dimethyl-propyl)-2-[(S)-1-(4-piperazin-1-ylmethyl-phenyl)-ethyl amino]-8H-pyrido[2,3-d]pyrimidin-7-one hydrochloride (55.0 mg, 0.12 mmol) and DIPEA (0.04 mL, 0.24 mmol) in DCM (1.0 mL) is added acryloyl chloride (0.01 mL, 0.13 mmol) at 0° C. After 30 minutes, the reaction is quenched with water. The mixture is extracted with DCM, dried over $Na_2SO_4$, filtered, and concentrated to yield a yellow oil. The crude product is purified by silica gel chromatography (1 to 10% MeOH/DCM) to give the title product as a white foam (37.5 mg, 66% yield).

$^1$H NMR (500 MHz, DMSO-$d_6$) δ=8.57 (s, 1H), 8.36 (d, J=7.2 Hz, 1H), 7.67 (d, J=9.3 Hz, 1H), 7.33 (d, J=8.1 Hz, 2H), 7.23 (d, J=7.9 Hz, 2H), 6.76 (dd, J=10.4, 16.7 Hz, 1H), 6.22 (d, J=9.3 Hz, 1H), 6.08 (dd, J=2.4, 16.7 Hz, 1H), 5.65 (dd, J=2.4, 10.4 Hz, 1H), 5.06 (quin, J=7.2 Hz, 1H), 4.40-3.87 (m, 2H), 3.50 (d, J=17.5 Hz, 4 H), 3.44 (s, 2H), 2.31 (br. s., 4H), 1.46 (d, J=6.9 Hz, 3H), 1.05-0.53 (m, 9H).

LCMS: m/z 489 [M+H]$^+$@ r.t. 5.88 min. HRMS (ESI) calcd for $C_{28}H_{37}N_6O_2$ [M+H]$^+$ 489.2973 found 489.2966.

According to the same method, the following compounds were prepared:

2-{(S)-1-[4-(4-Acryloyl-piperazin-1-ylmethyl)-phenyl]-ethylamino}-8-(3-hydroxy-2,2-dimethyl-propyl)-8H-pyrido[2,3-d]pyrimidin-7-one [(I), X═N, R2=3-hydroxy-2,2-dimethyl-propyl, A=phenyl, R1a=H, R1b=Me, R6a=4-CH$_2$NR7R8, R6b=H, R7-R8=4-piperazin-1-yl, R11=vinyl, R3=R4=R5=H] cpd 140

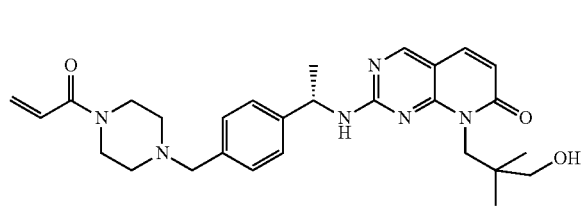 [SMILES: C=CC(=O)N1CCN(Cc2ccc([C@H](C)Nc3ncc4ccc(=O)n(CC(C)(C)CO)c4n3)cc2)CC1]

$^1$H NMR (500 MHz, DMSO-$d_6$) δ=8.60 (s, 1H), 8.43 (d, J=7.5 Hz, 1H), 7.72 (d, J=9.3 Hz, 1H), 7.36 (d, J=7.9 Hz, 2H), 7.23 (d, J=7.9 Hz, 2H), 6.76 (dd, J=10.5, 16.6 Hz, 1H), 6.26 (d, J=9.2 Hz, 1H), 6.08 (dd, J=2.4, 16.7 Hz, 1H), 5.65 (dd, J=2.4, 10.4 Hz, 1H), 5.11 (quin, J=6.9 Hz, 1H), 4.56 (br. s., 1H), 4.20-4.00 (m, 2H), 3.51 (d, J=14.2 Hz, 4H), 3.43 (s, 2H), 3.03 (br. s., 2H), 2.31 (br. s., 4H), 1.46 (d, J=7.0 Hz, 3H) 0.93-0.58 (m, 6H).

LCMS: m/z 505 [M+H]$^+$@ r.t. 5.01 min. HRMS (ESI) calcd for $C_{28}H_{36}N_6O_3$ [M+H]$^+$ 505.2922 found 505.2922;

2-{[(1S)-1-{4-[(4-acryloylpiperazin-1-yl)methyl]-3-fluorophenyl}ethyl]amino}-8-(2,2-dimethylpropyl)pyrido[2,3-d] pyrimidin-7(8H)-one [(I), X═N, R2=2,2-dimethyl-propyl, A=phenyl, R1a=H, R1b=Me, R6a=4-CH$_2$NR7R8, R6b=F, R7-R8=4-piperazin-1-yl, R11=vinyl, R3=R4=R5=H] cpd 141

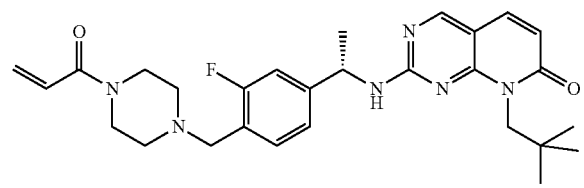 [SMILES: C=CC(=O)N1CCN(Cc2ccc([C@H](C)Nc3ncc4ccc(=O)n(CC(C)(C)C)c4n3)cc2F)CC1]

$^1$H NMR (500 MHz, DMSO-$d_6$) δ=8.59 (s, 1H), 8.38 (d, J=7.47 Hz, 1H), 7.68 (d, J=9.46 Hz, 1H), 7.33 (t, J=7.70 Hz, 1H), 7.08-7.23 (m, 2H), 6.76 (dd, J=10.52, 16.62 Hz, 1H), 6.24 (d, J=9.46 Hz, 1H), 6.07 (dd, J=2.29, 16.62 Hz, 1H), 5.64 (dd, J=2.29, 10.37 Hz, 1H), 5.06 (quin, J=7.13 Hz, 1H), 3.90-4.33 (m, 2H), 3.43-3.60 (m, 6H), 2.34 (br. s., 4H), 1.46 (d, J=7.02 Hz, 3H), 0.92 (br. s., 3H), 0.69 (br. s., 6H). LCMS: m/z 507 [M+H]$^+$@ r.t. 5.98 min.

HRMS (ESI) calcd for $C_{28}H_{36}N_6O_3$ [M+H]$^+$ 507.2879 found 507.2874;

2-{[(1S)-1-{4-[(4-acryloylpiperazin-1-yl)carbonyl]-3-fluorophenyl}ethyl]amino}-8-(2,2-dimethylpropyl)pyrido [2,3-d]pyrimidin-7(8H)-one [(I), X═N, R2=2,2-dimethyl-propyl, A=phenyl, R1a=H, R1b=Me, R6a=4-C(O)NR7R8, R6b=F, R7-R8=4-piperazin-1-yl, R11=vinyl, R3=R4=R5=H] cpd 142

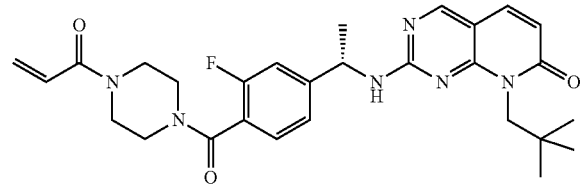 [SMILES: C=CC(=O)N1CCN(C(=O)c2ccc([C@H](C)Nc3ncc4ccc(=O)n(CC(C)(C)C)c4n3)cc2F)CC1]

$^1$H NMR (500 MHz, DMSO-$d_6$) δ=8.61 (s, 1H), 8.43 (d, J=7.17 Hz, 1H), 7.70 (d, J=9.30 Hz, 1H), 7.34-7.45 (m, 1H), 7.30 (d, J=6.86 Hz, 2H), 6.63-6.91 (m, 1H), 6.25 (d, J=9.30 Hz, 1H), 6.12 (dd, J=2.29, 16.78 Hz, 1H), 5.70 (s, 1H), 5.11 (quin, J=6.67 Hz, 1H), 3.89-4.32 (m, 2H), 3.39-3.78 (m, 6H), 3.22 (br. s., 2H), 1.48 (d, J=7.02 Hz, 3H), 0.93 (br. s., 3H), 0.73 (br. s., 6H). LCMS: m/z 521 [M+H]$^+$@ r.t. 5.44 min. HRMS (ESI) calcd for $C_{28}H_{34}FN_6O3$ [M+H]$^+$ 521.2671 found 521.2672;

2-({(1S)-1-[4-({4-[(2E)-but-2-enoyl]piperazin-1-yl}methyl)phenyl]ethyl}amino)-8-(2,2-dimethylpropyl) pyrido [2,3-d]pyrimidin-7(8H)-one [(I), X=N, R2=2,2-dimethyl-propyl, A=phenyl, R1a=H, R1b=Me, R6a=4-C(O)NR7R8, R6b=H, R7-R8=4-piperazin-1-yl, R11=propenyl, R3=R4=R5=H] cpd 143

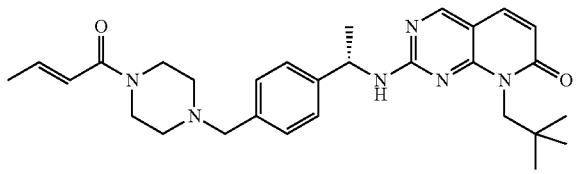 [SMILES: C/C=C/C(=O)N1CCN(Cc2ccc([C@H](C)Nc3ncc4ccc(=O)n(CC(C)(C)C)c4n3)cc2)CC1]

¹H NMR (500 MHz, DMSO-d₆) δ=8.57 (s, 1H), 8.36 (d, J=7.32 Hz, 1H), 7.67 (d, J=9.15 Hz, 1H), 7.33 (d, J=7.93 Hz, 2H), 7.23 (d, J=8.08 Hz, 2H), 6.64 (qd, J=6.90, 14.90 Hz, 1H), 6.46 (qd, J=1.50, 14.95 Hz, 1H), 6.22 (d, J=9.30 Hz, 1H), 5.06 (quin, J=7.20 Hz, 1H), 3.92-4.37 (m, 2H), 3.44-3.62 (m, 4H), 3.43 (s, 2H), 2.25-2.33 (m, 4H), 1.82 (dd, J=1.68, 6.8 Hz, 3H), 1.46 (d, J=7.02 Hz, 3H), 0.92 (br. s., 3H), 0.73 (br. s., 6H). LCMS: m/z 503 [M+H]+@ r.t. 6.11 min. HRMS (ESI) calcd for C₂₈H₃₉N₆O₂ [M+H]⁺ 503.3129 found 503.3117;

8-(2,2-dimethylpropyl)-2-{[(1S)-1-(4-{[4-(2-methyl-acryloyl)piperazin-1-yl]methyl}phenyl)ethyl]amino} pyrido [2,3-d]pyrimidin-7(8H)-one [(I), X=N, R2=2,2-dimethyl-propyl, A=phenyl, R1a=H, R1b=Me, R6a=4-C(O)NR7R8, R6b=H, R7-R8=4-piperazin-1-yl, R11=methylvinyl, R3=R4=R5=H] cpd 144

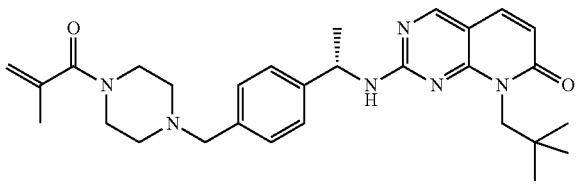 [SMILES: C=C(C)C(=O)N1CCN(Cc2ccc([C@H](C)Nc3ncc4ccc(=O)n(CC(C)(C)C)c4n3)cc2)CC1]

¹H NMR (500 MHz, DMSO-d₆) δ=8.57 (s, 1H), 8.36 (d, J=7.32 Hz, 1H), 7.67 (d, J=9.30 Hz, 1H), 7.33 (d, J=8.08 Hz, 2H), 7.23 (d, J=7.93 Hz, 2H), 6.22 (d, J=9.30 Hz, 1H), 5.15 (quin, J=1.40 Hz, 1H), 5.07 (quin, J=6.83 Hz, 1H), 4.92 (br. s, 1H), 3.89-4.33 (m, 2H), 3.44 (br. s., 6H), 2.30 (br. s., 4H), 1.81 (s, 3H), 1.45 (d, J=7.02 Hz, 3H), 0.92 (br. s., 3H), 0.73 (br. s., 6H). LCMS: m/z 503 [M+H]+@ r.t. 6.20 min. HRMS (ESI) calcd for C₂₉H₃₉N₆O₂ [M+H]⁺ 503.3129 found 503.3122;

8-(2,2-dimethylpropyl)-2-{[(1S)-1-(4-{[4-(2-methyl-propanoyl)piperazin-1-yl]methyl}phenyl)ethyl]amino}-pyrido [2,3-d]pyrimidin-7(8H)-one [(I), X=N, R2=2,2-dimethyl-propyl, A=phenyl, R1a=H, R1b=Me, R6a=O—R7, R6b=H, R7-=4-piperazin-1-yl, R11=2-isopropyl, R3=R4=R5=H] cpd 157

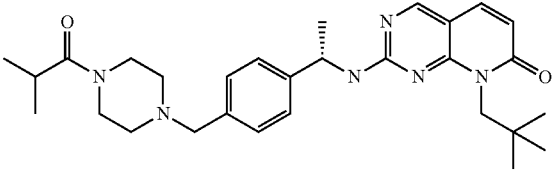

¹H NMR (500 MHz, DMSO-d₆) δ=8.57 (s, 1H), 8.36 (d, J=7.3 Hz, 1H), 7.67 (d, J=9.2 Hz, 1H), 7.33 (d, J=8.1 Hz, 2H), 7.13-7.28 (m, 2H), 6.22 (d, J=9.3 Hz, 1H), 5.06 (quin, J=6.9 Hz, 1H), 3.86-4.34 (m, 2H), 3.43 (s, 2H), 3.43 (br. s., 4H), 2.82 (spt, J=6.6 Hz, 1H), 2.32 (br. s., 2H), 2.25 (br. s., 2H), 1.46 (d, J=6.9 Hz, 3H), 0.95 (d, J=6.7 Hz, 6H), 0.74 (br. s., 9H). LCMS: m/z 505 [M+H]⁺@ r.t. 6.28 min. HRMS (ESI) calcd for C₂₉H₄₁N₆O₂ [M+H]⁺ 505.3286 found 505.3286;

2-{[(1S)-1-(4-{[4-(cyclopropylcarbonyl)piperazin-1-yl]methyl}phenyl)ethyl]amino}-8-(2,2-dimethylpropyl) pyrido[2,3-d]pyrimidin-7(8H)-one [(I), X=N, R2=2,2-dimethyl-propyl, A=phenyl, R1a=H, R1b=Me, R6a=0-R7, R6b=H, R7-=4-piperazin-4-yLR11=_cyclopropyl, R3_=R4=_R5=H]_cpd 158

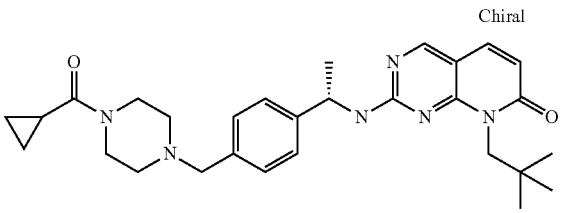 [SMILES: C[C@H](Nc1ncc2ccc(=O)n(CC(C)(C)C)c2n1)c1ccc(CN2CCN(C(=O)C3CC3)CC2)cc1]

¹H NMR (500 MHz, DMSO-d₆) δ=8.58 (s, 1H), 8.36 (d, J=7.3 Hz, 1H), 7.67 (d, J=9.3 Hz, 1H), 7.33 (d, J=8.1 Hz, 2H), 7.23 (d, J=7.9 Hz, 2H), 6.22 (d, J=9.3 Hz, 1H), 5.06 (quin, J=7.1 Hz, 1H), 3.89-4.32 (m, 2H), 3.63 (br. s., 2H), 3.44 (s, 2H), 3.42 (br. s., 2H), 2.35 (br. s., 2H), 2.26 (br. s., 2H), 1.86-1.99 (m, 1H), 1.46 (d, J=7.0 Hz, 3H), 0.74 (br. s., 9H), 0.57-0.74 (m, 4H). LCMS: m/z 503 [M+H]⁺@ r.t. 6.07 min HRMS (ESI) calcd for C₂₉H₃₉N₆O₂ [M+H]⁺ 503.3129 found 503.3137;

2-{(S)-1-[4-(4-Acryloyl-piperazin-1-ylmethyl)-phenyl]-ethylamino}-8-((S)-1,2-dimethyl-propyl)-8H-pyrido[2,3-d]pyrimidin-7-one [(I), X=N, R2=—(S)-1,2-Dimethyl-propyl, A=phenyl, R1a=H, R1b=Me, R6a=4-CH₂NR7R8, R6b=H, R7-R8=4-piperazin-1-yl, R11=vinyl, R3=R4=R5=H] cpd 161

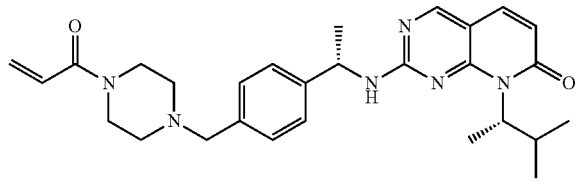

¹H NMR (500 MHz, DMSO-d₆) δ=8.56 (s, 1H), 7.64 (d, J=8.8 Hz, 1H), 7.20-7.33 (m, 4H), 6.76 (dd, J=16.6, 10.4 Hz, 1H), 6.10-6.22 (m, 1H), 6.07 (dd, J=16.6, 2.3 Hz, 1H), 5.64 (dd, J=10.4, 2.3 Hz, 1H), 4.78-5.07 (m, 2H), 3.41-3.55 (m, 6H), 2.30 (br. s., 4H), 1.36-2.07 (m, 4H), 0.07-1.09 (m, 9H). LCMS: m/z 489 [M+H]⁺@ r.t. 5.77 min. HRMS (ESI) calcd for C₂₈H₃₆N₆O₂ [M+H]⁺ 489.2973 found 489.2973;

8-((S)-1,2-Dimethyl-propyl)-2-((S)-1-{4-[4-(2-methyl-acryloyl)-piperazin-1-ylmethyl]-phenyl}-ethylamino)-8H-pyrido[2,3-d]pyrimidin-7-one [(I), X=N, R2=—(S)-1,2-Dimethyl-propyl, A=phenyl, R1a=H, R1b=Me, R6a=4-CH₂NR7R8, R6b=H, R7-R8=4-piperazin-1-yl, R11=methylvinyl, R3=R4=R5=H] cpd 162

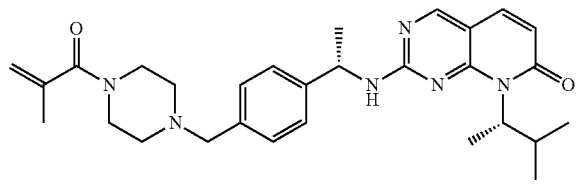 [SMILES: C=C(C)C(=O)N1CCN(Cc2ccc([C@H](C)Nc3ncc4ccc(=O)n([C@@H](C)C(C)C)c4n3)cc2)CC1]

¹H NMR (500 MHz, DMSO-d₆) δ=8.56 (s, 1H), 7.20-7.35 (m, 4H), 6.10-6.22 (m, 1H), 4.75-5.16 (m, 4H), 3.27-3.47 (m, 6H), 2.32 (br. s., 4H), 1.80-1.85 (m, 3H), 1.00-1.55 (m, 4H), 0.07-0.86 (m, 9H). LCMS: m/z 503 [M+H]+@ r.t. 6.08 min. HRMS (ESI) calcd for C₂₉H₃₉N₆O₂ [M+H]⁺ 503.3129 found 503.3136; 2-({(1S)-1-[4-(1-acryloyl-1,2,3,6-tetrahydropyridin-4-yl)phenyl]ethyl}amino)-8-[(2S)-3-methylbutan-2-yl]pyrido [2,3-d]pyrimidin-7(8H)-one [(I), X=N, R2=(2S)-3-methylbutan-2-yl, A=phenyl, R1a=H, R1b=Me, R6a=4-(1-acryloyl-1,2,3,6-tetrahydropyridin-4-yl, R6b=H, R8=H, R3=R4=R5=H] Cpd 168

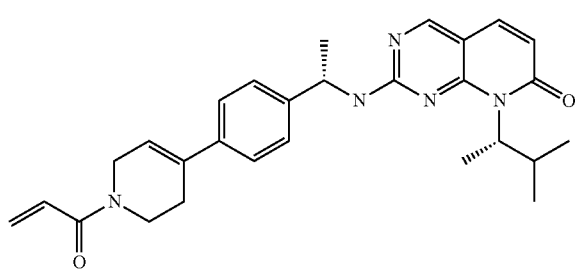

¹H NMR (500 MHz, DMSO-d₆) δ 8.58 (s, 1H), 8.40 (d, J=7.47 Hz, 1H), 7.63 (d, J=9.3 Hz, 1H), 7.23-7.42 (m, 4H), 6.88 (dd, J=10.68, 18.30 Hz, 1H), 6.21 (d, J=9.30 Hz, 1H), 6.04-6.16 (m, 2H), 5.70 (dd, J=2.29, 10.68 Hz, 1H), 4.95-5.10 (m, 1H), 4.74-4.87 (m, 1H), 4.24 (br. s., 1H), 4.14 (br. s., 1H), 2.44 (m, 2H), 1.86-1.94 (m, 1H), 1.47 (d, J=6.86 Hz, 3H), 0.99-1.14 (m, 3H), 0.70 (d, J=6.41 Hz, 3H), 0.05 (d, J=6.41 Hz, 3H). LCMS: m/z 472 [M+H]⁺ r.t. 6.24 min. HRMS (ESI) calcd for C₂₈H₃₄N₅O [M+H]⁺ 472.2707 found 472.2700;

2-{[(1S)-1-{4-[(4-acryloylpiperazin-1-yl)methyl]phenyl}ethyl]amino}-8-[(2S)-1,1,1-trifluoropropan-2-yl]pyrido [2,3-d]pyrimidin-7(8H)-one [(I), X=N, R2=2,2-dimethyl-propyl, A=phenyl, R1a=H, R1b=Me, R6a=4-CH₂NR7R8, R6b=H, R7-R8=4-piperazin-1-yl, R11=vinyl, R3=R4=R5=H] cpd 169

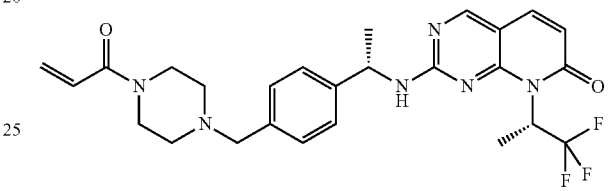

¹H NMR (500 MHz, DMSO-d₆) δ=8.63 (m, 2H), 7.72 (d, J=9.46 Hz, 1H), 7.22-7.35 (m, 4H), 6.76 (dd, J=10.37, 18.91 Hz, 1H), 6.18 (d, J=9.46 Hz, 1H), 6.01-6.10 (m, 2H), 5.65 (dd, J=2.29, 10.37 Hz, 1H), 4.79 (quin, J=6.71 Hz, 1H), 3.42-3.54 (m, 6H), 2.27-2.31 (m, 4H), 1.87 (d, J=7.17 Hz, 1H), 1.47 (d, J=6.86 Hz, 3H), 1.36 (d, J=7.17 Hz, 3H). LCMS: m/z 515 [M+H]⁺@ r.t. 5.71 min. HRMS (ESI) calcd for C₂₆H₃₀F₃N₆O₂[M+H]⁺ 515.2377 found 515.2363.

2-({(1S)-1-[4-(4-acryloylpiperazin-1-yl)phenyl]ethyl}amino)-8-[(2S)-3-methylbutan-2-yl]pyrido[2,3-d]pyrimidin-7(8H)-one [(I), X=N, R2=(2S)-3-methylbutan-2-yl, A=phenyl, R1a=H, R1b=Me, R6a=4-NR7R8, R6b=H, R7-R8=4-piperazin-1-yl, R11=vinyl, R3=R4=R5=H] cpd 175

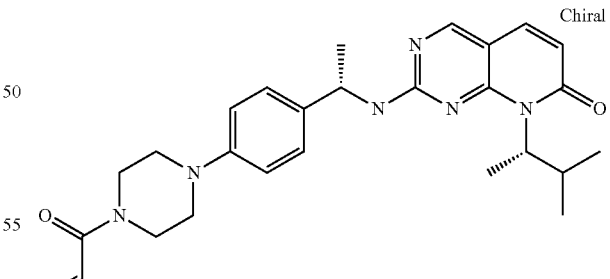

¹H NMR (500 MHz, DMSO-d₆) δ=8.55 (s, 1H), 8.27 (d, J=7.63 Hz, 1H), 7.63 (d, J=9.15 Hz, 1H), 7.24 (d, J=8.69 Hz, 1H), 7.16 (d, J=8.69 Hz, 1H), 6.90 (d, J=8.69 Hz, 2H), 6.84 (dd, J=10.45, 16.55 Hz, 1H), 6.20 (d, J=9.15 Hz, 1H), 6.12 (dd, J=2.29, 16.78 Hz, 1H), 5.69 (dd, J=2.30, 10.50 Hz, 1H), 5.11-5.22 (m, 1H), 4.76-4.96 (m, 1H), 3.66 (d, J=18.00 Hz, 4H), 3.06 (br. s., 4H), 1.39-1.53 (m, 4H), 0.98-1.21 (m, 3H), 0.60-0.80 (m, 3H), 0.13 (d, J=6.24 Hz, 3H). LCMS: m/z 475

[M+H]+@ r.t. 5.96 min. HRMS (ESI) calcd for $C_{27}H_{35}N_6O_2$ [M+H]+ 475.2816 found 475.2813.

2-({(1S)-1-[4-(4-acryloylpiperazin-1-yl)-3-fluorophenyl]ethyl}amino)-8-[(2S)-3-methylbutan-2-yl] pyrido[2,3-d]pyrimidin-7(8H)-one [(I), X=N, R2=(2S)-3-methylbutan-2-yl, A=phenyl, R1a=H, R1b=Me, R6a=4-NR7R8, R6b=F, R7-R8=4-piperazin-1-yl, R11=vinyl, R3=R4=R5=H] cpd 179

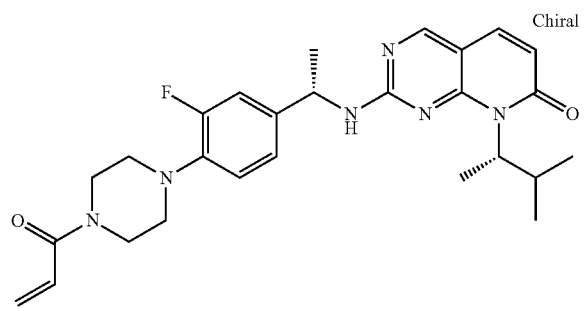 [SMILES: C=CC(=O)N1CCN(c2ccc([C@H](C)Nc3ncc4ccc(=O)n([C@@H](C)C(C)C)c4n3)cc2F)CC1]

$^1$H NMR (500 MHz, DMSO-$d_6$) δ=8.57 (s, 1H), 8.28-8.45 (m, 1H), 7.64-7.68 (m, 1H), 6.92-7.18 (m, 3H), 6.83 (dd, J=10.45, 16.40 Hz, 1H), 6.10-6.24 (m, 2H), 5.70 (dd, J=2.06, 10.45 Hz, 1H), 4.92 (m, 1H), 4.79 (m, 1H), 3.68 (d, J=16.93 Hz, 4H), 2.92 (br. s., 4H), 1.95 (m, 1H), 1.42-1.51 (m, 3H), 0.99-1.16 (m, 3H), 0.11 (d, J=6.56 Hz, 3H).

LCMS: m/z 493 [M+H]+@ r.t. 6.07 min. HRMS (ESI) calcd for $C_{27}H_{34}FN_6O_2$[M+H]+ 493.2722 found 493.2736.

2-({(1S)-1-[6-(4-acryloylpiperazin-1-yl)pyridin-3-yl] ethyl}amino)-8-[(2S)-3-methylbutan-2-yl]pyrido[2,3-d]pyrimidin-7(8H)-one [(I), X=N, R2=(2S)-3-methylbutan-2-yl, A=pyridin-3-yl, R1a=H, R1b=Me, R6a=4-NR7R8, R6b=H, R7-R8=4-piperazin-1-yl, R11=vinyl, R3=R4=R5=H] cpd 181

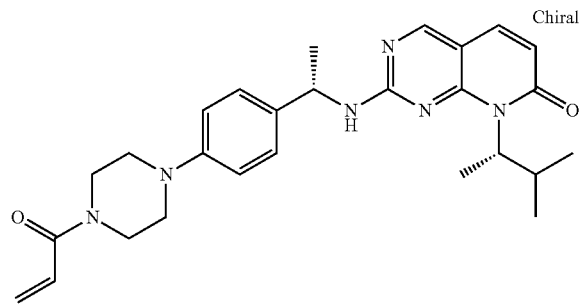 [SMILES: C=CC(=O)N1CCN(c2ccc([C@H](C)Nc3ncc4ccc(=O)n([C@@H](C)C(C)C)c4n3)cc2)CC1]

$^1$H NMR (500 MHz, DMSO-$d_6$) δ=8.57 (s, 1H), 8.30 (m, 1H), 8.15 (br., s, 1H), 7.65 (d, J=9.46 Hz, 1H), 7.49 (m, 1H), 6.80-6.87 (m, 2H), 5.70 (dd, J=2.70, 10.3 Hz, 1H), 4.90 (m, 1H), 4.81 (m, 1H), 3.62 (d, J=19.52 Hz, 4H), 3.44 (br. s., 4H), 2.10 (m, 1H), 1.44-1.51 (m, 3H); 0.99-1.07 (m, 3H); 0.55-0.65 (m, 3H), 0.17 (d, J=6.41 Hz, 3H).

LCMS: m/z 476 [M+H]+@ r.t. 5.49 min. HRMS (ESI) calcd for $C_{26}H_{34}N_7O_2$ [M+H]+ 476.2769 found 476.2777.

2-{[(1S)-1-{4-[(4-acryloylpiperazin-1-yl)methyl] phenyl}ethyl]amino}-8-(2-azidoethyl)pyrido[2,3-d] pyrimidin-7(8H)-one [(I), X=N, R2=2-azidoethyl, A=phenyl, R1a=H, R1b=Me, R6a=4-CH$_2$NR7R8, R6b=H, R7-R8=4-piperazin-1-yl, R1=vinyl, R3=R4=R5=H]cpd 182

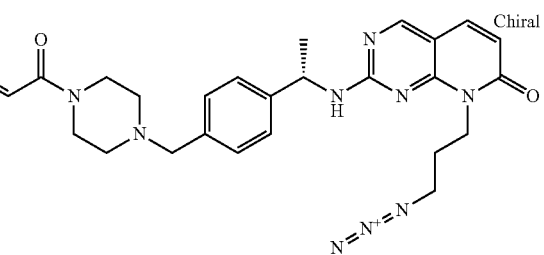

$^1$H NMR (500 MHz, DMSO-$d_6$) δ=8.60 (m, 1H), 8.50 (m, 1H), 7.63-7.73 (m, 1H), 7.17-7.37 (m, 2H), 6.75 (dd, J=10.22, 16.78 Hz, 1H), 6.12-6.29 (m, 2H), 6.08 (dd, J=2.36, 16.70 Hz, 1H), 5.26 (m, 2H), 5.04 (m, 1H), 4.44 (m, 1H), 4.17-4.37 (m, 2H), 3.34-3.71 (m, 6H), 2.20-2.34 (m, 4H), 1.41-1.49 (m, 3H). LCMS: m/z 488 [M+H]+@ r.t. 5.12 min. HRMS (ESI) calcd for $C_{25}H_{30}N_9O_2$ [M+H]+ 488.22517 found 488.2525.

2-{[(1S)-1-{4-[(4-acryloylpiperazin-1-yl)methyl]-3-fluorophenyl}ethyl]amino}-8-(propan-2-yl)pyrido[2,3-d]pyrimidin-7(8H)-one [(I), X=N, R2=propan-2-yl, A=phenyl, R1a=H, R1b=Me, R6a=4-CH$_2$NR7R8, R6b=F, R7-R8=4-piperazin-1-yl, R11=vinyl, R3=R4=R5=H] cpd 183

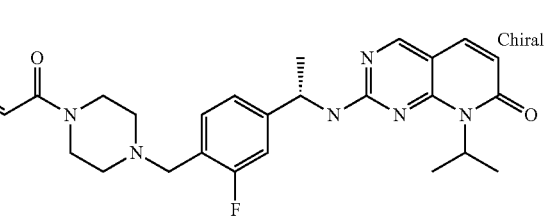

$^1$H NMR (500 MHz, DMSO-$d_6$) δ=8.57 (s, 1H), 8.37 (d, J=6.71 Hz, 1H), 7.63 (d, J=9.30 Hz, 1H), 7.32 (t, J=7.47 Hz, 1H), 7.10-7.24 (m, 2H), 6.75 (dd, J=10.52, 16.62 Hz, 1H), 6.17 (d, J=9.30 Hz, 1H), 6.07 (dd, J=1.83, 16.47 Hz, 1H), 5.64 (dd, J=1.98, 10.37 Hz, 1H), 5.49 (br., m, 1H), 4.99 (quin, J=6.98 Hz, 1H), 3.49 (br. s, 6H), 2.31 (br. s., 4H), 1.48 (d, J=6.86 Hz, 9H). LCMS: m/z 479 [M+H]+@ r.t. 6.74 min. HRMS (ESI) calcd for $C_{26}H_{32}FN_6O_2$[M+H]+479.2566 found 479.2577.

2-{[(1S)-1-{4-[(4-acryloylpiperazin-1-yl)methyl]
phenyl}ethyl]amino}-8-(propan-2-yl)pyrido[2,3-d]
pyrimidin-7(8H)-one [(I), X=N, R2=propan-2-yl,
A=phenyl, R1a=H, R1b=Me, R6a=4-CH$_2$NR7R8,
R6b=H, R7-R8=4-piperazin-1-yl, R11=vinyl,
R3=R4=R5=H] cpd 184

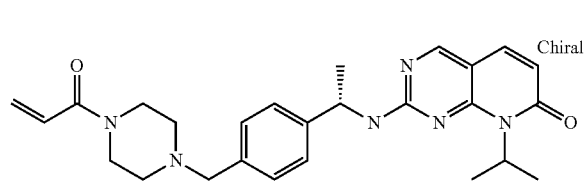 [SMILES: C=CC(=O)N1CCN(Cc2ccc([C@H](C)Nc3ncc4ccc(=O)n(C(C)C)c4n3)cc2)CC1]

$^1$H NMR (500 MHz, DMSO-d$_6$) δ=8.55 (s, 1H), 8.36 (d, J=6.86 Hz, 1H), 7.62 (d, J=9.30 Hz, 1H), 7.32 (d, J=7.63 Hz, 2H), 7.22 (d, J=7.47 Hz, 2H), 6.76 (dd, J=10.52, 16.62 Hz, 1H), 6.15 (d, J=9.30 Hz, 1H), 6.07 (dd, J=1.98, 16.62 Hz, 1H), 5.64 (dd, J=1.98, 10.52 Hz, 1H), 5.50 (br., s, 1H), 5.0 (m, 1H), 3.50 (br. s., 4H), 3.42 (br. s., 2H), 2.28 (br. s., 4H), 1.44-1.52 (m, 9H). LCMS: m/z 461 [M+H]$^+$@ r.t. 5.29 min. HRMS (ESI) calcd for C$_{26}$H$_{33}$N$_6$O$_2$ [M+H]$^+$ 461.266 found 461.2661.

2-{[(1S)-1-{4-[(4-acryloylpiperazin-1-yl)methyl]
phenyl}ethyl]amino}-8-ethylpyrido[2,3-d]pyrimidin-
7(8H)-one [(I), X=N, R2=ethyl, A=phenyl,
R1a=H, R1b=Me, R6a=4-CH$_2$NR7R8, R6b=H,
R7-R8=4-piperazin-1-yl, R11=vinyl,
R3=R4=R5=H] cpd 186

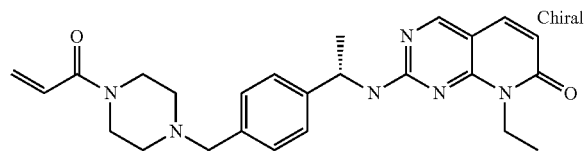 [SMILES: C=CC(=O)N1CCN(Cc2ccc([C@H](C)Nc3ncc4ccc(=O)n(CC)c4n3)cc2)CC1]

$^1$H NMR (500 MHz, DMSO-d$_6$) δ=8.58 (s, 1H), 8.43 (d, J=7.02 Hz, 1H), 7.67 (d, J=9.30 Hz, 1H), 7.35 (d, J=7.78 Hz, 2H), 7.23 (d, J=7.78 Hz, 2H), 6.75 (dd, J=10.52, 16.62 Hz, 1H), 6.20 (d, J=9.30 Hz, 1H), 6.07 (dd, J=2.21, 16.62 Hz, 1H), 5.65 (dd, J=2.21, 10.52 Hz, 1H), 5.02 (quin, J=7.05 Hz, 1H), 3.49 (m, 6H), 3.42 (s, 2H), 2.29 (br. s., 4H), 1.47 (d, J=7.17 Hz, 3H), 0.90 (t, J=6.86 Hz, 3H). LCMS: m/z 447 [M+H]$^+$@ r.t. 4.92 min. HRMS (ESI) calcd for C$_{25}$H$_{31}$N$_6$O$_2$ [M+H]$^+$ 447.2503 found 447.2518.

2-{[(1S)-1-{4-[1-(4-acryloylpiperazin-1-yl)propyl]
phenyl}ethyl]amino}-8-(propan-2-yl)pyrido[2,3-d]
pyrimidin-7(8H)-one [(I), X=N, R2=propan-2-yl,
A=phenyl, R1a=H, R1b=Me, R6a=4-CH(R14)
NR7R8, R6b=H, R7-R8=4-piperazin-1-yl,
R11=vinyl, R3=R4=R5=H, R14=ethyl] cpd 187

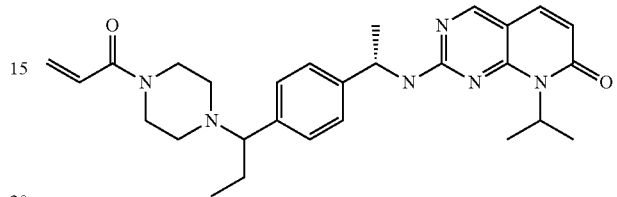

$^1$H NMR (500 MHz, DMSO-d$_6$) δ=8.56 (s, 1H), 8.34 (d, J=6.85 Hz, 1H), 7.62 (d, J=9.30 Hz, 1H), 7.30 (d, J=7.63 Hz, 2H), 7.14 (d, J=7.63 Hz, 2H), 6.69 (dd, J=10.98, 17.54 Hz, 1H), 6.15 (d, J=9.30 Hz, 1H), 6.01 (dd, J=1.98, 17.54 Hz, 1H), 5.59 (dd, J=1.98, 10.98 Hz, 1H), 5.44 (br., s, 1H), 4.98 (br. s, 1H), 3.40-3.52 (br. m, 4H), 3.222-3.26 (m, 1H), 2.28 (br. s., 4H), 1.80-1.89 (m, 1H), 1.61-1.67 (m, 1H), 1.44-1.52 (m, 9H), 0.65-0.72 (m, 3H).

LCMS: m/z 489 [M+H]$^+$@ r.t. 7.09 min. HRMS (ESI) calcd for C$_{28}$H$_{37}$N$_6$O$_2$ [M+H]$^+$ 489.2973 found 489.2981

2-{[(1S)-1-{4-[(4-acryloylpiperazin-1-yl)carbonyl]
phenyl}ethyl]amino}-8-ethylpyrido[2,3-d]pyrimidin-
7(8H)-one [(I), X=N, R2=ethyl, A=phenyl,
R1a=H, R1b=Me, R6a=4-CONR7R8, R6b=H,
R7-R8=4-piperazin-1-yl, R11=vinyl,
R3=R4=R5=H] cpd 190

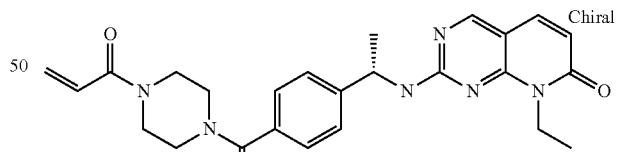

$^1$H NMR (500 MHz, DMSO-d$_6$) δ=8.59 (s, 1H), 8.50 (d, J=7.17 Hz, 1H), 7.68 (d, J=9.30 Hz, 1H), 7.47 (d, J=8.08 Hz, 2H), 7.37 (d, J=8.08 Hz, 2H), 6.61-6.95 (m, 1H), 6.22 (d, J=9.30 Hz, 1H), 6.12 (dd, J=2.29, 16.62 Hz, 1H), 5.70 (d, J=10.83 Hz, 1H), 5.05 (q, J=7.1 Hz, 1H), 3.99-4.27 (m, 2H), 3.57 (br. s., 8H), 1.49 (d, J=7.02 Hz, 3H), 0.89 (t, J=6.63 Hz, 3H). LCMS: m/z 461 [M+H]$^+$@ r.t. 4.58 min. HRMS (ESI) calcd for C$_{25}$H$_{29}$N$_6$O$_3$ [M+H]$^+$ 461.2296 found 461.2306

181

2-{[(1S)-1-{4-[(4-acryloylpiperazin-1-yl)carbonyl]-3-fluorophenyl}ethyl]amino}-8-[(2S)-3-methylbutan-2-yl]pyrido[2,3-d]pyrimidin-7(8H)-one [(I), X=N, R2=(2S)-3-methylbutan-2-yl, A=phenyl, R1a=H, R1b=Me, R6a=4-CONR7R8, R6b=F, R7-R8=4-piperazin-1-yl, R11=vinyl, R3=R4=R5=H] cpd 191

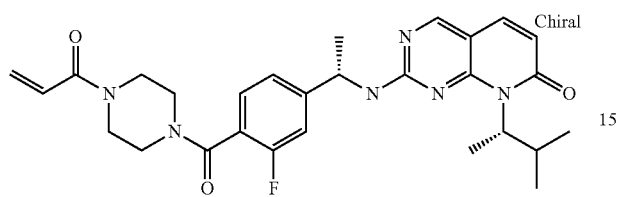

$^1$H NMR (500 MHz, DMSO-d$_6$) δ=8.60 (s, 1H), 8.41 (d, J=6.25 Hz, 1H), 7.66 (d, J=9.30 Hz, 1H), 7.37 (d, J=7.32 Hz, 1H), 7.18-7.32 (m, 2H), 6.68-6.86 (m, 1H), 6.24 (d, J=9.30 Hz, 1H), 6.11 (dd, J=2.29, 16.62 Hz, 1H), 5.66-5.73 (m, 1H), 5.01 (q, J=7.1 Hz, 1H), 4.77-4.99 (m, 1H), 3.45-3.69 (m, 6H), 3.18-3.25 (m, 2H), 1.91 (m, 1H), 1.50 (d, J=6.86 Hz, 3H), 0.76 (d, J=5.80 Hz, 3H), 0.64 (d, J=5.80 Hz, 3H), 0.12 (d, J=5.80 Hz, 3H). LCMS: m/z 521 [M+H]$^+$@ r.t. 5.44 min. HRMS (ESI) calcd for C$_{28}$H$_{33}$FN$_6$O$_3$[M+H]$^+$ 521.2671 found 521.2684.

N-(1-acryloylpiperidin-4-yl)-2-fluoro-4-[(1S)-1-{[7-oxo-8-(propan-2-yl)-7,8-dihydropyrido[2,3-d]pyrimidin-2-yl]amino}ethyl]benzamide [(I), X=N, R2=propan-2-yl, A=phenyl, R1a=H, R1b=Me, R6a=4-CONR7R8, R6b=H, R7=H, R8=4-piperidin-1-yl, R11=vinyl, R3=R4=R5=H] cpd 192

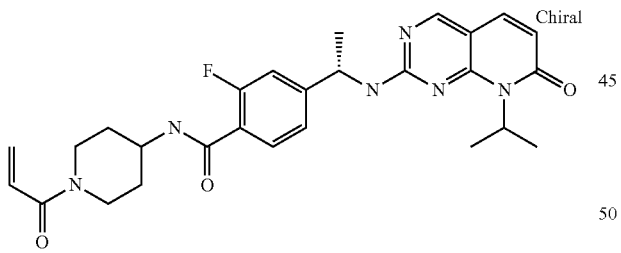

$^1$H NMR (500 MHz, DMSO-d$_6$) δ 8.57 (s, 1H), 8.42 (d, J=7.32 Hz, 1H), 8.15 (d, J=7.78 Hz, 1H), 7.63 (d, J=9.46 Hz, 1H), 7.49 (t, J=7.40 Hz, 1H), 7.27 (d, J=9.76 Hz, 2H), 6.81 (dd, J=10.45, 16.70 Hz, 1H), 6.17 (d, J=8.85 Hz, 1H), 6.08 (dd, J=2.36, 16.70 Hz, 1H), 5.66 (dd, J=2.36, 10.45 Hz, 1H), 5.54 (br. s., 1H), 5.06 (quin, J=7.00 Hz, 1H), 4.27 (d, J=12.51 Hz, 1H), 3.92-4.01 (m, 2H), 3.18 (t, J=11.90 Hz, 1H), 2.84 (t, J=11.74 Hz, 1H), 1.82 (br. s., 2H), 1.51 (d, J=4.88 Hz, 2H), 1.48 (d, J=7.02 Hz, 3H), 1.36 (br. s., 6H). LCMS: m/z 506 [M+H]$^+$@ r.t. 9.44 min.

HRMS (ESI) calcd for C$_{27}$H$_{32}$FN$_6$O$_3$[M+H]$^+$ 506.2515 found 506.2528.

182

2-{[(1S)-1-(1'-acryloyl-1',2',3',6'-tetrahydro-3,4'-bipyridin-6-yl)ethyl]amino}-8-[(2S)-3-methylbutan-2-yl]pyrido [2,3-d]pyrimidin-7(8H)-one [(I), X=N, R2=(2S)-3-methylbutan-2-yl, A=pyridin-2-yl, R1a=H, R1b=Me, R6a=4-(1-acryloyl-1,2,3,6-tetrahydropyridin-4-yl, R6b=H, R3=R4=R5=H] Cpd 194

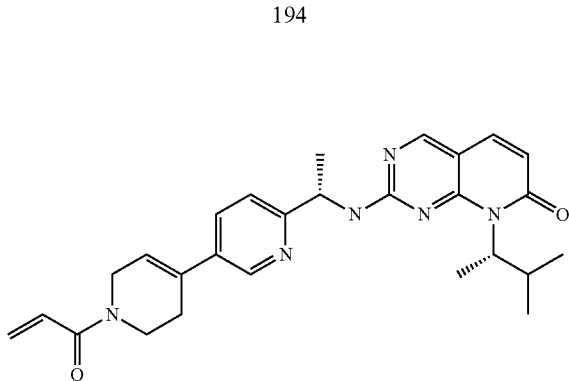

$^1$H NMR (500 MHz, DMSO-d$_6$) δ 8.61 (s, 1H), 8.59 (s, 1H), 8.34 (d, J=6.25 Hz, 1H), 7.62-7.80 (m, 2H), 7.21 (d, J=8.24 Hz, 1H), 7.46 (d, J=8.24 Hz, 2H), 6.89 (dd, J=10.37, 16.93 Hz, 1H), 6.09-6.23 (m, 3H), 5.70 (dd, J=2.29, 16.93 Hz, 1H), 4.97 (quin, J=6.90 Hz, 1H), 4.70-4.77 (m, 1H), 4.27 (br. m, 1H), 4.15-4.27 (br. m, 1H), 3.71-3.79 (m, 2H), 2.52-2.55 (m, 2H), 1.48-1.60 (m, 4H), 0.97-1.03 (m, 3H), 0.57-0.63 (m, 3H), 0.01 (d, J=6.71 Hz, 3H).

LCMS: m/z 473 [M+H]$^+$ r.t. 5.28 min. HRMS (ESI) calcd for C$_{27}$H$_{33}$N$_6$O$_2$ [M+H]$^+$ 473.266 found 473.2667;

2-({(1S)-1-[1'-(cyclopropylcarbonyl)-1',2',3',6'-tetrahydro-3,4'-bipyridin-6-yl]ethyl}amino)-8-[(2S)-3-methyl butan-2-yl]pyrido[2,3-d]pyrimidin-7(8H)-one [(I), X=N, R2=(2S)-3-methylbutan-2-yl, A=pyridin-2-yl, R1a=H, R1b=Me, R6a=4-(1-cyclopropylcarbonyl 1,2,3,6-tetrahydropyridin-4-yl, R6b=H, R3=R4=R5=H] Cpd 195

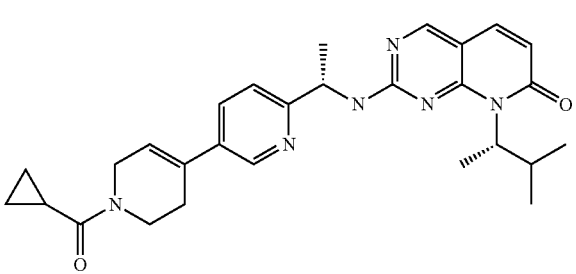

LCMS: m/z 487 [M+H]$^+$ r.t. 5.52 min. HRMS (ESI) calcd for C$_{28}$H$_{35}$N$_6$O$_2$ [M+H]$^+$ 487.2816 found 487.2813;

2-{[(1S)-1-{4-[(4-acryloylpiperazin-1-yl)methyl]
phenyl}ethyl]amino}-8-[(2S)-1-fluoropropan-2-yl]
pyrido[2,3-d]pyrimidin-7(8H)-one [(I), X=N, R2=
(2S)-1-fluoropropan-2-yl, A=phenyl, R1a=H,
R1b=Me, R6a=4-(4-acryloylpiperazin-1-yl)methyl,
R6b=H, R3=R4=R5=H] Cpd 198

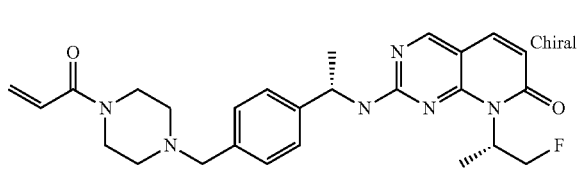

$^1$H NMR (500 MHz, DMSO-d$_6$) δ 8.60 (s, 1H), 8.47 (d, J=5.64 Hz, 1H), 7.68 (d, J=9.15 Hz, 1H), 7.21-7.37 (m, 4H), 6.75 (dd, J=10.29, 16.70 Hz, 1H), 6.20 (d, J=9.15 Hz, 1H), 6.07 (dd, J=2.21, 16.70 Hz, 1H), 5.64 (dd, J=2.21, 10.29 Hz, 1H), 4.91 (td, J=6.48, 12.96 Hz, 1H), 4.36 (m, 1H), 3.38-3.60 (m, 8H), 2.30 (br. s., 4H), 1.47 (d, J=7.02 Hz, 3H), 1.05 (dd, J=7.02 Hz, 3H). LCMS: m/z 479 [M+H]$^+$ r.t. 5.94 min. HRMS (ESI) calcd for C$_{26}$H$_{32}$FN$_6$O$_2$ [M+H]$^+$ 479.2566 found 479.2572;

2-{[(1S)-1-{4-[(4-acryloylpiperazin-1-yl)methyl]
phenyl}ethyl]amino}-8-[(2S)-1-hydroxypropan-2-yl]
pyrido[2,3-d]pyrimidin-7(8H)-one [(I), X=N, R2=
(2S)-1-hydroxypropan-2-yl, A=phenyl, R1a=H,
R1b=Me, R6a=4-(4-acryloylpiperazin-1-yl)methyl,
R6b=H, R3=R4=R5=H] Cpd 199

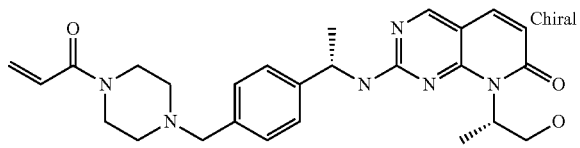

$^1$H NMR (500 MHz, DMSO-d$_6$) δ 8.56 (s, 1H), 7.63 (d, J=9.00 Hz, 1H), 7.19-7.49 (m, 4H), 6.76 (dd, J=10.52, 16.78 Hz, 1H), 6.04-6.22 (br. m, 2H), 5.61-5.77 (br. m, 1H), 5.27 (br. s, 1H), 5.01 (m, 1H), 4.68-4.79 (br. m, 1H), 4.42-4.52 (br. m, 1H), 4.17-4.37 (br. m, 2H), 3.39-3.60 (m, 6H), 2.29 (m, 4H), 1.36-1.51 (m, 6H). LCMS: m/z 477 [M+H]$^+$ r.t. 4.37 min. HRMS (ESI) calcd for C$_{26}$H$_{32}$N$_6$O$_3$ [M+H]$^+$ 477.2609 found 477.2605;

2-{[(1S)-1-{4-[(4-acryloylpiperazin-1-yl)methyl]
phenyl}ethyl]amino}-8-(2,2-dimethylpropyl)-4-
ethoxypyrido[2,3-d]pyrimidin-7(8H)-one [(I),
X=N, R2=2,2-dimethylpropyl, A=phenyl, R1a=H,
R1b=Me, R6a=4-(4-acryloylpiperazin-1-yl)methyl,
R6b=H, R3=OEthyl, R4=R5=H] Cpd 201

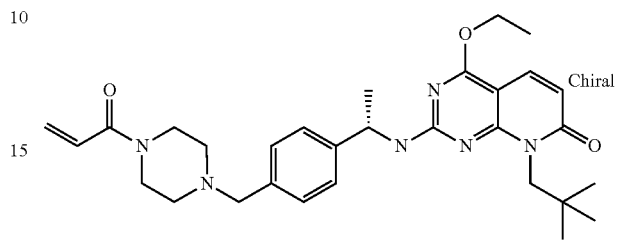

$^1$H NMR (500 MHz, DMSO-d$_6$) δ 8.19 (d, J=7.63 Hz, 1H), 7.67 (d, J=9.46 Hz, 1H), 7.30-7.37 (m, 2H), 7.18-7.28 (m, 2H), 6.76 (dd, J=10.29, 16.70 Hz, 1H), 6.05-6.10 (m, 2H), 5.64-5.68 (m, 1H), 4.98-5.23 (m, 1H), 4.28-4.53 (m, 2H), 4.02 (dd J=7.17, 15.56 Hz, 2H), 3.46-3.56 (m, 4H), 3.40-3.46 (m, 2H), 2.31 (br. s., 4H), 1.42-1.49 (m, 6H), 1.37 (t, J=7.09 Hz, 3H), 0.73 (br., m. 6H). LCMS: m/z 533 [M+H]$^+$ r.t. 10.12 min. HRMS (ESI) calcd for C$_{30}$H$_{41}$N$_6$O$_3$ [M+H]$^+$ 533.3235 found 533.3249;

2-{[(1S)-1-{4-[(4-acryloylpiperazin-1-yl)methyl]
phenyl}ethyl]amino}-8-(2,2-dimethylpropyl)-4-
(methylamino) pyrido[2,3-d]pyrimidin-7(8H)-one
[(I), X=N, R2=2,2-dimethylpropyl, A=phenyl,
R1a=H, R1b=Me, R6a=4-(4-acryloylpiperazin-1-yl)
methyl, R6b=H, R3=N-Methyl, R4=R5=H] Cpd
202

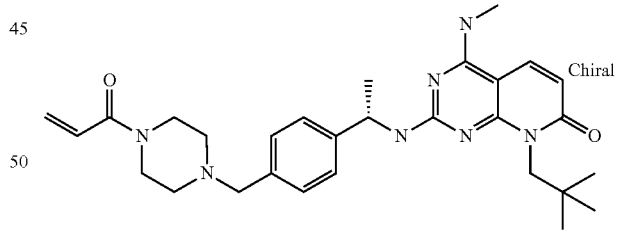

$^1$H NMR (500 MHz, DMSO-d$_6$) δ. 7.72-7.89 (m, 1H), 7.53-7.64 (m, 1H), 7.32 (d, J=8.08 Hz, 1H), 7.15-7.29 (m, 4H), 6.76 (ddd, J=4.27, 10.49, 16.66 Hz, 1H), 6.03-6.18 (m, 1H), 5.99 (d, J=9.46 Hz, 1H), 5.60-5.71 (m, 1H), 4.88 (dq J=7.32, 7.63 Hz, 1H), 4.11 (dd, J=5.19 Hz, 2H), 3.51 (br. s., 4H), 3.44 (d, J=6.86 Hz, 2H), 2.90 (d, J=4.27 Hz, 3H), 2.32 (br. s., 4H), 1.31 (d, J=7.02 Hz, 3H), 0.90 (br.s, 3H), 0.73 (br. s, 6H).

LCMS: m/z 518 [M+H]$^+$ r.t. 10.12 min. HRMS (ESI) calcd for C$_{29}$H$_{40}$N$_7$O$_2$ [M+H]$^+$ 518.3238 found 518.3239;

2-{[(1S)-1-{4-[(4-acryloylpiperazin-1-yl)methyl]phenyl}ethyl]amino}-4-(dimethylamino)-8-(propan-2-yl)pyrido[2,3-d]pyrimidin-7(8H)-one [(I), X=N, R2=propan-2-yl, A=phenyl, R1a=H, R1b=Me, R6a=4-(4-acryloylpiperazin-1-yl)methyl, R6b=H, R3=N N-diMethyl, R4=R5=H] Cpd 203

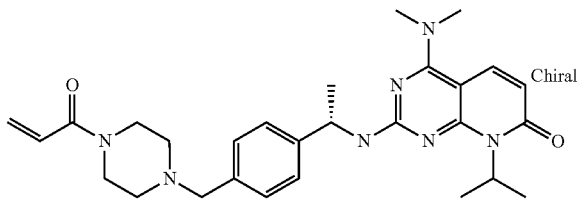

LCMS: m/z 505 [M+H]⁺ r.t. 6.05 min. HRMS (ESI) calcd for $C_{28}H_{38}N_7O_2$ [M+H]⁺ 504.3082 found 504.3095; 2-{[(1S)-1-{4-[(4-acryloylpiperazin-1-yl)methyl]phenyl}ethyl]amino}-7-oxo-8-(propan-2-yl)-7,8-dihydropyrido [2,3-d]pyrimidine-4-carbonitrile [(I), X=N, R2=propan-2-yl, A=phenyl, R1a=H, R1b=Me, R6a=4-(4-acryloylpiperazin-1-yl)methyl, R6b=H, R3=CN, R4=R5=H] Cpd 204

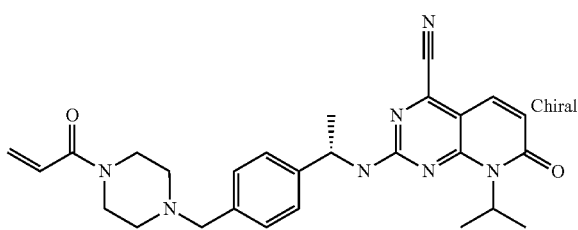

¹H NMR (500 MHz, DMSO-d₆) δ 8.92 (d, J=7.17 Hz, 1H), 7.66 (d, J=9.46 Hz, 1H), 7.32 (d, J=8.08 Hz, 2H), 7.23 (d, J=8.08 Hz, 2H), 6.76 (dd, J=10.45, 16.70 Hz, 1H), 6.35 (d, J=9.46 Hz, 1H), 6.07 (dd, J=2.36, 16.70 Hz, 1H), 5.64 (dd, J=2.36, 10.45 Hz, 1H), 4.98 (d, J=6.56 Hz, 1H), 3.50 (br. s., 4H), 3.43 (s, 2H), 2.28 (br. s., 4H), 1.48 (d, J=7.17 Hz, 3H). LCMS: m/z 486 [M+H]⁺ r.t. 6.18 min. HRMS (ESI) calcd for $C_{27}H_{32}N_7O_2$ [M+H]⁺ 486.2612 found 486.2614;

2-{[(1S)-1-{4-[(4-acryloylpiperazin-1-yl)methyl]phenyl}ethyl]amino}-4-[(2,4-dimethoxybenzyl)amino]-8-(propan-2-yl)pyrido[2,3-d]pyrimidin-7(8H)-one [(I), X=N, R2=propan-2-yl, A=phenyl, R1a=H, R1b=Me, R6a=4-(4-acryloylpiperazin-1-yl)methyl, R6b=H, R3=(2,4-dimethoxybenzyl)amino, R4=R5=H] Cpd 205

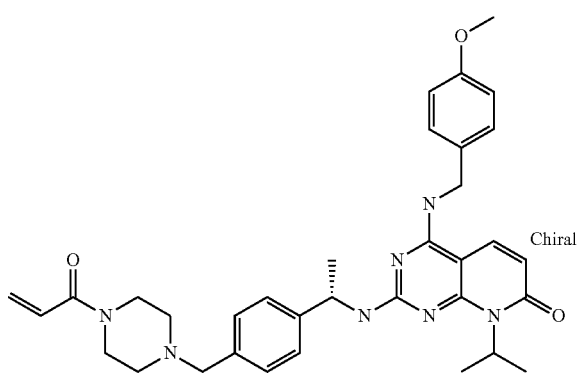

LCMS: m/z 626 [M+H]⁺ r.t. 6.67 min. HRMS (ESI) calcd for $C_{35}H_{43}N_7O_4$ [M+H]⁺ 626.345 found 626.3475;

2-{[(1S)-1-{4-[(4-acryloylpiperazin-1-yl)methyl]phenyl}ethyl]amino}-4-amino-8-(propan-2-yl)pyrido[2,3-d]pyrimidin-7(8H)-one [(I), X=N, R2=propan-2-yl, A=phenyl, R1a=H, R1b=Me, R6a=4-(4-acryloylpiperazin-1-yl)methyl, R6b=H, R3=NH2, R4=R5=H] Cpd 206

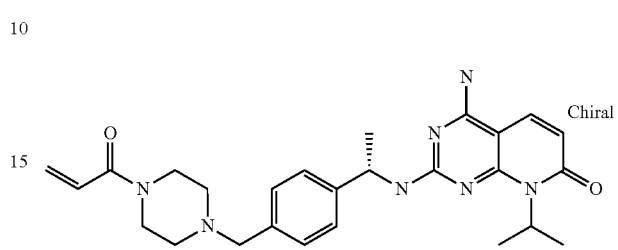

¹H NMR (500 MHz, DMSO-d₆) δ 7.82 (d, J=9.15 Hz, 1H), 6.75 (dd, J=10.52, 16.62 Hz, 1H), 6.07 (dd, J=2.21, 16.70 Hz, 1H), 5.91 (br. s., 1H), 4.98 (d, J=13.88 Hz, 1H), 3.49 (d, J=6.56 Hz, 6H), 2.29 (br. s., 4H), 1.17-1.58 (m, 9H). LCMS: m/z 476 [M+H]⁺ r.t. 4.81 min. HRMS (ESI) calcd for $C_{26}H_{34}N_7O_2$ [M+H]⁺ 476.2769 found 476.2777;

2-{[(1S)-1-(4-{[(2R)-4-acryloyl-2-methylpiperazin-1-yl]methyl}phenyl)ethyl]amino}-8-ethylpyrido[2,3-d]pyrimidin-7(8H)-one [(I), X=N, R2=Ethyl, A=phenyl, R1a=H, R1b=Me, R6a=4-(2R)-(4-acryloyl-2-methylpiperazin-1-yl)methyl, R6b=H, R3=R4=R5=H] Cpd 207

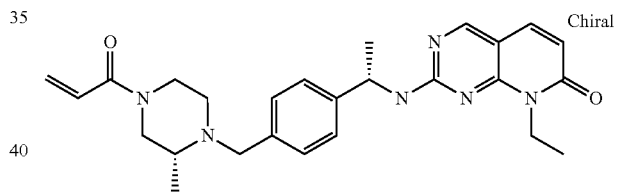

¹H NMR (500 MHz, DMSO-d₆) δ 8.57 (s, 1H), 8.42 (d, J=7.17 Hz, 1H), 7.67 (d, J=9.46 Hz, 1H), 7.34 (d, J=7.78 Hz, 2H), 7.23 (d, J=7.78 Hz, 2H), 6.63-6.90 (m, 1H), 6.20 (d, J=9.30 Hz, 1H), 6.01-6.14 (m, 1H), 5.57-5.71 (m, 1H), 5.01 (quin, J=6.30 Hz, 1H), 1.47 (d, J=7.02 Hz, 3H), 1.03 (dd, J=6.25, 10.68 Hz, 3H), 0.89 (q, J=6.81 Hz, 3H). LCMS: m/z 461 [M+H]⁺ r.t. 5.13 min. HRMS (ESI) calcd for $C_{26}H_{33}N_6O_2$ [M+H]⁺ 461.266 found 461.2656;

2-{[(1S)-1-(4-{[(3R)-4-acryloyl-3-methylpiperazin-1-yl]methyl}phenyl)ethyl]amino}-8-ethylpyrido[2,3-d]pyrimidin-7(8H)-one [(I), X=N, R2=Ethyl, A=phenyl, R1a=H, R1b=Me, R6a=4-(3R)-(4-acryloyl-2-methylpiperazin-1-yl)methyl, R6b=H, R3=R4=R5=H] Cpd 208

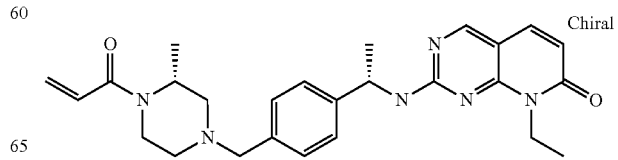

¹H NMR (500 MHz, DMSO-d₆) δ 8.57 (s, 1H), 8.42 (d, J=7.17 Hz, 1H), 7.67 (d, J=9.46 Hz, 1H), 7.34 (d, J=7.78 Hz, 2H), 7.23 (d, J=7.78 Hz, 2H), 6.63-6.90 (m, 1H), 6.20 (d, J=9.30 Hz, 1H), 6.01-6.14 (m, 1H), 5.57-5.71 (m, 1H), 5.01 (quin, J=6.30 Hz, 1H), 1.47 (d, J=7.02 Hz, 3H), 1.03 (dd, J=6.25, 10.68 Hz, 3H), 0.89 (q, J=6.81 Hz, 3H). LCMS: m/z 461 [M+H]⁺ r.t. 5.61 min. HRMS (ESI) calcd for C₂₆H₃₃N₆O₂ [M+H]⁺ 461.266 found 461.2655;

2-{[(1S)-1-(4-{[(2R)-4-acryloyl-2-(propan-2-yl)piperazin-1-yl]methyl}phenyl)ethyl]amino}-8-ethylpyrido[2,3-d]pyrimidin-7(8H)-one [(I), X=N, R2=Ethyl, A=phenyl, R1a=H, R1b=Me, R6a=4-(2R)-(4-acryloyl-2-(propan-2-yl)piperazin-1-yl)methyl, R6b=H, R3=R4=R5=H] Cpd 209

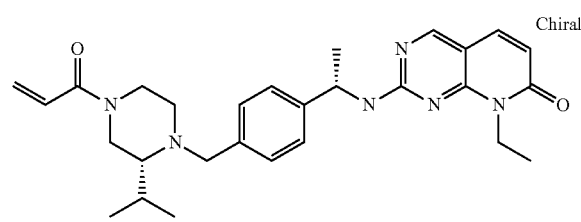

¹H NMR (500 MHz, DMSO-d₆) δ 8.57 (s, 1H), 8.42 (d, J=6.86 Hz, 1H), 7.67 (d, J=9.30 Hz, 1H), 7.34 (d, J=7.78 Hz, 2H), 7.23 (d, J=7.93 Hz, 2H), 6.59-6.85 (m, 1H), 6.20 (d, J=9.46 Hz, 1H), 6.07 (d, J=16.62 Hz, 1H), 5.65 (dd, J=11.29, 19.37 Hz, 1H), 5.00 (br. s., 1H), 4.14-4.28 (m, 3H), 3.95-4.08 (m, 4H), 3.71-3.80 (m, 2H), 3.08-3.20 (m, 1H), 2.87-2.95 (m, 1H), 2.11-2.20 (m, 1H), 1.47 (d, J=7.02 Hz, 3H), 0.74-1.08 (m, 9H). LCMS: m/z 489 [M+H]⁺ r.t. 6.25 min. HRMS (ESI) calcd for C₂₈H₃₇N₆O₂ [M+H]⁺ 489.2973 found 489.298;

2-{[(1S)-1-(4-{[(2S)-4-acryloyl-2-methylpiperazin-1-yl]methyl}phenyl)ethyl]amino}-8-ethylpyrido[2,3-d]pyrimidin-7(8H)-one [(I), X=N, R2=Ethyl, A=phenyl, R1a=H, R1b=Me, R6a=4-(2R)-(4-acryloyl-2-methylpiperazin-1-yl)methyl, R6b=H, R3=R4=R5=H] Cpd 210

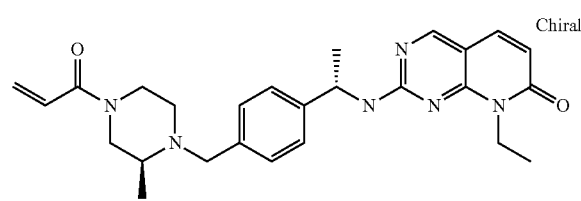

¹H NMR (500 MHz, DMSO-d₆) δ 8.58 (s, 1H), 8.42 (d, J=7.47 Hz, 1H), 7.67 (d, J=9.30 Hz, 1H), 7.34 (d, J=7.78 Hz, 2H), 7.23 (d, J=7.93 Hz, 2H), 6.65-6.87 (m, 1H), 6.20 (d, J=9.30 Hz, 1H), 6.09 (d, J=17.23 Hz, 1H), 5.64 (t, J=8.70 Hz, 1H), 5.02 (quin, J=6.83 Hz, 1H), 4.00-4.28 (m, 3H), 3.63-3.92 (m, 5H), 3.08-3.26 (m, 2H), 1.95-2.04 (m, 1H), 1.47 (d, J=7.02 Hz, 3H), 0.98-1.10 (m, 3H), 0.90 (t, J=6.33 Hz, 3H). LCMS: m/z 461 [M+H]⁺ r.t. 5.14 min. HRMS (ESI) calcd for C₂₆H₃₃N₆O₂ [M+H]⁺ 461.266 found 461.2675; 2-{[(1S)-1-(4-{[(3S)-4-acryloyl-3-methylpiperazin-1-yl]methyl}phenyl)ethyl]amino}-8-ethylpyrido[2,3-d]pyrimidin-7(8H)-one [(I), X=N, R2=Ethyl, A=phenyl, R1a=H, R1b=Me, R6a=4-(3R)-(4-acryloyl-2-methylpiperazin-1-yl)methyl, R6b=H, R3=R4=R5=H] Cpd 211

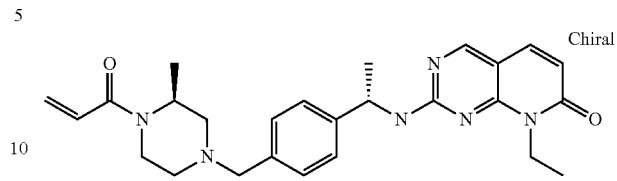

¹H NMR (500 MHz, DMSO-d₆) δ 8.58 (s, 1H), 8.42 (d, J=7.17 Hz, 1H), 7.67 (d, J=9.30 Hz, 1H), 7.35 (d, J=7.93 Hz, 2H), 7.24 (d, J=7.93 Hz, 2H), 6.74 (dd, J=10.60, 16.70 Hz, 1H), 6.21 (d, J=9.30 Hz, 1H), 6.07 (d, J=16.32 Hz, 1H), 5.64 (dd, J=1.37, 10.22 Hz, 1H), 5.02 (quin, J=7.32 Hz, 1H), 4.00-4.29 (m, 5H), 3.35-3.45 (m, 4H), 2.61 (br. s, 2H), (1.47 (d, J=7.02 Hz, 3H), 1.17 (q, J=7.10 Hz, 3H), 0.91 (t, J=6.86 Hz, 3H). LCMS: m/z 461 [M+H]++r.t. 5.61 min. HRMS (ESI) calcd for C₂₆H₃₃N₆O₂ [M+H]⁺ 461.266 found 461.2672;

2-{[(1S)-1-(4-{[(2S)-4-acryloyl-2-(propan-2-yl)piperazin-1-yl]methyl}phenyl)ethyl]amino}-8-ethylpyrido[2,3-d]pyrimidin-7(8H)-one [(I), X=N, R2=Ethyl, A=phenyl, R1a=H, R1b=Me, R6a=4-(2R)-(4-acryloyl-2-(propan-2-yl)piperazin-1-yl)methyl, R6b=H, R3=R4=R5=H] Cpd 212

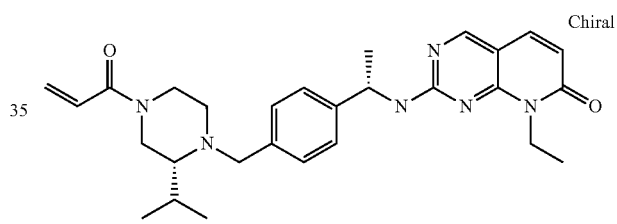

¹H NMR (500 MHz, DMSO-d₆) δ 8.57 (s, 1H), 8.42 (d, J=6.86 Hz, 1H), 7.67 (d, J=9.30 Hz, 1H), 7.34 (d, J=8.08 Hz, 2H), 7.23 (d, J=7.93 Hz, 2H), 6.72 (dd, J=10.37, 16.62 Hz, 1H), 6.20 (d, J=9.46 Hz, 1H), 6.07 (dd, J=2.21, 16.70 Hz, 1H), 5.56-5.73 (m, 1H), 5.01 (t, J=6.86 Hz, 1H), 3.66-4.29 (m, 6H), 2.87-3.28 (m, 3H), 2.66 (d, J=15.25 Hz, 1H), 2.17 (d, J=6.56 Hz, 1H), 2.01-2.09 (m, 2H), 1.47 (d, J=7.02 Hz, 3H), 0.78-0.98 (m, 9H). LCMS: m/z 489 [M+H]⁺ r.t. 6.13 min. HRMS (ESI) calcd for C₂₈H₃₇N₆O₂ [M+H]⁺ 489.2973 found 489.2977;

2-{[(1S)-1-{6-[(4-acryloylpiperazin-1-yl)methyl]pyridin-3-yl}ethyl]amino}-8-(propan-2-yl)pyrido[2,3-d]pyrimidin-7(8H)-one [(I), X=N, R2=Ethyl, A=Pyridin-3-yl, R1a=H, R1b=Me, R6a=6-(4-acryloylpiperazin-1-yl)methyl, R6b=H, R3=R4=R5=H] Cpd 213

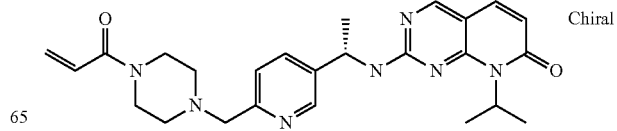

¹H NMR (500 MHz, DMSO-d₆) δ 8.57 (s, 1H), 8.51 (br. s., 1H), 8.42 (d, J=6.41 Hz, 1H), 7.74 (d, J=8.08 Hz, 1H), 7.63 (d, J=9.30 Hz, 1H), 7.38 (d, J=7.93 Hz, 1H), 6.76 (dd, J=10.37, 16.62 Hz, 1H), 6.17 (d, J=9.30 Hz, 1H), 6.08 (dd, J=1.91, 16.85 Hz, 1H), 5.65 (dd, J=1.75, 10.75 Hz, 1H), 5.20-5.58 (m, 1H), 5.04 (br. s., 1H), 3.56 (br. s., 2H), 3.51 (m, 4H), 2.22-2.44 (m, 4H), 1.51 (d, J=6.86 Hz, 9H). LCMS: m/z 462 [M+H]⁺ r.t. 4.57 min. HRMS (ESI) calcd for $C_{25}H_{32}N_7O_2$ [M+H]⁺ 462.2612 found 462.2606;

2-{[(1S)-1-{4-[1-(4-acryloylpiperazin-1-yl)propyl]phenyl}ethyl]amino}-8-ethylpyrido[2,3-d]pyrimidin-7(8H)-one [(I), X=N, R2=Ethyl, A=phenyl, R1a=H, R1b=Me, R6a=4-CH(R14)NR7R8, R6b=H, R7-R8=4-piperazin-1-yl, R11=vinyl, R3=R4=R5=H, R14=ethyl] Cpd 214

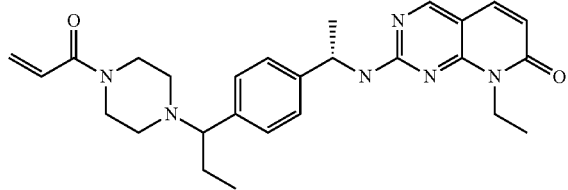 [SMILES: C=CC(=O)N1CCN(C(CC)c2ccc([C@H](C)Nc3ncc4ccc(=O)n(CC)c4n3)cc2)CC1]

¹H NMR (500 MHz, DMSO-d₆) δ 8.58 (s, 1H), 8.40 (d, J=4.42 Hz, 1H), 7.67 (d, J=9.30 Hz, 1H), 7.33 (d, J=7.63 Hz, 2H), 7.14 (d, J=7.93 Hz, 2H), 6.69 (dd, J=10.60, 16.55 Hz, 1H), 6.20 (d, J=9.30 Hz, 1H), 6.01 (d, J=16.78 Hz, 1H), 5.60 (d, J=10.52 Hz, 1H), 4.90-5.38 (m, 1H), 3.90-4.35 (m, 2H), 3.44 (br. s, 4H), 3.19-3.28 (m, 1H), 2.23 (br. s., 4H), 1.84 (qd, J=6.66, 13.27 Hz, 1H), 1.56-1.72 (m, 1H), 1.47 (d, J=7.02 Hz, 3H), 0.82 (td, J=7.02, 10.37 Hz, 3H), 0.57-0.75 (m, 3H). LCMS: m/z 475 [M+H]⁺ r.t. 5.4 min. HRMS (ESI) calcd for $C_{27}H_{35}N_6O_2$ [M+H]⁺ 475.2816 found 475.2824;

2-{[(1S)-1-{4-[1-(4-acryloylpiperazin-1-yl)propyl]phenyl}ethyl]amino}-8-methylpyrido[2,3-d]pyrimidin-7(8H)-one [(I), X=N, R2=Methyl, A=phenyl, R1a=H, R1b=Me, R6a=4-CH(R14)NR7R8, R6b=H, R7-R8=4-piperazin-1-yl, R11=vinyl, R3=R4=R5=H, R14=ethyl] Cpd 215

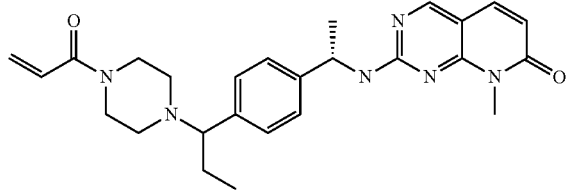 [SMILES: C=CC(=O)N1CCN(C(CC)c2ccc([C@H](C)Nc3ncc4ccc(=O)n(C)c4n3)cc2)CC1]

¹H NMR (500 MHz, DMSO-d₆) δ 8.57 (s, 1H), 8.39 (d, J=7.63 Hz, 1H), 7.69 (d, J=9.30 Hz, 1H), 7.37 (d, J=7.63 Hz, 2H), 7.15 (d, J=7.93 Hz, 2H), 6.70 (dd, J=10.52, 16.62 Hz, 1H), 6.18-6.28 (m, 1H), 6.02 (d, J=16.78 Hz, 1H), 5.60 (dd, J=1.98, 10.37 Hz, 1H), 5.13 (quin, J=6.90 Hz, 1H), 3.47 (d, J=17.54 Hz, 4H), 3.37 (d, J=3.51 Hz, 3H), 3.20-3.28 (m, 1H), 2.26 (br. s., 4H), 1.79-1.92 (m, 1H), 1.66 (dt, J=7.32, 14.41 Hz, 1H), 1.48 (d, J=6.71 Hz, 3H), 0.55-0.91 (m, 3H). LCMS: m/z 461 [M+H]⁺ r.t. 5.12 min. HRMS (ESI) calcd for $C_{26}H_{33}N_6O_2$ [M+H]⁺ 461.266 found 461.265;

2-{[(1S)-1-{4-[1-(4-acryloylpiperazin-1-yl)propyl]phenyl}ethyl]amino}-8-(2,6-difluorobenzyl)pyrido[2,3-d]pyrimidin-7(8H)-one one [(I), X=N, R2=2,6-difluorobenzyl, A=phenyl, R1a=H, R1b=Me, R6a=4-CH(R14)NR7R8, R6b=H, R7-R8=4-piperazin-1-yl, R11=vinyl, R3=R4=R5=H, R14=ethyl] Cpd 216

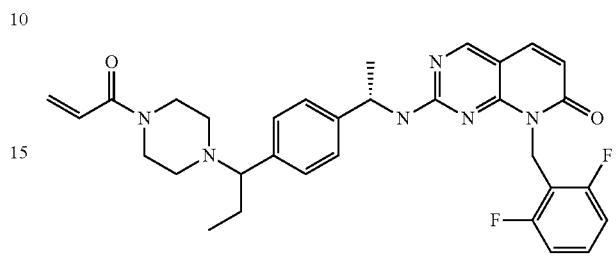

¹H NMR (500 MHz, DMSO-d₆) δ 8.59 (s, 1H), 8.32 (d, J=8.39 Hz, 1H), 7.73 (d, J=9.30 Hz, 1H), 7.27-7.39 (m, 1H), 7.25 (d, J=7.93 Hz, 2H), 7.07 (d, J=6.25 Hz, 2H), 6.96 (t, J=8.08 Hz, 2H), 6.71 (dd, J=10.45, 16.70 Hz, 1H), 6.25 (d, J=9.30 Hz, 1H), 6.03 (dd, J=2.36, 16.70 Hz, 1H), 5.59-5.65 (m, 1H), 5.55 (dd, J=6.90, 14.9 Hz, 1H), 5.36 (d, J=14.95 Hz, 1H), 5.10 (quin, J=7.55 Hz, 1H), 3.47 (br. s., 4H), 3.18-3.27 (m, 1H), 2.25 (br. s., 4H), 1.75-1.93 (m, J=6.71, 12.66 Hz, 1H), 1.56-1.72 (m, 1H), 1.36 (d, J=6.86 Hz, 3H), 0.60-0.77 (m, 3H). LCMS: m/z 461 [M+H]⁺ r.t. 6.17 min. HRMS (ESI) calcd for $C_{32}H_{34}F_2N_6O_2$[M+H]⁺ 573.2784 found 573.2791;

2-{[(1S)-1-{4-[1-(4-acryloylpiperazin-1-yl)propyl]phenyl}ethyl]amino}-8-cyclopropylpyrido[2,3-d]pyrimidin-7(8H)-one [(I), X=N, R2=cyclopropyl, A=phenyl, R1a=H, R1b=Me, R6a=4-CH(R14)NR7R8, R6b=H, R7-R8=4-piperazin-1-yl, R11=vinyl, R3=R4=R5=H, R14=ethyl] Cpd 218

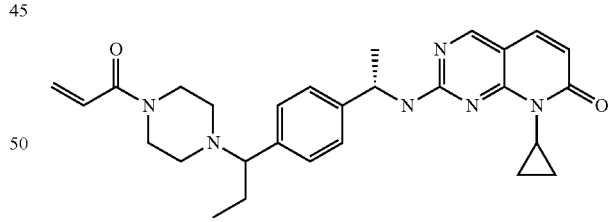

¹H NMR (500 MHz, DMSO-d₆) δ 8.53 (s, 1H), 8.29 (d, J=7.47 Hz, 1H), 7.63 (d, J=9.30 Hz, 1H), 7.35 (d, J=6.86 Hz, 2H), 7.15 (d, J=8.08 Hz, 2H), 6.70 (dd, J=10.75, 16.85 Hz, 1H), 6.14 (d, J=9.30 Hz, 1H), 6.02 (d, J=16.47 Hz, 1H), 5.55-5.67 (m, 1H), 5.08-5.39 (m, 1H), 3.40-3.58 (m, 4H), 3.21-3.29 (m, 1H), 2.57-2.67 (m, 1H), 2.26 (br. s., 4H), 1.59-1.94 (m, 2H), 1.49 (d, J=7.02 Hz, 3H), 1.01-1.06 (m, 1H), 0.79-0.86 (m, 1H), 0.70 (t, J=7.32 Hz, 3H), 0.61 (br. s 1H), 0.32 (br. s 1H). LCMS: m/z 487 [M+H]⁺ r.t. 6.25 min. HRMS (ESI) calcd for $C_{28}H_{35}N_6O_2$ [M+H]⁺ 487.2816 found 487.2829;

191

2-{[(1S)-1-{4-[1-(4-acryloylpiperazin-1-yl)-2-cyclopropylethyl]phenyl}ethyl]amino}-8-ethylpyrido[2,3-d]pyrimidin-7(8H)-one [(I), X=N, R2=Ethyl, A=phenyl, R1a=H, R1b=Me, R6a=4-CH(R14)NR7R8, R6b=H, R7-R8=4-piperazin-1-yl, R11=vinyl, R3=R4=R5=H, R14=cyclopropylmethyl] Cpd 219

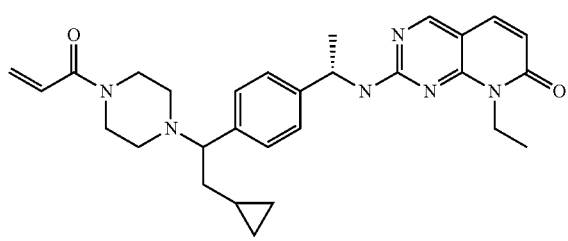 [SMILES: C=CC(=O)N1CCN(C(CC2CC2)c2ccc([C@H](C)Nc3ncc4ccc(=O)n(CC)c4n3)cc2)CC1]

$^1$H NMR (500 MHz, DMSO-$d_6$) δ 8.61 (s, 1H), 8.44 (d, J=5.03 Hz, 1H), 7.70 (d, J=9.30 Hz, 1H), 7.11-7.44 (m, 4H), 6.72 (dd, J=10.83, 16.32 Hz, 1H), 6.23 (d, J=9.30 Hz, 1H), 6.04 (d, J=16.32 Hz, 1H), 5.62 (d, J=10.37 Hz, 1H), 5.05 (d, J=6.86 Hz, 1H), 3.95-4.41 (m, 2H), 3.43-3.62 (m, 4H), 2.28 (br. s., 4H), 1.55-1.85 (m, 2H), 1.51 (d, J=6.86 Hz, 3H), 0.71-1.04 (m, 3H), 0.18-0.51 (m, 4H), −0.13-0.10 (m, 2H). LCMS: m/z 501 [M+H]$^+$ r.t. 7.27 min.

HRMS (ESI) calcd for $C_{29}H_{37}N_6O_2$ [M+H]$^+$ 501.2973 found 501.2978;

2-{[(1S)-1-{4-[1-(4-acryloylpiperazin-1-yl)-2-cyclopropylethyl]phenyl}ethyl]amino}-8-(propan-2-yl)pyrido[2,3-d]pyrimidin-7(8H)-one [(I), X=N, R2=propan-2-yl, A=phenyl, R1a=H, R1b=Me, R6a=4-CH(R14)NR7R8, R6b=H, R7-R8=4-piperazin-1-yl, R11 vinyl, R3=R4=R5=H, R14=cyclopropylmethyl] Cpd 220

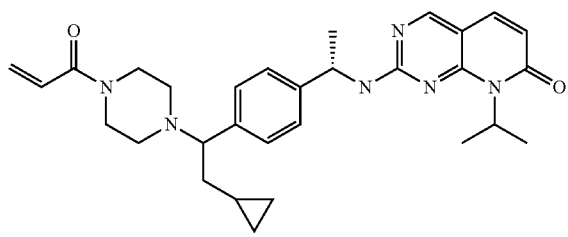 [SMILES: C=CC(=O)N1CCN(C(CC2CC2)c2ccc([C@H](C)Nc3ncc4ccc(=O)n(C(C)C)c4n3)cc2)CC1]

$^1$H NMR (500 MHz, DMSO-$d_6$) δ 8.56 (s, 1H), 8.34 (br. s., 1H), 7.62 (d, J=9.15 Hz, 1H), 7.27-7.40 (m, 2H), 7.17 (d, J=7.78 Hz, 2H), 6.68 (dd, J=10.37, 16.47 Hz, 1H), 6.15 (d, J=9.00 Hz, 1H), 6.01 (d, J=16.47 Hz, 1H), 5.59 (d, J=10.52 Hz, 1H), 4.99 (d, J=5.95 Hz, 1H), 3.40-3.56 (m, 5H), 2.23 (br. s., 4H), 1.54-1.84 (m, 2H), 1.22-1.52 (m, 7H), −0.18-0.50 (m, 6H), −0.05-0.02 (m, 2H). LCMS: m/z 515 [M+H]$^+$ r.t. 9.75 min. HRMS (ESI) calcd for $C_{30}H_{39}N_6O_2$ [M+H]$^+$ 515.3129 found 515.3143;

192

2-{[(1S)-1-(4-{1-[4-(2-methylacryloyl)piperazin-1-yl]propyl}phenyl)ethyl]amino}-8-(propan-2-yl)pyrido[2,3-d]pyrimidin-7(8H)-one [(I), X=N, R2=propan-2-yl, A=phenyl, R1a=H, R1b=Me, R6a=4-CH(R14)NR7R8, R6b=H, R7-R8=4-piperazin-1-yl, R11=2-methylvinyl, R3=R4=R5=H, R14=Ethyl] Cpd 221

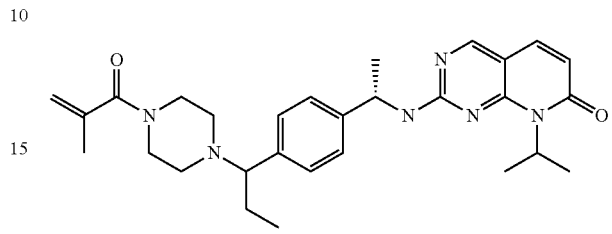

$^1$H NMR (500 MHz, DMSO-$d_6$) δ 8.56 (s, 1H), 8.12-8.39 (m, 1H), 7.63 (d, J=9.15 Hz, 1H), 7.23-7.42 (m, 2H), 7.09-7.18 (m, 2H), 6.15 (d, J=9.15 Hz, 1H), 5.21-5.56 (m, 1H), 5.07-5.17 (m, 1H), 4.92-5.04 (m, 1H), 4.74-4.89 (m, 1H), 3.36-3.48 (m, 4H), 3.18-3.28 (m, 1H), 2.14-2.35 (m, 4H), 1.81-1.91 (m, 1H), 1.71-1.81 (m, 3H), 1.58-1.69 (m, 1H), 1.21-1.56 (m, 9H), 0.61-0.74 (m, 3H). LCMS: m/z 503 [M+H]$^+$ r.t. 7.49 min. HRMS (ESI) calcd for $C_{29}H_{39}N_6O_2$ [M+H]$^+$ 503.3129 found 503.3141;

2-({(1S)-1-[4-(1-{4-[(2E)-but-2-enoyl]piperazin-1-yl}propyl)phenyl]ethyl}amino)-8-(propan-2-yl)pyrido[2,3-d]pyrimidin-7(8H)-one [(I), X=N, R2=propan-2-yl, A=phenyl, R1a=H, R1b=Me, R6a=4-CH(R14)NR7R8, R6b=H, R7-R8=4-piperazin-1-yl, R11=(2E)-propen-2-yl, R3=R4=R5=H, R14=Ethyl] Cpd 222

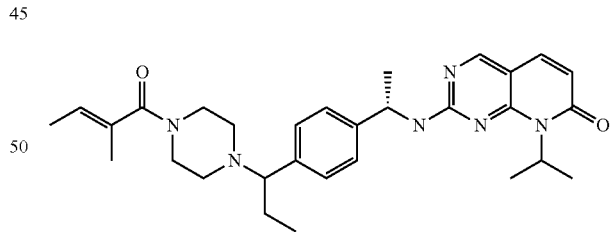

$^1$H NMR (500 MHz, DMSO-$d_6$) δ 8.56 (s, 1H), 8.13-8.38 (m, 1H), 7.62 (d, J=9.15 Hz, 1H), 7.27-7.37 (m, 2H), 7.09-7.18 (m, 2H), 6.51-6.66 (m, 1H), 6.32-6.47 (m, 1H), 6.15 (d, J=9.15 Hz, 1H), 5.36-5.76 (m, 1H), 4.89-5.32 (m, 1H), 3.38-3.58 (m, 4H), 3.16-3.29 (m, 1H), 2.21 (br. s., 4H), 1.81-1.91 (m, 1H), 1.73-1.80 (m, 3H), 1.60-1.71 (m, 1H), 1.25-1.57 (m, 9H), 0.62-0.77 (m, 3H). LCMS: m/z 503 [M+H]$^+$ r.t. 7.45 min. HRMS (ESI) calcd for $C_{29}H_{39}N_6O_2$ [M+H]$^+$ 503.3129 found 503.3132;

2-{[(1S)-1-{4-[(1S)-1-(4-acryloylpiperazin-1-yl)
propyl]phenyl}ethyl]amino}-8-(propan-2-yl)pyrido
[2,3-d]pyrimidin-7(8H)-one [(I), X=N, R2=propan-
2-yl, A=phenyl, R1a=H, R1b=Me, R6a=4-CH(R14)
NR7R8, R6b=H, R7-R8=4-piperazin-1-yl,
R11=vinyl, R3=R4=R5=H, R14=Ethyl] Cpd 227

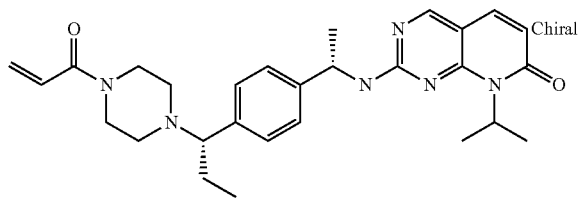 [SMILES: C=CC(=O)N1CCN([C@@H](CC)c2ccc([C@H](C)Nc3ncc4ccc(=O)n(C(C)C)c4n3)cc2)CC1]

$^1$H NMR (500 MHz, DMSO-d$_6$) δ 8.48-8.59 (m, 1H), 8.35 (d, J=6.56 Hz, 1H), 7.62 (d, J=9.30 Hz, 1H), 7.25-7.38 (m, 2H), 7.13 (d, J=7.78 Hz, 2H), 6.69 (dd, J=10.22, 16.62 Hz, 1H), 6.15 (d, J=9.30 Hz, 1H), 5.94-6.09 (m, 1H), 5.59 (d, J=10.22 Hz, 1H), 5.39-5.52 (br., s. 1H), 4.95-5.03 (m, 1H), 3.40-3.57 (m, 4H), 3.17-3.28 (m, 1H), 2.16-2.32 (m, 4H), 1.80-1.91 (m, 1H), 1.58-1.74 (m, 1H), 1.47 (d, J=7.02 Hz, 3H), 1.20-1.43 (m, 6H), 0.62-0.75 (m, 3H). LCMS: m/z 489 [M+H]$^+$ r.t. 7.12 min. HRMS (ESI) calcd for C$_{28}$H$_{37}$N$_6$O$_2$ [M+H]$^+$ 489.2973 found 489.2982;

2-{[(1S)-1-{4-[(1R)-1-(4-acryloylpiperazin-1-yl)
propyl]phenyl}ethyl]amino}-8-(propan-2-yl)pyrido
[2,3-d]pyrimidin-7(8H)-one [(I), X=N, R2=propan-
2-yl, A=phenyl, R1a=H, R1b=Me, R6a=4-CH(R14)
NR7R8, R6b=H, R7-R8=4-piperazin-1-yl,
R11=vinyl, R3=R4=R5=H, R14=Ethyl] Cpd 228

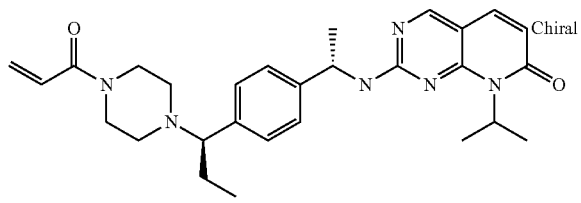 [SMILES: C=CC(=O)N1CCN([C@H](CC)c2ccc([C@H](C)Nc3ncc4ccc(=O)n(C(C)C)c4n3)cc2)CC1]

$^1$H NMR (500 MHz, DMSO-d$_6$) δ 8.56 (s, 1H), 8.11-8.38 (m, 1H), 7.62 (d, J=9.30 Hz, 1H), 7.25-7.37 (m, 2H), 7.13 (d, J=7.93 Hz, 2H), 6.69 (dd, J=10.37, 16.47 Hz, 1H), 6.15 (d, J=9.30 Hz, 1H), 6.01 (dd, J=1.98, 16.47 Hz, 1H), 5.55-5.66 (m, 1H), 5.39-5.52 (br., s. 1H), 4.87-5.32 (m, 1H), 3.39-3.52 (m, 4H), 3.25 (dd, J=6.25, 7.93 Hz, 1H), 2.23 (br. s., 4H), 1.60-1.91 (m, 2H), 1.47 (d, J=7.02 Hz, 3H), 1.20-1.43 (m, 6H), 0.62-0.75 (m, 3H). LCMS: m/z 489 [M+H]$^+$ r.t. 7.12 min. HRMS (ESI) calcd for C$_{28}$H$_{37}$N$_6$O$_2$ [M+H]$^+$ 489.2973 found 489.2975;

2-{[(1R)-1-{4-[(1R)-1-(4-acryloylpiperazin-1-yl)
propyl]phenyl}ethyl]amino}-8-(propan-2-yl)pyrido
[2,3-d]pyrimidin-7(8H)-one [(I), X=N, R2=propan-
2-yl, A=phenyl, R1a=H, R1b=Me, R6a=4-CH(R14)
NR7R8, R6b=H, R7-R8=4-piperazin-1-yl,
R11=vinyl, R3=R4=R5=H, R14=Ethyl] Cpd 229

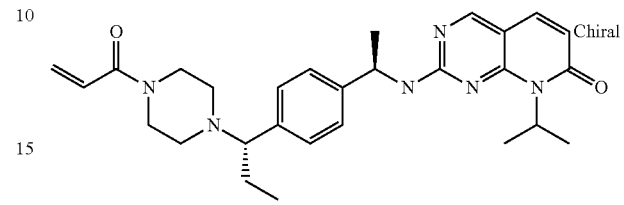

$^1$H NMR (500 MHz, DMSO-d$_6$) δ 8.56 (s, 1H), 8.35 (d, J=6.41 Hz, 1H), 7.62 (d, J=9.30 Hz, 1H), 7.25-7.38 (m, 2H), 7.10-7.19 (m, 2H), 6.69 (dd, J=10.37, 16.62 Hz, 1H), 6.15 (d, J=9.46 Hz, 1H), 5.97-6.08 (m, 1H), 5.59 (d, J=12.51 Hz, 1H), 5.42-5.52 (br., s. 1H), 4.90-5.06 (m, 1H), 3.41-3.56 (m, 4H), 3.20-3.29 (m, 1H), 2.14-2.34 (m, 4H), 1.80-1.92 (m, 1H), 1.59-1.72 (m, 1H), 1.47 (d, J=7.02 Hz, 3H), 1.20-1.43 (m, 6H), 0.63-0.75 (m, 6H).

LCMS: m/z 489 [M+H]$^+$ r.t. 6.74 min. HRMS (ESI) calcd for C$_{28}$H$_{37}$N$_6$O$_2$ [M+H]$^+$ 489.2973 found 489.2978;

2-{[(1S)-1-{4-[(1S)-1-(4-acryloylpiperazin-1-yl)-2-
cyclopropylethyl]phenyl}ethyl]amino}-8-(propan-2-
yl) pyrido [2,3-d]pyrimidin-7(8H)-one [(I), X=N,
R2=propan-2-yl, A=phenyl, R1a=H, R1b=Me,
R6a=4-CH(R14)NR7R8, R6b=H, R7-R8=4-piper-
azin-1-yl, R11=vinyl, R3=R4=R5=H,
R14=cyclopropylmethyl] cpd 230

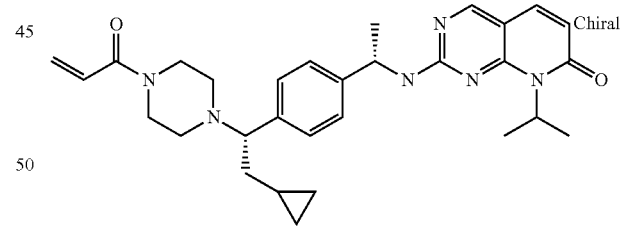

$^1$H NMR (500 MHz, DMSO-d$_6$) δ 8.56 (s, 1H), 8.35 (d, J=6.86 Hz, 1H), 7.62 (d, J=9.30 Hz, 1H), 7.28-7.39 (m, 2H), 7.17 (d, J=7.93 Hz, 2H), 6.68 (dd, J=10.52, 16.70 Hz, 1H), 6.15 (d, J=9.30 Hz, 1H), 6.01 (dd, J=2.06, 16.70 Hz, 1H), 5.59 (dd, J=1.98, 10.68 Hz, 1H), 5.37-5.49 (br., 1H), 4.98 (t, J=6.56 Hz, 1H), 3.38-3.56 (m, 5H), 2.23 (br. s., 4H), 1.54-1.82 (m, 2H), 1.47 (m, 10H), 0.25-0.37 (m, 2H), −0.09-0.02 (m, 2H). LCMS: m/z 515 [M+H]$^+$ r.t. 7.97 min. HRMS (ESI) calcd for C$_{30}$H$_{39}$N$_6$O$_2$ [M+H]$^+$ 515.3129 found 515.314;

2-{[(1S)-1-{4-[(1R)-1-(4-acryloylpiperazin-1-yl)-2-cyclopropylethyl]phenyl}ethyl]amino}-8-(propan-2-yl) pyrido [2,3-d]pyrimidin-7(8H)-one [(I), X=N, R2=propan-2-yl, A=phenyl, R1a=H, R1b=Me, R6a=4-CH(R14)NR7R8, R6b=H, R7-R8=4-piperazin-1-yl, R11=vinyl, R3=R4=R5=H, R14=cyclopropylmethyl] cpd 231 J

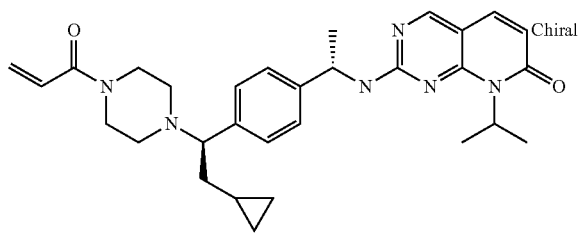 [SMILES: C=CC(=O)N1CCN([C@H](CC2CC2)c2ccc([C@H](C)Nc3ncc4ccc(=O)n(C(C)C)c4n3)cc2)CC1]

$^1$H NMR (500 MHz, DMSO-d$_6$) δ 8.56 (s, 1H), 8.12-8.37 (m, 1H), 7.62 (d, J=9.30 Hz, 1H), 7.27-7.40 (m, 2H), 7.11-7.23 (m, 2H), 6.68 (dd, J=10.37, 16.47 Hz, 1H), 6.15 (d, J=9.00 Hz, 1H), 6.00 (d, J=16.47 Hz, 1H), 5.59 (d, J=10.37 Hz, 1H), 5.39-5.51 (m, 1H), 4.93-5.30 (m, 1H), 3.39-3.53 (m, 5H), 2.23 (br. s., 4H), 1.53-1.81 (m, 3H), 0.95-1.50 (m, 9H), 0.24-0.45 (m, 3H), −0.12-0.05 (m, 2H). LCMS: m/z 515 [M+H]$^+$ r.t. 7.65 min. HRMS (ESI) calcd for C$_{30}$H$_{39}$N$_6$O$_2$ [M+H]$^+$ 515.3129 found 515.3135;

2-{[(1S)-1-{4-[1-(4-propanoylpiperazin-1-yl)propyl]phenyl}ethyl]amino}-8-(propan-2-yl)pyrido[2,3-d]pyrimidin-7(8H)-one [(I), X=N, R2=propan-2-yl, A=phenyl, R1a=H, R1b=Me, R6a=4-CH(R14)NR7R8, R6b=H, R7-R8=4-piperazin-1-yl, R11=Ethyl, R3=R4=R5=H, R14=Ethyl] Cpd 240

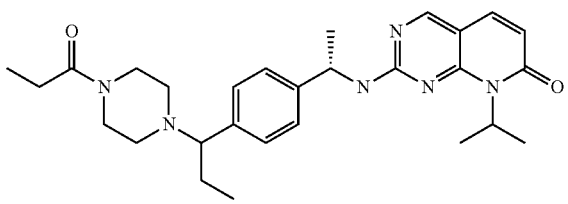 [SMILES: CCC(=O)N1CCN(C(CC)c2ccc([C@H](C)Nc3ncc4ccc(=O)n(C(C)C)c4n3)cc2)CC1]

$^1$H NMR (500 MHz, DMSO-d$_6$) δ 8.56 (s, 1H), 8.35 (br. s., 1H), 7.62 (d, J=9.15 Hz, 1H), 7.30 (d, J=7.78 Hz, 2H), 7.13 (d, J=7.78 Hz, 2H), 6.15 (d, J=9.30 Hz, 1H), 5.39-5.72 (m, 1H), 4.99 (br. s., 1H), 3.34 (br.s., 4H), 3.18-3.26 (m, 1H), 2.11-2.31 (m, 6H), 1.77-1.93 (m, 1H), 1.65 (dd, J=7.70, 13.50 Hz, 1H), 1.00-1.56 (m, 9H), 0.89 (dt, J=2.14, 7.40 Hz, 3H), 0.59-0.73 (m, 3H). LCMS: m/z 491 [M+H]$^+$ r.t. 5.64 min. HRMS (ESI) calcd for C$_{23}$H$_{39}$N$_6$O$_2$ [M+H]$^+$ 491.3129 found 491.313; 1-acryloyl-4-{4-[(1S)-1-{[7-oxo-8-(propan-2-yl)-7,8-dihydropyrido[2,3-d]pyrimidin-2-yl]amino}ethyl]phenyl}piperidine-4-carbonitrile [(I), X=N, R2=propan-2-yl, A=phenyl, R1a=H, R1b=Me, R6a=piperidine-4-carbonitrile, R6b=H, R11=vinyl, R3=R4=R5=H] Cpd 241

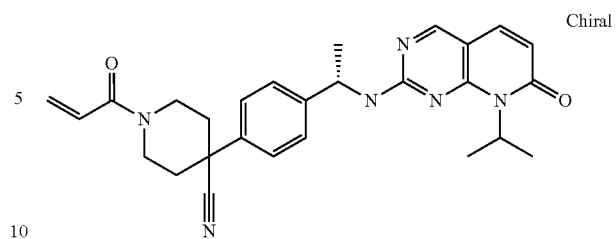

$^1$H NMR (500 MHz, DMSO-d$_6$) δ 8.50-8.58 (m, 1H), 8.19-8.43 (m, 1H), 7.62 (d, J=9.30 Hz, 1H), 7.37-7.53 (m, 4H), 6.83 (dd, J=10.52, 16.62 Hz, 1H), 6.05-6.18 (m, 2H), 5.66-5.73 (m, 1H), 5.39-5.57 (m, 1H), 4.94-5.30 (m, 1H), 4.61 (d, J=12.22 Hz, 1H), 4.24 (d, J=12.20 Hz, 1H), 3.31 (m, 1H), 2.88 (t, J=12.89 Hz, 1H), 2.05-2.22 (m, 2H), 1.80-2.02 (m, 2H), 1.12-1.62 (m, 9H). LCMS: m/z 471 [M+H]$^+$ r.t. 10.25 min. HRMS (ESI) calcd for C$_{28}$H$_{31}$N$_6$O$_2$ [M+H]$^+$ 471.2503 found 471.25;

2-{[(1S)-1-(4-{(1S)-1-[4-(3-chloropropanoyl)piperazin-1-yl]-2-cyclopropylethyl}phenyl)ethyl]amino}-8-(propan-2-yl)pyrido[2,3-d]pyrimidin-7(8H)-one [(I), X=N, R2=propan-2-yl, A=phenyl, R1a=H, R1b=Me, R6a=4-CH(R14)NR7R8, R6b=H, R7-R8=4-piperazin-1-yl, R11=2-chloroethyl, R3=R4=R5=H, R14=cyclopropylmethyl] Cpd 242

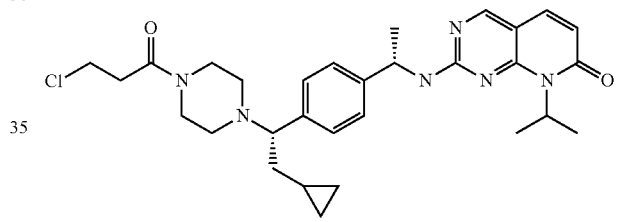

$^1$H NMR (500 MHz, DMSO-d$_6$) 8.56 (s, 1H), 8.35 (d, J=6.86 Hz, 1H), 7.62 (d, J=9.30 Hz, 1H), 7.28-7.39 (m, 2H), 7.18 (d, J=8.08 Hz, 2H), 6.15 (d, J=9.00 Hz, 1H), 5.40-5.55 (br.s., 1H), 4.91-5.02 (m, 1H), 3.70 (t, J=6.5 Hz, 2H), 3.35-3.45 (m, 5H), 2.71 (t, J=6.5 Hz, 2H), 2.14-2.33 (m, 4H), 1.69-1.81 (m, 1H), 1.21-1.57 (m, 10H), 0.24-0.37 (m, 3H), −0.11-0.02 (m, 2H). LCMS: m/z 551 [M+H]$^+$ r.t. 7.8 min. HRMS (ESI) calcd for C$_{30}$H$_{40}$ClN$_6$O$_2$[M+H]$^+$ 551.2896 found 551.2897;

2-{[(1S)-1-(4-{(1R)-1-[4-(3-hydroxypropanoyl)piperazin-1-yl]propyl}phenyl)ethyl]amino}-8-(propan-2-yl)pyrido 2,3-d]pyrimidin-7(8H)-one [(I), X=N, R2=propan-2-yl, A=phenyl, R1a=H, R1b=Me, R6a=4-CH(R14)NR7R8, R6b=H, R7-R8=4-piperazin-1-yl, R11=2-hydroxyethyl, R3=R4=R5=H, R14=ethyl] Cpd 243

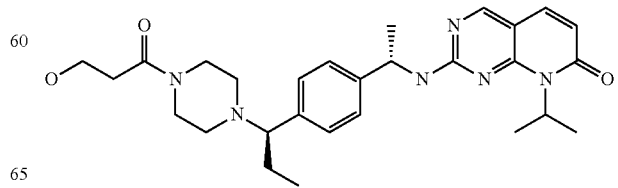

¹H NMR (500 MHz, DMSO-d₆) 8.56 (s, 1H), 8.12-8.39 (m, 1H), 7.62 (d, J=9.15 Hz, 1H), 7.28-7.38 (m, 2H), 7.08-7.17 (m, 2H), 6.15 (d, J=9.00 Hz, 1H), 5.39-5.77 (m, 1H), 4.92-5.32 (m, 1H), 3.88-4.01 (m, 2H), 3.17-3.30 (m, 5H), 2.09-2.32 (m, 6H), 1.59-1.90 (m, 3H), 1.48 (d, J=6.86 Hz, 3H), 1.03-1.14 (m, 6H), 0.62-0.75 (m, 3H).

LCMS: m/z 507 [M+H]⁺ r.t. 7.43 min. HRMS (ESI) calcd for C₂₈H₃₉N₆O₃ [M+H]⁺ 507.3078 found 507.3083;

Example 16

4-(4-{(S)-1-[8-(2,2-Dimethyl-propyl)-7-oxo-7,8-dihydro-pyrido[2,3-d]pyrimidin-2-ylamino]-ethyl}-phenoxy)-piperidine-1-carboxylic acid tert-butyl ester [(I), X=N, R2=2,2-dimethyl-propyl, A=phenyl, R1a=H, R1b=Me, R6a=—O—R7, R6b=H, R7=4-pipedine-1-carboxylic acid tert-butyl ester, R3=R4=R5=H] conv. 13, cpd 154

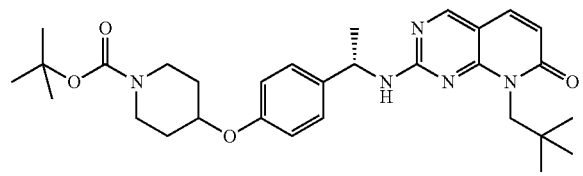 [SMILES: C[C@H](Nc1ncc2ccc(=O)n(CC(C)(C)C)c2n1)c1ccc(OC2CCN(C(=O)OC(C)(C)C)CC2)cc1]

8-(2,2-Dimethyl-propyl)-2-[(S)-1-(4-hydroxy-phenyl)-ethylamino]-8H-pyrido[2,3-d]pyrimidin-7-one (20.0 mg, 0.057 mmol) was dissolved in DMF (2.0 mL) to which cesium carbonate (37.0 mg, 0.113 mmol) and 4-hydroxy-piperidine-1-carboxylic acid tert-butyl ester (19.0 mg, 0.068 mmol) was added and stirred for 5 hours at 100° C. The cesium carbonate was filtered off and the solution was diluted with AcOEt and washed with water (3×10 mL), and then dried over Na₂SO₄. The crude material was purified through silica gel column chromatography (AcOEt) to give the title product (11.5 mg, 38% yield). ¹H NMR (500 MHz, DMSO-d₆) δ=8.56 (s, 1H), 8.31 (d, J=7.5 Hz, 1H), 7.67 (d, J=9.3 Hz, 1H), 7.28 (d, J=8.7 Hz, 2H), 6.90 (d, J=8.5 Hz, 2H), 6.22 (d, J=9.3 Hz, 1H), 5.04 (quin, J=7.1 Hz, 1H), 4.48 (tt, J=7.8, 3.7 Hz, 1H), 3.93-4.31 (m, 2H), 3.53-3.69 (m, 2H), 3.15 (br. s., 2H), 1.78-1.91 (m, 2H), 1.43-1.53 (m, 2H), 1.43 (d, J=6.9 Hz, 3H), 1.39 (s, 9H), 0.79 (br. s., 9H). LCMS: m/z 536 [M+H]⁺@ r.t. 7.78 min. HRMS (ESI) calcd for C₃₀H₄₂N₅O₄ [M+H]⁺ 536.3232 found 536.3243.

Example 17

8-((S)-1,2-Dimethyl-propyl)-2-{(S)-1-[4-(piperidin-4-yloxy)-phenyl]-ethylamino}-8H-pyrido[2,3-d]pyrimidin-7-one [(I), X=N, R2=(S)-1,2-Dimethyl-propyl, A=phenyl, R1a=H, R1b=Me, R6a=—O—R7, R6b=H, R7-R8=4-piperazin-1-yl, R3=R4=R5=H] conv. 14, cpd 155

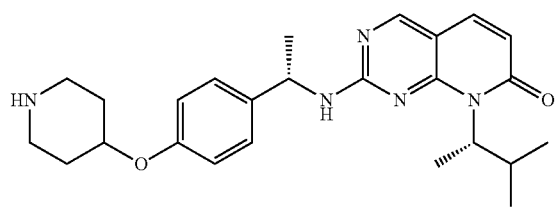 [SMILES: CC(C)[C@H](C)n1c(=O)ccc2cnc(N[C@@H](C)c3ccc(OC4CCNCC4)cc3)nc21]

To a stirred solution of 4-(4-{(S)-1-[8-((S)-1,2-Dimethyl-propyl)-7-oxo-7,8-dihydro-pyrido[2,3-d]pyrimidin-2-ylamino]-ethyl}-phenoxy)-piperidine-1-carboxylic acid benzyl ester (40.0 mg, 0.070 mmol) in absolute ethanol (1.0 mL) was added, under nitrogen atmosphere, 10% Pd/C (1:1 catalyst/substrate by weight) followed by cyclohexadiene (0.066 mL, 0.702 mmol). The suspension was stirred at 60° C. for 1 hour. The catalyst was removed by filtration through a pad of celite and the filtrate was evaporated to dryness under vacuum to give the title product (22.2 mg, 73% yield).

¹H NMR (500 MHz, DMSO-d₆) δ=8.55 (d, J=14.9 Hz, 1H), 8.27 (d, J=6.9 Hz, 1H), 7.64 (d, J=9.2 Hz, 1H), 7.12-7.33 (m, 2H), 6.86 (d, J=8.2 Hz, 2H), 6.21 (d, J=9.3 Hz, 1H), 4.18-5.34 (m, 3H), 2.03-3.01 (m, 4H), 1.13-1.95 (m, 7H), 0.09-1.12 (m, 9H). LCMS: m/z 436 [M+H]⁺@ r.t. 5.17 min HRMS (ESI) calcd for C₂₅H₃₄₃N₅O₂ [M+H]⁺ 436.2707 found 436.2719.

Example 18

2-{(S)-1-[4-(1-Acryloyl-piperidin-4-yloxy)-phenyl]-ethylamino}-8-(2,2-dimethyl-propyl)-8H-pyrido[2,3-d]pyrimidin-7-one [(I), X=N, R2=2,2-dimethyl-propyl, A=phenyl, R1a=H, R1b=Me, R6a=O—R7, R6b=H, R7=4-piperidin-4-yl, R11=vinyl, R3=R4=R5=H] conv. 15, cpd 156

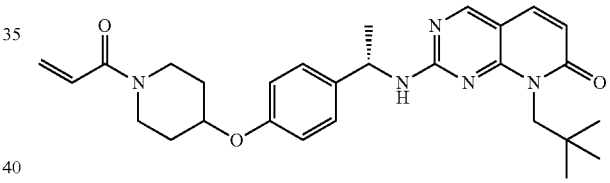

To a solution of 8-((S)-1,2-Dimethyl-propyl)-2-{(S)-1-[4-(piperidin-4-yloxy)-phenyl]-ethylamino}-8H-pyrido[2,3-d]pyrimidin-7-one hydrochloride (50.0 mg, 0.11 mmol) and DIPEA (0.04 mL, 0.22 mmol) in CH₂Cl₂ (1.0 mL) is added acryloyl chloride (8 μL, 0.12 mmol) at 0° C. After 30 minutes, the reaction is quenched with water. The mixture is extracted with DCM, dried over Na₂SO₄, filtered, and concentrated to yield a yellow oil. The crude product is purified by silica gel chromatography (1 to 10% MeOH/DCM) to give the title product as a white foam (32 mg, 60% yield).

¹H NMR (500 MHz, DMSO-d₆) δ=8.56 (s, 1H), 8.32 (d, J=7.6 Hz, 1H), 7.67 (d, J=9.2 Hz, 1H), 7.29 (d, J=8.5 Hz, 2H), 6.92 (d, J=8.4 Hz, 2H), 6.81 (dd, J=16.7, 10.4 Hz, 1H), 6.22 (d, J=9.3 Hz, 1H), 6.08 (dd, J=16.6, 2.4 Hz, 1H), 5.66 (dd, J=10.4, 2.3 Hz, 1H), 5.04 (quin, J=7.1 Hz, 1H), 4.56 (tt, J=7.6, 3.8 Hz, 1H), 4.02-4.20 (m, 2H), 3.76-3.90 (m, 2H), 3.28-3.37 (m, 2H), 1.90 (br. s., 2H), 1.53 (br. s., 2H), 1.44 (d, J=7.0 Hz, 3H), 0.79 (br. s., 9H).

LCMS: m/z 490 [M+H]⁺@ r.t. 6.31 min. HRMS (ESI) calcd for C₂₈H₃₆N₅O₃ [M+H]⁺ 490.2813 found 490.2813.

According to the same method, the following compounds were prepared:

2-{(S)-1-[4-(1-Acryloyl-piperidin-4-yloxy)-phenyl]-ethylamino}-8-((S)-1,2-dimethyl-propyl)-8H-pyrido[2,3-d]pyrimidin-7-one [(I), X=N, R2=—(S)-1,2-Dimethyl-propyl, A=phenyl, R1a=H, R1b=Me, R6a=O—R7, R6b=H, R7-=4-piperidin-4-yl, R11=vinyl, R3=R4=R5=H] cpd 159

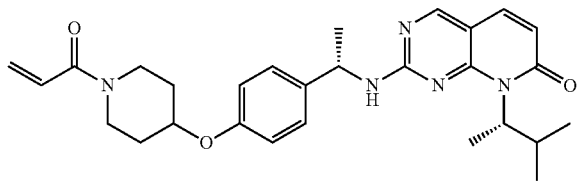 [SMILES: C=CC(=O)N1CCC(Oc2ccc([C@H](C)Nc3ncc4ccc(=O)n([C@@H](C)C(C)C)c4n3)cc2)CC1]

¹H NMR (500 MHz, DMSO-d₆) δ=8.50-8.60 (m, 1H), 7.64 (d, J=9.3 Hz, 1H), 7.15-7.30 (m, 2H), 6.91 (d, J=8.5 Hz, 2H), 6.81 (dd, J=16.7, 10.4 Hz, 1H), 6.10-6.22 (m, 1H), 6.08 (dd, J=10.4, 2.4 Hz, 1H), 5.66 (dd, J=10.4, 2.4 Hz, 1H), 4.77-5.20 (m, 2H), 4.56 (tt, J=7.3, 3.6 Hz, 1H), 3.35-3.80 (m, 4H), 1.02-2.11 (m, 8H), 0.10-0.89 (m, 9H). LCMS: m/z 490 [M+H]⁺@ r.t. 6.20 min. HRMS (ESI) calcd for C₂₈H₃₆N₅O₃ [M+H]⁺ 490.2813 found 490.2813;

8-((S)-1,2-Dimethyl-propyl)-2-{(S)-1-[4-(1-isobutyryl-piperidin-4-yloxy)-phenyl]-ethylamino}-8H-pyrido[2,3-d]pyrimidin-7-one [(I), X=N, R2=—(S)-1,2-Dimethyl-propyl, A=phenyl, R1a=H, R1b=Me, R6a=O—R7, R6b=H, R7-=4-piperidin-4-yl, R11=i-propyl, R3=R4=R5=H] cpd 160

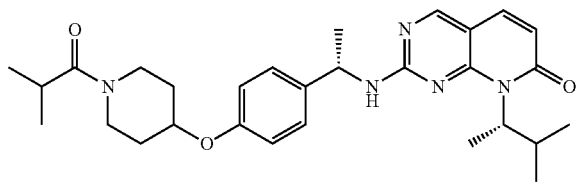

¹H NMR (500 MHz, DMSO-d₆) δ=8.54-8.57 (m, 1H), 7.64 (d, J=9.3 Hz, 1H), 7.19-7.26 (m, 2H), 6.90 (d, J=8.4 Hz, 2H), 6.11-6.22 (m, 1H), 4.82-5.31 (m, 2H), 4.44-4.63 (m, 1H), 3.19-3.72 (m, 4H), 2.87 (dt, J=13.4, 6.7 Hz, 1H), 1.11-2.12 (m, 5H), 0.13-1.07 (m, 12H). LCMS: m/z 506 [M+H]⁺@ r.t. 6.60 min HRMS (ESI) calcd for C₂₉H₄₀N₅O₃ [M+H]⁺ 506.3126 found 506.3130.

2-{[(1S)-1-(4-{[(3R)-1-acryloylpyrrolidin-3-yl]oxy}phenyl)ethyl]amino}-8-ethylpyrido[2,3-d]pyrimidin-7(8H)-one [(I), X=N, R2=Ethyl, A=phenyl, R1a=H, R1b=Me, R6a=O—R7, R6b=H, R7-=pyrrolidin-3-yl, R11=vinyl, R3=R4=R5=H] cpd 223

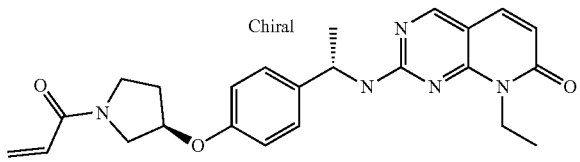

¹H NMR (500 MHz, DMSO-d₆) δ 8.57 (s, 1H), 8.14-8.44 (m, 1H), 7.67 (d, J=9.15 Hz, 1H), 7.32 (d, J=7.78 Hz, 2H), 6.88 (dd, J=3.36, 8.69 Hz, 2H), 6.46-6.68 (m, 1H), 6.21 (d, J=9.15 Hz, 1H), 6.07-6.15 (m, 1H), 5.58-5.71 (m, 1H), 4.88-5.27 (m, 2H), 4.03-4.30 (m, 2H), 3.37-3.89 (m, 4H), 1.98-2.22 (m, 2H), 1.45 (d, J=7.02 Hz, 3H), 0.94-1.19 (m, 3H). LCMS: m/z 434 [M+H]⁺@ r.t. 5.13 min HRMS (ESI) calcd for C₂₄H₂₇N₅O₃ [M+H]⁺ 434.2187 found 434.2191.

2-{[(1S)-1-(4-{[(3R)-1-acryloylpyrrolidin-3-yl]oxy}phenyl)ethyl]amino}-8-ethylpyrido[2,3-d]pyrimidin-7(8H)-one [(I), X=N, R2=Ethyl, A=phenyl, R1a=H, R1b=Me, R6a=O—R7, R6b=H, R7-=pyrrolidin-3-yl, R11=vinyl, R3=R4=R5=H] cpd 224

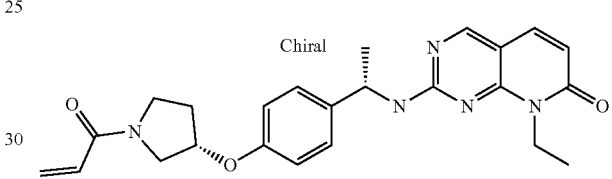

¹H NMR (500 MHz, DMSO-d₆) δ 8.56 (s, 1H), 8.38 (d, J=7.17 Hz, 1H), 7.67 (d, J=9.30 Hz, 1H), 7.32 (dd, J=1.98, 8.69 Hz, 2H), 6.80-6.93 (m, 2H), 6.47-6.66 (m, 1H), 6.19-6.25 (m, 1H), 6.07-6.17 (m, 1H), 5.59-5.71 (m, 1H), 4.89-5.28 (m, 2H), 4.03-4.33 (m, 2H), 3.45-3.90 (m, 4H), 2.00-2.25 (m, 2H), 1.45 (d, J=7.02 Hz, 3H), 0.87-1.08 (m, 3H). LCMS: m/z 434 [M+H]⁺@ r.t. 5.12 min HRMS (ESI) calcd for C₂₄H₂₇N₅O₃ [M+H]⁺ 434.2187 found 434.2191.

Example 19

2-{[(1S)-1-{4-[(1S)-1-(piperazin-1-yl)propyl]phenyl}ethyl]amino}-8-(propan-2-yl)pyrido[2,3-d]pyrimidin-7(8H)-one [(I), X=N, R2=propan-2-yl, A=phenyl, R1a=H, R1b=Me, R6a=4-CHR14NR7R8, R6b=H, R7-R8=4-piperazin-1-yl, R14=Ethyl, R3=R4=R5=H] conv. 6

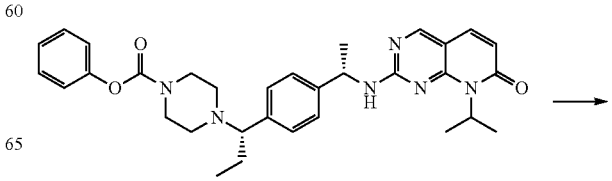

201
-continued

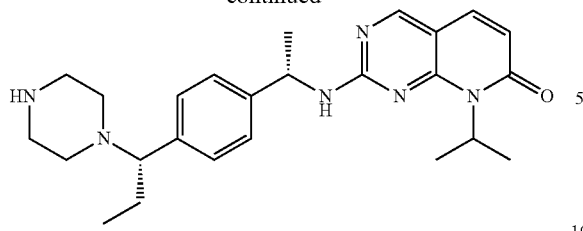

5

To a solution of Phenyl 4-[(1S)-1-{4-[(1S)-1-{[7-oxo-8-(propan-2-yl)-7,8-dihydropyrido[2,3-d]pyrimidin-2-yl]amino}ethyl]phenyl} propyl]piperazine-1-carboxylate (cpd 225) (155.0 mg, 0.279 mmol) in a mixture of i-propanol (4.0 mL) is added NaOH (1.0 mL, 12.5 mmol). The mixture is stirred 8 hours at 80 and then concentrated to dryness. The crude is dissolved in DCM and water, the organic phase is separated and washed with brine, died (Na$_2$SO$_4$) and volatiles removed in vacuo to provide the title compound as light yellow oil to give (140.0 mg, quantitative).

LCMS (HPLC Method 1): m/z 435 [M+H]$^+$@ r.t. 4.12 min. HRMS (ESI) calcd for C$_{25}$H$_{35}$N$_6$O [M+H]$^+$ 435. 5770 found 435.5765.

The following compound is prepared essentially by the method of Example 19

202

2-{[(1S)-1-{4-[(1R)-1-(piperazin-1-yl)propyl]phenyl}ethyl]amino}-8-(propan-2-yl)pyrido[2,3-d]pyrimidin-7(8H)-one [(I), X=N, R2=propan-2-yl, A=phenyl, R1a=H, R1b=Me, R6a=4-CHR14NR7R8, R6b=H, R7-R8=4-piperazin-1-yl, R14 Ethyl, R3 R4=R5=H] conv. 6

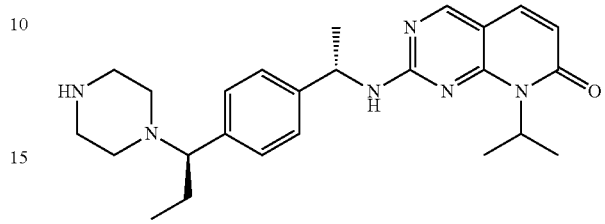

LCMS (HPLC Method 1): m/z 435 [M+H]$^+$@ r.t. 4.12 min. HRMS (ESI) calcd for C$_{25}$H$_{35}$N$_6$O [M+H]$^+$ 435. 5770 found 435.5771.

Example 20

2-{[(1S)-1-{4-[(4-acryloylpiperazin-1-yl)methyl]phenyl}ethyl]amino}-8-(4-ethynyl-2-fluorobenzyl)pyrido[2,3-d]pyrimidin-7(8H)-one [(I), X=N, R2=4-ethynyl-2-fluorobenzyl, A=phenyl, R1a=H, R1b=Me, R6a=O—R7, R6b=H, R6a=4-(4-acryloylpiperazin-1-yl)methyl, R6b=H, R3=R4=R5=H] conv. 16, Cpd 217

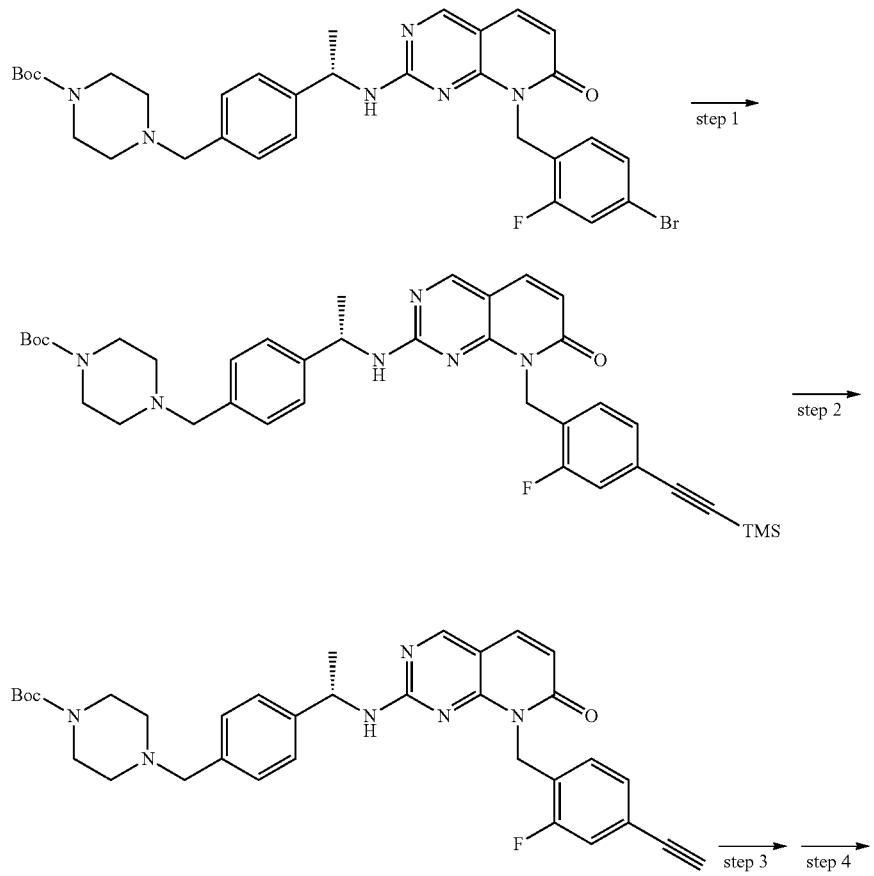

-continued

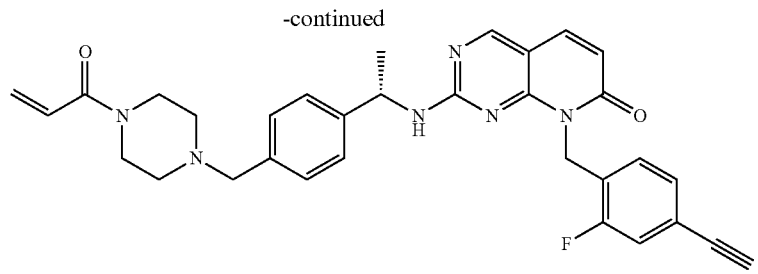

Step 1 conv. 16, Nitrogen is bubbled through a solution of tert-butyl 4-{4-[(1S)-1-{[8-(4-bromo-2-fluorobenzyl)-7-oxo-7,8-dihydropyrido[2,3-d]pyrimidin-2-yl]amino}ethyl]benzyl}piperazine-1-carboxylate (130 mg, 0.2 mmol), and TEA (195 uL, 1.4 mmol) in DMF (2.8 mL) for 30 minutes. Bis(triphenylphosphine)palladium(II) dichloride (28 mg 0.04 mmol, 20% mol) and CuI (8 mg 0.04 mmol, 20% mol) are added and degassing is continued for additional 5 minutes. Trimethylsilylacetylene (166 uL, 1.2 mmol) is added while degassing for 10 additional seconds. The reaction is heated to 70° C. for 2.5 hours, and then the heat is removed. The mixture is diluted with water and extracted with EtOAc and washed with brine, dried ($Na_2SO_4$) filtered, and concentrated to give the crude product that is purified by RP-HPLC eluting with a gradient of $H_2O$/ACN 7/3 to 0/10 to obtain 93 mg of tert-butyl 4-(4-{(1S)-1-[(8-{2-fluoro-4-[(trimethylsilyl)ethynyl]benzyl}-7-oxo-7,8-dihydropyrido[2,3-d]pyrimidin-2-yl)amino]ethyl}benzyl)piperazine-1-carboxylate.

$^1$H NMR (500 MHz, DMSO-$d_6$) δ 8.63 (s, 1H), 8.46 (d, J=7.78 Hz, 1H), 7.80 (d, J=9.46 Hz, 1H), 7.36 (d, J=10.68 Hz, 1H), 7.06 (d, J=7.93 Hz, 2H), 6.99 (dd, J=0.76, 8.39 Hz, 1H), 6.97 (d, J=7.93 Hz, 2H), 6.54 (t, J=7.93 Hz, 1H), 6.30 (d, J=9.30 Hz, 1H), 5.51 (d, J=15.56 Hz, 1H), 5.25 (d, J=15.56 Hz, 1H), 4.88 (quin, J=7.21 Hz, 1H), 3.30 (br. s., 2H), 3.28 (br. s., 4H), 2.18-2.33 (m, 4H), 1.37 (s, 12H), 0.23 (s, 9H). LCMS: m/z 669 [M+H]$^+$@ r.t. 8.71 min HRMS (ESI) calcd for $C_{37}H_{46}FN_6O_3Si$ [M+H]$^+$ 669.3379 found 669.3397.

Step 2 tert-butyl 4-(4-{(1S)-1-[(8-{2-fluoro-4-[(trimethylsilyl)ethynyl]benzyl}-7-oxo-7,8-dihydropyrido[2,3-d]pyrimidin-2-yl)amino]ethyl}benzyl)piperazine-1-carboxylate (88 mg 0.131 mmol) and $K_2CO_3$ (18 mg, 0.131 mmol) and MeOH (3 ml) were placed in a flask and stirred at room temperature for 45 minutes. The mixture was diluted with EtOAc and water. The organic phases was separated and washed with brine, dried ($Na_2SO_4$). The solvent was removed in vacuo to give the desired compound tert-butyl 4-{4-[(1S)-1-{[8-(4-ethynyl-2-fluorobenzyl)-7-oxo-7,8-dihydropyrido[2,3-d]pyrimidin-2-yl]amino}ethyl]benzyl}piperazine-1-carboxylate as light yellow oil (74 mg Y=95%).

$^1$H NMR (500 MHz, DMSO-$d_6$) δ 8.63 (s, 1H), 8.45 (d, J=7.93 Hz, 1H), 7.80 (d, J=9.46 Hz, 1H), 7.38 (d, J=10.83 Hz, 1H), 7.07-7.12 (m, 2H), 7.04 (d, J=7.78 Hz, 1H), 6.97-7.03 (m, 2H), 6.61 (t, J=7.93 Hz, 1H), 6.30 (d, J=9.30 Hz, 1H), 5.48 (d, J=15.71 Hz, 1H), 5.26 (d, J=15.71 Hz, 1H), 4.90 (quin, J=7.13 Hz, 1H), 4.29 (s, 1H), 3.28 (br. s., 4H), 2.24 (br. s., 4H), 1.37 (s, 9H). LCMS: m/z 597 [M+H]$^+$@ r.t. 7.30 min HRMS (ESI) calcd for $C_{34}H_{38}FN_6O_3$[M+H]$^+$ 597.2984 found 597.3001.

Step 3 conv. 6, tert-butyl 4-{4-[(1S)-1-{[8-(4-ethynyl-2-fluorobenzyl)-7-oxo-7,8-dihydropyrido[2,3-d]pyrimidin-2-yl]amino}ethyl]benzyl}piperazine-1-carboxylate was dissolved in DCM (5 ml) in a flask and added with HCl 4 M in dioxanne (2 ml). The solution is stirred at room temperature for 1 h. The volatiles were removed in vacuo and the residue dissolved in DCM and diluted with satured solution of $NaHCO_3$ up to pH 9. The organic phase were extracted and washed with brine, dried ($Na_2SO_4$) and evaporated in vacuo. The residue contening the compound 8-(4-ethynyl-2-fluorobenzyl)-2-({(1S)-1-[4-(piperazin-1-ylmethyl)phenyl]ethyl}amino)pyrido[2,3-d]pyrimidin-7(8H)-one as light yellow oil (60 mg Y=98%).

Step 4 conv. 7, To a solution of 8-(4-ethynyl-2-fluorobenzyl)-2-({(1S)-1-[4-(piperazin-1-ylmethyl)phenyl]ethyl}amino)pyrido-[2,3-d]pyrimidin-7(8H)-one (60.0 mg, 0.12 mmol) in $CH_2Cl_2$ (1.0 mL) is added acryloyl chloride (10 μL, 0.12 mmol) at 0° C. After 30 minutes, the reaction is quenched with water. The mixture is partioned with DCM and satured solution of $NaHCO_3$, dried over $Na_2SO_4$, filtered, and concentrated to yield a yellow oil. The crude product is purified by silica gel chromatography (1 to 10% MeOH/DCM) to give the title product as a off-white foam (40 mg, 60% yield).

$^1$H NMR (500 MHz, DMSO-$d_6$) δ=8.63 (s, 1H), 8.45 (d, J=7.93 Hz, 1H), 7.80 (d, J=9.46 Hz, 1H), 7.39 (d, J=10.68 Hz, 1H), 7.07-7.15 (m, 2H), 6.99-7.07 (m, 3H), 6.76 (dd, J=10.45, 16.70 Hz, 1H), 6.61 (t, J=7.93 Hz, 1H), 6.30 (d, J=9.30 Hz, 1H), 6.08 (dd, J=2.36, 16.70 Hz, 1H), 5.66 (dd, J=2.40, 10.50 Hz, 1H), 5.49 (d, J=15.56 Hz, 1H), 5.26 (d, J=15.71 Hz, 1H), 4.90 (quin, J=7.02 Hz, 1H), 4.30 (s, 1H), 3.51 (d, J=4.12 Hz, 4H), 3.38 (br. s, 2H), 2.29 (br. s., 4H), 1.37 (d, J=7.02 Hz, 3H). LCMS: m/z 551 [M+H]$^+$@ r.t. 5.94 min HRMS (ESI) calcd for $C_{32}H_{32}FN_6O_2$[M+H]$^+$551.2526 found 551.258.

Example 21

2-[(1-{4-[1-(4-acryloylpiperazin-1-yl)-2-cyclopropylethyl]phenyl}cyclopropyl)amino]-8-(propan-2-yl)pyrido[2,3-d]pyrimidin-7(8H)-one [(I), X=N, R2=propan-2-yl, A=phenyl, R1a-R1b=cyclopropyl, R6a=4-CH(R14)NR7R8, R6b=H, R7-R8=4-piperazin-1-yl, R11=vinyl, R3=R4=R5=H, R14=cyclopropylmethyl] cpd 244

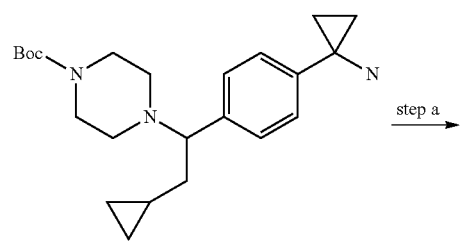

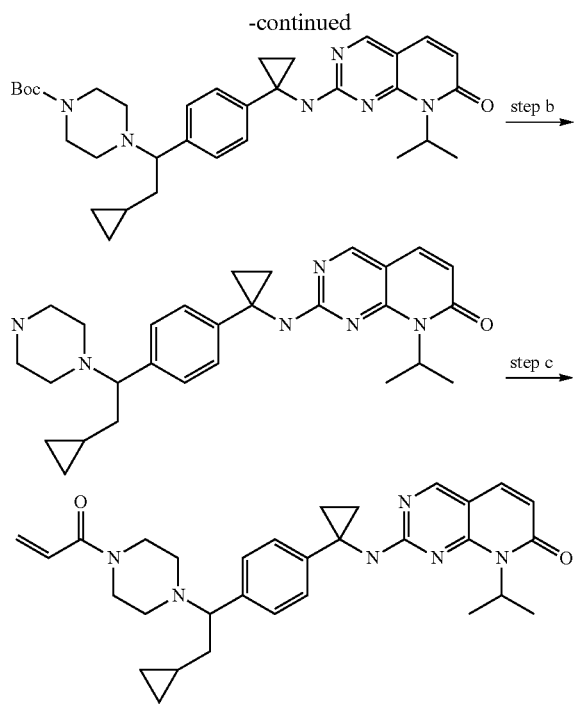

Step a. (Step 1a) tert-butyl 4-{1-[4-(1-aminocyclopropyl)phenyl]-2-cyclopropylethyl}piperazine-1-carboxylate 355 mg, 0.921 mmol, 1.1 eq.) was dissolved in DMSO (11 ml). To this solution is then sequentially added 2-(methylsulfonyl)-8-(propan-2-yl)pyrido[2,3-d]pyrimidin-7(8H)-one (223.7 mg, 0.837 mmol), CsF (140 mg, 0.920 mmol) and DIPEA (0.175 ml, 0.1 mmol). The reaction mixture is then heated at 75° C. for 4 hours and then allowed to warm to room temperature. The reaction mixture is slowly poured over cold water/brine. The precipitated solids are filtered, washed with water, and dried under vacuum. The dried solid obtained tert-butyl 4-{2-cyclopropyl-1-[4-(1-{[7-oxo-8-(propan-2-yl)-7,8-dihydropyrido[2,3-d]pyrimidin-2-yl]amino}cyclopropyl)phenyl]ethyl}piperazine-1-carboxylate (105 mg, 22%) is taken forward without further purification.

1H NMR (500 MHz, DMSO-d6) δ=8.58-8.63 (m, 2H), 7.65 (d, J=9.30 Hz, 1H), 7.00-7.14 (m, 4H), 6.20 (d, J=9.15 Hz, 1H), 5.33 (br. s., 1H), 3.38-3.42 (m, 1H), 3.21 (br. s., 4H), 2.04-2.27 (m, 4H), 1.73-1.84 (m, 1H), 0.21-0.43 (m, 4H), −0.14-0.06 (m, 2H).

Step b. conv. 6 To a solution of tert-butyl 4-{2-cyclopropyl-1-[4-(1-{[7-oxo-8-(propan-2-yl)-7,8-dihydropyrido[2,3-d]pyrimidin-2-yl]amino}cyclopropyl)phenyl]ethyl}piperazine-1-carboxylate (100 mg, 0.174 mmol) in a mixture of dioxane (4.0 mL) and MeOH (1.0 mL) is added HCl (4 M in dioxane, 1 mL). The mixture is stirred for 5 hours at room temperature. The volatiles were removed in vacuo and the residue dissolved in DCM and diluted with satured solution of NaHCO3 up to pH 9. The organic phase were extracted and washed with brine, dried (Na2SO4) and evaporated in vacuo. The residue containing the compound 2-[(1-{4-[2-cyclopropyl-1-(piperazin-1-yl)ethyl]phenyl}cyclopropyl)amino]-8-(propan-2-yl)pyrido[2,3-d]pyrimidin-7(8H)-one as a yellow viscous oil (95 mg, quantitative). LCMS (HPLC Method 1): m/z 435 [M+H]+@ r.t. 5.17 min.

Step c. conv. 7 To a solution of 2-[(1-{4-[2-cyclopropyl-1-(piperazin-1-yl)ethyl]phenyl}cyclopropyl)amino]-8-(propan-2-yl)pyrido[2,3-d]pyrimidin-7(8H)-one (95 mg, 0.174 mmol) in DCM (3.5 ml) is added acryloyl chloride (0.014 ml, 0.174 mmol, 1 eq.) at 0° C. After 10 minutes, the reaction is quenched with sat. aqueous NaHCO3 and extracted with DCM, dried over Na2SO4, filtered, and concentrated to yield a yellow oil. The crude product is purified by silica gel chromatography (1 to 5% EtOH/DCM) to give the title product as a white foam (56 mg, 61% yield).

1H NMR (500 MHz, DMSO-d6) δ=8.57-8.64 (m, 2H), 7.65 (d, J=9.30 Hz, 1H), 7.00-7.15 (m, 4H), 6.68 (dd, J=10.45, 16.70 Hz, 1H), 6.20 (d, J=9.15 Hz, 1H), 6.02 (dd, J=2.29, 16.62 Hz, 1H), 5.59 (dd, J=2.36, 10.45 Hz, 1H), 5.13-5.39 (m, 1H), 3.37-3.54 (m, 5H), 2.20 (br. s., 4H), 1.80 (br. s., 1H), 1.43-1.69 (m, 1H), 0.95-1.35 (br. m, 10 H), 0.13-0.42 (m, 3H), −0.03 (dd, J=4.96, 15.33 Hz, 2H) LCMS: m/z 527 [M+H]+@ r.t. 7.54 min. HRMS (ESI) calcd for C31H39N6O2 [M+H]+ 527.3129 found 527.3135.

The following compound was prepared essentially by the method of Example 21.

2-[(1-{4-[1-(4-acryloylpiperazin-1-yl)propyl]phenyl}cyclopropyl)amino]-8-(propan-2-yl)pyrido[2,3-d]pyrimidin-7(8H)-one [(I), X=N, R2=propan-2-yl, A=phenyl, R1a-R1b=cyclopropyl, R6a=4-CH(R14)NR7R8, R6b=H, R7-R8=4-piperazin-1-yl, R11=vinyl, R3=R4=R5=H, R14=ethyl] cpd 247

LCMS: m/z 501 [M+H]+@ r.t. 7.23 min. HRMS (ESI) calcd for C29H37N6O2 [M+H]+ 501.6351 found 501.6355.

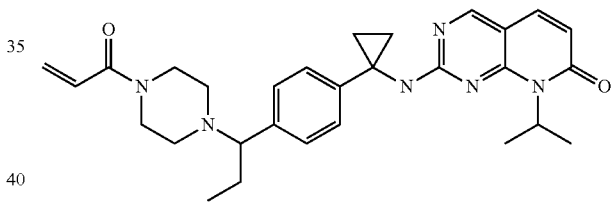

Example 22

2-[(1-{4-[(1R)-1-(4-acryloylpiperazin-1-yl)-2-cyclopropylethyl]phenyl}cyclopropyl)amino]-8-(propan-2-yl) pyrido[2,3-d]pyrimidin-7(8H)-one [(I), X=N, R2=propan-2-yl, A=phenyl, R1a-R1b=cyclopropyl, R6a=4-CH(R14)NR7R8, R6b=H, R7-R8=4-piperazin-1-yl, R11=vinyl, R3=R4=R5=H, R14=cyclopropylmethyl] cpd 245 Isopmer 1

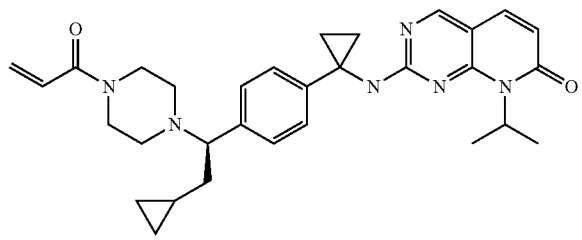 [SMILES: C=CC(=O)N1CCN([C@H](CC2CC2)c2ccc(C3(Nc4ncc5ccc(=O)n(C(C)C)c5n4)CC3)cc2)CC1]

and 2-[(1-{4-[(1S)-1-(4-acryloylpiperazin-1-yl)-2-cyclopropylethyl]phenyl}cyclopropyl)amino]-8-(propan-2-yl)pyrido[2,3-d]pyrimidin-7(8H)-one one [(I), X═N, R2=propan-2-yl, A=phenyl, R1a-R1b=cyclopropyl, R6a=4-CH(R14)NR7R8, R6b=H, R7-R8=4-piperazin-1-yl, R11=vinyl, R3=R4=R5=H, R14=cyclopropylmethyl] cpd 246 Isopmer 2

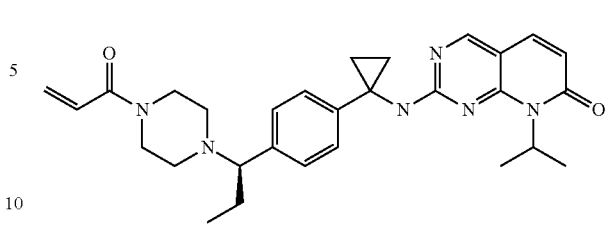

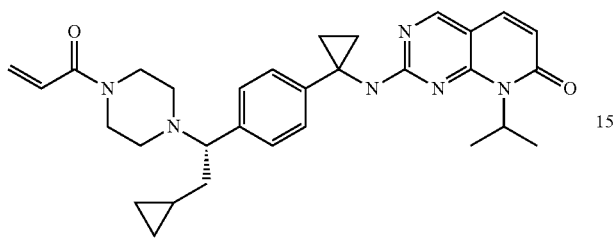

2-[(1-{4-[1-(4-acryloylpiperazin-1-yl)-2-cyclopropyl-ethyl]phenyl}cyclopropyl)amino]-8-(propan-2-yl)pyrido[2,3-d]pyrimidin-7(8H)-one (30 mg, 0.057 mmol) is dissolved in MeOH (1 ml) and resolved by chiral HPLC using the following conditions: column Chiralpak AD-H 5×50 cm; eluent Hexane/i-prOH 60/40 flow rate 50 ml/min; detection wavelength 334 nm; column temperature 25° C. Isomer 1 was isolated as the first eluting peak (7 mg, 0.013 mmol).

$^1$H NMR (DMSO-d6) δ: 8.60 (s, 1H), 8.59 (s, 1H), 7.65 (d, J=9.30 Hz, 1H), 7.02-7.16 (m, 4H), 6.68 (dd, J=10.45, 16.70 Hz, 1H), 6.20 (d, J=9.00 Hz, 1H), 6.02 (dd, J=2.29, 16.62 Hz, 1H), 5.59 (dd, J=2.29, 10.52 Hz, 1H), 5.18-5.42 (m, 1H), 3.37-3.53 (m, 5H), 2.20 (br. s., 4H), 1.80 (br. s., 1H), 1.40-1.61 (m, 1H), 1.20-1.36 (m, 6H), 0.97-1.15 (m, 4H), 0.34 (d, J=4.73 Hz, 1H), 0.17-0.29 (m, 2H), −0.11-0.05 (m, 2H). LCMS: m/z 527 [M+H]$^+$@ r.t. 7.54 min. HRMS (ESI) calcd for C$_{31}$H$_{39}$N$_6$O$_2$ [M+H]$^+$ 527.3129 found 527.3133.

Isomer 2 is isolated as second eluting peak (8 mg, 1.52 mmol).

$^1$H NMR (DMSO-d6) δ: 8.61 (s, 1H), 8.59 (s, 1H), 7.65 (d, J=9.30 Hz, 1H), 7.00-7.16 (m, 4H), 6.68 (dd, J=10.45, 16.70 Hz, 1H), 6.20 (d, J=9.30 Hz, 1H), 6.02 (dd, J=2.29, 16.62 Hz, 1H), 5.59 (dd, J=2.21, 10.45 Hz, 1H), 5.20-5.36 (m, 1H), 3.38-3.52 (m, 5H), 2.20 (br. s., 4H), 1.74-1.85 (m, 1H), 1.48-1.57 (m, 1H), 1.20-1.36 (m, 6H), 0.97-1.15 (m, 4H), 0.31-0.40 (m, 1H), 0.17-0.28 (m, 3H), −0.16-0.03 (m, 2H). LCMS: m/z 527 [M+H]$^+$@ r.t. 7.54 min.

HRMS (ESI) calcd for C$_{31}$H$_{39}$N$_6$O$_2$ [M+H]$^+$ 527.3129 found 527.3129.

The following compounds were obtained essentially by the method of Example 22.

Isomer 1 was isolated as the first eluting peak

2-[(1-{4-[(1R)-1-(4-acryloylpiperazin-1-yl)propyl]phenyl}cyclopropyl)amino]-8-(propan-2-yl)pyrido[2,3-d]pyrimidin-7(8H)-one [(I), X═N, R2=propan-2-yl, A=phenyl, R1a-R1b=cyclopropyl, R6a=4-CH(R14)NR7R8, R6b=H, R7-R8=4-piperazin-1-yl, R11=vinyl, R3=R4=R5=H, R14=ethyl] cpd 248

LCMS: m/z 501 [M+H]$^+$@ r.t. 7.23 min. HRMS (ESI) calcd for C$_{29}$H$_{37}$N$_6$O$_2$ [M+H]$^+$ 501.6351 found 501.6353.

Isomer 2 was isolated as the second eluting peak

2-[(1-{4-[(1S)-1-(4-acryloylpiperazin-1-yl)propyl]phenyl}cyclopropyl)amino]-8-(propan-2-yl)pyrido[2,3-d]pyrimidin-7(8H)-one [(I), X═N, R2=propan-2-yl, A=phenyl, R1a-R1b=cyclopropyl, R6a=4-CH(R14)NR7R8, R6b=H, R7-R8=4-piperazin-1-yl, R11=vinyl, R3=R4=R5=H, R14=ethyl] cpd 249

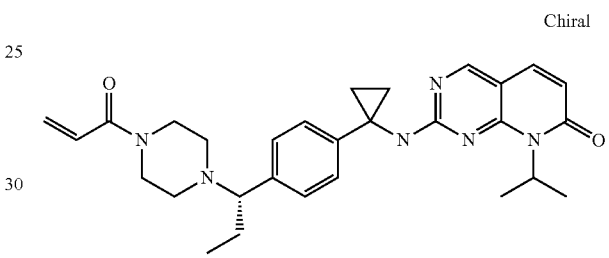

LCMS: m/z 501 [M+H]$^+$@ r.t. 7.23 min. HRMS (ESI) calcd for C$_{29}$H$_{37}$N$_6$O$_2$ [M+H]$^+$ 501.6351 found 501.6354.

Example 21

4-{4-[(S)-1-(1-Ethyl-2-oxo-1,2-dihydro-[1,6]naphthyridin-7-ylamino)-ethyl]-benzyl}-piperazine-1-carboxylic acid tert-butyl ester [(I), X═N, R2=Ethyl, X═CH, A=phenyl, R1a=H, R1b=Me, R6a=4-CH$_2$NR7R8, R6b=H, R7-R8=4-piperazine-1-carboxylic acid tert-butyl ester, R3=R4=R5=H] Step 1a, cpd 232

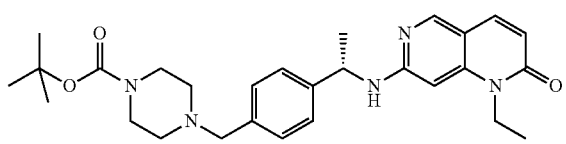 [SMILES: CCn1c(=O)ccc2cnc(N[C@@H](C)c3ccc(CN4CCN(C(=O)OC(C)(C)C)CC4)cc3)cc21]

To a solution of 4-[4-((S)-1-Amino-ethyl)-benzyl]-piperazine-1-carboxylic acid tert-butyl ester (0.30 g, 0.94 mmol), 7-Chloro-1-ethyl-1H-[1,6]naphthyridin-2-one (0.25 g, 1.17 mmol), and cesium carbonate (0.76 g, 2.35 mmol) in toluene (10 mL) under nitrogen is added dichloro[1,3-bis(2,6-di-3-pentylphenyl)imidazole-2-ylidene](3-chloropyridyl)palladium(II) (0.08 g, 0.12 mmol) and the mixture is heated at 100° C. overnight. After cooling to room temperature, the mixture is filtered through a plug of silica gel and eluted with ethyl acetate. The filtrate is concentrated under reduced pressure and the residue is purified by silica gel chromatography (0 to 20%) Acetone/EtOAc.

¹H NMR (DMSO-d₆) δ: 8.30 (s, 1H), 7.66 (d, J=9.3 Hz, 1H), 7.49 (d, J=7.5 Hz, OH), 7.35 (d, J=8.1 Hz, 2H), 7.22 (d, J=8.1 Hz, 2H), 6.18 (br. s., 1H), 6.15 (d, J=9.3 Hz, 1H), 5.00 (br. s., 1H), 4.08 (dq, J=13.9, 6.9 Hz, 1H), 3.85-3.96 (m, 1H), 3.41 (s, 2H), 3.27 (br. s., 4H), 2.25 (t, J=4.8 Hz, 4H), 1.45 (d, J=6.9 Hz, 3H), 1.37 (s, 9H), 1.00 (br. s., 3H). LCMS: m/z 492 [M+H]⁺@ r.t. 6.16 min HRMS (ESI) calcd for C₂₈H₃₈N₅O₃ [M+H]⁺ 492.2969 found 492.2974

4-(1-{4-[(S)-1-(1-Ethyl-2-oxo-1,2-dihydro-[1,6] naphthyridin-7-ylamino)-ethyl]-phenyl}-propyl)-piperazine-1-carboxylic acid tert-butyl ester [(I), X=N, R2=Ethyl, X=CH, A=phenyl, R1a=H, R1b=Me, R6a=4-CHR14NR7R8, R6b=H, R7-R8=4-piperazine-1-carboxylic acid tert-butyl ester, R14=Ethyl, R3=R4=R5=H] cpd 233

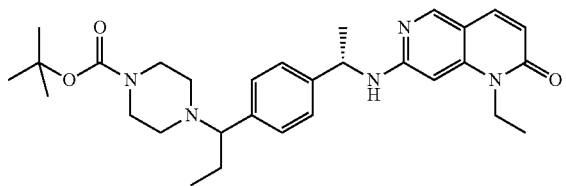 [SMILES: CCC(c1ccc([C@H](C)Nc2cc3c(ccc(=O)n3CC)cn2)cc1)N1CCN(C(=O)OC(C)(C)C)CC1]

¹H NMR (DMSO-d₆) δ: 8.31 (s, 1H), 7.66 (d, J=9.3 Hz, 1H), 7.49 (dd, J=6.9, 3.1 Hz, 1H), 7.35 (d, J=8.1 Hz, 2H), 7.14 (d, J=8.1 Hz, 2H), 6.14 (d, J=9.5 Hz, 1H), 4.96 (br. s., 1H), 4.02-4.17 (m, J=13.4, 7.2 Hz, 1H), 3.85 (br. s., 1H), 3.11-3.30 (m, 5H), 2.19 (br. s., 4H), 1.75-1.92 (m, 1H), 1.65 (tq, J=14.6, 7.4 Hz, 1H), 1.46 (d, J=6.9 Hz, 3H), 1.31 (d, J=3.7 Hz, 9H), 0.94 (br. s., 3H), 0.68 (td, J=7.2, 2.9 Hz, 3H). LCMS: m/z 520 [M+H]⁺@ r.t. 6.67 min HRMS (ESI) calcd for C₃₀H₄₂N₅O₃ [M+H]⁺ 520.3282 found 520.3284

According to the same method, the following compounds were prepared:

4-((S)-1-{4-[(S)-1-(1-Ethyl-2-oxo-1,2-dihydro-[1,6] naphthyridin-7-ylamino)-ethyl]-phenyl}-propyl)-piperazine-1-carboxylic acid phenyl ester [(I), X=N, R2=Ethyl, X=CH, A=phenyl, R1a=H, R1b=Me, R6a=4-CHR14NR7R8, R6b=H, R7-R8=4-piperazine-1-carboxylic acid phenyl ester, R14=Ethyl, R3=R4=R5=H] cpd 234

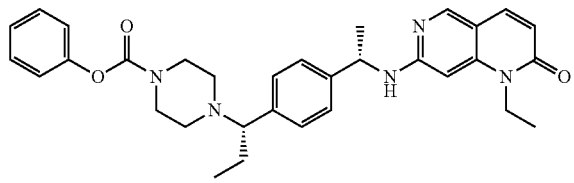 [SMILES: CC[C@@H](c1ccc([C@H](C)Nc2cc3c(ccc(=O)n3CC)cn2)cc1)N1CCN(C(=O)Oc2ccccc2)CC1]

¹H NMR (DMSO-d₆) δ:8.32 (s, 1H), 7.67 (d, J=9.3 Hz, 1H), 7.51 (d, J=7.2 Hz, 1H), 7.31-7.40 (m, 5H), 7.16-7.22 (m, 3H), 7.01-7.08 (m, 2H), 6.15 (d, J=9.3 Hz, 2H), 5.00 (br. s., 1H), 4.12 (dd, J=13.5, 6.9 Hz, 1H), 3.86 (br. s., 1H), 3.36-3.59 (m, 3H), 2.25-2.36 (m, 4H), 1.82-1.94 (m, 1H), 1.59-1.76 (m, 1H), 1.48 (d, J=6.9 Hz, 3H), 0.96 (br. s., 3H), 0.67-0.73 (m, 3H).

7-{(S)-1-[4-(3,3-Difluoro-piperidin-1-ylmethyl)-phenyl]-ethylamino}-1-(2,2-dimethyl-propyl)-1H-[1,6]naphthyridin-2-one [(I), X=N, R2=Ethyl, X=CH, A=phenyl, R1a=H, R1b=Me, R6a=4-CH₂NR7R8, R6b=H, R7-R8=4-(3,3-Difluoro-piperidin-1-yl), R3=R4=R5=H] cpd 235

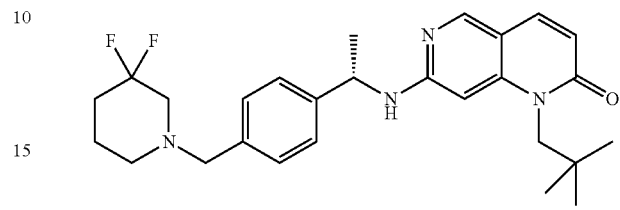

¹H NMR (DMSO-d₆) δ: 8.28 (s, 1H), 7.66 (d, J=9.5 Hz, 1H), 7.43 (d, J=7.0 Hz, 1H), 7.34 (d, J=8.1 Hz, 2H), 7.22 (d, J=7.9 Hz, 2H), 6.24 (br. s., 9H), 6.16 (d, J=9.3 Hz, 1H), 4.92-5.00 (m, 1H), 3.50-3.80 (m, 4H), 2.36-2.58 (m, 4H), 1.77-1.91 (m, 2H), 1.58-1.66 (m, 2H), 1.44 (d, J=6.9 Hz, 3H), 0.78 (br. s., 9H). LCMS: m/z 469 [M+H]⁺@ r.t. 7.05 min. HRMS (ESI) calcd for C₂₇H₃₅F₂N₄O [M+H]⁺ 469.2774 found 469.2765

Example 22

7-{(S)-1-[4-(4-Acryloyl-piperazin-1-ylmethyl)-phenyl]-ethylamino}-1-ethyl-1H-[1,6]naphthyridin-2-one [(I), X=N, R2=Ethyl, X=CH, A=phenyl, R1a=H, R1b=Me, R6a=4-CHR14NR7R8, R6b=H, R7-R8=4-piperazin-1-yl, R11=vinyl, R14 Ethyl, R3 R4=_R5=H]conv. 7, cpd 236

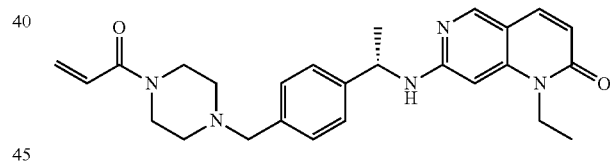

To a solution of 1-ethyl-7-({(1S)-1-[4-(piperazin-1-ylmethyl)phenyl]ethyl}amino)-1,6-naphthyridin-2-one (47.0 mg, 0.12 mmol) in CH₂Cl₂ (1.0 mL) is added acryloyl chloride (10 µL, 0.12 mmol) at 0° C. After 30 minutes, the reaction is quenched with water. The mixture is partioned with DCM and satured solution of NaHCO₃, dried over Na₂SO₄, filtered, and concentrated to yield a yellow oil. The crude product is purified by silica gel chromatography (1 to 10% MeOH/DCM) to give the title product as a off-white foam (38 mg, 71% yield).

¹H NMR (DMSO-d₆) δ: 8.30 (s, 1H), 7.66 (d, J=9.5 Hz, 1H), 7.49 (d, J=7.3 Hz, 1H), 7.36 (d, J=7.9 Hz, 2H), 7.24 (d, J=7.9 Hz, 2H), 6.66-6.82 (m, 1H), 6.15 (d, J=9.3 Hz, 1H), 6.08 (dd, J=16.7, 2.4 Hz, 1H), 5.65 (dd, J=10.4, 2.4 Hz, 1H), 5.00 (br. s., 1H), 4.09 (dq, J=13.9, 7.0 Hz, 1H), 3.81-3.97 (m, 1H), 3.49 (d, J=9.2 Hz, 4H), 3.43 (s, 2H), 2.30 (br. s., 4H), 1.46 (d, J=6.9 Hz, 3H), 1.00 (br. s, 2H). LCMS: m/z 446 [M+H]⁺@ r.t. 4.76 min. HRMS (ESI) calcd for C₂₆H₃₂N₅O₂ [M+H]⁺ 446.2551 found 446.2555.

According to the same method, the following compounds were prepared:

211

7-{[(1S)-1-{4-[(1S)-1-(4-acryloylpiperazin-1-yl)propyl]phenyl}ethyl]amino}-1-(propan-2-yl)-1,6-naphthyridin-2(1H)-one [(I), X=N, R2=propan-2-yl, X=CH, A=phenyl, R1a=H, R1b=Me, R6a=4-CHR14NR7R8, R6b=H, R7-R8=4-piperazin-1-yl, R11=vinyl, R14=Ethyl, R3=R4=R5=H], cpd 237

212

7-{[(1S)-1-{4-[(1S)-1-(4-acryloylpiperazin-1-yl)propyl]phenyl}ethyl]amino}-1-(propan-2-yl)-1,6-naphthyridin-2(1H)-one [(I), X=N, R2=propan-2-yl, X=CH, A=phenyl, R1a=H, R1b=Me, R6a=4-CHR14NR7R8, R6b=H, R7-R8=4-piperazin-1-yl, R11=vinyl, R14=Ethyl, R3=R4=R5=H] conv. 7, cpd 239

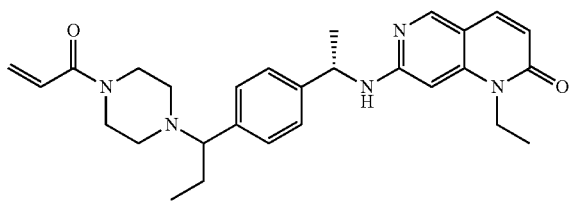

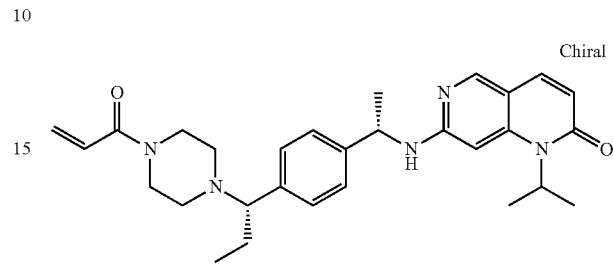

¹H NMR (DMSO-d₆) δ:8.31 (s, 1H), 7.66 (d, J=9.3 Hz, 1H), 7.46-7.51 (m, 1H), 7.31-7.41 (m, 2H), 7.12-7.19 (m, 2H), 6.70 (ddd, J=16.7, 10.4, 1.9 Hz, 1H), 6.07-6.22 (m, 2H), 6.02 (dt, J=16.7, 2.5 Hz, 1H), 5.56-5.64 (m, 1H), 4.99 (br. s., 1H), 4.04-4.12 (m, 1H), 3.78-3.93 (m, 1H), 3.41-3.55 (m, 4H), 3.21-3.30 (m, 1H), 2.25 (br. s., 4H), 1.58-1.89 (m, 2H), 1.46 (d, J=6.9 Hz, 3H), 0.82-1.06 (m, 3H), 0.64-0.76 (m, 3H) LCMS: m/z 474 [M+H]⁺@ r.t. 4.65 min. HRMS (ESI) calcd for $C_{28}H_{36}N_5O_2$ [M+H]⁺ 474.2864 found 474.2864

¹H NMR (DMSO-d₆) δ: 8.29 (s, 1H), 7.61 (d, J=9.30 Hz, 1H), 7.43 (d, J=7.02 Hz, 1H), 7.34 (d, J=8.08 Hz, 2H), 7.17 (d, J=8.08 Hz, 2H), 6.70 (dd, J=10.52, 16.62 Hz, 1H), 6.31 (br. s., 1H), 6.10 (d, J=9.15 Hz, 1H), 6.03 (dd, J=2.44, 16.62 Hz, 1H), 5.58-5.63 (m, 1H), 5.20 (br. s., 1H), 4.94 (br. s., 1H), 3.41-3.56 (m, 4H), 3.20-3.30 (m, 1H), 2.25 (d, J=4.27 Hz, 4H), 1.78-1.93 (m, 1H), 1.58-1.73 (m, 1H), 1.09-1.52 (m, 9H), 0.69 (t, J=7.32 Hz, 3H).

LCMS: m/z 488 [M+H]⁺@ r.t. 4.27 min. HRMS (ESI) calcd for $C_{28}H_{38}N_5O_2$ [M+H]⁺ 488.3020 found 488.3015

7-((S)-1-{4-[(S)-1-(4-Acryloyl-piperazin-1-yl)-propyl]-phenyl}-ethylamino)-1-ethyl-1H-[1,6]naphthyridin-2-one [(I), X=N, R2=Ethyl, X=CH, A=phenyl, R1a=H, R1b=Me, R6a=4-CHR14NR7R8, R6b=H, R7-R8=4-piperazin-1-yl, R11=vinyl, R14=Ethyl, R3=R4=R5=H] conv. 7, cpd 238

7-{[(1S)-1-{4-[(1S)-1-(4-acryloylpiperazin-1-yl)-2-cyclopropylethyl]phenyl}ethyl]amino}-1-(propan-2-yl)-1,6-naphthyridin-2(1H)-one [(I), X=N, R2=propan-2-yl, X=CH, A=phenyl, R1a=H, R1b=Me, R6a=4-CHR14NR7R8, R6b=H, R7-R8=4-piperazin-1-yl, R11=vinyl, R14=cyclopropylmethyl, R3=R4=R5=H] conv. 7, cpd 251

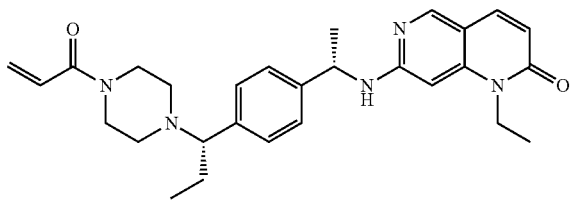 [SMILES: C=CC(=O)N1CCN([C@@H](CC)c2ccc([C@H](C)Nc3cc4c(ccc(=O)n4CC)cn3)cc2)CC1]

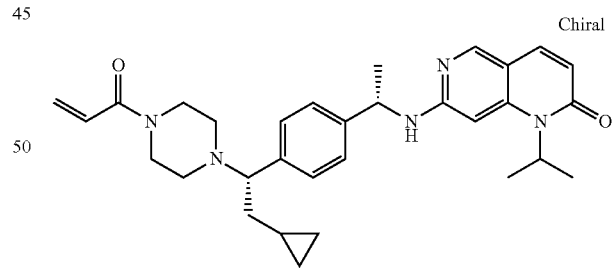

¹H NMR (DMSO-d₆) δ: 8.31 (s, 1H), 7.66 (d, J=9.3 Hz, 1H), 7.44-7.51 (m, 1H), 7.35 (d, J=8.1 Hz, 2H), 7.16 (d, J=8.1 Hz, 2H), 6.70 (dd, J=16.7, 10.4 Hz, 1H), 6.15 (d, J=9.3 Hz, 2H), 6.02 (dd, J=16.6, 2.4 Hz, 1H), 5.60 (dd, J=10.4, 2.2 Hz, 1H), 4.99 (br. s., 1H), 4.00-4.16 (m, 1H), 3.86 (br. s., 1H), 3.45 (br. s., 4H), 3.21-3.29 (m, 1H), 2.24 (br. s., 4H), 1.77-1.93 (m, 1H), 1.59-1.73 (m, 1H), 1.46 (d, J=6.9 Hz, 3H), 0.95 (br. s., 3H), 0.64-0.73 (m, 3H) LCMS: m/z 474 [M+H]⁺@ r.t. 4.27 min. HRMS (ESI) calcd for $C_{28}H_{36}N_5O_2$ [M+H]⁺ 474.2864 found 474.2861

¹H NMR (DMSO-d₆) δ:8.57 (s, 1H), 8.34 (d, J=6.86 Hz, 1H), 7.62 (d, J=9.30 Hz, 1H), 7.28-7.39 (m, 2H), 7.17 (d, J=7.90 Hz, 2H), 6.68 (dd, J=10.50, 16.70 Hz, 1H), 6.15 (d, J=9.30 Hz, 1H), 6.01 (dd, J=2.06, 16.70 Hz, 1H), 5.59 (dd, J=1.98, 10.68 Hz, 1H), 5.38-5.47 (br., 1H), 4.96 (t, J=6.55 Hz, 1H), 3.38-3.56 (m, 5H), 2.24 (br. s., 4H), 1.54-1.83 (m, 2H), 1.47 (m, 10H), 0.27-0.36 (m, 2H), −0.09-0.02 (m, 2H). LCMS: m/z 514 [M+H]⁺@ r.t. 4.85 min. HRMS (ESI) calcd for $C_{31}H_0N_5O_2$ [M+H]⁺ 514.6736 found 514.6732.

The invention claimed is:
1. A compound of formula (I):

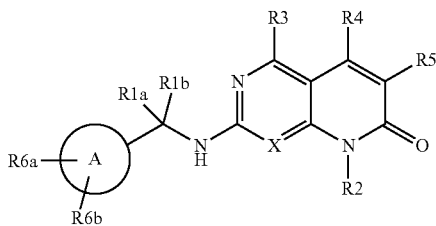

wherein:
X is nitrogen or —CH—
R1a is hydrogen or an optionally substituted straight or branched (C$_1$-C$_6$)alkyl;
R1b is an optionally substituted (C$_1$-C$_6$)alkyl, or together with the atom to which they are bound,
R1a and R1b may form a (C$_3$-C$_6$)cycloalkyl;
A is a (C$_3$-C$_6$)cycloalkyl, aryl or heteroaryl;
R6a is —CH(R14)NR7R8;
R6b is hydrogen:
  wherein:
  R14 is hydrogen or an optionally substituted straight or branched (C$_1$-C$_6$)alkyl;
  R7 and R8, together with the nitrogen atom to which they are bound, form a 5- to 7-membered heteroaryl or heterocyclyl group optionally containing one additional heteroatom selected from O, S and NR9;
    wherein:
    R9 is hydrogen, an optionally substituted straight or branched (C$_1$-C$_6$)alkyl, —COOR10 or —COR11;
      wherein:
      R10 is hydrogen or an optionally substituted straight or branched (C$_1$-C$_6$)alkyl;
      R11 is an optionally substituted straight or branched (C$_1$-C$_6$)alkyl, (C$_2$-C$_6$)alkenyl or (C$_2$-C$_6$)alkynyl;
R2 is an optionally substituted group selected from straight or branched (C$_1$-C$_6$)alkyl, (C$_3$-C$_6$)cycloalkyl-(C$_1$-C$_6$)alkyl, aryl-(C$_1$-C$_6$)alkyl, and heterocyclyl-(C$_1$-C$_6$)alkyl;
R3 is hydrogen, chloro, cyano, CONH$_2$, NH$_2$, NR13R13a, OR12, or an optionally substituted group selected from straight or branched (C$_1$-C$_6$)alkyl, (C$_3$-C$_6$)cycloalkyl-(C$_1$-C$_6$)alkyl, aryl and heteroaryl;
  wherein:
  R12 is an optionally substituted straight or branched (C$_1$-C$_6$)alkyl;
  R13, R13a are each independently selected from hydrogen or optionally substituted straight or branched (C$_1$-C$_6$)alkyl;
R4 is hydrogen or an optionally substituted straight or branched (C$_1$-C$_6$)alkyl;
R5 is hydrogen, fluoro, cyano, an optionally substituted straight or branched (C$_1$-C$_6$)alkyl or —OR12,
  wherein:
  R12 is as described above;
or a pharmaceutically acceptable salt thereof.

2. A compound of formula (I) or a pharmaceutically acceptable salt thereof, according to claim 1,
wherein:
R3 is hydrogen, chloro, cyano, CONH$_2$, NH$_2$, NR13R13a, OR12, or an optionally substituted straight or branched (C$_1$-C$_6$)alkyl;
  wherein:
  R12 is an optionally substituted straight or branched (C$_1$-C$_6$)alkyl;
  R13, R13a are each independently selected from hydrogen or optionally substituted straight or branched (C$_1$-C$_6$)alkyl;
R5 is hydrogen, fluoro or —OR12,
  wherein:
  R12 is as described above; and
R1a, R1b, A, X, R6a, R6b, R2 and R4 are as defined in claim 1.

3. A compound of formula (I) or a pharmaceutically acceptable salt thereof, according to claim 2,
wherein:
R5 is hydrogen or fluoro; and
R1a, R1b, A, X, R2, R3 and R4 are as defined in claim 2.

4. A compound of formula (I) or a pharmaceutically acceptable salt thereof, according to claim 3,
wherein:
A is aryl or heteroaryl;
R3 is hydrogen, cyano, CONH$_2$, NH$_2$, NR13R13a, or an optionally substituted straight or branched (C$_1$-C$_6$) alkyl;
  wherein:
  R13, R13a are each independently selected from hydrogen or optionally substituted straight or branched (C$_1$-C$_6$)alkyl; and
R1a, R1b, R6a, R6b, X, R2, R4 and R5 are as defined in claim 3.

5. A compound (cpd) selected from the group consisting of:
methyl 4-{(1S)-1-[(8-benzyl-7-oxo-pyrido[2,3-d]pyrimidin-2-yl)amino]ethyl}benzoate (cpd 1);
methyl 4-{(1S)-1-[(8-ethyl-7-oxo-pyrido[2,3-d]pyrimidin-2-yl)amino]ethyl}benzoate (cpd 2);
methyl 4-[(1S)-1-{[8-(methoxymethyl)-7-oxo-pyrido[2,3-d]pyrimidin-2-yl]amino}ethyl]benzoate (cpd 3);
methyl 4-1(1S)-1-[(8-methyl-7-oxo-pyrido[2,3-d]pyrimidin-2-yl)amino]ethyl}benzoate (cpd 4);
methyl 4-[(1S)-1-{[8-(2-methylpropyl)-7-oxo-pyrido[2,3-d]pyrimidin-2-yl]amino}ethyl]benzoate (cpd 5);
methyl 4-[(1S)-1-{[8-(4-fluorobenzyl)-7-oxo-pyrido[2,3-d]pyrimidin-2-yl]amino}ethyl]benzoate (cpd 6);
methyl 4-[(1S)-1-{[8-(3,5-difluorobenzyl)-7-oxo-pyrido[2,3-d]pyrimidin-2-yl]amino}ethyl]benzoate (cpd 7);
methyl 4-[(1S)-1-({8-[4-fluoro-2-(trifluoromethyl)benzyl]-7-oxo-pyrido[2,3-d]pyrimidin-2-yl}amino)ethyl]benzoate (cpd 8);
methyl 4-[(1S)-1-{[7-oxo-8-(propan-2-yl)-pyrido[2,3-d]pyrimidin-2-yl]amino}ethyl]benzoate (cpd 9);
methyl 4-[(1S)-1-({8-[(3-methyloxetan-3-yl)methyl]-7-oxo-pyrido[2,3-d]pyrimidin-2-yl}amino)ethyl]benzoate (cpd 10);
methyl 4-[(1S)-1-{[8-(2,2-dimethylpropyl)-7-oxo-pyrido[2,3-d]pyrimidin-2-yl]amino}ethyl]benzoate (cpd 11);
2-1[(1S)-1-cyclohexylethyl]amino}-8-ethylpyrido[2,3-d]pyrimidin-7(8H)-one (cpd 12);
8-ethyl-2-{[(1S)-1-(4-methoxyphenyl)ethyl]amino}pyrido[2,3-d]pyrimidin-7(8H)-one (cpd 13);
2-1[(1S)-1-(4-chlorophenyl)ethyl]amino}-8-ethylpyrido[2,3-d]pyrimidin-7(8H)-one (cpd 14);

2-1[(1S)-1-(4-chlorophenyl)ethyl]amino}-8-(pentan-3-yl)pyrido[2,3-d]pyrimidin-7(8H)-one (cpd 15);
8-benzyl-2-{[(1S)-1-(4-chlorophenyl)ethyl]amino}pyrido[2,3-d]pyrimidin-7(8H)-one (cpd 16);
2-1[(1S)-1-(4-chlorophenyl)ethyl]amino}-8-(2-fluoroethyl)pyrido[2,3-d]pyrimidin-7(8H)-one (cpd 17);
2-1[(1S)-1-(4-chlorophenyl)ethyl]amino}-8-(2,2,2-trifluoroethyl)pyrido[2,3-d]pyrimidin-7(8H)-one (cpd 18);
2-1[(1S)-1-(4-chlorophenyl)ethyl]amino}-8-(2-methylpropyl)pyrido[2,3-d]pyrimidin-7(8H)-one (cpd 19);
2-{[(1S)-1-(4-chlorophenyl)ethyl]amino}-8-(cyclopropylmethyl)pyrido[2,3-d]pyrimidin-7(8H)-one (cpd 20);
2-{[(1S)-1-(4-chlorophenyl)ethyl]amino}-8-(4-methoxybenzyl)pyrido[2,3-d]pyrimidin-7(8H)-one (cpd 21);
2-{[(1S)-1-(4-chlorophenyl)ethyl]amino}-8-(2-fluorobenzyl)pyrido[2,3-d]pyrimidin-7(8H)-one (cpd 22);
2-{[(1S)-1-(4-chlorophenyl)ethyl]amino}-8-(3,4-difluorobenzyl)pyrido[2,3-d]pyrimidin-7(8H)-one (cpd 23);
2-{[(1S)-1-(4-chlorophenyl)ethyl]amino}-8-[3-(trifluoromethyl)benzyl]pyrido[2,3-d]pyrimidin-7(8H)-one (cpd 24);
2-{[(1S)-1-(4-chlorophenyl)ethyl]amino}-8-(2,4-difluorobenzyl)pyrido[2,3-d]pyrimidin-7(8H)-one (cpd 25);
2-{[(1S)-1-(4-chlorophenyl)ethyl]amino}-8-[4-(trifluoromethoxy)benzyl]pyrido[2,3-d]pyrimidin-7(8H)-one (cpd 26);
4-{[2-{[(1S)-1-(4-chlorophenyl)ethyl]amino}-7-oxopyrido[2,3-d]pyrimidin-8(7H)-yl]methyl}benzonitrile (cpd 27);
2-{[(1S)-1-(4-chlorophenyl)ethyl]amino}-8-(4-fluorobenzyl)pyrido[2,3-d]pyrimidin-7(8H)-one (cpd 28);
2-{[(1S)-1-(4-chlorophenyl)ethyl]amino}-8-(3,5-difluorobenzyl)pyrido[2,3-d]pyrimidin-7(8H)-one (cpd 29);
2-{[(1S)-1-(4-chlorophenyl)ethyl]amino}-8-(3-methoxybenzyl)pyrido[2,3-d]pyrimidin-7(8H)-one (cpd 30);
2-{[(1S)-1-(4-chlorophenyl)ethyl]amino}-8-(2,6-difluorobenzyl)pyrido[2,3-d]pyrimidin-7(8H)-one (cpd 31);
2-{[(1S)-1-(4-chlorophenyl)ethyl]amino}-4-methyl-8-(2-methylpropyl)pyrido[2,3-d]pyrimidin-7(8H)-one (cpd 32);
8-(2,2-dimethylpropyl)-2-{[(1S)-1-(4-methoxyphenyl)ethyl]amino}pyrido[2,3-d]pyrimidin-7(8H)-one (cpd 33);
2-{[(1S)-1-(4-bromophenyl)ethyl]amino}-8-(2,2-dimethylpropyl)pyrido[2,3-d]pyrimidin-7(8H)-one (cpd 34);
2-{[(1S)-1-(4-bromophenyl)ethyl]amino}-8-(3-hydroxy-2,2-dimethylpropyl)pyrido[2,3-d]pyrimidin-7(8H)-one (cpd 35);
8-(2,2-dimethylpropyl)-2-{[(1S)-1-(naphthalen-2-yl)ethyl]amino}pyrido[2,3-d]pyrimidin-7(8H)-one (cpd 36);
methyl 2,2-dimethyl-3-[2-{[(1S)-1-(naphthalen-2-yl)ethyl]amino}-7-oxopyrido[2,3-d]pyrimidin-8(7H)-yl]propanoate (cpd 37);
8-(3-hydroxy-2,2-dimethylpropyl)-2-{[(1S)-1-(naphthalen-2-yl)ethyl]amino}pyrido[2,3-d]pyrimidin-7(8H)-one (cpd 38);
8-(2,2-dimethylpropyl)-2-1[(1R)-1-phenylethyl]amino}pyrido[2,3-d]pyrimidin-7(8H)-one (cpd 39);
8-(2,2-dimethylpropyl)-2-{[(1S)-1-phenylethyl]amino}pyrido[2,3-d]pyrimidin-7(8H)-one (cpd 40);
8-(2,2-dimethylpropyl)-2-[(2-phenylpropan-2-yl)amino]pyrido[2,3-d]pyrimidin-7(8H)-one (cpd 41);
8-(2,2-dimethylpropyl)-2-[(1-phenylcyclopropyl)amino]pyrido[2,3-d]pyrimidin-7(8H)-one (cpd 42);
8-(2,2-dimethylpropyl)-2-[(1-phenylcyclobutyl)amino]pyrido[2,3-d]pyrimidin-7(8H)-one (cpd 43);
8-(2,2-dimethylpropyl)-2-{[1-(tricyclo[3.3.1.1$^{3,7}$]dec-1-yl)ethyl]amino}pyrido[2,3-d]pyrimidin-7(8H)-one (cpd 44);
8-[(3-methyloxetan-3-yl)methyl]-2-{[(1S)-1-(naphthalen-2-yl)ethyl]amino}pyrido[2,3-d]pyrimidin-7(8H)-one (cpd 45);
8-(2-hydroxy-2-methylpropyl)-2-{[(1S)-1-phenylethyl]amino}pyrido[2,3-d]pyrimidin-7(8H)-one (cpd 46);
8-(2,2-Dimethyl-propyl)-6-fluoro-2-((S)-1-phenyl-ethylamino)-8H-pyrido[2,3-d]pyrimidin-7-one (cpd 47);
methyl 4-[(1S)-1-{[8-(2-hydroxy-2-methylpropyl)-7-oxo-7,8-dihydropyrido[2,3-d]pyrimidin-2-yl]amino}ethyl]benzoate (cpd 48);
8-(2,2-dimethylpropyl)-2-{[(1S)-1-(4-phenoxyphenyl)ethyl]amino}pyrido[2,3-d]pyrimidin-7(8H)-one (cpd 49);
2-{[(1S)-1-(6-chloro-2-oxo-quinolin-3-yl)ethyl]amino}-8-(2,2-dimethylpropyl)pyrido[2,3-d]pyrimidin-7(8H)-one (cpd 50);
8-benzyl-2-{[(1S)-1-(5-chloro-1H-benzimidazol-2-yl)ethyl]amino}pyrido[2,3-d]pyrimidin-7(8H)-one (cpd 51);
8-benzyl-2-(1(1S)-1-[3-(4-chlorophenyl)-1,2,4-oxadiazol-5-yl]ethyl}amino)pyrido[2,3-d]pyrimidin-7(8H)-one (cpd 52);
2-(1(1S)-1-[3-(4-chlorophenyl)-1,2,4-oxadiazol-5-yl]ethyl}amino)-8-(2,2-dimethylpropyl)pyrido[2,3-d]pyrimidin-7(8H)-one (cpd 53);
8-(2,2-dimethylpropyl)-2-{[(1S)-1-(4-oxo-3,4-dihydroquinazolin-2-yl)ethyl]amino}pyrido[2,3-d]pyrimidin-7(8H)-one (cpd 54);
2-{[(1S)-1-{4-[(4,4-difluoropiperidin-1-yl)methyl]phenyl}ethyl]amino}-8-(3-hydroxy-2,2-dimethylpropyl)pyrido[2,3-d]pyrimidin-7(8H)-one (cpd 55);
4-(4-1(S)-1-[8-(3-Hydroxy-2,2-dimethyl-propyl)-7-oxo-7,8-dihydro-pyrido[2,3-d]pyrimidin-2-ylamino]-ethyl}-benzyl)-piperazine-1-carboxylic acid tert-butyl ester (cpd 56);
2-1(S)-1-[4-(3,3-Difluoro-piperidin-1-ylmethyl)-phenyl]-ethylamino}-8-(2,2-dimethyl-propyl)-6-fluoro-8H-pyrido[2,3-d]pyrimidin-7-one (cpd 57);
2-1(S)-1-[4-(3,3-Difluoro-piperidin-1-ylmethyl)-phenyl]-ethylamino}-8-(2,2-dimethyl-propyl)-6-methoxy-8H-pyrido[2,3-d]pyrimidin-7-one (cpd 58);
4-(4-1(S)-1-[8-(2,2-Dimethyl-propyl)-7-oxo-7,8-dihydro-pyrido[2,3-d]pyrimidin-2-ylamino]-ethyl}-benzyl)-piperazine-1-carboxylic acid tert-butyl ester (cpd 59);
2-1[(1S)-1-{4-[(3,3-difluoropiperidin-1-yl)methyl]phenyl}ethyl]amino}-8-(2,2-dimethylpropyl)-5-methylpyrido[2,3-d]pyrimidin-7(8H)-one (cpd 60);
8-(butan-2-yl)-2-{[(1S)-1-{4-[(3,3-difluoropiperidin-1-yl)methyl]phenyl}ethyl]amino}pyrido[2,3-d]pyrimidin-7(8H)-one (cpd 61);
8-[(2S)-butan-2-yl]-2-{[(1S)-1-{4-[(3,3-difluoropiperidin-1-yl)methyl]phenyl}ethyl]amino}pyrido[2,3-d]pyrimidin-7(8H)-one (cpd 62);
ethyl 2-[2-1[(1S)-1-{4-[(3,3-difluoropiperidin-1-yl)methyl]phenyl}ethyl]amino}-7-oxopyrido[2,3-d]pyrimidin-8(7H)-yl] propanoate (cpd 63);
2-[2-1[(1S)-1-{4-[(3,3-difluoropiperidin-1-yl)methyl]phenyl}ethyl]amino}-7-oxopyrido[2,3-d]pyrimidin-8(7H)-yl] propanenitrile (cpd 64);

2-1[(1S)-1-{4-[(3,3-difluoropiperidin-1-yl)methyl] phenyl}ethyl]amino}-8-[(2S)-3-methylbutan-2-yl] pyrido[2,3-d]pyrimidin-7(8H)-one (cpd 65);

8-[(1S)-1-cyclohexylethyl]-2-{[(1S)-1-{4-[(3,3-difluoropiperidin-1-yl)methyl]phenyl}ethyl]amino}-pyrido[2,3-d]pyrimidin-7(8H)-one (cpd 66);

2-1[(1S)-1-{4-[(4,4-difluoropiperidin-1-yl)methyl]-3-fluorophenyl}ethyl]amino}-8-[(2S)-3-methylbutan-2-yl]pyrido[2,3-d] pyrimidin-7(8H)-one (cpd 67);

2-({(1S)-1-[3-fluoro-4-(morpholin-4-ylmethyl)phenyl] ethyl}amino)-8-[(2S)-3-methylbutan-2-yl]pyrido[2,3-d]pyrimidin-7 (8H)-one (cpd 68);

2-{[(1S)-1-{4-[(3,3-difluoropiperidin-1-yl)methyl] phenyl}ethyl]amino}-8-[(2S)-3,3-dimethylbutan-2-yl] pyrido[2,3-d] pyrimidin-7(8H)-one (cpd 69);

8-(2,2-dimethylpropyl)-2-{[(1S)-1-phenylpropyl] amino}pyrido[2,3-d]pyrimidin-7(8H)-one (cpd 70);

2-{[(1S)-1-(4-chlorophenyl)ethyl]amino}-8-(3-hydroxybenzyl)pyrido[2,3-d]pyrimidin-7(8H)-one (cpd 71);

2-{[(1S)-1-(4-chlorophenyl)ethyl]amino}-8-(4-hydroxybenzyl)pyrido[2,3-d]pyrimidin-7(8H)-one (cpd 72);

4-[(1S)-1-{[8-(2,6-difluorobenzyl)-7-oxo-pyrido[2,3-d] pyrimidin-2-yl]amino}ethyl]benzoic acid (cpd 73);

4-[(1S)-1-{[8-(2-fluorobenzyl)-7-oxo-pyrido[2,3-d]pyrimidin-2-yl]amino}ethyl]benzoic acid (cpd 74);

4-[(1S)-1-{[8-(2,6-difluorobenzyl)-7-oxo-pyrido[2,3-d] pyrimidin-2-yl]amino}ethyl]-N-(4,4-difluorocyclohexyl)benzamide (cpd 75);

4-[(1S)-1-{[8-(2,6-difluorobenzyl)-7-oxo-pyrido[2,3-d] pyrimidin-2-yl]amino}ethyl]-N-(1-methylpiperidin-4-yl)benzamide (cpd 76);

8-(2,6-difluorobenzyl)-2-{[(1S)-1-{4-[(4,4-difluoropiperidin-1-yl)carbonyl]phenyl}ethyl]amino}pyrido[2,3-d]pyrimidin-7 (8H)-one (cpd 77);

4-[(1S)-1-{[8-(2,6-difluorobenzyl)-7-oxo-pyrido[2,3-d] pyrimidin-2-yl]amino}ethyl]-N-(tetrahydro-2H-pyran-4-yl) benzamide (cpd 78);

N-(4,4-difluorocyclohexyl)-4-[(1S)-1-{[8-(2,2-dimethylpropyl)-7-oxo-pyrido[2,3-d]pyrimidin-2-yl] amino}ethyl]benzamide (cpd 79);

N-cyclopentyl-4-[(1S)-1-{[8-(2,2-dimethylpropyl)-7-oxo-pyrido[2,3-d]pyrimidin-2-yl]amino}ethyl]benzamide (cpd 80), N-cyclohexyl-4-[(1S)-1-{[8-(2,2-dimethylpropyl)-7-oxo-pyrido[2,3-d]pyrimidin-2-yl]amino}ethyl]benzamide (cpd 81);

2-chloro-N-(4,4-difluorocyclohexyl)-4-(1-{[8-(2,2-dimethylpropyl)-7-oxo-pyrido[2,3-d]pyrimidin-2-yl] amino} ethyl) benzamide (cpd 82);

2-{[(1S)-1-{4-[(4,4-difluoropiperidin-1-yl)carbonyl] phenyl}ethyl]amino}-8-(2,2-dimethylpropyl)pyrido[2,3-d]pyrimidin-7 (8H)-one (cpd 83);

N-(4,4-difluorocyclohexyl)-4-(1-{[8-(2,2-dimethylpropyl)-7-oxo-pyrido[2,3-d]pyrimidin-2-yl]amino}ethyl)-2-fluorobenzamide (cpd 84);

N-(3,3-difluorocyclobutyl)-4-[(1S)-1-{[8-(2,2-dimethylpropyl)-7-oxo-pyrido[2,3-d]pyrimidin-2-yl] amino}ethyl]benzamide (cpd 85);

4-[(1S)-1-{[8-(2,2-dimethylpropyl)-7-oxo-pyrido[2,3-d] pyrimidin-2-yl]amino}ethyl]benzamide (cpd 86);

8-(2,2-dimethylpropyl)-2-{[(1S)-1-{4-[(4-hydroxypiperidin-1-yl)carbonyl]phenyl}ethyl]amino}pyrido[2,3-d]pyrimidin-7(8H)-one (cpd 87);

2-chloro-N-(4,4-difluorocyclohexyl)-4-[(1S)-1-{[8-(2,2-dimethylpropyl)-7-oxo-7,8-dihydropyrido[2,3-d]pyrimidin-2-yl] amino}ethyl]benzamide (cpd 88);

N-(4,4-difluorocyclohexyl)-4-[(1S)-1-{[8-(2,2-dimethylpropyl)-7-oxo-7,8-dihydropyrido[2,3-d]pyrimidin-2-yl]amino}ethyl]-2-fluorobenzamide (cpd 89);

8-(2,2-dimethylpropyl)-2-(1(1S)-1-[3-fluoro-4-(hydroxymethyl)phenyl]ethyl}amino)pyrido[2,3-d]pyrimidin-7(8H)-one (cpd 90);

2-(1(1S)-1-[4-(hydroxymethyl)phenyl]ethyl}amino)-8-(2-methylpropyl)pyrido[2,3-d]pyrimidin-7(8H)-one (cpd 91);

8-(2,6-difluorobenzyl)-2-(1(1S)-1-[4-(hydroxymethyl) phenyl]ethyl}amino)pyrido[2,3-d]pyrimidin-7(8H)-one (cpd 92);

2-(1(1S)-1-[4-(hydroxymethyl)phenyl]ethyl}amino)-8-(2-hydroxy-2-methylpropyl)pyrido[2,3-d]pyrimidin-7 (8H)-one (cpd 93);

2-1[(1S)-1-{4-[(4,4-difluoropiperidin-1-yl)methyl]-3-fluorophenyl}ethyl]amino}-8-(2,2-dimethylpropyl) pyrido[2,3-d] pyrimidin-7(8H)-one (cpd 94);

2-1[(1S)-1-{4-[(4,4-difluoropiperidin-1-yl)methyl] phenyl}ethyl]amino}-8-(2-methylpropyl)pyrido[2,3-d] pyrimidin-7(8H)-one (cpd 95);

8-benzyl-2-[(1-{4-[(4,4-difluoropiperidin-1-yl)methyl] phenyl}ethyl)amino]pyrido[2,3-d]pyrimidin-7(8H)-one (cpd 96);

2-[(1-{4-[(4,4-difluoropiperidin-1-yl)methyl] phenyl}ethyl)amino]-8-(2-fluorobenzyl)pyrido[2,3-d] pyrimidin-7(8H)-one (cpd 97);

8-(2,6-difluorobenzyl)-2-[(1-{4-[(4,4-difluoropiperidin-1-yl)methyl]phenyl}ethyl)amino)pyrido[2,3-d]pyrimidin-7(8H)-one (cpd 98);

8-(2,6-difluorobenzyl)-2-{[(1S)-1-{4-[(4,4-difluoropiperidin-1-yl)methyl]phenyl}ethyl]amino}pyrido[2,3-d] pyrimidin-7(8H)-one (cpd 99);

2-[(1-{4-[(4,4-difluoropiperidin-1-yl)methyl] phenyl}ethyl)amino]-8-(2-fluoroethyl)pyrido[2,3-d] pyrimidin-7(8H)-one (cpd 100);

2-1[(1S)-1-{4-[(4,4-difluoropiperidin-1-yl)methyl] phenyl}ethyl]amino}-8-propylpyrido[2,3-d]pyrimidin-7(8H)-one (cpd 101);

2-(1(1S)-1-[4-(azepan-1-ylmethyl)phenyl]ethyl}amino)-8-propylpyrido[2,3-d]pyrimidin-7(8H)-one (cpd 102);

2-1[(1S)-1-{4-[(4-acetylpiperazin-1-yl)methyl] phenyl}ethyl]amino}-8-propylpyrido[2,3-d]pyrimidin-7(8H)-one (cpd 103);

2-1[(1S)-1-{4-[(4,4-difluoropiperidin-1-yl)methyl] phenyl}ethyl]amino}-8-(2-methylpropyl)pyrido[2,3-d] pyrimidin-7(8H)-one (cpd 104);

2-1[(1S)-1-{4-[(4,4-difluoropiperidin-1-yl)methyl] phenyl}ethyl]amino}-8-(2,2-dimethylpropyl)pyrido[2,3-d]pyrimidin-7(8H)-one (cpd 105);

2-1[(1S)-1-{4-[(4,4-difluoropiperidin-1-yl)methyl] phenyl}ethyl]amino}-8-(2,2,2-trifluoroethyl)pyrido[2,3-d]pyrimidin-7(8H)-one (cpd 106);

8-[2,3-difluoro-2-(fluoromethyl)propyl]-2-1[(1S)-1-{4-[(4,4-difluoropiperidin-1-yl)methyl]phenyl}ethyl] amino}pyrido[2,3-d]pyrimidin-7(8H)-one (cpd 107);

2-1[(1S)-1-{4-[(4,4-difluoropiperidin-1-yl)methyl] phenyl}ethyl]amino}-8-[3,3,3-trifluoro-2-(trifluoromethyl)propyl] pyrido [2,3-d]pyrimidin-7(8H)-one (cpd 108);

8-(cyclobutylmethyl)-2-{[(1S)-1-{4-[(4,4-difluoropiperidin-1-yl)methyl]phenyl}ethyl]amino}pyrido[2,3-d]pyrimidin-7(8H)-one (cpd 109);

8-(2,2-dimethylpropyl)-2-(1(1S)-1-[4-(morpholin-4-ylmethyl)phenyl]ethyl}amino)pyrido[2,3-d]pyrimidin-7 (8H)-one (cpd 110);

8-(2,2-dimethylpropyl)-2-(1(1S)-1-[4-(pyrrolidin-1-ylmethyl)phenyl]ethyl}amino)pyrido[2,3-d]pyrimidin-7(8H)-one (cpd 111);

2-1[(1S)-1-{4-[(4,4-difluoropiperidin-1-yl)methyl]phenyl}ethyl]amino}-8-(2-methylbenzyl)pyrido[2,3-d]pyrimidin-7(8H)-one (cpd 112);

8-(cyclohexylmethyl)-2-{[(1S)-1-{4-[(4,4-difluoropiperidin-1-yl)methyl]phenyl}ethyl]amino}pyrido[2,3-d]pyrimidin-7(8H)-one (cpd 113);

2-{[(1S)-1-{4-[(4,4-difluoropiperidin-1-yl)methyl]phenyl}ethyl]amino}-8-(2-methoxyethyl)pyrido[2,3-d]pyrimidin-7(8H)-one (cpd 114);

2-1[(1S)-1-{4-[(4,4-difluoropiperidin-1-yl)methyl]phenyl}ethyl]amino}-8-[4-fluoro-2-(trifluoromethyl)benzyl]pyrido[2,3-d] pyrimidin-7(8H)-one (cpd 115);

2-1[(1S)-1-{4-[(4,4-difluoropiperidin-1-yl)methyl]phenyl}ethyl]amino}-8-(3,3,3-trifluoro-2,2-dimethylpropyl)pyrido[2,3-d] pyrimidin-7(8H)-one (cpd 116);

2-1[(1S)-1-{4-[(3,3-difluoropiperidin-1-yl)methyl]phenyl}ethyl]amino}-8-(2,2-dimethylpropyl)pyrido[2,3-d]pyrimidin-7(8H)-one (cpd 117);

2-1[(1S)-1-{4-[(4,4-difluoropiperidin-1-yl)methyl]phenyl}ethyl]amino}-4-methyl-8-(2-methylpropyl)pyrido[2,3-d]pyrimidin-7(8H)-one (cpd 118);

2-1[(1S)-1-{4-[(4,4-difluoropiperidin-1-yl)methyl]phenyl}ethyl]amino}-8-(2-hydroxy-2-methylpropyl)pyrido[2,3-d] pyrimidin-7(8H)-one (cpd 119);

2-1[(1S)-1-{4-[(4,4-difluoropiperidin-1-yl)methyl]phenyl}ethyl]amino}-8-[2-(hydroxymethyl)-2-methylpentyl]pyrido[2,3-d] pyrimidin-7(8H)-one (cpd 120);

2,2-dimethyl-3-[2-1[(1S)-1-(naphthalen-2-yl)ethyl]amino}-7-oxopyrido[2,3-d]pyrimidin-8(7H)-yl]propanoic acid (cpd 121);

2,2-dimethyl-3-[2-1[(1S)-1-(naphthalen-2-yl)ethyl]amino}-7-oxopyrido[2,3-d]pyrimidin-8(7H)-yl]propanamide (cpd 122);

N,2,2-trimethyl-3-[7-oxo-2-{[(1S)-1-phenylethyl]amino}pyrido[2,3-d]pyrimidin-8(7H)-yl]propanamide (cpd 123);

N,N,2,2-tetramethyl-3-[7-oxo-2-{[(1S)-1-phenylethyl]amino}pyrido[2,3-d]pyrimidin-8(7H)-yl]propanamide (cpd 124);

2,2-dimethyl-N-(3-methylphenyl)-3-[7-oxo-2-{[(1S)-1-phenylethyl]amino}pyrido[2,3-d]pyrimidin-8(7H)-yl]propanamide (cpd 125);

N-(2-hydroxyethyl)-2,2-dimethyl-3-[7-oxo-2-{[(1S)-1-phenylethyl]amino}pyrido[2,3-d]pyrimidin-8(7H)-yl]propanamide (cpd 126);

N-(3-hydroxypropyl)-2,2-dimethyl-3-[7-oxo-2-{[(1S)-1-phenylethyl]amino}pyrido[2,3-d]pyrimidin-8(7H)-yl]propanamide (cpd 127);

N-[3-(1-hydroxyethyl)phenyl]-2,2-dimethyl-3-[7-oxo-2-{[(1S)-1-phenylethyl]amino}pyrido[2,3-d]pyrimidin-8(7H)-yl] propanamide (cpd 128);

2,2-dimethyl-3-[2-{[(1S)-1-(naphthalen-2-yl)ethyl]amino}-7-oxopyrido[2,3-d]pyrimidin-8(7H)-yl]propanenitrile (cpd 129);

8-(2,2-dimethylpropyl)-2-(1(1S)-1-[4-(1-methyl-1H-pyrazol-4-yl)phenyl]ethyl}amino)pyrido[2,3-d]pyrimidin-7(8H)-one (cpd 130);

8-(2,2-dimethylpropyl)-2-(1(1S)-1-[4-(pyridin-4-yl)phenyl]ethyl}amino)pyrido[2,3-d]pyrimidin-7(8H)-one (cpd 131);

8-(2,2-dimethylpropyl)-2-(1(1S)-1-[4-(2-fluoropyridin-4-yl)phenyl]ethyl}amino)pyrido[2,3-d]pyrimidin-7(8H)-one (cpd 132)

8-(2,2-dimethylpropyl)-2-(1(1S)-1-[4-(thiophen-3-yl)phenyl]ethyl}amino)pyrido[2,3-d]pyrimidin-7(8H)-one (cpd 133);

4'-[(1S)-1-{[8-(2,2-dimethylpropyl)-7-oxo-7,8-dihydropyrido[2,3-d]pyrimidin-2-yl]amino}ethyl]biphenyl-2-carbonitrile (cpd 134);

8-(3-hydroxy-2,2-dimethylpropyl)-2-(1(1S)-1-[4-(1-methyl-1H-pyrazol-4-yl)phenyl]ethyl}amino)pyrido[2,3-d]pyrimidin-7(8H)-one (cpd 135);

8-(3-hydroxy-2,2-dimethylpropyl)-2-(1(1S)-1-[4-(thiophen-3-yl)phenyl]ethyl}amino)pyrido[2,3-d]pyrimidin-7(8H)-one (cpd 136);

8-(2,2-dimethylpropyl)-2-(1(1S)-1-[4-(methylsulfonyl)phenyl]ethyl}amino)pyrido[2,3-d]pyrimidin-7(8H)-one (cpd 137);

8-(2,2-dimethylpropyl)-2-(1(1S)-1-[4-(piperazin-1-ylmethyl)phenyl]ethyl}amino)pyrido[2,3-d]pyrimidin-7(8H)-one dihydrochloride (cpd 138);

2-1[(1S)-1-{4-[(4-acryloylpiperazin-1-yl)methyl]phenyl}ethyl]amino}-8-(2,2-dimethylpropyl)pyrido[2,3-d]pyrimidin-7(8H)-one (cpd 139);

2-1[(1S)-1-{4-[(4-acryloylpiperazin-1-yl)methyl]phenyl}ethyl]amino}-8-(3-hydroxy-2,2-dimethylpropyl)pyrido[2,3-d] pyrimidin-7(8H)-one (cpd 140);

2-1[(1S)-1-{4-[(4-acryloylpiperazin-1-yl)methyl]-3-fluorophenyl}ethyl]amino}-8-(2,2-dimethylpropyl)pyrido[2,3-d] pyrimidin-7(8H)-one (cpd 141);

2-1[(1S)-1-{4-[(4-acryloylpiperazin-1-yl)carbonyl]phenyl}ethyl]amino}-8-(2,2-dimethylpropyl)pyrido[2,3-d]pyrimidin-7(8H)-one (cpd 142);

2-({(1S)-1-[4-({4-[(2E)-but-2-enoyl]piperazin-1-yl}methyl)phenyl]ethyl}amino)-8-(2,2-dimethylpropyl)pyrido[2,3-d] pyrimidin-7(8H)-one (cpd 143);

8-(2,2-dimethylpropyl)-2-{[(1S)-1-(4-1 [4-(2-methylacryloyl)piperazin-1-yl]methyl}phenyl)ethyl]amino} pyrido[2,3-d] pyrimidin-7(8H)-one (cpd 144);

8-(2,2-Dimethyl-propyl)-2-[(S)-1-(4-hydroxy-phenyl)-ethylamino]-8H-pyrido[2,3-d]pyrimidin-7-one (cpd 145);

4-(4-{(S)-1-[8-((S)-1,2-Dimethyl-propyl)-7-oxo-7,8-dihydro-pyrido[2,3-d]pyrimidin-2-ylamino]-ethyl}-phenoxy)-piperidine-1-carboxylic acid benzyl ester (cpd 146);

2-{[(1S)-1-{4-[(3,3-difluoroazetidin-1-yl)methyl]phenyl}ethyl]amino}-8-(2,2-dimethylpropyl)pyrido[2,3-d]pyrimidin-7(8H)-one (cpd 147);

2-{[(1S)-1-{4-[(3,3-difluoropyrrolidin-1-yl)methyl]phenyl}ethyl]amino}-8-(2,2-dimethylpropyl)pyrido[2,3-d]pyrimidin-7(8H)-one (cpd 148);

8-[(2R)-butan-2-yl]-2-1[(1S)-1-{4-[(3,3-difluoropiperidin-1-yl)methyl]phenyl}ethyl]amino}pyrido[2,3-d]pyrimidin-7(8H)-one (cpd 149);

2-1[(1S)-1-(4-1 [(2R,6S)-2,6-dimethylmorpholin-4-yl]methyl}-3-fluorophenyl)ethyl]amino}-8-[(2S)-3-methylbutan-2-yl] pyrido[2,3-d]pyrimidin-7(8H)-one (cpd 150);

2-1[(1S)-1-(4-1 [(2R,6S)-2,6-dimethylmorpholin-4-yl]methyl}-2-fluorophenyl)ethyl]amino}-8-(2,2-dimethylpropyl) pyrido [2,3-d]pyrimidin-7(8H)-one (cpd 151);

2-1[(1S)-1-{4-[(4,4-difluoropiperidin-1-yl)methyl]-2-fluorophenyl}ethyl]amino}-8-(2,2-dimethylpropyl)pyrido[2,3-d] pyrimidin-7(8H)-one (cpd 152);

8-(2,2-dimethylpropyl)-2-(1(1S)-1-[2-fluoro-4-(morpholin-4-ylmethyl)phenyl]ethyl}amino)pyrido[2,3-d]pyrimidin-7(8H)-one (cpd 153);

4-(4-1(S)-1-[8-(2,2-Dimethyl-propyl)-7-oxo-7,8-dihydro-pyrido[2,3-d]pyrimidin-2-ylamino]-ethyl}-phenoxy)-piperidine-1-carboxylic acid tert-butyl ester (cpd 154);

8-((S)-1,2-Dimethyl-propyl)-2-1(S)-1-[4-(piperidin-4-yloxy)-phenyl]-ethylamino}-8H-pyrido[2,3-d]pyrimidin-7-one (cpd 155);

2-1(S)-1-[4-(1-Acryloyl-piperidin-4-yloxy)-phenyl]-ethylamino}-8-(2,2-dimethyl-propyl)-8H-pyrido[2,3-d]pyrimidin-7-one (cpd 156);

8-(2,2-dimethylpropyl)-2-{[(1S)-1-(4-1 [4-(2-methylpropanoyl)piperazin-1-yl]methyl}phenyl)ethyl]amino}pyrido[2,3-d] pyrimidin-7(8H)-one (cpd 157);

2-1[(1S)-1-(4-1 [4-(cyclopropylcarbonyl)piperazin-1-yl]methyl}phenyl)ethyl]amino}-8-(2,2-dimethylpropyl) pyrido[2,3-d] pyrimidin-7(8H)-one (cpd 158);

2-1(S)-1-[4-(1-Acryloyl-piperidin-4-yloxy)-phenyl]-ethylamino}-8-((S)-1,2-dimethyl-propyl)-8H-pyrido[2,3-d]pyrimidin-7-one (cpd 159);

8-((S)-1,2-Dimethyl-propyl)-2-{(S)-1-[4-(1-isobutyryl-piperidin-4-yloxy)-phenyl]-ethylamino}-8H-pyrido[2,3-d]pyrimidin-7-one (cpd 160);

2-{(S)-1-[4-(4-Acryloyl-piperazin-1-ylmethyl)-phenyl]-ethylamino}-8-((S)-1,2-dimethyl-propyl)-8H-pyrido[2,3-d] pyrimidin-7-one (cpd 161);

8-((S)-1,2-Dimethyl-propyl)-2-((S)-1-{4-[4-(2-methylacryloyl)-piperazin-1-ylmethyl]-phenyl}-ethylamino)-8H-pyrido [2,3-d]pyrimidin-7-one (cpd 162);

2-{[(1S)-1-(4-bromophenyl)ethyl]amino}-8-[(2S)-3-methylbutan-2-yl]pyrido[2,3-d]pyrimidin-7(8H)-one (cpd 163);

2-{[(1S)-1-(4-{[(2R,6S)-2,6-dimethylmorpholin-4-yl]methyl}phenyl)ethyl]amino}-8-[(2S)-1,1,1-trifluoropropan-2-yl] pyrido[2,3-d]pyrimidin-7(8H)-one (cpd 164);

4'-[(1S)-1-({8-[(2S)-3-methylbutan-2-yl]-7-oxo-7,8-dihydropyrido[2,3-d]pyrimidin-2-yl}amino)ethyl]biphenyl-2-carbonitrile (cpd 165);

2-(1(1S)-1-[4-(2-fluoropyridin-4-yl)phenyl]ethyl}amino)-8-[(2S)-3-methylbutan-2-yl]pyrido[2,3-d]pyrimidin-7(8H)-one (cpd 166);

tert-butyl 4-{4-[(1S)-1-({8-[(2S)-3-methylbutan-2-yl]-7-oxo-7, 8-dihydropyrido[2,3-d]pyrimidin-2-yl}amino)ethyl]phenyl}-3,6-dihydropyridine-1(2H)-carboxylate (cpd 167);

2-(1(1S)-1-[4-(1-acryloyl-1,2,3,6-tetrahydropyridin-4-yl)phenyl]ethyl}amino)-8-[(2S)-3-methylbutan-2-yl] pyrido[2,3-d] pyrimidin-7(8H)-one (cpd 168);

2-1[(1S)-1-{4-[(4-acryloylpiperazin-1-yl)methyl]phenyl}ethyl]amino}-8-[(2S)-1,1,1-trifluoropropan-2-yl]pyrido[2,3-d] pyrimidin-7(8H)-one (cpd 169);

2-1[(1S)-1-{4-[(3,3-difluoropiperidin-1-yl)methyl]phenyl}ethyl]amino}-8-(propan-2-yl)pyrido[2,3-d]pyrimidin-7(8H)-one (cpd 170);

8-[(1S)-1-cyclopropylethyl]-2-1[(1S)-1-(4-{[(2R,6S)-2,6-dimethylmorpholin-4-yl]methyl}-3-fluorophenyl)ethyl] amino} pyrido[2,3-d]pyrimidin-7(8H)-one (cpd 171);

2-1[(1S)-1-(6-chloro-2-oxo-1,2-dihydroquinolin-3-yl)ethyl]amino}-8-[(2S)-3-methylbutan-2-yl]pyrido[2,3-d]pyrimidin-7(8H)-one (cpd 172);

8-[(2S)-3-methylbutan-2-yl]-2-({(1S)-1-[4-(morpholin-4-yl)phenyl]ethyl}amino)pyrido[2,3-d]pyrimidin-7 (8H)-one (cpd 173);

benzyl 4-{4-[(1S)-1-({8-[(2S)-3-methylbutan-2-yl]-7-oxo-7,8-dihydropyrido[2,3-d]pyrimidin-2-yl}amino)ethyl]phenyl} piperazine-1-carboxylate (cpd 174);

2-({(1S)-1-[4-(4-acryloylpiperazin-1-yl)phenyl]ethyl}amino)-8-[(2S)-3-methylbutan-2-yl]pyrido[2,3-d]pyrimidin-7(8H)-one (cpd 175);

8-[(2S)-3-methylbutan-2-yl]-2-(1(1S)-1-[4-(piperazin-1-yl)phenyl]ethyl}amino)pyrido [2,3-d]pyrimidin-7 (8H)-one (cpd 176);

2-(1(1S)-1-[4-(4-ethylpiperazin-1-yl)phenyl]ethyl}amino)-8-[(2S)-3-methylbutan-2-yl]pyrido[2,3-d]pyrimidin-7(8H)-one (cpd 177);

benzyl 4-{2-fluoro-4-[(1S)-1-({8-[(2S)-3-methylbutan-2-yl]-7-oxo-7,8-dihydropyrido [2,3-d]pyrimidin-2-yl}amino)ethyl] phenyl}piperazine-1-carboxylate (cpd 178);

2-(1(1S)-1-[4-(4-acryloylpiperazin-1-yl)-3-fluorophenyl]ethyl}amino)-8-[(2S)-3-methylbutan-2-yl]pyrido[2,3-d]pyrimidin-7(8H)-one (cpd 179);

8-[(2S)-3-methylbutan-2-yl]-2-(1(1S)-1-[6-(piperazin-1-yl)pyridin-3-yl]ethyl}amino)pyrido[2,3-d]pyrimidin-7 (8H)-one (cpd 180);

2-(1(1S)-1-[6-(4-acryloylpiperazin-1-yl)pyridin-3-yl]ethyl}amino)-8-[(2S)-3-methylbutan-2-yl]pyrido[2,3-d]pyrimidin-7(8H)-one (cpd 181);

2-{[(1S)-1-{4-[(4-acryloylpiperazin-1-yl)methyl]phenyl}ethyl]amino}-8-(2-azidoethyl)pyrido[2,3-d]pyrimidin-7(8H)-one (cpd 182);

2-1[(1S)-1-{4-[(4-acryloylpiperazin-1-yl)methyl]-3-fluorophenyl}ethyl]amino}-8-(propan-2-yl)pyrido[2,3-d]pyrimidin-7(8H)-one (cpd 183);

2-1[(1S)-1-{4-[(4-acryloylpiperazin-1-yl)methyl]phenyl}ethyl]amino}-8-(propan-2-yl)pyrido[2,3-d]pyrimidin-7(8H)-one (cpd 184);

tert-butyl 4-(4-{(1S)-1-[(8-ethyl-7-oxo-7,8-dihydropyrido[2,3-d]pyrimidin-2-yl)amino]ethyl}benzyl)piperazine-1-carboxylate (cpd 185);

2-1[(1S)-1-{4-[(4-acryloylpiperazin-1-yl)methyl]phenyl}ethyl]amino}-8-ethylpyrido[2,3-d]pyrimidin-7 (8H)-one (cpd 186);

2-1[(1S)-1-{4-[1-(4-acryloylpiperazin-1-yl)propyl]phenyl}ethyl]amino}-8-(propan-2-yl)pyrido[2,3-d]pyrimidin-7(8H)-one (cpd 187);

8-[(2S)-3-methylbutan-2-yl]-2-{[(1S)-1-{4-[(4-methyl-3-oxopiperazin-1-yl)methyl]phenyl}ethyl]amino}pyrido [2,3-d] pyrimidin-7(8H)-one (cpd 188);

tert-butyl 4-(4-1(1S)-1-[(8-ethyl-7-oxo-7,8-dihydropyrido[2,3-d]pyrimidin-2-yl)amino]ethyl}benzoyl)piperazine-1-carboxylate (cpd 189);

2-1[(1S)-1-{4-[(4-acryloylpiperazin-1-yl)carbonyl]phenyl}ethyl]amino}-8-ethylpyrido[2,3-d]pyrimidin-7 (8H)-one (cpd 190);

2-{1[(1S)-1-{4-[(4-acryloylpiperazin-1-yl)carbonyl]-3-fluorophenyl}ethyl]amino}-8-[(2S)-3-methylbutan-2-yl]pyrido[2,3-d]pyrimidin-7(8H)-one (cpd 191);

N-(1-acryloylpiperidin-4-yl)-2-fluoro-4-[(1S)-1-{[7-oxo-8-(propan-2-yl)-7,8-dihydropyrido[2,3-d]pyrimidin-2-yl] amino} ethyl]benzamide (cpd 192);

tert-butyl 6-[(1S)-1-({8-[(2S)-3-methylbutan-2-yl]-7-oxo-7,8-dihydropyrido[2,3-d]pyrimidin-2-yl}amino)ethyl]-3',6'-dihydro-3,4'-bipyridine-1'(2'H)-carboxylate (cps 193);

2-{[(1S)-1-(1'-acryloyl-1',2',3',6'-tetrahydro-3,4'-bipyridin-6-yl)ethyl]amino}-8-[(2S)-3-methylbutan-2-yl] pyrido[2,3-d] pyrimidin-7(8H)-one (cpd 194);

2-(1(1S)-1-[1'-(cyclopropylcarbonyl)-1',2',3',6'-tetrahydro-3,4'-bipyridin-6-yl]ethyl}amino)-8-[(2S)-3-methylbutan-2-yl] pyrido[2,3-d]pyrimidin-7(8H)-one (cpd 195);

8-[(2S)-3-methylbutan-2-yl]-2-(1(1S)-1-[2'-(trifluorom-ethyl)-3,4'-bipyridin-6-yl]ethyl}amino)pyrido[2,3-d]pyrimidin-7(8H)-one (cpd 196);

2-1[(1S)-1-(2'-fluoro-3,4'-bipyridin-6-yl)ethyl]amino}-8-[(2S)-3-methylbutan-2-yl]pyrido[2,3-d]pyrimidin-7(8H)-one (cpd 197);

2-1[(1S)-1-{4-[(4-acryloylpiperazin-1-yl)methyl]phenyl}ethyl]amino}-8-[(2S)-1-fluoropropan-2-yl]pyrido[2,3-d]pyrimidin-7(8H)-one (cpd 198);

2-1[(1S)-1-{4-[(4-acryloylpiperazin-1-yl)methyl]phenyl}ethyl]amino}-8-[(2S)-1-hydroxypropan-2-yl]pyrido[2,3-d] pyrimidin-7(8H)-one (cpd 199);

tert-butyl 4-{4-[(1S)-1-{[4-cyano-8-(2,2-dimethylpropyl)-7-oxo-7,8-dihydropyrido[2,3-d]pyrimidin-2-yl]amino} ethyl] benzyl}piperazine-1-carboxylate (cpd 200);

2-1[(1S)-1-{4-[(4-acryloylpiperazin-1-yl)methyl]phenyl}ethyl]amino}-8-(2,2-dimethylpropyl)-4-ethoxypyrido[2,3-d] pyrimidin-7(8H)-one (cpd 201);

2-1[(1S)-1-{4-[(4-acryloylpiperazin-1-yl)methyl]phenyl}ethyl]amino}-8-(2,2-dimethylpropyl)-4-(methylamino)pyrido[2,3-d]pyrimidin-7(8H)-one (cpd 202);

2-1[(1S)-1-{4-[(4-acryloylpiperazin-1-yl)methyl]phenyl}ethyl]amino}-4-(dimethylamino)-8-(propan-2-yl)pyrido[2,3-d] pyrimidin-7(8H)-one (cpd 203);

2-1[(1S)-1-{4-[(4-acryloylpiperazin-1-yl)methyl]phenyl}ethyl]amino}-7-oxo-8-(propan-2-yl)-7,8-dihydropyrido[2,3-d] pyrimidine-4-carbonitrile (cpd 204);

2-1[(1S)-1-{4-[(4-acryloylpiperazin-1-yl)methyl]phenyl}ethyl]amino}-4-[(2,4-dimethoxybenzyl)amino]-8-(propan-2-yl) pyrido[2,3-d]pyrimidin-7(8H)-one (cpd 205);

2-1[(1S)-1-{4-[(4-acryloylpiperazin-1-yl)methyl]phenyl}ethyl]amino}-4-amino-8-(propan-2-yl)pyrido[2,3-d]pyrimidin-7(8H)-one (cpd 206);

2-{[(1S)-1-(4-{[(2R)-4-acryloyl-2-methylpiperazin-1-yl]methyl}phenyl)ethyl]amino}-8-ethylpyrido[2,3-d]pyrimidin-7(8H)-one (cpd 207);

2-{[(1S)-1-(4-{[(3R)-4-acryloyl-3-methylpiperazin-1-yl]methyl}phenyl)ethyl]amino}-8-ethylpyrido[2,3-d]pyrimidin-7(8H)-one (cpd 208);

2-{[(1S)-1-(4-{[(2R)-4-acryloyl-2-(propan-2-yl)piperazin-1-yl]methyl}phenyl)ethyl]amino}-8-ethylpyrido[2,3-d]pyrimidin-7(8H)-one (cpd 209);

2-{[(1S)-1-(4-{[(2S)-4-acryloyl-2-methylpiperazin-1-yl]methyl}phenyl)ethyl]amino}-8-ethylpyrido[2,3-d]pyrimidin-7(8H)-one (cpd 210);

2-{[(1S)-1-(4-{[(3S)-4-acryloyl-3-methylpiperazin-1-yl]methyl}phenyl)ethyl]amino}-8-ethylpyrido[2,3-d]pyrimidin-7(8H)-one (cpd 211);

2-{[(1S)-1-(4-{[(2S)-4-acryloyl-2-(propan-2-yl)piperazin-1-yl]methyl}phenyl)ethyl]amino}-8-ethylpyrido[2,3-d]pyrimidin-7(8H)-one (cpd 212);

2-{[(1S)-1-{6-[(4-acryloylpiperazin-1-yl)methyl]pyridin-3-yl}ethyl]amino}-8-(propan-2-yl)pyrido[2,3-d]pyrimidin-7(8H)-one (cpd 213);

2-1[(1S)-1-{4-[1-(4-acryloylpiperazin-1-yl)propyl]phenyl}ethyl]amino}-8-ethylpyrido[2,3-d]pyrimidin-7(8H)-one (cpd 214);

2-1[(1S)-1-{4-[1-(4-acryloylpiperazin-1-yl)propyl]phenyl}ethyl]amino}-8-methylpyrido[2,3-d]pyrimidin-7(8H)-one (cpd 215);

2-1[(1S)-1-{4-[1-(4-acryloylpiperazin-1-yl)propyl]phenyl}ethyl]amino}-8-(2,6-difluorobenzyl)pyrido[2,3-d]pyrimidin-7(8H)-one (cpd 216);

2-1[(1S)-1-{4-[(4-acryloylpiperazin-1-yl)methyl]phenyl}ethyl]amino}-8-(4-ethynyl-2-fluorobenzyl)pyrido[2,3-d]pyrimidin-7(8H)-one (cpd 217);

2-1[(1S)-1-{4-[1-(4-acryloylpiperazin-1-yl)propyl]phenyl}ethyl]amino}-8-cyclopropylpyrido[2,3-d]pyrimidin-7(8H)-one (cpd 218);

2-1[(1S)-1-{4-[1-(4-acryloylpiperazin-1-yl)-2-cyclopropylethyl]phenyl}ethyl]amino}-8-ethylpyrido[2,3-d]pyrimidin-7(8H)-one (cpd 219);

2-1[(1S)-1-{4-[1-(4-acryloylpiperazin-1-yl)-2-cyclopropylethyl]phenyl}ethyl]amino}-8-(propan-2-yl)pyrido[2,3-d] pyrimidin-7(8H)-one (cpd 220);

2-1[(1S)-1-(4-{1-[4-(2-methylacryloyl)piperazin-1-yl]propyl}phenyl)ethyl]amino}-8-(propan-2-yl)pyrido[2,3-d]pyrimidin-7(8H)-one (cpd 221);

2-(1S)-1-[4-(1-{4-[(2E)-but-2-enoyl]piperazin-1-yl}propyl)phenyl]ethyl}amino)-8-(propan-2-yl)pyrido[2,3-d]pyrimidin-7(8H)-one (cpd 222);

2-{[(1S)-1-(4-{[(3R)-1-acryloylpyrrolidin-3-yl]oxy}phenyl)ethyl]amino}-8-ethylpyrido[2,3-d]pyrimidin-7(8H)-one (cpd 223);

2-{[(1S)-1-(4-{[(3S)-1-acryloylpyrrolidin-3-yl]oxy}phenyl)ethyl]amino}-8-ethylpyrido[2,3-d]pyrimidin-7(8H)-one (cpd 224);

phenyl 4-[(1S)-1-{4-[(1S)-1-{[7-oxo-8-(propan-2-yl)-7,8-dihydropyrido[2,3-d]pyrimidin-2-yl]amino}ethyl]phenyl} propyl] piperazine-1-carboxylate (cpd 225);

phenyl 4-[(1R)-1-{4-[(1S)-1-{[7-oxo-8-(propan-2-yl)-7,8-dihydropyrido[2,3-d]pyrimidin-2-yl]amino}ethyl]phenyl}propyl] piperazine-1-carboxylate (cpd 226);

2-1[(1S)-1-{4-[(1S)-1-(4-acryloylpiperazin-1-yl)propyl]phenyl}ethyl]amino}-8-(propan-2-yl)pyrido[2,3-d]pyrimidin-7(8H)-one (cpd 227);

2-1[(1S)-1-{4-[(1R)-1-(4-acryloylpiperazin-1-yl)propyl]phenyl}ethyl]amino}-8-(propan-2-yl)pyrido[2,3-d]pyrimidin-7(8H)-one (cpd 228);

2-1[(1R)-1-{4-[(1R)-1-(4-acryloylpiperazin-1-yl)propyl]phenyl}ethyl]amino}-8-(propan-2-yl)pyrido[2,3-d]pyrimidin-7(8H)-one (cpd 229);

2-1[(1S)-1-{4-[(1S)-1-(4-acryloylpiperazin-1-yl)-2-cyclopropylethyl]phenyl}ethyl]amino}-8-(propan-2-yl)pyrido[2,3-d] pyrimidin-7(8H)-one (cpd 230);

2-1[(1S)-1-{4-[(1R)-1-(4-acryloylpiperazin-1-yl)-2-cyclopropylethyl]phenyl}ethyl]amino}-8-(propan-2-yl)pyrido[2,3-d] pyrimidin-7(8H)-one (cpd 231);

4-{4-[(S)-1-(1-Ethyl-2-oxo-1,2-dihydro-[1,6]naphthyridin-7-ylamino)-ethyl]-benzyl}-piperazine-1-carboxylic acid tert-butyl ester (cpd 232);

4-(1-{4-[(S)-1-(1-Ethyl-2-oxo-1,2-dihydro-[1,6]naphthyridin-7-ylamino)-ethyl]-phenyl}-propyl)-piperazine-1-carboxylic acid tert-butyl ester (cpd 233);

4-((S)-1-{4-[(S)-1-(1-Ethyl-2-oxo-1,2-dihydro-[1,6]naphthyridin-7-ylamino)-ethyl]-phenyl}-propyl)-piperazine-1-carboxylic acid phenyl ester (cpd 234);

7-1(S)-1-[4-(3,3-Difluoro-piperidin-1-ylmethyl)-phenyl]-ethylamino}-1-(2,2-dimethyl-propyl)-1H-[1,6]naphthyridin-2-one (cpd 235);

7-1(S)-1-[4-(4-Acryloyl-piperazin-1-ylmethyl)-phenyl]-ethylamino}-1-ethyl-1H-[1,6]naphthyridin-2-one (cpd 236);

7-((S)-1-{4-[1-(4-Acryloyl-piperazin-1-yl)-propyl]-phenyl}-ethylamino)-1-ethyl-1H-[1,6]naphthyridin-2-one (cpd 237);

7-((S)-1-{4-[(S)-1-(4-Acryloyl-piperazin-1-yl)-propyl]-phenyl}-ethylamino)-1-ethyl-1H-[1,6]naphthyridin-2-one (cpd 238);

7-1[(1S)-1-{4-[(1S)-1-(4-acryloylpiperazin-1-yl)propyl]phenyl}ethyl]amino}-1-(propan-2-yl)-1,6-naphthyridin-2(1H)-one (cpd 239);

2-1[(1S)-1-{4-[1-(4-propanoylpiperazin-1-yl)propyl]phenyl}ethyl]amino}-8-(propan-2-yl)pyrido[2,3-d]pyrimidin-7(8H)-one (cpd 240);

1-acryloyl-4-{4-[(1S)-1-{[7-oxo-8-(propan-2-yl)-7,8-dihydropyrido[2,3-d]pyrimidin-2-yl]amino}ethyl]phenyl}piperidine-4-carbonitrile (cpd 241);

2-1[(1S)-1-(4-{(1S)-1-[4-(3-chloropropanoyl)piperazin-1-yl]-2-cyclopropylethyl}phenyl)ethyl]amino}-8-(propan-2-yl) pyrido[2,3-d]pyrimidin-7(8H)-one (cpd 242);

2-1[(1S)-1-(4-1(1R)-1-[4-(3-hydroxypropanoyl)piperazin-1-yl]propyl}phenyl)ethyl]amino}-8-(propan-2-yl) pyrido[2,3-d] pyrimidin-7(8H)-one (cpd 243);

2-[(1-{4-[1[-(4-acryloylpiperazin-1-yl)-2-cyclopropylethyl]phenyl}cyclopropyl)amino]-8-(propan-2-yl) pyrido[2,3-d] pyrimidin-7(8H)-one (cpd 244);

2-[(1-{4-1[(1R)-1-(4-acryloylpiperazin-1-yl)-2-cyclopropylethyl]phenyl}cyclopropyl)amino]-8-(propan-2-yl) pyrido[2,3-d] pyrimidin-7(8H)-one (cpd 245);

2-[(1-{4-1[(1S)-1-(4-acryloylpiperazin-1-yl)-2-cyclopropylethyl]phenyl}cyclopropyl)amino]-8-(propan-2-yl) pyrido[2,3-d] pyrimidin-7(8H)-one (cpd 246);

2-[(1-{4-[1-(4-acryloylpiperazin-1-yl)propyl]phenyl}cyclopropyl)amino]-8-(propan-2-yl)pyrido[2,3-d]pyrimidin-7(8H)-one (cpd 247);

2-[(1-{4-[(1R)-1-(4-acryloylpiperazin-1-yl)propyl]phenyl}cyclopropyl)amino]-8-(propan-2-yl)pyrido[2,3-d]pyrimidin-7(8H)-one (cpd 248);

2-[(1-{4-[(1S)-1-(4-acryloylpiperazin-1-yl)propyl]phenyl}cyclopropyl)amino]-8-(propan-2-yl)pyrido[2,3-d]pyrimidin-7(8H)-one (cpd 249);

2-1[(1S)-1-{4-[(2E)-pent-2-en-3-yl]phenyl}ethyl]amino}-8-(propan-2-yl)pyrido[2,3-d]pyrimidin-7(8H)-one (cpd 250); and 7-1[(1S)-1-{4-[(1S)-1-(4-acryloylpiperazin-1-yl)-2-cyclopropylethyl]phenyl}ethyl]amino}-1-(propan-2-yl)-1,6-naphthyridin-2(1H)-one (cpd 251).

6. A method of treating a disease caused by and/or associated with increased 2-hydroxyglutarate level, which comprises administering to a mammal, preferably a human, in need thereof, an effective amount of a compound of formula (I) as defined in claim 1.

7. A method of treating a disease caused by and/or associated with mutated IDH enzymes, which comprises administering to a mammal, preferably a human, in need thereof, an effective amount of compound of formula (I) as defined in claim 1.

8. A method of treating a disease caused by and/or associated with IDH wt over-functions, which comprises administering to a mammal, preferably a human, in need thereof, an effective amount of compound of formula (I) as defined in claim 1.

9. The method according to claim 6, wherein the disease is selected from the group consisting of cancer, cell proliferative disorders and immune-related disorders.

10. The method according to claim 9, wherein the disease is cancer.

11. The method according to claim 10, wherein said cancer is selected from the group consisting of: carcinomas, such as bladder, breast, kidney, liver, colon, lung, including small cell lung cancer, esophagus, gall-bladder, ovary, pancreas, stomach, cervix, prostate, and skin, including squamous cell carcinoma; hematopoietic tumors of lymphoid lineage including leukemia, acute lymphocitic leukemia, acute lymphoblastic leukemia, B-cell lymphoma, angioimmunoblastic T-cell lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including glioma, glioblastoma, glioblastoma multiforme, astrocytoma, oligodendroglioma, paraglioma, neuroblastoma, and schwannomas; and other tumors, including melanoma, seminoma, teratocarcinoma, osteosarcoma, xeroderma pigmentosum, keratoxanthoma, thyroid cancers, such as papillary thyroid carcinoma and medullary thyroid carcinoma, Kaposi's sarcoma, chondrosarcoma, and cholangiocarcinoma.

12. A pharmaceutical composition comprising a compound of formula (I) or a pharmaceutically acceptable salt thereof, as defined in claim 1, in association with a pharmaceutically acceptable excipient, carrier or diluent.

13. A pharmaceutical composition according to claim 12 further comprising one or more chemotherapeutic agents.

14. A kit comprising a compound of formula (I) or a pharmaceutically acceptable salt thereof, as defined in claim 1, and one or more chemotherapeutic agents, as a combined preparation for simultaneous, separate or sequential use in anticancer therapy.

15. The method according to claim 6 in combination with radiation therapy or with a chemotherapy regimen.

16. A compound of claim 1 having the following structure:

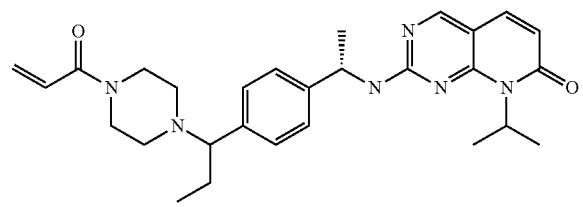 [SMILES: C=CC(=O)N1CCN(C(CC)c2ccc([C@H](C)Nc3ncc4ccc(=O)n(C(C)C)c4n3)cc2)CC1]

or a pharmaceutically acceptable salt thereof.

* * * * *